(12) United States Patent
Füßlein et al.

(10) Patent No.: US 10,820,591 B2
(45) Date of Patent: Nov. 3, 2020

(54) SUBSTITUTED SULFONYL AMIDES FOR CONTROLLING ANIMAL PESTS

(71) Applicants: Bayer Aktiengesellschaft, Leverkusen (DE); Bayer CropScience Aktiengesellschaft, Monheim am Rhein (DE)

(72) Inventors: Martin Füßlein, Düsseldorf (DE); Heinz-Jürgen Wroblowsky, Langenfeld (DE); Susanne Kübbeler, Düsseldorf (DE); Dominik Hager, Monheim (DE); Nina Kausch-Busies, Bergisch Gladbach (DE); Roland Andree, Langenfeld (DE); Johannes-Rudolf Jansen, Monheim (DE); Hans-Georg Schwarz, Dorsten (DE); Daniela Portz, Vettweiß (DE); Kerstin Ilg, Cologne (DE); Olga Malsam, Rösrath (DE); Sascha Eilmus, Leichlingen (DE); Peter Lösel, Leverkusen (DE); Stefan Herrmann, Langenfeld (DE); Angela Becker, Opio (FR); Arnd Voerste, Cologne (DE); Ulrich Görgens, Ratingen (DE); Anton Lishchynskyi, Langen (DE); Andreas Turberg, Haan (DE)

(73) Assignees: Bayer Aktiengesellschaft, Leverkusen (DE); Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 16/347,776

(22) PCT Filed: Nov. 6, 2017

(86) PCT No.: PCT/EP2017/078280
§ 371 (c)(1),
(2) Date: May 6, 2019

(87) PCT Pub. No.: WO2018/083288
PCT Pub. Date: May 11, 2018

(65) Prior Publication Data
US 2019/0269134 A1    Sep. 5, 2019

(30) Foreign Application Priority Data

Nov. 7, 2016  (EP) .................................... 16197465

(51) Int. Cl.
| | | |
|---|---|---|
| A01N 43/56 | (2006.01) |
| A01N 43/50 | (2006.01) |
| A01N 43/54 | (2006.01) |
| A01N 43/80 | (2006.01) |
| C07D 231/14 | (2006.01) |
| C07D 233/90 | (2006.01) |
| C07D 401/04 | (2006.01) |
| C07D 403/12 | (2006.01) |
| C07D 405/12 | (2006.01) |
| C07D 409/12 | (2006.01) |
| C07D 413/12 | (2006.01) |

(52) U.S. Cl.
CPC ............ *A01N 43/56* (2013.01); *A01N 43/50* (2013.01); *A01N 43/54* (2013.01); *A01N 43/80* (2013.01); *C07D 231/14* (2013.01); *C07D 233/90* (2013.01); *C07D 401/04* (2013.01); *C07D 403/12* (2013.01); *C07D 405/12* (2013.01); *C07D 409/12* (2013.01); *C07D 413/12* (2013.01)

(58) Field of Classification Search
CPC ........ A01N 43/50; A01N 43/54; A01N 43/80; C07D 231/14; C07D 233/90; C07D 401/04; C07D 403/12; C07D 405/12; C07D 409/12; C07D 413/12
USPC ........................................ 548/300.1
See application file for complete search history.

(56) References Cited

U.S. PATENT DOCUMENTS

| | | | | |
|---|---|---|---|---|
| 4,179,277 A | * | 12/1979 | Beck .................... | C07D 233/68 504/181 |
| 6,251,827 B1 | * | 6/2001 | Ziemer ................. | A01N 41/06 504/130 |

(Continued)

FOREIGN PATENT DOCUMENTS

| | | | | |
|---|---|---|---|---|
| CA | 3017547 A1 | * | 9/2017 | ........... C07D 401/04 |
| CN | 103483259 A | * | 1/2014 | ........... C07D 231/14 |

(Continued)

OTHER PUBLICATIONS

DiMauro; J. Med. Chem. 2016, 59, 17, 7818-7839, with Supporting Information, S1-S14. (Year: 2016).*
Song; Bioorganic & Medicinal Chemistry 2009, 17, 3080-3092. (Year: 2009).*
STN Registry Database, record for RN 2137594-63-7, Entered into STN on Nov. 1, 2017. (Year: 2017).*

(Continued)

*Primary Examiner* — Daniel R Carcanague
(74) *Attorney, Agent, or Firm* — Morrison and Foerster, LLP

(57) ABSTRACT

The present invention relates to the use of a compound of the general formula (I)

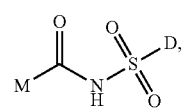

(I)

in which M and D have the meanings given in the description for controlling animal pests, in particular nematodes.

11 Claims, No Drawings

(56) References Cited

U.S. PATENT DOCUMENTS

| | | | |
|---|---|---|---|
| 8,623,898 B2 * | 1/2014 | Yasuhara | C07D 405/12 514/383 |
| 9,044,015 B2 * | 6/2015 | Bretschneider | A01N 43/40 |
| 2005/0009705 A1 * | 1/2005 | Feucht | A01N 47/38 504/277 |

FOREIGN PATENT DOCUMENTS

| | | | | |
|---|---|---|---|---|
| WO | WO2003040107 A1 | 5/2003 | | |
| WO | WO2005099705 A2 | 10/2005 | | |
| WO | WO2010129500 A2 | 11/2010 | | |
| WO | WO2015169776 A1 | 11/2015 | | |
| WO | WO-2017157735 A1 * | 9/2017 | | C07D 233/90 |

OTHER PUBLICATIONS

International Search Report, dated Mar. 15, 2018 for PCT/EP2017/078280, filed Nov. 6, 2017, 4 pages.

* cited by examiner

SUBSTITUTED SULFONYL AMIDES FOR CONTROLLING ANIMAL PESTS

CROSS REFERENCE TO RELATED APPLICATIONS

This application is a national stage application under 35 U.S.C. § 371 of International Application No. PCT/EP2017/078280, filed internationally on Nov. 6, 2017, which claims priority benefit to European Application No. 16197465.4, filed Nov. 7, 2016.

The present application relates to the use of substituted sulfonamides for controlling animal pests, in particular nematodes, to a composition comprising substituted sulfonamides for controlling animal pests, to a method for controlling animal pests and to an agrochemical formulation comprising the substituted sulfonamides. The invention also relates to novel substituted sulfonamides.

In the literature, sulfonamides and their suitability as active compounds are described, for example, in the patent applications WO 2005/099705, WO 2003/040107, WO 2014/077285 and WO 2014/023367.

In addition, it is known, for example from the documents WO 2010/129500, WO 2012/054233, WO 2013/055584, WO 2014/109933, WO 2015/007668, WO 2015/011082 and WO 2015/169776, that certain sulfonamides can be used as nematicides.

In addition, sulfonamides which can be used as insecticides are also known from EP 2092824.

Modern nematicides and insecticides have to meet many demands, for example in relation to extent, persistence and spectrum of their action and possible use. Questions of toxicity, sparing of beneficial species and pollinators, environmental properties, application rates, combinability with other active compounds or formulation auxiliaries play a role, as does the question of the effort required for the synthesis of an active compound; furthermore, resistances may occur, to mention only some parameters. For all these reasons alone, the search for novel crop protection compositions cannot be considered complete, and there is a constant need for novel compounds having equal or, at least in relation to individual aspects, improved properties compared to the known compounds.

It was an object of the present invention to provide compounds for use for controlling animal pests, which compounds widen the spectrum of the pesticides in various aspects.

This object, and further objects which are not stated explicitly but can be discerned or derived from the connections discussed herein, are achieved by the use of a compound of the formula (I)

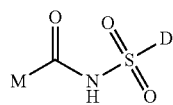
(I)

where
M represents a radical selected from formulae (IIa-IIc):

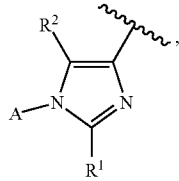
(IIa)

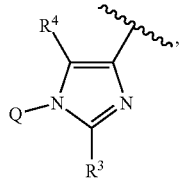
(IIb)

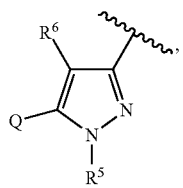
(IIc)

where (Embodiment 1-1)
$R^1$ represents hydrogen, hydroxy, cyano, carboxyl, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-alkylsulfoximino, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, halo-$(C_1-C_6)$-alkylthio-$(C_1-C_6)$-alkyl, halo-$(C_1-C_6)$-alkylsulfinyl-$(C_1-C_6)$-alkyl, halo$(C_1-C_6)$-alkylsulfonyl-$(C_1-C_6)$-alkyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl-$(C_1-C_6)$-alkyl or hetaryl-$(C_1-C_6)$-alkyl which is optionally monosubstituted or polysubstituted by identical or different substituents, where, in the case of hetaryl, optionally at least one carbonyl group may be present and where the substituent(s) in each case independently of one another are selected from:

cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, $R^2$ represents hydrogen, cyano, halogen, nitro, acetyl, hydroxy, carboxyl, amino, SCN, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-alkylsulfoximino, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl or hetaryl, optionally mono- or polysubstituted by identical or different substituents, where in the case of hetaryl optionally at least one carbonyl group may be present and where possible substituents in each case are as follows: cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, $R^3$ represents hydrogen, cyano, halogen, hydroxy, carboxyl, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbon-yl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-alkylsulfoximino, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl-$(C_1-C_6)$-alkyl or hetaryl-$(C_1-C_6)$-alkyl which is optionally monosubstituted or polysubstituted by identical or different substituents, where, in the case of hetaryl, optionally at least one carbonyl group may be present and where the substituent(s) in each case independently of one another are selected from:

cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, $R^4$ represents hydrogen, cyano, halogen, nitro, acetyl, hydroxy, carboxyl, amino, SCN, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkylsulfoximino, $(C_1-C_6)$-alkoxy-$(C_1-C_6)$-alkylsulfinyl, $(C_1-C_6)$-alkylsulfinyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl or hetaryl, optionally mono- or polysubstituted by identical or different substituents, where in the case of hetaryl optionally at least one carbonyl group may be present and where possible substituents in each case are as follows: cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, $R^5$ represents hydrogen, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$- alkyl, halo-$(C_1-C_6)$-alkylthio-$(C_1-C_6)$-alkyl, halo-$(C_1-C_6)$-alkylsulfinyl-$(C_1-C_6)$-alkyl or halo-$(C_1-C_6)$-alkylsulfonyl-$(C_1-C_6)$-alkyl, $R^6$ represents hydrogen, cyano, halogen, nitro, acetyl, hydroxy, carboxyl, amino, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl-$(C_1-C_6)$-alkyl or hetaryl-$(C_1-C_6)$-alkyl which is optionally monosubstituted or polysubstituted by identical or different substituents, where, in the case of hetaryl, optionally at least one carbonyl group may be present and where the substituent(s) in each case independently of one another are selected from:

cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, A represents $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_1-C_6)$-alkyl-$(C_3-C_8)$-cycloalkyl, halo-$(C_3-C_8)$-cycloalkyl, halo-$(C_1-C_3)$-alkoxy-$(C_1-C_4)$-alkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, halo-$(C_3-C_8)$-alkynyl, halo-$(C_3-C_8)$-alkenyl or an aryl-$(C_1-C_6)$-alkyl or hetaryl-$(C_1-C_6)$-alkyl radical which is optionally monosubstituted or polysubstituted by identical or different substituents, where, in the case of hetaryl, optionally at least one carbonyl group may be present and where the substituent(s) in each case independently of one another are selected from:

cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, Q represents a 6-membered aryl or hetaryl radical which is unsubstituted or substituted by one or more radicals $R^7$, where, in the case of hetaryl, optionally at least one carbonyl group may be present and where the substituent(s) $R^7$ in each case independently of one another are selected from:

cyano, halogen, nitro, acetyl, hydroxy, carboxyl, amino, SCN, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino and/or aryl or hetaryl, optionally mono- or polysubstituted by identical or different substituents, where, in the case of hetaryl, optionally at least one carbonyl group may be present and where possible substituents in each case are as follows: cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, and D represents a $C_1-C_6$-alkyl, phenyl, phenyl-$(C_1-C_2)$-alkyl, benzdioxolyl or 5- or 6-membered hetaryl radical which is unsubstituted or substituted by one or more radicals $R^8$ and which may contain one to three heteroatoms from the group consisting of oxygen, sulfur, nitrogen, where the substituent(s) $R^8$ in each case independently of one another are selected from:

cyano, halogen, nitro, acetyl, hydroxy, carboxyl, amino, SCN, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino), (1-pyrazolyl) $(C_1-C_3)$-alkyl and/or aryl or hetaryl or aryloxy or hetaryloxy, optionally mono- or polysubstituted by identical or different substituents, where, in the case of hetaryl, optionally at least one carbonyl group may be present and where possible substituents in each case are as follows: cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino,
for controlling animal pests.

Configuration (1-2)

Furthermore, the invention provides compounds of the formula (I) in which M represents a radical selected from formulae (IIa-IIc) and where
A represents $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_1-C_6)$-alkyl-$(C_3-C_8)$-cycloalkyl, halo-$(C_3-C_8)$-cycloalkyl, halo-$(C_1-C_3)$-alkoxy-$(C_1-C_4)$-alkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl or halo-$(C_1-C_6)$-alkylsulfonyl-$(C_1-C_6)$-alkyl
or an aryl-$(C_1-C_6)$-alkyl or hetaryl-$(C_1-C_6)$-alkyl radical which is optionally monosubstituted or polysubstituted by identical or different substituents, where, in the case of hetaryl, optionally at least one carbonyl group may be present and where the substituent(s) in each case independently of one another are selected from:
cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino,
and where $R^1$, $R^2$, $R^3$, $R^4$, $R^5$, $R^6$, $R^7$, $R^8$, Q and D are defined according to Configuration 1-1.

Preference is given to an embodiment (Configuration 2-1) in which M represents a radical selected from formulae (IIa-IIc) and where
$R^1$ represents hydrogen, cyano, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkoxycarbonyl, $(C_1-C_6)$-haloalkoxycarbonyl, $(C_1-C_6)$-alkylaminocarbonyl, $(C_1-C_6)$-alkylcarbonylamino or benzyl which is unsubstituted or monosubstituted or polysubstituted by identical or different substituents, where possible substituents in each case are as follows:
cyano, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl and/or $(C_1-C_6)$-alkylsulfonyl-$(C_1-C_6)$-alkyl,
$R^2$ represents hydrogen, cyano, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $C_1-C_6)$-alkoxy-$(C_1-C_6)$-alkoxy, $(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkoxycarbonyl, $(C_1-C_6)$-haloalkoxycarbonyl, $(C_1-C_6)$-alkylaminocarbonyl or $(C_1-C_6)$-alkylcarbonylamino,
$R^3$ represents hydrogen, cyano, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$- alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl, ($C_1$-$C_6$)-alkylcarbonylamino or benzyl which is unsubstituted or monosubstituted or polysubstituted by identical or different substituents, where possible substituents in each case are as follows:

cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl and/or ($C_1$-$C_6$)-alkylsulfonyl-($C_1$-$C_6$)-alkyl, $R^4$ represents hydrogen, cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl or ($C_1$-$C_6$)-alkylcarbonylamino, $R^5$ represents hydrogen, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, ($C_1$-$C_6$)-alkylthio-($C_1$-$C_6$)-alkyl, halo-($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, halo-($C_1$-$C_6$)-alkylsulfinyl-($C_1$-$C_6$)-alkyl or halo-($C_1$-$C_6$)-alkylsulfonyl-($C_1$-$C_6$)-alkyl, $R^6$ represents hydrogen, cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl or ($C_1$-$C_6$)-alkylcarbonylamino, A represents halo-($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, halo-($C_1$-$C_3$)-alkoxy-($C_1$-$C_4$)-alkyl ($C_1$-$C_6$)-alkylthio-($C_1$-$C_6$)-alkyl, ($C_1$-$C_6$)-alkylsulfinyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, halo-($C_3$-$C_6$)-alkenyl or a benzyl radical which is optionally monosubstituted or polysubstituted by identical or different substituents, where the substituent(s) in each case independently of one another are selected from:

cyano, halogen, ($C_3$-$C_6$)-cycloalkyl, ($C_3$-$C_6$)-cycloalkyloxy, ($C_3$-$C_6$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, ($C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl and/or halo-($C_1$-$C_6$)-alkylsulfonyl-($C_1$-$C_6$)-alkyl, Q represents a phenyl or pyridyl radical which is unsubstituted or substituted by one or more radicals $R^7$,
where the substituent(s) $R^7$ in each case independently of one another are selected from:
cyano, halogen, nitro, ($C_3$-$C_6$)-cycloalkyl, ($C_3$-$C_6$)-cycloalkyloxy, ($C_3$-$C_6$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, ($C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl, ($C_1$-$C_6$)-alkylcarbonylamino), halo-($C_1$-$C_6$)-alkylthio-($C_1$-$C_6$)-alkyl, halo-($C_1$-$C_6$)-alkylsulfinyl-($C_1$-$C_6$)-alkyl and/or halo-($C_1$-$C_6$)-alkylsulfonyl-($C_1$-$C_6$)-alkyl, and D represents a $C_1$-$C_6$-alkyl, phenyl, thiophenyl, isoxazolyl, phenyl-($C_1$-$C_2$)-alkyl or benzdioxolyl radical which is unsubstituted or substituted by one or more radicals $R^8$,
where the substituent(s) $R^8$ in each case independently of one another are selected from:
cyano, halogen, nitro, acetyl, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino, (1-pyrazolyl)($C_1$-$C_3$)-alkyl and/or ($C_1$-$C_3$)-alkoxypyrimidinyloxy.

Preference is furthermore given to an embodiment in which M represents a radical selected from formulae (IIa-IIc) and where (Configuration 2-2)

A represents halo-$(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, halo-$(C_1-C_3)$-alkoxy-$(C_1-C_4)$-alkyl $(C_1-C_6)$-alkylthio-$(C_1-C_6)$-alkyl, $(C_1-C_6)$-alkylsulfinyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl or a benzyl radical which is optionally monosubstituted or polysubstituted by identical or different substituents, where the substituent(s) in each case independently of one another are selected from:

cyano, halogen, $(C_3-C_6)$-cycloalkyl, $(C_3-C_6)$-cycloalkyloxy, $(C_3-C_6)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl and/or halo-$(C_1-C_6)$-alkylsulfonyl-$(C_1-C_6)$-alkyl, and where $R^1$, $R^2$, $R^3$, $R^4$, $R^5$, $R^6$, $R^7$, $R^8$, Q and D are defined according to Configuration 2-1.

Particular preference is furthermore given to an embodiment (Configuration 3-1) in which M represents a radical selected from formulae (IIa-IIc) and where $R^1$ represents hydrogen, cyano, halogen, cyclopropyl, $(C_1-C_4)$-alkyl, halocyclopropyl, halo-$(C_1-C_3)$-alkylcyclopropyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl, or benzyl which is unsubstituted, monosubstituted or polysubstituted by identical or different substituents, where possible substituents in each case are as follows: cyano, halogen, $(C_1-C_4)$-haloalkyl, $(C_1-C_4)$-alkoxy, $(C_1-C_4)$-haloalkoxy, $(C_1-C_6)$-alkylthio and/or $(C_1-C_6)$-haloalkylthio, $R^2$ represents hydrogen, cyano, halogen, $(C_1-C_4)$-haloalkyl, $(C_1-C_4)$-alkoxy, $(C_1-C_4)$-haloalkoxy, $(C_1-C_6)$-alkylthio or $(C_1-C_6)$-haloalkylthio, $R^1$ represents hydrogen, cyano, halogen, cyclopropyl, $(C_1-C_4)$-alkyl, halocyclopropyl, halo-$(C_1-C_3)$-alkylcyclopropyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylthio-$(C_1-C_4)$-alkyl, $(C_1-C_4)$-alkylsulfinyl-$(C_1-C_4)$-alkyl or $(C_1-C_4)$-alkylsulfonyl-$(C_1-C_4)$-alkyl, $R^4$ represents hydrogen, cyano, halogen, $(C_1-C_4)$-haloalkyl, $(C_1-C_4)$-alkoxy, $(C_1-C_4)$-alkyl, $(C_3-C_4)$-cycloalkyl, $(C_1-C_4)$-haloalkoxy, $(C_1-C_6)$-alkylthio or $(C_1-C_6)$-haloalkylthio, $R^5$ represents hydrogen, cyclopropyl, $(C_1-C_4)$-alkyl, halocyclopropyl, halo-$(C_1-C_3)$-alkylcyclopropyl or $(C_1-C_4)$-haloalkyl, $R^6$ represents hydrogen, cyano, halogen, $(C_1-C_4)$-haloalkyl, $(C_1-C_4)$-alkoxy, $(C_1-C_4)$-haloalkoxy, $(C_1-C_6)$-alkylthio or $(C_1-C_6)$-haloalkylthio, A represents halo-$(C_1-C_4)$-alkyl-$(C_3-C_4)$-cycloalkyl, halo-$(C_3-C_6)$-cycloalkyl, $(C_1-C_6)$-alkyl, $(C_1-C_5)$-haloalkyl, $(C_1-C_6)$-cyanoalkyl, $(C_1-C_4)$-alkoxy-$(C_1-C_4)$-alkyl, halo-$(C_1-C_3)$-alkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, halo-$(C_3-C_4)$-alkenyl or a benzyl radical which is optionally monosubstituted or polysubstituted by identical or different substituents, where the substituent(s) in each case independently of one another are selected from:

cyano, halogen, $(C_3-C_6)$-cycloalkyl, $(C_3-C_6)$-cycloalkyloxy, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkylthio and/or $(C_1-C_6)$-haloalkylthio, Q represents a phenyl or pyridyl radical which is unsubstituted or substituted by one or more radicals $R^7$, where the substituent(s) $R^7$ in each case independently of one another are selected from:

cyano, halogen, $(C_3-C_6)$-cycloalkyl, halo-$(C_3-C_8)$-cycloalkyl, $(C_1-C_6)$-alkyl, $(C_1-C_6)$-haloalkyl, $(C_1-C_6)$-alkoxy-$(C_1-C_6)$-alkyl, $(C_1-C_6)$-alkoxy and/or $(C_1-C_6)$-haloalkoxy, and D represents a $C_1-C_6$-alkyl, phenyl, thiophenyl, isoxazolyl, benzyl or benzdioxolyl radical which is unsubstituted or substituted by one or more radicals $R^8$, where the substituent(s) $R^8$ in each case independently of one another are selected from:

cyano, halogen, acetyl, $(C_3-C_6)$-cycloalkyl, $(C_3-C_6)$-cycloalkyloxy, $(C_3-C_6)$-cycloalkyl-$(C_3-C_8)$-cycloalkyl, $(C_1-C_6)$-alkyl-$(C_3-C_6)$-cycloalkyl, halo-$(C_3-C_6)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, $(C_3-C_8)$-cycloalkylamino, $(C_1-C_6)$-alkylcarbonylamino, (1-pyrazolyl)$(C_1-C_3)$-alkyl and/or $(C_1-C_3)$-alkoxypyrimidinyloxy.

Particular preference is furthermore given to an embodiment in which M represents a radical selected from formulae (IIa-IIc) and where (Configuration 3-2)

$R^4$ represents hydrogen, cyano, halogen, $(C_1-C_4)$-haloalkyl, $(C_1-C_4)$-alkoxy, $(C_1-C_4)$-haloalkoxy, $(C_1-C_6)$-alkylthio or $(C_1-C_6)$-haloalkylthio, A represents halo-$(C_1-C_4)$-alkyl-$(C_3-C_4)$-cycloalkyl, halo-$(C_3-C_6)$-cycloalkyl, $(C_1-C_6)$-alkyl, $(C_1-C_5)$-haloalkyl, $(C_1-C_6)$-cyanoalkyl, $(C_1-C_4)$-alkoxy-$(C_1-C_4)$-alkyl, halo-$(C_1-C_3)$-alkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl or a benzyl radical which is optionally monosubstituted or polysubstituted by identical or different substituents, where the substituent(s) in each case independently of one another are selected from:
cyano, halogen, $(C_3-C_6)$-cycloalkyl, $(C_3-C_6)$-cycloalkyloxy, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkylthio and/or $(C_1-C_6)$-haloalkylthio, and where $R^1$, $R^2$, $R^3$, $R^5$, $R^6$, $R^7$, $R^8$, Q and D are defined according to Configuration 3-1.

Very particular preference is furthermore given to an embodiment (Configuration 4-1) in which M represents a radical selected from formulae (IIa-IIc) and where
$R^1$ represents hydrogen, halogen, cyclopropyl, $(C_1-C_4)$-alkyl, $(C_1-C_4)$-alkylthio, halocyclopropyl, $(C_1-C_4)$-haloalkyl or benzyl which is unsubstituted or monosubstituted or polysubstituted by identical or different substituents, where possible substituents in each case are as follows: cyano, halogen, $(C_1-C_4)$-haloalkyl and/or $(C_1-C_4)$-alkoxy,
$R^2$ represents hydrogen, halogen, cyano, $(C_1-C_4)$-alkyl, $(C_1-C_4)$-haloalkyl,
$R^3$ represents hydrogen, halogen, cyclopropyl, $(C_1-C_4)$-alkyl, halocyclopropyl or $(C_1-C_4)$-haloalkyl,
$R^4$ represents hydrogen, halogen, cyano, $(C_1-C_4)$-alkyl, cyclopropyl or $(C_1-C_4)$-haloalkyl,
$R^5$ represents hydrogen, cyclopropyl, $(C_1-C_4)$-alkyl or halo-$(C_1-C_4)$-alkyl,
$R^6$ represents hydrogen, halogen, cyano, $(C_1-C_4)$-alkyl or $(C_1-C_4)$-haloalkyl,
A represents halo-$(C_1-C_4)$-alkyl-$(C_3-C_4)$-cycloalkyl, halo-$(C_3-C_6)$-cycloalkyl, $(C_1-C_6)$-alkyl, $(C_1-C_5)$-haloalkyl, $(C_1-C_6)$-cyanoalkyl, $(C_1-C_4)$-alkoxy-$(C_1-C_4)$-alkyl, halo-$(C_1-C_3)$-alkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, halo-$(C_3-C_4)$-alkenyl or
a benzyl radical which is optionally monosubstituted or polysubstituted by identical or different substituents, where the substituent(s) in each case independently of one another are selected from:
cyano, halogen, $(C_3-C_6)$-cycloalkyl, $(C_3-C_6)$-cycloalkyloxy, halo-$(C_3-C_8)$-cycloalkyl, $(C_1-C_6)$-alkyl, $(C_1-C_6)$-haloalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-alkylthio and/or $(C_1-C_6)$-haloalkylthio,
Q represents a phenyl or pyridyl radical which is unsubstituted or substituted by one or more radicals $R^7$,
where the substituent(s) $R^7$ in each case independently of one another are selected from:
cyano, halogen, $(C_3-C_6)$-cycloalkyl, halo-$(C_3-C_6)$-cycloalkyl, $(C_1-C_6)$-alkyl, $(C_1-C_6)$-haloalkyl, $(C_1-C_6)$-alkoxy-$(C_1-C_6)$-alkyl, $(C_1-C_6)$-alkoxy and/or $(C_1-C_6)$-haloalkoxy and
D represents a $C_1-C_6$-alkyl, phenyl, thiophenyl, isoxazolyl, benzyl or benzdioxolyl radical which is unsubstituted or substituted by one or more radicals $R^8$,
where the substituent(s) $R^8$ in each case independently of one another are selected from:
cyano, halogen, acetyl, $(C_3-C_6)$-cycloalkyl, $(C_3-C_6)$-cycloalkyloxy, $(C_3-C_6)$-cycloalkyl-$(C_3-C_8)$-cycloalkyl, $(C_1-C_6)$-alkyl-$(C_3-C_6)$-cycloalkyl, halo-$(C_3-C_6)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, $(C_3-C_6)$-cycloalkylamino, $(C_1-C_6)$-alkylcarbonylamino, (1-pyrazolyl)$(C_1-C_3)$-alkyl and/or $(C_1-C_3)$-alkoxypyrimidinyloxy.

Very particular preference is furthermore given to an embodiment in which M represents a radical selected from formulae (IIa-IIc) and where (Configuration 4-2)
$R^1$ represents hydrogen, halogen, cyclopropyl, $(C_1-C_4)$-alkyl, halocyclopropyl, $(C_1-C_4)$-haloalkyl or benzyl which is unsubstituted or monosubstituted or polysubstituted by identical or different substituents, where possible substituents in each case are as follows: cyano, halogen, $(C_1-C_4)$-haloalkyl and/or $(C_1-C_4)$-alkoxy,
$R^4$ represents hydrogen, halogen, cyano, $(C_1-C_4)$-alkyl or $(C_1-C_4)$-haloalkyl,
A represents halo-$(C_1-C_4)$-alkyl-$(C_3-C_4)$-cycloalkyl, halo-$(C_3-C_6)$-cycloalkyl, $(C_1-C_6)$-alkyl, $(C_1-C_5)$-haloalkyl, $(C_1-C_6)$-cyanoalkyl, $(C_1-C_4)$-alkoxy-$(C_1-C_4)$-alkyl, halo-$(C_1-C_3)$-alkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl or
a benzyl radical which is optionally monosubstituted or polysubstituted by identical or different substituents, where the substituent(s) in each case independently of one another are selected from:
cyano, halogen, $(C_3-C_6)$-cycloalkyl, $(C_3-C_6)$-cycloalkyloxy, halo-$(C_3-C_8)$-cycloalkyl, $(C_1-C_6)$-alkyl, $(C_1-C_6)$-haloalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-alkylthio and/or $(C_1-C_6)$-haloalkylthio
and where $R^2$, $R^3$, $R^5$, $R^6$, $R^7$, $R^8$, Q and D are defined according to Configuration 4-1.

Special preference is furthermore given to an embodiment (Configuration 5-1) in which M represents a radical selected from formulae (IIa-IIc) and where
$R^1$ represents hydrogen, chlorine, bromine, methyl, benzyl, 2-chlorobenzyl, 3-chlorobenzyl, 4-chlorobenzyl, trifluoromethyl, methylthio or isopropylthio,
$R^2$ represents hydrogen, cyano, chlorine, bromine or iodine,
$R^3$ represents hydrogen, chlorine, methyl, isopropyl, ethyl or bromine,
$R^4$ represents hydrogen, chlorine, bromine, iodine, fluorine, difluoromethyl, isopropyl or cyclopropyl,
$R^5$ represents methyl or 2,2,2-trifluoroethyl and
$R^6$ represents hydrogen or chlorine,
A represents a radical selected from the radicals of the formulae (III1-III19):

(III1)

(III2)

-continued
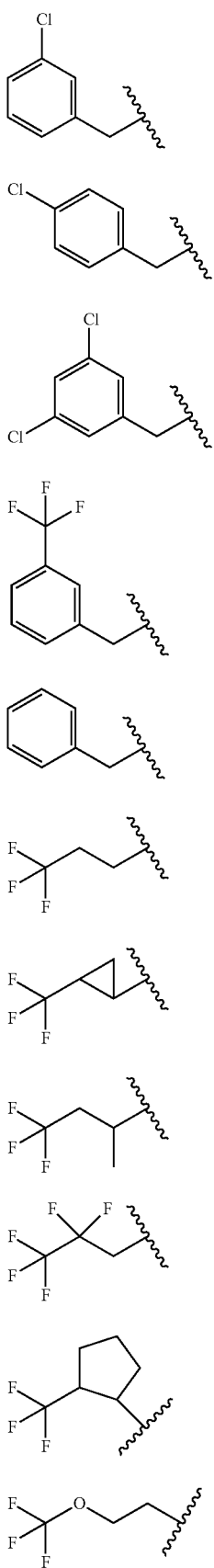
(III3)
(III4)
(III5)
(III6)
(III7)
(III8)
(III9)
(III10)
(III11)
(III12)
(III13)
-continued
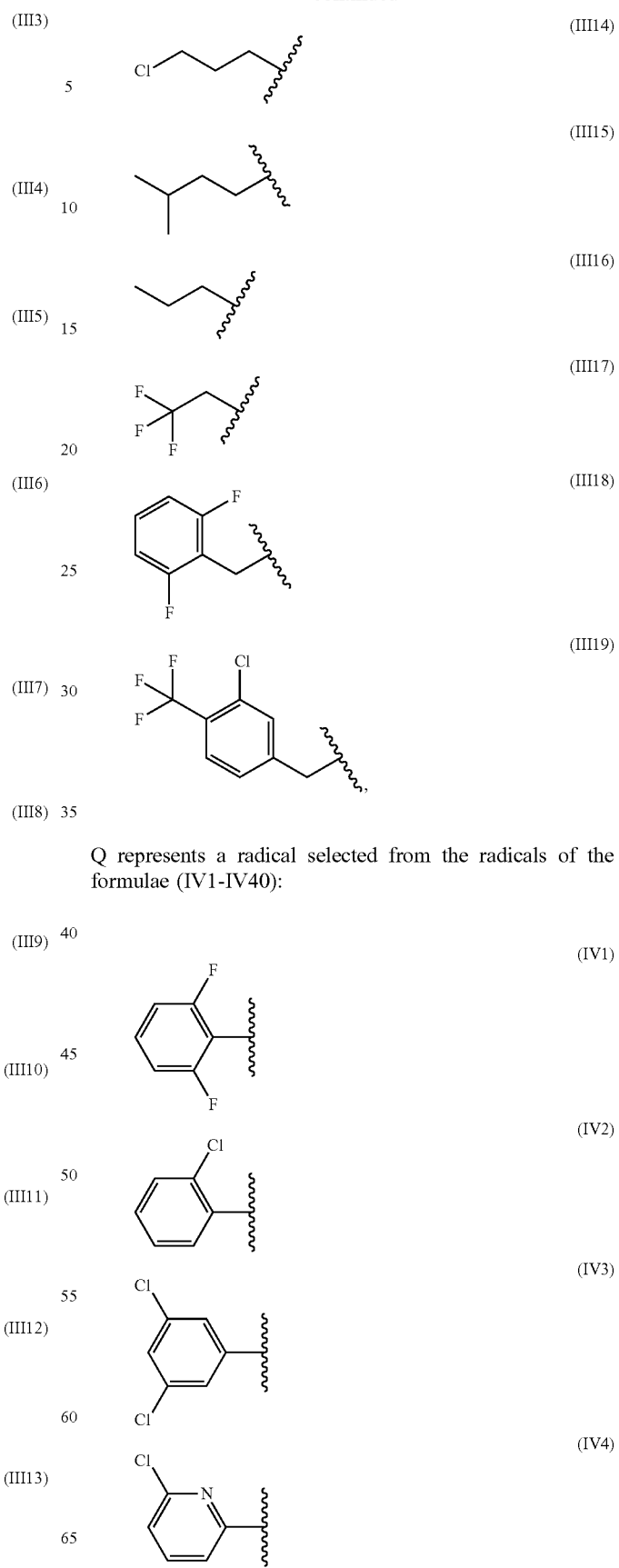
(III14)
(III15)
(III16)
(III17)
(III18)
(III19)
Q represents a radical selected from the radicals of the formulae (IV1-IV40):
(IV1)
(IV2)
(IV3)
(IV4)

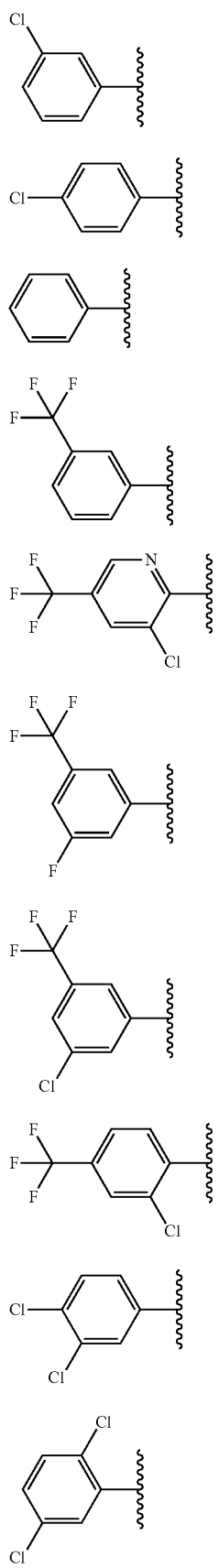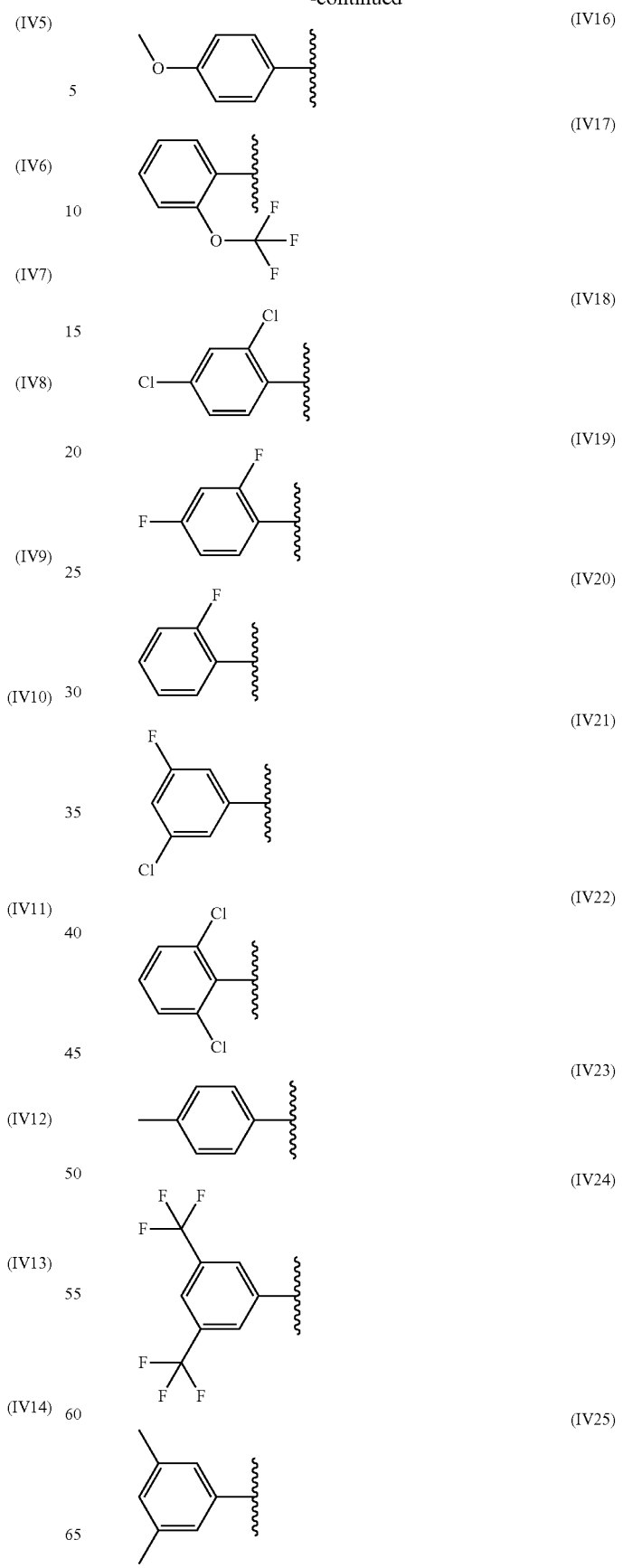

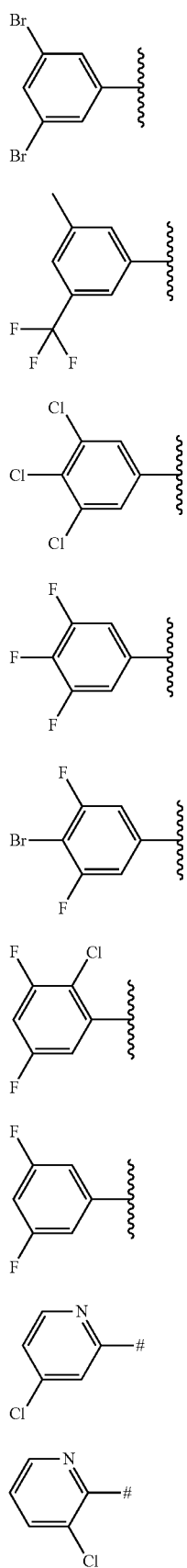
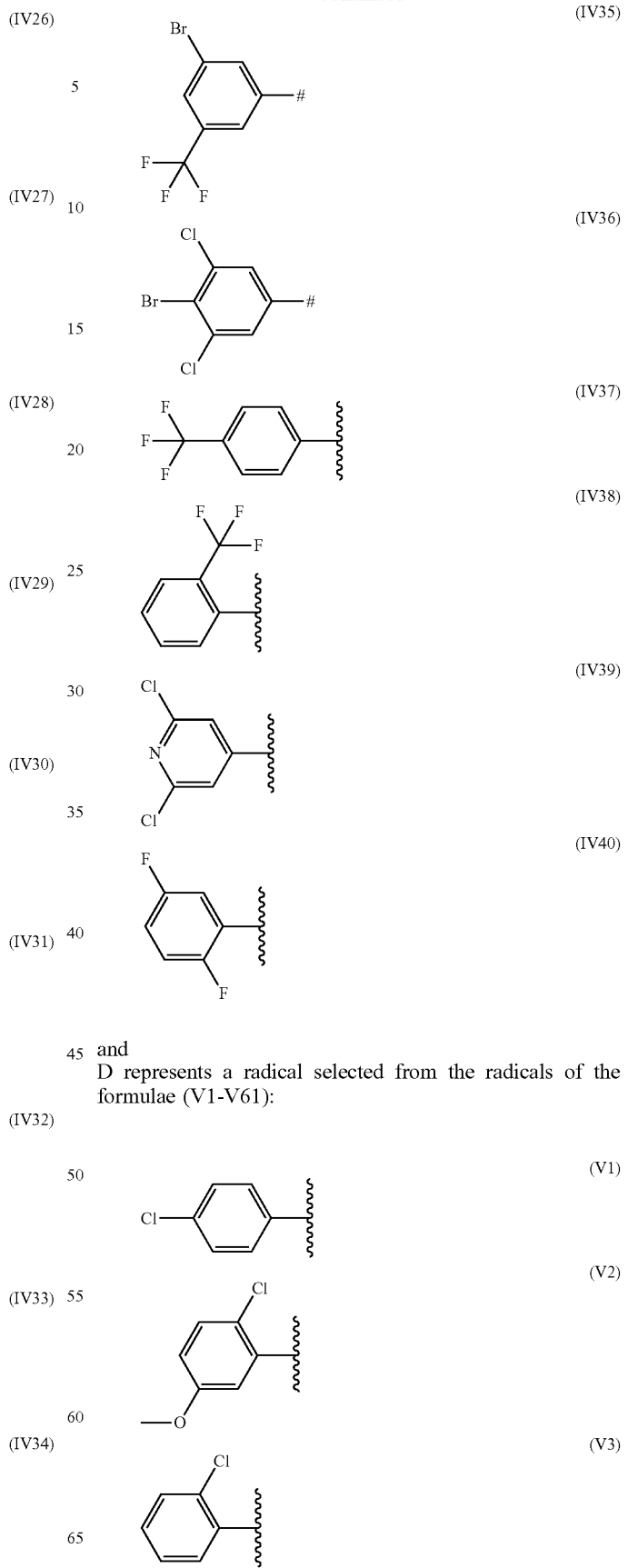
and
D represents a radical selected from the radicals of the formulae (V1-V61):

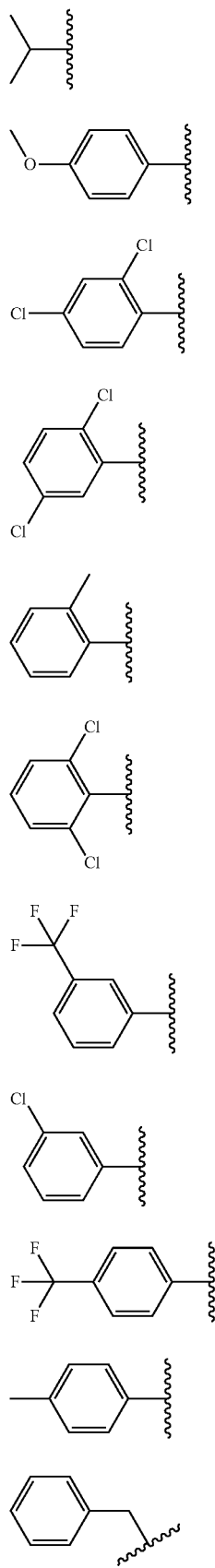
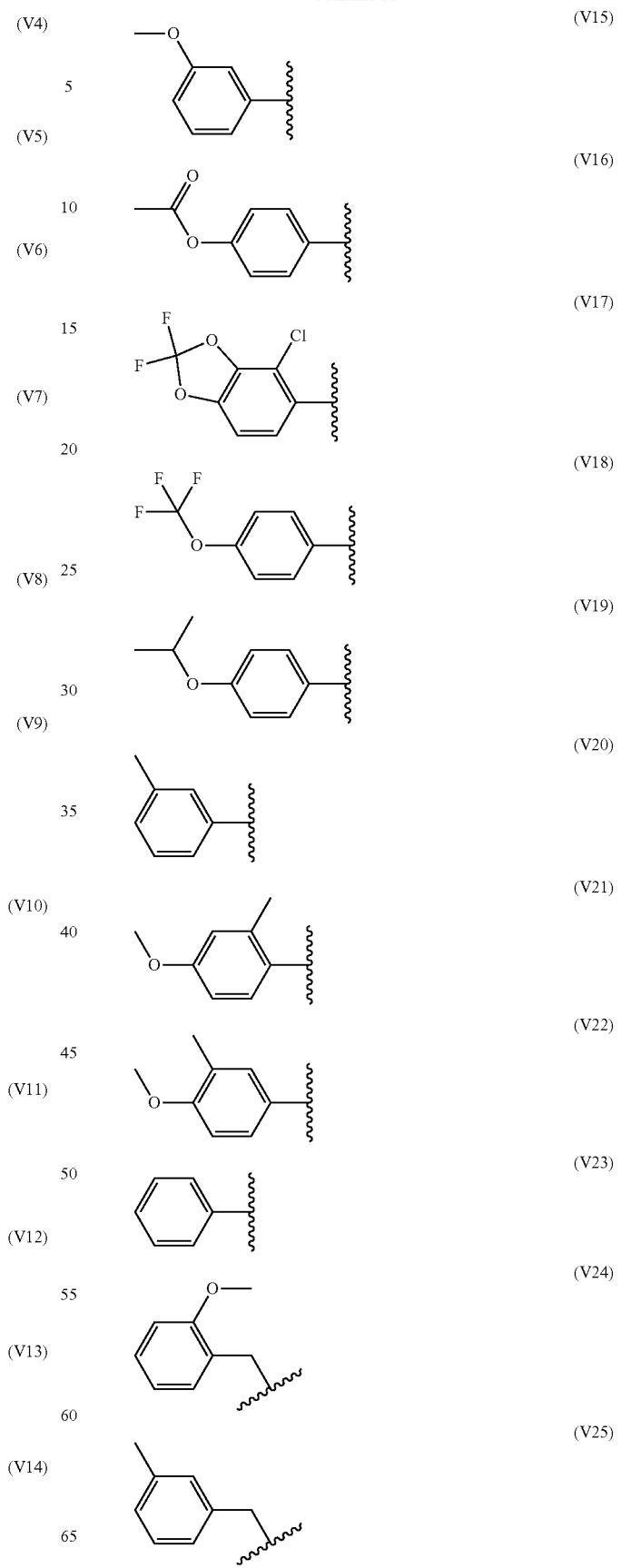

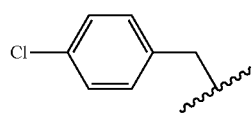
(V26)
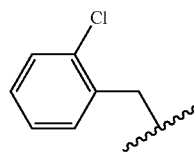
(V27)
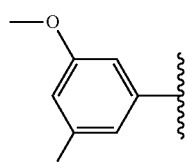
(V28)
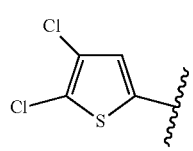
(V30)
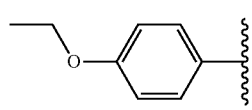
(V30)
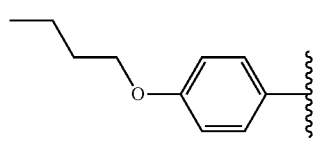
(V31)
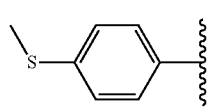
(V32)
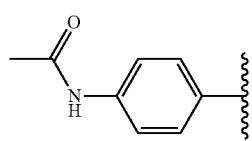
(V33)
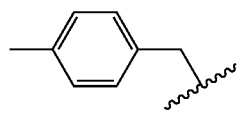
(V34)
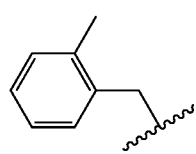
(V35)
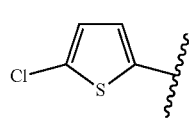
(V36)
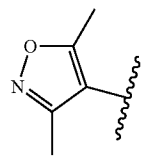
(V37)
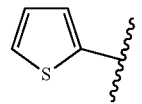
(V38)
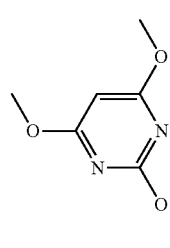
(V39)
(V40)
(V41)
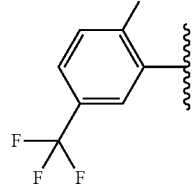
(V42)
(V43)
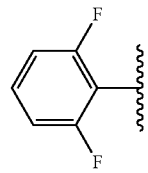
(V44)
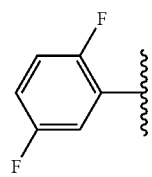
(V45)

-continued

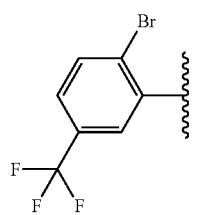 (V46)

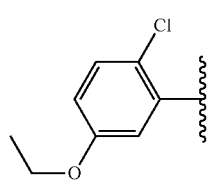 (V47)

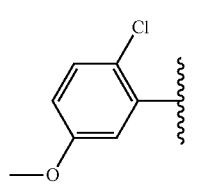 (V48)

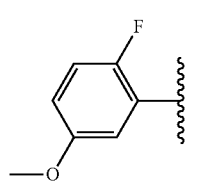 (V49)

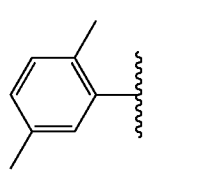 (V50)

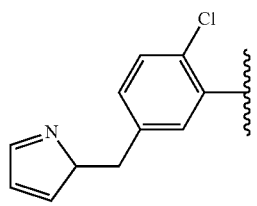 (V51)

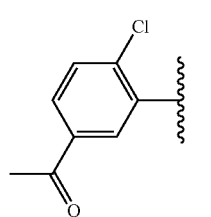 (V52)

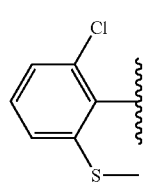 (V53)

-continued

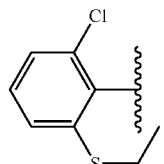 (V54)

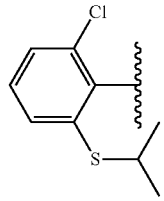 (V55)

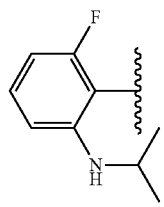 (V56)

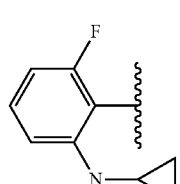 (V57)

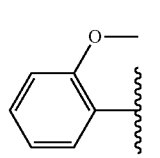 (V58)

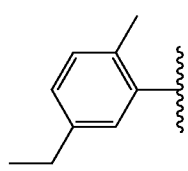 (V59)

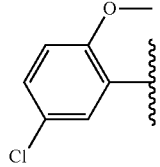 (V60)

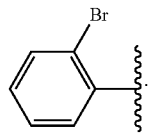 (V61)

Very particular preference is furthermore given to an embodiment in which M represents a radical selected from formulae (IIa-IIc) and where (Configuration 5-2)

$R^1$ represents hydrogen, chlorine, bromine, methyl, benzyl, 2-chlorobenzyl, 3-chlorobenzyl or 4-chlorobenzyl, $R^2$ represents hydrogen, cyano, chlorine, bromine or iodine, $R^3$ represents hydrogen, chlorine, methyl, isopropyl or ethyl, $R^4$ represents hydrogen, chlorine, bromine or iodine, $R^5$ represents methyl and
$R^6$ represents hydrogen or chlorine,
A represents a radical selected from the radicals of the formulae (III1-III18):
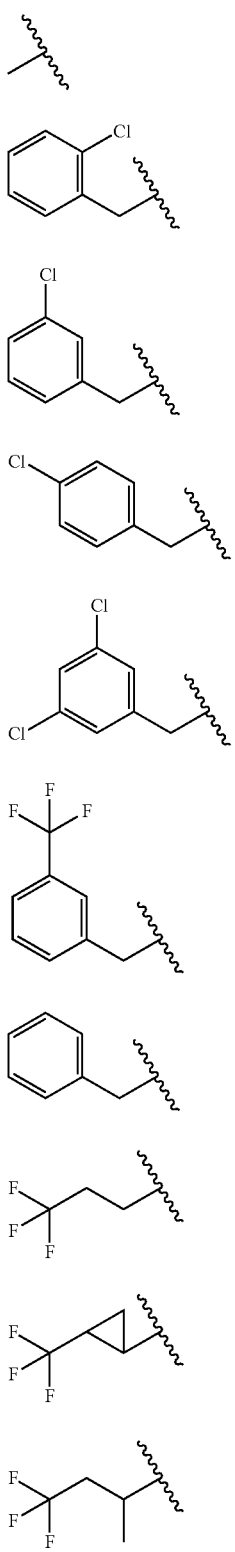
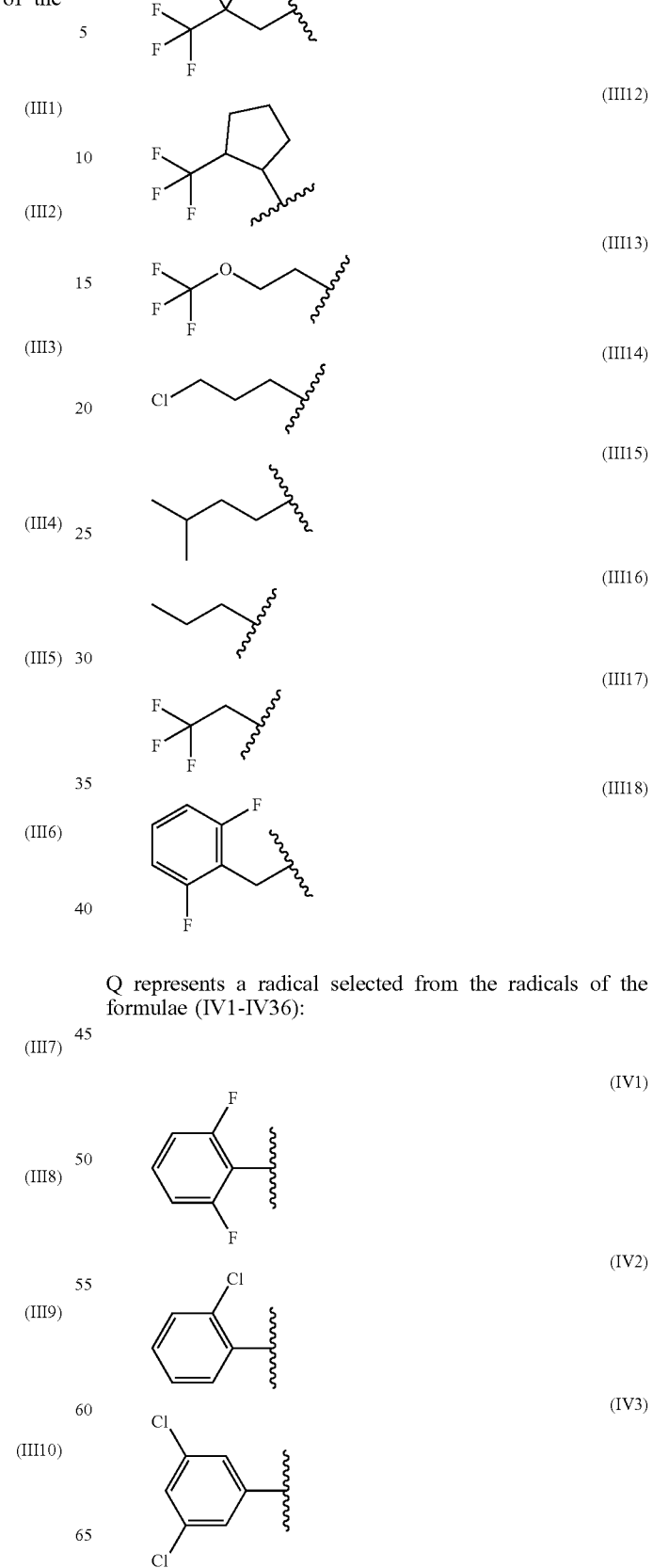
Q represents a radical selected from the radicals of the formulae (IV1-IV36):

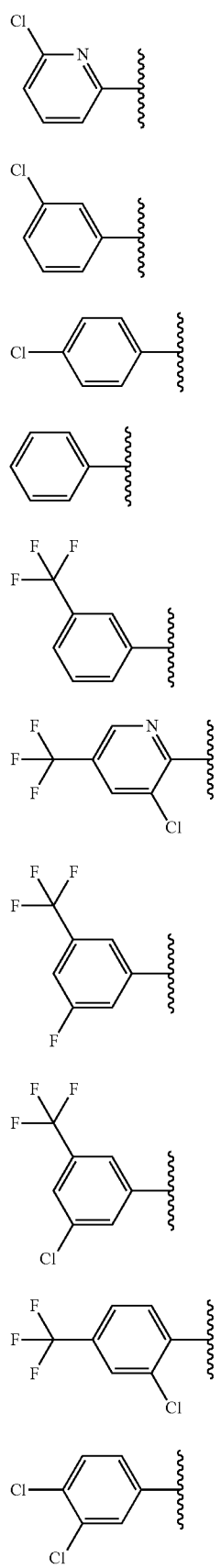
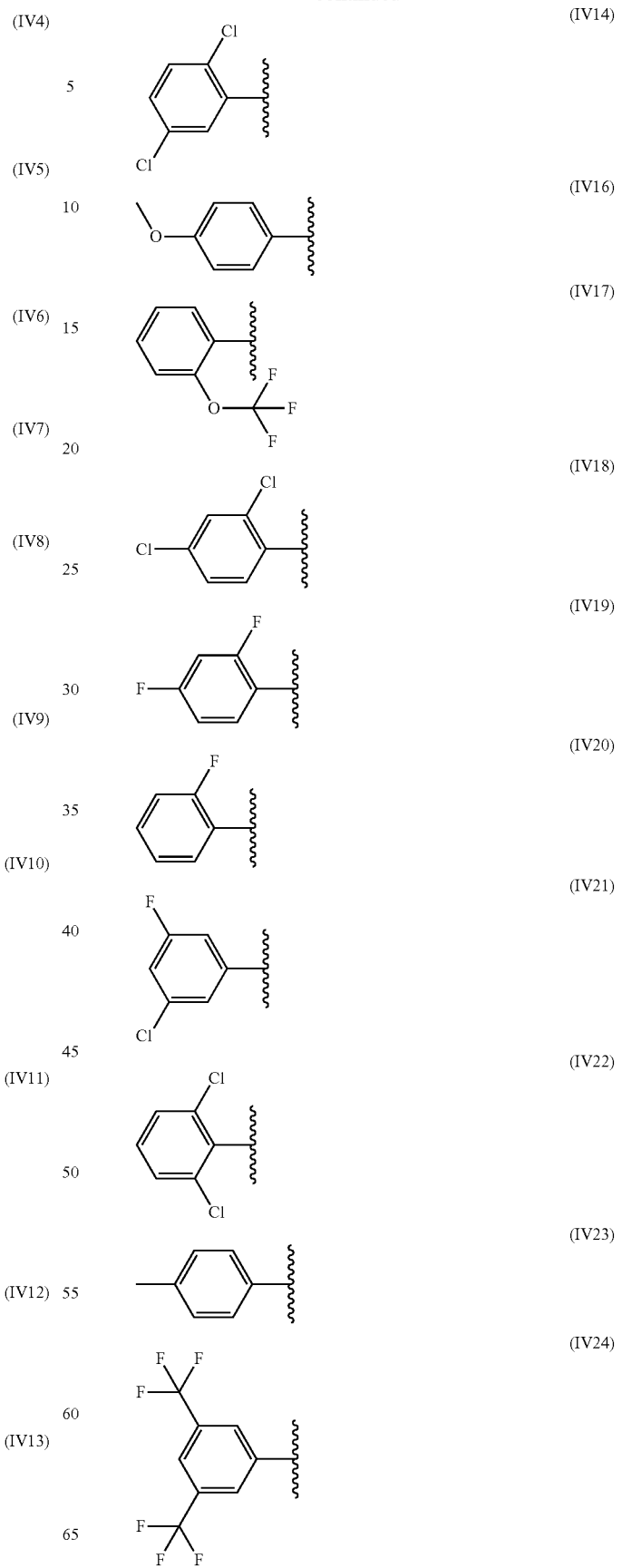

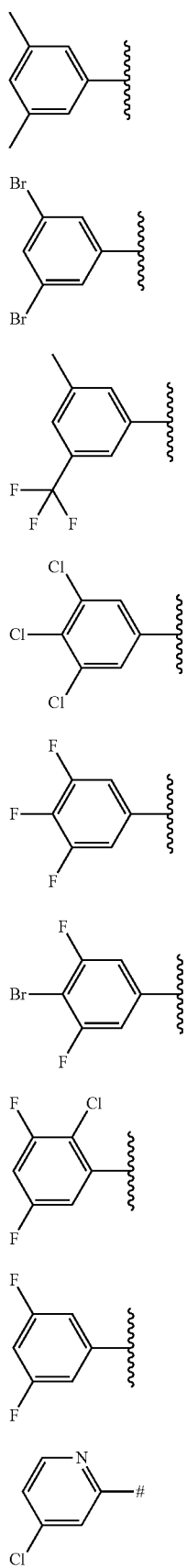
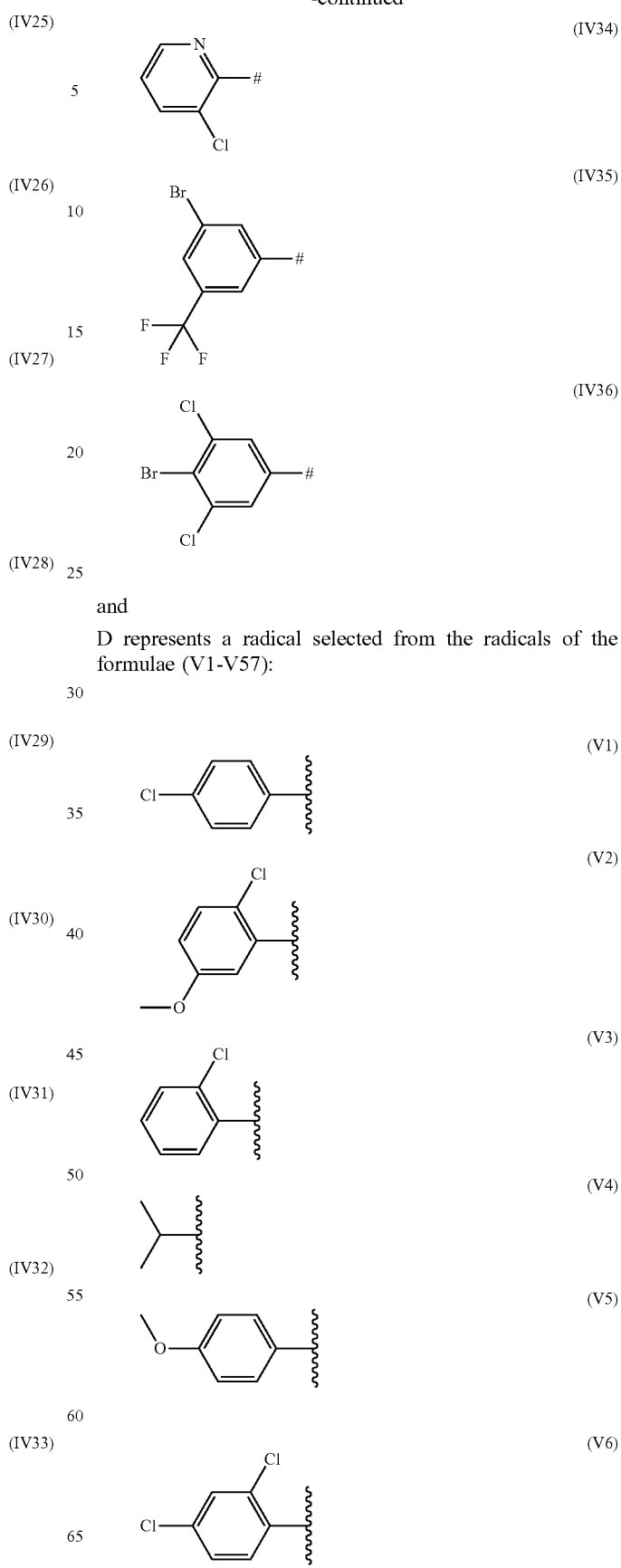
and
D represents a radical selected from the radicals of the formulae (V1-V57):

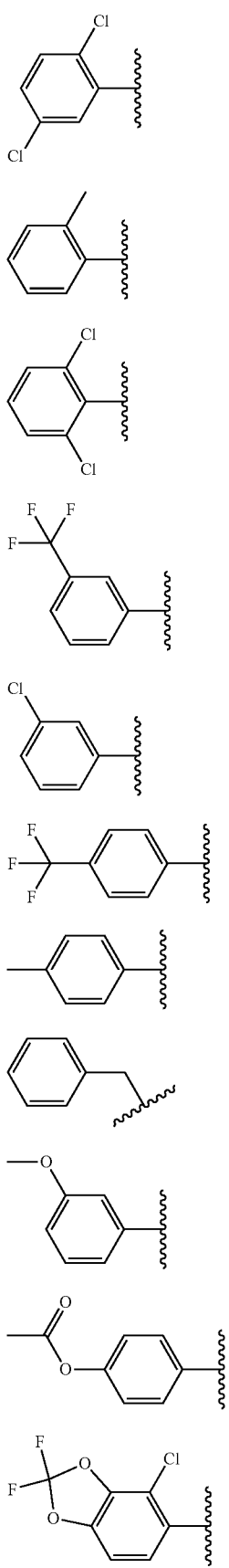
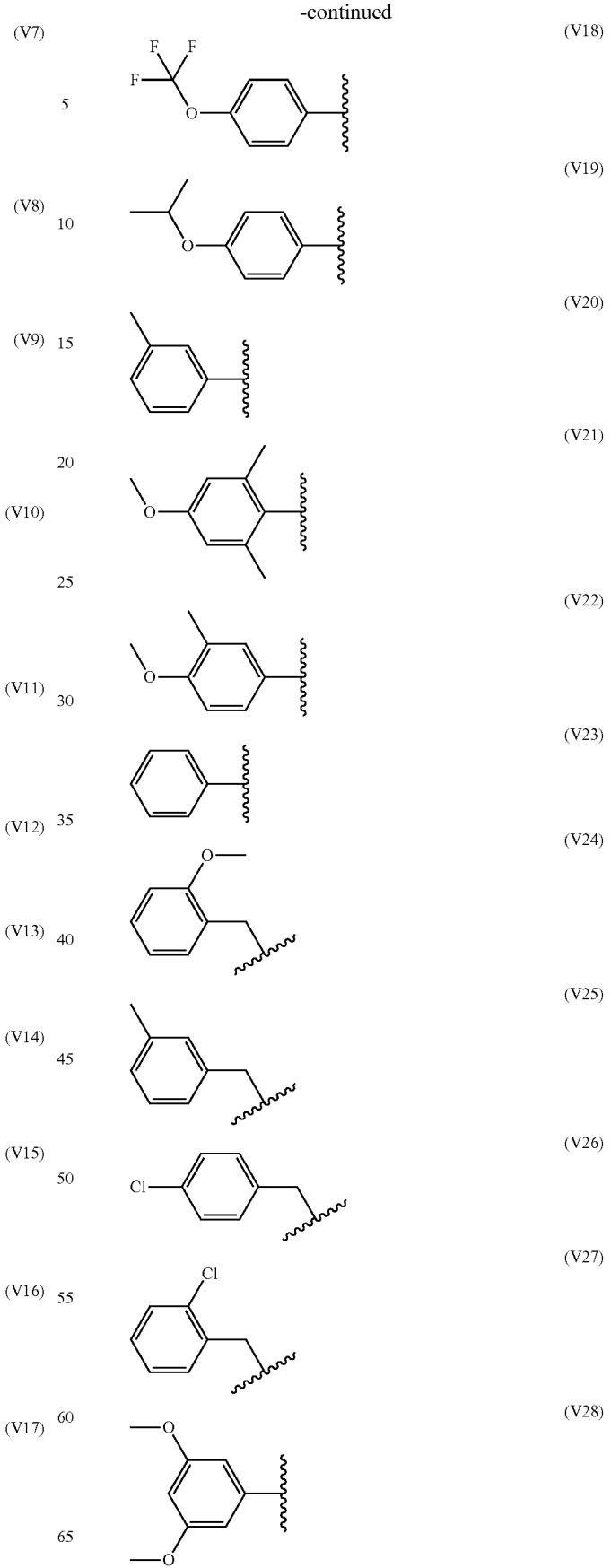

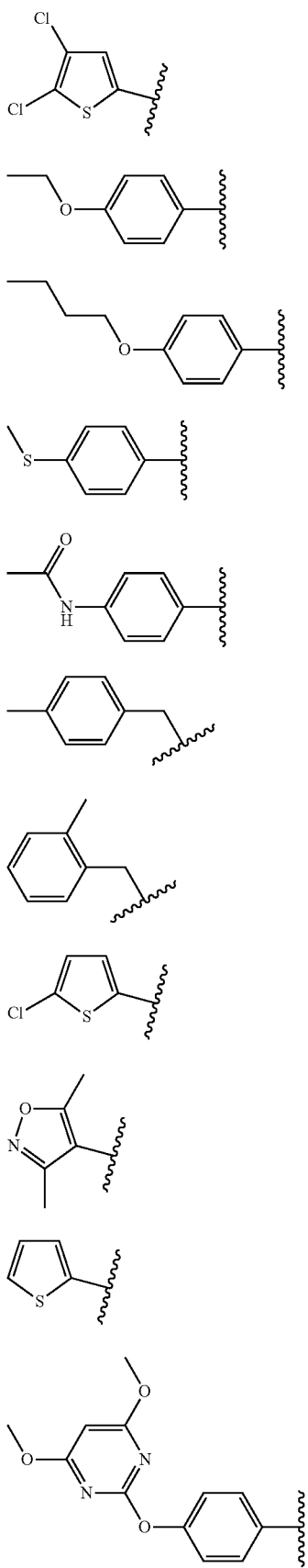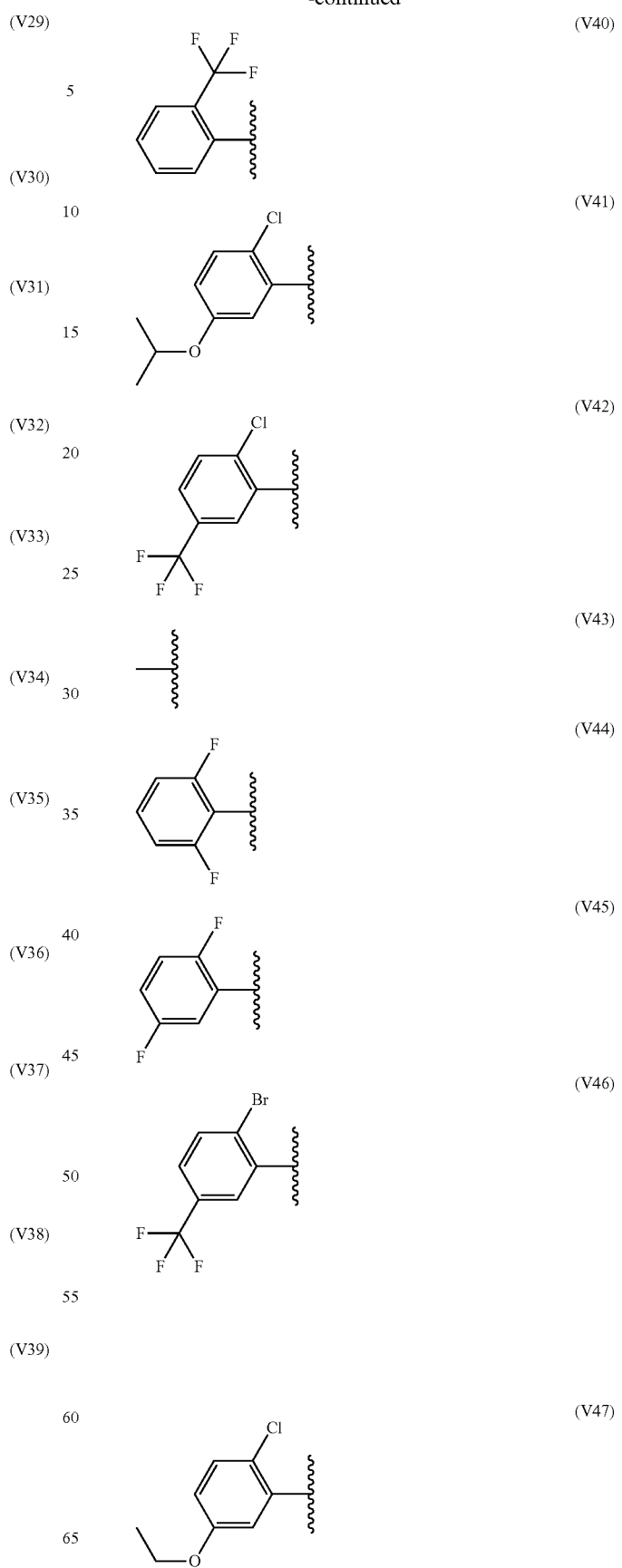

-continued (V48) 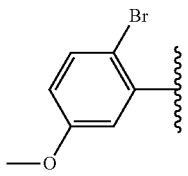

(V49) 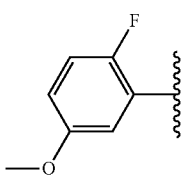

(V50) 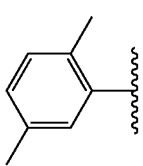

(V51) 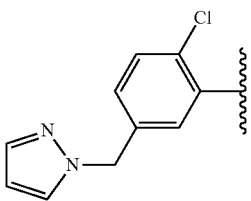

(V52) 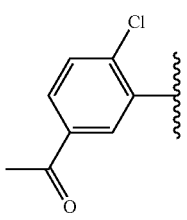

(V53) 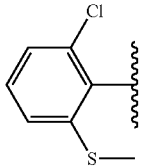

(V54) 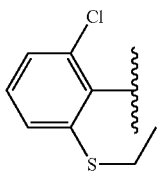

(V55) 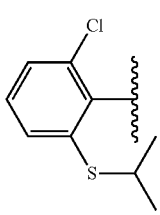

-continued (V56) 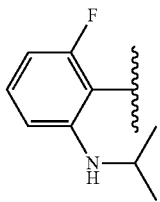

(V57) 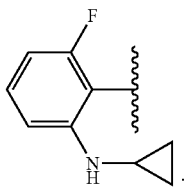

Hereinbelow, Configuration (x) is equivalent to Configuration (x-1) or (x-2) with x=1, 2, 3, 4 or 5.

In a preferred embodiment of the invention, M in formulae (I) represents a radical selected from the formulae IIa and IIb, where the radicals $R^1$, $R^2$, A, $R^3$, $R^4$, $R^7$, $R^8$, Q and D have the meanings described in Configuration (1) or Configuration (2) or Configuration (3) or Configuration (4) or Configuration (5).

In a further preferred embodiment, the invention relates to the use of compounds of the formula (I) where M, $R^1$, $R^2$, $R^3$, $R^4$, $R^5$, $R^6$, $R^7$, $R^8$, Q and D have the meanings described above, in particular the meanings described in Configuration (2) or Configuration (3) or Configuration (4) or Configuration (5) and A has the meanings described in Configuration (1).

In a further preferred embodiment, the invention relates to the use of compounds of the formula (I) where M, $R^1$, $R^2$, $R^3$, $R^4$, $R^5$, $R^6$, $R^7$, $R^8$, Q and D have the meanings described above, in particular the meanings described in Configuration (1) or Configuration (3) or Configuration (4) or Configuration (5) and A has the meanings described in Configuration (2).

In a further preferred embodiment, the invention relates to the use of compounds of the formula (I) where M, $R^1$, $R^2$, $R^3$, $R^4$, $R^5$, $R^6$, $R^7$, $R^8$, Q and D have the meanings described above, in particular the meanings described in Configuration (1) or Configuration (2) or Configuration (4) or Configuration (5) and A has the meanings described in Configuration (3).

In a further preferred embodiment, the invention relates to the use of compounds of the formula (I) where M, $R^1$, $R^2$, $R^3$, $R^4$, $R^5$, $R^6$, $R^7$, $R^8$, Q and D have the meanings described above, in particular the meanings described in Configuration (1) or Configuration (2) or Configuration (3) or Configuration (5) and A has the meanings described in Configuration (4).

In a further preferred embodiment, the invention relates to the use of compounds of the formula (I) where M, $R^1$, $R^2$, $R^3$, $R^4$, $R^5$, $R^6$, $R^7$, $R^8$, Q and D have the meanings described above, in particular the meanings described in Configuration (1) or Configuration (2) or Configuration (3) or Configuration (4) and A has the meanings described in Configuration (5).

In a further preferred embodiment, the invention relates to the use of compounds of the formula (I) where M, $R^1$, $R^2$, $R^3$, $R^4$, $R^5$, $R^6$, $R^8$, A and D have the meanings described above, in particular the meanings described in Configuration (2) or Configuration (3) or Configuration (4) or Configuration (5) and Q and R⁷ have the meanings described in Configuration (1).

In a further preferred embodiment, the invention relates to the use of compounds of the formula (I) where M, $R^1$, $R^2$, $R^3$, $R^4$, $R^5$, $R^6$, $R^8$, A and D have the meanings described above, in particular the meanings described in Configuration (1) or Configuration (3) or Configuration (4) or Configuration (5) and Q has the definitions described in configuration (2).

In a further preferred embodiment, the invention relates to the use of compounds of the formula (I) where M, $R^1$, $R^2$, $R^3$, $R^4$, $R^5$, $R^6$, $R^8$, A and D have the meanings described above, in particular the meanings described in Configuration (1) or Configuration (2) or Configuration (4) or Configuration (5) and Q and R⁷ have the meanings described in Configuration (3).

In a further preferred embodiment, the invention relates to the use of compounds of the formula (I) where M, $R^1$, $R^2$, $R^3$, $R^4$, $R^5$, $R^6$, $R^8$, A and D have the meanings described above, in particular the meanings described in Configuration (1) or Configuration (2) or Configuration (3) or Configuration (5) and Q and R⁷ have the meanings described in Configuration (4).

In a further preferred embodiment, the invention relates to the use of compounds of the formula (I) where M, $R^1$, $R^2$, $R^3$, $R^4$, $R^5$, $R^6$, $R^8$, A and D have the meanings described above, in particular the meanings described in Configuration (1) or Configuration (2) or Configuration (3) or Configuration (4) and Q and R⁷ have the meanings described in Configuration (5).

In a further preferred embodiment, the invention relates to the use of compounds of the formula (I) where M, $R^1$, $R^2$, $R^3$, $R^4$, $R^5$, $R^6$, $R^7$, Q and A have the meanings described above, in particular the meanings described in Configuration (2) or Configuration (3) or Configuration (4) or Configuration (5) and D and R⁸ have the meanings described in Configuration (1).

In a further preferred embodiment, the invention relates to the use of compounds of the formula (I) where M, $R^1$, $R^2$, $R^3$, $R^4$, $R^5$, $R^6$, $R^7$, Q and A have the meanings described above, in particular the meanings described in Configuration (1) or Configuration (3) or Configuration (4) or Configuration (5) and D and R⁸ have the meanings described in Configuration (2).

In a further preferred embodiment, the invention relates to the use of compounds of the formula (I) where M, $R^1$, $R^2$, $R^3$, $R^4$, $R^5$, $R^6$, $R^7$, Q and A have the meanings described above, in particular the meanings described in Configuration (1) or Configuration (2) or Configuration (4) or Configuration (5) and D and R⁸ have the meanings described in Configuration (3).

In a further preferred embodiment, the invention relates to the use of compounds of the formula (I) where M, $R^1$, $R^2$, $R^3$, $R^4$, $R^5$, $R^6$, $R^7$, Q and A have the meanings described above, in particular the meanings described in Configuration (1) or Configuration (2) or Configuration (3) or Configuration (5) and D and R⁸ have the meanings described in Configuration (4).

In a further preferred embodiment, the invention relates to the use of compounds of the formula (I) where M, $R^1$, $R^2$, $R^3$, $R^4$, $R^5$, $R^6$, $R^7$, Q and A have the meanings described above, in particular the meanings described in Configuration (1) or Configuration (2) or Configuration (3) or Configuration (4) and D and R⁸ have the meanings described in Configuration (5).

In a further preferred embodiment, the invention relates to the use of compounds of the formula (I) where M, $R^1$, $R^2$, $R^3$, $R^4$, $R^5$, $R^6$, $R^7$, $R^8$ Q and A have the meanings described above, in particular the meanings described in Configuration (1) or Configuration (2) or Configuration (3) or Configuration (4) or Configuration (5) and D represents a phenyl radical which is unsubstituted or mono- or disubstituted by $R^8$.

In a further preferred embodiment, the invention relates to the use of compounds of the formula (I) where M, $R^1$, $R^2$, $R^3$, $R^4$, $R^5$, $R^6$, $R^7$, $R^8$, Q and A have the meanings described above, in particular the meanings described in Configuration (1) or Configuration (2) or Configuration (3) or Configuration (4) or Configuration (5) and D represents a phenyl radical which is mono- or disubstituted by $R^8$.

In a further preferred embodiment, the invention relates to the use of compounds of the formula (I) where M, $R^1$, $R^2$, $R^3$, $R^4$, $R^5$, $R^6$, $R^7$, Q and A have the meanings described above, in particular the meanings described in Configuration (1) or Configuration (2) or Configuration (3) or Configuration (4) or Configuration (5) and D represents a phenyl radical which is unsubstituted or mono- or disubstituted by $R^8$, where $R^8$ is selected from halogen, $(C_1-C_4)$-alkyl, $(C_1-C_4)$-alkoxy, $(C_1-C_4)$-haloalkyl and $(C_1-C_4)$-alkylthio, particularly preferably from fluorine, bromine, chlorine, methyl, trifluoromethyl, methoxy, ethoxy, isopropoxy and methylthio.

In a further preferred embodiment, the invention relates to the use of compounds of the formula (I) where M, $R^1$, $R^2$, $R^3$, $R^4$, $R^5$, $R^6$, $R^7$, Q and A have the meanings described above, in particular the meanings described in Configuration (1) or Configuration (2) or Configuration (3) or Configuration (4) or Configuration (5) and D represents a phenyl radical which is mono- or disubstituted by $R^8$, where $R^8$ is selected from halogen, $(C_1-C_4)$-alkyl, $(C_1-C_4)$-alkoxy, $(C_1-C_4)$-haloalkyl and $(C_1-C_4)$-alkylthio, particularly preferably from fluorine, bromine, chlorine, methyl, trifluoromethyl, methoxy, ethoxy, isopropoxy and methylthio.

Preference is furthermore given to compounds of the formulae (Ia) or (Ib) or (Ic), particularly preferably (Ia) or (Ib),

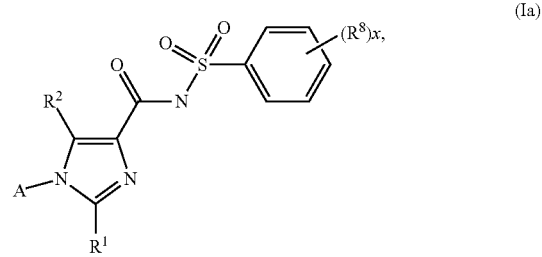

(Ia)

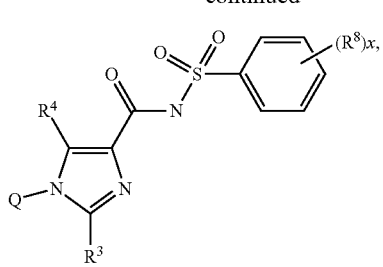

(Ib)

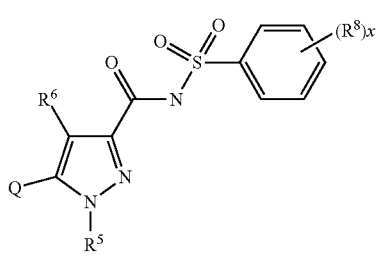

(Ic)

where $R^1$, $R^2$, $R^3$, $R^4$, $R^5$, $R^6$, $R^7$, A, Q and $R^8$ have the meanings described above, in particular the meanings described in Configuration (1) or Configuration (2) or Configuration (3) or Configuration (4) or Configuration (5), and x represents 1 or 2.

Particular preference is given to compounds of the formula (Ia) in which:

A represents $(C_1-C_4)$-haloalkyl or $(C_1-C_4)$-haloalkylcyclopropyl, preferably $(C_1-C_4)$-fluoroalkyl or $(C_1-C_4)$-fluoroalkylcyclopropyl, very particularly preferably 3,3,3-trifluoropropyl or 2-trifluoromethylcyclopropyl, x represents 1 or 2 and $R^1$, $R^2$ and $R^8$ have the meanings described above, in particular the meanings described in Configuration (1) or Configuration (2) or Configuration (3) or Configuration (4) or Configuration (5).

Particular preference is furthermore given to compounds of the formula (Ia) in which:

$R^1$ represents halogen, particularly preferably chlorine or bromine, $R^2$ represents halogen, particularly preferably chlorine, bromine or iodine, x represents 1 or 2 and A and $R^8$ have the meanings described above, in particular the meanings described in Configuration (1) or Configuration (2) or Configuration (3) or Configuration (4) or Configuration (5).

Particular preference is given to compounds of the formula (Ib) in which:

Q represents a phenyl radical which is unsubstituted or mono- or disubstituted by $R^7$, where $R^7$ is selected from halogen, $(C_1-C_4)$-alkyl, $(C_1-C_4)$-alkoxy and $(C_1-C_4)$-haloalkyl, particularly preferably from fluorine, bromine, chlorine and trifluoromethyl, x represents 1 or 2 and $R^3$, $R^4$ and $R^8$ have the meanings described above, in particular the meanings described in Configuration (1) or Configuration (2) or Configuration (3) or Configuration (4) or Configuration (5).

Particular preference is furthermore given to compounds of the formula (Ib) in which:

Q represents a phenyl radical which is unsubstituted or mono- or disubstituted by $R^7$, x represents 1 or 2 and $R^3$, $R^4$, $R^7$ and $R^8$ have the meanings described above, in particular the meanings described in Configuration (1) or Configuration (2) or Configuration (3) or Configuration (4) or Configuration (5).

Particular preference is furthermore given to compounds of the formula (Ib) in which:

$R^3$ represents hydrogen, halogen or $(C_1-C_4)$-alkyl, particularly preferably hydrogen, chlorine, methyl, isopropyl or ethyl, $R^4$ represents hydrogen or halogen, particularly preferably hydrogen, chlorine, bromine or iodine, x represents 0, 1 or 2 and Q and $R^8$ have the meanings described above, in particular the meanings described in Configuration (1) or Configuration (2) or Configuration (3) or Configuration (4) or Configuration (5).

Particular preference is given to compounds of the formula (Ic) in which:

Q represents a phenyl radical which is unsubstituted or mono- or disubstituted by $R^7$, where $R^7$ is selected from halogen, $(C_1-C_4)$-alkyl, $(C_1-C_4)$-alkoxy and $(C_1-C_4)$-haloalkyl, particularly preferably from fluorine, bromine, chlorine and trifluoromethyl, x represents 1 or 2 and $R^5$, $R^6$ and $R^8$ have the meanings described above, in particular the meanings described in Configuration (1) or Configuration (2) or Configuration (3) or Configuration (4) or Configuration (5).

Particular preference is furthermore given to compounds of the formula (Ic) in which:

Q represents a phenyl radical which is unsubstituted or mono- or disubstituted by $R^7$, x represents 1 or 2 and $R^3$, $R^4$, $R^7$ and $R^8$ have the meanings described above, in particular the meanings described in Configuration (1) or Configuration (2) or Configuration (3) or Configuration (4) or Configuration (5).

Particular preference is furthermore given to compounds of the formula (Ic) in which:

$R^5$ represents $(C_1-C_4)$-alkyl, particularly preferably methyl, $R^6$ represents hydrogen or halogen, particularly preferably hydrogen or chlorine, x represents 1 or 2 and Q and $R^8$ have the meanings described above, in particular the meanings described in Configuration (1) or Configuration (2) or Configuration (3) or Configuration (4) or Configuration (5).

Hereinbelow, the term formula (I) also comprises the specific embodiments formula (Ia), formula (Ib) and formula (Ic).

In a further preferred embodiment, the invention relates to compounds of the formula (I) where M, $R^2$, $R^3$, $R^4$, $R^5$, $R^6$, $R^7$, A, Q, D and $R^8$ have the meanings described above, in particular the meanings described in Configuration (1) or Configuration (2) or Configuration (3) or Configuration (4) or Configuration (5) and $R^1$ represents hydroxy, cyano, carboxyl, halogen, nitro, $(C_3-C_5)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_5)$-cycloalkyl, halo-$(C_3-C_5)$-cycloalkyl, methyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl- $(C_1-C_6)$-alkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-alkylsulfoximino, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl-$(C_2-C_6)$-alkyl or hetaryl-$(C_1-C_6)$-alkyl which is optionally monosubstituted or polysubstituted by identical or different substituents, where, in the case of hetaryl, optionally at least one carbonyl group may be present and where the substituent(s) in each case independently of one another are selected from:

cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino.

In a further preferred embodiment, the invention relates to compounds of the formula (I) where M, $R^2$, $R^3$, $R^4$, $R^5$, $R^6$, $R^7$, A, Q, D and $R^8$ have the meanings described above, in particular the meanings described in Configuration (1) or Configuration (2) or Configuration (3) or Configuration (4) or Configuration (5) and $R^1$ represents cyano, halogen, nitro, $(C_3-C_5)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_5)$-cycloalkyl, halo-$(C_3-C_5)$-cycloalkyl, methyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkoxycarbonyl, $(C_1-C_6)$-haloalkoxycarbonyl, $(C_1-C_6)$-alkylaminocarbonyl or $(C_1-C_6)$-alkylcarbonylamino).

In a further preferred embodiment, the invention relates to compounds of the formula (I) where M, $R^2$, $R^3$, $R^4$, $R^5$, $R^6$, $R^7$, A, Q, D and $R^8$ have the meanings described above, in particular the meanings described in Configuration (1) or Configuration (2) or Configuration (3) or Configuration (4) or Configuration (5) and $R^1$ represents cyano, halogen, cyclopropyl, methyl, halocyclopropyl, halo-$(C_1-C_3)$-alkylcyclopropyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylthio-$(C_1-C_4)$-alkyl, $(C_1-C_4)$-alkylsulfinyl-$(C_1-C_4)$-alkyl or $(C_1-C_4)$-alkylsulfonyl-$(C_1-C_4)$-alkyl.

In a further preferred embodiment, the invention relates to compounds of the formula (I) where M, $R^2$, $R^3$, $R^4$, $R^5$, $R^6$, $R^7$, A, Q, D and $R^8$ have the meanings described above, in particular the meanings described in Configuration (1) or Configuration (2) or Configuration (3) or Configuration (4) or Configuration (5) and $R^1$ represents halogen, cyclopropyl, methyl, $(C_1-C_4)$-alkylthio, halocyclopropyl or $(C_1-C_4)$-haloalkyl.

In a further preferred embodiment, the invention relates to compounds of the formula (I) where M, $R^2$, $R^3$, $R^4$, $R^5$, $R^6$, $R^7$, A, Q, D and $R^8$ have the meanings described above, in particular the meanings described in Configuration (1) or Configuration (2) or Configuration (3) or Configuration (4) or Configuration (5) and $R^1$ represents chlorine, bromine, methyl, trifluoromethyl, methylthio or isopropylthio.

In a preferred embodiment of the invention, the compounds of the formula (I) according to the configurations and preferred embodiments described above are used for controlling nematodes.

According to a further preferred embodiment of the invention, the use of a compound of the formula (I) according to the configurations and preferred embodiments described above for protecting the propagation material of plants is provided.

The invention also provides a composition comprising at least one compound of the formula (I) according to the configurations and preferred embodiments described above and customary extenders and/or surfactants, in particular for controlling animal pests, preferably nematodes.

The invention furthermore provides a method for controlling animal pests, preferably nematodes, in which at least one compound of the formula (I) according to the configurations and preferred embodiments described above or a composition according to the invention is allowed to act on the animal pests, preferably nematodes, and/or their habitat.

According to a preferred embodiment of the method, the surgical, therapeutic and diagnostic treatment of the human or animal body is excluded.

The invention furthermore still provides an agrochemical formulation comprising at least one compound of the formula (I) according to the configurations and preferred embodiments described above in biologically effective amounts of from 0.00000001 to 98% by weight, based on the weight of the agrochemical formulation, and also extenders and/or surfactants.

A preferred embodiment of the formulation according to the invention additionally comprises a further agrochemically active compound.

The invention also provides compounds of the formula (I')

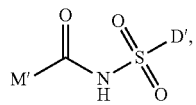
(I')

in which
M' represents a radical selected from formulae (IIa'-IIc'):

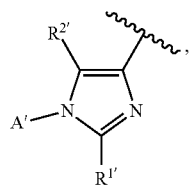
(IIa')

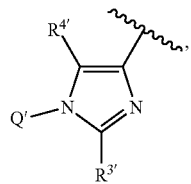
(IIb')

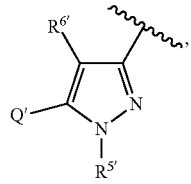
(IIc')

where (Configuration 1'-1)
$R^{1'}$ represents hydroxy, cyano, carboxyl, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-alkylsulfoximino, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or
aryl-$(C_1-C_6)$-alkyl or hetaryl-$(C_1-C_6)$-alkyl which is optionally monosubstituted or polysubstituted by identical or different substituents, where, in the case of hetaryl, optionally at least one carbonyl group may be present and where the substituent(s) in each case independently of one another are selected from:
cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino,
$R^{2'}$ represents hydrogen, cyano, halogen, nitro, acetyl, hydroxy, carboxyl, amino, SCN, tri-$(C_1-C_6)$-alkylsilyl, $(C_3-C_8)$-cycloalkyl, $(C_3-C_8)$-cycloalkyloxy, $(C_3-C_8)$-cycloalkyl- $(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-alkylsulfoximino, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino, or aryl or hetaryl, optionally mono- or polysubstituted by identical or different substituents, where in the case of hetaryl optionally at least one carbonyl group may be present and where possible substituents in each case are as follows: cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, $R^{3'}$ represents cyano, halogen, hydroxy, carboxyl, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-alkylsulfoximino, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl-$(C_1-C_6)$-alkyl or hetaryl-$(C_1-C_6)$-alkyl which is optionally monosubstituted or polysubstituted by identical or different substituents, where, in the case of hetaryl, optionally at least one carbonyl group may be present and where the substituent(s) in each case independently of one another are selected from:

cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$- alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, $R^{4'}$ represents hydrogen, cyano, halogen, nitro, acetyl, hydroxy, carboxyl, amino, SCN, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkylsulfoximino, $(C_1-C_6)$-alkoxy-$(C_1-C_6)$-alkylsulfinyl, $(C_1-C_6)$-alkylsulfinyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl or hetaryl, optionally mono- or polysubstituted by identical or different substituents, where in the case of hetaryl optionally at least one carbonyl group may be present and where possible substituents in each case are as follows: cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, $R^{5'}$ represents $((C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl or halo-$(C_1-C_6)$-alkylsulfonyl-$(C_1-C_6)$-alkyl, $R^{6'}$ represents hydrogen cyano, halogen, nitro, acetyl, hydroxy, carboxyl, amino, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl-$(C_1-C_6)$-alkyl or hetaryl-$(C_1-C_6)$-alkyl which is optionally monosubstituted or polysubstituted by identical or different substituents, where, in the case of hetaryl, optionally at least one carbonyl group may be present and where the substituent(s) in each case independently of one another are selected from:

cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, A' represents $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_1-C_6)$-alkyl-$(C_3-C_8)$-cycloalkyl, halo-$(C_3-C_8)$-cycloalkyl, halo-$(C_1-C_3)$-alkoxy-$(C_1-C_4)$-alkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, halo-$(C_3-C_8)$-alkynyl, halo-$(C_3-C_8)$-alkenyl or an aryl-$(C_1-C_6)$-alkyl or hetaryl-$(C_1-C_6)$-alkyl radical which is optionally monosubstituted or polysubstituted by identical or different substituents, where, in the case of hetaryl, optionally at least one carbonyl group may be present and where the substituent(s) in each case independently of one another are selected from:

cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, Q' represents a 6-membered aryl or hetaryl radical which is unsubstituted or substituted by one or more radicals $R^{7'}$, where, in the case of hetaryl, optionally at least one carbonyl group may be present and where the substituent(s) $R^{7'}$ in each case independently of one another are selected from:

cyano, halogen, nitro, acetyl, hydroxy, carboxyl, amino, SCN, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino and/or aryl or hetaryl, optionally mono- or polysubstituted by identical or different substituents, where, in the case of hetaryl, optionally at least one carbonyl group may be present and where possible substituents in each case are as follows: cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, and D' represents a $C_1-C_6$-alkyl, phenyl, phenyl-$(C_1-C_2)$-alkyl, benzdioxolyl or 5- or 6-membered hetaryl radical which is unsubstituted or substituted by one or more radicals $R^{8'}$ and which may contain one to three heteroatoms from the group consisting of oxygen, sulfur, nitrogen, where the substituent(s) $R^{8'}$ in each case independently of one another are selected from:

cyano, halogen, nitro, acetyl, hydroxy, carboxyl, amino, SCN, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino), (1-pyrazolyl) $(C_1-C_3)$-alkyl and/or aryl or hetaryl or aryloxy or hetaryloxy, optionally mono- or polysubstituted by identical or different substituents, where, in the case of hetaryl, optionally at least one carbonyl group may be present and where possible substituents in each case are as follows: cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino.

Configuration (1'-2)

Furthermore, the invention provides compounds of the formula (I') in which M' represents a radical selected from formulae (IIa'-IIc') and where A' represents $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_1-C_6)$-alkyl-$(C_3-C_8)$-cycloalkyl, halo-$(C_3-C_8)$-cycloalkyl, halo-$(C_1-C_3)$-alkoxy-$(C_1-C_4)$-alkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl or an aryl-$(C_1-C_6)$-alkyl or hetaryl-$(C_1-C_6)$- alkyl radical which is optionally monosubstituted or polysubstituted by identical or different substituents, where, in the case of hetaryl, optionally at least one carbonyl group may be present and where the substituent(s) in each case independently of one another are selected from:

cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino, and where $R^{1'}$, $R^{2'}$, $R^{3'}$, $R^{4'}$, $R^{5'}$, $R^{6'}$, $R^{7'}$, $R^{8'}$, Q' and D' are defined according to Configuration 1-1.

Preference is given to an embodiment (Configuration 2'-1) in which M' represents a radical selected from formulae (IIa'-IIc') and where $R^{1'}$ represents cyano, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkoxycarbonyl, $(C_1-C_6)$-haloalkoxycarbonyl, $(C_1-C_6)$-alkylaminocarbonyl, $(C_1-C_6)$-alkylcarbonylamino) or benzyl which is unsubstituted or monosubstituted or polysubstituted by identical or different substituents, where possible substituents in each case are as follows:

cyano, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $C_1-C_6)$-alkoxy-$(C_1-C_6)$-alkoxy, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl and/or $(C_1-C_6)$-alkylsulfonyl-$(C_1-C_6)$-alkyl, $R^{2'}$ represents hydrogen, cyano, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $C_1-C_6)$-alkoxy-$(C_1-C_6)$-alkoxy, $(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkoxycarbonyl, $(C_1-C_6)$-haloalkoxycarbonyl, $(C_1-C_6)$-alkylaminocarbonyl or $(C_1-C_6)$-alkylcarbonylamino), $R^{3'}$ represents cyano, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $C_1-C_6)$-alkoxy-$(C_1-C_6)$-alkoxy, $(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkoxycarbonyl, $(C_1-C_6)$-haloalkoxycarbonyl, $(C_1-C_6)$-alkylaminocarbonyl, $(C_1-C_6)$-alkylcarbonylamino) or benzyl which is unsubstituted or monosubstituted or polysubstituted by identical or different substituents, where possible substituents in each case are as follows:

cyano, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $C_1-C_6)$-alkoxy-$(C_1-C_6)$-alkoxy, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl and/or $(C_1-C_6)$-alkylsulfonyl-$(C_1-C_6)$-alkyl, $R^{4'}$ represents hydrogen, cyano, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $C_1-C_6)$-alkoxy-$(C_1-C_6)$-alkoxy, $(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkoxycarbonyl, $(C_1-C_6)$-haloalkoxycarbonyl, $(C_1-C_6)$-alkylaminocarbonyl or $(C_1-C_6)$-alkylcarbonylamino, $R^{5'}$ represents $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-alkylthio-$(C_1-C_6)$-alkyl, halo-$(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, halo-$(C_1-C_6)$-alkylsulfinyl-$(C_1-C_6)$-alkyl or halo-$(C_1-C_6)$-alkylsulfonyl-$(C_1-C_6)$-alkyl, $R^{6'}$ represents hydrogen, cyano, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-

$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl or ($C_1$-$C_6$)-alkylcarbonylamino, A' represents halo-($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, halo-($C_1$-$C_3$)-alkoxy-($C_1$-$C_4$)-alkyl ($C_1$-$C_6$)-alkylthio-($C_1$-$C_6$)-alkyl, ($C_1$-$C_6$)-alkylsulfinyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, halo-($C_3$-$C_6$)-alkenyl or a benzyl radical which is optionally monosubstituted or polysubstituted by identical or different substituents, where the substituent(s) in each case independently of one another are selected from:

cyano, halogen, ($C_3$-$C_6$)-cycloalkyl, ($C_3$-$C_6$)-cycloalkyloxy, ($C_3$-$C_6$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, ($C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl and/or halo-($C_1$-$C_6$)-alkylsulfonyl-($C_1$-$C_6$)-alkyl, Q' represents a phenyl or pyridyl radical which is unsubstituted or substituted by one or more radicals $R^{7'}$, where the substituent(s) $R^{7'}$ in each case independently of one another are selected from:

cyano, halogen, nitro, ($C_3$-$C_6$)-cycloalkyl, ($C_3$-$C_6$)-cycloalkyloxy, ($C_3$-$C_6$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, ($C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl, ($C_1$-$C_6$)-alkylcarbonylamino), halo-($C_1$-$C_6$)-alkylthio-($C_1$-$C_6$)-alkyl, halo-($C_1$-$C_6$)-alkylsulfinyl-($C_1$-$C_6$)-alkyl and/or halo-($C_1$-$C_6$)-alkylsulfonyl-($C_1$-$C_6$)-alkyl, and D' represents a $C_1$-$C_6$-alkyl, phenyl, thiophenyl, isoxazolyl, phenyl-($C_1$-$C_2$)-alkyl or benzdioxolyl radical which is unsubstituted or substituted by one or more radicals $R^{8'}$, where the substituent(s) $R^{8'}$ in each case independently of one another are selected from:

cyano, halogen, nitro, acetyl, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino, (1-pyrazolyl)($C_1$-$C_3$)-alkyl and/or ($C_1$-$C_3$)-alkoxypyrimidinyloxy.

Preference is furthermore given to an embodiment in which M' represents a radical selected from formulae (IIa'-IIc') and where (Configuration 2'-2)

A' represents halo-($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, halo-($C_1$-$C_3$)-alkoxy-($C_1$-$C_4$)-alkyl ($C_1$-$C_6$)-alkylthio-($C_1$-$C_6$)-alkyl, ($C_1$-$C_6$)-alkylsulfinyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl or a benzyl radical which is optionally monosubstituted or polysubstituted by identical or different substituents, where the substituent(s) in each case independently of one another are selected from:

cyano, halogen, ($C_3$-$C_6$)-cycloalkyl, ($C_3$-$C_6$)-cycloalkyloxy, ($C_3$-$C_6$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl and/or halo-($C_1$-$C_6$)-alkylsulfonyl-($C_1$-$C_6$)-alkyl, and where $R^{1'}$, $R^{2'}$, $R^{3'}$, $R^{4'}$, $R^{5'}$, $R^{6'}$, $R^{7'}$, $R^{8'}$, Q' and D' are defined according to Configuration 2'-1.

Particular preference is furthermore given to an embodiment (Configuration 3'-1) in which M' represents a radical selected from formulae (IIa'-IIc') and where $R^{1'}$ represents cyano, halogen, cyclopropyl, ($C_1$-$C_4$)-alkyl, halocyclopropyl, halo-($C_1$-$C_3$)-alkylcyclopropyl, ($C_1$-$C_4$)-haloalkyl, ($C_1$-$C_4$)-alkoxy, ($C_1$-$C_4$)-haloalkoxy, ($C_1$-$C_4$)-alkylthio, ($C_1$-$C_4$)-haloalkylthio, ($C_1$-$C_4$)-alkylthio-($C_1$-$C_4$)-alkyl, ($C_1$-$C_4$)-alkylsulfinyl-($C_1$-$C_4$)-alkyl, ($C_1$-$C_4$)-alkylsulfonyl-($C_1$-$C_4$)-alkyl, or benzyl which is unsubstituted, monosubstituted or polysubstituted by identical or different substituents, where possible substituents in each case are as follows:

cyano, halogen, $(C_1-C_4)$-haloalkyl, $(C_1-C_4)$-alkoxy, $(C_1-C_4)$-haloalkoxy, $(C_1-C_6)$-alkylthio and/or $(C_1-C_6)$-haloalkylthio, $R^{2'}$ represents hydrogen, cyano, halogen, $(C_1-C_4)$-haloalkyl, $(C_1-C_4)$-alkoxy, $(C_1-C_4)$-haloalkoxy, $(C_1-C_6)$-alkylthio or $(C_1-C_6)$-haloalkylthio, $R^{3'}$ represents cyano, halogen, cyclopropyl, $(C_1-C_4)$-alkyl, halocyclopropyl, halo-$(C_1-C_3)$-alkylcyclopropyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylthio-$(C_1-C_4)$-alkyl, $(C_1-C_4)$-alkylsulfinyl-$(C_1-C_4)$-alkyl, or $(C_1-C_4)$-alkylsulfonyl-$(C_1-C_4)$-alkyl, $R^{4'}$ represents hydrogen, cyano, halogen, $(C_1-C_4)$-haloalkyl, $(C_1-C_4)$-alkoxy, $(C_1-C_4)$-alkyl, $(C_3-C_4)$-cycloalkyl, $(C_1-C_4)$-haloalkoxy, $(C_1-C_6)$-alkylthio or $(C_1-C_6)$-haloalkylthio, $R^{5'}$ represents cyclopropyl, $(C_1-C_4)$-alkyl, halocyclopropyl, halo-$(C_1-C_3)$-alkylcyclopropyl or $(C_1-C_4)$-haloalkyl, $R^{6'}$ represents hydrogen, cyano, halogen, $(C_1-C_4)$-haloalkyl, $(C_1-C_4)$-alkoxy, $(C_1-C_4)$-haloalkoxy, $(C_1-C_6)$-alkylthio or $(C_1-C_6)$-haloalkylthio, A' represents halo-$(C_1-C_4)$-alkyl-$(C_3-C_4)$-cycloalkyl, halo-$(C_3-C_6)$-cycloalkyl, $(C_1-C_6)$-alkyl, $(C_1-C_5)$-haloalkyl, $(C_1-C_6)$-cyanoalkyl, $(C_1-C_4)$-alkoxy-$(C_1-C_4)$-alkyl, halo-$(C_1-C_3)$-alkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, halo-$(C_3-C_4)$-alkenyl or a benzyl radical which is optionally monosubstituted or polysubstituted by identical or different substituents, where the substituent(s) in each case independently of one another are selected from:

cyano, halogen, $(C_3-C_6)$-cycloalkyl, $(C_3-C_6)$-cycloalkyloxy, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $C_1-C_6)$-alkoxy-$(C_1-C_6)$-alkoxy, $(C_1-C_6)$-alkylthio and/or $(C_1-C_6)$-haloalkylthio, Q' represents a phenyl or pyridyl radical which is unsubstituted or substituted by one or more radicals $R^{7'}$, where the substituent(s) $R^{7'}$ in each case independently of one another are selected from:

cyano, halogen, $(C_3-C_6)$-cycloalkyl, halo-$(C_3-C_8)$-cycloalkyl, $(C_1-C_6)$-alkyl, $(C_1-C_6)$-haloalkyl, $(C_1-C_6)$-alkoxy-$(C_1-C_6)$-alkyl, $(C_1-C_6)$-alkoxy and/or $(C_1-C_6)$-haloalkoxy, and D' represents a $C_1-C_6$-alkyl, phenyl, thiophenyl, isoxazolyl, benzyl or benzdioxolyl radical which is unsubstituted or substituted by one or more radicals $R^{8'}$, where the substituent(s) $R^{8'}$ in each case independently of one another are selected from:

cyano, halogen, acetyl, $(C_3-C_6)$-cycloalkyl, $(C_3-C_6)$-cycloalkyloxy, $(C_3-C_6)$-cycloalkyl-$(C_3-C_8)$-cycloalkyl, $(C_1-C_6)$-alkyl-$(C_3-C_6)$-cycloalkyl, halo-$(C_3-C_6)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkyl- sulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, $(C_3-C_8)$-cycloalkylamino, $(C_1-C_6)$-alkylcarbonylamino, (1-pyrazolyl)$(C_1-C_3)$-alkyl and/or $(C_1-C_3)$-alkoxypyrimidinyloxy.

Particular preference is furthermore given to an embodiment in which M' represents a radical selected from formulae (IIa'-IIc') and where (Configuration 3'-2)

$R^{4'}$ represents hydrogen, cyano, halogen, $(C_1-C_4)$-haloalkyl, $(C_1-C_4)$-alkoxy, $(C_1-C_4)$-haloalkoxy, $(C_1-C_6)$-alkylthio or $(C_1-C_6)$-haloalkylthio, A' represents halo-$(C_1-C_4)$-alkyl-$(C_3-C_4)$-cycloalkyl, halo-$(C_3-C_6)$-cycloalkyl, $(C_1-C_6)$-alkyl, $(C_1-C_5)$-haloalkyl, $(C_1-C_6)$-cyanoalkyl, $(C_1-C_4)$-alkoxy-$(C_1-C_4)$-alkyl, halo-$(C_1-C_3)$-alkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl or a benzyl radical which is optionally monosubstituted or polysubstituted by identical or different substituents, where the substituent(s) in each case independently of one another are selected from:

cyano, halogen, $(C_3-C_6)$-cycloalkyl, $(C_3-C_6)$-cycloalkyloxy, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $C_1-C_6)$-alkoxy-$(C_1-C_6)$-alkoxy, $(C_1-C_6)$-alkylthio and/or $(C_1-C_6)$-haloalkylthio, and where $R^{1'}$, $R^{2'}$, $R^{3'}$, $R^{5'}$, $R^{6'}$, $R^{7'}$, $R^{8'}$, Q' and D' are defined according to Configuration 3'-1.

Very particular preference is furthermore given to an embodiment (Configuration 4'-1) in which M' represents a radical selected from formulae (IIa'-IIc') and where $R^{1'}$ represents halogen, cyclopropyl, $(C_1-C_4)$-alkyl, $(C_1-C_4)$-alkylthio, halocyclopropyl, $(C_1-C_4)$-haloalkyl or benzyl which is unsubstituted or monosubstituted or polysubstituted by identical or different substituents, where possible substituents in each case are as follows: cyano, halogen, $(C_1-C_4)$-haloalkyl and/or $(C_1-C_4)$-alkoxy, $R^{2'}$ represents hydrogen, halogen, cyano, $(C_1-C_4)$-alkyl, $(C_1-C_4)$-haloalkyl, $R^{3'}$ represents halogen, cyclopropyl, $(C_1-C_4)$-alkyl, halocyclopropyl or $(C_1-C_4)$-haloalkyl, $R^{4'}$ represents hydrogen, halogen, cyano, $(C_1-C_4)$-alkyl, cyclopropyl, or $(C_1-C_4)$-haloalkyl, $R^{5'}$ represents cyclopropyl, $(C_1-C_4)$-alkyl or halo-$(C_1-C_4)$-alkyl, $R^{6'}$ represents hydrogen, halogen, cyano, $(C_1-C_4)$-alkyl or $(C_1-C_4)$-haloalkyl, A' represents halo-$(C_1-C_4)$-alkyl-$(C_3-C_4)$-cycloalkyl, halo-$(C_3-C_6)$-cycloalkyl, $(C_1-C_6)$-alkyl, $(C_1-C_5)$-haloalkyl, $(C_1-C_6)$-cyanoalkyl, $(C_1-C_4)$-alkoxy-$(C_1-C_4)$-alkyl, halo-$(C_1-C_3)$-alkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, halo-$(C_3-C_4)$-alkenyl or a benzyl radical which is optionally monosubstituted or polysubstituted by identical or different substituents, where the substituent(s) in each case independently of one another are selected from:

cyano, halogen, $(C_3-C_6)$-cycloalkyl, $(C_3-C_6)$-cycloalkyloxy, halo-$(C_3-C_8)$-cycloalkyl, $(C_1-C_6)$-alkyl, $(C_1-C_6)$-haloalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-alkylthio and/or $(C_1-C_6)$-haloalkylthio, Q' represents a phenyl or pyridyl radical which is unsubstituted or substituted by one or more radicals $R^{7'}$, where the substituent(s) $R^{7'}$ in each case independently of one another are selected from:

cyano, halogen, $(C_3-C_6)$-cycloalkyl, halo-$(C_3-C_6)$-cycloalkyl, $(C_1-C_6)$-alkyl, $(C_1-C_6)$-haloalkyl, $(C_1-C_6)$-alkoxy-$(C_1-C_6)$-alkyl, $(C_1-C_6)$-alkoxy and/or $(C_1-C_6)$-haloalkoxy and D' represents a $C_1-C_6$-alkyl, phenyl, thiophenyl, isoxazolyl, benzyl or benzdioxolyl radical which is unsubstituted or substituted by one or more radicals $R^{8'}$, where the substituent(s) $R^{8'}$ in each case independently of one another are selected from:

cyano, halogen, acetyl, $(C_3-C_6)$-cycloalkyl, $(C_3-C_6)$-cycloalkyloxy, $(C_3-C_6)$-cycloalkyl-$(C_3-C_8)$-cycloalkyl, $(C_1-C_6)$-alkyl-$(C_3-C_6)$-cycloalkyl, halo-$(C_3-C_6)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, $(C_3-C_6)$-cycloalkylamino, $(C_1-C_6)$-alkylcarbonylamino, (1-pyrazolyl)$(C_1-C_3)$-alkyl and/or $(C_1-C_3)$-alkoxypyrimidinyloxy.

Particular preference is furthermore given to an embodiment in which M' represents a radical selected from formulae (IIa'-IIc') and where (Configuration 4'-2)

$R^{1'}$ represents halogen, cyclopropyl, $(C_1-C_4)$-alkyl, halocyclopropyl, $(C_1-C_4)$haloalkyl or benzyl which is unsubstituted or monosubstituted or polysubstituted by identical or different substituents, where possible substituents in each case are as follows: cyano, halogen, $(C_1-C_4)$-haloalkyl and/or $(C_1-C_4)$-alkoxy, $R^{2'}$ represents hydrogen, halogen, cyano, $(C_1-C_4)$-alkyl, $(C_1-C_4)$-haloalkyl, $R^{3'}$ represents halogen, cyclopropyl, $(C_1-C_4)$-alkyl, halocyclopropyl or $(C_1-C_4)$-haloalkyl, $R^{4'}$ represents hydrogen, halogen, cyano, $(C_1-C_4)$-alkyl or $(C_1-C_4)$-haloalkyl, $R^{5'}$ represents cyclopropyl, $(C_1-C_4)$-alkyl or halo-$(C_1-C_4)$-alkyl, $R^{6'}$ represents hydrogen, halogen, cyano, $(C_1-C_4)$-alkyl or $(C_1-C_4)$-haloalkyl, A' represents halo-$(C_1-C_4)$-alkyl-$(C_3-C_4)$-cycloalkyl, halo-$(C_3-C_6)$-cycloalkyl, $(C_1-C_6)$-alkyl, $(C_1-C_5)$-haloalkyl, $(C_1-C_6)$-cyanoalkyl, $(C_1-C_4)$-alkoxy-$(C_1-C_4)$-alkyl, halo-$(C_1-C_3)$-alkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl or a benzyl radical which is optionally monosubstituted or polysubstituted by identical or different substituents, where the substituent(s) in each case independently of one another are selected from:

cyano, halogen, $(C_3-C_6)$-cycloalkyl, $(C_3-C_6)$-cycloalkyloxy, halo-$(C_3-C_8)$-cycloalkyl, $(C_1-C_6)$-alkyl, $(C_1-C_6)$-haloalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-alkylthio and/or $(C_1-C_6)$-haloalkylthio, and where $R^{2'}$, $R^{3'}$, $R^{5'}$, $R^{6'}$, $R^{7'}$, $R^{8'}$, Q' and D' are defined according to Configuration 4'-1.

Particular preference is furthermore given to an embodiment (Configuration 5'-1) in which M' represents a radical selected from formulae (IIa'-IIc') and where $R^{1'}$ represents chlorine, bromine, methyl, benzyl, 2-chlorobenzyl, 3-chlorobenzyl, 4-chlorobenzyl, trifluoromethyl, methylthio or isopropylthio, $R^{2'}$ represents hydrogen, cyano, chlorine, bromine or iodine, $R^{3'}$ represents chlorine, methyl, isopropyl, ethyl or bromine, $R^{4'}$ represents hydrogen, chlorine, bromine, iodine, fluorine, difluoromethyl, isopropyl or cyclopropyl, $R^{5'}$ represents methyl or 2,2,2-trifluoroethyl, $R^{6'}$ represents hydrogen or chlorine, A' represents a radical selected from the radicals of the formulae (III1-III19):

(III1)

(III2)

(III3)

(III4)

(III5)

(III6)

(III7)

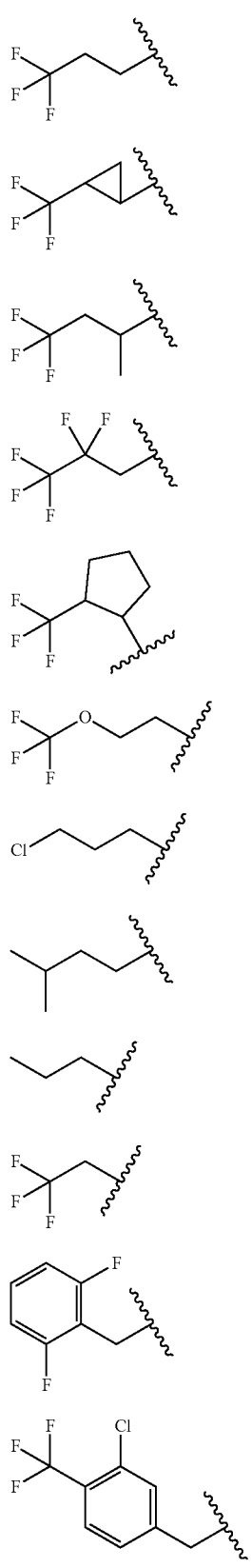
(III8)
(III9)
(III10)
(III11)
(III12)
(III13)
(III14)
(III15)
(III16)
(III17)
(III18)
(III19)
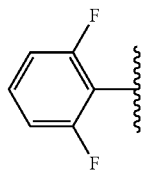 (IV1)
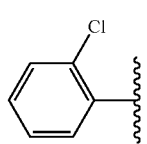 (IV2)
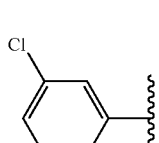 (IV3)
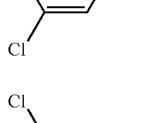 (IV4)
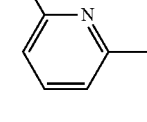 (IV5)
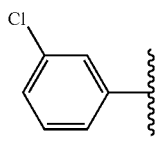 (IV6)
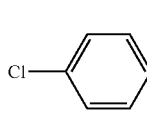 (IV7)
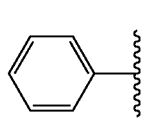 (IV8)
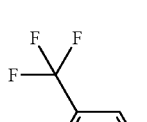 (IV9)
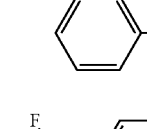 (IV10)
Q' represents a radical selected from the radicals of the formulae (IV1-IV40):

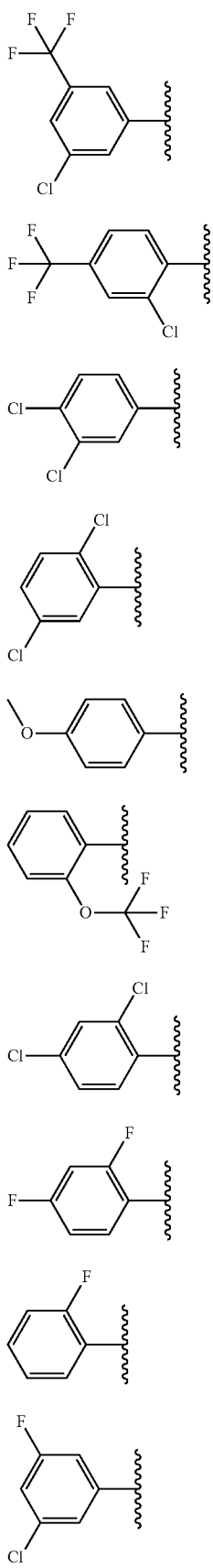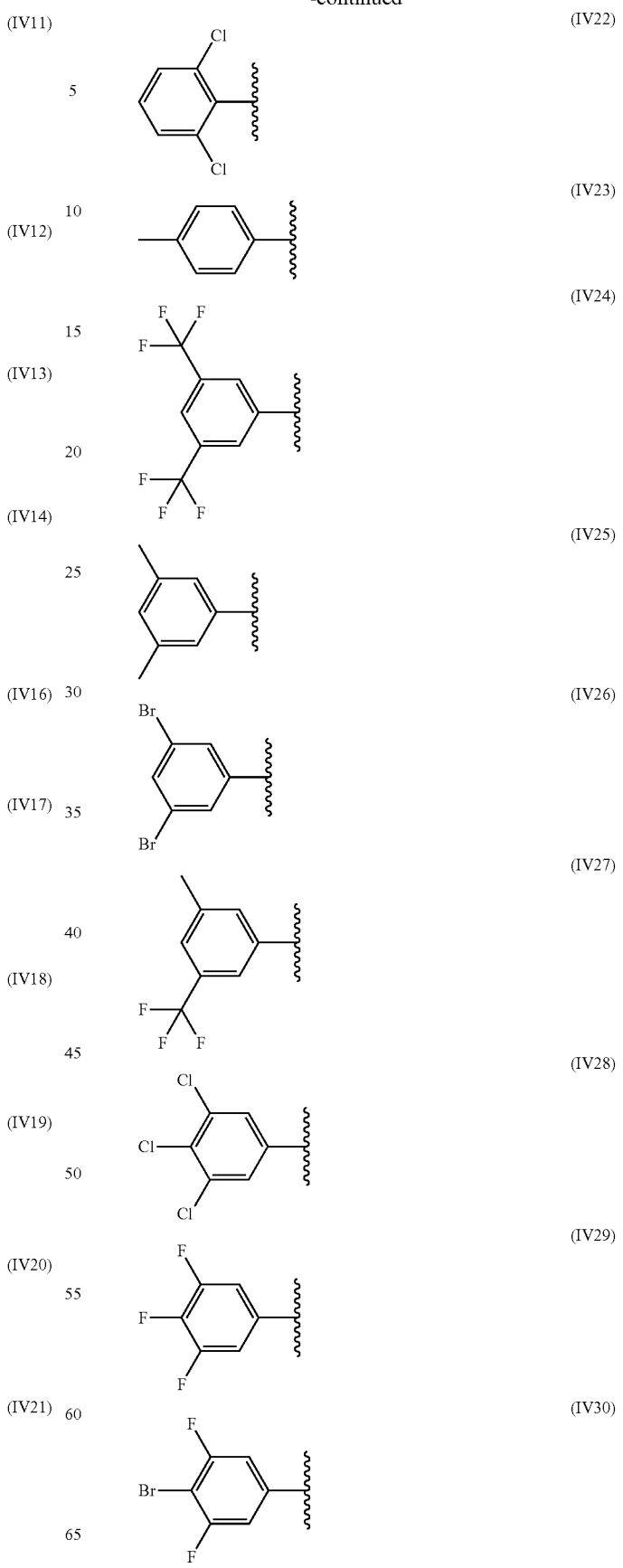

(IV31) 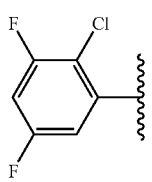
(IV32) 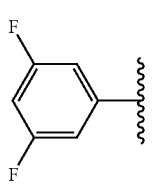
(IV33) 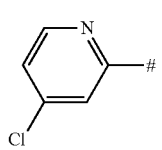
(IV34) 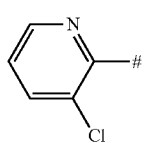
(IV35) 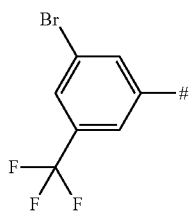
(IV36) 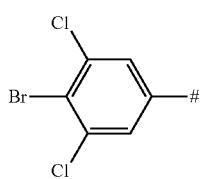
(IV37) 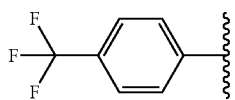
(IV38) 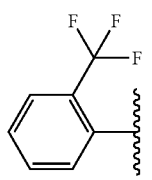
(IV39) 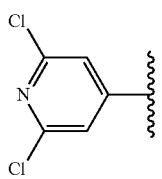
(IV40) 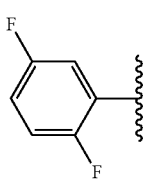
and
D' represents a radical selected from the radicals of the formulae (V1-V61):
(V1) 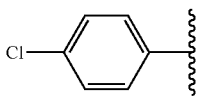
(V2) 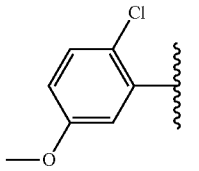
(V3) 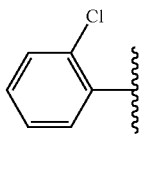
(V4) 
(V5) 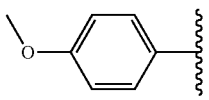
(V6) 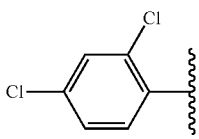
(V7) 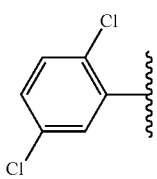
(V8) 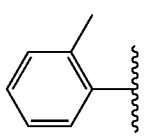

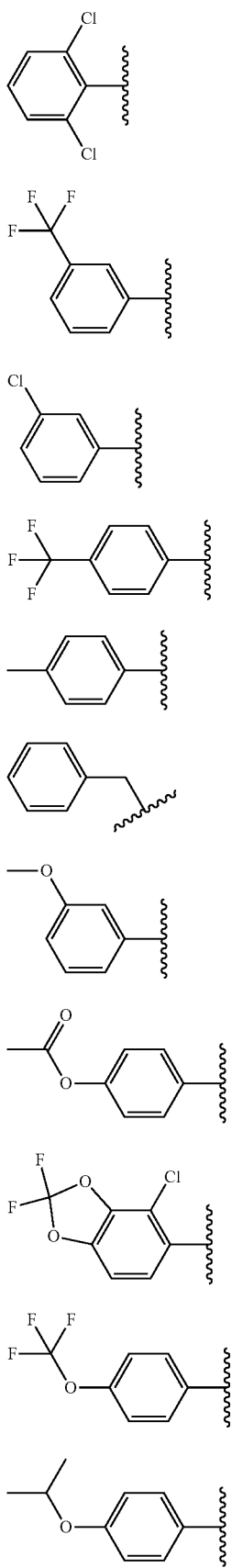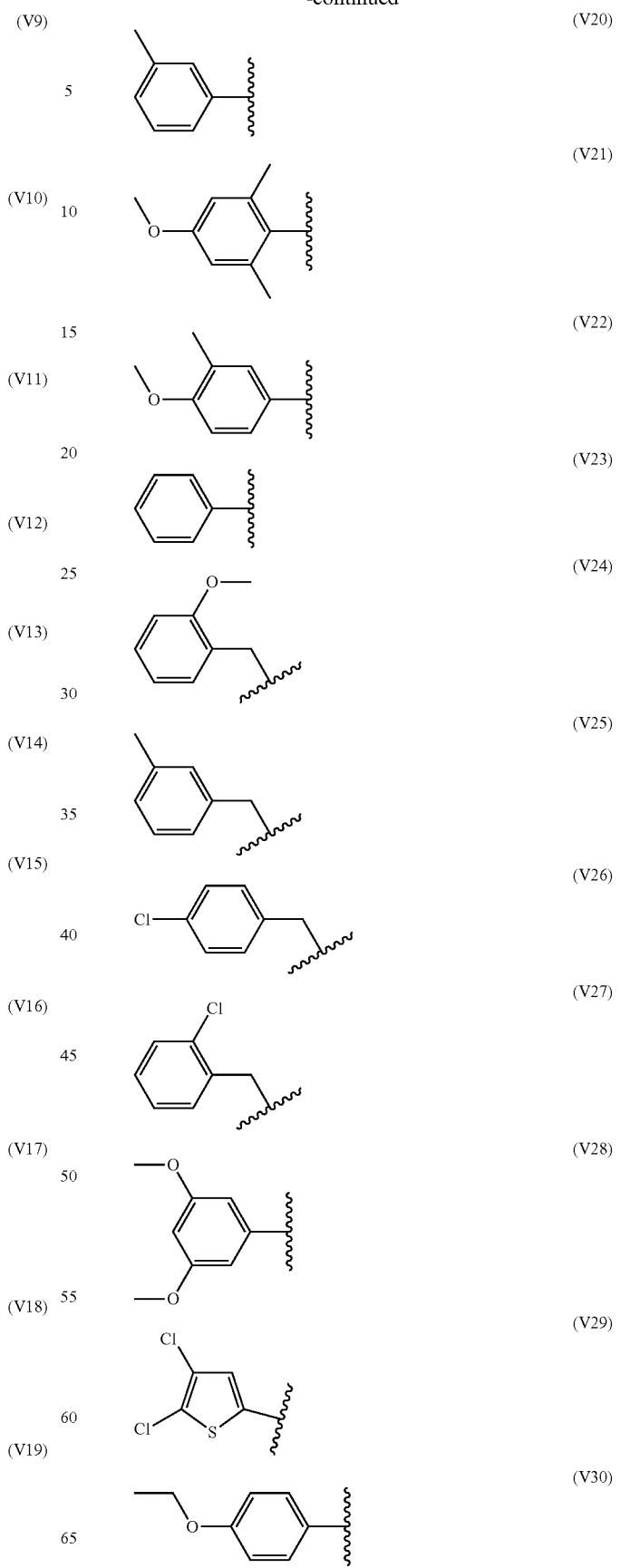

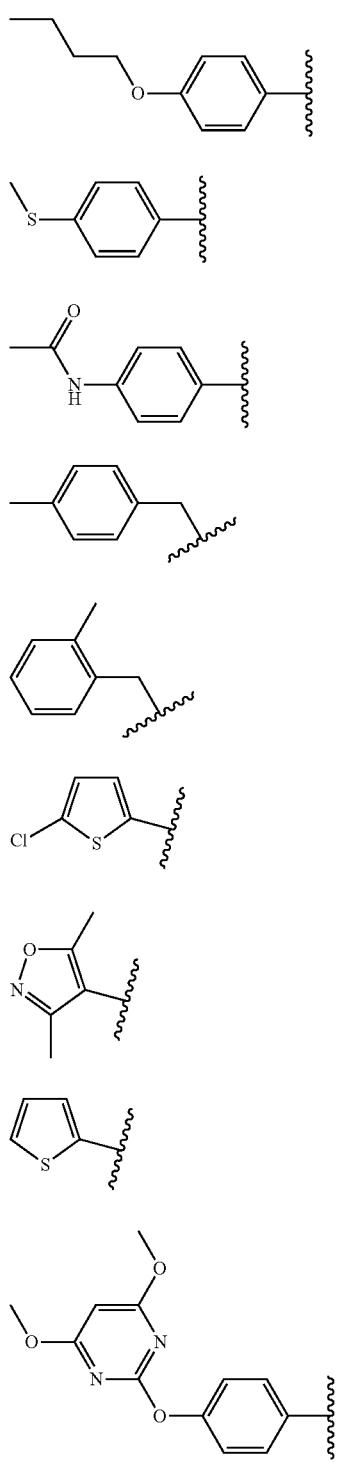
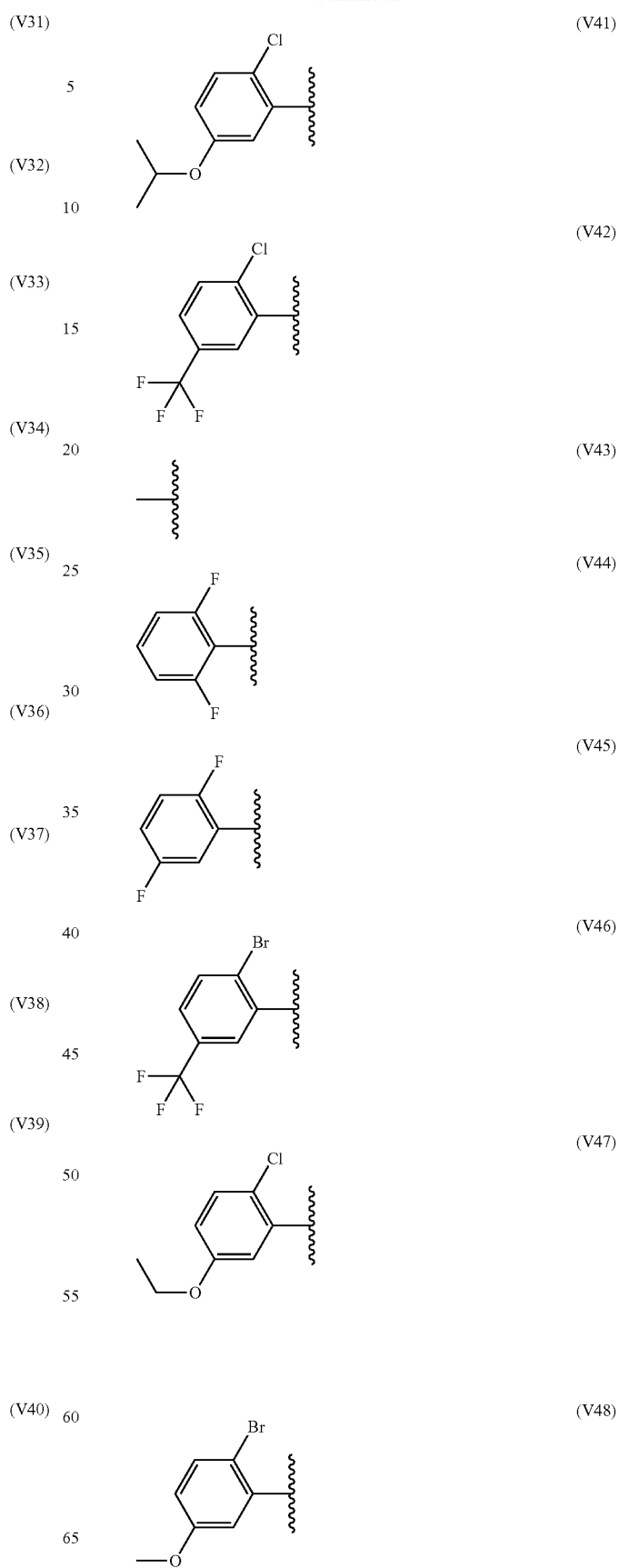

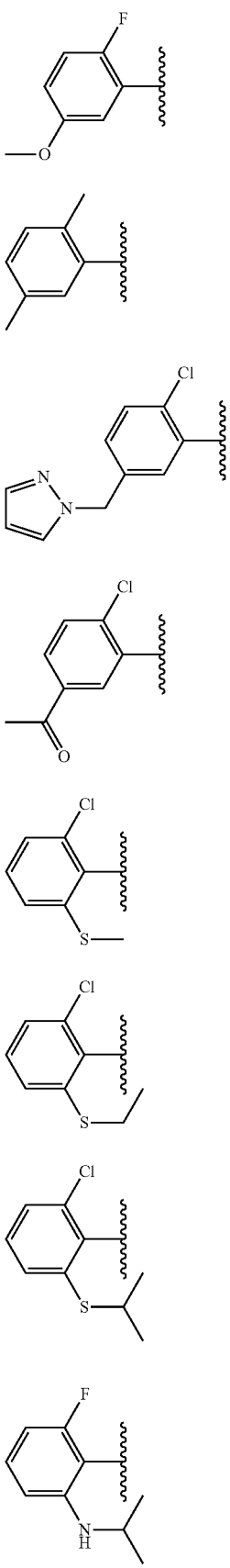

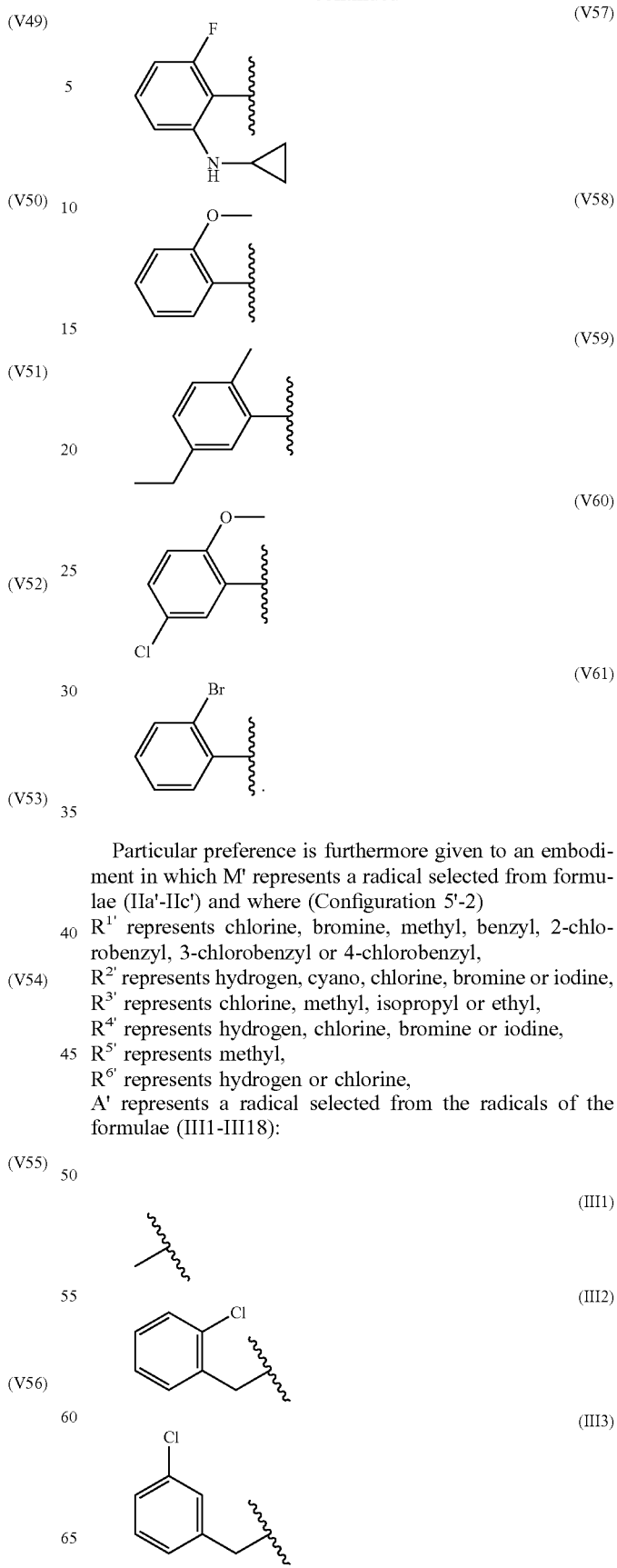

Particular preference is furthermore given to an embodiment in which M' represents a radical selected from formulae (IIa'-IIc') and where (Configuration 5'-2)
R$^{1'}$ represents chlorine, bromine, methyl, benzyl, 2-chlorobenzyl, 3-chlorobenzyl or 4-chlorobenzyl,
R$^{2'}$ represents hydrogen, cyano, chlorine, bromine or iodine,
R$^{3'}$ represents chlorine, methyl, isopropyl or ethyl,
R$^{4'}$ represents hydrogen, chlorine, bromine or iodine,
R$^{5'}$ represents methyl,
R$^{6'}$ represents hydrogen or chlorine,
A' represents a radical selected from the radicals of the formulae (III1-III18):

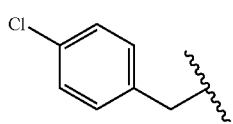 (III4)
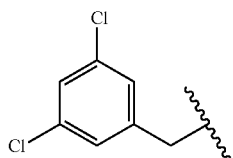 (III5)
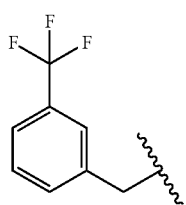 (III6)
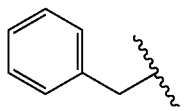 (III7)
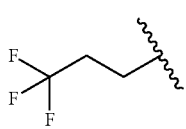 (III8)
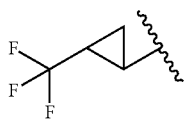 (III9)
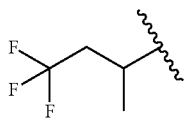 (III10)
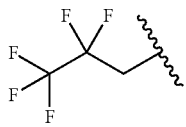 (III11)
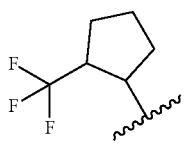 (III12)
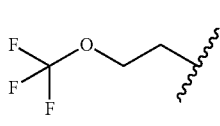 (III13)
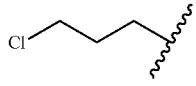 (III14)
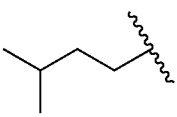 (III15)
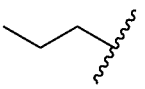 (III16)
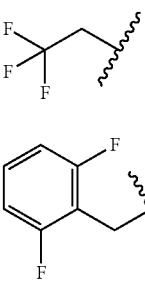 (III17)
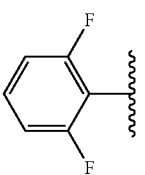 (III18),
Q' represents a radical selected from the radicals of the formulae (IV1-IV36):
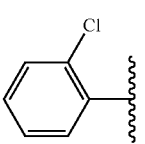 (IV1)
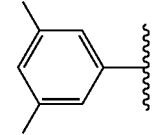 (IV2)
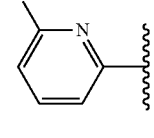 (IV3)
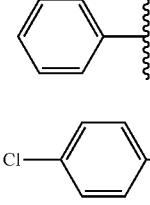 (IV4)
(IV5)
(IV6)

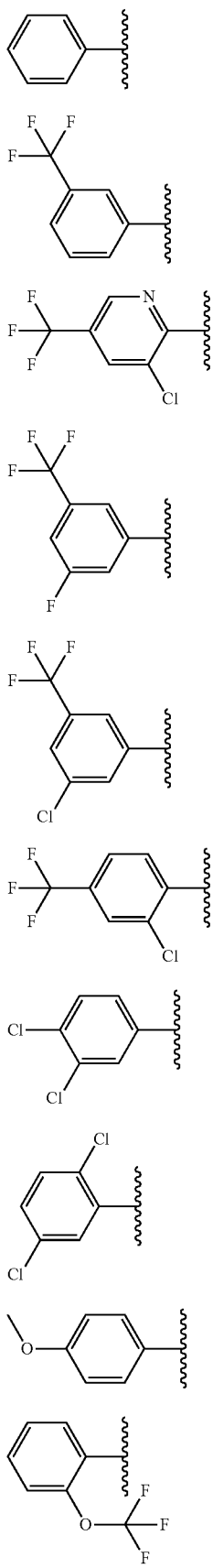
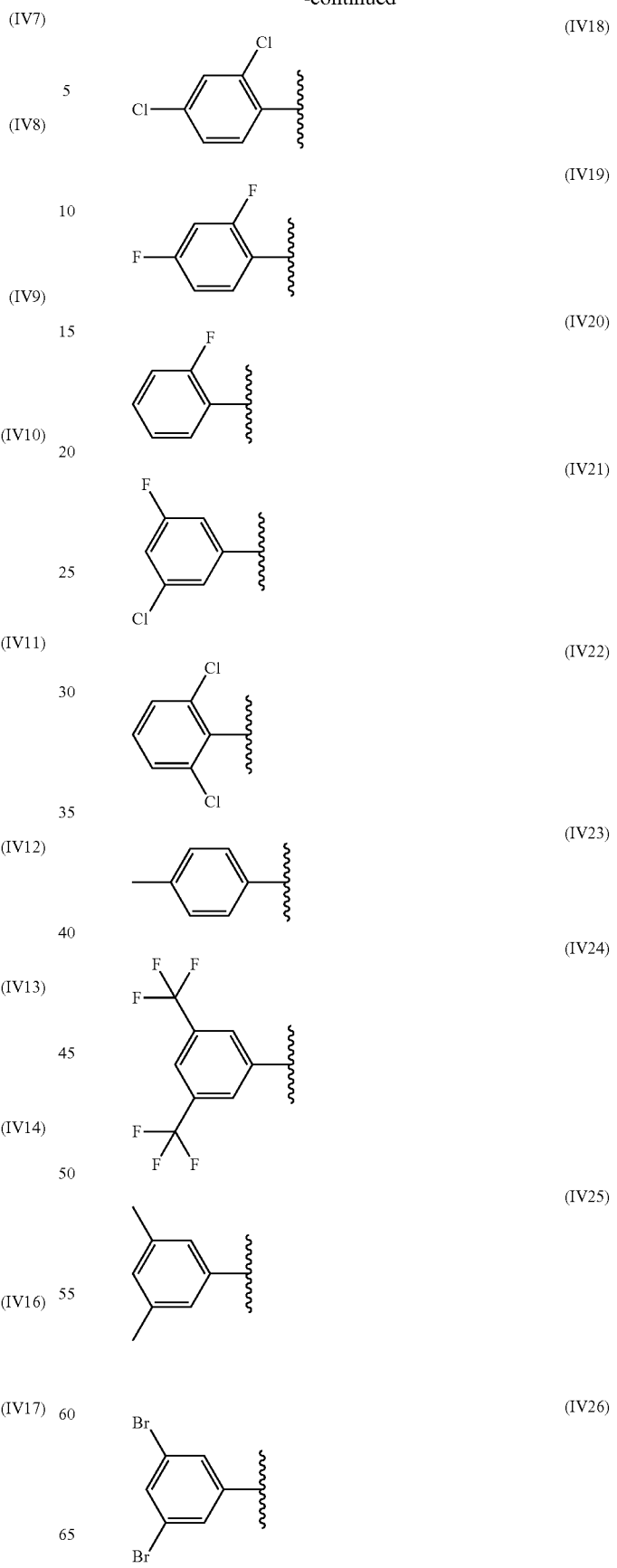

-continued
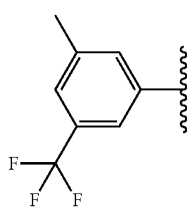 (IV27)
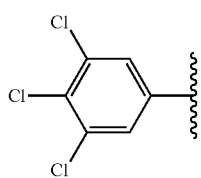 (IV28)
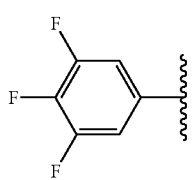 (IV29)
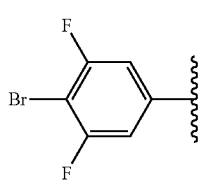 (IV30)
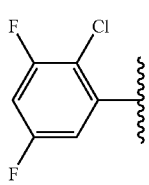 (IV31)
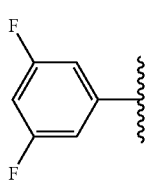 (IV32)
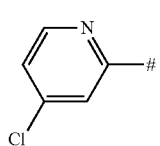 (IV33)
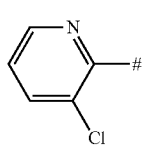 (IV34)
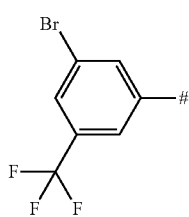 (IV35)
-continued
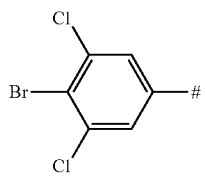 (IV36)
and
D' represents a radical selected from the radicals of the formulae (V1-V57):
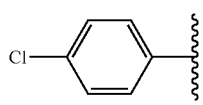 (V1)
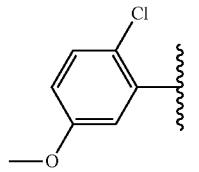 (V2)
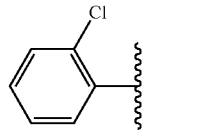 (V3)
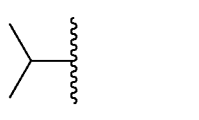 (V4)
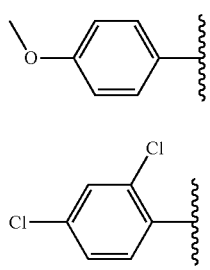 (V5)
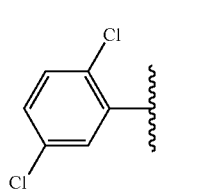 (V6)
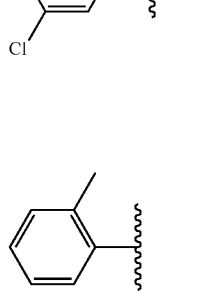 (V7)
(V8)

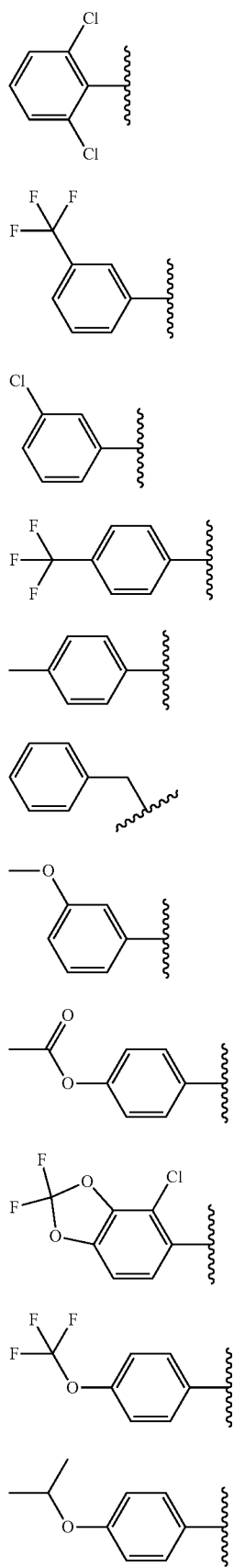
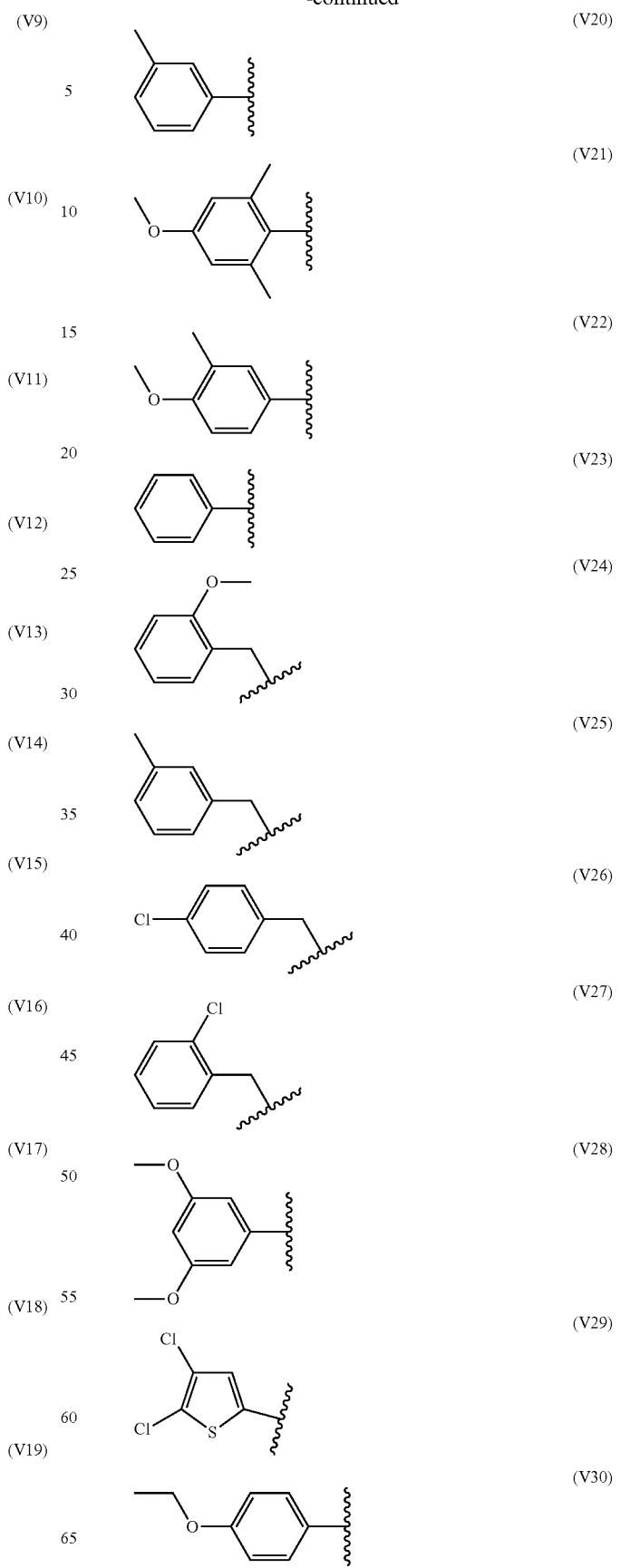

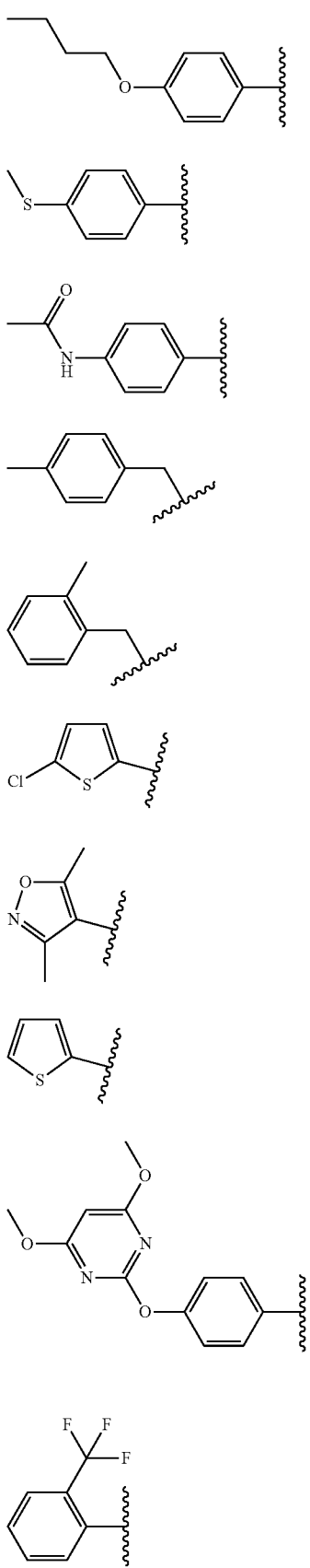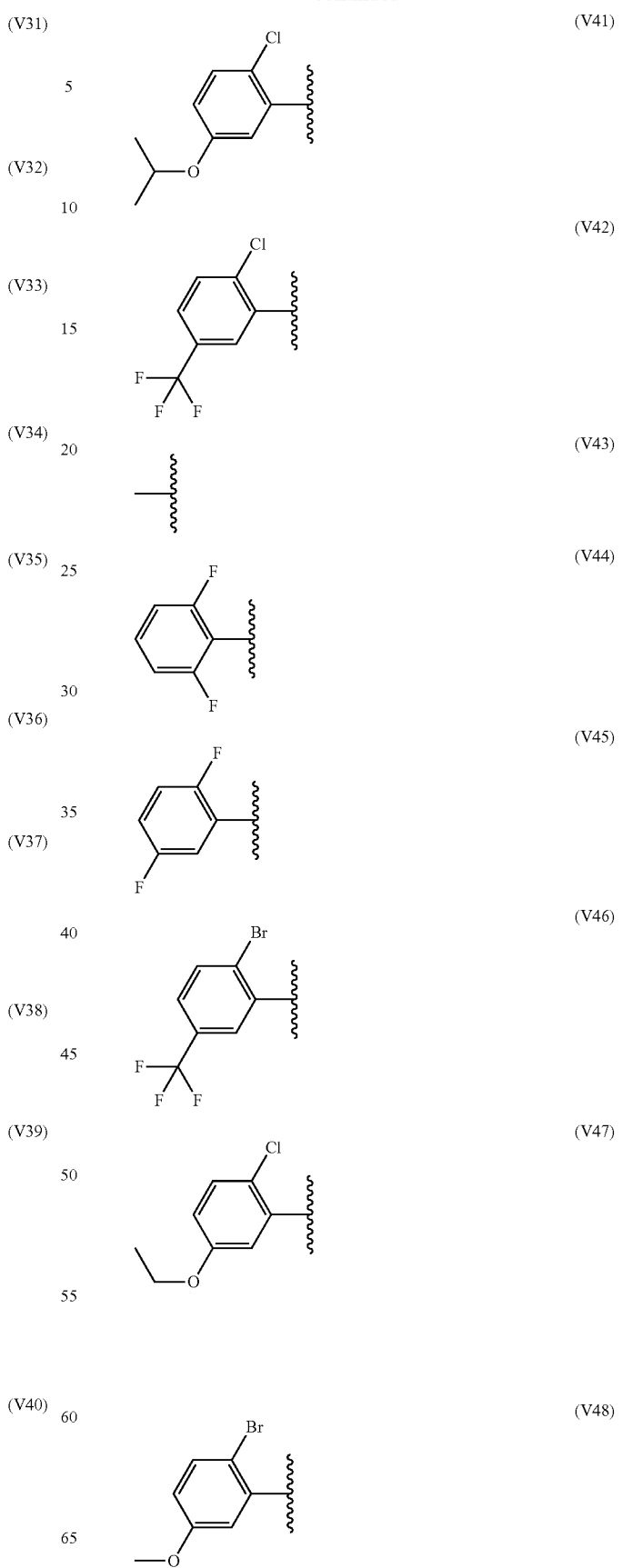

-continued (V49) 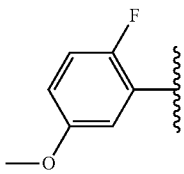

(V50) 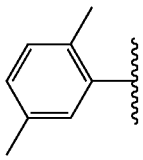

(V51) 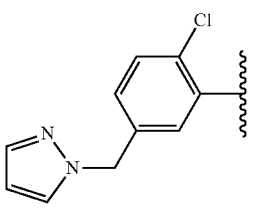

(V52) 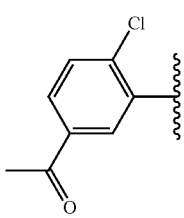

(V53) 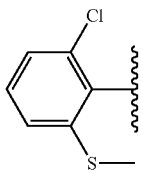

(V54) 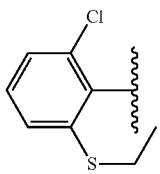

(V55) 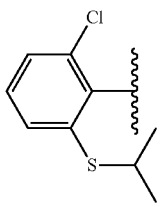

(V56) 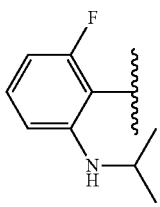

-continued (V57) 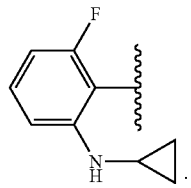

Hereinbelow, Configuration (x') is equivalent to Configuration (x'-1) or (x'-2) with x'=1', 2', 3', 4' or 5'.

In a preferred embodiment of the invention, M' in formulae (I') represents a radical selected from the formulae IIa' or IIb', where the radicals $R^{1'}$, $R^{2'}$, A', $R^{3'}$, $R^{4'}$, $R^{7'}$, $R^{8'}$, Q' and D' have the meanings described in Configuration (1') or Configuration (2') or Configuration (3') or Configuration (4') or Configuration (5').

In a further preferred embodiment, the invention relates to compounds of the formula (I') where M', $R^{1'}$, $R^{2'}$, $R^{3'}$, $R^{4'}$, $R^{5'}$, $R^{6'}$, $R^{7'}$, $R^{8'}$, Q' and D' have the meanings described above, in particular the meanings described in Configuration (2') or Configuration (3') or Configuration (4') or Configuration (5') and A' has the meanings described in Configuration (1').

In a further preferred embodiment, the invention relates to compounds of the formula (I') where M', R1', R2', R3', R4', R5', R6', R7', R8', Q' and D' have the meanings described above, in particular the meanings described in Configuration (1') or Configuration (3') or Configuration (4') or Configuration (5') and A' has the meanings described in Configuration (2').

In a further preferred embodiment, the invention relates to compounds of the formula (I') where M', R1', R2', R3', R4', R5', R6', R7', R8', Q' and D' have the meanings described above, in particular the meanings described in Configuration (1') or Configuration (2') or Configuration (4') or Configuration (5') and A' has the meanings described in Configuration (3').

In a further preferred embodiment, the invention relates to compounds of the formula (I') where M', R1', R2', R3', R4', R5', R6', R7', R8', Q' and D' have the meanings described above, in particular the meanings described in Configuration (1') or Configuration (2') or Configuration (3') or Configuration (5') and A' has the meanings described in Configuration (4').

In a further preferred embodiment, the invention relates to compounds of the formula (I') where M', R1', R2', R3', R4', R5', R6', R7', R8', Q' and D' have the meanings described above, in particular the meanings described in Configuration (1') or Configuration (2') or Configuration (3') or Configuration (4') and A' has the meanings described in Configuration (5').

In a further preferred embodiment, the invention relates to compounds of the formula (I') where M', $R^{1'}$, $R^{2'}$, $R^{3'}$, $R^{4'}$, $R^{5'}$, $R^{6'}$, $R^{8'}$, A' and D' have the meanings described above, in particular the meanings described in Configuration (2') or Configuration (3') or Configuration (4') or Configuration (5') and Q' and $R^{7'}$ have the meanings described in Configuration (1').

In a further preferred embodiment, the invention relates to compounds of the formula (I') where M', $R^{1'}$, $R^{2'}$, $R^{3'}$, $R^{4'}$, $R^{5'}$, $R^{6'}$, $R^{8'}$, A' and D' have the meanings described above, in particular the meanings described in Configuration (1') or Configuration (3') or Configuration (4') or Configuration (5') and Q' and $R^{7'}$ have the meanings described in Configuration (2').

In a further preferred embodiment, the invention relates to compounds of the formula (I') where M', $R^{1'}$, $R^{2'}$, $R^{3'}$, $R^{4'}$, $R^{5'}$, $R^{6'}$, $R^{8'}$, A' and D' have the meanings described above, in particular the meanings described in Configuration (1') or Configuration (2') or Configuration (4') or Configuration (5') and Q' and $R^{7'}$ have the meanings described in Configuration (3').

In a further preferred embodiment, the invention relates to compounds of the formula (I') where M', $R^{1'}$, $R^{2'}$, $R^{3'}$, $R^{4'}$, $R^{5'}$, $R^{6'}$, $R^{8'}$, A' and D' have the meanings described above, in particular the meanings described in Configuration (1') or Configuration (2') or Configuration (3') or Configuration (5') and Q' and $R^{7'}$ have the meanings described in Configuration (4').

In a further preferred embodiment, the invention relates to compounds of the formula (I') where M', $R^{1'}$, $R^{2'}$, $R^{3'}$, $R^{4'}$, $R^{5'}$, $R^{6'}$, $R^{8'}$, A' and D' have the meanings described above, in particular the meanings described in Configuration (1') or Configuration (2') or Configuration (3') or Configuration (4') and Q' and $R^{7'}$ have the meanings described in Configuration (5').

In a further preferred embodiment, the invention relates to compounds of the formula (I') where M', $R^{1'}$, $R^{2'}$, $R^{3'}$, $R^{4'}$, $R^{5'}$, $R^{6'}$, $R^{7'}$, A' and Q' have the meanings described above, in particular the meanings described in Configuration (2') or Configuration (3') or Configuration (4') or Configuration (5') and D' and $R^{8'}$ have the meanings described in Configuration (1').

In a further preferred embodiment, the invention relates to compounds of the formula (I') where M', $R^{1'}$, $R^{2'}$, $R^{3'}$, $R^{4'}$, $R^{5'}$, $R^{6'}$, $R^{7'}$, A' and Q' have the meanings described above, in particular the meanings described in Configuration (1') or Configuration (3') or Configuration (4') or Configuration (5') and D' and $R^{8'}$ have the meanings described in Configuration (2').

In a further preferred embodiment, the invention relates to compounds of the formula (I') where M', $R^{1'}$, $R^{2'}$, $R^{3'}$, $R^{4'}$, $R^{5'}$, $R^{6'}$, $R^{7'}$, A' and Q' have the meanings described above, in particular the meanings described in Configuration (1') or Configuration (2') or Configuration (4') or Configuration (5') and D' and $R^{8'}$ have the meanings described in Configuration (3').

In a further preferred embodiment, the invention relates to compounds of the formula (I') where M', $R^{1'}$, $R^{2'}$, $R^{3'}$, $R^{4'}$, $R^{5'}$, $R^{6'}$, $R^{7'}$, A' and Q' have the meanings described above, in particular the meanings described in Configuration (1') or Configuration (2') or Configuration (3') or Configuration (5') and D' and $R^{8'}$ have the meanings described in Configuration (4').

In a further preferred embodiment, the invention relates to compounds of the formula (I') where M', $R^{1'}$, $R^{2'}$, $R^{3'}$, $R^{4'}$, $R^{5'}$, $R^{6'}$, $R^{7'}$, A' and Q' have the meanings described above, in particular the meanings described in Configuration (1') or Configuration (2') or Configuration (3') or Configuration (4') and D' and $R^{8'}$ have the meanings described in Configuration (5').

In a further preferred embodiment, the invention relates to the use of compounds of the formula (I') where M', $R^{1'}$, $R^{2'}$, $R^{3'}$, $R^{4'}$, $R^{5'}$, $R^{6'}$, $R^{7'}$, $R^{8'}$, Q' and A' have the meanings described above, in particular the meanings described in Configuration (1') or Configuration (2') or Configuration (3') or Configuration (4') or Configuration (5') and D' represents a phenyl radical which is unsubstituted or mono- or disubstituted by $R^{8'}$.

In a further preferred embodiment, the invention relates to the use of compounds of the formula (I') where M', $R^{1'}$, $R^{2'}$, $R^{3'}$, $R^{4'}$, $R^{5'}$, $R^{6'}$, $R^{7'}$, $R^{8'}$, Q' and A' have the meanings described above, in particular the meanings described in Configuration (1') or Configuration (2') or Configuration (3') or Configuration (4') or Configuration (5') and D' represents a phenyl radical which is mono- or disubstituted by $R^{8'}$. In a further preferred embodiment, the invention relates to the use of compounds of the formula (I') where M', $R^{1'}$, $R^{2'}$, $R^{3'}$, $R^{4'}$, $R^{5'}$, $R^{6'}$, $R^{7'}$, $R^{8'}$, Q' and A' have the meanings described above, in particular the meanings described in Configuration (1') or Configuration (2') or Configuration (3') or Configuration (4') or Configuration (5') and D' represents a phenyl radical which is unsubstituted or mono- or disubstituted by $R^{8'}$, where $R^{8'}$ is selected from halogen, $(C_1$-$C_4)$-alkyl, $(C_1$-$C_4)$-alkoxy, $(C_1$-$C_4)$-haloalkyl and $(C_1$-$C_4)$-alkylthio, particularly preferably from fluorine, bromine, chlorine, methyl, trifluoromethyl, methoxy, ethoxy, isopropoxy and methylthio.

In a further preferred embodiment, the invention relates to the use of compounds of the formula (I') where M', $R^{1'}$, $R^{2'}$, $R^{3'}$, $R^{4'}$, $R^{5'}$, $R^{6'}$, $R^{7'}$, $R^{8'}$, Q' and A' have the meanings described above, in particular the meanings described in Configuration (1') or Configuration (2') or Configuration (3') or Configuration (4') or Configuration (5') and D' represents a phenyl radical which is mono- or disubstituted by $R^{8'}$, where $R^{8'}$ is selected from halogen, $(C_1$-$C_4)$-alkyl, $(C_1$-$C_4)$-alkoxy, $(C_1$-$C_4)$-haloalkyl and $(C_1$-$C_4)$-alkylthio, particularly preferably from fluorine, bromine, chlorine, methyl, trifluoromethyl, methoxy, ethoxy, isopropoxy and methylthio.

Preference is furthermore given to compounds of the formulae (Ia') or (Ib') or (Ic'), particularly preferably (Ia') or (Ib'),

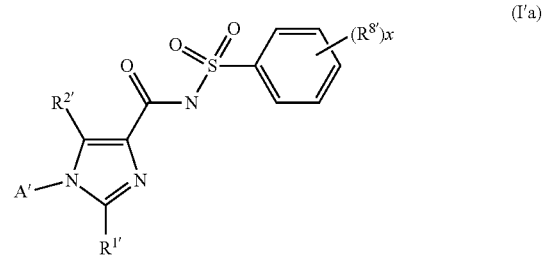

(I'a)

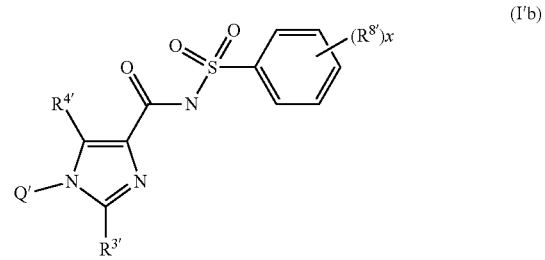

(I'b)

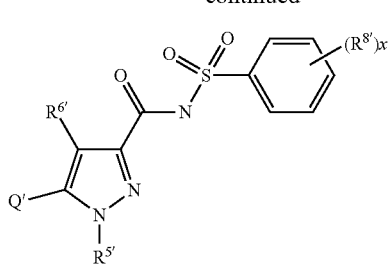

(I'c)

where $R^{1'}$, $R^{2'}$, $R^{3'}$, $R^{4'}$, $R^{5'}$, $R^{6'}$, $R^{7'}$, A', Q' and $R^{8'}$ have the meanings described above, in particular the meanings described in Configuration (1') or Configuration (2') or Configuration (3') or Configuration (4') or Configuration (5'),
and x represents 1 or 2.

Particular preference is given to compounds of the formula (Ia') in which:
A' represents $(C_1-C_4)$-haloalkyl or $(C_1-C_4)$-haloalkylcyclopropyl, preferably $(C_1-C_4)$-fluoroalkyl or $(C_1-C_4)$-fluoroalkylcyclopropyl, very particularly preferably 3,3,3-trifluoropropyl or 2-trifluoromethylcyclopropyl,
x represents 1 or 2 and
$R^{1'}$, $R^{2'}$ and $R^{8'}$ have the meanings described above, in particular the meanings described in Configuration (1') or Configuration (2') or Configuration (3') or Configuration (4') or Configuration (5').

Particular preference is furthermore given to compounds of the formula (Ia') in which:
$R^{1'}$ represents halogen, particularly preferably chlorine or bromine,
$R^{2'}$ represents halogen, particularly preferably chlorine, bromine or iodine,
x represents 1 or 2 and
A' and $R^{8'}$ have the meanings described above, in particular the meanings described in Configuration (1') or Configuration (2') or Configuration (3') or Configuration (4') or Configuration (5').

Particular preference is given to compounds of the formula (Ib') in which:
Q' represents a phenyl radical which is unsubstituted or mono- or disubstituted by $R^{7'}$, where
$R^{7'}$ is selected from halogen, $(C_1-C_4)$-alkyl, $(C_1-C_4)$-alkoxy and $(C_1-C_4)$-haloalkyl, particularly preferably from fluorine, bromine, chlorine and trifluoromethyl,
x represents 1 or 2 and
$R^{3'}$, $R^{4'}$ and $R^{8'}$ have the meanings described above, in particular the meanings described in Configuration (1') or Configuration (2') or Configuration (3') or Configuration (4') or Configuration (5').

Particular preference is furthermore given to compounds of the formula (Ib') in which:
Q' represents a phenyl radical which is unsubstituted or mono- or disubstituted by $R^{7'}$,
x represents 1 or 2 and
$R^{3'}$, $R^{4'}$, $R^{7'}$ and $R^{8'}$ have the meanings described above, in particular the meanings described in Configuration (1') or Configuration (2') or Configuration (3') or Configuration (4') or Configuration (5').

Particular preference is furthermore given to compounds of the formula (Ib') in which:
$R^{3'}$ represents hydrogen, halogen or $(C_1-C_4)$-alkyl, particularly preferably hydrogen, chlorine, methyl, isopropyl or ethyl,
$R^{4'}$ represents hydrogen or halogen, particularly preferably hydrogen, chlorine, bromine or iodine,
x represents 0, 1 or 2 and
Q' and $R^{8'}$ have the meanings described above, in particular the meanings described in Configuration (1') or Configuration (2') or Configuration (3') or Configuration (4') or Configuration (5').

Particular preference is given to compounds of the formula (Ic') in which:
Q' represents a phenyl radical which is unsubstituted or mono- or disubstituted by $R^{7'}$, where
$R^{7'}$ is selected from halogen, $(C_1-C_4)$-alkyl, $(C_1-C_4)$-alkoxy and $(C_1-C_4)$-haloalkyl, particularly preferably from fluorine, bromine, chlorine and trifluoromethyl,
x represents 1 or 2 and
$R^{5'}$, $R^{6'}$ and $R^{8'}$ have the meanings described above, in particular the meanings described in Configuration (1') or Configuration (2') or Configuration (3') or Configuration (4') or Configuration (5').

Particular preference is furthermore given to compounds of the formula (Ic') in which:
Q represents a phenyl radical which is unsubstituted or mono- or disubstituted by $R^{7'}$,
x represents 1 or 2 and
$R^{3'}$, $R^{4'}$, $R^{7'}$ and $R^{8'}$ have the meanings described above, in particular the meanings described in Configuration (1') or Configuration (2') or Configuration (3') or Configuration (4') or Configuration (5').

Particular preference is furthermore given to compounds of the formula (Ic') in which:
$R^{5'}$ represents $(C_1-C_4)$-alkyl, particularly preferably methyl,
$R^{6'}$ represents hydrogen or halogen, particularly preferably hydrogen or chlorine,
x represents 1 or 2 and
Q' and $R^{8'}$ have the meanings described above, in particular the meanings described in Configuration (1') or Configuration (2') or Configuration (3') or Configuration (4') or Configuration (5').

Hereinbelow, the term formula (I') also comprises the specific embodiments formula (Ia'), formula (Ib') and formula (Ic').

In a further preferred embodiment, the invention relates to compounds of the formula (I') where M', $R^{2'}$, $R^{3'}$, $R^{4'}$, $R^{5'}$, $R^{6'}$, $R^{7'}$, A', Q', D' and $R^{8'}$ have the meanings described above, in particular the meanings described in Configuration (1') or Configuration (2') or Configuration (3') or Configuration (4') or Configuration (5') and
$R^{1'}$ represents hydroxy, cyano, carboxyl, halogen, nitro, $(C_3-C_5)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_5)$-cycloalkyl, halo-$(C_3-C_5)$-cycloalkyl, methyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyloxy, $(C_1-C_6)$- alkylcarbonyl, $(C_1-C_6)$-alkylthiocarbonyl, $(C_1-C_6)$-alkylsulfoximino, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl-$(C_2-C_6)$-alkyl or hetaryl-$(C_1-C_6)$-alkyl which is optionally monosubstituted or polysubstituted by identical or different substituents, where, in the case of hetaryl, optionally at least one carbonyl group may be present and where the substituent(s) in each case independently of one another are selected from:
cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino and/or $(C_1-C_6)$-alkylcarbonylamino.

In a further preferred embodiment, the invention relates to compounds of the formula (I') where M', $R^{2'}$, $R^{3'}$, $R^{4'}$, $R^{5'}$, $R^{6'}$, $R^{7'}$, A', Q', D' and $R^{8'}$ have the meanings described above, in particular the meanings described in Configuration (1') or Configuration (2') or Configuration (3') or Configuration (4') or Configuration (5') and $R^{1'}$ represents cyano, halogen, nitro, $(C_3-C_5)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_5)$-cycloalkyl, halo-$(C_3-C_5)$-cycloalkyl, methyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkoxycarbonyl, $(C_1-C_6)$-haloalkoxycarbonyl, $(C_1-C_6)$-alkylaminocarbonyl or $(C_1-C_6)$-alkylcarbonylamino).

In a further preferred embodiment, the invention relates to compounds of the formula (I') where M', $R^{2'}$, $R^{3'}$, $R^{4'}$, $R^{5'}$, $R^{6'}$, $R^{7'}$, A', Q', D' and $R^{8'}$ have the meanings described above, in particular the meanings described in Configuration (1') or Configuration (2') or Configuration (3') or Configuration (4') or Configuration (5'), and $R^{1'}$ represents cyano, halogen, cyclopropyl, methyl, halocyclopropyl, halo-$(C_1-C_3)$-alkylcyclopropyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylthio-$(C_1-C_4)$-alkyl, $(C_1-C_4)$-alkylsulfinyl-$(C_1-C_4)$-alkyl or $(C_1-C_4)$-alkylsulfonyl-$(C_1-C_4)$-alkyl.

In a further preferred embodiment, the invention relates to compounds of the formula (I') where M', $R^{2'}$, $R^{3'}$, $R^{4'}$, $R^{5'}$, $R^{6'}$, $R^{7'}$, A', Q', D' and $R^{8'}$ have the meanings described above, in particular the meanings described in Configuration (1') or Configuration (2') or Configuration (3') or Configuration (4') or Configuration (5') and $R^{1'}$ represents halogen, cyclopropyl, methyl, $(C_1-C_4)$-alkylthio, halocyclopropyl or $(C_1-C_4)$-haloalkyl.

In a further preferred embodiment, the invention relates to compounds of the formula (I') where M', $R^{2'}$, $R^{3'}$, $R^{4'}$, $R^{5'}$, $R^{6'}$, $R^{7'}$, A', Q', D' and $R^{8'}$ have the meanings described above, in particular the meanings described in Configuration (1') or Configuration (2') or Configuration (3') or Configuration (4') or Configuration (5') and $R^{1'}$ represents chlorine, bromine, methyl, trifluoromethyl, methylthio or isopropylthio.

Hereinbelow, formula (I) is equivalent to formula (I) or (I').

By definition, unless stated otherwise, halogen is selected from the group of fluorine, chlorine, bromine and iodine, preferably in turn from the group of fluorine, chlorine and bromine.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1-C_{12}$alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl.

According to the invention, unless defined differently elsewhere, the term "alkenyl", either on its own or else in combination with further terms, is understood to mean a straight-chain or branched $C_2-C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl.

According to the invention, unless defined differently elsewhere, the term "alkynyl", either on its own or else in combination with further terms, is understood to mean a straight-chain or branched $C_2-C_{12}$-alkynyl radical which has at least one triple bond, for example ethynyl, 1-propynyl and propargyl. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl.

The term "alkoxy", either on its own or else in combination with further terms, for example haloalkoxy, is understood in the present case to mean an O-alkyl radical, where the term "alkyl" is as defined above.

According to the invention, unless defined differently elsewhere, the term "aryl" is understood to mean a mono-, bi- or tricyclic radical having 6 to 14 carbon atoms, where at least one cycle is aromatic, preferably phenyl, naphthyl, anthryl or phenanthrenyl, more preferably phenyl.

Unless defined differently elsewhere, the term "arylalkyl" is understood to mean a combination of the radicals "aryl" and "alkyl" defined according to the invention, where the radical is generally attached via the alkyl group. Examples of these are benzyl, phenylethyl or □-methylbenzyl, benzyl being particularly preferred.

Unless defined differently elsewhere, "hetaryl" denotes a mono-, bi- or tricyclic heterocyclic group of carbon atoms and at least one heteroatom, where at least one cycle is aromatic. Preferably, the hetaryl group contains 3, 4, 5, 6, 7 or 8 carbon atoms selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl, imidazopyridinyl and indolizinyl.

Halogen-substituted radicals, for example haloalkyl, are mono- or polyhalogenated, up to the maximum number of possible substituents. In the case of polyhalogenation, the halogen atoms may be identical or different. Unless stated otherwise, optionally substituted radicals may be mono- or polysubstituted, where the substituents in the case of polysubstitutions may be the same or different.

Description of the Processes and Intermediates

By way of example and supplementarily, the preparation of compounds of the formula (I) or (I') is illus-trated in the formula schemes below. Here, reference is also made to the preparation examples.

All statements made hereinbelow for formula (I) also apply analogously to formula (I'). Hereinbelow, all radicals specified, such as, for example, M, D, Q etc., also represent the respective' variant, i.e., for example, M', D', Q' etc.

Formula Scheme 1

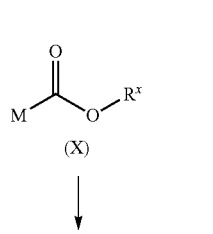

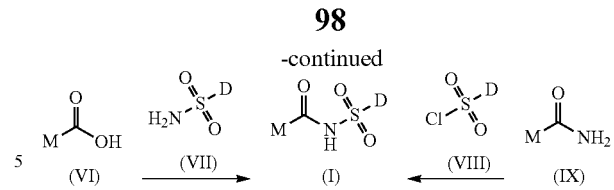

According to formula scheme 1, the compounds of the formula (I) according to the invention are prepared in general terms from carboxylic acids of the formula (VI) by reaction with a coupling agent and sulfonamides of the formula (VII), see, for example, WO2012/80447, WO2006/114313, WO2015/11082, WO2010/129500, US2008/227769 and WO2009/67108. Alternatively, the compounds of the formula (I) can also be prepared by reacting a carboxamide of the formula (IX) with a sulfonyl chloride of the formula (VIII) in the presence of a base such as, for example, sodium hydride, see, for example, US2004/6143. The required amides of the formula (IX) can be obtained from the acids of the formula (VI), for example by reaction with a coupling agent and ammonium acetate, see, for example, U.S. Pat. No. 5,300,498.

The required sulfonamides and sulfonyl chlorides of the formulae (VII) and (VIII) are known or can be prepared by generally known methods. Here, the sulfonamides can be obtained from the sulfonyl chlorides by reaction with ammonia, see WO2014/146490, Eur. J. Med. Chem. 2013, 62, 597-604; Bioorg. Med. Chem. 2005, 13, 7, 2459-2468.

Further examples are:
3-chlorobenzenesulfonamide: Coll. Czech. Chem. Comm. 1984, 49, 5, 1182-1192
2-chlorobenzenesulfonyl chloride: U.S. Pat. No. 5,099,025
2-chloro-5-methoxybenzenesulfonamide: WO2010/129500
isopropylsulfonamide: US542803

The required carboxylic acids of the formula (VI) are obtained by hydrolysis from the esters of the formula (X). The hydrolysis of the esters of the formula (X) to the acids of the formula (VI) is carried out according to generally known conditions (LiOH, $H_2O$, THF or NaOH, EtOH).

For the esters of the formula (X), $R^x$ may be, for example, alkyl (including cyclic).

The preparation of the compounds of the formula (I) according to the invention in which $R^1$, $R^2$, $R^3$, $R^4$, $R^6$ independently of one another represent halogen can be obtained either according to formula scheme 2 by reaction of suitable compounds of the formula (I) in which accordingly $R^1$, $R^2$, $R^3$, $R^4$, $R^6$ represent hydrogen with a halogenating agent such as N-bromosuccinimide or bromine or 1-chloromethyl-4-fluoro-1,4-diazoniabicyclo[2.2.2]octane bis(tetrafluoroborate) in a solvent such as acetonitrile.

Formula Scheme 2

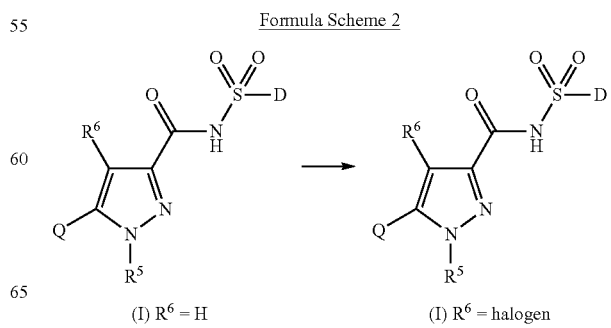

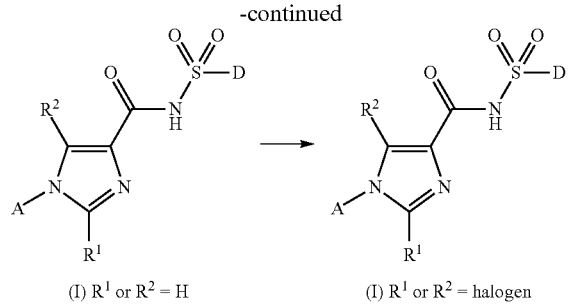

(I) R¹ or R² = H   (I) R¹ or R² = halogen

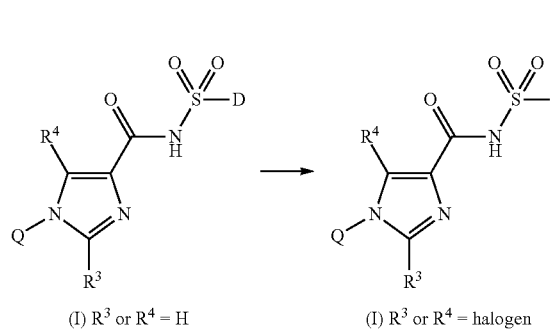

(I) R³ or R⁴ = H   (I) R³ or R⁴ = halogen

Alternatively, the introduction of halogen at the positions mentioned may also take place prior to the coupling described in Formula Scheme 1 at an appropriate intermediate such as, for example, the ester (X) analogously to the reaction described in Formula Scheme 2, see, for example, WO2014/191894 A1, page 63.

The esters of the formula (X) and the corresponding acids of the formula (VI) are known or can be prepared by generally known processes or according to the processes described below.

Examples of esters of the formula (X) and corresponding acids of the formula (VI) and their preparation processes are:

for 1-benzyl-1H-imidazole-4-carboxylic acud see WO 2014125444 A1, Tetrahedron 2004, vol 60, #29, 6079 for 1-(3-chlorobenzyl)-1H-imidazole-4-carboxylic acid and 1-[3-(trifluoromethyl)benzyl]-1H-imidazole-4-carboxylic acid se. Bioorganic and Medicinal Chemistry Letters, 2011, vol. 21, #6 pp. 1621-162 for 1-(3-chlorophenyl)-1H-imidazole-4-carboxylic acid and 1-[3-(trifluoromethyl)phenyl]-1H-imidazole-4-carboxylic acid see U.S. Pat. No. 4,952,698 A1 for 1-(4-chlorophenyl)-1H-imidazole-4-carboxylic acid see US2002/151715 A1, for 1-phenyl-1H-imidazole-4-carboxylic acid see US2009/239810 A1 for 2-methyl-1-phenyl-1H-imidazole-4-carboxylic acid see Bioorganic and Medicinal Chemistry Letters, 2010, vol. 20, #3 pp. 1084-1089 for ethyl 1-benzyl-1H-imidazole-4-carboxylate see Organic Letters, 2002, vol. 4, #23 pp. 4133-4134 and WO2015/96884 A1 and U.S. Pat. No. 5,089,499 A1 and Chemical and Pharmaceutical Bulletin, 2006, vol. 54, #5 pp. 706-710.

for 5-(2,6-difluorophenyl)-1-methyl-1H-pyrazole-3-carboxylic acid see WO2014/108336 A1, page 58.

A preparation process for esters of the formula (X) is described in Formula Scheme 3.

Formula Scheme 3

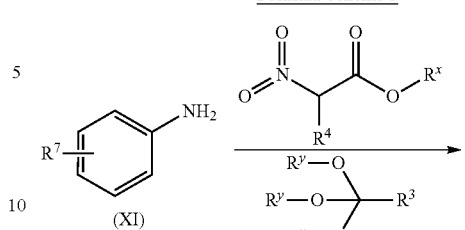

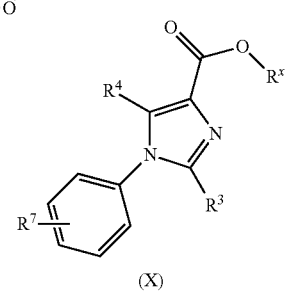

The reaction of an aromatic amine of the formula (XI) with nitroacetic esters and an orthoester in acetic acid with a reducing agent such as iron according to, for example, US2005/256113A1 page 20 or U.S. Pat. No. 6,642,237 B1 page 115 leads to a suitable ester of the formula (X).

Alternatively, according to Formula Scheme 4, the esters of the formula (X) can be obtained by reacting the enamine of the formula (XII) during transition metal-catalysed hydrogenation, for example according to WO2013/22818 A1 paragraph 00400 or Bioorganic and Medicinal Chemistry Letters, 2010, vol. 20, #3 pp. 1084-1089 or Bioorganic and Medicinal Chemistry Letters, 2011, vol. 21, #21 pp. 6515-6518, or under reducing conditions according to WO2015/110369 A1 page 31.

Formula Scheme 4

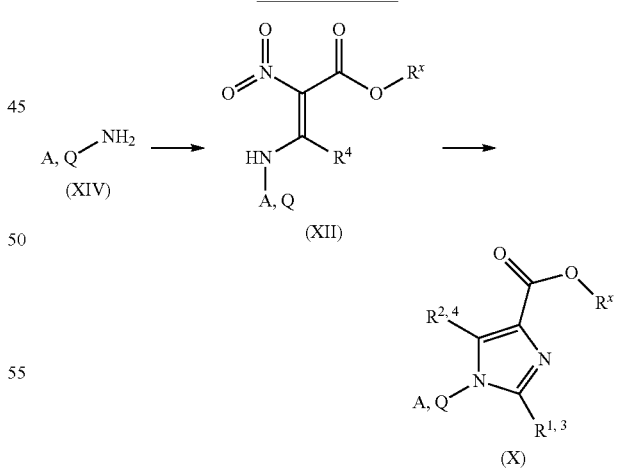

For their part, the enamines of the formula (XII) are obtained from the amines of the formula (XIV) in a manner similar to Formula Scheme 3 according to Chemische Berichte, 1977, vol. 110, pp. 2480-2493 or WO2013/22818 A1 paragraph 00372, or by direct reaction with a nitroacetic acid enol ether according to WO2015/110369 A1, page 32 or WO2013/22818 A1 paragraph 00372. For their part, the nitroacetic acid enol ethers are prepared, for example, according to WO2013/40790 page 100.

Furthermore, esters of the formula (X) can be obtained by reacting a suitable imidazole of the formula (XIII), this takes place according to Formula Scheme 5 and, for example, according to US2012/94837 A1 page 35, Molecules, 2013, vol. 18, #11 pp. 13385-13397, WO2010/3626 A1, page 133, WO2013/22818 A1 paragraph 00341, US2006/194779 A1 page 13, US2016/185785 A1 paragraph 2173, WO2006/135627 A2 page 140, WO2005/9965 A1 page 49, WO2012/143599 A1 page 46.

Formula Scheme 5:

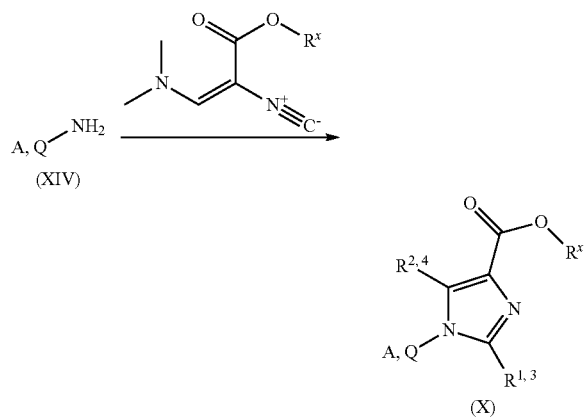

A further preparation route to esters of the formula (X) is described in Formula Scheme 6.

Formula Scheme 6:

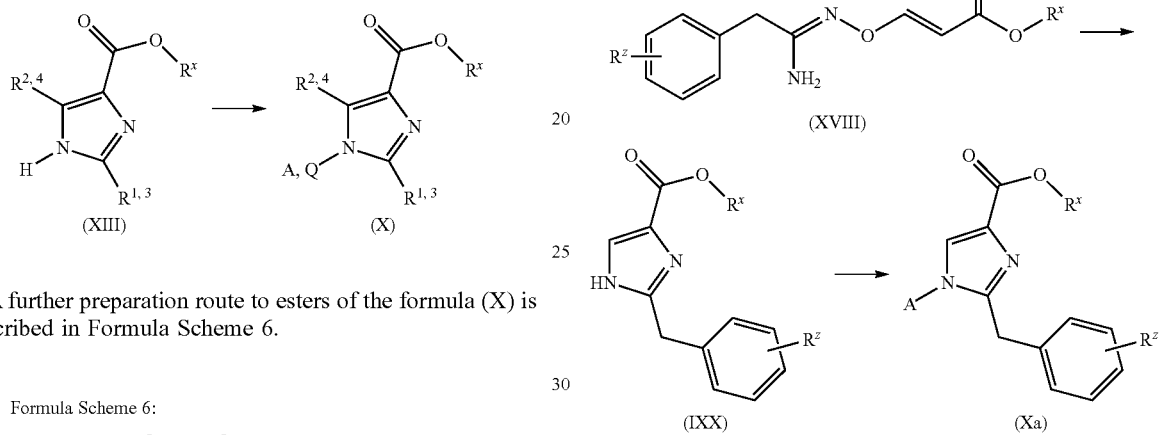

The reaction of amines of the formula (XIV) with isonitriles of the formula (XV), for example according to WO2014/115077 A1 page 60, US2012/35168 A1 page 30, EP2548871 A1 Paragraph 0264, WO2014/191894 A1 page 62, WO2007/42546 A1 page 25, WO2015/96884 A1 page 39, Organic Letters, 2002, vol. 4, #23 pp. 4133-4134, WO2007/42545 A1 page 19, Bioorganic and Medicinal Chemistry Letters, 2011, vol. 21, #6 pp. 1621-1625, leads to the esters of the formula (X).

The required isonitriles are known, for example from Chemische Berichte, 1983, vol. 116, #9 pp. 3205-3211, WO2015/96884 A page 38 and WO2014/115077 A1 page 64.

The esters of the formula (Xa) where $R^1/R^3$=benzyl, optionally substituted by an appropriate substituent $R^z$, are preferably prepared by the method described in Formula Scheme 7:

Formula Scheme 7:

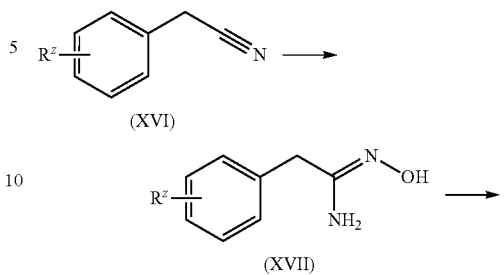

With hydroxylamine, the nitriles of the formula (XVI) give, using for example sodium bicarbonate in methanol/water, the hydroxamic acids of the formula (XVII), see WO2015/140130 A1, page 143 or WO2013/49119 A1 page 39. The reaction with propoxide gives initially, on heating in ethanol, the intermediate of the formula (XVIII) and finally, on heating in a high-boiling solvent such as diphenyl ether, the imidazole of the formula (IXX), see WO2016/44441 A1 page 175 or US2010/22599 A1 page 51 or WO2004/63169 page 137. The imidazole of the formula (IXX) is obtained by reacting the esters of the formula (X) with an alkylating agent, see Journal of the American Chemical Society, 2014, vol. 136, #34 pp. 11914-11917 or US2010/22599 A1, page 51.

Halogen-substituted esters of the formula (X) can be obtained both via the process described in Formula Scheme 2 and via the route described in Formula Scheme 8; moreover, the esters of the formula (X) obtained by Formula Scheme 8 can be reacted further according to Formula Scheme 2; in addition, Formula Scheme 8 describes, in general terms, a further access to esters of the formula (X).

Formula Scheme 8:

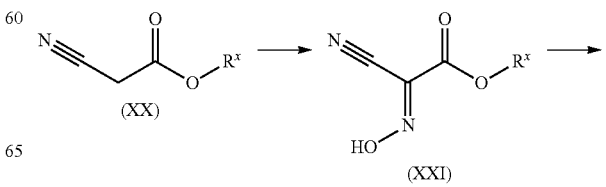

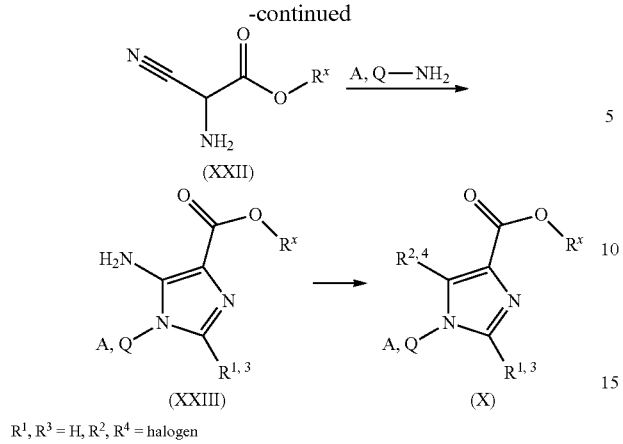

R¹, R³ = H, R², R⁴ = halogen

Cyanoacetic esters (XX) give, by reaction with sodium nitrite, the oxime of the formula (XXI), see, for example, WO2010/140168 page 14. Reduction, for example with sodium dithionite, affords the amine of the formula (XXII), which directly, by reaction with an amine A/Q-N, furnishes the aminoimidazole of the formula (XXIII), see WO2011/79000 A1 page 36 or Journal of Medicinal Chemistry, 1997, vol. 40, #14 pp. 2196-2210 or European Journal of Medicinal Chemistry, 2012, vol. 49, pp. 164-171 or Journal of the Chemical Society, Perkin Transactions 1: Organic and Bio-Organic Chemistry (1972-1999), 1980, pp. 2316-2321. Finally, using the principle of the Sandmeyer reaction, the aminoimidazoles of the formula (XXIII) afford the esters of the formula (X), see, for example, Journal of Medicinal Chemistry, 1991, vol. 34, #3 pp. 1187-1192 or Journal of the Chemical Society, Perkin Transactions 1: Organic and Bio-Organic Chemistry (1972-1999), 1980, pp. 2310-2315.

The pyrazole esters of the formula (X) are obtained by the process described in Formula Scheme 9.

Formula Scheme 9:

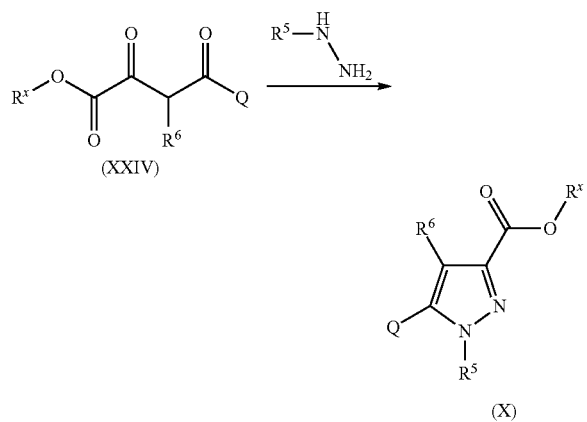

Esters of the formula (X) are prepared starting with an appropriate alkylhydrazine and a diketo ester of the formula (XXIV). This cyclization can by catalysed by base or acid, as described, for example, in US2007/287734 A1, 2007 or U.S. Pat. No. 6,020,357 A1, 2000.

The required diketo esters of the formula (XXIV) are known or can be prepared by generally known methods.

The invention further provides intermediates of the formulae (VIa), (Xa) and (IXa),

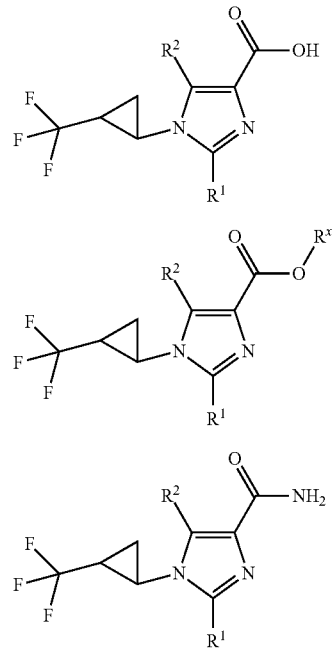

in which R¹ and R² have the meanings mentioned in Configuration 2 or Configuration 3 or Configuration 4 or Configuration 5 and $R^x$ represents $(C_1-C_6)$-alkyl or $(C_3-C_8)$-cycloalkyl.

The intermediates of the formula (VIa), (Xa) or (IXa) may be present as geometric and/or optically active isomers or corresponding isomer mixtures in different compositions. The invention therefore encompasses both pure stereoisomers and any desired mixtures of these isomers.

Salts

The compounds of the formula (I) can also be present as salts, in particular acid addition salts and metal salt complexes. The compounds of the formula (I) and their acid addition salts and metal salt complexes have good efficacy, especially for control of animal pests.

Suitable salts of the compounds of the general formula (I) include customary nontoxic salts, i.e. salts with appropriate bases and salts with added acids. Preference is given to salts with inorganic bases, such as alkali metal salts, for example sodium, potassium or caesium salts, alkaline earth metal salts, for example calcium or magnesium salts, ammonium salts, salts with organic bases and with inorganic amines, for example triethylammonium, dicyclohexylammonium, N,N'-dibenzylethylenediammonium, pyridinium, picolinium or ethanolammonium salts, salts with inorganic acids, for example hydrochlorides, hydrobromides, dihydrosulfates, trihydrosulfates, or phosphates, salts with organic carboxylic acids or organic sulfonic acids, for example formates, acetates, trifluoroacetates, maleates, tartrates, methanesulfonates, benzenesulfonates or para-toluenesulfonates, salts with basic amino acids, for example arginates, aspartates or glutamates, and the like.

Isomers

Depending on the nature of the substituents, the compounds of the formula (I) or (I') may be in the form of geometric and/or optically active isomers or corresponding isomer mixtures in different compositions. These stereoisomers are, for example, enantiomers, diastereomers, atropisomers or geometric isomers. The invention therefore encompasses both pure stereoisomers and any desired mixtures of these isomers.

Methods and Uses

The invention also relates to methods for controlling animal pests, in which compounds of the formula (I) or (I') are allowed to act on animal pests, in particular nematodes, and/or their habitat. The control of the animal pests is preferably carried out in agriculture and forestry, and in material protection. This preferably excludes methods for surgical or therapeutic treatment of the human or animal body and diagnostic methods carried out on the human or animal body.

The invention further relates to the use of the compounds of the formula (I) or (I') as pesticides, especially crop protection compositions.

In the context of the present application, the term "pesticide" in each case also always encompasses the term "crop protection composition".

The compounds of the formula (I) or (I'), having good plant tolerance, favourable endotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, especially nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environ-ment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are carried out on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stables, animal keeping, etc.

The term "hygiene pest" should therefore be understood to mean one or more animal pests whose presence in the hygiene sector is problematic, especially for reasons of health. A main aim is therefore that of avoiding, or limiting to a minimum degree, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of the formula (I) or (I') can preferably be used as pesticides. They are active against normally sensitive and resistant species and also against all or specific stages of development. The abovementioned pests include: pests from the phylum of the Arthropoda, especially from the class of the Arachnida, for example *Acarus* spp., e.g. *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., e.g. *Eotetranychus hicoriae, Epitrimerus pyri, Eutetranychus* spp., e.g. *Eutetranychus banksi, Eriophyes* spp., e.g. *Eriophyes pyri, Glycyphagus domesticus, Halotydeus destructor, Hemitarsonemus* spp., e.g. *Hemitarsonemus latus (=Polyphagotarsonemus latus), Hyalomma* spp., *Ixodes* spp., *Latrodectus* spp., *Loxosceles* spp., *Neutrombicula autumnalis, Nuphersa* spp., *Oligonychus* spp., e.g. *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., e.g. *Panonychus citri (=Metatetranychus citri), Panonychus ulmi (=Metatetranychus ulmi), Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., e.g. *Tarsonemus confusus, Tarsonemus pallidus, Tetranychus* spp., e.g. *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, e.g. *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., e.g. *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agrilus* spp., for example *Agrilus planipennis, Agrilus coxalis, Agrilus bilineatus, Agrilus anxius, Agriotes* spp., for example *Agriotes linneatus, Agriotes mancus, Alphitobius diaperinus, Amphimallon solstitialis, Anobium punctatum, Anoplophora* spp., for example *Anoplophora glabripennis, Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetoc-*

*nema ectypa, Cleonus mendicus, Conoderus* spp., *Cosmopolites* spp., for example *Cosmopolites sordidus, Costelytra zealundica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dendroctonus* spp., for example *Dendroctonus ponderosae, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloborerus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Listronotus (=Hyperodes)* spp., *Lixus* spp., *Luperodes* spp., *Luperomorpha xanthodera, Lyctus* spp., *Megacyllene* spp., for example *Megacyllene robiniae, Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., for example *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Scolytus* spp., for example *Scolytus multistriatus, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Dermaptera, for example *Anisolabis maritime, Forficula auricularia, Labidura riparia;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* or *Pegomyia* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda;* from the order of the Hemiptera, for example *Acizzia acaciaebaileyanae, Acizzia dodonaeae, Acizzia uncatoides, Acrida turrita, Acyrthosipon* spp., e.g. *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., e.g. *Amrasca bigutulla, Amrasca devastans, Anuraphis cardui, Aonidiella* spp., e.g. *Aonidiella aurantii, Aonidiella citrina, Aonidiella inornata, Aphanostigma piri, Aphis* spp., e.g. *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., e.g. *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., e.g. *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., e.g. *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., e.g. *Dysaphis apiifolia, Dysaphis plantaginea, Dysaphis tulipae, Dysmicoccus* spp., *Empoasca* spp., e.g. *Empoasca abrupta, Empoasca fabae, Empoasca maligna, Empoasca solana, Empoasca stevensi, Eriosoma* spp., e.g. *Eriosoma americanum, Eriosoma lanigerum, Eriosoma pyricola, Erythroneura* spp., *Eucalyptolyma* spp.,

*Euphyllura* spp., *Euscelis bilobatus*, *Ferrisia* spp., *Fiorinia* spp., *Furcaspis oceanica*, *Geococcus coffeae*, *Glycaspis* spp., *Heteropsylla cubana*, *Heteropsylla spinulosa*, *Homalodisca coagulata*, *Hyalopterus arundinis*, *Hyalopterus pruni*, *Icerya* spp., e.g. *Icerya purchasi*, *Idiocerus* spp., *Idioscopus* spp., *Laodelphax striatellus*, *Lecanium* spp., e.g. *Lecanium corni* (=*Parthenolecanium corni*), *Lepidosaphes* spp., e.g. *Lepidosaphes ulmi*, *Lipaphis erysimi*, *Lopholeucaspis japonica*, *Lycorma delicatula*, *Macrosiphum* spp., e.g. *Macrosiphum euphorbiae*, *Macrosiphum lilii*, *Macrosiphum rosae*, *Macrosteles facifrons*, *Mahanarva* spp., *Melanaphis sacchari*, *Metcalfiella* spp., *Metcalfa pruinosa*, *Metopolophium dirhodum*, *Monellia costalis*, *Monelliopsis pecanis*, *Myzus* spp., e.g. *Myzus ascalonicus*, *Myzus cerasi*, *Myzus ligustri*, *Myzus ornatus*, *Myzus persicae*, *Myzus nicotianae*, *Nasonovia ribisnigri*, *Neomaskellia* spp., *Nephotettix* spp., e.g. *Nephotettix cincticeps*, *Nephotettix nigropictus*, *Nettigoniclla spectra*, *Nilaparvata lugens*, *Oncometopia* spp., *Orthezia praelonga*, *Oxya chinensis*, *Pachypsylla* spp., *Parabemisia myricae*, *Paratrioza* spp., e.g. *Paratrioza cockerelli*, *Parlatoria* spp., *Pemphigus* spp., e.g. *Pemphigus bursarius*, *Pemphigus populivenae*, *Peregrinus maidis*, *Perkinsiella* spp., *Phenacoccus* spp., e.g. *Phenacoccus madeirensis*, *Phloeomyzus passerinii*, *Phorodon humuli*, *Phylloxera* spp., e.g. *Phylloxera devastatrix*, *Phylloxera notabilis*, *Pinnaspis aspidistrae*, *Planococcus* spp., e.g. *Planococcus citri*, *Prosopidopsylla flava*, *Protopulvinaria pyriformis*, *Pseudaulacaspis pentagona*, *Pseudococcus* spp., e.g. *Pseudococcus calceolariae*, *Pseudococcus comstocki*, *Pseudococcus longispinus*, *Pseudococcus maritimus*, *Pseudococcus viburni*, *Psyllopsis* spp., *Psylla* spp., e.g. *Psylla buxi*, *Psylla mali*, *Psylla pyri*, *Pteromalus* spp., *Pulvinaria* spp., *Pyrilla* spp., *Quadraspidiotus* spp., e.g. *Quadraspidiotus juglansregiae*, *Quadraspidiotus ostreaeformis*, *Quadraspidiotus perniciosus*, *Quesada gigas*, *Rastrococcus* spp., *Rhopalosiphum* spp., e.g. *Rhopalosiphum maidis*, *Rhopalosiphum oxyacanthae*, *Rhopalosiphum padi*, *Rhopalosiphum rufiabdominale*, *Saissetia* spp., e.g. *Saissetia coffeae*, *Saissetia miranda*, *Saissetia neglecta*, *Saissetia oleae*, *Scaphoideus titanus*, *Schizaphis graminum*, *Selenaspidus articulatus*, *Sipha flava*, *Sitobion avenae*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., e.g. *Toxoptera aurantii*, *Toxoptera citricidus*, *Trialeurodes vaporariorum*, *Trioza* spp., e.g. *Trioza diospyri*, *Typhlocyba* spp., *Unaspis* spp., *Viteus vitifolii*, *Zygina* spp.;

from the suborder of the Heteroptera, for example *Aelia* spp., *Anasa tristis*, *Antestiopsis* spp., *Boisea* spp., *Blissus* spp., *Calocoris* spp., *Campylomma livida*, *Cavelerius* spp., *Cimex* spp., e.g. *Cimex adjunctus*, *Cimex hemipterus*, *Cimex lectularius*, *Cimex pilosellus*, *Collaria* spp., *Creontiades dilutus*, *Dasynus piperis*, *Dichelops furcatus*, *Diconocoris hewetti*, *Dysdercus* spp., *Euschistus* spp., e.g. *Euschistus heros*, *Euschistus servus*, *Euschistus tristigmus*, *Euschistus variolarius*, *Eurydema* spp., *Eurygaster* spp., *Halyomorpha halys*, *Heliopeltis* spp., *Horcias nobilellus*, *Leptocorisa* spp., *Leptocorisa varicornis*, *Leptoglossus occidentalis*, *Leptoglossus phyllopus*, *Lygocoris* spp., e.g. *Lygocoris pabulinus*, *Lygus* spp., e.g. *Lygus elisus*, *Lygus hesperus*, *Lygus lineolaris*, *Macropes excavatus*, *Megacopta cribraria*, *Miridae*, *Monalonion atratum*, *Nezara* spp., e.g. *Nezara viridula*, *Nysius* spp., *Oebalus* spp., *Pentomidae*, *Piesma quadrata*, *Piezodorus* spp., e.g. *Piezodorus guildinii*, *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order of the Hymenoptera, for example *Acromyrmex* spp., *Athalia* spp., e.g. *Athalia rosae*, *Atta* spp., *Camponotus* spp., *Dolichovespula* spp., *Diprion* spp., e.g. *Diprion similis*, *Hoplocampa* spp., e.g. *Hoplocampa cookei*, *Hoplocampa testudinea*, *Lasius* spp., *Linepithema* (*Iridiomyrmex*) *humile*, *Monomorium pharaonis*, *Paratrechina* spp., *Paravespula* spp., *Plagiolepis* spp., *Sirex* spp., e.g. *Sirex noctilio*, *Solenopsis invicta*, *Tapinoma* spp., *Technomyrmex albipes*, *Urocerus* spp., *Vespa* spp., e.g. *Vespa crabro*, *Wasmannia auropunctata*, *Xeris* spp.;

from the order of the Isopoda, for example *Armadillidium vulgare*, *Oniscus asellus*, *Porcellio scaber*;

from the order of the Isoptera, for example *Coptotermes* spp., e.g. *Coptotermes formosanus*, *Cornitermes cumulans*, *Cryptotermes* spp., *Incisitermes* spp., *Kalotermes* spp., *Microtermes obesi*, *Nasutitermes* spp., *Odontotermes* spp., *Porotermes* spp., *Reticulitermes* spp., e.g. *Reticulitermes flavipes*, *Reticulitermes hesperus*;

from the order of the Lepidoptera, for example *Achroia grisella*, *Acronicta major*, *Adoxophyes* spp., e.g. *Adoxophyes orana*, *Aedia leucomelas*, *Agrotis* spp., e.g. *Agrotis segetum*, *Agrotis ipsilon*, *Alabama* spp., e.g. *Alabama argillacea*, *Amyelois transitella*, *Anarsia* spp., *Anticarsia* spp., e.g. *Anticarsia gemmatalis*, *Argyroploce* spp., *Autographa* spp., *Barathra brassicae*, *Blastodacna atra*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., e.g. *Chilo plejadellus*, *Chilo suppressalis*, *Choreutis pariana*, *Choristoneura* spp., *Chrysodeixis chalcites*, *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., e.g. *Cydia nigricana*, *Cydia pomonella*, *Dalaca noctuides*, *Diaphania* spp., *Diparopsis* spp., *Diatraea saccharalis*, *Dioryctria* spp., e.g. *Dioryctria zimmermani*, *Earias* spp., *Ecdytolopha aurantium*, *Elasmopalpus lignosellus*, *Eldana saccharina*, *Ephestia* spp., e.g. *Ephestia elutella*, *Ephestia kuehniella*, *Epinotia* spp., *Epiphyas postvittana*, *Erannis* spp., *Erschoviella musculana*, *Etiella* spp., *Eudocima* spp., *Eulia* spp., *Eupoecilia ambiguella*, *Euproctis* spp., e.g. *Euproctis chrysorrhoea*, *Euxoa* spp., *Feltia* spp., *Galleria mellonella*, *Gracillaria* spp., *Grapholitha* spp., e.g. *Grapholita molesta*, *Grapholita prunivora*, *Hedylepta* spp., *Helicoverpa* spp., e.g. *Helicoverpa armigera*, *Helicoverpa zea*, *Heliothis* spp., e.g. *Heliothis virescens* *Hofmannophila pseudospretella*, *Homoeosoma* spp., *Homona* spp., *Hyponomeuta padella*, *Kakivoria flavofasciata*, *Lampides* spp., *Laphygma* spp., *Laspeyresia molesta*, *Leucinodes orbonalis*, *Leucoptera* spp., e.g. *Leucoptera coffeella*, *Lithocolletis* spp., e.g. *Lithocolletis blancardella*, *Lithophane antennata*, *Lobesia* spp., e.g. *Lobesia botrana*, *Loxagrotis albicosta*, *Lymantria* spp., e.g. *Lymantria dispar*, *Lyonetia* spp., e.g. *Lyonetia clerkella*, *Malacosoma neustria*, *Maruca testulalis*, *Mamestra brassicae*, *Melanitis leda*, *Mocis* spp., *Monopis obviella*, *Mythimna separata*, *Nemapogon cloacellus*, *Nymphula* spp., *Oiketicus* spp., *Omphisa* spp., *Operophtera* spp., *Oria* spp., *Orthaga* spp., *Ostrinia* spp., e.g. *Ostrinia nubilalis*, *Panolis flammea*, *Parnara* spp., *Pectinophora* spp., e.g. *Pectinophora gossypiella*, *Perileucoptera* spp., *Phthorimaea* spp., e.g. *Phthorimaea operculella*, *Phyllocnistis citrella*, *Phyllonorycter* spp., e.g. *Phyllonorycter blancardella*, *Phyllonorycter crataegella*, *Pieris* spp., e.g. *Pieris rapae*, *Platynota stultana*, *Plodia interpunctella*, *Plusia* spp., *Plutella xylostella* (=*Plutella maculipennis*), *Podesia* spp., e.g. *Podesia syringae*, *Prays* spp., *Prodenia* spp., *Protoparce* spp., *Pseudaletia* spp., e.g. *Pseudaletia unipuncta*, *Pseudoplusia includens*, *Pyrausta nubilalis*, *Rachiplusia nu*, *Schoenobius* spp., e.g. *Schoenobius bipunctifer*, *Scirpophaga* spp., e.g. *Scirpophaga innotata*, *Scotia segetum*, *Sesamia* spp., e.g. *Sesamia inferens*, *Sparganothis* spp., *Spodoptera* spp., e.g. *Spodoptera eradiana*, *Spodoptera exigua*, *Spodoptera frugiperda*, *Spodoptera praefica*, *Stathmopoda* spp., *Stenoma* spp., *Stomopteryx subsecivella*, *Synanthedon* spp., *Tecia solanivora*, *Thaumetopoea* spp., *Thermesia gemmatalis*, *Tinea cloacella*, *Tinea pellionella*, *Tineola bisselliella*, *Tortrix* spp., *Trichophaga tapetzella*, *Trichoplusia* spp., for example *Trichoplusia ni*, *Tryporyza incertulas*, *Tuta absoluta*, *Virachola* spp.;

from the order of the Orthoptera or Saltatoria, for example *Acheta domesticus*, *Dichroplus* spp., *Gryllotalpa* spp., e.g. *Gryllotalpa gryllotalpa*, *Hieroglyphus* spp., *Locusta* spp., e.g. *Locusta migratoria*, *Melanoplus* spp., e.g. *Melanoplus devastator*, *Paratlanticus ussuriensis*, *Schistocerca gregaria*;

from the order of the Phthiraptera, for example *Damalinia* spp., *Haematopinus* spp., *Linognathus* spp., *Pediculus* spp., *Phylloxera vastatrix*, *Phthirus pubis*, *Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., e.g. *Ctenocephalides canis*, *Ctenocephalides felis*, *Pulex irritans*, *Tunga penetrans*, *Xenopsylla cheopis*;

from the order of the Thysanoptera, for example *Anaphothrips obscurus*, *Baliothrips biformis*, *Chaetanaphothrips leeuweni*, *Drepanothrips reuteri*, *Enneothrips flavens*, *Frankliniella* spp., e.g. *Frankliniella fusca*, *Frankliniella occidentalis*, *Frankliniella schultzei*, *Frankliniella tritici*, *Frankliniella vaccinii*, *Frankliniella williamsi*, *Haplothrips* spp., *Heliothrips* spp., *Hercinothrips femoralis*, *Kakothrips* spp., *Rhipiphorothrips cruentatus*, *Scirtothrips* spp., *Taeniothrips cardamomi*, *Thrips* spp., e.g. *Thrips palmi*, *Thrips tabaci*;

from the order of the Zygentoma (=*Thysanura*), for example *Ctenolepisma* spp., *Lepisma saccharina*, *Lepismodes inquilinus*, *Thermobia domestica*;

from the class of the Symphyla, for example *Scutigerella* spp., e.g. *Scutigerella immaculata*;

pests from the phylum of the Mollusca, for example from the class of the Bivalvia, e.g. *Dreissena* spp.;

and also from the class of the Gastropoda, for example *Arion* spp., e.g. *Arion ater rufus*, *Biomphalaria* spp., *Bulinus* spp., *Deroceras* spp., e.g. *Deroceras laeve*, *Galba* spp., *Lymnaea* spp., *Oncomelania* spp., *Pomacea* spp., *Succinea* spp.;

plant pests from the phylum of the Nematoda, i.e. plant-parasitic nematodes, in particular *Aglenchus* spp., for example *Aglenchus agricola*, *Anguina* spp., for example *Anguina tritici*, *Aphelenchoides* spp., for example *Aphelenchoides arachidis*, *Aphelenchoides fragariae*, *Belonolaimus* spp., for example *Belonolaimus gracilis*, *Belonolaimus longicaudatus*, *Belonolaimus nortoni*, *Bursaphelenchus* spp., for example *Bursaphelenchus cocophilus*, *Bursaphelenchus eremus*, *Bursaphelenchus xylophilus*, *Cacopaurus* spp., for example *Cacopaurus pestis*, *Criconemella* spp., for example *Criconemella curvata*, *Criconemella onoensis*, *Criconemella ornata*, *Criconemella rusium*, *Criconemella xenoplax* (=*Mesocriconema xenoplax*), *Criconemoides* spp., for example *Criconemoides ferniae*, *Criconemoides onoense*, *Criconemoides ornatum*, *Ditylenchus* spp., for example *Ditylenchus dipsaci*, *Dolichodorus* spp., *Globodera* spp., for example *Globodera pallida*, *Globodera rostochiensis*, *Helicotylenchus* spp., for example *Helicotylenchus dihystera*, *Hemicriconemoides* spp., *Hemicycliophora* spp., *Heterodera* spp., for example *Heterodera avenae*, *Heterodera glycines*, *Heterodera schachtii*, *Hirschmaniella* spp., *Hoplolaimus* spp., *Longidorus* spp., for example *Longidorus africanus*, *Meloidogyne* spp., for example *Meloidogyne chitwoodi*, *Meloidogyne fallax*, *Meloidogyne hapla*, *Meloidogyne incognita*, *Meloinema* spp., *Nacobbus* spp., *Neotylenchus* spp., *Paralongidorus* spp., *Paraphelenchus* spp., *Paratrichodorus* spp., for example *Paratrichodorus minor*, *Paratylenchus* spp., *Pratylenchus* spp., for example *Pratylenchus penetrans*, *Pseudohalenchus* spp., *Psilenchus* spp., *Punctodera* spp., *Quinisulcius* spp., *Radopholus* spp., for example *Radopholus citrophilus*, *Radopholus similis*, *Rotylenchulus* spp., *Rotylenchus* spp., *Scutellonema* spp., *Subanguina* spp., *Trichodorus* spp., for example *Trichodorus obtusus*, *Trichodorus primitivus*, *Tylenchorhynchus* spp., for example *Tylenchorhynchus annulatus*, *Tylenchulus* spp., for example *Tylenchulus semipenetrans*, *Xiphinema* spp., for example *Xiphinema index*.

Nematodes

In the present context, the term "nematodes" comprises all species of the phylum Nematoda and here in particular species acting as parasites on plants or fungi (for example species of the order Aphelenchida, *Meloidogyne*, Tylenchida and others) or else on humans and animals (for example species of the orders Trichinellida, Tylenchida, Rhabditina and Spirurida) and causing damage in or on these living organisms, and also other parasitic helminths.

A nematicide in crop protection, as described herein, is capable of controlling nematodes.

The term "controlling nematodes" means killing the nematodes or preventing or impeding their development or their growth or preventing or impeding their penetration into or their sucking on plant tissue.

Here, the efficacy of the compounds is determined by comparing mortalities, gall formation, cyst formation, nematode density per volume of soil, nematode density per root, number of nematode eggs per volume of soil, mobility of the nematodes between a plant or plant part treated with the compound of the formula (I) or (I') or the treated soil and an untreated plant or plant part or the untreated soil (100%). Preferably, the reduction achieved is 25-50% in comparison to an untreated plant, plant part or the untreated soil, more preferably 51-79% and most preferably the complete kill or the complete prevention of development and growth of the nematodes by a reduction of 80 to 100% is achieved. The control of nematodes as described herein also comprises the control of proliferation of the nematodes (development of cysts and/or eggs). Compounds of the formula (I) or (I') can likewise be used to maintain the health of the plants or animals, and they can be used for the control of nematodes in a curative, preventa-tive or systemic manner.

The person skilled in the art knows methods for determining mortalities, gall formation, cyst formation, nematode density per volume of soil, nematode density per root, number of nematode eggs per volume of soil, mobility of the nematodes.

The use of a compound of the formula (I) or (I') may keep the plant healthy and also comprises a reduction of the damage caused by nematodes and an increase of the harvest yield.

In the present context, the term "nematodes" refers to plant nematodes which comprise all nematodes which damage plants. Plant nematodes comprise phytoparasitic nematodes and soil-borne nematodes. The phytoparasitic nematodes include ectoparasites such as *Xiphinema* spp., *Longidorus* spp. and *Trichodorus* spp.; semiparasites such as *Tylenchulus* spp.; migratory endoparasites such as *Pratylenchus* spp., *Radopholus* spp. and *Scutellonema* spp.; non-migratory parasites such as *Heterodera* spp., *Globodera* spp. and *Meloidogyne* spp., and also stem and leaf endoparasites such as *Ditylenchus* spp., *Aphelenchoides* spp. and *Hirschmaniella* spp. Particularly damaging root-parasitic soil nematodes are, for example, cyst-forming nematodes of the genera *Heterodera* or *Globodera*, and/or root gall nematodes of the genus *Meloidogyne*. Damaging species of these genera are, for example, *Meloidogyne incognita*, *Heterodera glycines* (soya bean cyst nematode), *Globodera pallida* and *Globodera rostochiensis* (yellow potato cyst nematode), these species being controlled effectively by the compounds described in the present text. However, the use of the compounds described in the present text is by no means restricted to these genera or species, but also extends in the same manner to other nematodes.

The plant nematodes include, for example, *Aglenchus agricola*, *Anguina tritici*, *Aphelenchoides arachidis*, *Aphelenchoides fragaria*, and the stem and leaf endoparasites *Aphelenchoides* spp., *Belonolaimus gracilis*, *Belonolaimus longicaudatus*, *Belonolaimus nortoni*, *Bursaphelenchus cocophilus*, *Bursaphelenchus eremus*, *Bursaphelenchus xylophilus* and *Bursaphelenchus* spp., *Cacopaurus pestis*, *Criconemella curvata*, *Criconemella onoensis*, *Criconemella ornata*, *Criconemella rusium*, *Criconemella xenoplax* (=*Mesocriconema xenoplax*) and *Criconemella* spp., *Criconemoides ferniae*, *Criconemoides onoense*, *Criconemoides ornatum* and *Criconemoides* spp., *Ditylenchus destructor*, *Ditylenchus dipsaci*, *Ditylenchus myceliophagus* and also the stem and leaf endoparasites *Ditylenchus* spp., *Dolichodorus heterocephalus*, *Globodera pallida* (=*Heterodera pallida*), *Globodera rostochiensis* (yellow potato cyst nematode), *Globodera solanacearum*, *Globodera tabacum*, *Globodera virginia* and the non-migratory cyst-forming parasites *Globodera* spp., *Helicotylenchus digonicus*, *Helicotylenchus dihystera*, *Helicotylenchus erythrine*, *Helicotylenchus multicinctus*, *Helicotylenchus nannus*, *Helicotylenchus pseudorobustus und Helicotylenchus* spp., *Hemicriconemoides*, *Hemicycliophora arenaria*, *Hemicycliophora nudata*, *Hemicycliophora parvana*, *Heterodera avenae*, *Heterodera cruciferae*, *Heterodera glycines* (soya bean cyst nematode), *Heterodera oryzae*, *Heterodera schachtii*, *Heterodera zeae* and the non-migratory cyst-forming parasites *Heterodera* spp., *Hirschmaniella gracilis*, *Hirschmaniella oryzae*, *Hirschmaniella spinicaudata* and the stem and leaf endoparasites *Hirschmaniella* spp., *Hoplolaimus aegyptii*, *Hoplolaimus californicus*, *Hoplolaimus columbus*, *Hoplolaimus galeatus*, *Hoplolaimus indicus*, *Hoplolaimus magnistylus*, *Hoplolaimus pararobustus*, *Longidorus africanus*, *Longidorus breviannulatus*, *Longidorus elongatus*, *Longidorus laevicapitatus*, *Longidorus vineacola* and the ectoparasites *Longidorus* spp., *Meloidogyne acronea*, *Meloidogyne africana*, *Meloidogyne arenaria*, *Meloidogyne arenaria thamesi*, *Meloidogyne artiella*, *Meloidogyne chitwoodi*, *Meloidogyne coffeicola*, *Meloidogyne ethiopica*, *Meloidogyne exigua*, *Meloidogyne fallax*, *Meloidogyne graminicola*, *Meloidogyne graminis*, *Meloidogyne hapla*, *Meloidogyne incognita*, *Meloidogyne incognita acrita*, *Meloidogyne javanica*, *Meloidogyne kikuyensis*, *Meloidogyne minor*, *Meloidogyne naasi*, *Meloidogyne paranaensis*, *Meloidogyne thamesi* and the non-migratory parasites *Meloidogyne* spp., *Meloinema* spp., *Nacobbus aberrans*, *Neotylenchus vigissi*, *Paraphelenchus pseudoparietinus*, *Paratrichodorus allius*, *Paratrichodorus lobatus*, *Paratrichodorus minor*, *Paratrichodorus nanus*, *Paratrichodorus porosus*, *Paratrichodorus teres und Paratrichodorus* spp., *Paratylenchus hamatus*, *Paratylenchus minutus*, *Paratylenchus projectus und Paratylenchus* spp., *Pratylenchus agilis*, *Pratylenchus alleni*, *Pratylenchus andinus*, *Pratylenchus brachyurus*, *Pratylenchus cerealis*, *Pratylenchus coffeae*, *Pratylenchus crenatus*, *Pratylenchus delattrei*, *Pratylenchus giibbicaudatus*, *Pratylenchus goodeyi*, *Pratylenchus hamatus*, *Pratylenchus hexincisus*, *Pratylenchus loosi*, *Pratylenchus neglectus*, *Pratylenchus penetrans*, *Pratylenchus pratensis*, *Pratylenchus scribneri*, *Pratylenchus teres*, *Pratylenchus thornei*, *Pratylenchus vulnus*, *Pratylenchus zeae* and the migratory endoparasites *Pratylenchus* spp., *Pseudohalenchus minutus*, *Psilenchus magnidens*, *Psilenchus tumidus*, *Punctodera chalcoensis*, *Quinisulcius acutus*, *Radopholus citrophilus*, *Radopholus similis*, the migratory endoparasites *Radopholus* spp., *Rotylenchulus borealis*, *Rotylenchulus parvus*, *Rotylenchulus reniformis* and *Rotylenchulus* spp., *Rotylenchus laurentinus*, *Rotylenchus macrodoratus*, *Rotylenchus robustus*, *Rotylenchus uniformis* and *Rotylenchus* spp., *Scutellonema brachyurum*, *Scutellonema bradys*, *Scutellonema clathricaudatum* and the migratory endoparasites *Scutellonema* spp., *Subanguina radiciola*, *Tetylenchus nicotianae*, *Trichodorus cylindricus*, *Trichodorus minor*, *Trichodorus primitivus*, *Trichodorus proximus*, *Trichodorus similis*, *Trichodorus sparsus* and the ectoparasites *Trichodorus* spp., *Tylenchorhynchus agri*, *Tylenchorhynchus brassicae*, *Tylenchorhynchus clarus*, *Tylenchorhynchus claytoni*, *Tylenchorhynchus digitatus*, *Tylenchorhynchus ebriensis*, *Tylenchorhynchus maximus*, *Tylenchorhynchus nudus*, *Tylenchorhynchus vulgaris* and *Tylenchorhynchus* spp., *Tylenchulus semipenetrans* and the semiparasites *Tylenchulus* spp., *Xiphinema americanum*, *Xiphinema brevicolle*, *Xiphinema dimorphicaudatum*, *Xiphinema index* and the ectoparasites *Xiphinema* spp.

Nematodes for the control of which a compound of the formula (I) or (I') may be used include nematodes of the genus *Meloidogyne* such as the Southern root-knot nematode (*Meloidogyne incognita*), the Javanese root-knot nematode (*Meloidogyne javanica*), the Northern root-knot nematode (*Meloidogyne hapla*) and the peanut root-knot nematode (*Meloidogyne arenaria*); nematodes of the genus *Ditylenchus* such as the potato rot nematode (*Ditylenchus destructor*) and stem and bulb eelworm (*Ditylenchus dipsaci*); nematodes of the genus *Pratylenchus* such as the cob root-lesion nematode (*Pratylenchus penetrans*), the chrysanthemum root-lesion nematode (*Pratylenchus fallax*), the coffee root nematode (*Pratylenchus coffeae*), the tea root nematode (*Pratylenchus loosi*) and the walnut root-lesion nematode (*Pratylenchus vulnus*); nematodes of the genus *Globodera* such as the yellow potato cyst nematode (*Globodera rostochiensis*) and the white potato cyst nematode (*Globodera pallida*); nematodes of the genus *Heterodera* such as the soya bean cyst nematode (*Heterodera glycines*) and the beet cyst eelworm (*Heterodera schachtii*); nematodes of the genus *Aphelenchoides* such as the rice white-tip nematode (*Aphelenchoides besseyi*), the chrysanthemum nematode (*Aphelenchoides ritzemabosi*) and the straw-berry nematode (*Aphelenchoides fragariae*); nematodes of the genus *Aphelenchus* such as the fungivor-ous nematode (*Aphelenchus avenae*); nematodes of the genus *Radopholus*, such as the burrowing nematode (*Radopholus similis*); nematodes of the genus *Tylenchulus* such as the citrus root nematode (*Tylenchulus semipenetrans*); nematodes of the genus *Rotylenchulus* such as the reniform nematode (*Rotylenchulus reniformis*); tree-dwelling nematodes such as the pine wood nematode (*Bursaphelenchus xylophilus*) and the red ring nematode (*Bursaphelenchus cocophilus*) and the like.

Plants for the protection of which a compound of the formula (I) or (I') can be used include plants such as cereals (for example rice, barley, wheat, rye, oats, maize and the like), beans (soya bean, azuki bean, bean, broadbean, peas, peanuts and the like), fruit trees/fruits (apples, citrus species, pears, grapevines, peaches, Japanese apricots, cherries, walnuts, almonds, bananas, strawberries and the like), vegetable species (cabbage, tomato, spinach, broccoli, lettuce, onions, spring onion, bell pepper and the like), root crops (carrot, potato, sweet potato, radish, lotus root, turnip and the like), plants for industrial raw materials (cotton, hemp, paper mulberry, mitsumata, rape, beet, hops, sugar cane, sugar beet, olive, rubber, palm trees, coffee, tobacco, tea and the like), cucurbits (pumpkin, cucumber, watermelon, melon and the like), meadow plants (cocksfoot, sorghum, timothygrass, clover, alfalfa and the like), lawn grasses (mascarene grass, bentgrass and the like), spice plants etc. (lavender, rosemary, thyme, parsley, pepper, ginger and the like) and flowers (chrysanthemums, rose, orchid and the like).

The compounds of the formula (I) or (I') are particularly suitable for controlling coffee nematodes, in particular *Pratylenchus brachyurus, Pratylenchus coffeae, Meloidogyne exigua, Meloidogyne incognita, Meloidogyne coffeicola, Helicotylenchus* spp. and also *Meloidogyne paranaensis, Rotylenchus* spp., *Xiphinema* spp., *Tylenchorhynchus* spp. and *Scutellonema* spp.

The compounds of the formula (I) or (I') are particularly suitable for controlling potato nematodes, in particular *Pratylenchus brachyurus, Pratylenchus pratensis, Pratylenchus scribneri, Pratylenchus penetrans, Pratylenchus coffeae, Ditylenchus dipsaci* and also *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne fallax, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae* and *Meloinema* spp.

The compounds of the formula (I) or (I') are particularly suitable for controlling tomato nematodes, in particular *Meloidogyne arenaria, Meloidogyne hapla, Meloidogyne javanica, Meloidogyne incognita, Pratylenchus penetrans* and also *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus* and *Rotylenchulus reniformis*.

The compounds of the formula (I) or (I') are particularly suitable for controlling cucumber plant nematodes, in particular *Meloidogyne arenaria, Meloidogyne hapla, Meloidogyne javanica, Meloidogyne incognita, Rotylenchulus reniformis* and *Pratylenchus* thornei.

The compounds of the formula (I) or (I') are particularly suitable for controlling cotton nematodes, in particular *Belonolaimus longicaudatus, Meloidogyne incognita, Hoplolaimus columbus, Hoplolaimus galeatus* and *Rotylenchulus reniformis*.

The compounds of the formula (I) or (I') are particularly suitable for controlling maize nematodes, in particular *Belonolaimus longicaudatus, Paratrichodorus minor* and also *Pratylenchus brachyurus, Pratylenchus delattrei, Pratylenchus hexincisus, Pratylenchus penetrans, Pratylenchus zeae, (Belonolaimus gracilis), Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyurum* and *Subanguina radiciola*.

The compounds of the formula (I) or (I') are particularly suitable for controlling soya bean nematodes, in particular *Pratylenchus brachyurus, Pratylenchus pratensis, Pratylenchus penetrans, Pratylenchus scribneri, Belonolaimus longicaudatus, Heterodera glycines, Hoplolaimus columbus* and also *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus, (Belonolaimus gracilis), Meloidogyne arenaria, Meloidogyne incognita, Meloidogyne javanica, Meloidogyne hapla, Hoplolaimus columbus, Hoplolaimus galeatus* and *Rotylenchulus reniformis*.

The compounds of the formula (I) or (I') are particularly suitable for controlling tobacco nematodes, in particular *Meloidogyne incognita, Meloidogyne javanica* and also *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp. and *Tetylenchus nicotianae*.

The compounds of the formula (I) or (I') are particularly suitable for controlling citrus nematodes, in particular *Pratylenchus coffeae* and also *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americanum, Xiphinema brevicolle, Xiphinema index, Criconemella* spp., *Hemicriconemoides, Radopholus similis* and *Radopholus citrophilus, Hemicycliophora arenaria, Hemicycliophora nudata* and *Tylenchulus semipenetrans*.

The compounds of the formula (I) or (I') are particularly suitable for controlling banana nematodes, in particular *Pratylenchus coffeae, Radopholus similis* and also *Pratylen-*

*chus giibbicaudatus, Pratylenchus loosi, Meloidogyne* spp., *Helicotylenchus multicinctus, Helicotylenchus dihystera* and *Rotylenchulus* spp.

The compounds of the formula (I) or (I') are particularly suitable for controlling pineapple nematodes, in particular *Pratylenchus zeae, Pratylenchus pratensis, Pratylenchus brachyurus, Pratylenchus goodeyi., Meloidogyne* spp., *Rotylenchulus reniformis* and also *Longidorus elongatus, Longidorus laevicapitatus, Trichodorus primitivus, Trichodorus minor, Heterodera* spp., *Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides ferniae, Criconemoides onoense* and *Criconemoides ornatum*.

The compounds of the formula (I) or (I') are particularly suitable for controlling grapevine nematodes, in particular *Pratylenchus vulnus, Meloidogyne arenaria, Meloidogyne incognita, Meloidogyne javanica, Xiphinema americanum, Xiphinema index* and also *Pratylenchus pratensis, Pratylenchus scribneri, Pratylenchus neglectus, Pratylenchus brachyurus, Pratylenchus thornei* and *Tylenchulus semipenetrans*.

The compounds of the formula (I) or (I') are particularly suitable for controlling nematodes in tree crops—pome fruit, in particular *Pratylenchus penetrans* and also *Pratylenchus vulnus, Longidorus elongatus, Meloidogyne incognita* and *Meloidogyne hapla*.

The compounds of the formula (I) or (I') are particularly suitable for controlling nematodes in tree crops—stone fruit, in particular *Pratylenchus penetrans, Pratylenchus vulnus, Meloidogyne arenaria, Meloidogyne hapla, Meloidogyne javanica, Meloidogyne incognita, Criconemella xenoplax* and also *Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum* and *Hoplolaimus galeatus*.

The compounds of the formula (I) or (I') are particularly suitable for controlling nematodes in tree crops, sugar cane and rice, in particular *Trichodorus* spp., *Criconemella* spp. and also *Pratylenchus* spp., *Paratrichodorus* spp., *Meloidogyne* spp., *Helicotylenchus* spp., *Tylenchorhynchus* spp., *Aphelenchoides* spp., *Heterodera* spp., *Xiphinema* spp. and *Cacopaurus pestis*.

The compounds of the formula (I) or (I') can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). They can, as the case may be, also be used as intermediates or precursors for the synthesis of other active compounds.

Formulations

The present invention further relates to formulations and use forms prepared therefrom as pesticides, for example drench, drip and spray liquors, comprising at least one compound of the formula (I) or (I'). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I) or (I'), optionally comprise further agrochemically active compounds.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which en-hances the biological effect of the formulation, without the component itself having any biological effect. Examples of adjuvants are agents which promote retention, spreading, attachment to the leaf surface or penetration.

These formulations are produced in a known manner, for example by mixing the compounds of the formula (I) or (I') with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I) or (I'), or to the use forms prepared from these formulations (for example ready-to-use pesticides such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents, for example dimethyl sulfoxide, and water.

In principle, it is possible to use all suitable carriers. Suitable carriers include more particularly the following: e.g. ammonium salts and natural, finely ground rocks, such as kaolins, aluminas, talc, chalk, quartz, attapulgite, montmorillonite or diatomaceous earth, and synthetic, finely ground rocks, such as highly disperse silica, aluminium oxide and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as saw-dust, paper, coconut shells, maize cobs and tobacco stalks.

It is also possible to use liquefied gaseous extenders or solvents. Especially suitable extenders or carriers are those which are gaseous at standard temperature and under atmospheric pressure, for example aero-sol propellants such as halogenated hydrocarbons, and also butane, propane, nitrogen and carbon diox-ide.

Examples of emulsifiers and/or foam formers, dispersants or wetting agents having ionic or nonionic properties or mixtures of these surface-active substances are salts of polyacrylic acid, salts of lignosul-fonic acid, salts of phenolsulfonic acid or naphthalenesulfonic acid, polycondensates of ethylene oxide with fatty alcohols or with fatty acids or with fatty amines, with substituted phenols (preferably al-kylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is advantageous if one of the compounds of the formula (I) or (I') and/or one of the inert carriers is insoluble in water and if the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) or (I') can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of agrochemically active compounds into plants. Penetrants are defined in this context by their ability to penetrate from the (generally aqueous) application liquor and/or from the spray coating into the cuticle of the plant and hence to increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I) or (I'), more preferably between 0.01% and 95% by weight of the compound of the formula (I) or (I'), most preferably between 0.5% and 90% by weight of the compound of the formula (I) or (I'), based on the weight of the formulation.

The content of the compound of the formula (I) or (I') in the use forms prepared from the formulations (in particular pesticides) may vary within wide ranges. The concentration of the compound of the formula (I) or (I') in the use forms may typically be between 0.00000001% and 95% by weight of the compound of the formula (I) or (I'), preferably between 0.00001% and 1% by weight, based on the weight of the use form. Application is accomplished in a customary manner appropriate for the use forms.

Mixtures

The compounds of the formula (I) or (I') can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processi-bility of the harvested products.

In addition, the compounds of the formula (I) or (I') may be present in a mixture with other active compounds or semiochemicals such as attractants and/or bird repellents and/or plant activators and/or growth regulators and/or fertilizers. Likewise, the compounds of the formula (I) or (I') can be used to improve plant properties, for example growth, yield and quality of the harvested material.

In a particular embodiment according to the invention, the compounds of the formula (I) or (I') are present in formulations or in the use forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/Acaricides/Nematicides

The active compounds specified here with their common names are known and are described for example in "The Pesticide Manual", 16th ed., British Crop Protection Council 2012, or can be searched for on the Internet (e.g. http://www.alanwood.net/pesticides). The classification is based on the IRAC Mode of Action Classification Scheme applicable at the time of filing of this patent application.

(1) Acetylcholinesterase (AChE) inhibitors, for example carbamates, e.g. alanycarb, aldicarb, bendio-carb, benfuracarb, butocarboxim, butoxycarboxim, carbaryl, carbofuran, carbosulfan, ethiofencarb, fe-nobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfen-vinphos, chlormephos, chlorpyrifos-methyl, coumaphos, cyanophos, demeton-S-methyl, diazinon, di-chlorvos/DDVP, dicrotophos, dimethoate, dimethylvinphos, disulfoton, EPN, ethion, ethoprophos, fam-phur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methida-thion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, for example cyclodiene-organochlorines, e.g. chlordane and endosulfan or phenylpyrazoles (fiproles), e.g. ethiprole and fipronil.

(3) Sodium channel modulators, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer], tralomethrin and transfluthrin or DDT or methoxychlor.

(4) Nicotinic acetylcholine receptor (nAChR) competitive modulators, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, for example spinosyns, e.g. spinetoram and spinosad.

(6) Glutamate-gated chloride channel (GluCl) allosteric modulators, for example avermec-tins/milbemycins, e.g. abamectin, emamectin benzoate, lepimectin and milbemectin.

(7) Juvenile hormone mimetics, for example juvenile hormone analogues, e.g. hydroprene, kinoprene and methoprene or fenoxycarb or pyriproxyfen.

(8) Miscellaneous non-specific (multisite) inhibitors, for example alkyl halides, e.g. methyl bromide and other alkyl halides; or chloropicrin or sulfuryl fluoride or borax or tartar emetic or methyl isocyanate generator, e.g. diazomet and metam.

(9) Chordotonal organ modulators, e.g. pymetrozine or flonicamide.

(10) Mite growth inhibitors, for example clofentezine, hexythiazox and diflovidazin or etoxazole.

(11) Microbial disruptors of the insect midgut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis* and B.t. plant proteins: Cry1Ab, Cry1Ac, Cry1Fa, Cry1A.105, Cry2Ab, Vip3A, mCry3A, Cry3Ab, Cry3Bb, Cry34 Ab1/35Ab1.

(12) Inhibitors of mitochondrial ATP synthase, such as ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the proton gradient, for example chlorfenapyr, DNOC and sulfluramid.

(14) Nicotinic acetylcholine receptor channel blockers, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptors (especially in the case of Diptera), for example cyromazine.

(18) Ecdysone receptor agonists, for example chromafenozide, halofenozide, methoxyfenozide and tebufenozide.

(19) Octopamine receptor agonists, for example amitraz.

(20) Mitochondrial complex III electron transport inhibitors, for example hydramethylnon or acequi-nocyl or fluacrypyrim.

(21) Mitochondrial complex I electron transport inhibitors, for example METI acaricides, e.g. fena-zaquin, fenpyroximate, pyrimidifen, pyridaben, tebufenpyrad and tolfenpyrad or rotenone (Derris).

(22) Voltage-dependent sodium channel blockers, for example indoxacarb or metaflumizone.

(23) Inhibitors of acetyl CoA carboxylase, for example tetronic and tetramic acid derivatives, e.g. spi-rodiclofen, spiromesifen and spirotetramat.

(24) Mitochondrial complex IV electron transport inhibitors, for example phosphines, e.g. aluminium phosphide, calcium phosphide, phosphine and zinc phosphide, or cyanides, calcium cyanide, potassium cyanide and sodium cyanide.

(25) Mitochondrial complex II electron transport inhibitors, for example beta-keto nitrile derivatives, e.g. cyenopyrafen and cyflumetofen and carboxanilides, for example pyflubumide.

(28) Ryanodine receptor modulators, for example diamides, e.g. chlorantraniliprole, cyantraniliprole and flubendiamide, further active compounds, for example afidopyropen, afoxolaner, azadirachtin, benclothiaz, benzoxi-mate, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidacloothiz, iprodione, kappa bifenthrin, kappa tefluthrin, lotilaner, meperfluthrin, paichongding, pyridalyl, pyriflu-quinazon, pyriminostrobin, spirobudiclofen, tetramethylfluthrin, tetraniliprole, tetrachlorantraniliprole, tioxazafen, thiofluoximate, triflumezopyrim and iodomethane; additionally preparations based on *Bacillus firmus* (1-1582, BioNeem, Votivo), and the following compounds: 1-{2-fluoro-4-methyl-5-[(2,2,2-trifluoroethyl)sulfinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indole-3,4'-piperidine]-1(2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS-1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS Reg. No. 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoropropan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]propanamide, (+)-N-[3-chloro-1-(3-pyridinyl)-1H-pyrazol-4-yl]-N-ethyl-3-[(3,3,3-trifluoropropyl)sulfinyl]propanamide and (−)-N-[3-chloro-1-(3-pyridinyl)-1H-pyrazol-4-yl]-N-ethyl-3-[(3,3,3-trifluoropropyl)sulfinyl]propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (known from WO 2012/034403A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl) pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-(1H-benzimidazol-2-yl)phenyl ester (known from CN 103524422 A) (CAS 1542271-46-4); (4aS)-7-chloro-2,5-dihydro-2-[[(methoxycarbonyl) [4-[(trifluoromethyl)thio]phenyl]amino]carbonyl]indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-1-[N-[4-[1-[4-(1,1,2,2,2-pentafluoroethoxy)phenyl]-1H-1,2,4-triazole-3-yl]phenyl]carbamate]-α-L-mannopyranose (known from US 2014/0275503A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 933798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8) and N-[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9).

Fungicides

The active compounds specified herein by their common name are known and described, for example, in "Pesticide Manual" (16th Ed. British Crop Protection Council) or on the internet (for example: http://www.alanwood.net/pesticides).

All the mixing components mentioned in classes (1) to (15), as the case may be, may form salts with suitable bases or acids if they are capable of doing so on the basis of their functional groups. All the fungicidal mixing components mentioned in classes (1) to (15), as the case may be, may include tautomeric forms.

1) ergosterol biosynthesis inhibitors, for example (1.001) cyproconazole, (1.002) difenoconazole, (1.003) epoxiconazole, (1.004) fenhexamid, (1.005) fenpropidin, (1.006) fenpropimorph, (1.007) fenpy-razamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazole, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenole, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl))-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-(({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl) sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl) sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) mefentrifluconazole, (1.082) ipfentrifluconazole.

2) Inhibitors of the respiratory chain in complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of the syn-epimeric racemate 1RS,4SR,9RS and the anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro- 1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain in complex III, for example (3.001) ametoctradin, (3.002) amisul-brom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyrao-xystrobin, (3.020) trifloxystrobin (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multisite activity, for example (5.001) Bordeaux mixture, (5.002) captafol, (5.003) captan, (5.004) chlorthalonil, (5.005) copper hydroxide, (5.006) copper naphthenate, (5.007) copper oxide, (5.008) copper oxychloride, (5.009) copper(2+) sulfate, (5.010) dithianon, (5.011) dodin, (5.012) folpet, (5.013) mancozeb, (5.014) maneb, (5.015) metiram, (5.016) zinc metiram, (5.017) copper oxine, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable of triggering host defense, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

(8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) pro-cymidone, (13.004) proquinazid, (13.005) quinoxyfen, (13.006) vinclozolin.

14) Compounds that can act as uncouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufen-amid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone) (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl} piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl-}1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts thereof, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one.

Biological Pesticides as Mixing Components

The compounds of the formula (I) or (I') can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562 or *Bacillus firmus*, strain I-1582 (Accession number CNCM I-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus*

*subtilis* strain OST 30002 (Accession No. NRRL B-50421), *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:
*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii* (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (accession number CNCM I-952).

Examples of viruses which are used or can be used as biological pesticides are:
*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:
*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:
*Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, For-tune Aza, Fungastop, Heads Up (*Chenopodium quinoa* saponin extract), pyrethrum/pyrethrins, *Quassia amara, Quercus, Quillaja*, Regalia, "Requiem™ Insecticide", rotenone, ryania/ryanodine, *Symphytum officinale, Tanacetum vulgare*, thymol, Triact 70, TriCon, *Tropaeulum majus, Urtica dioica, Veratrin, Viscum album*, Brassicaceae extract, especially oilseed rape powder or mustard powder.

Safener as Mixing Components

The compounds of the formula (I) or (I') can be combined with safeners, for example benoxacor, clo-quintocet (-mexyl), cyometrinil, cyprosulfamide, dichlormid, fenchlorazole (-ethyl), fenclorim, flu-razole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The treatment according to the invention of the plants and parts of plants with the compounds of the formula (I) or (I') is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants to animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants to phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain active herbicidal compounds, for example imidazolinones, sulfonylureas, glyphosate or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (the fruits being apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) or (I') directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) or (I') by the ultra-low volume method or to inject the application form or the compound of the formula (I) or (I') itself into the soil.

A preferred direct treatment of the plants is foliar application, meaning that the compounds of the formula (I) or (I') are applied to the foliage, in which case the treatment frequency and the application rate should be adjusted according to the level of infestation with the pest in question.

In the case of systemically active compounds, the compounds of the formula (I) or (I') also access the plants via the root system. The plants are then treated by the action of the compounds of the formula (I) or (I') on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I) or (I'), or by soil application, meaning that the compounds of the formula (I) or (I') according to the invention are introduced in solid form (e.g. in the form of granules) into the locus of the plants. In the case of paddy rice crops, this can also be accomplished by metering the compound of the formula (I) or (I') in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides.

The present invention therefore in particular also relates to a method for the protection of seed and germinating plants from attack by pests, by treating the seed with one of the compounds of the formula (I) or (I'). The method according to the invention for protecting seed and germinating plants against attack by pests further comprises a method in which the seed is treated simultaneously in one operation or sequentially with a compound of the formula (I) or (I') and a mixing component. It further also comprises a method where the seed is treated at different times with a compound of the formula (I) or (I') and a mixing component.

The invention also relates to the use of the compounds of the formula (I) or (I') for the treatment of seed for protecting the seed and the resulting plant from animal pests.

The invention further relates to seed which has been treated with a compound of the formula (I) or (I') according to the invention for protection from animal pests. The invention also relates to seed which has been treated simultaneously with a compound of the formula (I) or (I') and a mixing component. The invention further relates to seed which has been treated at different times with a compound of the formula (I) or (I') and a mixing component. In the case of seed which has been treated at different times with a compound of the formula (I) or (I') and a mixing component, the individual substances may be present on the seed in different layers. In this case, the layers comprising a compound of the formula (I) or (I') and mixing components may optionally be separated by an intermediate layer. The invention also relates to seed in which a compound of the formula (I) or (I') and a mixing component have been applied as part of a coating or as a further layer or further layers in addition to a coating.

The invention further relates to seed which, after the treatment with a compound of the formula (I) or (I'), is subjected to a film-coating process to prevent dust abrasion on the seed.

One of the advantages that occur when a compound of the formula (I) or (I') acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) or (I') can enhance germination and emergence of the treated seed.

It is likewise considered to be advantageous that compounds of the formula (I) or (I') can especially also be used for transgenic seed.

Furthermore, compounds of the formula (I) or (I') can be employed in combination with compositions of signalling technology, leading to better colonization by symbionts such as, for example, rhizobia, mycorrhizae and/or endophytic bacteria or fungi, and/or to optimized nitrogen fixation.

The compounds of the formula (I) or (I') are suitable for the protection of seed of any plant variety which is used in agriculture, in greenhouses, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beets (for example sugar beets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) or (I') is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of the formula (I) or (I') is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

When treating the seed, care must generally be taken that the amount of the compound of the formula (I) or (I') applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) or (I') are applied to the seed in the form of a suitable formulation. Suitable formulations and processes for seed treatment are known to the person skilled in the art.

The compounds of the formula (I) or (I') can be converted to the customary seed-dressing formulations, such as solutions, emulsions, suspensions, powders, foams, slurries or other coating compositions for seed, and also ULV formulations.

These formulations are prepared in a known manner, by mixing the compounds of the formula (I) or (I') with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active compounds. Usable with preference are alkyl naphthalenesulfonates, such as diisopropyl or diisobutyl naphthalenesulfonates.

Suitable dispersants and/or emulsifiers which may be present in the seed-dressing formulations usable in accordance with the invention are all nonionic, anionic and cationic dispersants customary for the formulation of agrochemically active compounds. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schidlingsbekimpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or the use forms prepared therefrom through the addition of water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) or (I') in the formulations and by the seed. The application rates of the compound of the formula (I) or (I') are generally between 0.001 and 50 g per kilogram of seed, preferably between 0.01 and 15 g per kilogram of seed.

Animal Health

In the animal health field, i.e. the field of veterinary medicine, the compounds of the formula (I) or (I') are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of the formula (I) or (I') having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets, and particularly dogs, cats, caged birds; reptiles, amphibians or aquarium fish.

In a specific embodiment, the compounds of the formula (I) or (I') are administered to mammals.

In another specific embodiment, the compounds of the formula (I) or (I') are administered to birds, namely caged birds or particularly poultry.

Use of the compounds of the formula (I) or (I') for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" in the present context means that the compounds of the formula (I) or (I') are effective in reducing the incidence of the particular parasite in an animal infected with such parasites to an innocuous degree. More specifically, "controlling" in the present context means that the compounds of the formula (I) or (I') kill the respective parasite, inhibit its growth, or inhibit its proliferation.

The arthropods include, for example, but are not limited to, from the order of Anoplurida, for example, *Haematopinus* spp., *Linognathus* spp., *Pediculus* spp., *Phtirus* spp. and *Solenopotes* spp.;

from the order of Mallophagida and the suborders Amblycerina and Ischnocerina, for example, *Bovicola* spp., *Damalina* spp., *Felicola* spp.; *Lepikentron* spp., *Menopon* spp., *Trichodectes* spp., *Trimenopon* spp., *Trinoton* spp., *Werneckiella* spp;

from the order of Diptera and the suborders Nematocerina and Brachycerina, for example, *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.;

from the order of Siphonapterida, for example, *Ceratophyllus* spp., *Ctenocephalides* spp., *Pulex* spp., *Tunga* spp., *Xenopsylla* spp.;

from the order of heteropterida, for example, *Cimex* spp., *Panstrongylus* spp., *Rhodnius* spp., *Triatoma* spp.; and also nuisance and hygiene pests from the order Blattarida.

In addition, in the case of the arthropods, mention should be made by way of example, without limita-tion, of the following Acari:

from the subclass of Acari (Acarina) and the order of Metastigmata, for example from the family of Argasidae such as *Argas* spp., *Ornithodorus* spp., *Otobius* spp., from the family of Ixodidae such as *Amblyomma* spp., *Dermacentor* spp., *Haemaphysalis* spp., *Hyalomma* spp., *Ixodes* spp., *Rhipicephalus* (*Boophilus*) spp., *Rhipicephalus* spp. (the original genus of multi-host ticks); from the order of Mesostigmata such as *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (Prostigmata), for example, *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of the Acaridida (Astigmata), for example, *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (Flagellata), such as:

Metamonada: from the order of Diplomonadida, for example, *Giardia* spp., *Spironucleus* spp.

Parabasala: from the order of Trichomonadida, for example, *Histomonas* spp., *Pentatrichomonas* spp., *Tetratrichomonas* spp., *Trichomonas* spp., *Tritrichomonas* spp.

Euglenozoa: from the order of Trypanosomatida, for example, *Leishmania* spp., *Trypanosoma* spp.

Sarcomastigophora (Rhizopoda) such as Entamoebidae, for example, *Entamoeba* spp., Centramoebidae, for example *Acanthamoeba* sp., Euamoebidae, e.g. *Hartmanella* sp.

Alveolata such as Apicomplexa (Sporozoa): e.g. *Cryptosporidium* spp.; from the order of Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order of Adeleida, for example, *Hepatozoon* spp., *Klossiella* spp.; from the order of Haemosporida, for example, *Leucocytozoon* spp., *Plasmodium* spp.; from the order of Piroplasmida, for example, *Babesia* spp., *Ciliophora* spp., *Echinozoon* spp., *Theileria* spp.; from the order of Vesibuliferida, for example, *Balantidium* spp., *Buxtonella* spp.

Microspora such as *Encephalitozoon* spp., *Enterocytozoon* spp., *Globidium* spp., *Nosema* spp., and also, for example, *Myxozoa* spp.

The helminths that are pathogenic to humans or animals include, for example, Acanthocephala, nematodes, Pentastoma and Platyhelminthes (e.g. Monogenea, cestodes and trematodes).

Illustrative helminths include, but are not limited to:

Monogenea: e.g. *Dactylogyrus* spp., *Gyrodactylus* spp., *Microbothrium* spp., *Polystoma* spp., *Troglecephalus* spp.;

Cestodes: from the order of Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

From the order of cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acanthocephala: from the order of Oligacanthorhynchida, for example: *Macracanthorhynchus* spp., *Prosthenorchis* spp.; from the order of Moniliformida, for example: *Moniliformis* spp.

From the order of Polymorphida, for example: *Filicollis* spp.; from the order of Echinorhynchida, for example *Acanthocephalus* spp., *Echinorhynchus* spp., *Leptorhynchoides* spp.

Pentastoma: from the order of Porocephalida, for example, *Linguatula* spp.

In the veterinary field and in animal husbandry, the compounds of the formula (I) or (I') are administered by methods generally known in the art, such as via the enteral, parenteral, dermal or nasal route in the form of suitable preparations. Administration may be prophylactic, metaphylactic or therapeutic.

Thus, one embodiment of the present invention relates to the compounds of the formula (I) or (I') for use as a medicament.

A further aspect relates to the compounds of the formula (I) or (I') for use as an antiendoparasitic agent.

A further specific aspect of the invention relates to the compounds of the formula (I) or (I') for use as an antithelminthic agent, especially for use as a nematicide, platyhelminthicide, acanthocephalicide or pen-tastomicide.

A further specific aspect of the invention relates to the compounds of the formula (I) or (I') for use as an antiprotozoic agent.

A further aspect relates to the compounds of the formula (I) or (I') for use as an antiectoparasitic agent, especially an arthropodicide, very particularly an insecticide or an acaricide.

Further aspects of the invention are veterinary medicine formulations comprising an effective amount of at least one compound of the formula (I) or (I') and at least one of the following: a pharmaceutically acceptable excipient (e.g. solid or liquid diluents), a pharmaceutically acceptable auxiliary (e.g. surfactants), especially a pharmaceutically acceptable excipient used conventionally in veterinary medicine formulations and/or a pharmaceutically acceptable auxiliary conventionally used in veterinary medicine formulations.

A related aspect of the invention is a method for production of a veterinary medicine formulation as described here, which comprises the step of mixing at least one compound of the formula (I) or (I') with pharmaceutically acceptable excipients and/or auxiliaries, especially with pharmaceutically acceptable excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalicidal, pentastomicidal, insecticidal and acaricidal formulations, according to the aspects mentioned, and methods for production thereof.

Another aspect relates to a method for treatment of a parasitic infection, especially an infection caused by a parasite selected from the group of the ectoparasites and endoparasites mentioned here, by use of an effective amount of a compound of the formula (I) or (I') in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of the formula (I) or (I') in the treatment of a parasite infection, especially an infection caused by a parasite selected from the group of the ectoparasites and endoparasites mentioned here, in an animal, especially a nonhuman animal.

In the present context of animal health or veterinary medicine, the term "treatment" includes prophylactic, metaphylactic and therapeutic treatment.

In a particular embodiment, in this way, mixtures of at least one compound of the formula (I) or (I') with other active compounds, especially with endo- and ectoparasiticides, are provided for the field of veterinary medicine.

In the field of animal health, "mixture" means not just that two (or more) different active compounds are formulated in a common formulation and are correspondingly employed together, but also relates to products comprising formulations separated for each active compound. Accordingly, when more than two active compounds are to be employed, all active compounds can be formulated in a common formulation or all active compounds can be formulated in separate formulations; likewise conceivable are mixed forms in which some of the active compounds are formulated together and some of the active compounds are formulated separately. Separate formulations allow the separate or successive application of the active compounds in question.

The active compounds specified here by their "common names" are known and are described, for example, in the "Pesticide Manual" (see above) or can be searched for on the Internet (e.g.: http://www.alanwood.net/pesticides).

Illustrative active compounds from the group of the ectoparasiticides as mixing components include, without any intention that this should constitute a restriction, the insecticides and acaricides listed in detail above. Further usable active compounds are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluCl) allosteric modulators; (7) juvenile hormone mimetics; (8) miscellaneous non-specific (multi-site) inhibitors; (9) chordotonal organ modulators; (10) mite growth inhibitors; (12) inhibitors of mitochondrial ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in Diptera); (18) ecdysone receptor agonists; (19) octopamine receptor agonists; (21) mitochondrial complex I electron transport inhibitors; (25) mitochondrial complex II electron transport inhibitors; (20) mitochondrial complex III electron transport inhibitors; (22) voltage-dependent sodium channel blockers; (23) inhibitors of acetyl CoA carboxylase; (28) ryanodine receptor modulators;

active compounds having unknown or non-specific mechanisms of action, e.g. fentrifanil, fenoxacrim, cycloprene, chlorobenzilate, chlordimeform, flubenzimin, dicyclanil, amidoflumet, quinomethionat, triarathene, clothiazoben, tetrasul, potassium oleate, petroleum, metoxadiazone, gossyplur, flutenzine, brompropylate, cryolite;

compounds from other classes, for example butacarb, dimetilan, cloethocarb, phosphocarb, pirimiphos(-ethyl), parathion(-ethyl), methacrifos, isopropyl o-salicylate, trichlorfon, sulprofos, propaphos, sebufos, pyridathion, prothoate, dichlofenthion, demeton-S-methyl sulfone, isazofos, cyanofenphos, dialifos, carbophenothion, autathiofos, aromfenvinfos(-methyl), azinphos(-ethyl), chlorpyrifos(-ethyl), fosmethi-lan, iodofenphos, dioxabenzofos, formothion, fonofos, flupyrazofos, fensulfothion, etrimfos;

organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-)metofluthrin, profluthrin, flufenprox, flubrocythrinate, fubfenprox, fen-fluthrin, protrifenbut, pyresmethrin, RU15525, terallethrin, cis-resmethrin, heptafluthrin, bioethanome-thrin, biopermethrin, fenpyrithrin, cis-cypermethrin, cis-permethrin, clocythrin, cyhalothrin (lambda-), chlovaporthrin, or halogenated hydrocarbon compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz beehive varroa acaricides, for example organic acids, e.g. formic acid, oxalic acid.

Illustrative active compounds from the group of the endoparasiticides, as mixing components, include, but are not limited to, active anthelmintic ingredients and active antiprotozoic ingredients.

The active anthelmintic ingredients include, but are not limited to, the following active nematicidal, trematicidal and/or cestocidal ingredients:
from the class of the macrocyclic lactones, for example: eprinomectin, abamectin, nemadectin, moxidectin, doramectin, selamectin, lepimectin, latidectin, milbemectin, ivermectin, emamectin, milbemycin; from the class of the benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole;
from the class of the depsipeptides, preferably cyclic depsipeptides, especially 24-membered cyclic depsipeptides, for example: emodepside, PF1022A;
from the class of the tetrahydropyrimidines, for example: morantel, pyrantel, oxantel;
from the class of the imidazothiazoles, for example: butamisole, levamisole, tetramisole;
from the class of the aminophenylamidines, for example: amidantel, deacylated amidantel (dAMD), tribendimidine;
from the class of the aminoacetonitriles, for example: monepantel;
from the class of the paraherquamides, for example: paraherquamide, derquantel;
from the class of the salicylanilides, for example: tribromsalan, bromoxanide, brotianide, clioxanide, closantel, niclosamide, oxyclozanide, rafoxanide;
from the class of the substituted phenols, for example: nitroxynil, bithionol, disophenol, hexachloro-phene, niclofolan, meniclopholan;
from the class of the organophosphates, for example: trichlorfon, naphthalofos, dichlorvos/DDVP, crufomate, coumaphos, haloxon;
from the class of the piperazinones/quinolines, for example: praziquantel, epsiprantel;
from the class of the piperazines, for example: piperazine, hydroxyzine;
from the class of the tetracyclines, for example: tetracycline, chlorotetracycline, doxycycline, oxytetracycline, rolitetracycline;
from various other classes, for example: bunamidine, niridazole, resorantel, omphalotin, oltipraz, nitros-canate, nitroxynil, oxamniquin, mirasan, miracil, lucanthon, hycanthon, hetolin, emetin, diethylcarbam-azine, dichlorophen, diamfenetide, clonazepam, bephenium, amoscanate, clorsulon.

Active antiprotozoic ingredients include, but are not limited to, the following active compounds:
from the class of the triazines, for example: diclazuril, ponazuril, letrazuril, toltrazuril;
from the class of polyether ionophores, for example: monensin, salinomycin, maduramicin, narasin;
from the class of the macrocyclic lactones, for example: milbemycin, erythromycin;
from the class of the quinolones, for example: enrofloxacin, pradofloxacin;
from the class of the quinines, for example: chloroquine;
from the class of the pyrimidines, for example: pyrimethamine;
from the class of the sulfonamides, for example: sulfaquinoxaline, trimethoprim, sulfaclozin;
from the class of the thiamines, for example: amprolium;
from the class of the lincosamides, for example: clindamycin;
from the class of the carbanilides, for example: imidocarb;
from the class of the nitrofurans, for example: nifurtimox;
from the class of the quinazolinone alkaloids, for example: halofuginone;
from various other classes, for example: oxamniquin, paromomycin;
from the class of the vaccines or antigens from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All the mixing components mentioned, as the case may be, may also form salts with suitable bases or acids if they are capable of doing so on the basis of their functional groups.

Vector Control

The compounds of the formula (I) or (I') can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) onto a host or after injection into a host (for example malaria parasites by mosquitoes).

Examples of vectors and the diseases or pathogens they transmit are:
1) Mosquitoes
  *Anopheles*: malaria, filariasis;
  *Culex*: Japanese encephalitis, filariasis, other viral diseases, transmission of other worms;
  *Aedes*: yellow fever, dengue fever, further viral disorders, filariasis;
  Simuliidae: transmission of worms, especially *Onchocerca volvulus;*
  Psychodidae: transmission of leishmaniasis
2) Lice: skin infections, epidemic typhus;
3) Fleas: plague, endemic typhus, tapeworms;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia bungdorferi* sensu lato., *Borrelia duttoni*, tick-borne encephalitis, Q fever (*Coxiella burnetii*), babesioses (*Babesia canis canis*), ehrlichiosis.

Examples of vectors in the context of the present invention are insects, for example aphids, flies, leaf-hoppers or thrips, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, Psychodidae such as *Phlebotomus, Lutzomyia*, lice, fleas, flies, mites and ticks, which can transmit pathogens to animals and/or humans.

Vector control is also possible if the compounds of the formula (I) or (I') are resistance-breaking.

Compounds of the formula (I) or (I') are suitable for use in the prevention of diseases and/or pathogens transmitted by vectors. Thus, a further aspect of the present invention is the use of compounds of the formula (I) or (I') for vector control, for example in agriculture, in horticulture, in forests, in gardens and in leisure facilities, and also in the protection of materials and stored products.

Protection of Industrial Materials

The compounds of the formula (I) or (I') are suitable for protecting industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) or (I') are used together with at least one further insecticide and/or at least one fungicide.

In a further embodiment, the compounds of the formula (I) or (I') take the form of a ready-to-use pesticide, meaning that they can be applied to the material in question without further modifications. Useful further insecticides or fungicides especially include those mentioned above.

Surprisingly, it has also been found that the compounds of the formula (I) or (I') can be employed for protecting objects which come into contact with saltwater or brackish water, in particular hulls, screens, nets, buildings, moorings and signalling systems, against fouling. It is equally possible to use the compounds of the formula (I) or (I'), alone or in combinations with other active compounds, as antifouling agents.

Control of Animal Pests in the Hygiene Sector

The compounds of the formula (I) or (I') are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For controlling animal pests the compounds of the formula (I) or (I') are used alone or in combination with other active compounds and/or auxiliaries. They are preferably used in domestic insecticide products. The compounds of the formula (I) or (I') are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Mal-acostraca the order Isopoda.

Application is effected, for example, in aerosols, unpresurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES

The preparation and use examples which follow illustrate the invention without limiting it.

Methods

The log P values were determined according to EEC Directive 79/831 Annex V.A8 by HPLC (high-performance liquid chromatography) on a reversed-phase column (C18). Temperature 43° C. The calibration is effected with unbranched alkan-2-ones (having 3 to 16 carbon atoms), for which the log P values are known. Here, the terms acidic and neutral are defined analogously to the definitions below for the determination of $M^+$.

The determination of the $M^+$ by LC-MS in the acidic range was carried out at pH 2.7 using the mobile phases 0.1% aqueous formic acid and acetonitrile (contains 0.1% formic acid); linear gradient from 10% acetonitrile to 95% acetonitrile, instrument: Agilent 1100 LC system, Agilent MSD system, HTS PAL.

The determination of the $M^+$ by LC-MS in the neutral range was carried out at pH 7.8 using the mobile phases 0.001 molar aqueous ammonium bicarbonate solution and acetonitrile; linear gradient from 10% acetonitrile to 95% acetonitrile.

b) The determination of the $^1H$ NMR data was effected with a Bruker Avance 400 equipped with a sample flow head (capacity 60 µl), with tetramethylsilane as reference (0.0) and the solvents $CD_3CN$, $CDCl_3$ or $D_6$-DMSO, or with a Bruker Avance III HD 300 MHz Digital NMR with a 5 mm sample head.

The NMR data of selected examples are listed either in conventional form (δ values, multiplet splitting, number of hydrogen atoms) or as NMR peak lists.

NMR Peak List Method

The $^1H$ NMR data of selected examples are stated in the form of $^1H$ NMR peak lists. For each signal peak, first the δ value in ppm and then the signal intensity in round brackets are listed. The δ value—signal intensity number pairs for different signal peaks are listed with separation from one another by semicolons.

The peak list for one example therefore takes the form of: $δ_1$ (intensity$_1$); $δ_2$ (intensity$_2$); ... ; $δ_i$ (intensity$_i$); ... ; $δ_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of $^1H$ NMR spectra was accomplished using tetramethylsilane and/or the chemical shift of the solvent, particularly in the case of spectra which were measured in DMSO. Therefore, the tetramethylsilane peak may but need not occur in NMR peak lists.

The lists of the $^1H$ NMR peaks are similar to the conventional $^1H$ NMR printouts and thus usually contain all peaks listed in a conventional NMR interpretation.

In addition, like conventional $^1H$ NMR printouts, they may show solvent signals, signals of stereoisomers of the target compounds which are likewise provided by the invention, and/or peaks of impurities.

In the reporting of compound signals within the delta range of solvents and/or water, our lists of $^1H$ NMR peaks show the standard solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to peak picking in conventional $^1$H NMR interpretation.

Further details of $^1$H NMR peak lists can be found in the Research Disclosure Database Number 564025.

Preparation of ethyl 1-methyl-5-[3-(trifluoromethyl)phenyl]-1H-pyrazole-3-carboxylate

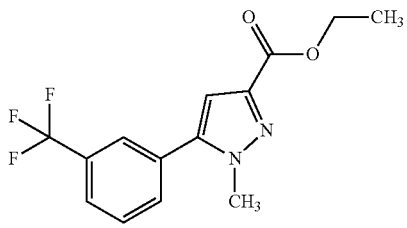 [SMILES: CCOC(=O)c1cc(-c2cccc(C(F)(F)F)c2)n(C)n1]

10 g (34.72 mmol) of ethyl 2,4-dioxo-4-[3-(trifluoromethyl)phenyl]butanoate (known from WO2005/121134 A1) were dissolved in 200 ml of ethanol, and 7.51 g (52.08 mmol) of methylhydrazine sulfate and 1 ml of conc. HCl were added. The reaction mixture was stirred at room temperature overnight and then concentrated under reduced pressure. The residue was dissolved in ethyl acetate, dried over sodium sulfate, filtered and once more concentrated under reduced pressure. By column chromatography (silica gel, mobile phase petroleum ether:ethyl acetate=5:1), the residue was removed from the isomeric ethyl 1-methyl-3-[3-(trifluoromethyl)phenyl]-1H-pyrazole-5-carboxylate. This gave 4.1 g (39.6% of theory).

LC-MS (M+1): 299; RT=1.61 min

Preparation of 1-methyl-5-[3-(trifluoromethyl)phenyl]1H-pyrazole-3-carboxylic acid

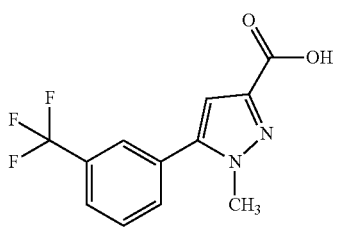 [SMILES: Cn1nc(C(=O)O)cc1-c1cccc(C(F)(F)F)c1]

4.1 g (12.76 mmol) of ethyl 1-methyl-5-[3-(trifluoromethyl)phenyl]-1H-pyrazole-3-carboxylate were dissolved in 100 ml of ethanol, and 2.75 g (68.79 mmol) of NaOH, dissolved in 30 ml of water, were added. The reaction mixture was stirred at room temperature for 3 h and then concentrated under reduced pressure. Using 1N HCl, the aqueous solution that remained was acidified to pH 2. This resulted in the precipitation of a solid which was filtered off with suction and air-dried. This gave 2.7 g (78.4% of theory) which were used for the next step without further purification.

LC-MS (M+1): 271; RT=1.44 min

Preparation of N-[(2,5-dichlorophenyl)sulfonyl]-1-methyl-5-[3-(trifluoromethyl)phenyl]-1H-pyrazole-3-carboxamide

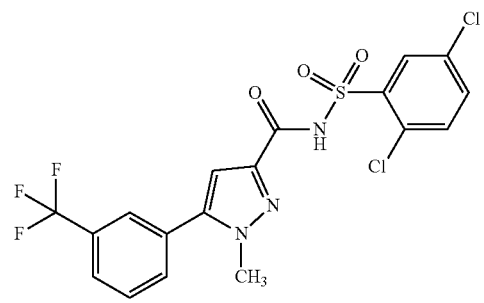 [SMILES: Cn1nc(C(=O)NS(=O)(=O)c2cc(Cl)ccc2Cl)cc1-c1cccc(C(F)(F)F)c1]

0.324 g (1.2 mmol) of 1-methyl-5-[3-(trifluoromethyl)phenyl]-1H-pyrazole-3-carboxylic acid and 0.407 g (1.8 mmol) of 2,5-dichlorobenzenesulfonamide were dissolved in 5 ml of DMF, and 0.684 g (1.8 mmol) of HATU and 0.220 g (1.8 mmol) of DMAP were added. The reaction mixture was stirred at room temperature overnight and then concentrated under reduced pressure. The residue was chromatographed by preparative HPLC. This gave 0.25 g of a colourless solid (43.7% of theory).

LC-MS: log P (acidic): 3.84 MH+: 478.0

1H-NMR (400 MHz, D6-DMSO) ☐ ppm: 8.11 (s, 1H), 7.93-7.71 (m, 6H), 7.14 (s, 1H), 3.96 (s, 3H)—NH proton not detected.

Preparation of ethyl 5-amino-1-propyl-1H-imidazole-4-carboxylate

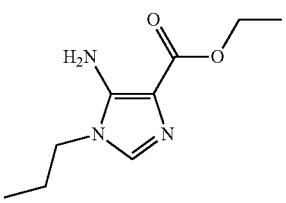

A solution of ethyl 3-nitriloalaninate (10.2 g, 79.6 mmol, known from WO2008/59368) and (diethox-ymethoxy)ethane (13.9 g, 93.9 mmol) in nitromethane (200 ml) was stirred at room temperature for 45 minutes. Subsequently, propan-1-amine (4.71 g, 79.6 mmol) was added and the mixture was stirred at room temperature overnight. The solvent was removed and the residue was purified by column chromatography, giving 4.20 g (21.3 mmol, 27%) of the desired product.

log P (neutral): 0.9; MH+: 198.1; $^1$H-NMR (400 MHz, D6-DMSO) ☐ ppm: 7.11 (s, 1H), 6.00 (s, 2H), 4.15 (q, 2H), 3.75 (m, 2H), 1.63 (m, 2H), 1.24 (m, 3H), 0.83 (m, 3H).

Preparation of ethyl 5-chloro-1-propyl-1H-imidazole-4-carboxylate

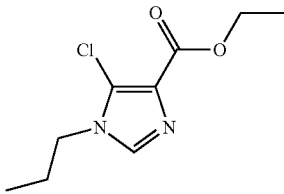

An aqueous HCl solution (6 N, 200 ml) was cooled to −25° C., and a solution of ethyl 5-amino-1-propyl-1H-imidazole-4-carboxylate (4.00 g, 20.3 mmol) in acetonitrile (140 ml) and a solution of sodium nitrite (7.00 g, 2101 mmol) in water (25 ml) were added dropwise. The mixture was stirred at −25° C. for another 5 minutes, and a solution of copper(I) chloride (10.3 g, 104 mmol) in aqueous HCl (6 N, 25 ml) was then added. Over 2 hours, the reaction mixture was warmed to −10° C., and then neutralized using saturated $NaHCO_3$ solution. The mixture was repeatedly extracted with dichloromethane, and the combined organic phases were washed with water, dried and concentrated under reduced pressure. The residue was purified by column chromatography, giving the desired product (1.90 g, 43%).

log P (neutral): 1.7; MH+: 217.1; $^1$H-NMR (400 MHz, D6-DMSO) □ ppm: 7.93 (s, 1H), 4.24 (q, 2H), 3.98 (m, 2H), 1.72 (m, 2H), 1.27 (m, 3H), 0.84 (m, 3H).

Preparation of 5-chloro-1-propyl-1H-imidazole-4-carboxylic acid

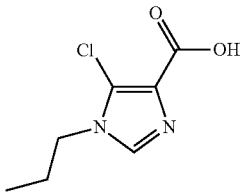

A solution of ethyl 5-chloro-1-propyl-1H-imidazole-4-carboxylate (2.20 g, 10.2 mmol) and sodium hydroxide (516 mg, 12.9 mmol) in ethanol (30 ml) and water (3 ml) was stirred at room temperature overnight. The solvent was removed under reduced pressure, the residue was dissolved in water and the pH of the aqueous phase was then adjusted to 2 using aqueous HCl solution (2 N). The solid formed was collected, washed with water and dried, giving the desired product (1.40 g, 72%).

log P (acidic): 0.6; MH+: 189.0; $^1$H-NMR (400 MHz, D6-DMSO) □ ppm: 7.90 (s, 1H), 3.97 (m, 2H), 1.72 (m, 2H), 0.84 (m, 3H).

Preparation of 5-chloro-N-[(4-methoxyphenyl)sulfonyl]-1-propyl-1H-imidazole-4-carboxamide

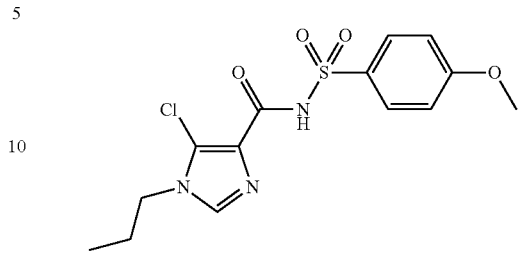

A solution of 5-chloro-1-propyl-1H-imidazole-4-carboxylic acid (100 mg, 0.53 mmol), N,N-dimethylpyridin-4-amine (194 mg, 1.59 mmol) and 1-ethyl-3-(3-dimethylaminopropyl)carbodiimide hydrochloride (305 mg, 1.59 mmol) was stirred at room temperature for 5 minutes, and 4-methoxybenzenesulfonamide (99.3 mg, 0.53 mmol) was then added. Stirring of the reaction mixture was continued at room temperature overnight. The solvent was then removed under reduced pressure, the residue was dissolved in aqueous HCl (2 N) and the mixture was repeatedly extracted with ethyl acetate. The combined organic phases were dried and the solvent was removed. The residue was purified by column chromatography (RP18), giving the desired product (100 mg, 52%).

log P (neutral): 0.56; MH+: 358.0; $^1$H-NMR (400 MHz, D6-DMSO) □ ppm: 7.99 (s, 1H), 7.93 (m, 2H), 7.14 (m, 2H), 3.96 (m, 2H), 3.85 (s, 3H), 1.69 (m, 2H), 0.82 (m, 3H).

Preparation of ethyl (3-[(2-chlorophenyl)amino]-2-nitroacrylate

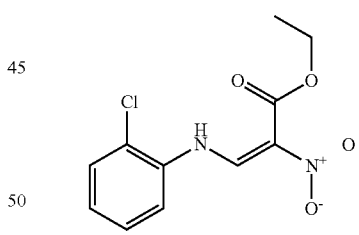

5.99 g (45 mmol) of nitroethyl acetate and 4.775 g (45 mmol) of trimethyl orthoformate were dissolved in 50 ml of methanol, 5.74 g (45 mmol) of 2-chloroaniline were added and the mixture was heated at reflux overnight. The precipitated solid was filtered off with suction, washed with methanol and dried.

Yield 7.4 g (60% of theory)

log P (HCOOH): 2.92; MH+: 271.0

$^1$H-NMR (400 MHz, D6-DMSO) □ ppm: 1.3 (m 3H), 4.3 (m, 1H), 4.4 (m, 1H), 7.3 (m, 1H), 7.5 (m, 1H), 7.65 (m, 1H), 7.75 (m, 1H), 8.6 (m) 9.2 (m) (both together 1H), 11 (s) 11.5 (s) (both together 1H)

Preparation of ethyl 1-(2-chlorophenyl)-2-methyl-1H-imidazole-4-carboxylate

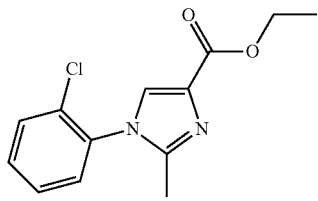 [SMILES: CCOC(=O)c1cn(-c2ccccc2Cl)c(C)n1]

16.5 g (60.96 mmol) of ethyl (2E)-3-[(2-chlorophenyl)amino]-2-nitroacrylate were reacted in 60 ml of triethyl orthoacetate at 70° C. and 2.5 bar of hydrogen and 3.2 g of platinum on carbon (10%) for 1.5 h. The mixture was filtered off through Celite, washed with methanol and concentrated. The residue was purified chromatographically on silica gel (cyclohexane/ethyl acetate).

Yield 9.94 g (59% of theory)

log P (neutral): 2.06; MH+: 265.1

$^1$H-NMR (400 MHz, D6-DMSO) ☐ ppm: 1.3 (t, 3H), 2.3 (s, 3H), 4.2-4.3 (q, 2H), 7.6-7.7 (m, 4H), 7.75 (m, 1H), 7.95 (s, 1H)

Preparation of 1-(2-chlorophenyl)-2-methyl-1H-imidazole-4-carboxylic acid

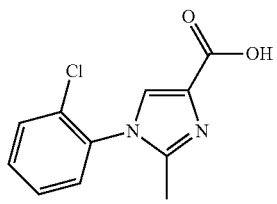 [SMILES: Cc1nc(C(=O)O)cn1-c1ccccc1Cl]

At −10° C., 2.1 g (7.9 mmol) of ethyl 1-(2-chlorophenyl)-2-methyl-1H-imidazole-4-carboxylate were stirred with 11.925 g (47.6 mmol) of boron tribromide for 2 h. Water was then added, the mixture was stirred at RT for 1 h, the dichloromethane was evaporated, the mixture was stirred overnight and filtered off with suction, aqueous ammonia was added to pH=7 and the mixture was extracted with ethyl acetate. Dilute hydrochloric acid was added to pH=5 and the mixture was once more extracted with ethyl acetate. The combined organic phases were dried and concentrated. This gave 0.65 g (30% of theory). A further fraction of 1 g could be obtained by concentration of the aqueous phases, stirring with THF, filtration with suction and concentration of the THF phase.

log P (HCOOH): 0.67; log P (neutral): −0.01 MH+: 237.0

Preparation of 1-(2-chlorophenyl)-N-[(2-chlorophenyl)sulfonyl]-2-methyl-1H-imidazole-4-carboxamide

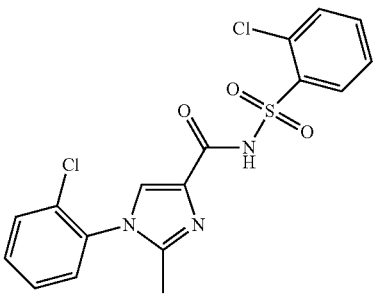 [SMILES: Cc1nc(C(=O)NS(=O)(=O)c2ccccc2Cl)cn1-c1ccccc1Cl]

0.2 g (0.845 mmol) of 1-(2-chlorophenyl)-2-methyl-1H-imidazole-4-carbxylic acid in THF was heated under reflux with 0.21 g (1.27 mmol) of carbonyldiimidazole for 1 h, and 0.243 g (1.27 mmol) of 2-chlorophenylsulfonamide and 0.193 g (1.27 mmol) of DBU were added after cooling. The mixture was stirred overnight and then concentrated and dissolved in dichloromethane and dilute hydrochloric acid. The organic phase was washed two more times with dilute hydrochloric acid, dried and concentrated. The residue was stirred with acetonitrile, filtered off with suction and dried.

Yield 0.22 g (63% of theory)

log P (neutral): 0.85; MH+: 410.0

$^1$H-NMR (400 MHz, D6-DMSO) ☐ ppm: 2.4 (s, 3H), 7.5-7.8 (m, 7H), 8.1-8.2 (m, 2H)

Preparation of methyl 1-(2,6-difluorobenzyl)-1H-imidazole-4-carboxylate

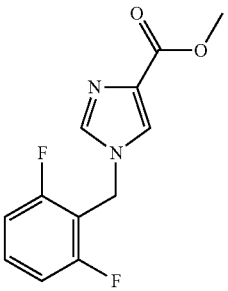 [SMILES: COC(=O)c1cn(Cc2c(F)cccc2F)cn1]

3.0 g (23.788 mmol) of methyl imidazole-4-carboxylate were initially charged in 100 ml of acetonitrile, 3.29 g (23.788 mmol) of potassium carbonate were added and the mixture was stirred at room temperature for 20 minutes. 3.87 g (23.788 mmol) of 2,6-difluorobenzyl chloride, dissolved in 5 ml of acetonitrile, were then added dropwise and the reaction mixture was stirred at 50° C. for four hours. After cooling, the mixture was added to sodium chloride solution and extracted exhaustively with ethyl acetate. Chromatography on silica gel (cyclohexane/ethyl acetate 1/1) gave 2.7 g (45% of theory) of the desired product.

log P (acidic/neutral): 1.45/1.55; MH+: 253.1

1H-NMR (400 MHz, D6-DMSO), ☐☐ ppm: 3.72 (s, 3H); 5.36 (s, 2H); 7.17-7.21 (m, 2H); 7.47-7.53 (m, 2H); 7.78 (s, 1H); 7.81 (s, 1H)

Preparation of 1-(2,6-difluorobenzyl)-1H-imidazole-4-carboxylic acid

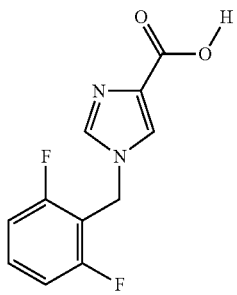 [SMILES: O=C(O)c1cn(Cc2c(F)cccc2F)cn1]

800 mg (3.172 mmol) of methyl 1-(2,6-difluorobenzyl)-1H-imidazole-4-carboxylate were initially charged in 10 ml of THF p.a., and 266.2 mg (6.344 mmol) of lithium hydroxide monohydrate, dissolved in 2 ml of water, were added. The reaction was stirred at room temperature for four hours. After removal of the volatile constituents under reduced pressure, the pH was adjusted to 2 using 2N HCl solution, resulting in the crystallization of 500 mg (66% of theory) of 1-(2,6-difluorobenzyl)-1H-imidazole-4-carboxylic acid. A further 200 mg (26% of theory) of the product were obtained by extraction of the aqueous phase.

log P (acidic): 0.42; MH+: 239.1

1H-NMR (400 MHz, D6-DMSO) ☐ ppm: 5.27 (s, 2H); 7.14-7.21 (m, 3H); 7.46-7.54 (m, 1H); 7.69 (s, 1H).

Preparation of N-[(2-chloro-5-methoxyphenyl)sulfonyl]-1-(2,6-difluorobenzyl)-1H-imidazole-4-carboxamide

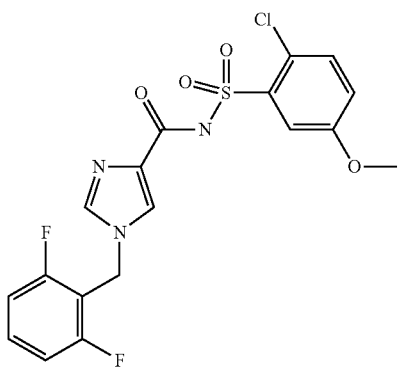 [SMILES: COc1ccc(Cl)c(S(=O)(=O)NC(=O)c2cn(Cc3c(F)cccc3F)cn2)c1]

150 mg (0.63 mmol) of 1-(2,6-difluorobenzyl)-1H-imidazole-4-carboxylic acid were initially charged in 20 ml of dichloromethane, and 230.8 mg (1.889 mmol) of 4-dimethylaminopyridine and 362.2 mg (1.889 mmol) of 1-(3-dimethylaminopropyl)-3-ethylcarbodiimide hydrochloride (EDC×HCl) were then added. The mixture was stirred for five minutes, 139.59 mg (0.63 mmol) of 2-chloro-5-methoxybenzene-1-sulfonamide were then added and the mixture was stirred at room temperature for 18 hours. Dilute hydrochloric acid was then added, the mixture was extracted twice with dichloromethane and the organic phase was washed with sat. sodium chloride solution, dried over sodium sulfate and concentrated by evaporation. Purification by preparative HPLC (water/acetonitrile) gave 40 mg (14.4% of theory) of N-[(2-chloro-5-methoxyphenyl)sulfonyl]-1-(2,6-difluorobenzyl)-1H-imidazole-4-carboxamide.

log P (acidic): 2.18; MH+: 442.0

Preparation of methyl 1-(3,3,3-trifluoropropyl)-1H-imidazole-4-carboxylate

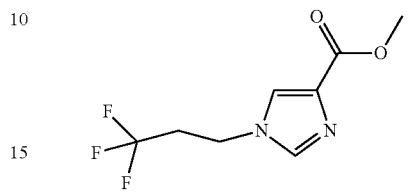

10.55 g (68.46 mmol) of methyl (2Z)-3-(dimethylamino)-2-isocyanoacrylate (commercially available, see also WO2016/57924), 9.75 g (66.2 mmol) of 2,2,2-trifluoropropylamine hydrochloride (commercially available) and 9.27 g (71.7 mmol) of diisopropylethylamine in 32 g of 1-butanol were stirred in an autoclave at 95° for 16 hours. After cooling, the mixture was concentrated, dissolved in water/ethyl acetate, extracted at pH=8; the organic phase was dried with Na2SO4 and concentrated. Yield 13.3 g.

log P (HCOOH): 0.87; MH+: 223.1;

Preparation of methyl 2,5-dibromo-1-(3,3,3-trifluoropropyl)-1H-imidazole-4-carboxylate

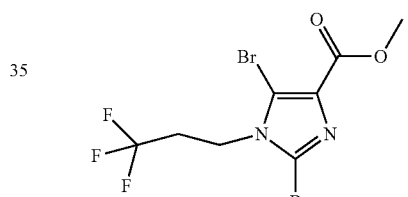

5 g (27.8 mmol) of N-bromosuccinimide were successively added to 1.52 g (6.84 mmol) of methyl 1-(3,3,3-trifluoropropyl)-1H-imidazole-4-carboxylate in 50 ml of acetonitrile, and the mixture was stirred for 2 days in total. Aqueous sodium bisulfite solution and then ethyl acetate were added. At pH=8, the mixture was extracted 3 times with ethyl acetate, and the combined organic phases were dried with Na2SO4 and concentrated. The residue was purified chromatographically on silica gel using petroleum ether/acetone. Yield 0.4 g.

log P (HCOOH): 2.13; MH+: 380.9.

Preparation of 2,5-dibromo-1-(3,3,3-trifluoropropyl)-1H-imidazole-4-carboxylic acid

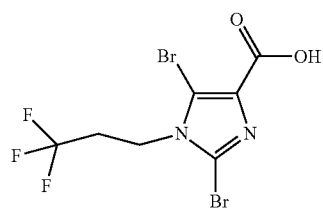 [SMILES: O=C(O)c1nc(Br)n(CCC(F)(F)F)c1Br]

0.4 g (1 mmol) of methyl 2,5-dibromo-1-(3,3,3-trifluoropropyl)-1H-imidazole-4-carboxylate was dissolved in tetrahydrofuran, aqueous sodium hydroxide solution was added and the mixture was stirred. The mixture was concentrated, water and dilute hydrochloric acid were added and the precipitated product was filtered off with suction and dried. Yield 0.34 g.

log P (HCOOH): 1.49; MH+: 366.9.

Preparation of 2,5-dibromo-N-[(2-chlorophenyl)sulfonyl]-1-(3,3,3-trifluoropropyl)-1H-imidazole-4-carboxamide

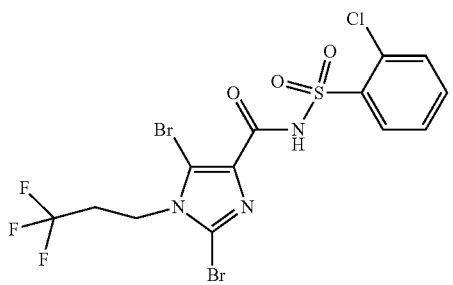 [SMILES: O=C(NS(=O)(=O)c1ccccc1Cl)c1nc(Br)n(CCC(F)(F)F)c1Br]

0.17 g (0.46 mmol) of 2,5-dibromo-1-(3,3,3-trifluoropropyl)-1H-imidazole-4-carboxylic acid, 2-chlorophenylsulfonamide, 0.55 g (2.86 mmol) of EDC-HCl and 0.3 g of 4-dimethylaminopyridine (DMAP) were dissolved in tetrahydrofuran-dichloromethane-diisopropylamine and stirred for 3 d. The mixture was concentrated, dissolved in ethyl acetate, aqueous sodium chloride, citric acid, extracted 3 times with ethyl acetate; the combined organic phases were dried with $Na_2SO_4$ and concentrated. The residue was purified chromatographically on silica gel RP-18, water/formic acid/acetonitrile. Yield 0.08 g.

log P (HCOOH): 2.99; MH+: 539.6.

Preparation of ethyl 5-amino-1-[2-(trifluoromethyl)cyclopropyl]-1H-imidazole-4-carboxylate

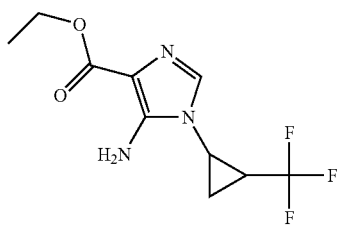 [SMILES: CCOC(=O)c1ncn(C2CC2C(F)(F)F)c1N]

11.0 g (109 mmol) of triethylamine were added to a mixture of 30.0 g (97.9 mmol) of ethyl 3-nitriloalaninate (as tosylate salt) and 15.0 g (101 mmol) of $HC(OEt)_3$ in acetonitrile (500 ml), and the solution was heated under reflux for 1 h. 16.2 g (100 mmol) of 2-(trifluoromethyl)cyclopropanamine (as hydrochloride) and a further 11.0 g (109 mmol) of triethylamine were added and the reaction solution was heated under reflux for 1 h. All volatiles were removed under reduced pressure and the residue was suspended in 200 ml of water. The insoluble solid was filtered off and recrystallized from a mixture of hexane/MTBE (7:3), giving 12.0 g (45.6 mmol, 45%) of the desired product.

Preparation of ethyl 5-amino-2-chloro-1-[2-(trifluoromethyl)cyclopropyl]-1H-imidazole-4-carboxylate

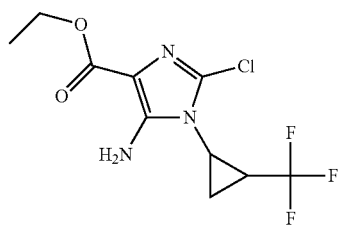 [SMILES: CCOC(=O)c1nc(Cl)n(C2CC2C(F)(F)F)c1N]

9.30 g (54.6 mmol) of $CuCl_2.2H_2O$ were added to a solution of 12.0 g (45.6 mmol) of ethyl 5-amino-1-[2-(trifluoromethyl)cyclopropyl]-1H-imidazole-4-carboxylate in acetonitrile (200 ml), and the reaction mixture was heated under reflux for 72 h. All volatiles were removed under reduced pressure and potassium carbonate solution was added to the residue. The mixture was extracted with dichloromethane (3×300 ml) and the combined organic phases were dried ($Na_2CO_3$) and then concentrated under reduced pressure. The residue was recrystallized from hexane/ethyl acetate (9:1), giving 7.50 g (25.2 mmol, 55%) of the desired product.

Preparation of ethyl 2,5-dichloro-1-[2-(trifluoromethyl)cyclopropyl]-1H-imidazole-4-carboxylate

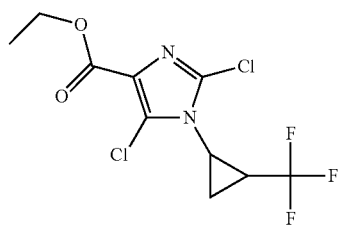 [SMILES: CCOC(=O)c1nc(Cl)n(C2CC2C(F)(F)F)c1Cl]

A solution of 7.0 g (23.5 mmol) of ethyl 5-amino-2-chloro-1-[2-(trifluoromethyl)cyclopropyl]-1H-imidazole-4-carboxylate and 3.50 g (35.4 mmol) of CuCl in acetonitrile (150 ml) was cooled to −10° C., and 3.65 g (35.4 mmol) of t-BuONO were slowly added dropwise over 30 min. The reaction mixture was warmed to room temperature and stirred for 1 h. All volatiles were removed under reduced pressure and potassium carbonate solution was added to the residue. The mixture was extracted with dichloromethane (3×100 ml). The combined organic phases were filtered off over silica gel and then concentrated under reduced pressure. The residue was recrystallized from hexane, giving 3.40 g (10.7 mmol, 46%) of the desired product.

157
Preparation of 2,5-dichloro-1-[2-(trifluoromethyl)cyclopropyl]-1H-imidazole-4-carboxylic acid

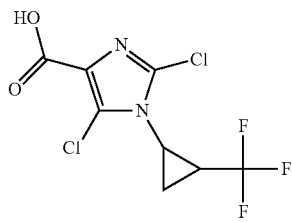 [SMILES: O=C(O)c1nc(Cl)n(C2CC2C(F)(F)F)c1Cl]

A solution of 2.30 g (54.8 mmol) of LiOH.H$_2$O in water was added to a solution of 3.40 g (10.7 mmol) of ethyl 2,5-dichloro-1-[2-(trifluoromethyl)cyclopropyl]-1H-imidazole-4-carboxylate in THF (100 ml). The reaction mixture was stirred at room temperature overnight. THF was then distilled off from the mixture and the aqueous phase was acidified with 1N HCl. The solid was filtered off, recrystallized from ethyl acetate and dried. The desired product was obtained in a yield of 77% (2.40 g, 8.30 mmol).

Ret_time: 1.162 min

[M+H]$^+$: 289.0

158
Preparation of N-[(2-chloro-5-methoxyphenyl)sulfonyl]-1-(3,5-dichlorophenyl)-5-fluoro-2-methyl-1H-imidazole-4-carboxamide

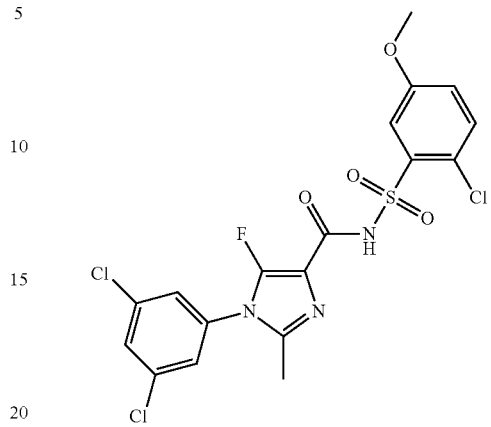

In a pressure vessel, under argon, acetonitrile (2.5 ml) was added to a mixture of N-[(2-chloro-5-methoxyphenyl)sulfonyl]-1-(3,5-dichlorophenyl)-2-methyl-1H-imidazole-4-carboxamide (50 mg, 0.11 mmol) and 1-chloromethyl-4-fluoro-1,4-diazoniabicyclo[2.2.2]octanebis(tetrafluoroborate) (149 mg, 0.42 mmol). The reaction mixture was stirred vigorously at 80° C. for 1.5 hours and then cooled to room temperature and filtered. The precipitate formed was additionally washed with acetonitrile (1 ml). The mother liquor was then concentrated to dryness under reduced pressure. The residue was purified by column chromatography (RP18), Yield 6 mg (11%).

log P (acidic): 3.71; MH+: 494.0;

Table 1 below lists further compounds of the formula (I) which were prepared analogously to the examples given above. The synthesis of the acid precursors was either as described above, or the acids were commercially available.

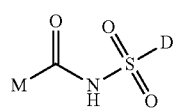

(I)

| Example No. | Structure | NMR peak list |
|---|---|---|
| I-001 | 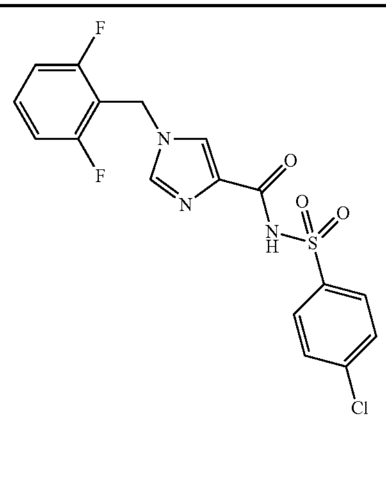 | Example I-1001: 1H-NMR(400.0 MHz, d6-DMSO): δ = 8.134(1.4); 8.013(6.4); 7.949(11.32); 7.928(13.44); 7.88(9.12); 7.67 (12.78); 7.649(11.13); 7.551(0.85); 7.534(1.95); 7.53(2.01); 7.513(3.82); 7.496(2.06); 7.492(2.35); 7.475(1.02); 7.214(0.99); 7.205(6.21); 7.185 (9.96); 7.164(5.31); 7.155(0.89); 5.754(10.6); 5.353(16); 4.278(0.33); 4.243(0.34); 4.121(0.4); 4.076(0.41); 4.046(0.44); 3.989(0.43); 3.91(0.43); 3.9(0.43); 3.874(0.46); 3.85(0.42); 3.816(0.41); 3.791(0.47); 3.777 (0.39); 3.744(0.44); 3.716(0.55); 2.677(0.59); 2.672(0.82); 2.668(0.61); 2.542(0.33); 2.525(1.97); 2.507(102.25); 2.503(140.59); 2.498(108.84); 2.334(0.67); 2.33(0.88); 2.326(0.68); 0.146(0.78); 0.008(6.03); 0(171.7); −0.008(8.75); −0.15(0.85) |

-continued
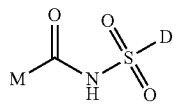
(I)
| Example No. | Structure | NMR peak list |
|---|---|---|
| I-002 | 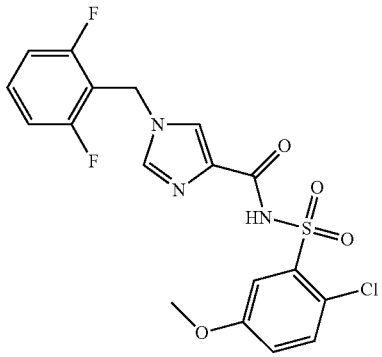 [SMILES: COc1ccc(Cl)c(S(=O)(=O)NC(=O)c2cn(Cc3c(F)cccc3F)cn2)c1] | Example I-1002: 1H-NMR(400.0 MHz, d6-DMSO): δ = 8.111(1.44); 7.974(3.36); 7.572(3.02); 7.564(3.23); 7.55(0.81); 7.546 (0.77); 7.529(1.43); 7.507(3.16); 7.485(2.91); 7.232(1.85); 7.224(3.34); 7.21(1.91); 7.203(4.86); 7.183(1.93); 7.173(0.37); 5.374(5.96); 3.831 (16); 2.671(0.34); 2.506(45.04); 2.502(58.65); 2.498(44.46); 2.329(0.35); 2.074(0.43); 0(17.74) |
| I-003 | 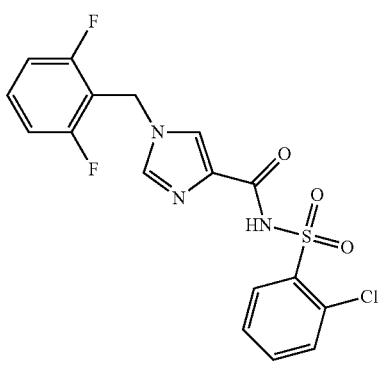 [SMILES: O=C(NS(=O)(=O)c1ccccc1Cl)c1cn(Cc2c(F)cccc2F)cn1] | Example I-1003: 1H-NMR(400.0 MHz, d6-DMSO): δ = 8.114(4.31); 8.094(4.67); 8.066(5.81); 7.974(8.32); 7.665(1.2); 7.647 (3.54); 7.629(3.82); 7.606(6.79); 7.583(4.06); 7.562(4.65); 7.545(3.68); 7.528(3.7); 7.508(2.32); 7.49(0.98); 7.232(1.06); 7.223(5.8); 7.203(9.68); 7.183(5.02); 7.173(0.98); 6.961(0.49); 5.368(16); 4.855(0.71); 4.758 (0.33); 4.746(0.4); 4.737(0.35); 4.725(0.32); 3.738(1.72); 3.17(1.46); 2.672(0.92); 2.542(0.75); 2.503(165.65); 2.33(1); 0.147(0.85); 0(177.13); −0.149(0.93) |
| I-004 | 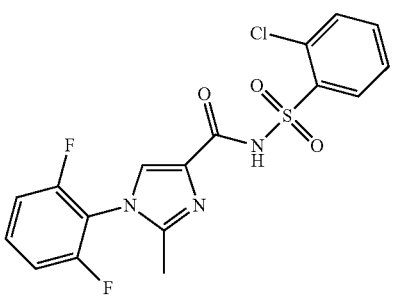 [SMILES: Cc1nc(C(=O)NS(=O)(=O)c2ccccc2Cl)cn1-c1c(F)cccc1F] | Example I-1004: 1H-NMR(400.0 MHz, d6-DMSO): δ = 8.314(0.38); 8.186(2.21); 8.151(1.96); 8.148(2.14); 8.131(2.11); 8.128 (2.23); 7.747(0.38); 7.731(0.85); 7.726(0.81); 7.709(1.71); 7.704(1.09); 7.693(1.03); 7.687(1.56); 7.683(1.66); 7.672(0.85); 7.662(1.91); 7.65 (3.09); 7.634(1.09); 7.611(1.28); 7.607(1.18); 7.591(1.81); 7.574(0.81); 7.57(0.76); 7.476(2.75); 7.454(4.65); 7.434(2.22); 3.65(0.32); 3.637 (0.33); 3.604(0.35); 3.583(0.35); 3.569(0.35); 3.547(0.35); 3.512(0.35); 3.488(0.35); 3.435(0.33); 2.675(0.77); 2.67(1.11); 2.666(0.84); 2.524(2.1); 2.506(136.37); 2.501(181.02); 2.497(136.48); 2.384(0.32); 2.332(0.95); 2.328(1.27); 2.324(1); 2.223(16); 0(3.59) |
| I-005 | 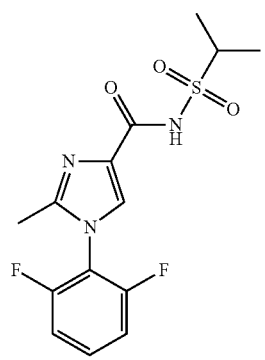 [SMILES: Cc1nc(C(=O)NS(=O)(=O)C(C)C)cn1-c1c(F)cccc1F] | Example I-005: 1H-NMR(400.0 MHz, d6-DMSO): δ = 8.229(4.62); 7.732(0.7); 7.727(0.69); 7.711(1.37); 7.694(0.78); 7.689 (0.88); 7.673(0.39); 7.48(2.24); 7.459(3.96); 7.438(1.87); 3.798(0.45); 3.781(1.19); 3.764(1.65); 3.746(1.23); 3.729(0.48); 3.326(1.02); 2.671 (0.43); 2.502(66.57); 2.329(0.43); 2.215(14.37); 1.318(16); 1.301(15.8); 0.146(0.34); 0(66.84); −0.15(0.35) |

-continued
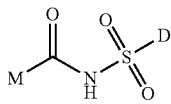
(I)
| Example No. | Structure | NMR peak list |
|---|---|---|
| I-006 | 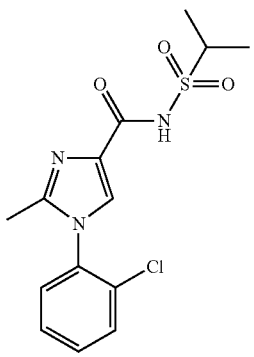 [SMILES: Cc1nc(C(=O)NS(=O)(=O)C(C)C)cn1-c1ccccc1Cl] | Example I-006: 1H-NMR(400.0 MHz, d6-DMSO): δ = 8.107(5.18); 7.78(1.46); 7.777(1.63); 7.76(1.87); 7.757(2.05); 7.669 (1.16); 7.665(1.38); 7.651(1.75); 7.646(2.33); 7.638(0.87); 7.623(1.83); 7.618(1.46); 7.604(1.35); 7.599(1.04); 7.591(1.54); 7.587(1.61); 7.572 (1.57); 7.569(1.54); 7.553(0.53); 7.55(0.5); 3.804(0.45); 3.787(1.13); 3.77(1.54); 3.752(1.19); 3.735(0.47); 3.339(0.8); 2.671(0.4); 2.506(48.6); 2.502(63.69); 2.498(48.56); 2.328(0.4); 2.151(16); 1.317(14.68); 1.3 (14.49); 0.146(0.34); 0.007(3.03); 0(66.15); −0.15(0.35) |
| I-007 | 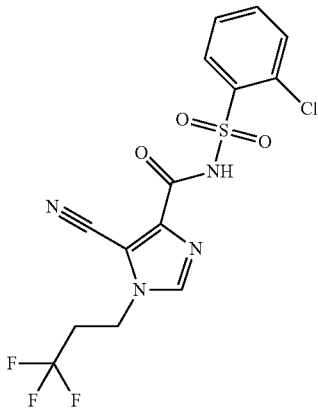 [SMILES: N#Cc1c(C(=O)NS(=O)(=O)c2ccccc2Cl)ncn1CCC(F)(F)F] | Example I-007: 1H-NMR(400.0 MHz, d6-DMSO): δ = 8.462(0.41); 8.315(16); 8.17(5.61); 8.166(6.27); 8.15(6.1); 8.147(6.65); 7.732(1.54); 7.728(1.82); 7.709(4.79); 7.694(4.88); 7.69(5.37); 7.667 (9.46); 7.65(4.28); 7.647(4.19); 7.64(4.38); 7.636(4.21); 7.619(5.95); 7.602(2.59); 7.598(2.61); 4.626(0.42); 4.608(0.33); 4.447(7.03); 4.43 (14.63); 4.413(7.24); 3.995(0.34); 3.854(0.51); 3.78(0.48); 3.716(0.53); 3.672(0.53); 3.637(0.55); 3.602(0.56); 3.562(0.55); 3.532(0.56); 3.505 (0.54); 3.484(0.54); 3.452(0.52); 3.393(0.48); 3.314(0.41); 3.286(0.39); 3.235(0.36); 3.228(0.35); 3.186(0.36); 3.021(1.06); 3.004(2.17); 2.993 (3.22); 2.976(5.97); 2.966(3.93); 2.959(3.71); 2.949(6.13); 2.932(3.11); 2.921(2.28); 2.904(1.08); 2.675(1.4); 2.67(1.83); 2.666(1.39); 2.506 (234.23); 2.501(297.02); 2.497(220.35); 2.387(0.37); 2.332(1.6); 2.328 (2.04); 2.324(1.6); 2.073(4.19); 0.146(1.51); 0.008(19.99); 0(346.46); −0.008(18.84); −0.042(0.73); −0.064(0.37); −0.15(1.69) |
| I-008 | 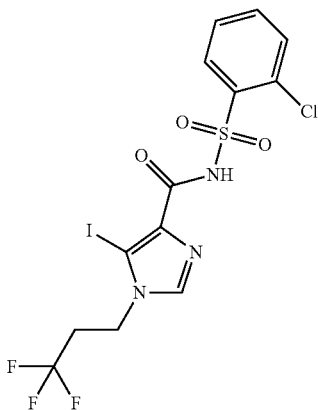 [SMILES: O=C(NS(=O)(=O)c1ccccc1Cl)c1ncn(CCC(F)(F)F)c1I] | Example I-008: 1H-NMR(400.0 MHz, d6-DMSO): δ = 8.313(0.62); 8.242(16); 8.153(5.29); 8.15(5.97); 8.134(5.84); 8.131 (6.31); 7.725(1.42); 7.722(1.68); 7.702(4.65); 7.688(5.03); 7.684(5.53); 7.666(9.47); 7.649(3.79); 7.646(3.47); 7.635(4.09); 7.632(3.93); 7.615 (5.64); 7.598(2.46); 7.594(2.5); 4.312(6.28); 4.295(12.1); 4.277(6.81); 2.904(0.59); 2.885(1.5); 2.876(2.58); 2.858(4.72); 2.848(3.36); 2.841 (3.14); 2.83(4.95); 2.82(1.77); 2.813(2.66); 2.803(1.78); 2.785(0.72); 2.67(1.25); 2.505(191,74); 2.501 (253.16); 2.497(201.42); 2.332(1.84); 2.328(2.26); 2.21(0.42); 2.139(0.33); 2.135(0.33); 2.073(1.4); 0(6.04) |

(I)
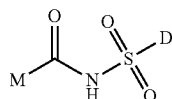
| Example No. | Structure | NMR peak list |
|---|---|---|
| I-009 | 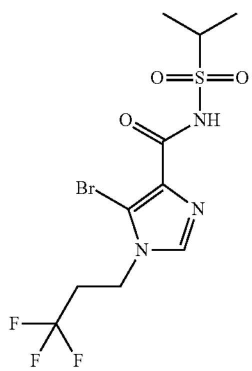 [SMILES: CC(C)S(=O)(=O)NC(=O)c1ncn(CCC(F)(F)F)c1Br] | Example I-009: 1H-NMR(400.0 MHz, d6-DMSO): δ = 8.148(5.41); 4.354(2.22); 4.336(4.55); 4.319(2.3); 3.778(0.45); 3.761 (1.16); 3.744(1.58); 3.727(1.2); 3.71(0.47); 3.319(4.42); 2.928(0.61); 2.918(0.97); 2.901(1.78); 2.89(1.12); 2.884(1.04); 2.873(1.83); 2.863 (0.56); 2.856(0.9); 2.845(0.64); 2.675(0.42); 2.671(0.54); 2.506(65.63); 2.502(84.73); 2.498(65.01); 2.328(0.55); 1.301(16); 1.284(15.77); 0(0.48) |
| I-010 | 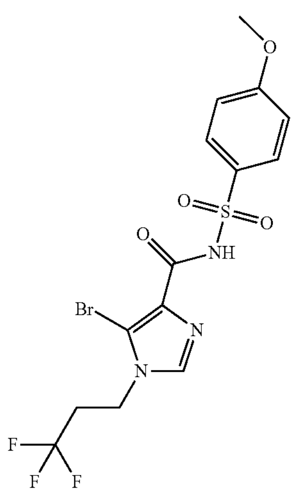 [SMILES: COc1ccc(S(=O)(=O)NC(=O)c2ncn(CCC(F)(F)F)c2Br)cc1] | Example I-010: 1H-NMR(400.0 MHz, d6-DMSO): δ = 8.12(4.93); 7.948(0.48); 7.94(4.06); 7.936(1.56); 7.923(1.33); 7.918 (4.44); 7.911(0.54); 7.154(0.53); 7.147(4.19); 7.129(1.3); 7.124(4.05); 4.315(1.7); 4.297(3.55); 4.28(1.75); 3.847(16); 3.32(0.95); 2.886(0.49); 2.876(0.75); 2.858(1.39); 2.848(0.89); 2.841(0.82); 2.83(1.42); 2.819 (0.45); 2.813(0.71); 2.803(0.51); 2.671(0.36); 2.51(21.3); 2.506(41.07); 2.502(54.7); 2.497(42.04); 2.328(0.36); 2.073(3.3); 0(0.41) |
| I-011 | 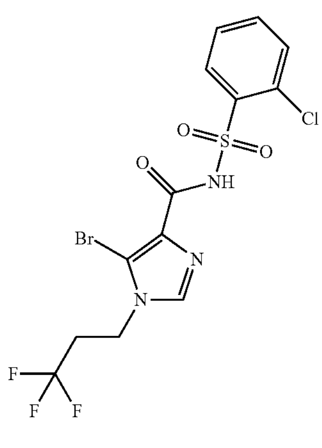 [SMILES: O=C(NS(=O)(=O)c1ccccc1Cl)c1ncn(CCC(F)(F)F)c1Br] | Example I-011: 1H-NMR(400.0 MHz, d6-DMSO): δ = 8.313(0.35); 8.171(16); 8.15(5.15); 8.147(5.97); 8.13(5.48); 8.127 (6.15); 7.724(1.47); 7.721(1.7); 7.704(4.7); 7.701(4.8); 7.686(5); 7.683 (5.46); 7.665(9.29); 7.648(3.58); 7.645(3.36); 7.63(3.8); 7.627(3.83); 7.61(5.55); 7.593(2.35); 7.59(2.43); 4.323(6.42); 4.305(12.81); 4.288 (6.81); 3.952(0.33); 3.932(0.33); 3.894(0.34); 3.848(0.38); 3.816(0.36); 3.782(0.37); 3.754(0.38); 3.69(0.38); 3.676(0.38); 3.635(0.37); 3.608 (0.37); 3.599(0.37); 3.586(0.36); 3.569(0.37); 3.548(0.35); 3.517(0.34); 3.504(0.34); 3.482(0.33); 3.461(0.32); 3.441(0.32); 2.923(0.8); 2.905 (1.73); 2.895(2.8); 2.878(5.06); 2.868(3.55); 2.861(3.43); 2.85(5.27); 2.833(2.78); 2.822(2.01); 2.805(0.86); 2.671(0.95); 2.667(0.79); 2.506 (125.21); 2.502(167.3); 2.498(143.33); 2.328(1.4); 2.256(0.44); 2.073 (1.66); 0(0.83) |

(I)

| Example No. | Structure | NMR peak list |
|---|---|---|
| I-012 | 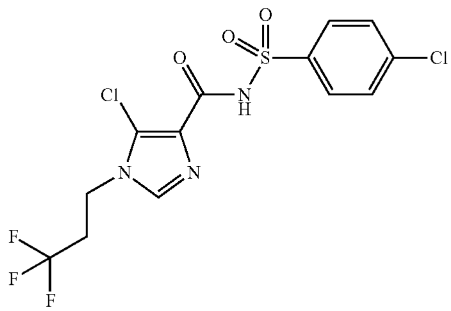 [SMILES: O=C(NS(=O)(=O)c1ccc(Cl)cc1)c1ncn(CCC(F)(F)F)c1Cl] | Example I-012: 1H-NMR(400.0 MHz, d6-DMSO): δ = 8.076(14.94); 8.013(1.49); 8.006(13.39); 8.002(4.45); 7.989(4.66); 7.985(16); 7.978(1.96); 7.885(0.36); 7.863(0.44); 7.742(1.82); 7.736 (14.47); 7.714(12.49); 7.68(0.33); 4.318(5.9); 4.3(12.74); 4.283(6.17); 4.146(0.34); 4.116(0.36); 4.099(0.38); 4.086(0.37); 4.066(0.36); 4.059 (0.38); 4.044(0.38); 4.026(0.4); 4.001(0.42); 3.983(0.46); 3.954(0.49); 3.911(0.56); 3.901(0.57); 3.895(0.63); 3.87(0.62); 3.851(0.83); 3.836 (0.68); 3.813(0.7); 3.754(0.96); 3.746(0.97); 3.738(1.03); 3.375(42.67); 3.194(3.39); 3.002(1.03); 2.967(0.81); 2.94(0.71); 2.924(1.29); 2.908 (2.08); 2.897(2.96); 2.88(5.3); 2.869(3.35); 2.863(3.03); 2.852(5.39); 2.841(1.8); 2.835(2.72); 2.824(2.08); 2.807(1.08); 2.787(0.56); 2.769 (0.53); 2.751(0.47); 2.739(0.48); 2.717(0.91); 2.7(0.45); 2.682(2.72); 2.678(3.73); 2.673(2.69); 2.669(1.49); 2.654(0.44); 2.624(0.49); 2.619 (0.47); 2.581(0.71); 2.548(143.66); 2.531(11.01); 2.517(208.17); 2.513 (409.48); 2.509(534.67); 2.504(390.07); 2.5(190.65); 2.462(0.79); 2.446(0.64); 2.413(0.42); 2.401(0.66); 2.374(0.69); 2.34(2.64); 2.335 (3.47); 2.331(2.56); 1.512(0.43); 1.305(0.35); 1.265(0.45); 1.258(0.37); 1.242(1.05); 1.153(0.38); 0.007(0.59) |
| I-013 | 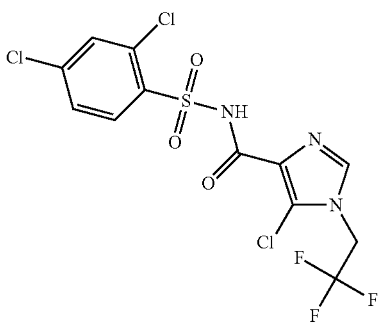 [SMILES: O=C(NS(=O)(=O)c1ccc(Cl)cc1Cl)c1ncn(CC(F)(F)F)c1Cl] | Example I-013: 1H-NMR(400.0 MHz, d6-DMSO): δ = 8.14(8.85); 8.118(16); 7.88(5.64); 7.726(3.78); 7.714(2.43); 7.704 (3.61); 7.693(2.3); 7.545(1.27); 7.54(1.35); 7.4(0.84); 7.395(0.86); 7.379 (0.75); 7.373(0.75); 7.208(0.63); 7.08(0.69); 6.953(0.67); 5.175(2.33); 5.153(6.53); 5.13(6.76); 5.108(2.42); 4.132(0.35); 4.099(0.38); 4.083 (0.4); 4.076(0.38); 4.025(0.42); 4.01(0.45); 3.987(0.51); 3.973(0.51); 3.923(0.62); 3.911(0.63); 3.899(0.64); 3.869(0.71); 3.832(0.83); 3.634 (2.42); 3.374(153.96); 3.193(5.22); 3.002(1.31); 2.985(1.06); 2.916 (0.82); 2.846(0.62); 2.811(0.56); 2.766(0.52); 2.737(0.48); 2.731(0.48); 2.726(0.51); 2.718(0.63); 2.682(5.66); 2.678(7.64); 2.673(5.67); 2.641 (0.48); 2.589(0.77); 2.548(53.37); 2.531(22.4); 2.513(883.54); 2.509 (1144.63); 2.504(842.05); 2.5(418.8); 2.411(0.83); 2.375(0.68); 2.34 (5.63); 2.336(7.47); 2.331(5.61); 2.297(0.66); 2.288(0.41); 2.268(0.34); 2.2(0.33); 1.304(0.55); 1.265(0.74); 1.242(1.68); 1.154(0.83); 0.861 (0.34); 0.007(0.4) |
| I-014 | 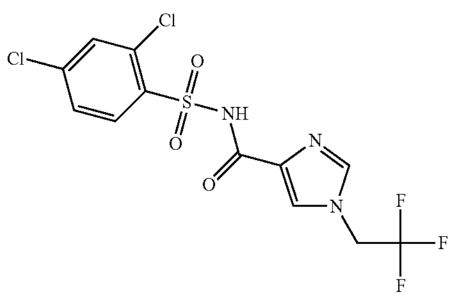 [SMILES: O=C(NS(=O)(=O)c1ccc(Cl)cc1Cl)c1cn(CC(F)(F)F)cn1] | Example I-014: 1H-NMR(400.0 MHz, d6-DMSO): δ = 8.136(1.34); 8.114(2.18); 8.062(1.21); 7.859(0.96); 7.854(1.09); 7.713 (0.66); 7.708(0.68); 7.691(0.62); 7.686(0.65); 5.177(0.91); 5.154(0.98); 5.131(0.35); 3.452(16); 2.684(0.41); 2.679(0.56); 2.674(0.41); 2.549 (11.21); 2.532(1.7); 2.519(31.46); 2.515(62.36); 2.51(81.38); 2.506 (58.53); 2.501(27.81); 2.341(0.37); 2.337(0.52); 2.332(0.35) |
| I-015 | 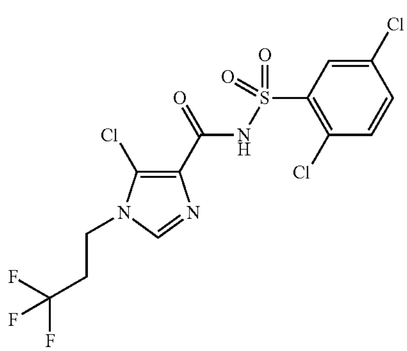 [SMILES: O=C(NS(=O)(=O)c1cc(Cl)ccc1Cl)c1ncn(CCC(F)(F)F)c1Cl] | Example I-015: 1H-NMR(400.0 MHz, d6-DMSO): δ = 8.18(7.29); 8.077(4.17); 8.07(4.35); 7.816(1.94); 7.809(1.83); 7.794 (2.94); 7.788(2.85); 7.716(5.31); 7.695(3.49); 7.62(0.49); 7.613(0.53); 7.477(0.39); 7.471(0.35); 7.409(0.66); 7.388(0.42); 4.33(2.35); 4.313(5); 4.296(2.48); 3.555(16); 2.949(0.34); 2.932(0.67); 2.921(1.03); 2.904 (1.96); 2.894(1.17); 2.887(1.07); 2.876(2.03); 2.866(0.55); 2.859(0.97); 2.848(0.73); 2.831(0.34); 2.718(0.34); 2.682(0.58); 2.678(0.77); 2.673 (0.55); 2.548(81.38); 2.531(2.19); 2.518(42.82); 2.513(85.39); 2.509 (112.12); 2.504(80.93); 2.5(38.74); 2.374(0.33); 2.34(0.52); 2.335(0.71); 2.331(0.51) |

-continued
(I)

| Example No. | Structure | NMR peak list |
|---|---|---|
| I-016 | 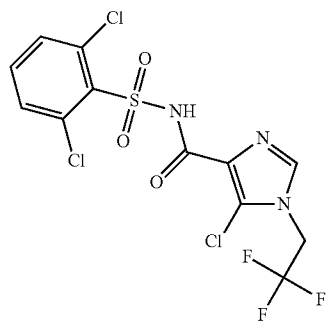 [SMILES: O=C(NS(=O)(=O)c1c(Cl)cccc1Cl)c1ncn(CC(F)(F)F)c1Cl] | Example I-016: 1H-NMR(400.0 MHz, d6-DMSO): δ = 8.222(0.35); 8.132(10.6); 7.683(5.27); 7.678(6.94); 7.671(0.8); 7.661 (15.14); 7.654(1.53); 7.628(7.28); 7.619(0.62); 7.611(4.44); 7.604(3.27); 7.596(0.35); 7.588(2.28); 5.18(1.76); 5.158(5.69); 5.135(6.01); 5.113 (2.09); 3.489(16); 3.003(0.66); 2.719(0.74); 2.688(0.54); 2.684(0.97); 2.679(1.25); 2.674(0.93); 2.67(0.5); 2.549(170.03); 2.532(3.54); 2.528 (5.46); 2.519(63.29); 2.514(126.49); 2.51(165.68); 2.505(117.84); 2.501 (54.66); 2.376(0.59); 2.346(0.36); 2.341(0.78); 2.337(1.07); 2.332(0.74); 2.328(0.35) |
| I-017 | 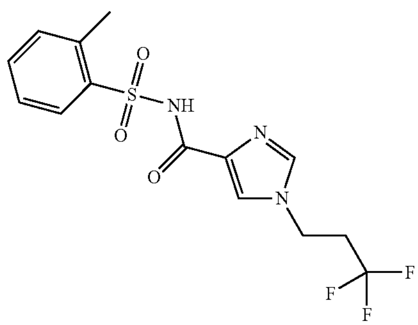 [SMILES: Cc1ccccc1S(=O)(=O)NC(=O)c1cn(CCC(F)(F)F)cn1] | Example I-017: 1H-NMR(400.0 MHz, d6-DMSO): δ = 8.029(3.74); 8.002(4.98); 7.984(2.05); 7.981(1.99); 7.561(0.74); 7.558 (0.76); 7.542(1.84); 7.539(1.78); 7.523(1.21); 7.52(1.14); 7.431(1.16); 7.412(1.85); 7.394(0.84); 7.374(2.07); 7.355(1.66); 4.336(2.37); 4.318 (5.03); 4.301(2.51); 3.708(0.37); 3.393(81.35); 3.105(0.38); 3.001(0.33); 2.963(0.48); 2.945(0.78); 2.935(1.15); 2.928(0.63); 2.917(2.07); 2.907 (1.27); 2.9(1.17); 2.889(2.11); 2.878(0.63); 2.872(1.05); 2.862(0.8); 2.844(0.41); 2.718(0.38); 2.687(0.7); 2.682(1.41); 2.678(1.9); 2.673(1.4); 2.669(0.7); 2.589(16); 2.548(85.39); 2.531(5.46); 2.526(8.75); 2.518 (106.15); 2.513(212.57); 2.509(278.75); 2.504(201.24); 2.5(96.41); 2.374(0.34); 2.345(0.64); 2.34(1.34); 2.335(1.83); 2.331(1.32); 2.326 (0.64); 1.242(0.4) |
| I-018 | 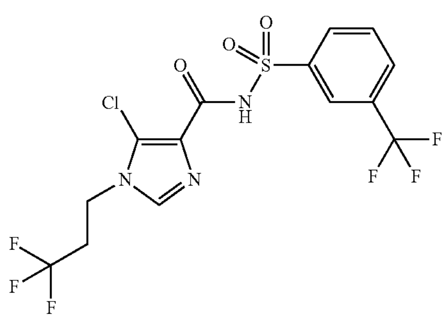 [SMILES: O=C(NS(=O)(=O)c1cccc(C(F)(F)F)c1)c1ncn(CCC(F)(F)F)c1Cl] | Example I-018: 1H-NMR(400.0 MHz, d6-DMSO): δ = 8.32(0.34); 8.308(3.8); 8.286(10.71); 8.133(3.41); 8.113(4.39); 8.1(16); 7.93(3.03); 7.91(5.24); 7.891(2.46); 4.318(5.87); 4.301(12.79); 4.284 (6.13); 3.938(0.32); 3.928(0.32); 3.925(0.33); 3.916(0.34); 3.857(0.44); 3.844(0.43); 3.816(0.49); 3.4(246.28); 3.174(1.6); 3.056(0.64); 3.008 (0.5); 3.001(0.52); 2.974(0.43); 2.955(0.41); 2.924(1.04); 2.906(1.91); 2.896(2.72); 2.89(1.52); 2.879(5.19); 2.868(3.09); 2.862(2.86); 2.851 (5.35); 2.84(1.54); 2.834(2.55); 2.823(2); 2.806(0.96); 2.718(0.58); 2.687 (1.23); 2.682(2.37); 2.678(3.17); 2.673(2.34); 2.669(1.16); 2.596(0.35); 2.548(110.22); 2.531(9.47); 2.526(14.93); 2.518(174.42); 2.513(349.41); 2.509(458.33); 2.504(328.48); 2.5(154.99); 2.442(0.33); 2.425(0.85); 2.374(0.48); 2.345(1.07); 2.34(2.23); 2.335(3.03); 2.331(2.18); 2.326 (1.01); 1.264(0.35); 1.241(0.73) |
| I-019 | 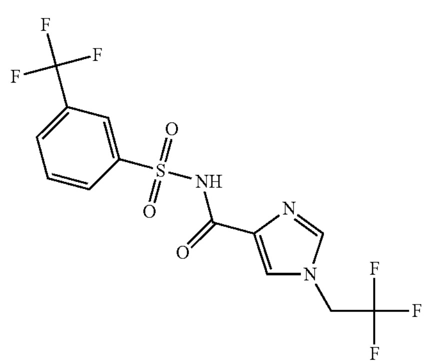 [SMILES: O=C(NS(=O)(=O)c1cccc(C(F)(F)F)c1)c1cn(CC(F)(F)F)cn1] | Example I-019: 1H-NMR(400.0 MHz, d6-DMSO): δ = 8.288(1.01); 8.272(3.07); 8.12(0.87); 8.1(1.08); 8.062(2.64); 8.044 (2.54); 7.915(0.73); 7.894(1.24); 7.874(0.54); 5.177(0.54); 5.154(1.73); 5.131(1.84); 5.108(0.64); 3.502(16); 2.548(26.78); 2.531(0.82); 2.526 (1.27); 2.518(16.16); 2.513(32.31); 2.509(42.28); 2.504(30.25); 2.5 (14.34) |

-continued
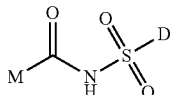
(I)
| Example No. | Structure | NMR peak list |
|---|---|---|
| I-020 | 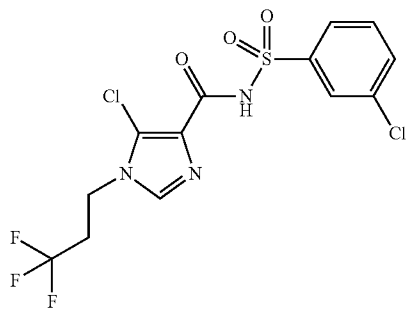 [SMILES: O=C(NS(=O)(=O)c1cccc(Cl)c1)c1ncn(CCC(F)(F)F)c1Cl] | Example I-020: 1H-NMR(400.0 MHz, d6-DMSO): δ = 8.316(0.42); 8.086(16); 7.993(5.58); 7.988(10.09); 7.984(7.07); 7.957 (5.28); 7.938(5.94); 7.812(3.81); 7.789(5.21); 7.696(5.99); 7.676(9.27); 7.656(3.86); 5.756(1.32); 4.315(6.81); 4.298(14.61); 4.28(7.16); 3.47 (0.73); 3.423(0.76); 3.417(0.75); 3.382(0.75); 3.285(0.64); 3.263(0.61); 3.259(0.6); 3.187(0.51); 3.109(0.37); 2.921(1.02); 2.904(2.02); 2.893 (3.05); 2.876(5.76); 2.865(3.62); 2.86(3.43); 2.848(5.97); 2.831(2.94); 2.821(2.21); 2.803(0.99); 2.675(1.1); 2.671(1.48); 2.667(1.17); 2.644 (0.34); 2.541(0.62); 2.524(3.01); 2.506(167.11); 2.502(220.75); 2.498 (167.57); 2.333(1.13); 2.329(1.53); 2.324(1.2); 1.505(0.78); 0.146(0.95); 0.008(7.71); 0(229.05); −0.008(12.48); −0.15(1.05) |
| I-021 | 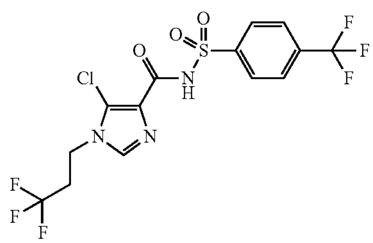 [SMILES: O=C(NS(=O)(=O)c1ccc(C(F)(F)F)cc1)c1ncn(CCC(F)(F)F)c1Cl] | Example I-021: 1H-NMR(400.0 MHz, d6-DMSO): δ = 8.21(9.74); 8.19(12.76); 8.094(16); 8.053(12.87); 8.032(10.01); 8.011 (0.41); 7.213(0.34); 7.085(0.39); 4.319(6.94); 4.302(15); 4.285(7.31); 4.12(0.34); 4.089(0.32); 4.072(0.32); 4.04(0.36); 3.981 (0.41); 3.949(0.43); 3.892(0.53); 3.869(0.55); 3.818(0.69); 3.8(0.74); 3.791(0.76); 3.381(822.34); 3.067(1.11); 3.001(0.88); 2.967(0.65); 2.924(1.39); 2.906(2.42); 2.896(3.4); 2.879(6.26); 2.868(3.94); 2.862 (3.62); 2.851(6.5); 2.834(3.19); 2.823(2.48); 2.806(1.27); 2.786(0.47); 2.777(0.45); 2.752(0.44); 2.719(1.16); 2.683(4.62); 2.679(6.16); 2.674 (4.55); 2.67(2.29); 2.625(0.54); 2.549(231.23); 2.532(17.98); 2.527 (28.7); 2.518(347.95); 2.514(689.63); 2.51(898.56); 2.505(646.66); 2.5(308.12); 2.426(0.72); 2.375(1.01); 2.345(2.12); 2.341(4.35); 2.336(5.87); 2.332(4.19); 2.3(0.47); 1.512(0.52); 1.336(0.37); 1.305(0.4); 1.265(0.6); 1,242(1.58); 1.155(0.62) |
| I-022 | 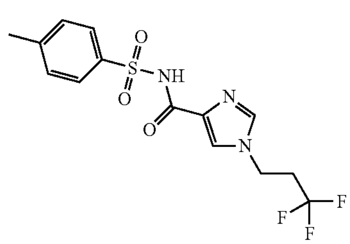 [SMILES: Cc1ccc(S(=O)(=O)NC(=O)c2cn(CCC(F)(F)F)cn2)cc1] | Example I-022: 1H-NMR(400.0 MHz, d6-DMSO): δ = 8.009(4.28); 7.937(3.65); 7.863(5.21); 7.842(5.72); 7.407(4.45); 7.386 (4.01); 4.318(2.57); 4.3(5.47); 4.283(2.66); 3.694(0.52); 3.657(0.65); 3.385(26.85); 3.089(0.52); 2.995(0.4); 2.943(0.56); 2.925(0.89); 2.914 (1.26); 2.908(0.7); 2.897(2.26); 2.886(1.4); 2.88(1.24); 2.869(2.32); 2.858(0.7); 2.852(1.15); 2.841(0.88); 2.824(0.45); 2.68(0.71); 2.675 (1.4); 2.671(1.87); 2.666(1.37); 2.662(0.67); 2.541(6.44); 2.524(5.88); 2.519(9.35); 2.511(106.54); 2.506(211.15); 2.502(275.58); 2.497 (197.66); 2.492(93.42); 2.381(16); 2.337(0.7); 2.333(1.38); 2.328 (1.83); 2.324(1.33); 2.319(0.64); 1.235(0.4); 0(0.88) |
| I-023 | 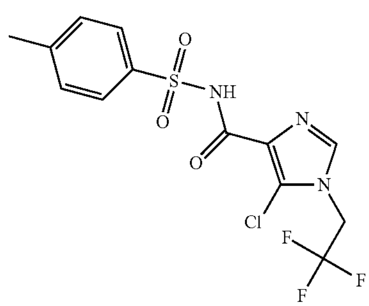 [SMILES: Cc1ccc(S(=O)(=O)NC(=O)c2ncn(CC(F)(F)F)c2Cl)cc1] | Example I-023: 1H-NMR(400.0 MHz, d6-DMSO): δ = 8.085(5.82); 7.888(5.1); 7.867(5.63); 7.842(0.4); 7.439(4.45); 7.419 (4.16); 5.161(1.02); 5.138(3.27); 5.116(3.44); 5.093(1.18); 3.331(46.78); 2.675(0.72); 2.671(0.97); 2.666(0.7); 2.541(63.01); 2.524(2.93); 2.511 (59.34); 2.506(115.57); 2.502(149.35); 2.497(108.18); 2.493(52.95); 2.459(0.35); 2.395(16); 2.368(0.36); 2.333(0.74); 2.329(0.98); 2.324 (0.73); 0(0.37) |

-continued
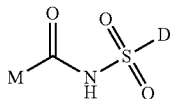
(I)
| Example No. | Structure | NMR peak list |
|---|---|---|
| I-024 | 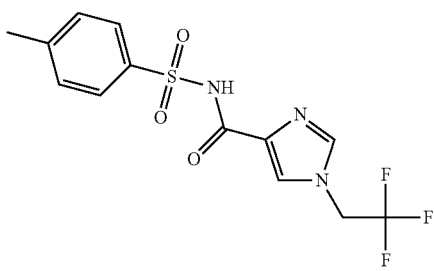 [SMILES: Cc1ccc(S(=O)(=O)NC(=O)c2cn(CC(F)(F)F)cn2)cc1] | Example I-024: 1H-NMR(400.0 MHz, d6-DMSO): δ = 8.022(4.27); 7.913(4.41); 7.875(5.34); 7.854(5.88); 7.428(4.59); 7.408 (4.23); 5.159(0.96); 5.136(3.07); 5.113(3.24); 5.09(1.12); 3.574(0.64); 3.526(1.06); 3.358(4.5); 2.676(0.56); 2.671(0.73); 2.666(0.55); 2.541 (13.12); 2.524(2.37); 2.511(42.85); 2.506(82.53); 2.502(105.92); 2.497 (76.08); 2.493(36.33); 2.389(16); 2.333(0.56); 2.329(0.7); 2.324(0.52) |
| I-025 | 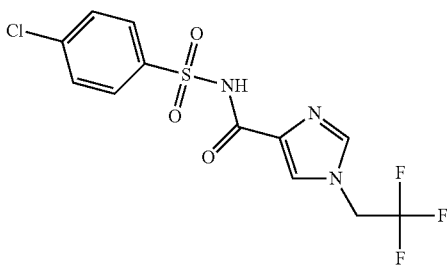 [SMILES: O=C(NS(=O)(=O)c1ccc(Cl)cc1)c1cn(CC(F)(F)F)cn1] | Example I-025: 1H-NMR(400.0 MHz, d6-DMSO): δ = 8.048(8.63); 8.005(1.5); 7.998(13.59); 7.994(4.11); 7.982(4.63); 7.977 (16); 7.97(2.46); 7.964(8.85); 7.733(1.87); 7.726(15.79); 7.721(4.39); 7.709(4.12); 7.704(13.1); 7.698(1.41); 5.174(1.9); 5.152(6.16); 5.128 (6.55); 5.106(2.26); 4.019(0.39); 3.904(0.62); 3.536(7.46); 3.511(7.73); 3.505(7.74); 3.174(0.93); 3.066(0.48); 3.057(0.46); 3.053(0.45); 3.02 (0.39); 3.002(0.56); 2.964(0.35); 2.718(0.43); 2.687(0.62); 2.682(1.07); 2.678(1.4); 2.673(1.01); 2.669(0.54); 2.579(0.34); 2.548(74.35); 2.531 (3.66); 2.526(5.99); 2.518(73.57); 2.513(145.82); 2.508(189.52); 2.504 (134.42); 2.499(62.56); 2.344(0.45); 2.34(0.92); 2.335(1.25); 2.331(0.87) |
| I-026 | 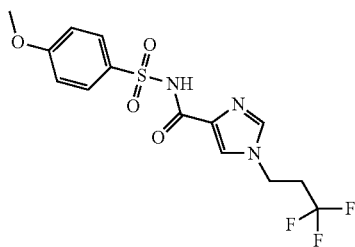 [SMILES: COc1ccc(S(=O)(=O)NC(=O)c2cn(CCC(F)(F)F)cn2)cc1] | Example I-026: 1H-NMR(400.0 MHz, d6-DMSO): δ = 8.012(3.25); 8.009(3.12); 7.922(4.33); 7.916(2.24); 7.911(2.48); 7.905 (2.18); 7.899(4.5); 7.892(0.74); 7.126(4.2); 7.121(1.41); 7.108(1.54); 7.104(3.92); 7.096(0.52); 4.316(1.77); 4.299(3.77); 4.281(1.93); 3.837 (16); 2.922(0.59); 2.912(0.84); 2.894(1.53); 2.884(0.98); 2.877(0.93); 2.867(1.53); 2.856(0.52); 2.849(0.76); 2.839(0.55); 2.671(0.36); 2.51 (21.79); 2.506(39.95); 2.502(49.8); 2.497(35.79); 2.493(17.77); 1.488 (2); 1.2.33(0.32); 0.146(0.4); 0(86.75); −0.008(4.78); −0.15(0.39) |
| I-027 | 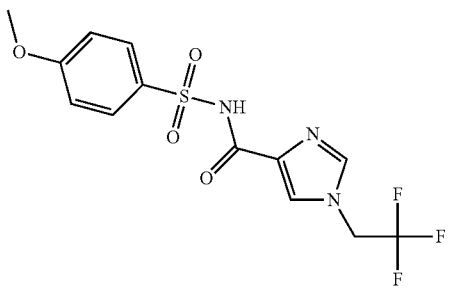 [SMILES: COc1ccc(S(=O)(=O)NC(=O)c2cn(CC(F)(F)F)cn2)cc1] | Example I-027: 1H-NMR(400.0 MHz, d6-DMSO): δ = 8.026(2.84); 7.94(1.51); 7.936(4.4); 7.93(1.53); 7.913(7.13); 7.153 (1.52); 7.149(4.44); 7.144(1.41); 7.131(2.11); 7.126(3.96); 7.119(0.42); 5.164(0.74); 5.141(2.08); 5.118(2.12); 5.095(0.72); 3.853(5.43); 3.848 (16); 3.664(0.41); 3.367(6.38); 2.682(0.44); 2.677(0.5); 2.672(0.36); 2.552(16.99); 2.548(57.02); 2.517(35.83); 2.513(58.88); 2.508(67.24); 2.504(45.88); 2.499(20.42); 2.34(0.37); 2.335(0.44); 1.502(0.5) |

-continued
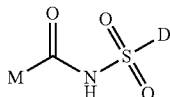
(I)
| Example No. | Structure | NMR peak list |
|---|---|---|
| I-028 | 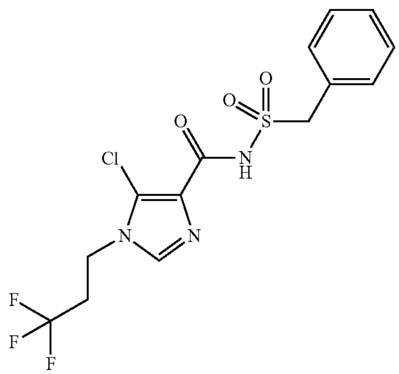 [SMILES: O=C(NS(=O)(=O)Cc1ccccc1)c1ncn(CCC(F)(F)F)c1Cl] | Example I-028: 1H-NMR(400.0 MHz, d6-DMSO): δ = 20.007(1.29); 8.052(7); 7.99(1.2); 7.374(10.13); 7.367(16); 7.346 (8.34); 7.338(6); 7.327(4.28); 4.803(9.02); 4.359(4.81); 4.342(9.81); 4.325(5.06); 3.334(1103.06); 3.216(3.24); 2.973(1.43); 2.944(2.52); 2.928(4.6); 2.916(3.17); 2.9(5); 2.883(2.97); 2.872(2.27); 2.682(12.02); 2.678(15.93); 2.673(11.77); 2.548(85.22); 2.531(45.08); 2.518(943.45); 2.513(1881.46); 2.509(2461.77); 2.504(1774.37); 2.5(849.47); 2.34 (11.74); 2.335(15.4); 2.331(10.87); 2.295(1.36); 1.512(2.91); 1.335 (1.22); 1.304(1.23); 1.265(2.03); 1.257(1.75); 1.242(4.65); 1.155(1.68); 0.904(1.49); 0.007(3.23) |
| I-029 | 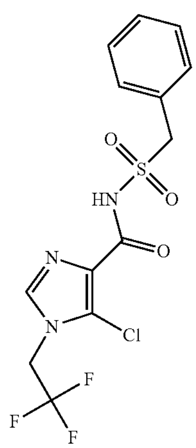 [SMILES: O=C(NS(=O)(=O)Cc1ccccc1)c1ncn(CC(F)(F)F)c1Cl] | Example I-029: 1H-NMR(400.0 MHz, d6-DMSO): δ = 17.914(0.47); 11.402(0.48); 8.086(7.1); 7.938(0.46); 7.405(0.56); 7.386(5.24); 7.373(16); 7.355(8.38); 7.346(5.62); 7.336(3.75); 7.316 (0.74); 5.221(0.59); 5.211(1.82); 5.189(5.67); 5.167(5.89); 5.144 (2.33); 5.121(0.53); 4.809(10.15); 3.905(0.52); 3.866(0.51); 3.794 (0.51); 3.73(0.61); 3.704(0.47); 3.671(0.66); 3.653(0.53); 3.632(0.73); 3.588(0.78); 3.559(0.93); 3.548(1.11); 3.538(1.27); 3.522(1.33); 3.496 (1.69); 3.482(1.66); 3.344(2638.83); 3.21(2.59); 3.176(1.98); 3.137 (1.07); 3.103(1.06); 3.098(0.99); 3.082(0.98); 3.031(0.77); 3.01(0.73); 2.937(0.66); 2.918(0.48); 2.898(0.5); 2.887(0.52); 2.877(0.53); 2.859 (0.56); 2.855(0.52); 2.849(0.5); 2.84(0.49); 2.815(0.56); 2.734(0.6); 2.716(0.63); 2.682(6.69); 2.678(8.95); 2.673(6.46); 2.604(0.9); 2.586 (0.6); 2.548(97.21); 2.517(557.81); 2.513(1063.86); 2.509(1377.3); 2.504(1008.9); 2.44(1.86); 2.373(1.08); 2.34(6.76); 2.335(8.96); 2.331 (6.56); 2.298(0.73); 2.282(0.51); 2.275(0.56); 1.9(0.48); 1.52(3.21); 1.498(0.51); 1.305(0.77); 1.265(0.98); 1.252(1.14); 1.242(2.37); 1.156(1); 0.908(0.56); 0.86(0.54); −3.449(0.47) |
| I-030 | 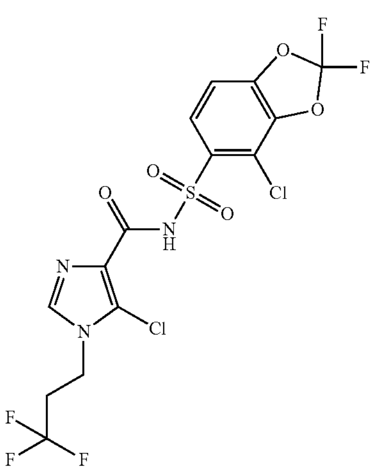 [SMILES: O=C(NS(=O)(=O)c1ccc2c(c1Cl)OC(F)(F)O2)c1ncn(CCC(F)(F)F)c1Cl] | Example I-030: 1H-NMR(400.0 MHz, d6-DMSO): δ = 8.316(0.41); 8.149(14.19); 8.134(16); 7.907(15.3); 4.322(5.18); 4.305 (10.78); 4.288(5.47); 2.94(0.64); 2.922(1.38); 2.912(2.17); 2.895(4.15); 2.884(2.65); 2.878(2.44); 2.867(4.32); 2.85(2.11); 2.839(1.56); 2.822 (0.67); 2.676(0.74); 2.671(0.99); 2.667(0.74); 2.524(2); 2.507(126.58); 2.502(162.86); 2.498(120.15); 2.333(0.85); 2.329(1.08); 2.325(0.84); 0.146(0.39); 0.008(3.13); 0(92.07); −0.008(5.4); −0.15(0.44) |

(I)

| Example No. | Structure | NMR peak list |
|---|---|---|
| I-031 | 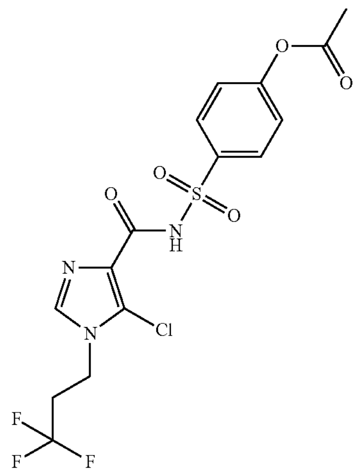 [SMILES: CC(=O)Oc1ccc(S(=O)(=O)NC(=O)c2ncn(CCC(F)(F)F)c2Cl)cc1] | Example I-031: 1H-NMR(400.0 MHz, d6-DMSO): δ = 12.171(0.34); 12.164(0.33); 8.142(5.63); 8.137(2.93); 8.037(0.52); 8.014(0.42); 8.007(4.01); 8.003(1.9); 7.991(1.36); 7.985(4.72); 7.979(1.36); 7.912(1.28); 7.907(0.6); 7.896(0.44); 7.89(1.54); 7.827(0.4); 7.805(0.42); 7.531(0.47); 7.524(4.38); 7.519(1.95); 7.507(1.31); 7.502(4.31); 7.495(1.06); 7.468(0.33); 7.461(1.51); 7.456(0.68); 7.445(0.57); 7.439(1.66); 7.433(2.25); 6.926(0.38); 6.904(0.39); 4.4(2.43); 4.383(5.3); 4.366(2.61); 4.288(0.36); 3.328(11.51); 2.985(0.34); 2.968(0.7); 2.958(1.1); 2.941(2.05); 2.93(1.35); 2.924(1.3); 2.913(2.18); 2.896(1.1); 2.885(0.85); 2.867(0.46); 2.689(0.32); 2.675(0.38); 2.671(0.55); 2.666(0.45); 2.524(1.37); 2.51(27.22); 2.506(58.61); 2.502(82.35); 2.497(67.21); 2.329(0.53); 2.324(0.43); 2.075(0.77); 1.948(16); 0.146(0.36); 0.008(2.68); 0(78.74); −0.007(9.88); −0.15(0.34) |
| I-032 | 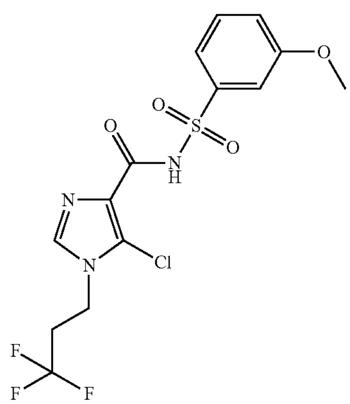 [SMILES: COc1cccc(S(=O)(=O)NC(=O)c2ncn(CCC(F)(F)F)c2Cl)c1] | Example I-032: 1H-NMR(400.0 MHz, d6-DMSO): δ = 8.066(4.92); 7.951(0.99); 7.577(0.38); 7.573(0.39); 7.559(3.67); 7.553(1.56); 7.542(2.06); 7.522(0.58); 7.508(1.59); 7.505(1.75); 7.501(1.33); 7.289(0.83); 7.283(1.24); 7.276(0.76); 7.271(0.74); 7.265(1.23); 7.259(0.66); 4.312(1.78); 4.295(3.73); 4.278(1.78); 3.826(16); 2.902(0.53); 2.891(0.81); 2.874(1.52); 2.863(0.93); 2.857(0.85); 2.846(1.56); 2.829(0.74); 2.819(0.56); 2.525(0.45); 2.511(10.14); 2.507(20.31); 2.502(26.35); 2.498(18.6); 2.494(8.7); 1.91(0.85); 1.505(9.87); 1.252(0.42); 1.236(0.42); 1.111(3.28); 0.898(0.4); 0.008(0.41); 0(11.12); −0.008(0.36) |
| I-033 | 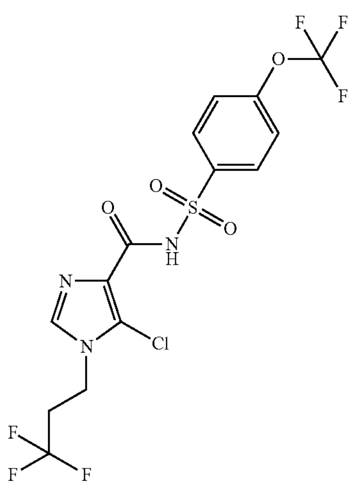 [SMILES: O=C(NS(=O)(=O)c1ccc(OC(F)(F)F)cc1)c1ncn(CCC(F)(F)F)c1Cl] | Example I-033: 1H-NMR(400.0 MHz, d6-DMSO): δ = 8.316(0.54); 8.14(1.67); 8.133(13.15); 8.128(4.35); 8.116(4.77); 8.111(14.44); 8.104(1.65); 8.077(16); 7.65(8.39); 7.629(7.69); 4.312(5.51); 4.295(11.74); 4.278(5.68); 3.383(0.74); 2.918(0.85); 2.901(1.66); 2.89(2.49); 2.873(4.67); 2.862(2.92); 2.856(2.68); 2.846(4.79); 2.828(2.34); 2.818(1.75); 2.801(0.83); 2.676(1.15); 2.671(1.5); 2.667(1.13); 2.541(1.25); 2.511(89.16); 2.507(170.43); 2.502(217.14); 2.498(154.39); 2.494(73.8); 2.334(1.03); 2.329(1.36); 2.325(1); 0.008(2.09); 0(44.44); −0.008(1.6) |

-continued

(I)
| Example No. | Structure | NMR peak list |
|---|---|---|
| I-034 | 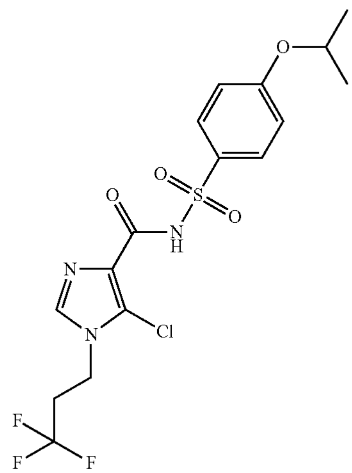 [SMILES: CC(C)Oc1ccc(S(=O)(=O)NC(=O)c2ncn(CCC(F)(F)F)c2Cl)cc1] | Example I-034: 1H-NMR(400.0 MHz, d6-DMSO): δ = 8.045(4.56); 7.904(3.91); 7.882(4.17); 7.111(3.87); 7.089(3.68); 5.757 (0.67); 4.769(0.39); 4.754(1.03); 4.738(1.4); 4.723(1.04); 4.708(0.4); 4.307(1.66); 4.29(3.57); 4.273(1.73); 4.097(0.66); 3.34(0.56); 3.169 (14.87); 2.896(0.47); 2.885(0.72); 2.868(1.38); 2.857(0.86); 2.851(0.8); 2.84(1.43); 2.823(0.69); 2.812(0.51); 2.525(0.47); 2.511(14.4); 2.507 (28.68); 2.502(37.09); 2.498(26.9); 1.505(0.33); 1.299(16); 1.284(15.82); 0.008(0.46); 0(13.3); −0.008(0.51) |
| I-035 | 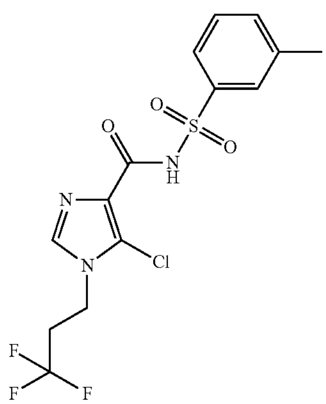 [SMILES: Cc1cccc(S(=O)(=O)NC(=O)c2ncn(CCC(F)(F)F)c2Cl)c1] | Example I-035: 1H-NMR(400.0 MHz, d6-DMSO): δ = 8.058(6.06); 7.95(1.3); 7.795(4.52); 7.782(1.45); 7.518(5.05); 7.51 (3.17); 7.503(3.05); 4.309(3.02); 4.292(6.26); 4.274(3.11); 3.494(0.38); 3.341(0.8); 3.223(0.43); 3.169(0.51); 2.916(0.44); 2.899(0.86); 2.888 (1.35); 2.871(2.39); 2.86(1.63); 2.854(1.44); 2.843(2.46); 2.826(1.23); 2.816(0.91); 2.798(0.43); 2.506(36.91); 2.502(46.23); 2.498(34.29); 2.403(16); 1.505(12.95); 1.251(0.52); 1.236(0.56); 0.897(0.49); 0.008 (1.82); 0.003(11.84); 0(43.72); −0.008(2.22) |
| I-036 | 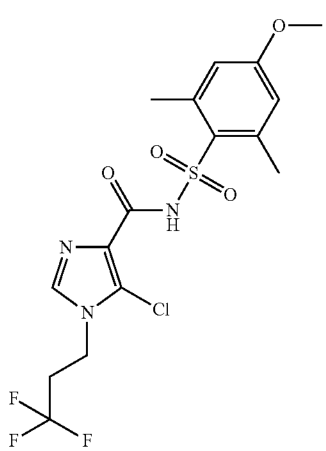 [SMILES: COc1cc(C)c(S(=O)(=O)NC(=O)c2ncn(CCC(F)(F)F)c2Cl)c(C)c1] | Example I-036: 1H-NMR(400.0 MHz, d6-DMSO): δ = 8.074(0.53); 8.054(1.82); 6.777(4.03); 4.304(1.17); 4.296(0.7); 4.287 (2.41); 4.269(1.17); 3.792(9.72); 3.776(1.54); 3.329(4.12); 2.901(0.39); 2.89(0.56); 2.873(1.01); 2.862(0.66); 2.857(0.67); 2.845(1.02); 2.829 (0.51); 2.818(0.38); 2.675(0.32); 2.67(0.42); 2.632(16); 2.584(1.23); 2.506(45.22); 2.502(58.78); 2.497(43.35); 2.329(0.37); 2.295(1.13); 0.007(0.83); 0(20.01); −0.008(0.93) |

(I)

| Example No. | Structure | NMR peak list |
|---|---|---|
| I-037 | 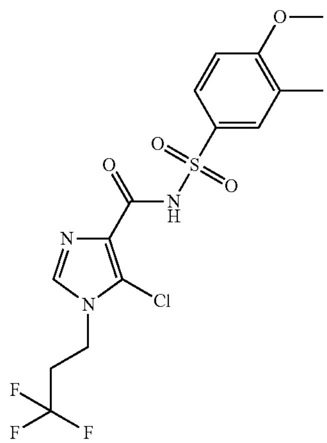 [SMILES: COc1ccc(S(=O)(=O)NC(=O)c2ncn(CCC(F)(F)F)c2Cl)cc1C] | Example I-037: 1H-NMR(400.0 MHz, d6-DMSO): δ = 8.044(5.02); 7.85(2.02); 7.829(2.15); 7.749(3.87); 7.154(2.77); 7.133 (2.61); 5.758(0.73); 4.305(2.84); 4.289(5.27); 4.272(2.87); 3.878(16); 3.503(0.47); 3.331(11.57); 2.911(0.52); 2.884(1.51); 2.867(2.43); 2.855(2.06); 2.84(2.4); 2.824(1.44); 2.795(0.49); 2.672(0.84); 2.503 (115.35); 2.33(0.85); 2.198(15.23); 1.505(1.04); 0(12.18); −0.003(11.3) |
| I-038 | 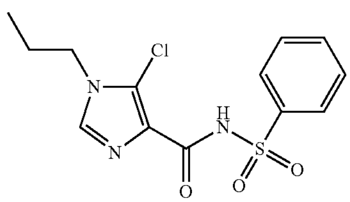 [SMILES: CCCn1cnc(C(=O)NS(=O)(=O)c2ccccc2)c1Cl] | Example I-038: 1H-NMR(400.0 MHz, d6-DMSO): δ = 8.004(15.73); 7.987(7.27); 7.879(0.4); 7.724(1.18); 7.706(3.65); 7.687 (2.9); 7.646(5.29); 7.626(7.31); 7.608(2.8); 3.976(4.43); 3.959(8.1); 3.941(4.56); 3.612(0.33); 3.594(0.37); 3.578(0.35); 3.507(0.4); 3.484 (0.39); 3.458(0.4); 3.451(0.4); 3.437(0.39); 3.425(0.41); 3.37(0.39); 3.355(0.39); 3.339(0.37); 3.33(0.37); 3.318(0.36); 3.304(0.36); 3.261 (0.32); 2.672(0.38); 2.507(40.6); 2.503(52.43); 2.499(40.87); 2.33 (0.37); 1.741(0.57); 1.723(2.61); 1.705(5.06); 1.686(5.12); 1.668 (2.73); 1.65(0.66); 1.503(4.07); 0.854(0.48); 0.837(8.28); 0.818 (16); 0.8(7.23); 0(2.35) |
| I-039 | 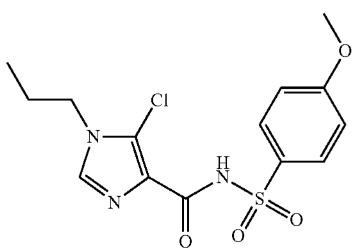 [SMILES: CCCn1cnc(C(=O)NS(=O)(=O)c2ccc(OC)cc2)c1Cl] | Example I-039: 1H-NMR(400.0 MHz, d6-DMSO): δ = 7.987(5.1); 7.946(0.45); 7.939(3.98); 7.934(1.31); 7.922(1.31); 7.916 (4.34); 7.909(0.47); 7.154(0.49); 7.147(4.17); 7.142(1.35); 7.129(1.26); 7.124(3.98); 7.117(0.42); 5.757(3.88); 3.975(1.85); 3.958(3.33); 3.94 (1.85); 3.846(16); 2.511(9.85); 2.507(19.79); 2.503(25.9); 2.498(18.68); 2.494(8.95); 1.722(1.13); 1.704(2.16); 1.686(2.16); 1.668(1.15); 1.503 (2.97); 0.836(4.1); 0.817(7.74); 0.798(3.32); 0(0.86) |
| I-040 | 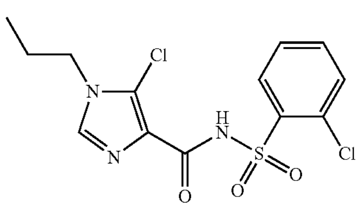 [SMILES: CCCn1cnc(C(=O)NS(=O)(=O)c2ccccc2Cl)c1Cl] | Example I-040: 1H-NMR(400.0 MHz, d6-DMSO): δ = 8.146(2.94); 8.142(3.04); 8.126(3.21); 8.123(3.14); 8.056(10.3); 7.72 (0.87); 7.716(0.9); 7.7(2.45); 7.697(2.32); 7.683(3.13); 7.679(3.02); 7.667(4); 7.663(5.04); 7.647(1.99); 7.643(1.44); 7.626(2.31); 7.622 (1.97); 7.606(2.89); 7.602(2.34); 7.589(1.47); 7.584(1.33); 3.986(3.86); 3.969(6.64); 3.951(3.97); 2.671(0.43); 2.511(28.82); 2.507(55.68); 2.502 (71.76); 2.498(52.5); 2.494(26.14); 2.334(0.39); 2.329(0.5); 2.325(0.39); 2.086(0.74); 1.758(0.47); 1.74(2.29); 1.722(4.41); 1.704(4.47); 1.686 (2.44); 1.667(0.57); 1.503(2.57); 0.854(7.61); 0.835(16); 0.817(7.11); 0(2.36) |
| I-041 | 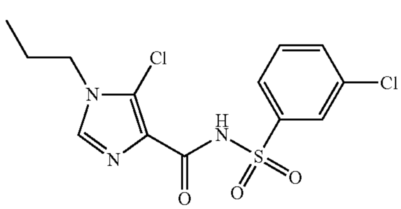 [SMILES: CCCn1cnc(C(=O)NS(=O)(=O)c2cccc(Cl)c2)c1Cl] | Example I-041: 1H-NMR(400.0 MHz, d6-DMSO): δ = 8.05(10.55); 7.99(5.66); 7.986(4.17); 7.957(3.26); 7.937(3.65); 7.808 (2.37); 7.788(3.19); 7.786(3.2); 7.694(3.63); 7.674(5.52); 7.654(2.35); 5.757(0.5); 3.987(4.4); 3.969(8.05); 3.951(4.56); 2.672(0.53); 2.507 (62.31); 2.503(80.92); 2.499(65.85); 2.33(0.62); 1.749(0.59); 1.731 (2.67); 1.712(5.2); 1.694(5.27); 1.676(2.84); 1.658(0.73); 1503(159); 0.843(8); 0.824(16); 0.806(7.4); 0(2.04) |

-continued (I)

M-C(=O)-NH-S(=O)₂-D

| Example No. | Structure | NMR peak list |
|---|---|---|
| I-042 | 1-propyl-5-chloro-imidazole-4-carboxamide N-(4-chlorophenylsulfonyl) | Example I-042: 1H-NMR(400.0 MHz, d6-DMSO): δ = 8.024(11.01); 8.009(1.07); 8.002(8.3); 7.985(3); 7.981(9.89); 7.733 (1.24); 7.727(9.7); 7.71(2.73); 7.705(8.35); 5.757(1.75); 3.983(4.19); 3.965(7.61); 3.947(4.36); 3.877(0.34); 3.871(0.35); 3.822(0.36); 3.803 (0.39); 3.785(0.41); 3.766(0.39); 3.706(0.4); 3.7(0.4); 3.68(0.41); 3.643 (0.41); 3.614(0.41); 3.61(0.4); 3.588(0.4); 3.548(0.38); 3.477(0.35); 2.672(0.37); 2.508(42.46); 2.503(57.16); 2.499(44.25); 2.33(0.43); 2.326(0.35); 1.745(0.49); 1.727(2.45); 1.709(4.84); 1.691(4.92); 1.673 (2.63); 1.654(0.61); 1.503(1.07); 0.839(7.72); 0.821(16); 0.802(7.21); 0(1.71) |
| I-043 | 1-propyl-5-chloro-imidazole-4-carboxamide N-(3-methoxyphenylsulfonyl) | Example I-043: 1H-NMR(400.0 MHz, d6-DMSO): δ = 8.01(4.75); 7.576(0.39); 7.572(0.4); 7.561(1.61); 7.557(3.85); 7.553 (1.63); 7.539(2.11); 7.52(0.65); 7.509(1.5); 7.506(1.79); 7.502(1.36); 7.286(0.77); 7.28(1.12); 7.274(0.74); 7.268(0.7); 7.262(1.12); 7.256 (0.65); 5.757(0.44); 3.981(1.69); 3.963(3.03); 3.946(1.74); 3.826(16); 2.511(10.27); 2.507(21.24); 2.502(28.31); 2.498(20.59); 2.494(10.01); 1.728(1.06); 1.709(2.02); 1.691(2.03); 1.673(1.09); 1.503(2.03); 0.841 (3.47); 0.823(7.3); 0.804(3.18); 0(0.87) |
| I-044 | 1-isopentyl-5-chloro-imidazole-4-carboxamide N-(phenylsulfonyl) | Example I-044: 1H-NMR(400.0 MHz, d6-DMSO): δ = 8.024(5.23); 8.004(2.95); 7.985(3.48); 7.982(2.53); 7.723(0.52); 7.71 (0.39); 7.705(1.76); 7.686(1.34); 7.644(2.52); 7.625(3.5); 7.607(1.33); 5.756(0.64); 4.021(1.9); 4.003(2.66); 3.984(1.96); 3.411(0.34); 3.404 (0.34); 3.392(0.34); 2.525(0.45); 2.507(23.81); 2.503(31.68); 2.498 (23.76); 1.597(0.83); 1.58(1.99); 1.561(2.02); 1.543(1.23); 1.517(0.51); 1.502(2.94); 1.485(0.96); 1.468(0.74); 1.452(0.39); 0.919(0.87); 0.9(16); 0.884(14.96); 0.008(0.73); 0(21.16); −0.008(0.8) |
| I-045 | 1-isopentyl-5-chloro-imidazole-4-carboxamide N-(4-methoxyphenylsulfonyl) | Example I-045: 1H-NMR(400.0 MHz, d6-DMSO): δ = 8.007(4.47); 7.944(0.42); 7.936(4); 7.931(1.21); 7.919(1.25); 7.914 (4.22); 7.906(0.44); 7.899(0.56); 7.152(0.44); 7.145(4.01); 7.14(1.23); 7.128(1.18); 7.122(3.77); 7.115(0.39); 5.756(0.38); 4.02(1.65); 4.002 (2.3); 3.982(1.64); 3.846(16); 3.335(0.9); 2.524(0.88); 2.511(17.55); 2.507(34.76); 2.502(45.86); 2.498(33.46); 2.493(15.98); 1.596(0.8); 1.579(1.78); 1.56(1.74); 1.542(1.04); 1.514(0.49); 1.502(5.08); 1.482 (0.82); 1.465(0.64); 1.448(0.32); 0.918(1.81); 0.9(15.23); 0.883(13.99); 0.008(1.25); 0(34.26); −0.008(1.11) |
| I-046 | 1-isopentyl-5-chloro-imidazole-4-carboxamide N-(4-chlorophenylsulfonyl) | Example I-046: 1H-NMR(400.0 MHz, d6-DMSO): δ = 8.045(5.15); 8.001(3.8); 7.979(4.62); 7.9(0.51); 7.726(4.52); 7.704(4); 5.756(1.67); 4.027(1.9); 4.008(2.82); 3.99(1.99); 2.507(23.16); 2.503 (30.41); 2.499(23.5); 1.601(0.85); 1.584(2.03); 1.564(2.09); 1.547(1.21); 1.519(0.57); 1.502(5.17); 1.486(1.05); 1.47(0.78); 1.453(0.41); 0.919 (1.79); 0.902(16); 0.886(14.03); 0(18.62); −0.008(1) |
| I-047 | 1-isopentyl-5-chloro-imidazole-4-carboxamide N-(3-methoxyphenylsulfonyl) | Example I-047: 1H-NMR(400.0 MHz, d6-DMSO): δ = 8.03(4.9); 7.9(0.57); 7.574(0.39); 7.57(0.39); 7.556(3.93); 7.551(1.66); 7.538(2.14); 7.519(0.66); 7.507(1.6); 7.504(1.86); 7.5(1.41); 7.285 (0.79); 7.279(1.18); 7.273(0.76); 7.267(0.74); 7.262(1.17); 7.255(0.66); 5.756(0.74); 4.026(1.64); 4.007(2.41); 3.988(1.72); 3.826(16); 3.383 (0.32); 3.371(0.32); 2.525(0.38); 2.511(11.26); 2.507(22.87); 2.502 (30.71); 2.498(22.99); 2.494(11.52); 1.602(0.74); 1.585(1.76); 1.566 (1.77); 1.548(1.06); 1.521(0.5); 1.502(5.53); 1.489(0.92); 1.472(0.68); 1.455(0.35); 0.918(1.96); 0.903(15.78); 0.886(13.57); 0.008(0.68); 0(21.63); −0.008(0.9) |

-continued

(I)
| Example No. | Structure | NMR peak list |
|---|---|---|
| I-048 | 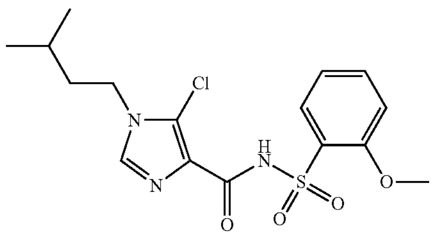 [SMILES: COc1ccccc1S(=O)(=O)NC(=O)c1ncn(CCC(C)C)c1Cl] | Example I-048: 1H-NMR(400.0 MHz, d6-DMSO): δ = 8.035(3.99); 7.899(0.44); 7.89(1.5); 7.886(1.6); 7.871(1.63); 7.866 (1.64); 7.69(0.61); 7.686(0.61); 7.669(1.18); 7.651(0.75); 7.647(0.71); 7.239(1.81); 7.218(1.66); 7.164(0.98); 7.144(1.8); 7.126(0.89); 4.027 (1.74); 4.009(2.37); 3.99(1.81); 3.843(16); 3.326(1.23); 2.671(0.33); 2.524(0.81); 2.311(18.94); 2.506(38.1); 2.502(50.8); 2.497(37.43); 2.493 (18.16); 2.328(0.34); 1.611(0.78); 1.595(1.91); 1.576(1.93); 1.557(1.25); 1.538(0.48); 1.522(0.79); 1.502(4.06); 1.489(0.73); 1.472(0.36); 0.918 (1.67); 0.909(15.85); 0.903(2.65); 0.892(14.89); 0.008(1.18); 0(35.28); −0.008(1.18) |
| I-049 | 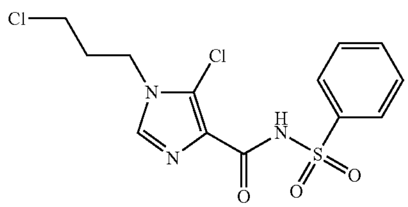 [SMILES: O=C(NS(=O)(=O)c1ccccc1)c1ncn(CCCCl)c1Cl] | Example I-049: 1H-NMR(400.0 MHz, d6-DMSO): δ = 8.007(16); 7.991(1.69); 7.986(7.25); 7.982(5.11); 7.887(1.05); 7.726 (0.61); 7.723(1.12); 7.72(0.71); 7.71(0.83); 7.705(3.61); 7.699(1.1); 7.689(1.75); 7.686(2.88); 7.683(1.52); 7.645(4.99); 7.628(3.87); 7.625 (7.14); 7.611(1.14); 7.607(2.76); 5.756(7.96); 4.153(3.83); 4.136(6.23); 4.118(3.79); 3.652(0.69); 3.642(4.81); 3.637(1.84); 3.626(9.38); 3.611 (4.91); 2.672(0.38); 2.525(0.94); 2.511(21.28); 2.507(43.19); 2.502(57.2); 2.498(41.66); 2.494(20.09); 2.329(0.39); 2.192(1.11); 2.176(3.26); 2.158 (4.18); 2.141(3.1); 2.125(0.98); 1.504(9.15); 1.249(0.33); 1.234(0.37); 0.008(2.11); 0(60.33); −0.008(2.11) |
| I-050 | 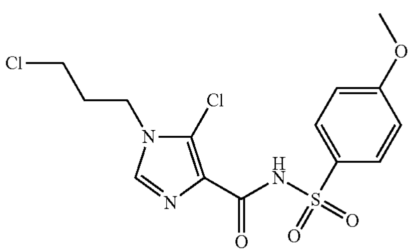 [SMILES: COc1ccc(S(=O)(=O)NC(=O)c2ncn(CCCCl)c2Cl)cc1] | Example I-050: 1H-NMR(400.0 MHz, d6-DMSO): δ = 7.992(5.24); 7.945(0.44); 7.937(4.05); 7.933(1.38); 7.92(1.43); 7.915 (4.38); 7.908(0.5); 7.887(0.81); 7.153(0.48); 7.146(4.28); 7.141(143); 7.128(1.31); 7.123(4.09); 7.116(0.47); 5.756(3.04); 4.152(1.88); 4.135 (3.13); 4.117(1.79); 3.846(16); 3.652(0.49); 3.64(2.3); 3.625(4.4); 3.609 (2.27); 3.364(0.35); 3.347(0.37); 3.329(0.34); 3.318(0.35); 3.304(0.35); 2.511(12.83); 2.507(25.27); 2.502(33.16); 2.498(24.66); 2.19(0.58); 2.174(1.64); 2.157(2.17); 2.14(1.51); 2.124(0.45); 1.504(7); 1.234(0.32); 0.008(1.17); 0(29.62); −0.008(1.24) |
| I-051 | 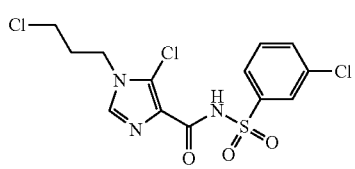 [SMILES: O=C(NS(=O)(=O)c1cccc(Cl)c1)c1ncn(CCCCl)c1Cl] | Example I-051: 1H-NMR(400.0 MHz, d6-DMSO): δ = 8.316(0.44); 8.133(0.35); 8.046(16); 7.991(4.52); 7.987(8.22); 7.982 (5.36); 7.957(3.32); 7.954(4.18); 7.951(2.87); 7.937(3.79); 7.935(4.58); 7.931(3.31); 7.808(2.64); 7.806(3.06); 7.803(2.81); 7.801(2.61); 7.788 (3.81); 7.786(4.02); 7.783(4.04); 7.781(3.42); 7.692(5.51); 7.672(8.42); 7.652(3.54); 5.756(1.34); 4.162(5.58); 4.144(9.22); 4.126(5.71); 4.063 (0.35); 3.847(0.33); 3.836(0.37); 3.828(0.34); 3.821(0.39); 3.807(0.37); 3.796(0.35); 3.777(0.36); 3.768(0.37); 3.751(0.37); 3.726(0.38); 3.72 (0.38); 3.711(0.39); 3.648(7.35); 3.633(14.25); 3.617(7.56); 3.569(0.43); 3.507(0.47); 3.497(0.4); 3.49(0.4); 3.486(0.41); 3.476(0.39); 3.455 (0.41); 3.44(0.44); 3.424(0.39); 3.405(0.37); 3.38(0.38); 3.363(0.46); 3.346 (0.46); 3.34(0.39); 3.328(0.42); 3.313(0.42); 3.298(0.36); 3.187(0.47); 3.169(10.49); 2.891(0.42); 2.731(0.33); 2.676(0.72); 2.672(0.97); 2.667 (0.73); 2.663(0.39); 2.644(0.51); 2.525(2.67); 2.511(52.6); 2.507(102.88); 2.502(133.57); 2.498(97.06); 2.494(47.13); 2.334(0.69); 2.329(0.94); 2.325(0.72); 2.199(1.65); 2.183(4.96); 2.165(6.44); 2.149(4.78); 2.133 (1.51); 1.504(2.18); 0.146(0.5); 0.008(4.84); 0(118.45); −0.008(4.78); −0.02(0.35); −0.15(0.53) |
| I-052 | 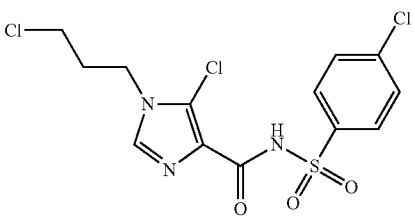 [SMILES: O=C(NS(=O)(=O)c1ccc(Cl)cc1)c1ncn(CCCCl)c1Cl] | Example I-052: 1H-NMR(400.0 MHz, d6-DMSO): δ = 8.026(16); 8.014(0.38); 8.007(1.48); 8.001(12.23); 7.996(4.06); 7.984 (4.4); 7.979(14.84); 7.973(1.78); 7.733(1.71); 7.726(13.83); 7.721 (4.22); 7.71(3.86); 7.705(12.01); 7.698(1.38); 5.756(3.28); 4.159(4.77); 4.141(7.87); 4.123(5.01); 3.645(6.25); 3.63(12.49); 3.614(6.64); 2.672 (0.42); 2.525(0.46); 2.512(27.74); 2.508(57.41); 2.503(76.77); 2.498 (56.26); 2.494(27.64); 2.334(0.47); 2.33(0.62); 2.325(0.48); 2.196(1.38); 2.18(4.23); 2.162(5.56); 2.146(4.26); 2.129(1.44); 2.087(3.01); 1.504(1.11); 0.008(1.34); 0(48.26); −0.008(1.95) |

-continued
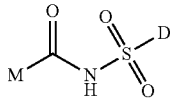
(I)
| Example No. | Structure | NMR peak list |
|---|---|---|
| I-053 | 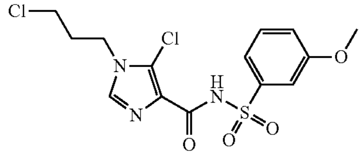 [SMILES: COc1cccc(S(=O)(=O)NC(=O)c2ncn(CCCCl)c2Cl)c1] | Example I-053: 1H-NMR(400.0 MHz, d6-DMSO): δ = 8.012(4.91); 7.887(0.6); 7.574(0.36); 7.57(0.37); 7.555(3.77); 7.55 (1.58); 7.538(2.11); 7.518(0.64); 7.507(1.5); 7.503(1.74); 7.499(1.33); 7.284(0.77); 7.278(1.15); 7.272(0.73); 7.266(0.7); 7.26(1.14); 7.254(0.64); 5.756(0.57); 4.157(1.73); 4.139(2.85); 4.122(1.77); 3.826(16); 3.646 (2.23); 3.636(1.02); 3.63(4.15); 3.62(0.71); 3.614(2.16); 2.524(0.63); 2.511(14.13); 2.507(28.61); 2.502(37.86); 2.498(27.49); 2.493(13.19); 2.196(0.5); 2.18(1.44); 2.162(1.82); 2.145(1.34); 2.129(0.41); 1.504(5.1); 0.008(0.66); 0(18.97); −0.008(0.63) |
| I-054 | 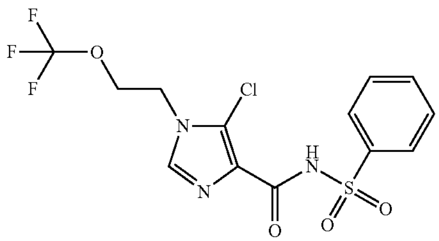 [SMILES: O=C(NS(=O)(=O)c1ccccc1)c1ncn(CCOC(F)(F)F)c1Cl] | Example I-054: 1H-NMR(400.0 MHz, d6-DMSO): δ = 8.029(6.48); 8.005(3.66); 7.993(4.16); 7.99(3.26); 7.918(1.11); 7.722 (0.78); 7.71(2.05); 7.697(1.42); 7.645(2.81); 7.632(4.16); 7.619(1.82); 4.405(0.65); 4.386(16); 3.344(1.25); 2.615(0.37); 2.525(0.58); 2.522 (0.71); 2.518(0.78); 2.509(22.13); 2.506(47.73); 2.504(66.53); 2.5(49.91); 2.498(24.5); 2.388(0.38); 1.508(8.77); 1.252(0.38); 1.242(0.41); 0.899 (0.38); 0.005(2.38); 0(65.85); −0.006(3.06) |
| I-055 | 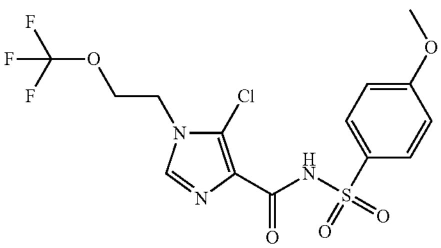 [SMILES: COc1ccc(S(=O)(=O)NC(=O)c2ncn(CCOC(F)(F)F)c2Cl)cc1] | Example I-055: 1H-NMR(400.0 MHz, d6-DMSO): δ = 8.017(4.64); 7.952(0.36); 7.938(4.01); 7.935(1.31); 7.927(1.38); 7.923 (4.32); 7.918(1.88); 7.147(3.94); 7.144(1.32); 7.132(3.84); 5.761(3.38); 4.406(0.7); 4.386(12.72); 3.847(16); 3.351(1.58); 2.522(0.44); 2.51 (14.21); 2.507(29.6); 2.504(39.99); 2.501(28.87); 2.498(13.38); 1.509 (11.37); 1.253(0.52); 1.242(0.51); 0.899(0.5); 0.005(1.63); 0(44.51); −0.006(1.59) |
| I-056 | 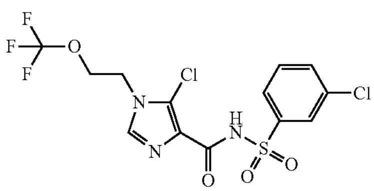 [SMILES: O=C(NS(=O)(=O)c1cccc(Cl)c1)c1ncn(CCOC(F)(F)F)c1Cl] | Example I-056: 1H-NMR(400.0 MHz, d6-DMSO): δ = 8.046(4.67); 7.995(1.43); 7.99(2.77); 7.986(1.92); 7.96(1.39); 7.948 (0.34); 7.94(1.56); 7.914(0.55); 7.81(0.96); 7.807(0.94); 7.789(1.29); 7.786(1.35); 7.695(1.67); 7.675(2.58); 7.655(1.1); 5.757(3.31); 4.392(16); 2.672(0.35); 2.525(1.09); 2.512(18.25); 2.507(36.04); 2.503(47.06); 2.498(33.84); 2.494(16.01); 1.79(0.41); 1.509(4.34); 1.256(0.35); 1.24 (0.64); 1.236(0.63); 0.008(0.45); 0(10.82) |
| I-057 | 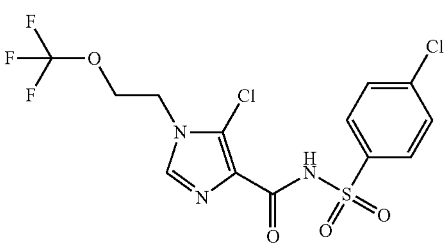 [SMILES: O=C(NS(=O)(=O)c1ccc(Cl)cc1)c1ncn(CCOC(F)(F)F)c1Cl] | Example I-057: 1H-NMR(400.0 MHz, d6-DMSO): δ = 8.035(6.38); 8.011(0.56); 8.005(4.73); 8(1.61); 7.988(1.67); 7.983 (5.73); 7.977(0.72); 7.735(0.68); 7.729(5.42); 7.724(1.73); 7.712(1.5); 7.707(4.7); 7.701(0.57); 5.757(1.2); 4.39(16); 2.672(0.36); 2.525(0.92); 2.511(19.25); 2.507(38.52); 2.502(50.69); 2.498(36.69); 2.494(17.56); 1.509(0.6); 0.008(0.44); 0(12.17); −0.008(0.36) |
| I-058 | 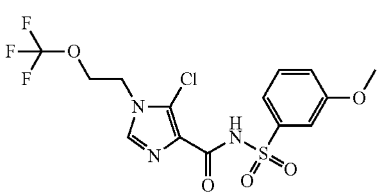 [SMILES: COc1cccc(S(=O)(=O)NC(=O)c2ncn(CCOC(F)(F)F)c2Cl)c1] | Example I-058: 1H-NMR(400.0 MHz, d6-DMSO): δ = 8.027(3.64); 7.948(0.4); 7.914(1.91); 7.578(0.39); 7.574(0.39); 7.563 (1.51); 7.559(3.43); 7.54(1.77); 7.521(0.58); 7.509(1.41); 7.506(1.69); 7.502(1.28); 7.286(0.64); 7.281(0.94); 7.274(0.64); 7.268(0.59); 7.262 (0.88); 7.257(0.53); 5.757(0.56); 4.403(1.27); 4.39(13.95); 3.827(15.56); 3.345(0.55); 3.315(0.52); 2.525(0.86); 2.511(16.37); 2.507(32.72); 2.502 (43.04); 2.498(31.16); 2.493(14.97); 1.509(16); 1.256(0.6); 1.24(0.62); 0.9(0.57); 0.008(0.37); 0(10.91); −0.008(0.36) |

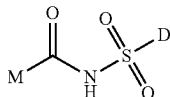
(I)
| Example No. | Structure | NMR peak list |
|---|---|---|
| I-059 | 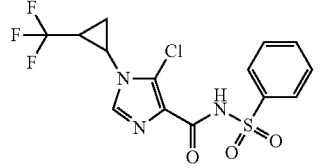 [SMILES: O=C(NS(=O)(=O)c1ccccc1)c1ncn(C2CC2C(F)(F)F)c1Cl] | Example I-059: 1H-NMR(400.0 MHz, d6-DMSO): δ = 8(1.56); 7.989(1.44); 7.97(1.46); 7.927(0.38); 7.893(1.9); 7.694(0.62); 7.676(0.51); 7.635(0.99); 7.616(1.35); 7.597(0.53); 5.756(1.76); 3.864 (0.35); 3.852(0.7); 3.844(0.87); 3.832(0.85); 3.823(0.58); 3.335(0.61); 2.716(0.52); 2.711(0.5); 2.702(0.52); 2.676(0.38); 2.671(0.37); 2.506 (25.84); 2.502(32.11); 2.498(23.81); 1.85(0.49); 1.834(0.67); 1.824(0.64); 1.809(0.47); 1.606(0.54); 1.589(1.07); 1.569(1.01); 1.552(0.42); 1.503 (16); 1.247(0.59); 1.232(0.61); 0.896(0.52); 0(35.67) |
| I-060 | 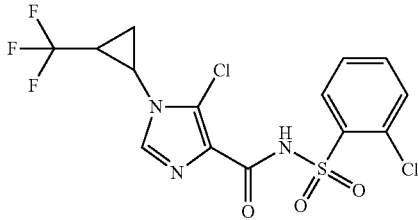 [SMILES: O=C(NS(=O)(=O)c1ccccc1Cl)c1ncn(C2CC2C(F)(F)F)c1Cl] | Example I-060: 1H-NMR(400.0 MHz, d6-DMSO): δ = 8.145(1.09); 8.14(1.14); 8.125(1.2); 8.121(1.19); 8.041(3.22); 7.927 (0.4); 7.892(1.86); 7.699(0.8); 7.695(0.77); 7.681(0.98); 7.677(0.95); 7.66(1.3); 7.657(1.71); 7.64(0.74); 7.637(0.56); 7.627(0.81); 7.623(0.66); 7.607(1); 7.589(0.5); 7.585(0.44); 5.756(3.57); 3.877(0.49); 3.866(0.72); 3.857(0.97); 3.848(0.79); 3.845(0.79); 3.836(0.62); 3.831(0.6); 3.822 (0.39); 2.75(0.39); 2.742(0.54); 2.733(0.51); 2.725(0.6); 2.718(0.49); 2.708(0.38); 2.701(0.38); 2.524(0.77); 2.511(15.43); 2.506(31.05); 2.502 (40.96); 2.497(29.49); 2.493(14.04); 1.871(0.32); 1.858(0.48); 1.853 (0.52); 1.844(0.7); 1.833(0.63); 1.817(0.43); 1.614(0.53); 1.598(0.96); 1.577(0.91); 1.569(0.46); 1.56(0.38); 1.503(16); 1.247(0.67); 1.232(0.69); 0.896(0.54); 0.008(2.27); 0(61.06); −0.009(2.25) |
| I-061 | 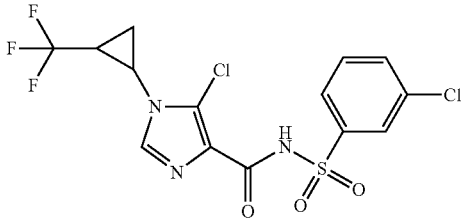 [SMILES: O=C(NS(=O)(=O)c1cccc(Cl)c1)c1ncn(C2CC2C(F)(F)F)c1Cl] | Example I-061: 1H-NMR(400.0 MHz, d6-DMSO): δ= 8.316(0.51); 8.04(16); 7.984(4.47); 7.979(8.43); 7.974(5.46); 7.951 (3.19); 7.949(4.03); 7.945(2.72); 7.931(3.67); 7.928(4.66); 7.925(3.37); 7.893(108); 7.811(2.59); 7.808(2.98); 7.806(2.71); 7.803(2.55); 7.79 (3.77); 7.788(3.85); 7.785(3.94); 7.783(3.3); 7.693(5.3); 7.673(8.17); 7.653(3.42); 3.878(1.95); 3.867(2.86); 3.858(3.84); 3.848(2.98); 3.837 (2.2); 3.82(0.64); 3.81(0.61); 3.755(0.6); 3.743(0.63); 3.532(1.13); 3.507 (1.25); 3.486(1.19); 3.476(1.19); 3.461(1.19); 3.378(1.06); 3.292(0.82); 3.259(0.72); 3.187(0.8); 3.169(1.86); 3.123(0.44); 3.116(0.43); 3.076(0.37); 3.055(0.36); 3.039(0.35); 3.021(0.33); 2.762(0.45); 2.752(0.88); 2.744 (1.07); 2.735(1.51); 2.727(1.97); 2.718(1.84); 2.709(2.07); 2.701(1.58); 2.692(1.19); 2.683(1); 2.676(1.01); 2.671(1.12); 2.666(0.93); 2.524 (2.46); 2.511(53.15); 2.507(107.03); 2.502(141.26); 2.498(102.11); 2.493 (49.3); 2.338(0.41); 2.333(0.76); 2.329(1); 2.324(0.73); 2.32(0.4); 1.859 (1.3); 1.842(1.87); 1.831(2.16); 1.821(1.72); 1.818(1.68); 1.805(1.35); 1.616(1.73); 1.598(3.43); 1.578(3.35); 1.561(1.4); 1.503(8.96); 1.248 (0.81); 1.232(0.89); 0.896(0.64); 0.146(0.85); 0.008(7.25); 0(197.4); −0.008(7.73); −0.033(0.33); −0.15(0.9) |
| I-062 | 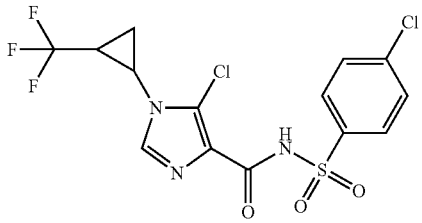 [SMILES: O=C(NS(=O)(=O)c1ccc(Cl)cc1)c1ncn(C2CC2C(F)(F)F)c1Cl] | Example I-062: 1H-NMR(400.0 MHz, d6-DMSO): δ = 8.316(0.49); 8.02(14.48); 7.995(1.68); 7.988(13.15); 7.984(5.03); 7.97 2(4.87); 7.967(16); 7.961(2.22); 7.927(0.37); 7.893(0.67); 7.723(14.1); 7.706(4.19); 7.702(12.32); 3.875(1.99); 3.864(3.18); 3.854(4.17); 3.84 5(3.22); 3.834(2.23); 3.822(0.39); 3.64(0.45); 3.508(0.83); 3.371(1.11) ; 2.747(0.97); 2.738(1.18); 2.73(1.71); 2.721(2.24); 2.713(2.06); 2.704 (2.35); 2.696(1.76); 2.687(1.32); 2.676(1.45); 2.671(1.43); 2.667(1.03); 2.662(0.66); 2.524(2.78); 2.511(63.98); 2.506(128.75); 2.502(169.38); 2.497(122.76); 2.493(59.51); 2.333(0.9); 2.329(1.18); 2.324(0.89); 1.855(1.5); 1.838(2.22); 1.827(2.56); 1.818(2.04); 1.814(1.98); 1.801 (1.62); 1.612(2); 1.594(4.05); 1.574(4.04); 1.557(1.67); 1.503(5.58); 1.247 (0.57); 1.232(0.66); 0.896(0.45); 0.146(0.63); 0.008(5.51); 0(150.86); −0.008(5.68); −0.15(0.66) |
| I-063 | 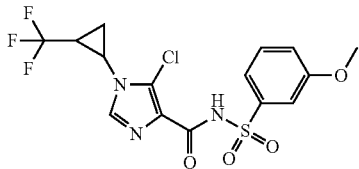 [SMILES: COc1cccc(S(=O)(=O)NC(=O)c2ncn(C3CC3C(F)(F)F)c2Cl)c1] | Example I-063: 1H-NMR(400.0 MHz, d6-DMSO): δ = 7.835(0.72); 7.456(0.8); 7.438(1.64); 7.419(2.64); 7.402(1.02); 7.094 (0.72); 5.756(2.92); 3.791(16); 3.335(2.97); 3.201(0.39); 2.786(0.47); 2.767(0.33); 2.671(0.89); 2.667(0.86); 2.65(0.61); 2.569(0.41); 2.506 (46.23); 2.502(58.17); 2.498(45.07); 2.328(0.35); 1.989(0.44); 1.813(0.68); 1.803(0.76); 1.791(0.67); 1.776(0.42); 1.582(0.43); 1.564(0.9); 1.546 (0.9); 1.528(0.53); 1.506(0.45); 1.487(0.33); 1.329(0.41); 1.309(0.42); 0.901(0.81); 0.883(1.57); 0.865(0.69); 0(11.03) |

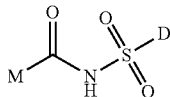
(I)
| Example No. | Structure | NMR peak list |
|---|---|---|
| I-064 | 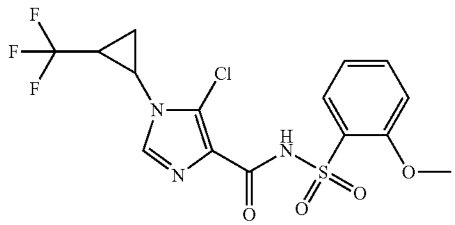 [SMILES: COc1ccccc1S(=O)(=O)NC(=O)c1ncn(C2CC2C(F)(F)F)c1Cl] | Example I-064: 1H-NMR(400.0 MHz, d6-DMSO): δ = 8.018(3.01); 7.888(1.55); 7.884(1.64); 7.868(1.67); 7.864(1.69); 7.684 (0.56); 7.666(1.15); 7.647(0.67); 7.236(1.73); 7.215(1.57); 7.161(0.96); 7.142(1.74); 7.123(0.85); 3.876(0.57); 3.866(0.95); 3.856(1.37); 3.841 (16); 3.324(1.45); 2.753(0.33); 2.745(0.49); 2.736(0.63); 2.727(0.6); 2.719(0.69); 2.71(0.52); 2.702(0.4); 2.675(0.39); 2.671(0.43); 2.51(25.51); 2.506(49.83); 2.502(64.42); 2.497(46.61); 2.493(22.68); 2.328(0.41); 2.324(0.32); 1.867(0.44); 1.85(0.68); 1.839(0.79); 1.83(0.63); 1.826 (0.62); 1.813(0.48); 1.615(0.58); 1.598(1.2); 1.578(1.18); 1.561(0.49); 1.503(1.94); 0.008(2.17); 0(50.56); −0.008(1.88) |
| I-065 | 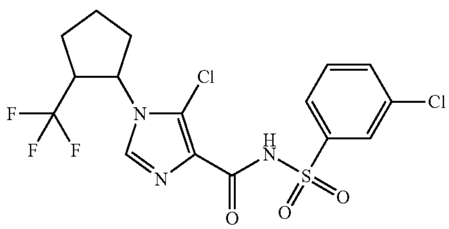 [SMILES: O=C(NS(=O)(=O)c1cccc(Cl)c1)c1ncn(C2CCCC2C(F)(F)F)c1Cl] | Example I-065: 1H-NMR(400.0 MHz, d6-DMSO): δ = 8.185(9.64); 8.001(5.45); 7.997(7.79); 7.992(4.84); 7.967(4.15); 7.947 (4.51); 7.817(3.24); 7.797(4.23); 7.794(3.94); 7.702(4.41); 7.682(6.67); 7.662(2.84); 5.757(16); 4.891(1.39); 4.871(3.72); 4.851(3.73); 4.831 (1.41); 3.732(0.36); 3.689(0.39); 3.654(0.42); 3.607(0.44); 3.508(0.5); 3.478(0.48); 3.464(0.48); 3.428(0.47); 3.354(0.59); 3.327(1.06); 3.306 (2.02); 3.285(2.32); 3.259(1.97); 3.238(1.02); 3.213(0.49); 3.186(0.36); 2.676(0.6); 2.672(0.7); 2.507(90.09); 2.503(102.22); 2.499(72.85); 2.334 (0.75); 2.33(0.88); 2.325(0.75); 2.296(2.51); 2.276(4.81); 2.257(4.02); 2.234(1.46); 2.202(0.38); 2.147(1.02); 2.13(1.87); 2.125(1.99); 2.119 (1.79); 2.109(1.48); 2.097(2.49); 2.076(1.3); 2.071(1.2); 2.018(1.66); 2.011(1.66); 1.996(1.81); 1.98(1.59); 1.966(1.95); 1.944(2.38); 1.934 (1.32); 1.922(2.31); 1.912(1.83); 1.9(1.16); 1.889(1.58); 1.868(0.67); 1.757 (0.52); 1.734(1.57); 1.711(2.23); 1.704(1.71); 1.688(1.69); 1.682(1.87); 1.66(1.05); 1.509(0.48); 0(6.71) |
| I-066 | 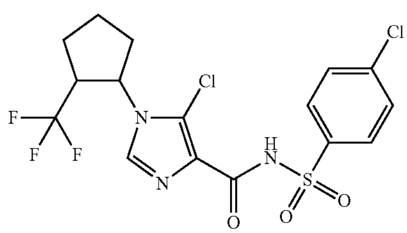 [SMILES: O=C(NS(=O)(=O)c1ccc(Cl)cc1)c1ncn(C2CCCC2C(F)(F)F)c1Cl] | Example I-066: 1H-NMR(400.0 MHz, d6-DMSO): δ = 8.169(12.39); 8.01(13.32); 7.993(5.23); 7.989(16); 7.734(15.38); 7.712 (13.45); 5.757(14.9); 4.887(1.55); 4.867(4.45); 4.847(4.56); 4.827 (1.69); 3.624(0.44); 3.51(0.55); 3.442(0.57); 3.423(0.57); 3.395(0.56); 3.384(0.56); 3.35(0.69); 3.325(1.23); 3.303(2.26); 3.282(2.44); 3.277(2.6); 3.256(2.31); 3.235(1.12); 3.23(1.11); 3.209(0.59); 2.677(0.54); 2.673 (0.73); 2.668(0.58); 2.508(77.08); 2.504(103.06); 2.499(79.63); 2.335(0.6); 2.33(0.84); 2.326(0.68); 2.293(2.4); 2.288(2.38); 2.272(4.94); 2.254 (4.11); 2.232(1.54); 2.199(0.4); 2.145(1.16); 2.128(1.8); 2.124(2.09); 2.118(1.89); 2.108(1.39); 2.096(2.54); 2.092(2.62); 2.075(1.39); 2.07 (1.43); 2.017(1.66); 2.01(1.66); 1.995(1.82); 1.978(1.56); 1.963(2.11); 1.942(2.74); 1.932(1.33); 1.92(2.62); 1.91(2.09); 1.899(1.22); 1.887(1.89); 1.866(0.77); 1.756(0.57); 1.733(1.78); 1.71(2.43); 1.703(1.94); 1.687 (1.64); 1.68(2.21); 1.658(1.25); 1.509(0.64); 0(8.23) |
| I-067 | 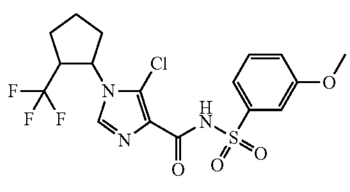 [SMILES: COc1cccc(S(=O)(=O)NC(=O)c2ncn(C3CCCC3C(F)(F)F)c2Cl)c1] | Example I-067: 1H-NMR(400.0 MHz, d6-DMSO): δ = 8.144(2.63); 8.134(0.33); 8.012(1.27); 7.575(0.41); 7.571(0.37); 7.56 (1.23); 7.556(2.76); 7.535(1.75); 7.516(0.65); 7.505(1.71); 7.501(1.33); 7.278(0.62); 7.274(0.87); 7.267(0.66); 7.26(0.59); 7.255(0.84); 7.249 (0.57); 5.757(5.56); 4.881(0.41); 4.861(1.25); 4.841(1.27); 4.821(0.45); 3.826(14.05); 3.347(0.52); 3.322(0.67); 3.3(0.94); 3.274(0.98); 3.253 (0.83); 3.232(0.45); 2.891(0.52); 2.732(0.41); 2.52(0.38); 2.512(11.53); 2.507(25.05); 2.503(34.31); 2.498(25.91); 2.494(13.43); 2.292(0.69); 2.271(1.35); 2.253(1.14); 2.23(0.44); 2.128(0.58); 2.123(0.57); 2.117 (0.53); 2.106(0.53); 2.101(0.57); 2.096(0.64); 2.091(0.61); 2.075(0.33); 2.069(0.34); 2.016(0.5); 2.007(0.5); 1.99(0.56); 1.973(0.54); 1.963(0.62); 1.951(0.43); 1.942(0.76); 1.93(0.53); 1.92(0.81); 1.909(0.58); 1.898(0.46); 1.887(0.46); 1.733(0.43); 1.724(0.43); 1.71(0.59); 1.702(0.58); 1.693 (0.39); 1.688(0.41); 1.68(0.55); 1.509(16); 1.257(0.65); 1.241(0.7); 0.902 (0.33) |

-continued
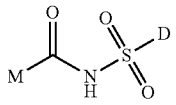
(I)
| Example No. | Structure | NMR peak list |
|---|---|---|
| I-068 | 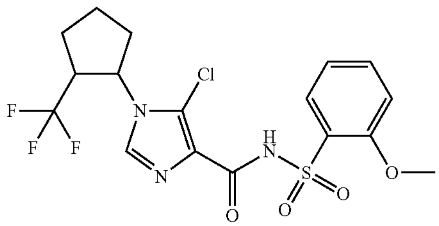 [SMILES: COc1ccccc1S(=O)(=O)NC(=O)c1ncn(C2CCCC2C(F)(F)F)c1Cl] | Example I-068: 1H-NMR(400.0 MHz, d6-DMSO): δ = 8.157(2); 8.012(1.28); 7.892(1.27); 7.888(1.41); 7.872(1.4); 7.868 (1.45); 7.686(0.45); 7.682(0.47); 7.664(0.95); 7.646(0.55); 7.643(0.54); 7.238(1.44); 7.217(1.32); 7.164(0.79); 7.145(1.45); 7.127(0.72); 5.757 (2.84); 4.879(0.52); 4.859(1.5); 4.839(1.52); 4.819(0.55); 3.822(13.64); 3.328(1.92); 3.324(1.91); 3.309(1.5); 3.302(1.63); 3.281(1.19); 3.276 (1.16); 3.255(0.9); 3.235(0.41); 3.229(0.39); 2.525(0.54); 2.52(0.8); 2.511 (13.43); 2.507(28.01); 2.502(37.44); 2.498(27.42); 2.494(13.55); 2.305 (0.67); 2.283(1.46); 2.274(1.01); 2.264(1.41); 2.242(0.71); 2.132(0.65); 2.127(0.68); 2.121(0.52); 2.111(0.44); 2.105(0.62); 2.1(0.85); 2.095(0.67); 2.078(0.44); 2.073(0.37); 2.015(0.51); 1.995(0.54); 1.984(0.5); 1.969 (0.76); 1.948(0.85); 1.938(0.38); 1.927(0.79); 1.917(0.62); 1.905(0.34); 1.894(0.55); 1.738(0.52); 1.715(0.8); 1.708(0.49); 1.693(0.62); 1.685 (0.55); 1.663(0.37); 1.509(16); 1.256(0.47); 1.241(0.49) |
| I-069 | 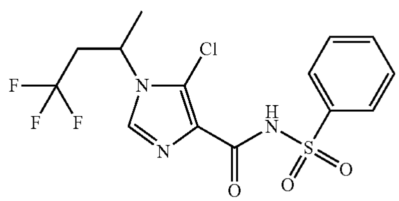 [SMILES: CC(CC(F)(F)F)n1cnc(C(=O)NS(=O)(=O)c2ccccc2)c1Cl] | Example I-069: 1H-NMR(400.0 MHz, d6-DMSO): δ = 8.317(0.37); 8.28(9.49); 8.165(1.54); 8.004(6.81); 7.986(7.71); 7.983 (5.99); 7.724(1.13); 7.706(3.57); 7.687(2.84); 7.645(5.47); 7.626(7.6); 7.608(2.94); 4.708(0.94); 4.697(1.35); 4.691(1.42); 4.681(1.56); 4.673 (1.44); 4.668(1.3); 4.656(1); 3.504(0.43); 3.336(2.04); 3.186(0.66); 3.178 (0.67); 3.17(0.63); 3.151(1.11); 3.138(0.79); 3.124(1.37); 3.112(1.58); 3.099(1.14); 3.086(1.9); 3.072(0.59); 3.06(1.37); 3.032(0.74); 3.02(0.56); 3.002(1.32); 2.991(1.6); 2.974(1.44); 2.963(2.12); 2.952(0.92); 2.946 (0.72); 2.935(1.29); 2.924(0.82); 2.908(0.34); 2.763(0.36); 2.676(0.58); 2.672(0.77); 2.667(0.59); 2.507(86.72); 2.502(113.92); 2.498(86.42); 2.334(0.59); 2.329(0.81); 2.325(0.6); 1.989(0.42); 1.514(13.15); 1.505 (16); 1.497(13.18); 1.235(0.33); 1.11(0.77); 0.008(1.26); 0(32.96); −0.008(1.73) |
| I-070 | 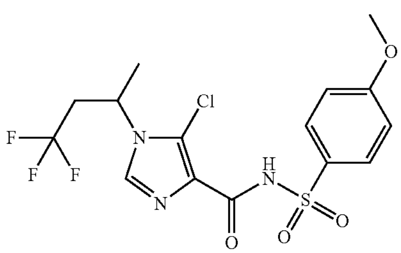 [SMILES: COc1ccc(S(=O)(=O)NC(=O)c2ncn(C(C)CC(F)(F)F)c2Cl)cc1] | Example I-070: 1H-NMR(400.0 MHz, d6-DMSO): δ = 8.267(4.13); 8.166(1.52); 7.938(4.01); 7.916(4.27); 7.146(4.1); 7.124 (3.91); 5.758(0.66); 4.708(0.56); 4.697(0.81); 4.691(0.86); 4.681(0.93); 4.673(0.86); 4.657(0.55); 3.846(16); 3.331(1.48); 3.17(0.66); 3.149 (0.57); 3.132(0.46); 3.123(0.7); 3.11(0.85); 3.098(0.58); 3.084(0.96); 3.059 (0.65); 3.031(0.38); 3.002(0.68); 2.991(0.81); 2.974(0.78); 2.963(1.1); 2.953(0.52); 2.935(0.67); 2.925(0.42); 2.507(33.29); 2.503(41.68); 2.499 (32.31); 1.513(7.21); 1.505(15.24); 1.497(6.96); 1.251(0.36); 1.236 (0.43); 0(9.73) |
| I-071 | 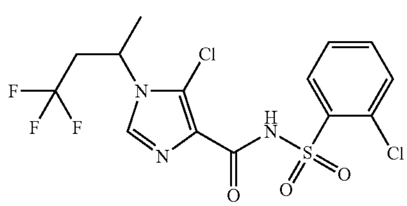 [SMILES: CC(CC(F)(F)F)n1cnc(C(=O)NS(=O)(=O)c2ccccc2Cl)c1Cl] | Example I-071: 1H-NMR(400.0 MHz, d6-DMSO): δ = 8.313(13.31); 8.166(0.51); 8.149(4.38); 8.145(4.64); 8.129(4.86); 8.125(4.89); 7.723(1.14); 7.719(1.22); 7.702(3.57); 7.685(4.08); 7.682 (4.11); 7.665(7.26); 7.649(2.84); 7.628(3.15); 7.624(2.83); 7.608(4.39); 7.59(2.02); 7.587(1.85); 4.733(0.36); 4.716(1.21); 4.705(1.65); 4.699 (1.78); 4.688(1.91); 4.681(1.83); 4.664(1.29); 4.648(0.39); 3.189(0.45); 3.162(1.12); 3.15(0.75); 3.136(1.55); 3.123(1.82); 3.111(1.32); 3.098(2.22); 3.084(0.67); 3.072(1.65); 3.044(0.7); 3.028(0.62); 3.012(1.47); 3.001 (1.8); 2.984(1.64); 2.972(2.43); 2.962(1.14); 2.945(1.51); 2.934(0.99); 2.916(0.43); 2.905(0.39); 2.676(0.66); 2.672(0.87); 2.667(0.66); 2.507 (90.75); 2.503(118.13); 2.498(89.08); 2.334(0.6); 2.329(0.8); 2.325(0.61); 2.075(1.63); 1.532(15.77); 1.514(16); 1.505(5.58); 0.008(1.28); 0(32.05); −0.008(1.66) |
| I-072 | 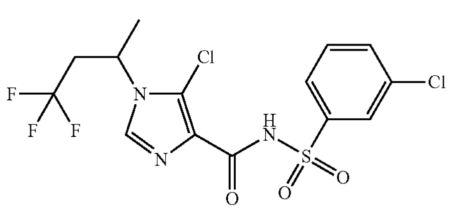 [SMILES: CC(CC(F)(F)F)n1cnc(C(=O)NS(=O)(=O)c2cccc(Cl)c2)c1Cl] | Example I-072: 1H-NMR(400.0 MHz, d6-DMSO): δ = 8.314(7.22); 8.166(1.2); 7.996(1.79); 7.992(3.57); 7.987(2.51); 7.962 (1.88); 7.941(2.1); 7.815(1.35); 7.812(1.3); 7.81(1.25); 7.795(1.8); 7.792 (1.86); 7.699(2.32); 7.679(3.59); 7.659(1.54); 4.721(0.54); 4.709(0.73); 4.704(0.84); 4.694(0.92); 4.686(0.88); 4.68(0.81); 4.669(0.62); 3.157 (0.53); 3.144(0.42); 3.131(0.79); 3.118(0.88); 3.106(0.72); 3.092(1.05); 3.08(0.39); 3.066(0.74); 3.039(0.41); 3.01(0.66); 2.999(0.84); 2.982 (0.76); 2.971(1.14); 2.96(0.54); 2.953(0.44); 2.942(0.69); 2.932(0.46); 2.645(0.68); 2.526(0.54); 2.512(15.27); 2.508(31.63); 2.504(43.08); 2.499 (33.41); 2.076(4.13); 1.521(7.91); 1.505(16); 1.252(0.38); 1.236(0.39); 0(2.22) |

(I)
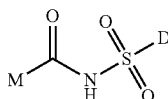
| Example No. | Structure | NMR peak list |
|---|---|---|
| I-073 | 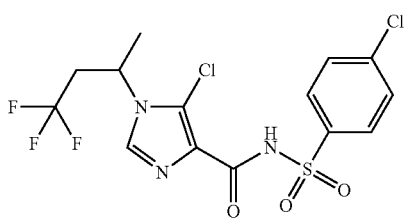 [SMILES: CC(CC(F)(F)F)n1cnc(C(=O)NS(=O)(=O)c2ccc(Cl)cc2)c1Cl] | Example I-073: 1H-NMR(400.0 MHz, d6-DMSO): δ = 8.317(0.45); 8.299(14.82); 8.004(11.49); 7.983(13.58); 7.954(0.77); 7.731(13.24); 7.709(11.36); 5.758(2.76); 4.734(0.38); 4.717(1.26); 4.706 (1.74); 4.7(1.91); 4.691(2.19); 4.682(2.02); 4.665(1.42); 4.65(0.47); 3.763(0.38); 3.682(0.5); 3.676(0.52); 3.584(0.71); 3.464(0.97); 3.456 (0.98); 3.435(1); 3.401(1.03); 3.384(1.01); 3.316(0.92); 3.286(0.85); 3.201(0.65); 3.182(0.82); 3.155(1.45); 3.142(1.11); 3.128(1.91); 3.116 (2.18); 3.103(1.69); 3.09(2.67); 3.064(1.94); 3.037(1.14); 3.025(0.86); 3.008(1.66); 2.997(1.99); 2.98(1.84); 2.969(2.58); 2.958(1.35); 2.941(1.64); 2.93(1.14); 2.912(0.59); 2.892(4.26); 2.733(3.59); 2.673(0.73); 2.508(76.36); 2.504(98.83); 2.5(80.12); 2.33(0.78); 1.91(1.71); 1.518(15.42); 1.501(16); 0(3.95) |
| I-074 | 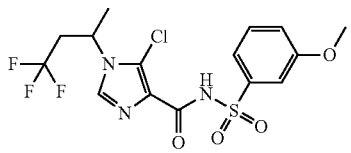 [SMILES: COc1cccc(S(=O)(=O)NC(=O)c2ncn(C(C)CC(F)(F)F)c2Cl)c1] | Example I-074: 1H-NMR(400.0 MHz, d6-DMSO): δ = 8.287(3.88); 8.165(0.78); 7.576(0.38); 7.572(0.4); 7.558(3.99); 7.54 (1.98); 7.521(0.6); 7.503(2.04); 7.287(0.73); 7.281(1.16); 7.275(0.72); 7.269(0.7); 7.264(1.07); 7.257(0.62); 4.714(0.4); 4.703(0.56); 4.697 (0.58); 4.687(0.66); 4.679(0.6); 4.674(0.56); 4.662(0.44); 3.827(16); 3.335 (0.64); 3.154(0.42); 3.142(0.32); 3.128(0.56); 3.115(0.63); 3.103(0.5); 3.089(0.76); 3.063(0.54); 3.006(0.48); 2.995(0.58); 2.978(0.51); 2.967 (0.78); 2.956(0.35); 2.939(0.48); 2.671(0.33); 2.507(38.41); 2.502(50.85); 2.498(38.64); 2.329(0.33); 2.075(3.14); 1.518(5.68); 1.505(8.59); 0(2.03) |
| I-075 | 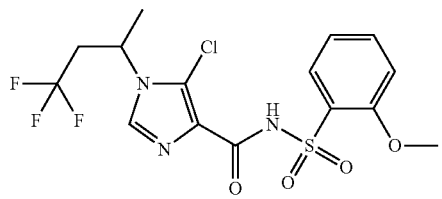 [SMILES: COc1ccccc1S(=O)(=O)NC(=O)c1ncn(C(C)CC(F)(F)F)c1Cl] | Example I-075: 1H-NMR(400.0 MHz, d6-DMSO): δ = 8.29(4.49); 7.893(1.58); 7.89(1.67); 7.874(1.74); 7.87(1.75); 7.691 (0.71); 7.687(0.73); 7.67(1.49); 7.652(0.88); 7.648(0.84); 7.241(2.15); 7.22(1.97); 7.166(1.17); 7.146(2.15); 7.127(1.08); 4.714(0.44); 4.703(0.6); 4.697(0.65); 4.686(0.72); 4.679(0.67); 4.662(0.48); 3.835(16); 3.441 (0.37); 3.332(5.41); 3.157(0.49); 3.146(0.35); 3.131(0.64); 3.119(0.72); 3.106(0.54); 3.093(0.86); 3.067(0.61); 3.041(0.35); 3.012(0.54); 3.001 (0.66); 2.984(0.6); 2.973(0.89); 2.962(0.43); 2.945(0.54); 2.934(0.35); 2.507(38.45); 2.502(49.32); 2.498(37.94); 2.33(0.34); 1.532(5.69); 1.515(5.89); 1.505(3.07); 0.008(2.96); 0(56.38) |
| I-076 | 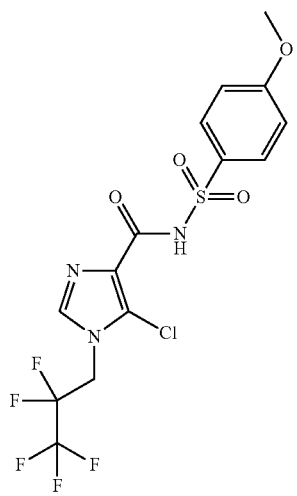 [SMILES: COc1ccc(S(=O)(=O)NC(=O)c2ncn(CC(F)(F)C(F)(F)F)c2Cl)cc1] | Example I-076: 1H-NMR(400.0 MHz, d6-DMSO): δ = 8.092(3.6); 7.952(0.4); 7.944(4); 7.94(1.34); 7.927(1.28); 7.922(4.38); 7.914(0.47); 7.163(0.43); 7.155(4.06); 7.15(1.37); 7.138(1.19); 7.133 (3.89); 7.125(0.44); 5.215(1.03); 5.175(2.18); 5.135(1.12); 3.849(16); 3.332(9.32); 2.672(0.42); 2.525(1.16); 2.511(24.89); 2.507(50.85); 2.502 (67.51); 2.498(50.17); 2.494(25.19); 2.329(0.43); 2.325(0.33); 0.008 (1.94); 0(60.71); −0.008(2.25) |

-continued
(I)
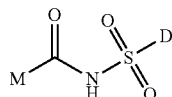
| Example No. | Structure | NMR peak list |
|---|---|---|
| I-077 | 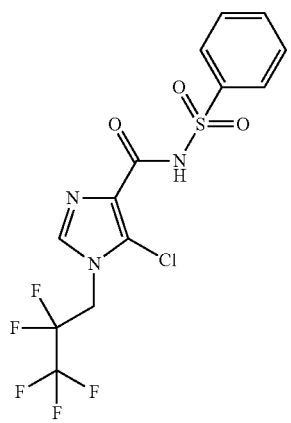 [SMILES: O=C(NS(=O)(=O)c1ccccc1)c1ncn(CC(F)(F)C(F)(F)F)c1Cl] | Example I-077: 1H-NMR(400.0 MHz, d6-DMSO): δ = 12.026(0.34); 8.317(0.52); 8.103(16); 8.011(12.58); 7.993(14.77); 7.989(11.02); 7.735(2.19); 7.722(1.65); 7.716(7.01); 7.698(5.41); 7.654 (10.22); 7.635(14.39); 7.617(5.42); 5.757(1.07); 5.216(5); 5.176(10.66); 5.136(5.51); 3.33(4.73); 2.676(1.36); 2.671(1.92); 2.666(1.42); 2.662(0.7); 2.524(4.63); 2.52(7.28); 2.511(108.27); 2.506(223.69); 2.502(298.62); 2.497(219.98); 2.493(108.76); 2.39(0.53); 2.333(1.41); 2.329(1.97); 2.324(1.46); 1.305(0.33); 0.146(1.49); 0.008(11.21); 0(338.45); −0.009(12.73); −0.15(1.5) |
| I-078 | 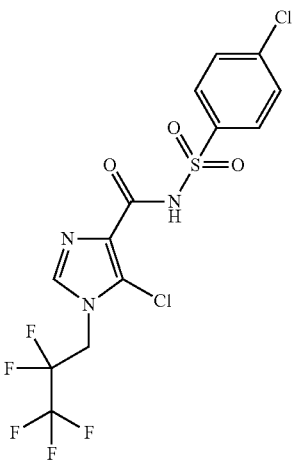 [SMILES: O=C(NS(=O)(=O)c1ccc(Cl)cc1)c1ncn(CC(F)(F)C(F)(F)F)c1Cl] | Example I-078: 1H-NMR(400.0 MHz, d6-DMSO): δ = 8.313(0.44); 8.133(1.39); 8.1(4.21); 8.004(4.74); 7.982(5.65); 7.73 (4.92); 7.709(4.31); 5.217(1.54); 5.177(3.26); 5.137(1.69); 3.807(0.35); 3.778(0.4); 3.768(0.45); 3.733(0.47); 3.709(0.54); 3.621(0.9); 3.359 (238.96); 3.134(1.01); 3.108(0.8); 3.001(0.39); 2.961(0.32); 2.677(1.49); 2.672(2.05); 2.668(1.52); 2.566(0.36); 2.526(4.87); 2.512(107.63); 2.508 (220.15); 2.504(293.62); 2.499(217.05); 2.495(108.14); 2.335(1.42); 2.33(1.95); 2.326(1.44); 2.074(16); 0.146(0.74); 0.008(5.27); 0(164.16); −0.008(6.01); −0.06(0.48); −0.15(0.76) |
| I-079 | 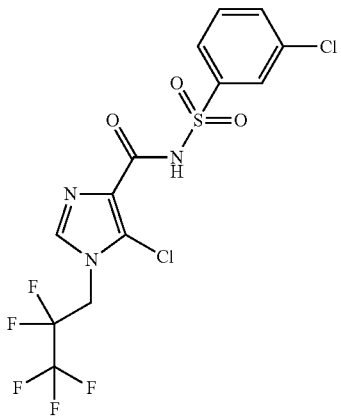 [SMILES: O=C(NS(=O)(=O)c1cccc(Cl)c1)c1ncn(CC(F)(F)C(F)(F)F)c1Cl] | Example I-079: 1H-NMR(400.0 MHz, d6-DMSO): δ = 8.124(16); 8(5.69); 7.995(10.83); 7.991(7.45); 7.971(5.6); 7.951(6.13); 7.831(3.47); 7.828(4.09); 7.826(3.86); 7.824(3.56); 7.81(4.94); 7.808 (5.35); 7.806(5.49); 7.803(4.65); 7.709(6.77); 7.689(10.52); 7.669(4.46); 5.759(7.55); 5.228(4.66); 5.189(9.78); 5.149(5.07); 3.509(0.44); 3.428 (0.52); 3.416(0.53); 3.372(0.54); 3.357(0.56); 3.329(0.51); 3.303(0.51); 3.29(0.49); 3.274(0.47); 3.254(0.45); 3.235(0.41); 2.677(0.7); 2.673 (0.95); 2.668(0.72); 2.526(2.63); 2.513(51.2); 2.508(103.46); 2.504 (136.32); 2.499(99.62); 2.495(48.82); 2.335(0.64); 2.33(0.87); 2.326(0.64); 2.087(3.32); 2.077(3.15); 0.146(0.35); 0.008(2.74); 0(79.8); −0.008(2.86); −0.15(0.34) |

-continued
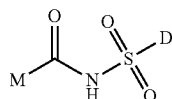
(I)
| Example No. | Structure | NMR peak list |
|---|---|---|
| I-080 | 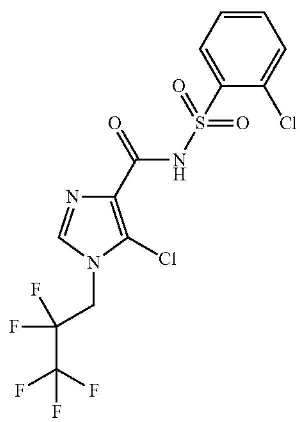 [SMILES: O=C(NS(=O)(=O)c1ccccc1Cl)c1ncn(CC(F)(F)C(F)(F)F)c1Cl] | Example I-080: 1H-NMR(400.0 MHz, d6-DMSO): δ = 8.317(0.42); 8.157(6.45); 8.153(7.03); 8.144(1.52); 8.137(8); 8.133 (9.15); 8.127(16); 7.733(1.6); 7.729(1.74); 7.713(4.7); 7.71(4.56); 7.695 (5.53); 7.692(5.57); 7.677(7.67); 7.673(10.09); 7.657(4.09); 7.653(3.22); 7.635(4.37); 7.632(4.14); 7.624(1.19); 7.615(5.82); 7.598(2.82); 7.594 (2.73); 5.222(4.72); 5.182(9.99); 5.162(0.88); 5.142(5.18); 5.123(0.38); 3.38(1.12); 3.353(1.14); 3.304(1.04); 2.68(0.5); 2.676(1.11); 2.671(1.56); 2.667(1.15); 2.662(0.54); 2.525(3.58); 2.52(5.81); 2.511(86.42); 2.507 (178.72); 2.502(238.58); 2.498(174.53); 2.493(84.84); 2.338(0.58); 2.334(1.18); 2.329(1.63); 2.325(1.22); 2.32(0.62); 2.075(6.51); 0.146 (0.58); 0.008(4.39); 0(142.8); −0.008(4.97); −0.15(0.6) |
| I-081 | 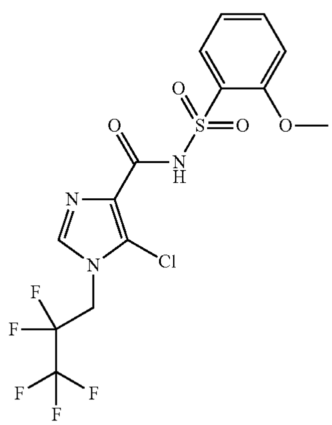 [SMILES: COc1ccccc1S(=O)(=O)NC(=O)c1ncn(CC(F)(F)C(F)(F)F)c1Cl] | Example I-081: 1H-NMR(400.0 MHz, d6-DMSO): δ = 8.119(3.76); 7.898(1.54); 7.894(1.68); 7.879(1.7); 7.875(1.74); 7.697 (0.73); 7.693(0.76); 7.675(1.31); 7.672(1.12); 7.658(0.92); 7.653(0.9); 7.244(2); 7.223(1.8); 7.167(1.12); 7.149(1.98); 7.131(0.98); 7.129(0.96); 5.757(1.36); 5.221(1.09); 5.182(2.33); 5.141(1.21); 3.847(16); 3.332 (17.86); 2.676(0.33); 2.672(0.47); 2.667(0.34); 2.525(1.17); 2.52(1.74); 2.511(25.47); 2.507(52.53); 2.502(69.98); 2.498(51.49); 2.493(25.28); 2.329(0.45); 2.324(0.33); 2.075(1.82); 0.008(2.06); 0(62.5); −0.008(2.13) |
| I-082 | 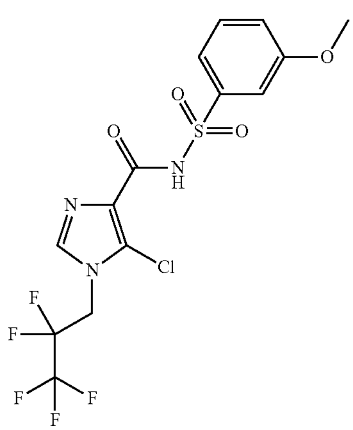 [SMILES: COc1cccc(S(=O)(=O)NC(=O)c2ncn(CC(F)(F)C(F)(F)F)c2Cl)c1] | Example I-082: 1H-NMR(400.0 MHz, d6-DMSO): δ = 8.109(3.81); 7.584(0.39); 7.58(0.44); 7.566(4.2); 7.549(2.19); 7.53 (0.61); 7.506(2.24); 7.298(0.83); 7.292(1.36); 7.286(0.83); 7.281(0.83); 7.275(1.27); 7.269(0.72); 5.222(1.18); 5.182(2.49); 5.142(1.28); 3.83(16); 3.336(3.14); 2.672(0.38); 2.507(44.76); 2.503(58.48); 2.498(45.39); 2.33(0.37); 0(43.29) |

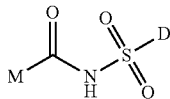
(I)
| Example No. | Structure | NMR peak list |
|---|---|---|
| I-083 | 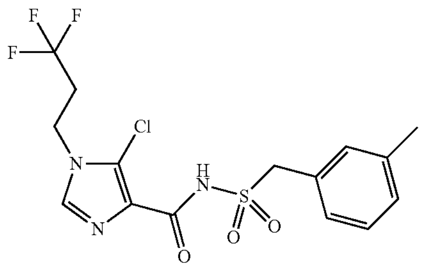 [SMILES: Cc1cccc(CS(=O)(=O)NC(=O)c2ncn(CCC(F)(F)F)c2Cl)c1] | Example I-083: 1H-NMR(400.0 MHz, d6-DMSO): δ = 8.051(7.03); 7.949(0.37); 7.268(1.12); 7.249(3.08); 7.23(2.47); 7.184 (2.38); 7.165(1.64); 7.141(3.6); 7.122(2.4); 7.103(1.8); 4.745(9.04); 4.358 (2.52); 4.34(5.6); 4.323(2.95); 4.292(0.44); 3.329(0.94); 2.964(0.36); 2.947(0.74); 2.936(1.16); 2.92(2.21); 2.909(1.54); 2.903(1.46); 2.892 (2.37); 2.881(0.91); 2.875(1.27); 2.864(0.97); 2.846(0.47); 2.675(0.45); 2.671(0.63); 2.666(0.52); 2.524(1.89); 2.51(32.85); 2.506(67.07); 2.502 (91.68); 2.497(74.5); 2.493(45.33); 2.333(0.46); 2.328(0.63); 2.324(0.52); 2.309(0.45); 2.264(16); 2.074(1.07); 1.505(3.41); 0.146(0.55); 0.008 (5.1); 0(118.57); −0.008(12.81); −0.15(0.54) |
| I-084 | 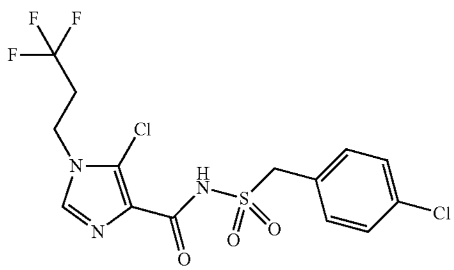 [SMILES: O=C(NS(=O)(=O)Cc1ccc(Cl)cc1)c1ncn(CCC(F)(F)F)c1Cl] | Example I-084: 1H-NMR(400.0 MHz, d6-DMSO): δ = 8.054(14.14); 7.949(0.33); 7.462(0.85); 7.456(8.98); 7.452(3.36); 7.44 (3.57); 7.435(14.17); 7.429(1.94); 7.357(1.55); 7.351(12.47); 7.335 (2.83); 7.33(8.53); 4.815(16); 4.353(4.56); 4.336(10); 4.318(4.83); 4.291 (0.34); 3.507(0.33); 3.487(0.34); 3.351(0.9); 3.344(0.92); 3.186(0.33); 2.965(0.61); 2.947(1.26); 2.937(1.93); 2.92(3.83); 2.909(2.24); 2.903 (2.07); 2.892(4.02); 2.881(1.07); 2.875(1.93); 2.864(1.47); 2.847(0.68); 2.762(1.73); 2.675(0.64); 2.671(0.91); 2.666(0.7); 2.524(2.12); 2.519 (3.16); 2.51(51.92); 2.506(109.01); 2.502(146.75); 2.497(108.22); 2.492 (53.34); 2.338(0.38); 2.333(0.73); 2.328(1.02); 2.324(0.78); 2.075(7.23); 1.505(2.94); 1.202(0.33); 0.986(0.63); 0.146(0.36); 0.008(2.56); 0 (88.71); −0.009(2.94); −0.15(0.38) |
| I-085 | 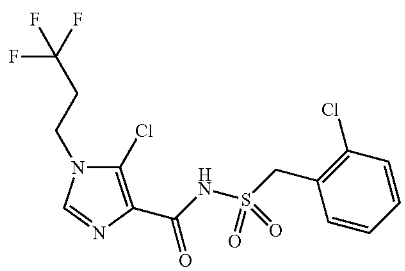 [SMILES: O=C(NS(=O)(=O)Cc1ccccc1Cl)c1ncn(CCC(F)(F)F)c1Cl] | Example I-085: 1H-NMR(400.0 MHz, d6-DMSO): δ = 8.058(12.04); 7.949(0.58); 7.515(3.01); 7.51(3.6); 7.494(6.35); 7.492 (6.57); 7.476(4.02); 7.47(4.4); 7.428(1.33); 7.423(1.69); 7.41(3.95); 7.404(3.36); 7.389(4.9); 7.384(5.57); 7.37(3.55); 7.366(3.19); 7.352(1.11); 7.348(0.94); 5.757(1.41); 4.964(16); 4.358(4.44); 4.34(9.67); 4.323(4.7); 4.309(0.42); 4.292(0.57); 3.505(0.55); 3.338(2.34); 2.968(0.66); 2.951 (1.29); 2.94(1.96); 2.923(3.74); 2.912(2.26); 2.906(2.08); 2.895(3.9); 2.884(1.14); 2.878(1.9); 2.868(1.45); 2.85(0.68); 2.675(0.91); 2.671(1.26); 2.666(0.93); 2.524(3.14); 2.519(4.79); 2.51(67.59); 2.506(137.75); 2.502(182.31); 2.497(133.72); 2.493(65.52); 2.333(0.85); 2.328(1.19); 2.324(0.86); 1.505(5.36); 1.235(0.33); 0.146(0.46); 0.008(3.28); 0(103.8); −0.008(3.34); −0.15(0.44) |
| I-086 | 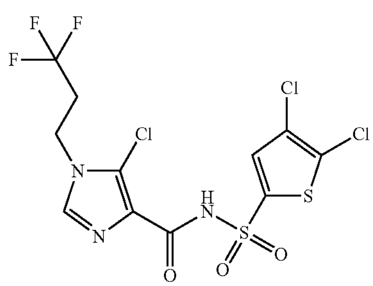 [SMILES: O=C(NS(=O)(=O)c1cc(Cl)c(Cl)s1)c1ncn(CCC(F)(F)F)c1Cl] | Example I-086: 1H-NMR(400.0 MHz, d6-DMSO): δ = 8.307(13.23); 8.294(0.8); 8.285(0.45); 7.786(16); 7.764(0.67); 7.752 (0.43); 4.763(0.49); 4.668(0.59); 4.545(0.64); 4.534(0.66); 4.516(0.67); 4.501(0.65); 4.443(0.62); 4.437(0.62); 4.354(5.96); 4.337(12.17); 4.32 (6.3); 4.22(0.46); 4.151(0.42); 4.134(0.37); 2.955(0.67); 2.938(1.48); 2.927(2.35); 2.91(4.49); 2.9(2.86); 2.894(2.71); 2.882(4.67); 2.865(2.3); 2.855(1.68); 2.838(0.72); 2.672(0.81); 2.507(100.21); 2.503(134.01); 2.499(106.24); 2.33(0.94); 2.076(2.92); 0.008(1.96); 0(55.07); −0.008 (2.98) |
| I-087 | 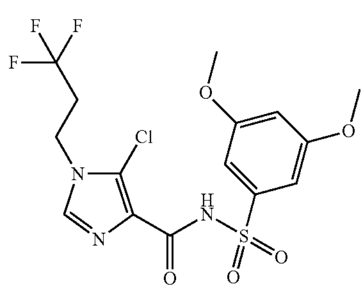 [SMILES: COc1cc(OC)cc(S(=O)(=O)NC(=O)c2ncn(CCC(F)(F)F)c2Cl)c1] | Example I-087: 1H-NMR(400.0 MHz, d6-DMSO): δ = 8.134(0.35); 8.058(1.37); 7.953(1.7); 7.103(2.72); 7.097(2.85); 6.809 (0.59); 6.804(0.97); 4.313(0.81); 4.296(1.75); 4.279(0.85); 3.808(16); 2.891(12.71); 2.877(0.71); 2.866(0.43); 2.86(0.4); 2.849(0.71); 2.832 (0.35); 2.732(10.81); 2.525(0.51); 2.511(11.47); 2.507(23.32); 2.502(30.9); 2.498(22.77); 2.494(11.35); 0.008(1.35); 0(37.94); −0.008(1.35); −0.008(1.35) |

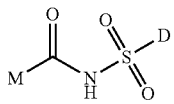
(I)
| Example No. | Structure | NMR peak list |
|---|---|---|
| I-088 | 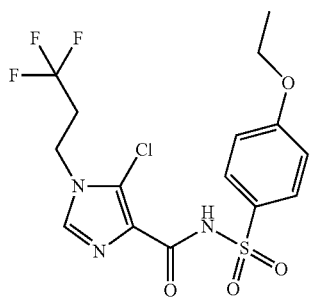 [SMILES: CCOc1ccc(S(=O)(=O)NC(=O)c2ncn(CCC(F)(F)F)c2Cl)cc1] | Example I-088: 1H-NMR(400.0 MHz, d6-DMSO): δ = 8.045(9.94); 7.927(0.85); 7.919(8.24); 7.914(2.69); 7.902(2.58); 7.897 (8.95); 7.89(0.92); 7.133(0.93); 7.126(8.33); 7.121(2.8); 7.108(2.49); 7.103(8); 7.096(0.87); 4.306(3.36); 4.289(7.3); 4.272(3.5); 4.15(2.11); 4.132(7.03); 4.115(7.11); 4.097(2.19); 3.332(1.31); 2.913(0.46); 2.896 (0.95); 2.885(1.45); 2.868(2.83); 2.857(1.7); 2.851(1.57); 2.84(2.92); 2.829(0.82); 2.823(1.39); 2.812(1.04); 2.795(0.46); 2.676(0.37); 2.671 (0.52); 2.667(0.37); 2.525(1.26); 2.511(28.44); 2.507(57.12); 2.502(75.26); 2.498(55.11); 2.494(27.12); 2.334(0.36); 2.329(0.48); 2.324(0.36); 2.075 (1.04); 1.361(7.54); 1.344(16); 1.326(7.34); 0.008(2.07); 0(58.49); −0.008(2.04) |
| I-089 | 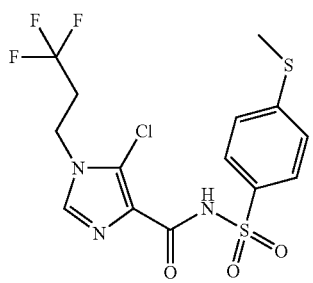 [SMILES: CSc1ccc(S(=O)(=O)NC(=O)c2ncn(CCC(F)(F)F)c2Cl)cc1] | Example I-089: 1H-NMR(400.0 MHz, d6-DMSO): δ = 8.054(16); 7.885(12.85); 7.864(14.64); 7.464(13.98); 7.442(12.89); 4.308(5.8); 4.291(12.37); 4.274(6.07); 3.343(0.66); 3.325(0.66); 3.32 (0.64); 2.914(0.82); 2.897(1.72); 2.886(2.67); 2.869(4.88); 2.858(3.16); 2.852(2.96); 2.841(5.03); 2.824(2.51); 2.814(1.82); 2.797(0.82); 2.731 (0.52); 2.671(0.78); 2.541(53.26); 2.506(86.17); 2.502(110.65); 2.498 (84.81); 2.362(0.34); 2.329(0.76); 2.075(0.8); 0.146(0.38); 0(80.22); −0.008(4.53); −0.15(0.39) |
| I-090 | 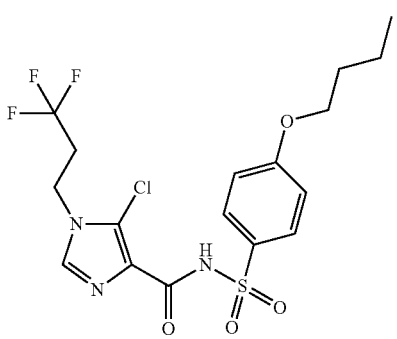 [SMILES: CCCCOc1ccc(S(=O)(=O)NC(=O)c2ncn(CCC(F)(F)F)c2Cl)cc1] | Example I-090: 1H-NMR(400.0 MHz, d6-DMSO): δ = 8.133(0.82); 8.037(1.29); 7.952(2.59); 7.911(1.25); 7.889(1.36); 7.127 (1.24); 7.104(1.22); 4.303(0.59); 4.288(1.26); 4.269(0.62); 4.078(0.7); 4.061(1.45); 4.045(0.73); 3.33(3.05); 2.89(16); 2.866(0.58); 2.855(0.36); 2.849(0.35); 2.838(0.54); 2.731(14.16); 2.506(36.36); 2.502(47.94); 2.498(37.91); 1.728(0.53); 1.711(0.71); 1.692(0.59); 1.458(0.44); 1.439 (0.75); 1.42(0.74); 1.402(0.42); 0.947(1.48); 0.929(2.89); 0.91(1.29); 0.008(1.02); 0(25.4) |
| I-091 | 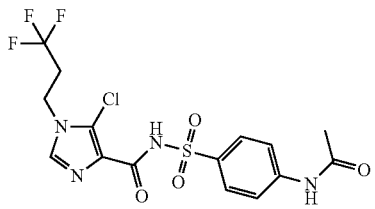 [SMILES: CC(=O)Nc1ccc(S(=O)(=O)NC(=O)c2ncn(CCC(F)(F)F)c2Cl)cc1] | Example I-091: 1H-NMR(400.0 MHz, d6-DMSO): δ = 10.378(2.55); 8.047(5.63); 7.924(3.69); 7.906(1.38); 7.902(5.21); 7.78 (4.72); 7.758(3.62); 4.305(1.73); 4.288(3.79); 4.271(1.82); 3.348(1.5); 3.339(0.76); 2.894(0.5); 2.883(0.77); 2.866(1.5); 2.855(0.89); 2.849 (0.83); 2.838(1.56); 2.827(0.44); 2.821(0.75); 2.81(0.56); 2.672(0.32); 2.525(0.72); 2.52(1.12); 2.511(18.22); 2.507(37.95); 2.502(50.84); 2.498 (37.55); 2.494(18.68); 2.329(0.33); 2.085(16); 2.075(1.36); 0.008(1.61); 0(49.84); −0.008(1.82) |

-continued
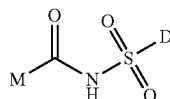
(I)
| Example No. | Structure | NMR peak list |
|---|---|---|
| I-092 | 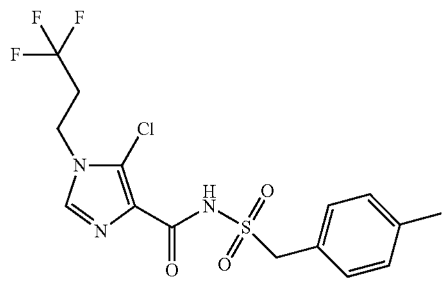 [SMILES: Cc1ccc(CS(=O)(=O)NC(=O)c2ncn(CCC(F)(F)F)c2Cl)cc1] | Example I-092: 1H-NMR(400.0 MHz, d6-DMSO): δ = 8.047(7.68); 7.218(2.52); 7.198(7.95); 7.178(6.94); 7.158(2.3); 4.744 (8.83); 4.354(2.51); 4.336(5.44); 4.319(2.62); 3.334(1.43); 3.235(0.43); 2.966(0.35); 2.949(0.7); 2.938(1.08); 2.921(2.07); 2.91(1.24); 2.904 (1.15); 2.893(2.16); 2.882(0.61); 2.876(1.02); 2.866(0.78); 2.848(0.34); 2.675(0.36); 2.67(0.5); 2.666(0.35); 2.524(1.06); 2.51(29.82); 2.506(59.34); 2.501(77.66); 2.497(56.61); 2.493(27.64); 2.333(0.4); 2.328(0.52); 2.324(0.41); 2.289(16); 2.074(0.61); 0(4.74) |
| I-093 | 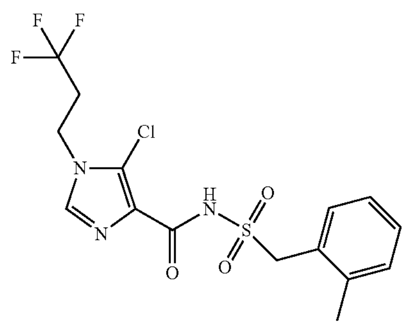 [SMILES: Cc1ccccc1CS(=O)(=O)NC(=O)c1ncn(CCC(F)(F)F)c1Cl] | Example I-093: 1H-NMR(400.0 MHz, d6-DMSO): δ = 8.075(6.87); 7.292(0.32); 7.288(0.38); 7.272(1.37); 7.269(1.7); 7.256 (4.56); 7.254(4.93); 7.242(2.93); 7.201(1.26); 7.197(1.17); 7.181(1.23); 7.176(0.8); 7.167(0.45); 7.161(0.46); 4.827(8.99); 4.364(2.22); 4.347 (4.88); 4.33(2.34); 3.337(0.81); 3.332(0.8); 3.308(0.74); 3.247(0.43); 2.954(0.62); 2.944(0.95); 2.926(1.84); 2.916(1.11); 2.909(1.03); 2.899 (1.92); 2.888(0.54); 2.882(0.91); 2.871(0.69); 2.67(0.35); 2.524(0.76); 2.51(19.91); 2.506(40.43); 2.501(53.73); 2.497(39.94); 2.492(19.95); 2.406(16); 2.328(0.37); 2.074(1.08); 0(3.39) |
| I-094 | 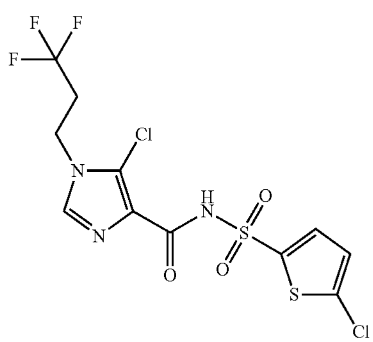 [SMILES: O=C(NS(=O)(=O)c1ccc(Cl)s1)c1ncn(CCC(F)(F)F)c1Cl] | Example I-094: 1H-NMR(400.0 MHz, d6-DMSO): δ = 8.132(16); 7.687(10.27); 7.677(10.85); 7.278(11.03); 7.268(10.45); 4.336(5.19); 4.318(11.43); 4.301(5.52); 2.94(0.57); 2.923(1.32); 2.912 (2.08); 2.895(4.23); 2.884(2.46); 2.878(2.24); 2.867(4.46); 2.856(1.13); 2.85(2.07); 2.839(1.56); 2.822(0.66); 2.672(0.48); 2.667(0.34); 2.525 (0.65); 2.52(1.15); 2.512(29.24); 2.507(62.28); 2.503(84.46); 2.498(63.09); 2.494(31.94); 2.334(0.44); 2.329(0.61); 2.325(0.47); 2.076(0.51); 0.146 (0.33); 0.008(1.99); 0(80.54); −0.008(3.41); −0.15(0.4) |
| I-095 | 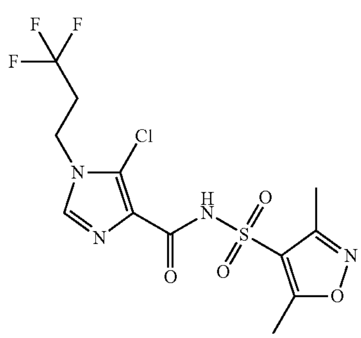 [SMILES: Cc1noc(C)c1S(=O)(=O)NC(=O)c1ncn(CCC(F)(F)F)c1Cl] | Example I-095: 1H-NMR(400.0 MHz, d6-DMSO): δ = 8.104(5.36); 4.328(1.74); 4.311(3.78); 4.294(1.83); 2.918(0.46); 2.907 (0.71); 2.89(1.42); 2.879(0.82); 2.872(0.76); 2.862(1.49); 2.851(0.38); 2.845(0.78); 2.834(0.53); 2.682(16); 2.525(0.53); 2.52(0.8); 2.511 (14.05); 2.507(29.38); 2.502(39.54); 2.498(29.32); 2.493(14.61); 2.383 (15.67); 0.008(1.07); 0(36.46); −0.008(1.33) |

-continued
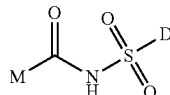
(I)
| Example No. | Structure | NMR peak list |
|---|---|---|
| I-096 | 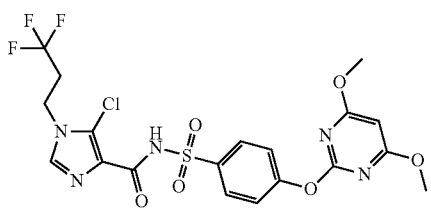 [SMILES: COc1cc(OC)nc(Oc2ccc(S(=O)(=O)NC(=O)c3ncn(CCC(F)(F)F)c3Cl)cc2)n1] | Example I-096: 1H-NMR(400.0 MHz, d6-DMSO): δ = 8.064(2.8); 8.056(2.52); 8.034(2.48); 7.516(2.27); 7.495(2.13); 6.068 (2.72); 6.066(2.91); 4.313(1.05); 4.296(2.19); 4.279(1.14); 3.784(16); 3.34(0.6); 2.904(0.35); 2.892(0.53); 2.876(0.92); 2.864(0.69); 2.848 (0.96); 2.832(0.52); 2.821(0.38); 2.502(40.48); 2.5(40.59); 0(25.74); −0.002(24.96) |
| I-097 | 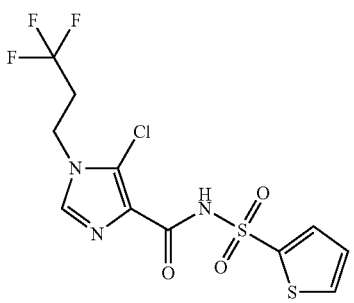 [SMILES: O=C(NS(=O)(=O)c1cccs1)c1ncn(CCC(F)(F)F)c1Cl] | Example I-097: 1H-NMR(400.0 MHz, d6-DMSO): δ = 8.068(16); 8.024(7.74); 8.015(6.82); 8.012(8.52); 7.818(8.44); 7.813 (8.85); 7.809(9.74); 7.211(5.11); 7.208(4.95); 7.198(9.56); 7.189(6.33); 7.187(5.36); 4.318(7.75); 4.302(15.93); 4.285(8.6); 3.92(0.38); 3.875 (0.38); 3.856(0.41); 3.841(0.43); 3.79(0.49); 3.716(0.59); 3.642(0.71); 3.633(0.72); 3.603(0.77); 3.566(0.84); 3.505(0.91); 3.491(0.9); 3.426(0.93); 3.406(0.91); 3.368(0.89); 3.345(0.86); 3.276(0.76); 3.255(0.73); 3.066 (0.46); 2.988(0.37); 2.968(0.34); 2.924(1.27); 2.907(2.51); 2.897(3.91); 2.88(6.64); 2.865(5.36); 2.853(6.95); 2.836(3.97); 2.826(2.95); 2.809 (1.31); 2.67(1.69); 2.501(248.98); 2.498(243.16); 2.376(0.36); 2.328 (1.76); 0.145(0.71); −0.001(140.93); −0.002(132.28); −0.15(0.78) |
| I-098 | 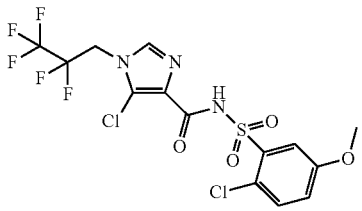 [SMILES: COc1ccc(Cl)c(S(=O)(=O)NC(=O)c2ncn(CC(F)(F)C(F)(F)F)c2Cl)c1] | Example I-098: 1H-NMR(400.0 MHz, d6-DMSO): δ = 8.129(3.51); 8.055(0.69); 7.598(2.75); 7.59(2.97); 7.582(2.54); 7.56 (2.89); 7.436(0.57); 7.418(0.34); 7.4(0.65); 7.304(1.44); 7.297(1.47); 7.282(1.27); 7.275(1.26); 5.313(1.43); 5.237(0.33); 5.225(1.04); 5.197 (0.69); 5.185(2.2); 5.157(0.37); 5.145(1.14); 3.855(16); 3.385(1.37); 3.366 (1.15); 2.676(0.38); 2.672(0.54); 2.667(0.41); 2.525(1.1); 2.511(29.5); 2.507(61.38); 2.503(82.33); 2.498(62.12); 2.334(0.42); 2.329(0.56); 2.325(0.44); 0(5.68) |
| I-099 | 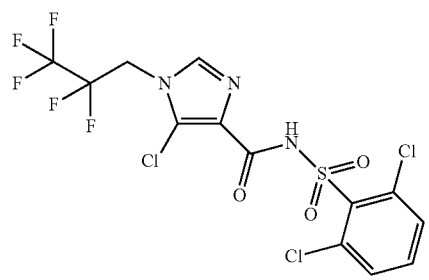 [SMILES: O=C(NS(=O)(=O)c1c(Cl)cccc1Cl)c1ncn(CC(F)(F)C(F)(F)F)c1Cl] | Example I-099: 1H-NMR(400.0 MHz, d6-DMSO): δ = 8.318(0.82); 8.121(9.35); 8.055(0.95); 7.666(5.2); 7.662(6.37); 7.644 (16); 7.61(5.73); 7.593(3.56); 7.587(2.68); 7.57(1.73); 7.456(0.42); 7.438 (0.81); 7.418(0.44); 7.4(0.87); 7.382(0.46); 7.364(0.34); 7.347(0.32); 5.313(1.93); 5.237(0.49); 5.22(3.54); 5.198(1.11); 5.18(7.43); 5.157(0.7); 5.14(3.82); 3.788(0.32); 3.766(0.36); 3.761(0.38); 3.647(0.67); 3.629 (0.71); 3.619(0.77); 3.602(0.81); 3.484(1.51); 3.382(2.04); 3.127(0.56); 2.676(1.54); 2.671(2.28); 2.667(1.68); 2.525(3.47); 2.511(140.4); 2.507 (294.05); 2.502(395.65); 2.498(296.22); 2.494(152.8); 2.352(0.6); 2.333 (2.25); 2.329(3.01); 2.325(2.37); 2.275(0.42); 2.244(0.39); 2.234 (0.34); 2.075(7.93); 2.063(0.34); 1.598(0.34); 1.581(0.46); 1.563(0.35); 1.36(0.33); 1.342(0.57); 1.324(0.58); 1.306(0.39); 1.171(0.48); 1.15(0.54); 1.13(0.45); 0.92(0.89); 0.902(1.75); 0.892(0.38); 0.884(0.84); 0.873 (0.55); 0.008(1.5); 0(65.25); −0.008(3.36); −0.15(0.34) |
| I-100 | 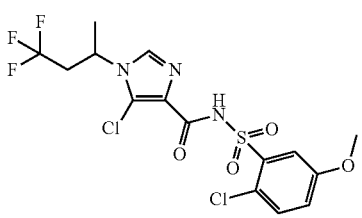 [SMILES: COc1ccc(Cl)c(S(=O)(=O)NC(=O)c2ncn(C(C)CC(F)(F)F)c2Cl)c1] | Example I-100: 1H-NMR(400.0 MHz, d6-DMSO): δ = 8.322(4.89); 7.593(2.82); 7.585(3.02); 7.577(2.71); 7.555(3.08); 7.297 (1.57); 7.289(1.5); 7.275(1.35); 7.267(1.31); 4.722(0.34); 4.71(0.46); 4.705(0.49); 4.698(0.51); 4.694(0.53); 4.687(0.51); 4.682(0.47); 4.67 (0.37); 3.854(16); 3.137(0.43); 3.125(0.5); 3.112(0.36); 3.098(0.63); 3.074 (0.46); 3.015(0.41); 3.004(0.51); 2.987(0.46); 2.976(0.69); 2.948(0.42); 2.525(0.49); 2.512(13.67); 2.508(28.43); 2.503(37.83); 2.498(28.25); 2.494(14.34); 2.076(3.33); 1.536(4.51); 1.518(4.52); 0(4.56) |

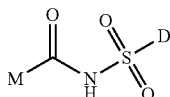
(I)
| Example No. | Structure | NMR peak list |
|---|---|---|
| I-101 | 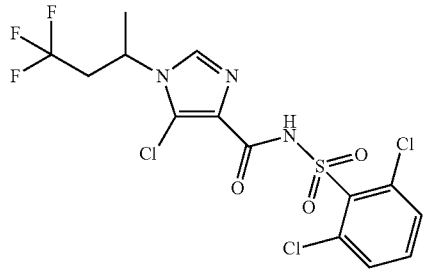 [SMILES: CC(CC(F)(F)F)n1cnc(C(=O)NS(=O)(=O)c2c(Cl)cccc2Cl)c1Cl] | Example I-101: 1H-NMR(400.0 MHz, d6-DMSO): δ = 8.355(12.88); 8.317(0.34); 7.665(5.26); 7.66(6.69); 7.642(16); 7.607 (6.57); 7.59(4.05); 7.584(3.02); 7.567(2.11); 4.744(0.34); 4.728(0.98); 4.716(1.3); 4.71(1.4); 4.703(1.44); 4.699(1.5); 4.692(1.47); 4.688(1.34); 4.675(1.09); 4.658(0.41); 4.24(0.34); 4.205(0.36); 4.177(0.37); 4.163 (0.38); 4.146(0.41); 4.136(0.41); 4.12(0.57); 4.078(0.56); 4.053(0.46); 4.042(0.46); 4.022(0.47); 4.004(0.47); 3.994(0.48); 3.982(0.48); 3.934 (0.49); 3.919(0.49); 3.86(0.49); 3.831(0.63); 3.778(0.44); 3.764(0.44); 3.704(0.4); 3.666(0.37); 3.618(0.33); 3.164(0.8); 3.152(0.48); 3.137(1.11); 3.125(1.37); 3.113(0.93); 3.099(1.69); 3.086(0.44); 3.074(1.26); 3.046 (0.62); 3.033(0.41); 3.016(1.1); 3.005(1.38); 2.988(1.24); 2.977(1.87); 2.966(0.79); 2.949(1.14); 2.938(0.71); 2.676(0.61); 2.672(0.89); 2.667 (0.65); 2.525(1.23); 2.52(2.36); 2.511(53.34); 2.507(112.08); 2.502 (150.71); 2.498(112.4); 2.494(57.27); 2.334(0.87); 2.329(1.14); 2.325(0.91); 1.538(12.72); 1.521(12.85); 0(10.3); −0.008(0.47) |
| I-102 | 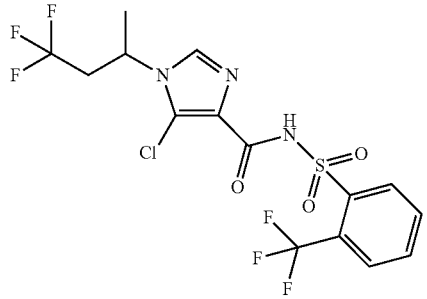 [SMILES: CC(CC(F)(F)F)n1cnc(C(=O)NS(=O)(=O)c2ccccc2C(F)(F)F)c1Cl] | Example I-102: 1H-NMR(400.0 MHz, d6-DMSO): δ = 8.334(16); 8.318(4.89); 8.011(3.16); 7.992(4.82); 7.974(1.63); 7.958 (3.93); 7.955(3.64); 7.939(3.21); 7.936(2.72); 7.925(3.48); 7.907(3.45); 7.888(1.12); 4.723(1.05); 4.711(1.44); 4.706(1.55); 4.695(1.7); 4.688 (1.61); 4.683(1.49); 4.671(1.17); 4.654(0.38); 3.188(0.32); 3.162(0.92); 3.149(0.56); 3.135(1.29); 3.123(1.54); 3.11(1.07); 3.096(1.97); 3.084 (0.52); 3.071(1.44); 3.043(0.76); 3.031(0.48); 3.015(1.23); 3.003(1.55); 2.987(1.39); 2.975(2.1); 2.964(0.92); 2.947(1.27); 2.937(0.8); 2.92(0.33); 2.676(0.65); 2.672(0.95); 2.668(0.72); 2.525(1.73); 2.507(121.81); 2.503 (162.61); 2.498(125.34); 2.334(0.97); 2.33(1.25); 2.325(1.01); 2.076 (4.87); 1.531(14.19); 1.514(14.34); 0(5.28) |
| I-103 | 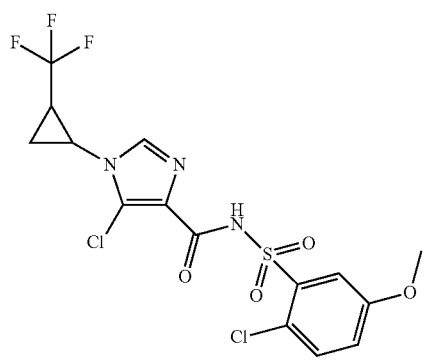 [SMILES: COc1ccc(Cl)c(S(=O)(=O)NC(=O)c2ncn(C3CC3C(F)(F)F)c2Cl)c1] | Example I-103: 1H-NMR(400.0 MHz, d6-DMSO): δ = 8.051(4.47); 7.587(2.67); 7.579(2.83); 7.568(2.42); 7.546(2.82); 7.29 (1.42); 7.282(1.36); 7.268(1.24); 7.26(1.18); 3.884(0.7); 3.873(1.01); 3.864(1.52); 3.854(16); 3.844(0.98); 3.796(0.33); 3.773(0.33); 3.753 (0.32); 3.738(0.35); 3.67(0.44); 3.637(0.39); 3.628(0.39); 3.617(0.39); 3.596(0.39); 3.548(0.37); 3.508(0.34); 2.758(0.42); 2.75(0.55); 2.741(0.49); 2.733(0.58); 2.724(0.42); 2.716(0.32); 2.671(0.34); 2.525(0.69); 2.511(19.41); 2.507(39.29); 2.502(51.65); 2.498(37.71); 2.494(18.62); 2.329(0.37); 1.874(0.37); 1.858(0.54); 1.847(0.63); 1.837(0.5); 1.832(0.49); 1.82(0.39); 1.618(0.47); 1.601(0.97); 1.581(0.98); 1.564(0.41); 0(4.47) |
| I-104 | 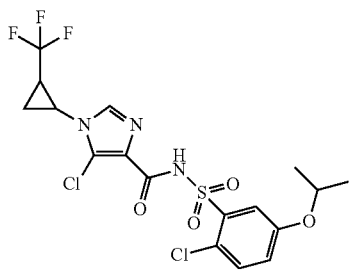 [SMILES: CC(C)Oc1ccc(Cl)c(S(=O)(=O)NC(=O)c2ncn(C3CC3C(F)(F)F)c2Cl)c1] | Example I-104: 1H-NMR(400.0 MHz, d6-DMSO): δ = 8.05(4.9); 7.546(2.8); 7.538(3.03); 7.533(2.78); 7.511(3.1); 7.265 (1.42); 7.258(1.38); 7.243(1.22); 7.236(1.19); 4.714(0.4); 4.699(1.02); 4.684(1.39); 4.669(1.03); 4.654(0.42); 3.886(0.67); 3.874(0.97); 3.865 (1.27); 3.856(1); 3.844(0.74); 3.693(0.35); 3.657(0.38); 3.616(0.4); 3.593 (0.4); 3.557(0.39); 3.55(0.39); 3.507(0.38); 3.497(0.36); 3.489(0.36); 3.487 (0.36); 3.45(0.33); 2.757(0.44); 2.748(0.56); 2.74(0.52); 2.732(0.6); 2.723(0.44); 2.714(0.33); 2.671(0.37); 2.525(0.68); 2.52(1.12); 2.511 (20.43); 2.507(42.85); 2.502(57.22); 2.498(42.1); 2.493(20.87); 2.329(0.4); 1.873(0.38); 1.856(0.56); 1.845(0.65); 1.832(0.51); 1.819(0.41); 1.619 (0.48); 1.602(1.02); 1.582(1.04); 1.564(0.42); 1.313(16); 1.298(15.92); 0(4.87) |

-continued
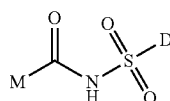
(I)
| Example No. | Structure | NMR peak list |
|---|---|---|
| I-105 | 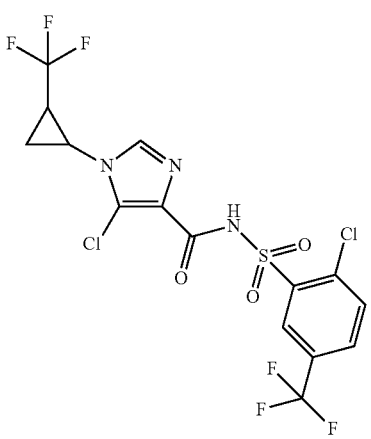 [SMILES: O=C(NS(=O)(=O)c1cc(C(F)(F)F)ccc1Cl)c1ncn(C2CC2C(F)(F)F)c1Cl] | Example I-105: 1H-NMR(400.0 MHz, d6-DMSO): δ = 8.329(7.22); 8.324(7.73); 8.198(16); 8.096(3.45); 8.091(3.49); 8.075 (4.37); 8.07(4.33); 7.92(7.03); 7.9(5.62); 4.301(0.48); 3.965(3.44); 3.9 (4.67); 3.889(5.68); 3.88(6.54); 3.87(5.37); 3.859(4.22); 2.778(0.86); 2.77 (1.06); 2.761(1.6); 2.753(2.12); 2.744(1.95); 2.735(2.25); 2.727(1.68); 2.718(1.22); 2.71(0.94); 2.676(0.86); 2.672(1.23); 2.667(0.93); 2.525 (2.5); 2.52(4.29); 2.512(66.93); 2.507(138.75); 2.503(184.71); 2.498 (136.9); 2.494(68.66); 2.334(0.94); 2.33(1.31); 2.325(0.99); 1.884(1.42); 1.867(2.15); 1.856(2.53); 1.846(1.96); 1.842(1.97); 1.83(1.56); 1.627(1.86); 1.61(3.89); 1.59(3.97); 1.573(1.61); 0.008(0.51); 0(16.5); −0.008(0.65) |
| I-106 | 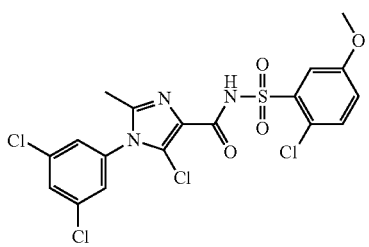 [SMILES: COc1ccc(Cl)c(S(=O)(=O)NC(=O)c2nc(C)n(-c3cc(Cl)cc(Cl)c3)c2Cl)c1] | Example I-106: 1H-NMR(400.0 MHz, CDCl3): δ = 7.852(2.68); 7.844(2.76); 7.582(1.74); 7.578(3.09); 7.574(1.92); 7.387 (2.56); 7.365(2.95); 7.261(9.41); 7.169(6.26); 7.165(6.36); 7.079(1.55); 7.071(1.55); 7.057(1.36); 7.049(1.34); 5.3(2.4); 3.887(16); 2.279(15.6); 1.562(0.83); 0(9.45) |
| I-107 | 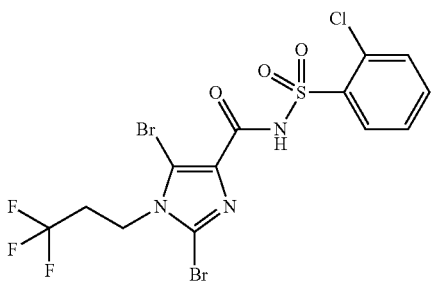 [SMILES: O=C(NS(=O)(=O)c1ccccc1Cl)c1nc(Br)n(CCC(F)(F)F)c1Br] | Example I-107: 1H-NMR(400.0 MHz, d6-DMSO): δ = 8.14(0.87); 8.136(0.88); 8.12(0.97); 8.116(0.93); 7.704(0.71); 7.686 (0.83); 7.682(0.8); 7.666(1.43); 7.649(0.58); 7.627(0.62); 7.623(0.54); 7.607(0.86); 7.589(0.41); 7.586(0.36); 4.304(0.88); 4.287(1.67); 4.269 (0.93); 3.351(0.35); 2.843(0.41); 2.826(0.69); 2.816(0.49); 2.808(0.44); 2.798(0.7); 2.78(0.37); 2.506(25.26); 2.502(32.43); 2.497(23.42); 2.086 (16); 0.008(1.52); 0(34.62); −0.008(1.59) |
| I-108 | 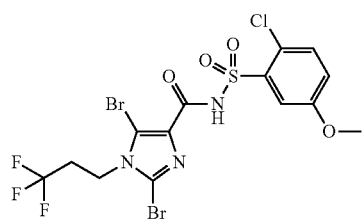 [SMILES: COc1ccc(Cl)c(S(=O)(=O)NC(=O)c2nc(Br)n(CCC(F)(F)F)c2Br)c1] | Example I-108: 1H-NMR(400.0 MHz, d6-DMSO): δ = 7.582(3.02); 7.574(5.36); 7.552(2.81); 7.293(1.42); 7.286(1.39); 7.271 (1.24); 7.264(1.19); 4.307(1.5); 4.289(2.86); 4.272(1.58); 3.852(16); 3.343(1.24); 2.856(0.43); 2.847(0.71); 2.83(1.2); 2.819(0.84); 2.812(0.76); 2.802(1.22); 2.784(0.63); 2.774(0.45); 2.671(0.37); 2.506(48.63); 2.502 (63.66); 2.497(45.96); 2.328(0.37); 2.086(2.72); 0.146(0.36); 0.008 (2.86); 0(76.31); −0.008(3.08); −0.15(0.37) |

-continued
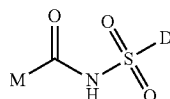
(I)
| Example No. | Structure | NMR peak list |
|---|---|---|
| I-109 | 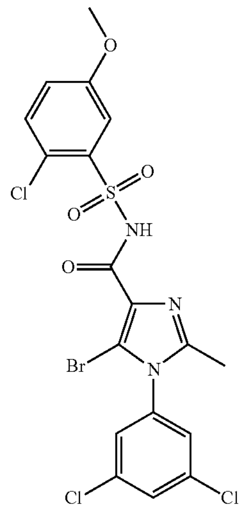 [SMILES: COc1ccc(Cl)c(S(=O)(=O)NC(=O)c2nc(C)n(-c3cc(Cl)cc(Cl)c3)c2Br)c1] | Example I-109: 1H-NMR(400.0 MHz, d6-DMSO): δ = 7.927(2.01); 7.923(3.68); 7.918(2.25); 7.787(7.58); 7.783(7.26); 7.605 (3); 7.597(3.23); 7.586(2.93); 7.564(3.3); 7.292(1.68); 7.284(1.66); 7.27 (1.5); 7.262(1.44); 5.757(3.16); 3.857(16); 2.506(19.48); 2.502(25.65); 2.498(20.48); 2.256(14.03); 0(1.07) |
| I-110 | 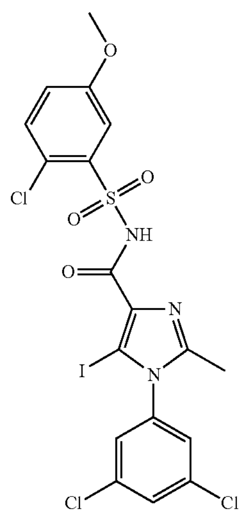 [SMILES: COc1ccc(Cl)c(S(=O)(=O)NC(=O)c2nc(C)n(-c3cc(Cl)cc(Cl)c3)c2I)c1] | Example I-110: 1H-NMR(400.0 MHz, d6-DMSO): δ = 7.925(2.11); 7.921(3.82); 7.916(2.26); 7.727(7.68); 7.722(7.45); 7.605 (3.1); 7.597(3.26); 7.581(2.81); 7.559(3.29); 7.285(1.68); 7.277(1.61); 7.263(1.47); 7.255(1.41); 3.862(16); 2.506(25.28); 2.502(32.51); 2.497 (24.73); 2.297(13.61); 2.256(0.47); 2.074(1.6); 0.008(1.28); 0(33.1); −0.008(1.9) |
| I-111 | 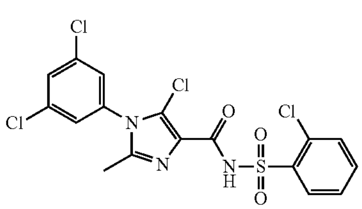 [SMILES: Cc1nc(C(=O)NS(=O)(=O)c2ccccc2Cl)c(Cl)n1-c1cc(Cl)cc(Cl)c1] | Example I-111: 1H-NMR(400.0 MHz, d6-DMSO): δ = 8.156(1.64); 8.153(1.67); 8.136(1.84); 8.133(1.78); 7.924(1.96); 7.919 (3.82); 7.914(2.2); 7.808(7.89); 7.803(7.31); 7.722(0.37); 7.718(0.38); 7.702(1.29); 7.698(1.14); 7.685(1.74); 7.681(1.81); 7.676(2.36); 7.672 (2.76); 7.656(0.98); 7.627(1.13); 7.623(0.96); 7.607(1.49); 7.59(0.78); 7.586(0.68); 3.616(0.43); 2.675(0.39); 2.671(0.52); 2.666(0.4); 2.524 (1.09); 2.51(34.27); 2.506(68.84); 2.502(89.08); 2.497(63.06); 2.333(0.4); 2.328(0.54); 2.324(0.4); 2.236(16); 1.481(0.79); 0.146(0.37); 0.008 (3.19); 0(90.36); −0.008(3.44); −0.15(0.39) |

-continued
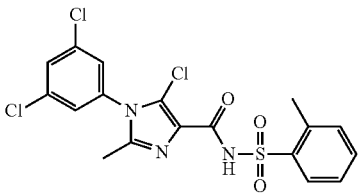 [SMILES: Cc1ccccc1S(=O)(=O)NC(=O)c1nc(C)n(-c2cc(Cl)cc(Cl)c2)c1Cl]
(I)
| Example No. | Structure | NMR peak list |
|---|---|---|
| I-112 | 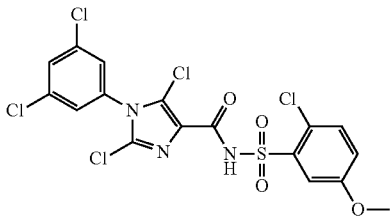 [SMILES: COc1ccc(Cl)c(S(=O)(=O)NC(=O)c2nc(Cl)n(-c3cc(Cl)cc(Cl)c3)c2Cl)c1] | Example I-112: 1H-NMR(400.0 MHz, d6-DMSO): δ = 8.032(1.77); 8.012(1.88); 7.918(1.85); 7.913(3.71); 7.908(2.24); 7.787 (7.51); 7.783(7.4); 7.588(0.7); 7.569(1.68); 7.55(1.08); 7.455(1.05); 7.436 (1.69); 7.417(0.84); 7.406(1.9); 7.387(1.53); 2.671(0.36); 2.626(13.1); 2.506(44.34); 2.502(59.7); 2.497(44.58); 2.329(0.36); 2.226(16); 2.074(3.91); 0.008(1.24); 0(34.39) |
| I-113 | 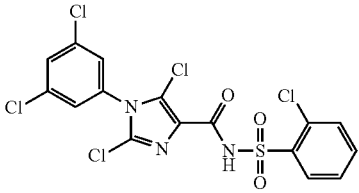 [SMILES: O=C(NS(=O)(=O)c1ccccc1Cl)c1nc(Cl)n(-c2cc(Cl)cc(Cl)c2)c1Cl] | Example I-113: 1H-NMR(400.0 MHz, d6-DMSO): δ = 7.975(1.64); 7.97(3.4); 7.966(2.15); 7.909(7.13); 7.905(6.37); 7.602 (2.95); 7.595(3.41); 7.591(2.55); 7.568(2.49); 7.297(1.28); 7.29(1.24); 7.275(1.11); 7.268(1.07); 5.756(0.46); 3.856(16); 3.357(1.03); 2.67(0.44); 2.506(61.21); 2.502(79.57); 2.497(58.27); 2.333(0.36); 2.328(0.47); 2.086(15.26); 0.007(1.74); 0(43.27) |
| I-114 | 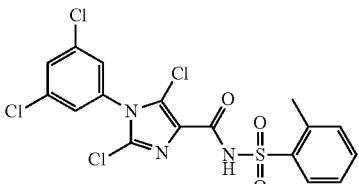 | Example I-114: 1H-NMR(400.0 MHz, d6-DMSO): δ = 8.159(3.74); 8.139(4.2); 7.968(7.45); 7.964(4.67); 7.903(16); 7.898 (14.1); 7.728(0.79); 7.708(2.73); 7.68(5.63); 7.663(1.84); 7.63(2.22); 7.611(3.19); 7.594(1.45); 5.756(6.74); 3.346(4.92); 3.286(1.18); 2.671 (1.25); 2.666(0.96); 2.506(175.48); 2.502(220.52); 2.497(158.05); 2.328 (1.28); 1.294(0.36); 1.236(0.49); 0.146(0.52); 0.008(4.85); 0(121.56); −0.008(5.47); −0.15(0.55) |
| I-115 | 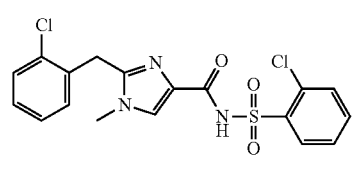 [SMILES: Cn1cc(C(=O)NS(=O)(=O)c2ccccc2Cl)nc1Cc1ccccc1Cl] | Example I-115: 1H-NMR(400.0 MHz, d6-DMSO): δ = 12.628(0.46); 8.034(2.23); 8.015(2.38); 7.972(2.22); 7.967(4.51); 7.962(2.82); 7.885(9.24); 7.88(8.81); 7.594(0.83); 7.576(1.99); 7.557(1.3); 7.46(1.29); 7.44(2.07); 7.42(1.15); 7.412(2.3); 7.393(1.81); 5.756 (3.58); 3.328(6.58); 3.286(0.33); 2.67(0.63); 2.629(16); 2.506(77.92); 2.501 (104.72); 2.497(79.36); 2.328(0.6); 0.008(2.05); 0(56.12) |
| I-116 | 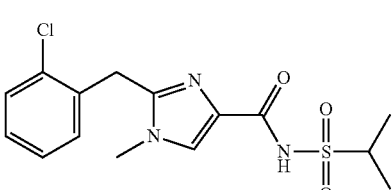 | Example I-116: 1H-NMR(400.0 MHz, d6-DMSO): δ = 8.132(6.22); 8.087(1.63); 8.083(1.71); 8.064(1.77); 7.953 (5.97); 7.596(0.69); 7.592(0.51); 7.576(1.24); 7.572(1.17); 7.559(2.11); 7.555(3.52); 7.549(3.22); 7.534(1.11); 7.525(1.42); 7.52(1.14); 7.501 (2.6); 7.495(1.57); 7.488(1.04); 7.483(1.66); 7.478(2.01); 7.35(0.39); 7.345 (0.56); 7.332(1.6); 7.326(1.84); 7.323(1.81); 7.316(3.18); 7.305(2.04); 7.3(1.7); 7.286(0.58); 7.282(0.36); 7.119(1.57); 7.114(1.09); 7.103 (1.25); 7.096(1.22); 4.287(7.28); 4.056(0.51); 4.038(1.06); 4.02(1.07); 4.003(0.56); 3.945(0.32); 3.874(0.35); 3.864(0.36); 3.851(0.36); 3.812(0.5); 3.784(0.38); 3.609(16); 2.523(0.84); 2.51(19.53); 2.506(39.2); 2.502 (51.54); 2.497(37.26); 2.493(18.11); 1.988(3.54); 1.193(0.9); 1.175 (1.78); 1.157(0.86); 0.008(1.15); 0(30.67); −0.008(1.19) |
| I-117 | 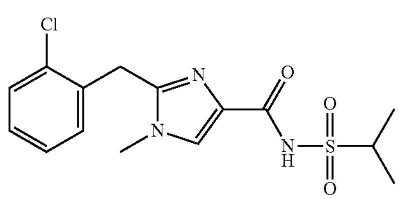 [SMILES: CC(C)S(=O)(=O)NC(=O)c1cn(C)c(Cc2ccccc2Cl)n1] | Example I-117: 1H-NMR(400.0 MHz, d6-DMSO): δ = 8.006(5.44); 7.49(1.32); 7.478(1.18); 7.474(0.86); 7.467(1.72); 7.325 (0.37); 7.314(3.11); 7.306(1.91); 7.304(2.12); 7.301(1.94); 7.298(2.09); 7.29(3.3); 7.279(0.42); 7.142(1.46); 7.131(1.18); 7.128(1.13); 7.118 (1.13); 4.189(8.17); 3.765(0.61); 3.748(1.34); 3.73(1.81); 3.713(1.41); 3.696(0.72); 3.68(0.37); 3.655(0.36); 3.61(16); 3.552(0.54); 3.545(0.54); 3.507(0.58); 3.491(0.59); 3.483(0.6); 3.473(0.6); 3.431(0.64); 3.388(0.54); 2.67(0.34); 2.506(42.55); 2.501(56.87); 2.497(42.75); 2.328(0.39); 1.283(15.35); 1.266(15.21); 0(0.75) |

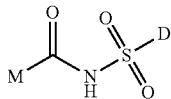
(I)
| Example No. | Structure | NMR peak list |
|---|---|---|
| I-118 | 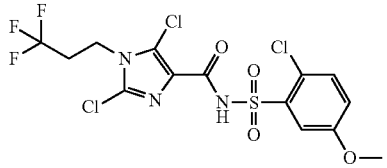 [SMILES: COc1ccc(Cl)c(S(=O)(=O)NC(=O)c2nc(Cl)n(CCC(F)(F)F)c2Cl)c1] | Example I-118: 1H-NMR(400.0 MHz, d6-DMSO): δ = 7.582(2.95); 7.575(3.48); 7.572(3.27); 7.55(3.07); 7.293(1.49); 7.285 (1.45); 7.271(1.3); 7.263(1.24); 4.291(1.44); 4.274(3.15); 4.257(1.51); 3.851(16); 3.362(0.42); 2.886(0.4); 2.875(0.61); 2.858(1.2); 2.847(0.74); 2.841(0.68); 2.83(1.25); 2.813(0.59); 2.802(0.45); 2.524(0.7); 2.51 (15.8); 2.506(32.98); 2.501(45.88); 2.497(34.71); 2.492(17.09); 2.073 (1.37); 0(3.16) |
| I-119 | 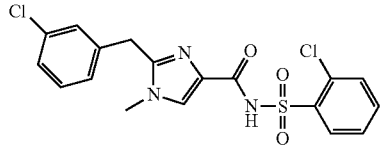 [SMILES: Cn1cc(C(=O)NS(=O)(=O)c2ccccc2Cl)nc1Cc1cccc(Cl)c1] | Example I-119: 1H-NMR(400.0 MHz, d6-DMSO): δ = 8.083(1.79); 8.08(1.89); 8.063(2.01); 8.061(2.03); 7.87(5.4); 7.569 (0.41); 7.553(1.25); 7.533(4.17); 7.528(3.69); 7.51(1.85); 7.49(1.6); 7.474 (0.72); 7.469(0.6); 7.388(0.8); 7.367(4.67); 7.35(4.41); 7.344(3.16); 7.329 (0.56); 7.324(0.72); 7.269(0.32); 7.25(0.86); 7.231(0.83); 7.204(1.98); 7.186(2.07); 7.163(0.84); 7.144(0.4); 4.23(7.44); 3.621(16); 2.756 (0.98); 2.506(29.37); 2.502(37.62); 2.3(3.51); 1.989(0.71); 1.175(0.39); 0(4.74) |
| I-120 | 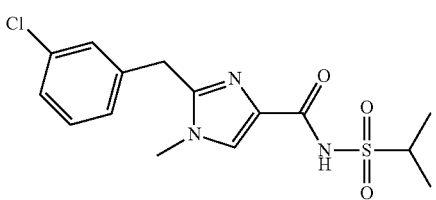 [SMILES: CC(C)S(=O)(=O)NC(=O)c1cn(C)c(Cc2cccc(Cl)c2)n1] | Example I-120: 1H-NMR(400.0 MHz, d6-DMSO): δ = 8.132(2.26); 7.959(5.54); 7.376(0.68); 7.371(0.33); 7.358(1.15); 7.355 (1.75); 7.342(0.52); 7.336(2.33); 7.32(4.42); 7.317(5.23); 7.303(0.9); 7.3(0.87); 7.204(1.71); 7.185(1.35); 4.141(7.04); 3.776(0.54); 3.759(1.27); 3.742(1.73); 3.725(1.32); 3.708(0.6); 3.575(16); 3.456(0.44); 3.433 (0.44); 3.415(0.44); 3.397(0.49); 3.314(0.34); 2.67(0.39); 2.524(1.07); 2.51(22.5); 2.506(45.13); 2.502(59.17); 2.497(42.88); 2.493(20.95); 2.328(0.35); 1.988(0.6); 1.292(15.27); 1.275(15.03); 1.233(0.42); 1.216 (0.33); 0.008(0.4); 0(10.5); −0.008(0.38) |
| I-121 | 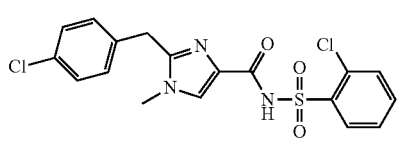 [SMILES: Cn1cc(C(=O)NS(=O)(=O)c2ccccc2Cl)nc1Cc1ccc(Cl)cc1] | Example I-121: 1H-NMR(400.0 MHz, d6-DMSO): δ = 8.132(2.48); 8.078(1.71); 8.074(1.79); 8.059(1.86); 8.055(1.86); 7.869 (5.31); 7.567(0.33); 7.564(0.35); 7.548(1.19); 7.544(1.2); 7.528(4.04); 7.523(3.64); 7.509(1.17); 7.504(1.78); 7.499(1.03); 7.485(1.49); 7.48 (1.08); 7.469(0.72); 7.464(0.62); 7.409(4.25); 7.388(5.87); 7.279(5.09); 7.258(3.69); 4.223(7.08); 4.164(0.41); 4.145(0.44); 4.121(0.46); 4.083 (0.49); 4.067(0.5); 4.056(0.54); 4.038(0.56); 4.02(0.57); 4.009(0.54); 4.002 (0.54); 3.988(0.55); 3.981(0.55); 3.922(0.56); 3.84(0.56); 3.781(0.54); 3.75(0.44); 3.605(16); 2.675(0.35); 2.67(0.48); 2.666(0.35); 2.506 (68.49); 2.501(90.05); 2.497(66.4); 2.332(0.45); 2.328(0.58); 2.324(0.45); 0.008(0.38); 0(9.87); −0.008(0.48) |
| I-122 | 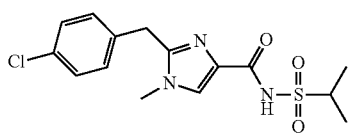 [SMILES: CC(C)S(=O)(=O)NC(=O)c1cn(C)c(Cc2ccc(Cl)cc2)n1] | Example I-122: 1H-NMR(400.0 MHz, d6-DMSO): δ = 8.133(6.19); 7.951(5.71); 7.389(3.87); 7.368(5.47); 7.268(4.69); 7.247 (3.33); 4.121(7.38); 3.774(0.58); 3.757(1.28); 3.74(1.72); 3.722(1.35); 3.705(0.62); 3.558(16); 3.502(0.34); 3.472(0.34); 3.456(0.33); 3.449 (0.33); 3.379(0.36); 2.671(0.38); 2.506(44.48); 2.502(57.74); 2.497(41.9); 2.329(0.36); 1.988(0.83); 1.291(15.24); 1.274(14.97); 1.175(0.45); 0.008(0.38); 0(9.25); −0.008(0.36) |
| I-123 | 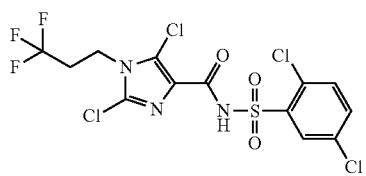 [SMILES: O=C(NS(=O)(=O)c1cc(Cl)ccc1Cl)c1nc(Cl)n(CCC(F)(F)F)c1Cl] | Example I-123: 1H-NMR(400.0 MHz, d6-DMSO): δ = 8.068(13.58); 8.062(14.32); 7.819(5.17); 7.812(4.87); 7.798(7.78); 7.791(7.6); 7.719(14.82); 7.697(9.69); 4.292(7.44); 4.275(16); 4.258 (7.83); 2.902(0.91); 2.885(1.99); 2.874(3.12); 2.858(6.09); 2.846(3.84); 2.841(3.6); 2.83(6.31); 2.813(3.05); 2.802(2.24); 2.785(0.98); 2.676(0.58); 2.672(0.8); 2.668(0.6); 2.525(1.65); 2.507(98.82); 2.502(137.67); 2.498(106.15); 2.334(0.62); 2.329(0.86); 2.325(0.65); 2.074(2.88); 0.008 (0.89); 0(28.85); −0.008(1.39) |
| I-124 | 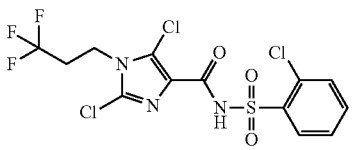 [SMILES: O=C(NS(=O)(=O)c1ccccc1Cl)c1nc(Cl)n(CCC(F)(F)F)c1Cl] | Example I-124: 1H-NMR(400.0 MHz, d6-DMSO): δ = 8.138(6.2); 8.119(6.67); 7.992(0.74); 7.972(0.77); 7.719(1.69); 7.7 (5.08); 7.681(5.53); 7.663(9.56); 7.644(3.97); 7.623(4.62); 7.604(7.73); 7.586(3.14); 7.536(0.51); 7.518(0.73); 7.501(0.33); 5.753(16); 4.289 (6.72); 4.272(13.72); 4.255(6.93); 4.056(0.4); 4.039(1.2); 4.021(1.2); 4.003 (0.43); 3.353(0.9); 3.275(0.57); 2.898(0.93); 2.882(1.96); 2.87(3.06); 2.854(5.52); 2.842(3.91); 2.826(5.63); 2.809(2.92); 2.798(2.07); 2.782 (0.88); 2.671(0.52); 2.502(77.56); 2.329(0.45); 1.989(4.86); 1.235(0.58); 1.193(1.3); 1.175(2.54); 1.158(1.26); 0(3.73) |

(I)
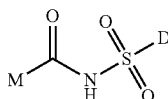
| Example No. | Structure | NMR peak list |
|---|---|---|
| I-125 | 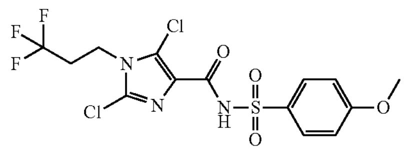 [SMILES: COc1ccc(S(=O)(=O)NC(=O)c2nc(Cl)n(CCC(F)(F)F)c2Cl)cc1] | Example I-125: 1H-NMR(400.0 MHz, d6-DMSO): δ = 11.931(0.63); 7.925(4.07); 7.903(4.36); 7.761(0.47); 7.739(0.5); 7.196 (0.53); 7.145(4.14); 7.123(3.93); 7.093(0.51); 7.071(0.46); 5.754(3.3); 4.286(1.7); 4.27(3.58); 4.253(1.78); 4.038(0.53); 4.021(0.54); 3.846(16); 3.824(2.04); 3.32(5.15); 2.868(0.46); 2.856(0.74); 2.84(1.38); 2.828 (0.91); 2.812(1.42); 2.795(0.7); 2.784(0.5); 2.506(20.92); 2.502(27.3); 2.498(20.26); 1.989(2.21); 1.193(0.58); 1.175(1.15); 1.158(0.56); 0(1.51) |
| I-126 | 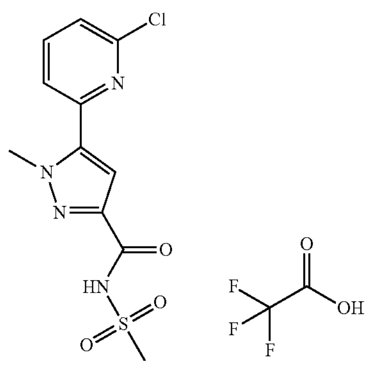 [SMILES: Cn1nc(C(=O)NS(C)(=O)=O)cc1-c1cccc(Cl)n1 ; O=C(O)C(F)(F)F] | Example I-126: 1H-NMR(400.0 MHz, d6-DMSO): δ = 8.036(1.34); 8.016(3.14); 7.996(2.02); 7.911(3.S2); 7.892(2.62); 7.584 (3.16); 7.564(2.91); 7.44(3.97); 4.213(16); 4.153(0.83); 4.107(0.38); 4.099(0.38); 4.074(0.39); 4.032(0.5); 4.002(0.48); 3.974(0.52); 3.969 (0.54); 3.933(0.62); 3.903(6.38); 3.74(1.55); 3.508(6.73); 3.45(7.38); 3.302 (4.16); 3.276(14.48); 3.169(2.83); 2.944(0.73); 2.909(0.54); 2.89(0.46); 2.88(0.44); 2.844(0.36); 2.695(0.77); 2.672(0.96); 2.542(1.9); 2.507 (127.41); 2.503(164.89); 2.499(132.47); 2.33(1.36); 2.198(0.36); 2.178 (0.43); 2.157(0.37); 1.265(0.36); 1.259(0.36); 1.235(0.68); 0(4.6) |
| I-127 | 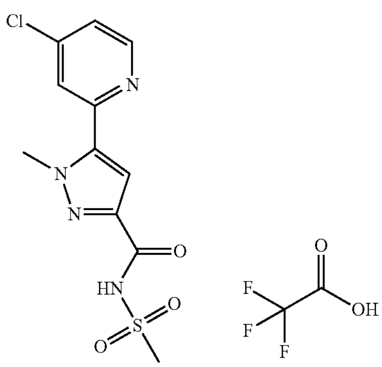 [SMILES: Cn1nc(C(=O)NS(C)(=O)=O)cc1-c1cc(Cl)ccn1 ; O=C(O)C(F)(F)F] | Example I-127: 1H-NMR(400.0 MHz, d6-DMSO): δ = 8.693(3.34); 8.68(3.47); 8.08(3.95); 8.076(4.1); 7.61(2); 7.606(2.14); 7.596(2.03); 7.593(2.05); 7.529(4.14); 4.595(0.46); 4.232(16); 4.206 (0.99); 4.178(0.42); 4.156(0.41); 4.144(0.39); 4.098(0.42); 4.053(0.52); 4.012(0.49); 4(0.51); 3.989(0.52); 3.962(0.55); 3.957(0.59); 3.943(0.6); 3.902(9.74); 3.83(1.01); 3.764(1.36); 3.418(16.39); 3.318(20.48); 3.219 (4.27); 3.169(13.35); 2.993(1.08); 2.91(1.19); 2.892(0.77); 2.87(0.58); 2.771(0.38); 2.75(0.33); 2.731(0.34); 2.695(0.52); 2.69(0.9); 2.672(1.54); 2.647(0.44); 2.55(2.78); 2.543(2.75); 2.507(217.6); 2.503(278.75); 2.499(217.29); 2.33(2.16); 2.297(0.62); 2.276(0.56); 2.263(0.52); 2.23 (0.49); 2.198(0.47); 2.178(0.49); 2.157(0.43); 2.106(0.36); 2.094(0.33); 2.088(0.33); 2.042(0.32); 1.258(0.44); 1.235(1.04); 1.213(0.34); 1.194 (0.39); 1.184(0.36); 1.178(0.34); 0(8.31) |
| I-128 | 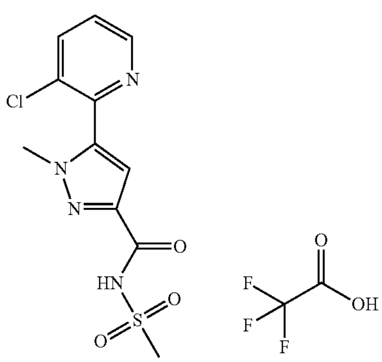 [SMILES: Cn1nc(C(=O)NS(C)(=O)=O)cc1-c1ncccc1Cl ; O=C(O)C(F)(F)F] | Example I-128: 1H-NMR(400.0 MHz, d6-DMSO): δ = 11.914(0.64); 8.722(1.8); 8.713(1.8); 8.71(1.8); 8.184(1.67); 8.164 (1.78); 7.597((1.48); 7.585(1.48); 7.576(1.42); 7.565(1.4); 7.321(5.7); 7.204(1.52); 7.076(1.73); 6.948(1.53); 4.596(0.44); 4.03(0.33); 3.949(16); 3.924(0.78); 3.911(1.09); 3.903(4.13); 3.878(0.68); 3.872(0.67); 3.829 (0.99); 3.768(1.25); 3.526(7.06); 3.509(6.86); 3.355(15.8); 3.324(1.53); 3.304(1.34); 3.219(0.91); 3.169(8.4); 3.13(0.44); 3.075(0.35); 2.91(0.6); 2.672(0.89); 2.542(1.28); 2.507(113.97); 2.503(144.31); 2.499 (111.51); 2.33(0.83); 0(1.5) |

-continued
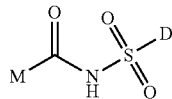
(I)
| Example No. | Structure | NMR peak list |
|---|---|---|
| I-129 | 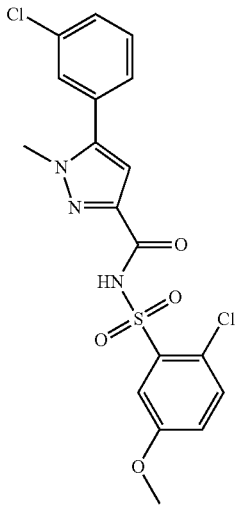 [SMILES: COc1ccc(Cl)c(S(=O)(=O)NC(=O)c2cc(-c3cccc(Cl)c3)n(C)n2)c1] | Example I-129: 1H-NMR(400.0 MHz, d6-DMSO): δ = 7.67(2.99); 7.617(2.97); 7.609(3.11); 7.586(2.36); 7.563(3.91); 7.555 (8.42); 7.539(1.09); 7.306(1.4); 7.299(1.35); 7.284(1.23); 7.277(1.14); 7.065(4.56); 3.941(14.79); 3.902(1.84); 3.86(16); 3.338(64.09); 3.169 (0.58); 2.672(0.55); 2.507(73.01); 2.503(92.19); 2.499(71.15); 2.329(0.51); 0(4.17) |
| I-130 | 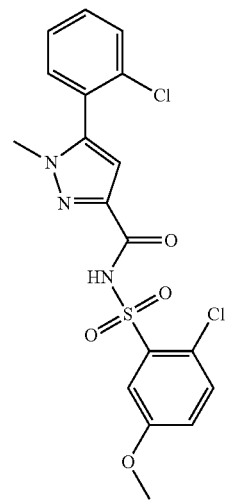 [SMILES: COc1ccc(Cl)c(S(=O)(=O)NC(=O)c2cc(-c3ccccc3Cl)n(C)n2)c1] | Example I-130: 1H-NMR(400.0 MHz, d6-DMSO): δ = 7.681(1.95); 7.661(2.76); 7.622(3.05); 7.615(3.18); 7.591(2.72); 7.584 (1.29); 7.57(3.88); 7.552(0.95); 7.546(1.42); 7.538(1.15); 7.524(3.41); 7.518(3.94); 7.499(1.61); 7.48(0.45); 7.31(1.44); 7.303(1.4); 7.288(1.24); 7.281(1.17); 6.966(4.37); 3.902(2.58); 3.86(16); 3.728(14.96); 3.713 (1.08); 3.342(99.08); 3.169(0.69); 2.672(0.6); 2.503(104.25); 2.329(0.57); 1.299(0.4); 1.259(0.66); 1.244(0.52); 1.236(0.34); 0(3.46) |

-continued
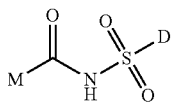
(I)
| Example No. | Structure | NMR peak list |
|---|---|---|
| I-131 | 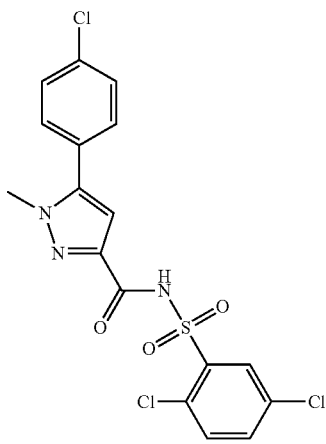 [SMILES: Cn1nc(C(=O)NS(=O)(=O)c2cc(Cl)ccc2Cl)cc1-c1ccc(Cl)cc1] | Example I-131: 1H-NMR(400.0 MHz, d6-DMSO): δ = 8.101(2.29); 8.095(2.39); 7.831(0.86); 7.825(0.83); 7.809(1.3); 7.803 (1.26); 7.73(2.36); 7.708(1.57); 7.596(16); 7.023(3.73); 3.928(11.01); 3.902(1.96); 3.509(0.43); 3.349(20.18); 3.17(0.71); 2.672(0.38); 2.508 (49.34); 2.503(63.19); 2.499(47.1); 2.33(0.38); 0(2.47) |
| I-132 | 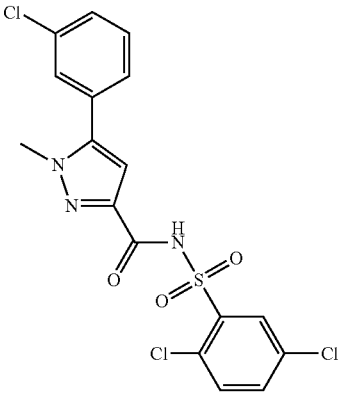 [SMILES: Cn1nc(C(=O)NS(=O)(=O)c2cc(Cl)ccc2Cl)cc1-c1cccc(Cl)c1] | Example I-132: 1H-NMR(400.0 MHz, d6-DMSO): δ = 8.102(3.32); 8.096(3.46); 7.83(1.23); 7.824(1.2); 7.809(1.85); 7.803 (1.83); 7.731(3.28); 7.709(2.18); 7.67(3.31); 7.569(1.3); 7.554(8.9); 7.539 (1.24); 7.053(5.23); 4.597(0.33); 3.942(16); 3.902(2.33); 3.353(41.64); 3.17(0.65); 2.673(0.54); 2.508(72.11); 2.504(90.62); 2.5(70.45); 2.33 (0.53); 0(2.46) |
| I-133 | 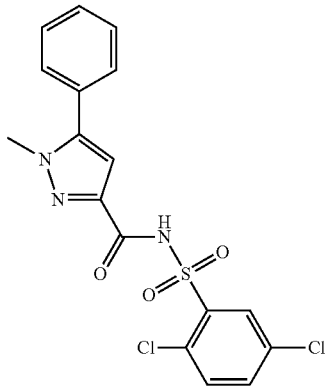 [SMILES: Cn1nc(C(=O)NS(=O)(=O)c2cc(Cl)ccc2Cl)cc1-c1ccccc1] | Example I-133: 1H-NMR(400.0 MHz, d6-DMSO): δ = 8.104(3.26); 8.098(3.42); 7.833(1.14); 7.828(1.08); 7.812(1.7); 7.806 (1.62); 7.734(3.06); 7.712(2.02); 7.572(1.77); 7.553(4.77); 7.528(4.18); 7.509(2.97); 7.504(2.34); 7.487(1.39); 7.47(0.38); 6.996(4.29); 3.932 (16); 3.903(2.14); 3.508(0.44); 3.345(6.58); 3.169(0.37); 2.671(0.53); 2.506(67.41); 2.502(86.42); 2.498(66.85); 2.329(0.48); 0(3.49) |

-continued
(I)
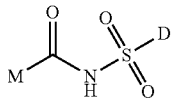
| Example No. | Structure | NMR peak list |
|---|---|---|
| I-134 | 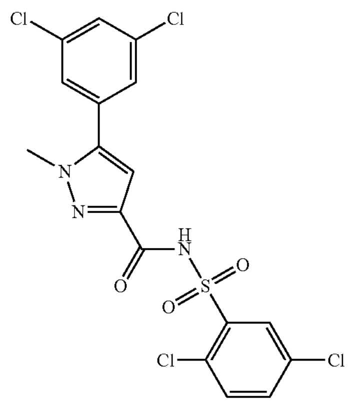 [SMILES: Cn1nc(C(=O)NS(=O)(=O)c2cc(Cl)ccc2Cl)cc1-c1cc(Cl)cc(Cl)c1] | Example I-134: 1H-NMR(400.0 MHz, d6-DMSO): δ = 8.09(2.74); 8.086(2.72); 7.803(0.77); 7.792(0.96); 7.755(1.92); 7.752 (3.56); 7.749(2.09); 7.71(1.67); 7.696(1.33); 7.681(8.84); 7.678(8.1); 7.081(1.6); 3.947(16); 3.336(2.23); 2.616(0.5); 2.613(0.67); 2.61(0.49); 2.522(2.86); 2.519(3.52); 2.516(4.08); 2.507(40.71); 2.504(79.18); 2.501 (104.2); 2.498(75.78); 2.495(35.83); 2.388(0.5); 2.385(0.66); 2.382 (0.47); 1.908(1.07); 0.005(0.49); 0(10.44); −0.006(0.33) |
| I-135 | 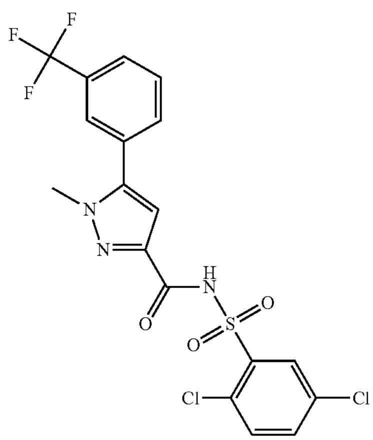 [SMILES: Cn1nc(C(=O)NS(=O)(=O)c2cc(Cl)ccc2Cl)cc1-c1cccc(C(F)(F)F)c1] | Example I-135: 1H-NMR(400.0 MHz, d6-DMSO): δ = 8.107(3.05); 8.101(3.41); 7.927(3.34); 7.914(1.86); 7.894(2.14); 7.873 (1.47); 7.853(2.19); 7.831(1.26); 7.809(1.89); 7.79(1.68); 7.771(2.18); 7.751(0.91); 7.734(2.69); 7.712(1.78); 7.135(3.91); 3.955(16); 3.902 (3.86); 3.509(0.55); 3.346(15.26); 3.169(2.28); 2.672(0.67); 2.507(86.95); 2.503(112.52); 2.499(88.88); 2.33(0.62); 0(5.25) |
| I-136 | 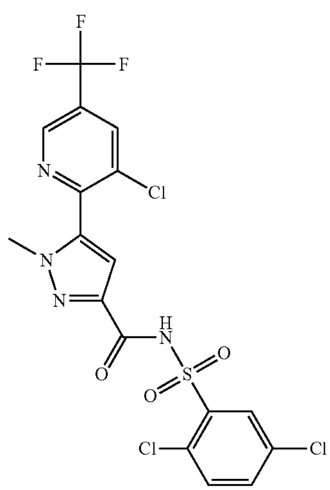 [SMILES: Cn1nc(C(=O)NS(=O)(=O)c2cc(Cl)ccc2Cl)cc1-c1ncc(C(F)(F)F)cc1Cl] | Example I-136: 1H-NMR(400.0 MHz, d6-DMSO): δ = 9.109(3.91); 8.711(3.96); 8.103(3.36); 8.097(3.46); 7.81(1.16); 7.79 (1.73); 7.716(2.55); 7.695(1.71); 7.413(2.72); 4.022(0.33); 3.984(16); 3.902(5.4); 3.508(0.81); 3.343(33.51); 3.169(1.08); 2.859(0.41); 2.672 (0.93); 2.507(121.65); 2.503(152.84); 2.499(116.39); 2.329(0.83); 1.249 (0.33); 1.235(0.48); 0.94(0.44); 0.923(0.44); 0(7.67) |

-continued
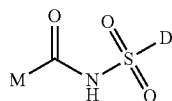
(I)
| Example No. | Structure | NMR peak list |
|---|---|---|
| I-137 | 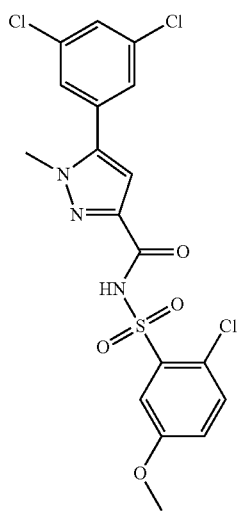 [SMILES: COc1ccc(Cl)c(S(=O)(=O)NC(=O)c2cc(-c3cc(Cl)cc(Cl)c3)n(C)n2)c1] | Example I-137: 1H-NMR(400.0 MHz, d6-DMSO): δ = 7.755(4.09); 7.712(0.45); 7.683(8.73); 7.611(3.26); 7.604(3.44); 7.578 (2.1); 7.556(2.43); 7.292(1.63); 7.274(1.43); 7.102(3.54); 4.222(0.32); 4.022(0.33); 4.006(0.35); 3.95(14.52); 3.902(3.72); 3.857(16); 3.816 (0.51); 3.674(0.32); 3.338(390.16); 2.672(1.34); 2.503(214.55); 2.329 (1.21); 1.237(0.45); 0.94(0.45); 0.923(0.48); 0.912(0.41); 0(4.52) |
| I-138 | 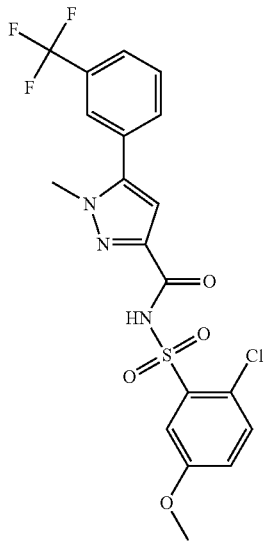 [SMILES: COc1ccc(Cl)c(S(=O)(=O)NC(=O)c2cc(-c3cccc(C(F)(F)F)c3)n(C)n2)c1] | Example I-138: 1H-NMR(400.0 MHz, d6-DMSO): δ = 7.927(3.03); 7.916(1.74); 7.896(1.89); 7.874(1.3); 7.854(1.91); 7.792 (1.44); 7.772(1.91); 7.753(0.73); 7.621(2.95); 7.614(3.06); 7.589(2.41); 7.566(2.81); 7.31(1.53); 7.302(1.47); 7.287(1.33); 7.28(1.24); 7.143 (4.93); 3.955(14.91); 3.902(2.7); 3.862(16); 3.341(80.08); 3.17(0.92); 2.672 (0.55); 2.507(76.32); 2.503(93.25); 2.33(0.52); 0(3.36) |

US 10,820,591 B2
227                                                                                                                            228
-continued
(I)
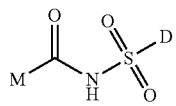
| Example No. | Structure | NMR peak list |
|---|---|---|
| I-139 | 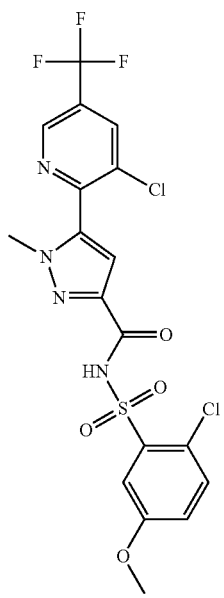 [SMILES: COc1ccc(Cl)c(S(=O)(=O)NC(=O)c2cc(-c3ncc(C(F)(F)F)cc3Cl)n(C)n2)c1] | Example I-139: 1H-NMR(400.0 MHz, d6-DMSO): δ = 9.112(3.03); 8.713(3.05); 7.626(2.93); 7.618(3.04); 7.586(1.81); 7.564 (2.09); 7.454(2.94); 7.307(1.17); 7.3(1.19); 7.286(1.04); 7.279(0.99); 3.988(14.57); 3.968(0.39); 3.902(3.1); 3.862(16); 3.51(0.34); 3.342 (111.04); 3.17(1.98); 2.672(0.65); 2.508(87.69); 2.504(110.16); 2.5(83.97); 2.33(0.59); 0(3.38) |
| I-140 | 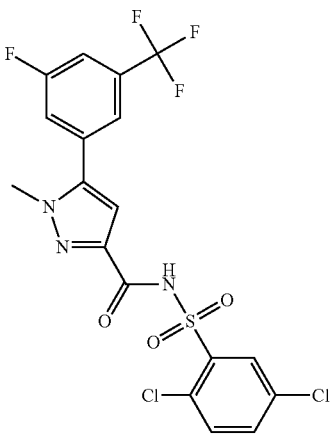 [SMILES: Cn1nc(C(=O)NS(=O)(=O)c2cc(Cl)ccc2Cl)cc1-c1cc(F)cc(C(F)(F)F)c1] | Example I-140: 1H-NMR(400.0 MHz, d6-DMSO): δ = 8.104(3.27); 8.098(3.48); 7.879(1.45); 7.856(2.83); 7.833(2.57); 7.828 (1.93); 7.811(4.89); 7.732(3.17); 7.71(2.13); 7.177(4.85); 4.596(0.51); 3.98(16); 3.902(2.9); 3.351(51.88); 3.17(0.62); 2.673(0.65); 2.508 (84.71); 2.504(108.82); 2.499(82.27); 2.33(0.63); 0(3.58) |

(I)
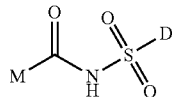
| Example No. | Structure | NMR peak list |
|---|---|---|
| I-141 | 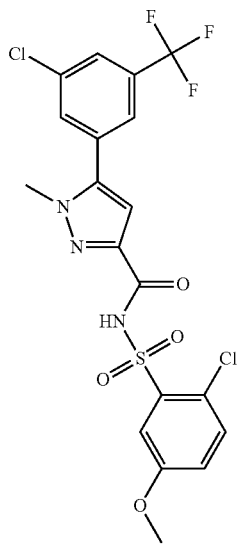 [SMILES: COc1ccc(Cl)c(S(=O)(=O)NC(=O)c2cc(-c3cc(Cl)cc(C(F)(F)F)c3)n(C)n2)c1] | Example I-141: 1H-NMR(400.0 MHz, d6-DMSO): δ = 8.036(2.91); 8.009(2.78); 7.93(2.87); 7.617(2.94); 7.609(3.06); 7.385 (1.82); 7.563(2.12); 7.306(1.16); 7.299(1.18); 7.284(1.01); 7.277(1); 7.188(3.34); 3.968(14.23); 3.903(2.93); 3.86(16); 3.333(36.85); 2.671 (0.62); 2.507(80.21); 2.502(103.14); 2.498(78.51); 2.329(0.56); 0(4.69) |
| I-142 | 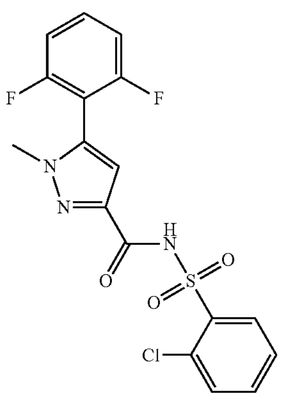 [SMILES: Cn1nc(C(=O)NS(=O)(=O)c2ccccc2Cl)cc1-c1c(F)cccc1F] | Example I-142: 1H-NMR(400.0 MHz, d6-DMSO): δ = 8.165(2.23); 8.146(2.36); 7.712(1.43); 7.695(3.05); 7.674(4.15); 7.663 (3.54); 7.637(1.27); 7.624(1.45); 7.605(1.95); 7.586(0.88); 7.357(3.18); 7.337(5.28); 7.317(2.66); 7.054(2.12); 5.139(0.37); 3.902(11.16); 3.777(16); 3.575(0.98); 3.508(0.39); 3.338(97.18); 3.304(6.08); 3.286 (3.04); 3.169(0.8); 3.048(0.34); 2.88(0.52); 2.866(0.99); 2.852(0.92); 2.838 (0.5); 2.696(7.08); 2.676(0.79); 2.672(1.03); 2.668(0.82); 2.542(0.75); 2.512(64.74); 2.508(130.84); 2.503(173.6); 2.499(129.04); 2.494(65.84); 2.334(0.72); 2.33(0.98); 2.325(0.75); 2.197(0.8); 2.177(1.54); 2.157 (1.07); 1.938(0.38); 1.921(0.92); 1.918(0.76); 1.902(1.06); 1.882(0.85); 1.235(0.44); 0(7.59) |
| I-143 | 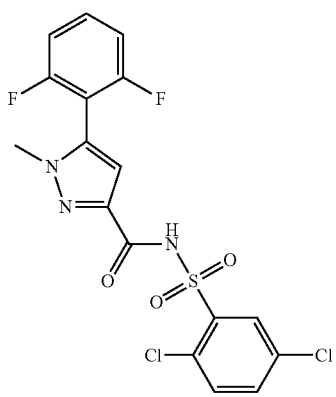 [SMILES: Cn1nc(C(=O)NS(=O)(=O)c2cc(Cl)ccc2Cl)cc1-c1c(F)cccc1F] | Example I-143: 1H-NMR(400.0 MHz, d6-DMSO): δ = 7.968(3.31); 7.662(0.57); 7.641(1.48); 7.624(2.35); 7.605(1.69); 7.586 (0.64); 7.492(2.29); 7.463(2.65); 7.443(1.33); 7.321(2.54); 7.301(4.08); 7.282(2.17); 7.053(0.39); 7.035(0.41); 6.67(0.6); 6.652(0.93); 6.632 (2.01); 6.024(0.43); 6.016(0.45); 4.107(0.33); 4.1(0.35); 3.902(16); 3.67 (11.06); 3.508(0.74); 3.493(0.43); 3.479(0.61); 3.469(0.69); 3.465(0.67); 3.458(0.68); 3.434(1.08); 3.338(345.99); 3.267(2.8); 3.222(0.55); 3.173(1.8); 3.164(1.79); 2.892(0.53); 2.731(0.33); 2.695(0.33); 2.69(0.5); 2.676(1.47); 2.672(2.01); 2.668(1.53); 2.542(6.09); 2.507(274.83); 2.503 (360.79); 2.499(268.17); 2.451(0.43); 2.334(1.49); 2.33(2.05); 2.325 (1.51); 1.298(0.34); 1.259(0.47); 1.249(0.66); 1.236(1.16); 0.008(0.62); 0(18.57); −0.008(0.76) |

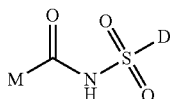
(I)
| Example No. | Structure | NMR peak list |
|---|---|---|
| I-144 | 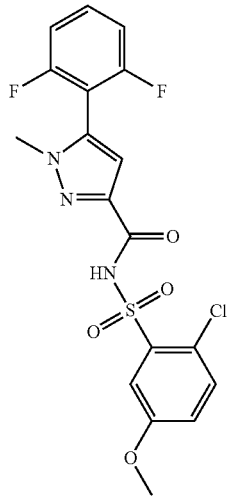 [SMILES: COc1ccc(Cl)c(S(=O)(=O)NC(=O)c2cc(-c3c(F)cccc3F)n(C)n2)c1] | Example I-144: 1H-NMR(400.0 MHz, d6-DMSO): δ = 7.681(0.83); 7.676(0.79); 7.66(1.68); 7.644(2.04); 7.627(1.47); 7.607 (0.68); 7.577(2.91); 7.474(0.43); 7.452(0.52); 7.414(0.75); 7.403(0.71); 7.349(1.88); 7.336(3); 7.33(3.21); 7.317(4.44); 7.297(2.32); 7.118(0.58); 7.049(0.46); 7.031(0.43); 6.828(0.37); 6.755(1.94); 6.025(0.4); 6.016 (0.42); 3.903(16); 3.82(13.05); 3.801(1.79); 3.737(6.4); 3.717(6.83); 3.508 (0.57); 3.479(0.61); 3.47(0.69); 3.466(0.7); 3.459(0.69); 3.434(1); 3.338 (177.88); 3.292(5.15); 3.268(2.83); 3.252(1.71); 3.17(1.55); 3.147 (0.42); 3.024(1.29); 2.988(3.05); 2.853(2.22); 2.677(0.96); 2.672(1.28); 2.668(0.97); 2.542(1.62); 2.512(88.83); 2.508(175.36); 2.503(229.74); 2.499(170.48); 2.334(0.95); 2.33(1.27); 2.326(0.95); 1.259(0.37); 1.25 (0.53); 1.235(1.13); 0.008(0.39); 0(12.45); −0.008(0.55) |
| I-145 | 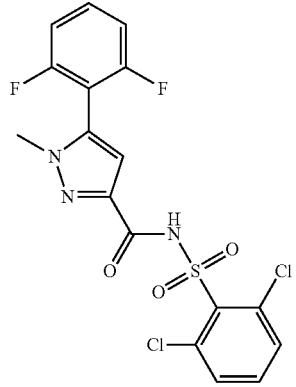 [SMILES: Cn1nc(C(=O)NS(=O)(=O)c2c(Cl)cccc2Cl)cc1-c1c(F)cccc1F] | Example I-145: 1H-NMR(400.0 MHz, d6-DMSO): δ = 7.684(0.56); 7.666(1.26); 7.647(1.87); 7.628(1.35); 7.609(0.65); 7.598 (0.34); 7.545(1.77); 7.526(2.72); 7.443(0.81); 7.428(0.99); 7.409(0.78); 7.388(0.46); 7.338(2.93); 7.318(4.67); 7.298(2.37); 6.824(0.35); 6.819 (0.35); 3.902(16); 3.821(0.46); 3.723(8.26); 3.508(0.67); 3.49(0.53); 3.479(0.72); 3.47(0.8); 3.466(0.83); 3.458(0.9); 3.434(1.36); 3.337 (139.16); 3.268(2.78); 3.169(2.06); 2.85(9.93); 2.69(0.66); 2.676(0.94); 2.672(1.25); 2.668(0.95); 2.542(1.44); 2.507(172); 2.503(225.06); 2.499 (168.13); 2.334(0.91); 2.33(1.28); 2.325(0.97); 1.259(0.32); 1.249(0.4); 1.236(0.73); 0.008(0.37); 0(11.46); −0.008(0.52) |
| I-146 | 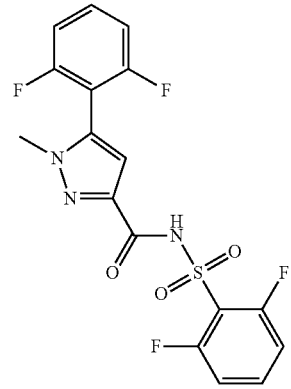 [SMILES: Cn1nc(C(=O)NS(=O)(=O)c2c(F)cccc2F)cc1-c1c(F)cccc1F] | Example I-146: 1H-NMR(400.0 MHz, d6-DMSO): δ = 7.659(0.69); 7.64(1.7); 7.622(2.63); 7.602(1.8); 7.584(0.7); 7.425 (1.85); 7.353(0.46); 7.342(0.64); 7.32(3.67); 7.3(5.83); 7.28(3); 7.03(2.78); 7.009(4.45); 6.99(2.36); 6.915(0.38); 6.67(0.73); 6.654(0.85); 6.602 (3.19); 5.845(0.47); 5.836(0.4); 5.791(0.54); 4.614(0.34); 4.596(0.58); 4.577(0.33); 3.902(10.67); 3.82(0.55); 3.762(0.88); 3.665(16); 3.543(0.34); 3.508(0.83); 3.487(0.7); 3.477(0.66); 3.342(602.47); 3.267(1.36); 3.22 (0.45); 3.175(0.73); 3.162(0.69); 2.689(0.49); 2.676(1.46); 2.672(2); 2.566(0.34); 2.542(7.36); 2.507(273.24); 2.503(359.09); 2.499(271.98); 2.334(1.5); 2.33(2.02); 2.326(1.56); 1.298(0.45); 1.258(0.69); 1.248(0.63); 1.235(1.27); 0.007(0.44); 0(13.17) |

-continued
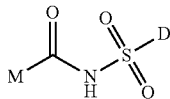
(I)
| Example No. | Structure | NMR peak list |
|---|---|---|
| I-147 | 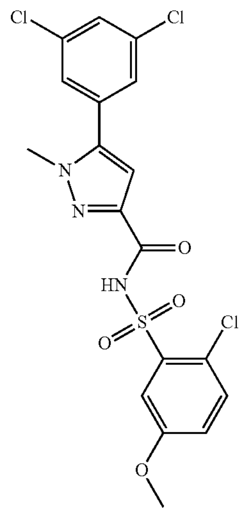 [SMILES: COc1ccc(Cl)c(S(=O)(=O)NC(=O)c2cc(-c3cc(Cl)cc(Cl)c3)n(C)n2)c1] | Example I-147: 1H-NMR(400.0 MHz, d6-DMSO): δ = 7.777(1.8); 7.772(3.59); 7.767(2.14); 7.608(7.16); 7.603(7.11); 7.554 (2.72); 7.546(2.79); 7.312(1.66); 7.29(1.91); 6.993(0.98); 6.986(1.02); 6.972(0.91); 6.964(0.87); 5.756(4.46); 3.791(16); 3.759(13.41); 3.323 (34.63); 2.671(0.45); 2.565(2.31); 2.506(56.32); 2.502(74.46); 2.497 (56.62); 2.329(0.42); 2.324(0.33); 1.989(1.24); 1.235(0.71); 1.192(0.36); 1.175(0.64); 1.157(0.35); 0.854(0.32); 0.008(2.64); 0(64.84); −0.15(0.32) |
| I-148 | 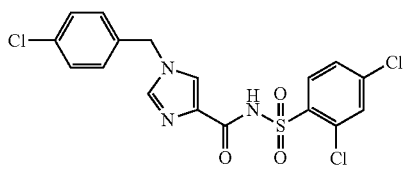 [SMILES: O=C(NS(=O)(=O)c1ccc(Cl)cc1Cl)c1cn(Cc2ccc(Cl)cc2)cn1] | Example I-148: 1H-NMR(400.0 MHz, d6-DMSO): δ = 8.586(3.13); 8.318(0.35); 8.063(7.14); 8.042(7.95); 8.026(8.63); 8.022 (8.23); 7.978(0.45); 7.956(0.48); 7.855(0.46); 7.85(0.47); 7.73(0.8); 7.716 (6.08); 7.711(6.54); 7.639(0.32); 7.617(0.4); 7.607(4.44); 7.601(4.07); 7.585(3.98); 7.58(3.76); 7.478(6.07); 7.473(2.49); 7.462(3.7); 7.457 (16); 7.452(2.83); 7.429(13.82); 7.424(3.38); 7.413(2.21); 7.408(5.37); 5.301(15.47); 4.756(0.35); 4.72(0.36); 4.67(0.4); 4.625(0.4); 4.616(0.41); 4.596(0.42); 4.547(0.42); 4.502(0.41); 4.454(0.39); 4.427(0.37); 4.348 (0.32); 2.944(0.82); 2.784(0.67); 2.676(0.52); 2.672(0.73); 2.668(0.54); 2.525(2.48); 2.52(4.01); 2.512(41.71); 2.507(83.46); 2.503(108.93); 2.498(78.6); 2.494(37.98); 2.334(0.57); 2.33(0.77); 2.325(0.56); 1.958 (0.71); 0(2.9) |
| I-149 | 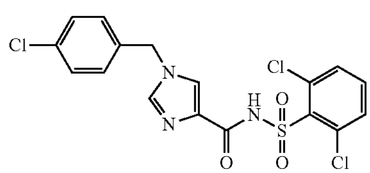 [SMILES: O=C(NS(=O)(=O)c1c(Cl)cccc1Cl)c1cn(Cc2ccc(Cl)cc2)cn1] | Example I-149: 1H-NMR(400.0 MHz, d6-DMSO): δ = 8.551(1.53); 7.97(3.42); 7.609(0.38); 7.569(0.34); 7.505(7.7); 7.492 (11.73); 7.476(0.95); 7.472(8.47); 7.469(3.12); 7.462(3.91); 7.458(16); 7.454(2.24); 7.435(0.39); 7.429(3.85); 7.423(11.94); 7.417(4.1); 7.415 (4.14); 7.412(3.59); 7.409(6.9); 7.403(2.25); 7.36(0.36); 7.347(0.49); 5.297 (14.63); 3.616(0.52); 3.419(124.87); 3.107(0.95); 3.012(0.64); 2.944 (1.75); 2.784(1.22); 2.62(0.85); 2.617(1.88); 2.614(2.63); 2.61(1.88); 2.607(0.87); 2.541(0.7); 2.538(0.48); 2.523(5.74); 2.52(6.98); 2.517(6.8); 2.508(135.6); 2.505(293.61); 2.502(407.76); 2.499(296.55); 2.496 (136.11); 2.392(0.78); 2.389(1.78); 2.386(2.52); 2.383(1.79); 2.38(0.8); 2.349(0.52); 1.957(1.26); 1.909(1.45); 0.096(0.67); 0.005(5.53); 0(191.57); −0.006(5.64); −0.009(0.35); −0.1(0.68) |
| I-150 | 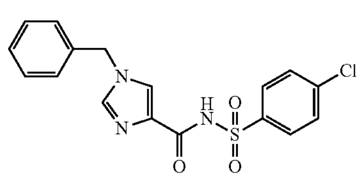 [SMILES: O=C(NS(=O)(=O)c1ccc(Cl)cc1)c1cn(Cc2ccccc2)cn1] | Example I-150: 1H-NMR(400.0 MHz, d6-DMSO): δ = 8.215(2.7); 7.973(7.76); 7.971(7.29); 7.935(9.04); 7.914(10.43); 7.644 (9.04); 7.622(7.73); 7.538(0.56); 7.391(1.87); 7.388(1.47); 7.37(5.06); 7.356(10.05); 7.34(6.95); 7.333(11.61); 7.325(5.47); 7.315(5.16); 5.259 (16); 2.676(0.4); 2.671(0.56); 2.667(0.4); 2.525(1.88); 2.511(36.3); 2.507 (71.01); 2.502(92.19); 2.498(68.32); 2.494(35.07); 2.333(0.54); 2.329 (0.69); 2.325(0.53); 0.008(1.2); 0(35.86); −0.008(2.06) |
| I-151 | 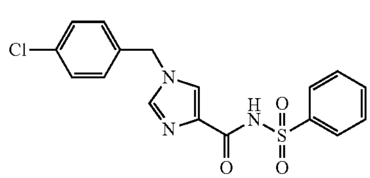 [SMILES: O=C(NS(=O)(=O)c1ccccc1)c1cn(Cc2ccc(Cl)cc2)cn1] | Example I-151: 1H-NMR(400.0 MHz, d6-DMSO): δ = 8.036(4.94); 7.995(8.79); 7.967(7.38); 7.948(7.91); 7.838(0.35); 7.822 (0.37); 7.687(1.32); 7.669(3.9); 7.651(3.16); 7.609(5.96); 7.59(8.43); 7.571(3.46); 7.446(7.34); 7.424(10.98); 7.347(10.45); 7.326(6.9); 5.246 (16); 2.672(0.47); 2.503(68.54); 2.33(0.49); 1.356(0.43); 0(10.23) |

-continued (I)

| Example No. | Structure | NMR peak list |
|---|---|---|
| I-152 | 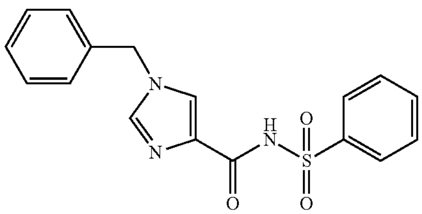 [SMILES: O=C(NS(=O)(=O)c1ccccc1)c1cn(Cc2ccccc2)cn1] | Example I-152: 1H-NMR(400.0 MHz, d6-DMSO): δ = 8.055(4.04); 7.993(7.98); 7.991(7.92); 7.965(6.81); 7.946(7.51); 7.943 (5.95); 7.682(1.2); 7.663(3.83); 7.645(3); 7.604(5.76); 7.585(8.1); 7.567 (3.23); 7.389(1.19); 7.385(1.8); 7.367(4.94); 7.362(3.75); 7.35(7.12); 7.334(3.33); 7.331(3.78); 7.318(11.36); 7.298(4.91); 5.759(0.32); 5.245 (16); 2.507(35.67); 2.503(45.85); 2.498(34.74); 0(9.01) |
| I-153 | 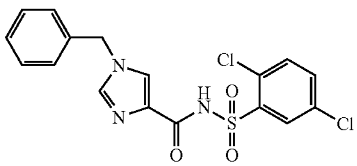 [SMILES: O=C(NS(=O)(=O)c1cc(Cl)ccc1Cl)c1cn(Cc2ccccc2)cn1] | Example I-153: 1H-NMR(400.0 MHz, d6-DMSO): δ = 8.855(4.05); 8.014(6.81); 7.997(4.83); 7.992(4.69); 7.609(2.34); 7.604 (2.34); 7.588(3.49); 7.533(4.92); 7.512(2.92); 7.403(16); 7.383(4.76); 5.326(12.22); 2.672(0.36); 2.504(49.08); 2.33(0.4); 2.076(2.1); 0(0.85) |
| I-154 | 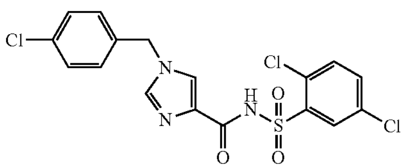 [SMILES: O=C(NS(=O)(=O)c1cc(Cl)ccc1Cl)c1cn(Cc2ccc(Cl)cc2)cn1] | Example I-154: 1H-NMR(400.0 MHz, d6-DMSO): δ = 8.816(3.36); 8.037(7.04); 8.033(6.94); 8.002(6.14); 7.996(6.27); 7.623 (2.65); 7.617(2.51); 7.602(4.42); 7.595(4.38); 7.545(8.05); 7.524(4.62); 7.486(3.11); 7.48(1.66); 7.47(2.78); 7.464(16); 7.452(13.84); 7.446 (2.38); 7.436(1.32); 7.43(2.78); 5.322(13.31); 2.676(0.43); 2.672(0.62); 2.667(0.44); 2.525(2.85); 2.512(36.35); 2.507(71.95); 2.503(93.8); 2.498 (68.05); 2.494(33.38); 2.334(0.45); 2.33(0.61); 2.325(0.46); 0(3.86) |
| I-155 | 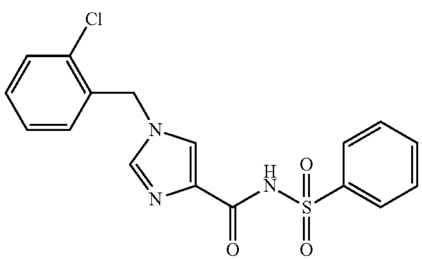 [SMILES: O=C(NS(=O)(=O)c1ccccc1)c1cn(Cc2ccccc2Cl)cn1] | Example I-155: 1H-NMR(400.0 MHz, d6-DMSO): δ = 8(5.17); 7.977(6.84); 7.959(8.06); 7.955(6.08); 7.947(8.32); 7.944 (7.79); 7.697(1.26); 7.684(0.97); 7.678(4.05); 7.673(1.36); 7.66(3.07); 7.618(5.75); 7.598(7.94); 7.588(1.05); 7.584(1.55); 7.58(3.09); 7.569(0.44); 7.524(2.9); 7.518(3.24); 7.504(2.74); 7.5(4.24); 7.415(1.02); 7.41(1.4); 7.396(3.36); 7.391(3.71); 7.384(3.31); 7.378(5.9); 7.372(3.21); 7.366 (4.01); 7.362(3.95); 7.347(1.35); 7.343(1.01); 7.228(3.3); 7.223(2.55); 7.211(2.73); 7.205(2.54); 5.76(1.9); 5.368(16); 2.526(0.93); 2.512(13.02); 2.508(25.89); 2.504(33.93); 2.499(24.83); 2.495(12.34); 1.357(1.3); 0(0.97) |
| I-156 | 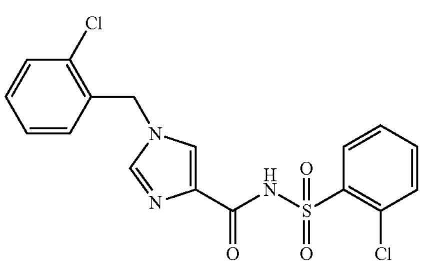 [SMILES: O=C(NS(=O)(=O)c1ccccc1Cl)c1cn(Cc2ccccc2Cl)cn1] | Example I-156: 1H-NMR(400.0 MHz, d6-DMSO): δ = 8.202(3.88); 8.116(3.4); 8.112(3.59); 8.096(3.65); 8.093(3.69); 7.995 (7.72); 7.657(0.98); 7.653(1.06); 7.637(2.98); 7.62(3.6); 7.616(3.67); 7.602(5.88); 7.585(2.42); 7.574(2.76); 7.57(2.36); 7.554(3.7); 7.542(3.18); 7.537(4.22); 7.523(2.93); 7.519(3.81); 7.437(0.98); 7.432(1.31); 7.419 (3.41); 7.413(3.98); 7.41(3.71); 7.403(5.45); 7.392(4.3); 7.387(3.58); 7.373(1.22); 7.369(0.88); 7.302(3.61); 7.285(2.56); 7.279(2.3); 5.398(16); 2.672(0.46); 2.506(57.16); 2.503(70.75); 2.329(0.51); 0(0.7) |
| I-157 | 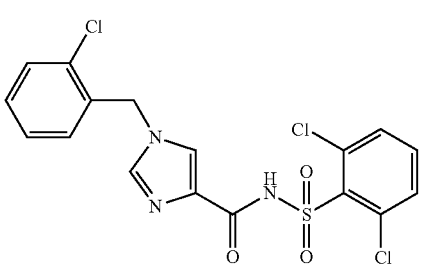 [SMILES: O=C(NS(=O)(=O)c1c(Cl)cccc1Cl)c1cn(Cc2ccccc2Cl)cn1] | Example I-157: 1H-NMR(400.0 MHz, d6-DMSO): δ = 8.538(2.66); 7.954(7.85); 7.95(7.54); 7.606(0.37); 7.548(7.05); 7.545 (8.23); 7.531(4.53); 7.527(16); 7.476(5.31); 7.459(3.83); 7.453(3.31); 7.445(1.61); 7.436(2.63); 7.432(3.69); 7.427(3.83); 7.42(3.21); 7.414 (5.37); 7.408(3.3); 7.401(4.19); 7.397(3.97); 7.383(1.57); 7.378(1.19); 7.374(0.48); 7.33(3.85); 7.326(2.75); 7.313(2.73); 7.307(2.27); 5.435 (15.19); 2.676(0.42); 2.671(0.57); 2.667(0.41); 2.525(1.77); 2.511(32.22); 2.507(63.26); 2.502(81.92); 2.498(59.27); 2.493(28.65); 2.334(0.41); 2.329 (0.56); 2.325(0.41); 2.075(0.47); 0.008(1.61); 0(42.43); −0.008(1.69) |

-continued
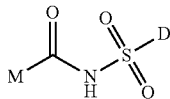
(I)
| Example No. | Structure | NMR peak list |
|---|---|---|
| I-158 | 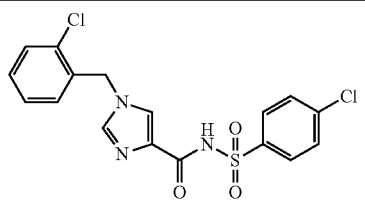 | Example I-158: 1H-NMR(400.0 MHz, d6-DMSO): δ = 8.128(4.09); 7.96(8.06); 7.938(16); 7.674(8.88); 7.652(7.63); 7.528 (2.48); 7.523(2.76); 7.508(2.89); 7.505(3.6); 7.421(1); 7.416(1.26); 7.403 (2.92); 7.398(3.21); 7.384(4.42); 7.379(2.95); 7.37(3.34); 7.367(3.14); 7.352(1.18); 7.348(0.97); 7.24(3.12); 7.236(2.7); 7.223(2.56); 7.218 (2.34); 5.382(14.14); 2.673(0.35); 2.508(43.28); 2.504(54.52); 2.5(41.79); 2.331(0.41); 0(0.62) |
| I-159 | 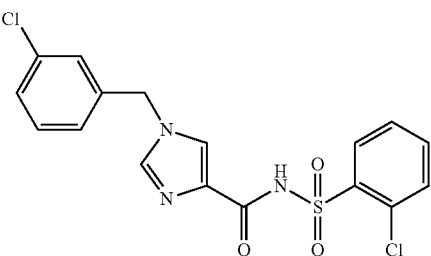 [SMILES: O=C(NS(=O)(=O)c1ccccc1Cl)c1cn(Cc2cccc(Cl)c2)cn1] | Example I-159: 1H-NMR(400.0 MHz, d6-DMSO): δ = 8.318(0.56); 8.296(3.23); 8.108(3.53); 8.104(3.74); 8.088(3.97); 8.084 (4.13); 8.074(8.28); 8.071(8.24); 7.64(1); 7.636(1.18); 7.62(2.85); 7.616 (2.78); 7.603(3.85); 7.599(3.75); 7.588(4.5); 7.584(6.26); 7.568(2.51); 7.562(3.32); 7.557(2.37); 7.542(3.45); 7.538(2.83); 7.524(1.75); 7.52 (1.62); 7.492(5.67); 7.446(0.43); 7.426(8.02); 7.422(4.31); 7.416(8.59); 7.413(9.74); 7.407(0.78); 7.402(0.61); 7.348(0.54); 7.345(0.6); 7.337 (2.37); 7.333(2.39); 7.326(3.35); 7.315(1.63); 7.312(1.47); 5.285(16); 2.512(14.68); 2.508(29.98); 2.503(40.28); 2.499(29.82); 2.494(14.83); 0.008(1.08); 0(32.15); −0.008(1.45) |
| I-160 | 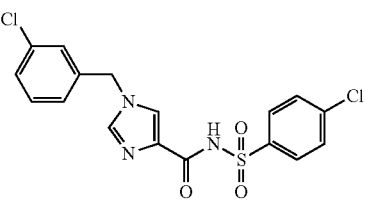 [SMILES: O=C(NS(=O)(=O)c1ccc(Cl)cc1)c1cn(Cc2cccc(Cl)c2)cn1] | Example I-160: 1H-NMR(400.0 MHz, d6-DMSO): δ = 8.19(3.18); 8.008(5.92); 7.944(7.37); 7.923(8.87); 7.839(1.63); 7.835 (0.61); 7.818(2.07); 7.67(2.26); 7.665(1); 7.649(8.01); 7.629(6.27); 7.474 (2.13); 7.459(6.51); 7.428(0.45); 7.418(0.66); 7.409(8.9); 7.396(10.38); 7.378(0.33); 7.357(0.34); 7.31(0.66); 7.302(2.58); 7.3(2.56); 7.291 (3.75); 7.281(1.89); 7.278(1.75); 5.264(16); 2.508(24.63); 2.504(31.81); 2.5(23.76); 1.357(1.03); 0.007(0.89); 0(21.16); −0.001(20.42); −0.008(1.13) |
| I-161 | 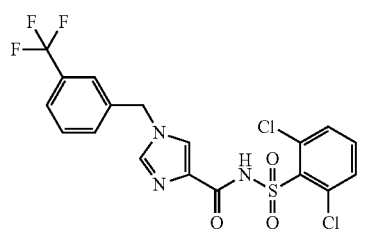 [SMILES: O=C(NS(=O)(=O)c1c(Cl)cccc1Cl)c1cn(Cc2cccc(C(F)(F)F)c2)cn1] | Example I-161: 1H-NMR(400.0 MHz, d6-DMSO): δ = 9.106(0.36); 8.699(3.57); 8.096(9.01); 7.925(4.79); 7.856(6.32); 7.752 (2.88); 7.733(4.25); 7.712(3.03); 7.695(4.89); 7.664(4.05); 7.645(4.54); 7.628(4.48); 7.609(6.1); 7.538(2.77); 7.528(7.06); 7.521(3.04); 7.509 (14.06); 7.499(1.78); 7.457(4.7); 7.44(3.55); 7.435(3.11); 7.418(1.93); 7.394(0.77); 7.376(1.68); 7.331(0.61); 7.315(0.45); 7.309(0.39); 5.419 (16); 2.674(0.5); 2.504(87.53); 2.33(0.6); 0(19.54) |
| I-162 | 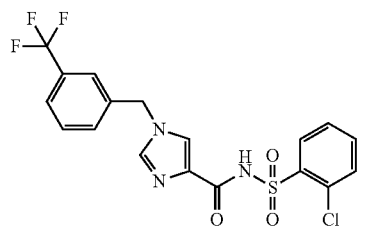 [SMILES: O=C(NS(=O)(=O)c1ccccc1Cl)c1cn(Cc2cccc(C(F)(F)F)c2)cn1] | Example I-162: 1H-NMR(400.0 MHz, d6-DMSO): δ = 8.329(2.65); 8.102(12.23); 8.099(9.41); 8.087(4.24); 8.083(4.2); 7.993 (1.47); 7.99(1.53); 7.974(1.7); 7.97(1.69); 7.807(5.56); 7.736(2.23); 7.719 (3.54); 7.672(1.34); 7.653(8.01); 7.65(8.39); 7.638(4.2); 7.634(5.79); 7.617(7.15); 7.609(3.81); 7.604(5.72); 7.6(4.23); 7.588(5.33); 7.585 (7.03); 7.568(2.71); 7.562(3.54); 7.558(2.5); 7.542(4.76); 7.538(4.02); 7.525(2.87); 7.523(2.68); 7.521(2.87); 7.505(0.86); 7.501(0.77); 5.76 (0.82); 5.385(16); 2.677(0.46); 2.672(0.66); 2.668(0.49); 2.512(40.64); 2.508(79.78); 2.503(104.25); 2.499(78.06); 2.495(41.04); 2.334(0.58); 2.33(0.76); 2.325(0.6); 0.008(1.43); 0(36.75); −0.008(1.89) |
| I-163 | 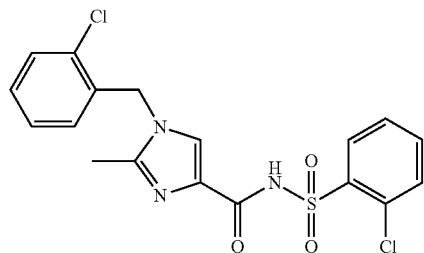 [SMILES: Cc1nc(C(=O)NS(=O)(=O)c2ccccc2Cl)cn1Cc1ccccc1Cl] | Example I-163: 1H-NMR(400.0 MHz, d6-DMSO): δ = 8.051(1.63); 8.048(1.71); 8.038(1.7); 8.036(1.69); 7.989(0.74); 7.986 (0.76); 7.976(0.81); 7.973(0.79); 7.708(5.35); 7.649(0.46); 7.647(0.54); 7.636(1.05); 7.634(1.07); 7.618(0.59); 7.615(0.63); 7.606(1.15); 7.601 (1.95); 7.593(0.57); 7.59(0.49); 7.566(1.6); 7.564(1.74); 7.552(1.94); 7.55 (2.02); 7.534(0.56); 7.531(0.58); 7.52(1.09); 7.509(1.43); 7.507(1.42); 7.498(1.82); 7.496(1.94); 7.492(2.22); 7.49(2.87); 7.479(0.96); 7.476 (0.54); 7.468(1.28); 7.465(1.01); 7.455(1.49); 7.452(1.16); 7.444(1.37); 7.441(1.42); 7.431(1.56); 7.428(1.57); 7.418(1.1); 7.415(1.02); 7.402 (1.19); 7.399(1.23); 7.389(1.84); 7.387(1.87); 7.377(0.79); 7.374(0.74); 7.153(1.46); 7.15(1.45); 7.14(1.36); 7.138(1.29); 5.383(7.17); 3.501(5.79); 2.617(0.41); 2.614(0.58); 2.611(0.41); 2.523(0.94); 2.52(1.2); 2.517 |

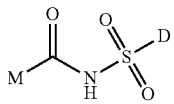
| Example No. | Structure | NMR peak list |
|---|---|---|
| | | (1.27); 2.508(30.18); 2.505(65.05); 2.502(89.79); 2.499(65.02); 2.496 (30.21); 2.456(16); 2.389(0.44); 2.386(0.59); 2.383(0.43); 0.005(1.92); 0(62.21); −0.006(2.13) |
| I-164 | 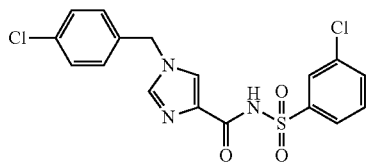 [SMILES: O=C(NS(=O)(=O)c1cccc(Cl)c1)c1cn(Cc2ccc(Cl)cc2)cn1] | Example I-164: 1H-NMR(400.0 MHz, d6-DMSO): δ = 8.357(1.16); 8.018(9.06); 8.015(8.96); 7.937(3.49); 7.934(6.11); 7.931 (3.83); 7.875(2.37); 7.873(3); 7.871(2.31); 7.862(2.64); 7.86(3.19); 7.858 (2.48); 7.711(2.05); 7.709(1.99); 7.704(0.71); 7.698(2.52); 7.696(2.5); 7.606(3.64); 7.593(5.91); 7.586(0.34); 7.58(2.64); 7.456(1.02); 7.451 (8.82); 7.448(3.14); 7.44(3.78); 7.4.37(13.47); 7.433(1.76); 7.381(10.74); 7.378(3.35); 7.37(2.76); 7.367(7.13); 5.278(16); 2.615(0.46); 2.612 (0.33); 2.524(0.81); 2.521(1.02); 2.518(1.01); 2.509(23.05); 2.506(51.07); 2.503(71.11); 2.5(51.75); 2.497(23.91); 2.39(0.34); 2.387(0.46); 2.384 (0.32); 0.005(1.93); 0(63.51); −0.006(2.23) |
| I-165 | 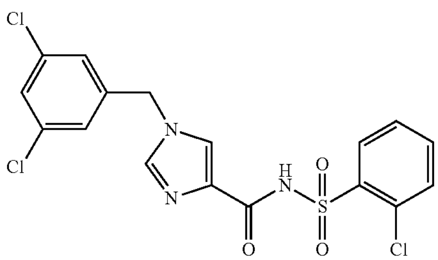 [SMILES: O=C(NS(=O)(=O)c1ccccc1Cl)c1cn(Cc2cc(Cl)cc(Cl)c2)cn1] | Example I-165: 1H-NMR(400.0 MHz, d6-DMSO): δ = 8.317(0.35); 8.272(3.7); 8.113(3.79); 8.109(4.16); 8.101(9.48); 8.097 (9.34); 8.094(4.84); 8.09(4.29); 7.994(1.52); 7.99(1.52); 7.974(1.79); 7.97 (1.74); 7.657(0.77); 7.653(1.16); 7.65(1.16); 7.645(1.21); 7.637(2.59); 7.633(3.9); 7.629(3.2); 7.625(4.54); 7.621(5.45); 7.617(7.98); 7.612 (10.08); 7.608(9.52); 7.604(3.86); 7.597(4.94); 7.593(6.8); 7.588(1.48); 7.584(1.16); 7.577(2.65); 7.573(1.95); 7.569(3.48); 7.565(2.52); 7.55 (3.51); 7.546(2.85); 7.541(1.7); 7.537(1.55); 7.532(2.03); 7.528(1.8); 7.523 (1.29); 7.522(1.59); 7.518(1.51); 7.5(16); 7.495(14.29); 5.758(0.76); 5.276(15.01); 4.51(0.33); 4.467(0.36); 4.445(0.37); 4.436(0.38); 4.416 (0.39); 4.388(0.4); 4.372(0.4); 4.363(0.41); 4.356(0.41); 4.353(0.41); 4.317 (0.41); 4.29(0.41); 4.249(0.4); 4.144(0.34); 4.111(0.33); 2.676(0.5); 2.672(0.72); 2.667(0.51); 2.525(1.73); 2.52(2.61); 2.512(37.49); 2.507 (77.1); 2.503(103.45); 2.498(75.61); 2.494(35.95); 2.334(0.53); 2.33(0.74); 2.325(0.54); 1.356(1.42); 0.146(0.36); 0.008(2.61); 0(90.79); −0.008(2.91); −0.15(0.37) |
| I-166 | 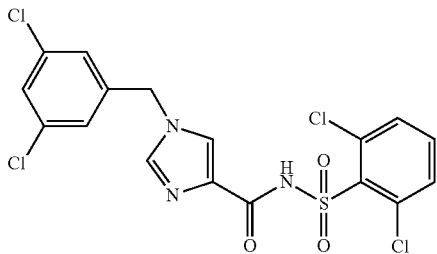 [SMILES: O=C(NS(=O)(=O)c1c(Cl)cccc1Cl)c1cn(Cc2cc(Cl)cc(Cl)c2)cn1] | Example I-166: 1H-NMR(400.0 MHz, d6-DMSO): δ = 8.602(3.61); 8.086(9.09); 8.083(8.82); 7.636(3.44); 7.631(6.79); 7.627 (4.16); 7.608(0.48); 7.544(16); 7.539(15.06); 7.536(8.44); 7.532(7.68); 7.514(15.21); 7.462(5.92); 7.445(4.22); 7.44(3.48); 7.422(2.41); 7.375 (0.34); 5.301(15.77); 4.832(0.32); 4.778(0.36); 4.758(0.37); 4.709(0.4); 4.694(0.4); 4.674(0.4); 4.653(0.41); 4.633(0.41); 4.611(0.41); 4.582 (0.41); 4.576(0.41); 4.564(0.41); 4.558(0.41); 4.542(0.41); 4.536(0.4); 4.513(0.39); 4.483(0.38); 4.391(0.32); 2.676(0.56); 2.672(0.77); 2.667 (0.56); 2.542(0.46); 2.525(2.2); 2.512(41.49); 2.507(82.19); 2.503(107.19); 2.498(77.89); 2.494(37.74); 2.334(0.53); 2.33(0.73); 2.325(0.53); 2.076 (2.98); 0.008(1.57); 0(44.22); −0.008(1.6) |
| I-167 | 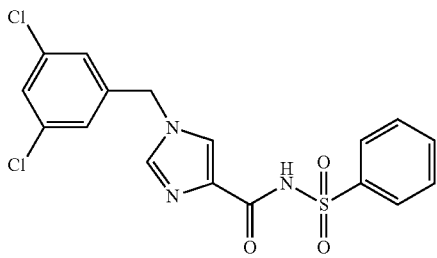 [SMILES: O=C(NS(=O)(=O)c1ccccc1)c1cn(Cc2cc(Cl)cc(Cl)c2)cn1] | Example I-167: 1H-NMR(400.0 MHz, d6-DMSO): δ = 8.05(10.33); 7.971(4.73); 7.953(5.45); 7.95(4.11); 7.91(3.01); 7.892 (3.63); 7.889(2.7); 7.84(2.22); 7.837(2.44); 7.821(2.61); 7.817(2.54); 7.742(0.64); 7.724(1.76); 7.705(1.41); 7.691(0.97); 7.673(2.81); 7.656 (4.41); 7.637(3.69); 7.613(4.69); 7.593(10.69); 7.588(7.07); 7.575(3.3); 7.568(3.03); 7.557(0.63); 7.553(0.78); 7.545(0.58); 7.449(9.47); 7.445 (8.78); 7.354(4.08); 6.871(0.54); 5.245(10.64); 3.746(0.39); 3.728(1.2); 3.694(0.43); 3.564(16); 3.509(0.76); 3.465(0.52); 3.431(0.47); 3.412(0.47); 3.404(0.47); 3.377(0.51); 3.362(0.44); 3.338(0.49); 3.326(0.47); 3.272 (0.38); 3.255(0.41); 3.236(0.34); 3.169(0.42); 2.676(0.64); 2.672(0.77); 2.668(0.61); 2.507(79.01); 2.502(97.25); 2.498(72.62); 2.329(0.69); 2.325(0.52); 2.184(0.84); 1.356(5.83); 1.234(0.47); 0(36.01); −0.008(2.1) |

-continued
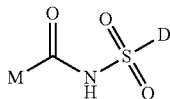
(I)
| Example No. | Structure | NMR peak list |
|---|---|---|
| I-168 | 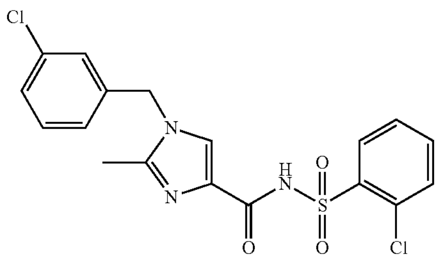 [SMILES: Cc1nc(C(=O)NS(=O)(=O)c2ccccc2Cl)cn1Cc1cccc(Cl)c1] | Example I-168: 1H-NMR(400.0 MHz, d6-DMSO): δ = 8.05(1.74); 8.047(1.78); 8.031(1.91); 8.029(1.94); 7.896(7.42); 7.497 (1.08); 7.492(1.22); 7.48(4.22); 7.475(4.75); 7.463(5.15); 7.444(2.09); 7.438(6.29); 7.429(3.79); 7.425(5.42); 7.405(0.36); 7.281(1.18); 7.277 (1.22); 7.272(1.04); 7.266(1.77); 7.259(0.99); 7.255(0.91); 5.294(8.18); 2.671(0.38); 2.525(1.32); 2.511(21.87); 2.507(42.43); 2.502(54.62); 2.498 (39.56); 2.493(19.23); 2.463(16); 2.329(0.38); 2.075(2.78); 0.008 (0.98); 0(23.85); −0.008(0.87) |
| I-169 | 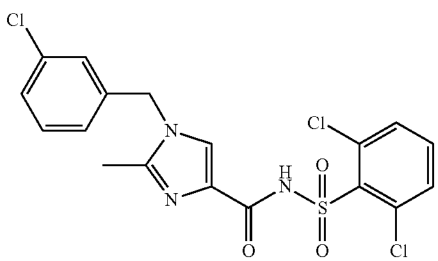 [SMILES: Cc1nc(C(=O)NS(=O)(=O)c2c(Cl)cccc2Cl)cn1Cc1cccc(Cl)c1] | Example I-169: 1H-NMR(400.0 MHz, d6-DMSO): δ = 8.317(0.59); 7.878(14.93); 7.497(5.56); 7.457(0.96); 7.445(15.95); 7.442(16); 7.438(5.84); 7.432C8.14); 7.424(15.33); 7.411(0.88); 7.357 (5.74); 7.34(4.41); 7.335(3.85); 7.318(3.04); 7.308(2.26); 7.304(2.43); 7.294(3.18); 7.286(1.79); 7.282(1.58); 5.312(14.66); 3.675(0.33); 3.64 (0.33); 3.601(0.34); 3.567(0.33); 3.518(0.32); 2.676(1.05); 2.671(1.41); 2.666(1.19); 2.541(1.02); 2.524(5.67); 2.511(74.88); 2.506(147.24); 2.502 (201.91); 2.498(132.66); 2.493(63.96); 2.333(0.98); 2.329(1.23); 2.324 (0.89); 2.32(0.42); 2.075(0.61); 0.146(0.43); 0.008(4.6); 0(99.54); −0.008(3.71); −0.15(0.43) |
| I-170 | 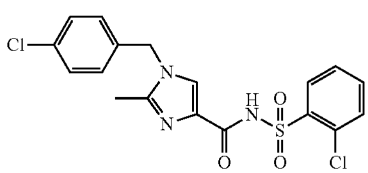 [SMILES: Cc1nc(C(=O)NS(=O)(=O)c2ccccc2Cl)cn1Cc1ccc(Cl)cc1] | Example I-170: 1H-NMR(400.0 MHz, d6-DMSO): δ = 8.043(2.2); 8.025(2.38); 7.88(6.25); 7.509(0.66); 7.488(2.13); 7.475 (9.92); 7.454(8.16); 7.442(2.47); 7.426(1.01); 7.42(0.83); 7.361(5.81); 7.34(4.16); 5.291(8.75); 4.181(0.33); 4.176(0.34); 4.158(0.35); 4.103 (0.37); 4.077(0.38); 4.068(0.38); 4.05(0.38); 4.013(0.39); 3.962(0.39); 3.95(0.39); 3.902(0.38); 3.889(0.37); 3.87(0.37); 3.851(0.37); 3.847(0.37); 3.835(0.36); 3.823(0.35); 3.801(0.35); 3.787(0.34); 2.671(0.67); 2.611 (0.36); 2.502(78.91); 2.45(16); 2.329(0.57); 2.076(1.63); 0(1.75) |
| I-171 | 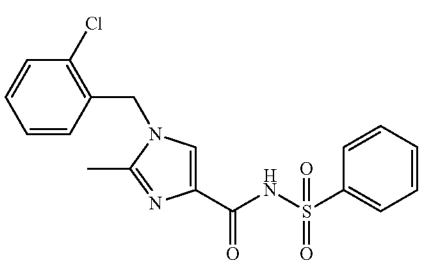 [SMILES: Cc1nc(C(=O)NS(=O)(=O)c2ccccc2)cn1Cc1ccccc1Cl] | Example I-171: 1H-NMR(400.0 MHz, d6-DMSO): δ = 7.935(4.36); 7.917(4.96); 7.914(3.88); 7.841(0.47); 7.837(0.53); 7.821 (0.55); 7.816(0.61); 7.767(5.34); 7.709(0.46); 7.706(0.48); 7.632(0.65); 7.613(1.97); 7.595(1.88); 7.588(1.31); 7.564(3.68); 7.557(3.25); 7.553 (3.53); 7.544(4.81); 7.538(3.68); 7.534(3.77); 7.527(1.92); 7.432(0.91); 7.427(1.1); 7.413(2.33); 7.409(2.39); 7.394(1.85); 7.389(1.87); 7.385 (2.16); 7.381(2.19); 7.366(2.9); 7.362(3.27); 7.348(1.18); 7.344(1.09); 7.048(1.74); 7.032(1.59); 6.87(0.51); 5.76(6.89); 5.339(9.78); 2.512 (18.98); 2.507(42.66); 2.503(60.79); 2.498(49.26); 2.494(28.08); 2.379(16); 2.334(0.69); 2.329(0.8); 2.325(0.69); 2.183(0.94); 1.355(5.72); 0(2.25) |
| I-172 | 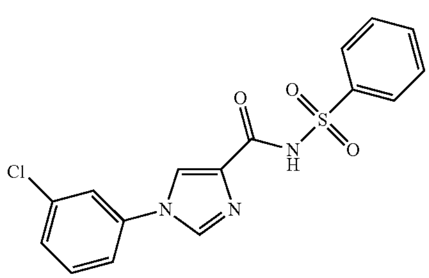 [SMILES: O=C(NS(=O)(=O)c1ccccc1)c1cn(-c2cccc(Cl)c2)cn1] | Example I-172: 1H-NMR(400.0 MHz, d6-DMSO): δ = 8.569(13.72); 8.566(16); 8.51(14.55); 8.507(14.36); 8.318(0.34); 8.022 (12.8); 8.003(14.18); 8(11.37); 7.922(6.74); 7.916(12.71); 7.912(7.79); 7.73(2.64); 7.721(5.15); 7.717(6.08); 7.711(8.84); 7.701(6.71); 7.696 (9.23); 7.653(10.84); 7.633(15.11); 7.615(5.76); 7.591(5.44); 7.57(11.55); 7.55(6.99); 7.507(6.86); 7.486(4.04); 5.759(1.4); 3.503(0.44); 3.47 (0.47); 3.367(0.49); 3.341(0.49); 3.212(0.39); 2.676(0.82); 2.672(1.07); 2.668(0.86); 2.507(108.9); 2.503(144.5); 2.499(112.39); 2.334(0.68); 2.33 (0.95); 2.326(0.74); 1.233(0.33); 1.18(0.53); 0(1.41) |

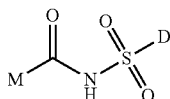
(I)
| Example No. | Structure | NMR peak list |
|---|---|---|
| I-173 | 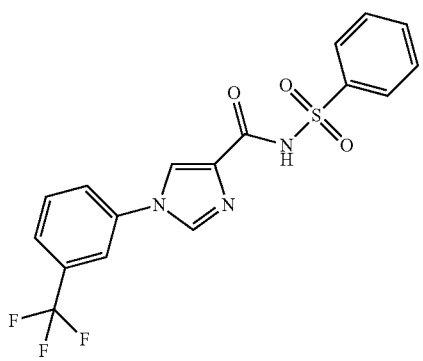 [SMILES: O=C(NS(=O)(=O)c1ccccc1)c1cn(-c2cccc(C(F)(F)F)c2)cn1] | Example I-173: 1H-NMR(400.0 MHz, d6-DMSO): δ = 8.653(13.23); 8.65(14.09); 8.581(13.69); 8.578(12.81); 8.319(0.39); 8.149(8.54); 8.064(2.6); 8.058(3.63); 8.049(4.51); 8.044(4.39); 8.036 (3.23); 8.025(12.54); 8.006(13.69); 8.003(10.28); 7.95(0.33); 7.848(0.47); 7.841(2.81); 7.837(3.25); 7.821(3.61); 7.817(3.84); 7.808(1.72); 7.798 (16); 7.792(7.15); 7.789(6.85); 7.784(7.5); 7.764(1.09); 7.731(2.18); 7.718(1.74); 7.712(7.18); 7.707(2.46); 7.694(5.6); 7.654(10.28); 7.634 (14.13); 7.616(5.55); 7.603(1.59); 7.593(2.26); 7.587(5.8); 7.576(1.33); 7.568(3.7); 7.557(0.67); 7.553(0.95); 7.546(0.72); 7.356(5.12); 6.87(0.88); 6.65(0.46); 5.759(1.6); 3.529(0.41); 3.406(0.61); 3.337(0.71); 3.326 (0.7); 3.311(0.68); 3.226(0.5); 3.206(0.48); 3.187(0.44); 2.676(1.1); 2.672 (1.48); 2.667(1.17); 2.507(153.35); 2.503(200.07); 2.498(150.26); 2.334(0.97); 2.33(1.33); 2.325(0.97); 2.184(1.46); 1.355(9.64); 1.259(0.49); 1.234(4.33); 1.19(0.39); 1.17(0.45); 0.854(0.55); 0.836(0.33); 0.008 (0.83); 0(20.14); −0.008(1.03) |
| I-174 | 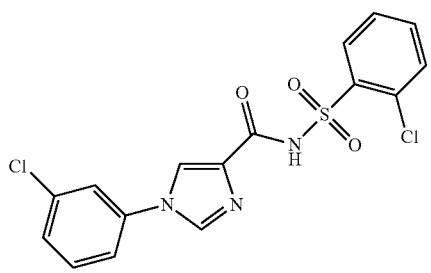 [SMILES: O=C(NS(=O)(=O)c1ccccc1Cl)c1cn(-c2cccc(Cl)c2)cn1] | Example I-174: 1H-NMR(400.0 MHz, d6-DMSO): δ = 8.634(14.75); 8.631(16); 8.562(13.93); 8.56(13.46); 8.179(6.38); 8.176 (6.96); 8.16(7.11); 8.156(7.32); 7.922(7.14); 7.918(13.12); 7.913(7.88); 7.724(6.43); 7.72(6.33); 7.704(11.61); 7.701(11.33); 7.687(7.09); 7.683 (7.05); 7.671(9.04); 7.667(11.97); 7.651(4.78); 7.648(3.66); 7.635(5.4); 7.632(4.59); 7.615(7.25); 7.607(6.84); 7.598(3.78); 7.594(3.66); 7.587 (12.3); 7.566(7.27); 7.524(7.43); 7.504(4.27); 7.502(4.25); 5.759(2.17); 2.678(0.39); 2.673(0.52); 2.669(0.39); 2.508(61.23); 2.504(79.62); 2.5(60.74); 2.336(0.39); 2.331(0.53); 0(0.91) |
| I-175 | 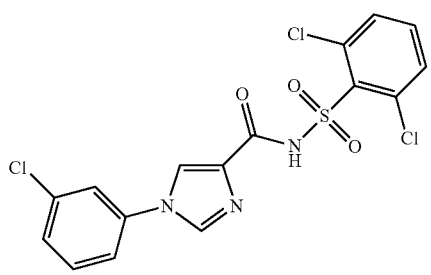 [SMILES: O=C(NS(=O)(=O)c1c(Cl)cccc1Cl)c1cn(-c2cccc(Cl)c2)cn1] | Example I-176: 1H-NMR(400.0 MHz, d6-DMSO): δ = 8.689(6.64); 8.628(8.74); 8.626(8.01); 7.942(4.05); 7.937(7.25); 7.932 (4.32); 7.739(2.73); 7.736(2.59); 7.719(3.47); 7.716(3.48); 7.65(5.4); 7.647(6.42); 7.629(16); 7.614(3.39); 7.608(1.04); 7.594(6.84); 7.586(6.2); 7.574(4.62); 7.569(4.27); 7.563(3.3); 7.545(2.68); 7.538(4.62); 7.518 (2.45); 2.672(0.49); 2.507(60.09); 2.503(76.51); 2.499(58.37); 2.33(0.51); 2.077(4.32); 0(0.73) |
| I-176 | 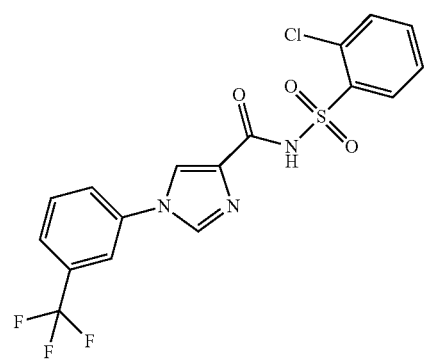 [SMILES: O=C(NS(=O)(=O)c1ccccc1Cl)c1cn(-c2cccc(C(F)(F)F)c2)cn1] | Example I-176: 1H-NMR(400.0 MHz, d6-DMSO): δ = 8.713(13.25); 8.632(11.99); 8.184(5.38); 8.181(5.85); 8.164(6.12); 8.161(6.51); 8.148(8.67); 8.063(3.53); 8.054(4.09); 8.048(4.29); 8.041 (2.73); 8.03(0.63); 7.817(16); 7.801(6.95); 7.782(1.09); 7.727(1.49); 7.723 (1.61); 7.707(4.83); 7.705(4.73); 7.689(5.56); 7.686(5.54); 7.67(9.86); 7.654(3.91); 7.639(4.39); 7.636(3.79); 7.619(5.96); 7.602(2.61); 7.598 (2.4); 5.76(0.62); 2.674(0.58); 2.509(67.25); 2.505(86.27); 2.501(67.01); 2.331(0.58); 0(0.95) |

-continued
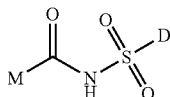
(I)
| Example No. | Structure | NMR peak list |
|---|---|---|
| I-177 | 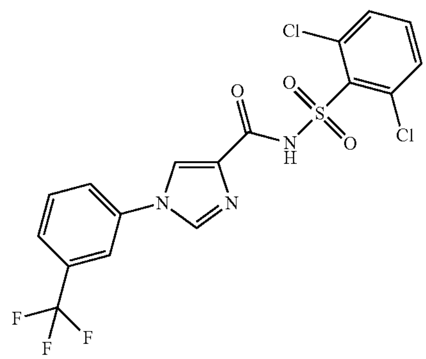 [SMILES: O=C(NS(=O)(=O)c1c(Cl)cccc1Cl)c1cn(-c2cccc(C(F)(F)F)c2)cn1] | Example I-177: 1H-NMR(400.0 MHz, d6-DMSO): δ = 8.76(6.51); 8.712(9.37); 8.709(8.53); 8.173(5.55); 8.078(2.57); 8.067 (2.45); 8.062(3.5); 8.056(1.91); 8.045(0.35); 8.041(0.33); 7.839(1.08); 7.825(11.05); 7.809(4.09); 7.789(1.02); 7.654(6.07); 7.65(7.29); 7.632 (16); 7.608(0.54); 7.588(6.62); 7.571(4.46); 7.566(3.59); 7.549(2.48); 2.513(19.32); 2.509(36.87); 2.505(47.67); 2.5(35.72); 2.078(1.55); 0(0.62) |
| I-178 | 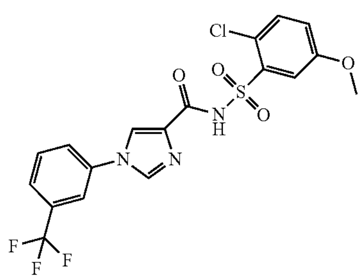 [SMILES: COc1ccc(Cl)c(S(=O)(=O)NC(=O)c2cn(-c3cccc(C(F)(F)F)c3)cn2)c1] | Example I-178: 1H-NMR(400.0 MHz, d6-DMSO): δ = 8.706(3.4); 8.64(3.1); 8.638(3.07); 8.146(2.27); 8.068(0.66); 8.062 (0.93); 8.052(1.1); 8.047(1.16); 8.04(0.74); 7.828(0.38); 7.818(4.26); 7.803 (1.87); 7.627(2.71); 7.62(2.91); 7.573(2.56); 7.551(3.04); 7.291(1.53); 7.283(1.51); 7.269(1.34); 7.261(1.31); 3.861(16); 3.818(0.63); 2.508 (27.43); 2.503(35.74); 2.499(27.52); 0.008(0.41); 0.001(10.16); 0(9.96) |
| I-179 | 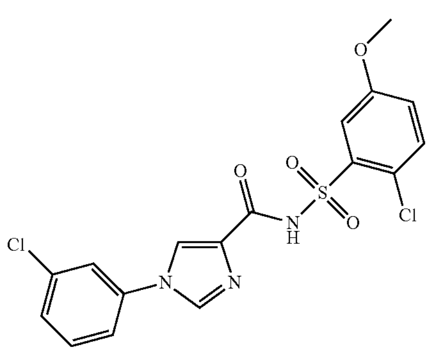 [SMILES: COc1ccc(Cl)c(S(=O)(=O)NC(=O)c2cn(-c3cccc(Cl)c3)cn2)c1] | Example I-179: 1H-NMR(400.0 MHz, d6-DMSO): δ = 8.603(3.16); 8.6(3.49); 8.564(3.22); 8.562(2.95); 7.921(1.65); 7.916 (3.05); 7.911(1.82); 7.724(1.09); 7.721(1.04); 7.704(1.43); 7.701(1.45); 7.669(0.37); 7.666(0.37); 7.622(2.89); 7.614(3.12); 7.605(1.54); 7.585 (2.81); 7.565(1.77); 7.557(2.79); 7.535(3.19); 7.521(1.76); 7.5(0.98); 7.274(1.62); 7.267(1.59); 7.252(1.42); 7.245(1.38); 5.756(1.13); 3.856(16); 3.817(0.67); 2.508(13.53); 2.504(17.6); 2.499(13.34); 0(4.35) |
| I-180 | 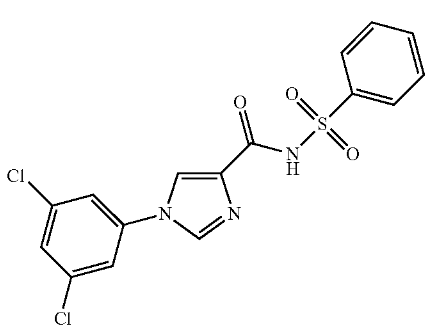 [SMILES: O=C(NS(=O)(=O)c1ccccc1)c1cn(-c2cc(Cl)cc(Cl)c2)cn1] | Example I-180: 1H-NMR(400.0 MHz, d6-DMSO): δ = 8.624(7.06); 8.621(8.15); 8.556(7.58); 8.553(7.48); 8.03(0.64); 8.022 (6.52); 8.009(1.8); 8.004(7.91); 8.001(5.78); 7.951(15.01); 7.947(16); 7.731(1.26); 7.728(0.87); 7.719(0.9); 7.713(4.08); 7.708(1.37); 7.698 (1.95); 7.694(3.39); 7.689(4.48); 7.685(7.06); 7.68(3.85); 7.654(5.68); 7.634(7.91); 7.62(1.3); 7.616(3.06); 5.757(0.34); 2.526(1.02); 2.512(14.35); 2.508(28.62); 2.504(37.85); 2.499(28.09); 2.495(14.3); 2.076(2.93); 0(1.83) |

-continued
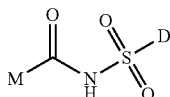
(I)
| Example No. | Structure | NMR peak list |
|---|---|---|
| I-181 | 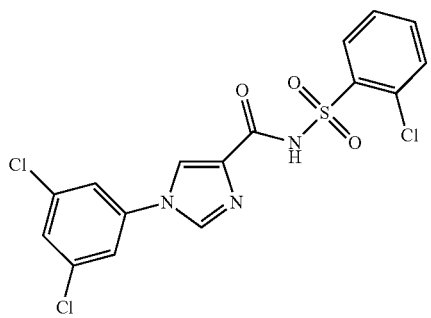 [SMILES: O=C(NS(=O)(=O)c1ccccc1Cl)c1cn(-c2cc(Cl)cc(Cl)c2)cn1] | Example I-181: 1H-NMR(400.0 MHz, d6-DMSO): δ = 8.677(7.08); 8.674(7.6); 8.588(7.4); 8.585(7.09); 8.177(3.31); 8.173 (3.61); 8.158(3.72); 8.154(3.81); 7.996(0.4); 7.959(0.52); 7.954(0.75); 7.945(15.23); 7.941(16); 7.732(0.37); 7.727(1.12); 7.723(1.18); 7.707 (6.4); 7.703(9.31); 7.699(4.14); 7.69(3.68); 7.686(3.6); 7.672(4.45); 7.668 (6.02); 7.652(2.52); 7.649(1.86); 7.637(2.78); 7.633(2.39); 7.617(3.26); 7.614(2.89); 7.608(0.64); 7.6(1.77); 7.596(1.57); 5.756(2.37); 2.677 (0.33); 2.672(0.46); 2.668(0.36); 2.525(1.64); 2.512(25.94); 2.507(51.37); 2.503(67.92); 2.498(50.69); 2.494(26.35); 2.33(0.44); 2.325(0.32); 0 (1.62) |
| I-182 | 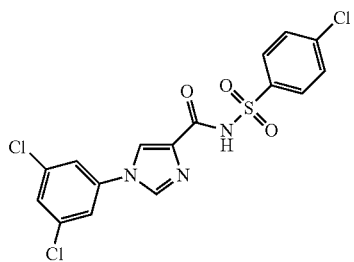 [SMILES: O=C(NS(=O)(=O)c1ccc(Cl)cc1)c1cn(-c2cc(Cl)cc(Cl)c2)cn1] | Example I-182: 1H-NMR(400.0 MHz, d6-DMSO): δ = 8.633(6.82); 8.63(7.89); 8.582(7.34); 8.579(6.81); 8.026(1.03); 8.019 (8.86); 8.014(3.22); 8.002(3.13); 7.997(10.81); 7.991(1.64); 7.959(15.23); 7.955(16); 7.74(1.32); 7.733(10.48); 7.728(3.52); 7.717(2.92); 7.712 (9.25); 7.705(1.41); 7.694(3.78); 7.69(6.78); 7.686(3.65); 2.527(0.93); 2.513(13.69); 2.509(27.84); 2.504(37.29); 2.5(27.86); 2.495(14.46); 2.077 (0.65); 0(1.61) |
| I-183 | 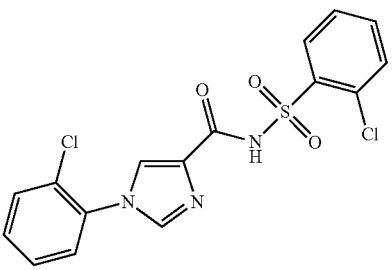 [SMILES: O=C(NS(=O)(=O)c1ccccc1Cl)c1cn(-c2ccccc2Cl)cn1] | Example I-183: 1H-NMR(400.0 MHz, d6-DMSO): δ = 8.327(13.03); 8.324(13.94); 8.182(16); 8.161(5.92); 8.158(6.51); 7.758 (4.67); 7.753(5.26); 7.739(4.95); 7.735(6.58); 7.728(2.21); 7.724(1.98); 7.708(4.71); 7.705(4.58); 7.691(5.84); 7.687(6.24); 7.678(7.72); 7.674 (10.3); 7.663(5); 7.658(7.48); 7.646(6.4); 7.64(7.92); 7.633(4.61); 7.624 (1.32); 7.616(5.66); 7.599(3.79); 7.596(4.6); 7.583(5.75); 7.578(5.55); 7.568(6.91); 7.565(8.33); 7.563(8.17); 7.559(5.77); 7.55(5.38); 7.545 (4.87); 7.531(1.7); 7.527(1.4); 2.672(0.33); 2.507(40.13); 2.503(53.01); 2.498(41.87); 2.33(0.35); 2.075(0.65); 0(0.63) |
| I-184 | 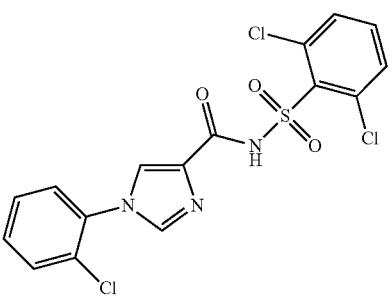 [SMILES: O=C(NS(=O)(=O)c1c(Cl)cccc1Cl)c1cn(-c2ccccc2Cl)cn1] | Example I-184: 1H-NMR(400.0 MHz, d6-DMSO): δ = 8.331(7.88); 8.328(10.63); 8.313(6.85); 7.914(1.15); 7.765(3.17); 7.76 (3.57); 7.746(3.36); 7.742(4.36); 7.707(0.41); 7.704(0.44); 7.686(2.93); 7.681(2.78); 7.668(4.26); 7.661(7.36); 7.656(7.21); 7.638(16); 7.627 (1.32); 7.625(1.3); 7.612(1.35); 7.606(3.44); 7.596(7.24); 7.588(4.03); 7.579(5.26); 7.575(8.55); 7.57(6.21); 7.557(5.9); 7.553(3.8); 7.535(1.59); 7.518(0.69); 7.514(0.62); 7.496(0.45); 7.394(0.4); 7.391(0.47); 7.373 (0.97); 7.328(0.45); 2.672(0.33); 2.524(1.07); 2.511(19.56); 2.507(38.86); 2.502(50.98); 2.498(37.89); 2.329(0.33); 2.075(4.52); 1.356(2.06); 0.008(0.37); 0(9.13); −0.008(0.37) |

(I)
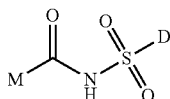
| Example No. | Structure | NMR peak list |
|---|---|---|
| I-185 | 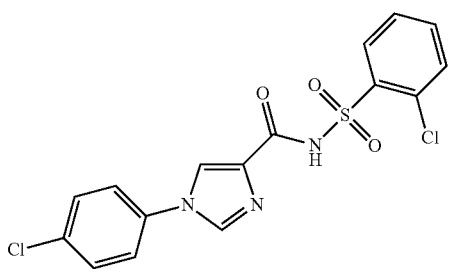 [SMILES: O=C(NS(=O)(=O)c1ccccc1Cl)c1cn(-c2ccc(Cl)cc2)cn1] | Example I-185: 1H-NMR(400.0 MHz, d6-DMSO): δ = 8.578(9.38); 8.575(10.62); 8.514(8.49); 8.511(8.12); 8.175(4.3); 8.171 (4.73); 8.155(4.78); 8.152(4.96); 7.775(0.99); 7.768(10.51); 7.762(3.89); 7.751(4.19); 7.745(15.86); 7.738(2.12); 7.719(1.28); 7.715(1.39); 7.698 (3.47); 7.695(3.5); 7.681(4.68); 7.677(4.71); 7.665(6.09); 7.661(9.18); 7.652(16); 7.646(6.56); 7.641(3.26); 7.635(4.08); 7.63(14.4); 7.611 (4.39); 7.607(3.97); 7.593(2.28); 7.589(2.11); 2.676(0.33); 2.672(0.46); 2.667(0.34); 2.525(1.38); 2.512(26.48); 2.507(53.86); 2.503(71.86); 2.498(53.36); 2.494(27.25); 2.334(0.35); 2.33(0.49); 2.325(0.37); 2.075 (0.65); 0(1.07) |
| I-186 | 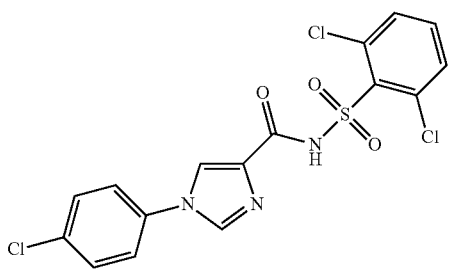 [SMILES: O=C(NS(=O)(=O)c1c(Cl)cccc1Cl)c1cn(-c2ccc(Cl)cc2)cn1] | Example I-186: 1H-NMR(400.0 MHz, d6-DMSO): δ = 8.657(6.12); 8.57(8.71); 8.567(8.43); 7.913(1.21); 7.792(0.98); 7.785 (8.91); 7.78(3.63); 7.768(3.98); 7.763(12.97); 7.756(2.06); 7.669(1.61); 7.662(12.84); 7.656(4.42); 7.64(13.58); 7.628(2.29); 7.619(16); 7.606 (2.38); 7.575(6.48); 7.558(4.36); 7.553(3.58); 7.536(3.11); 7.518(0.63); 7.514(0.56); 7.496(0.37); 2.676(0.44); 2.671(0.62); 2.667(0.46); 2.511 (35.34); 2.507(68.53); 2.502(89.62); 2.498(67.81); 2.494(36.4); 2.334 (0.42); 2.329(0.59); 2.325(0.44); 0(1.08) |
| I-187 | 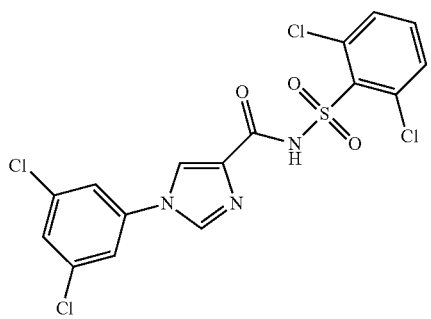 [SMILES: O=C(NS(=O)(=O)c1c(Cl)cccc1Cl)c1cn(-c2cc(Cl)cc(Cl)c2)cn1] | Example I-187: 1H-NMR(400.0 MHz, d6-DMSO): δ = 8.676(16); 7.958(10.92); 7.954(11.47); 7.72(2.84); 7.715(5); 7.711 (2.79); 7.66(3.58); 7.656(4.46); 7.638(10.52); 7.606(0.38); 7.598(4.08); 7.581(2.65); 7.575(2.09); 7.558(1.41); 2.508(28.54); 2.503(37.83); 2.499 (29.08); 2.076(4.51); 0(3.96) |
| I-188 | 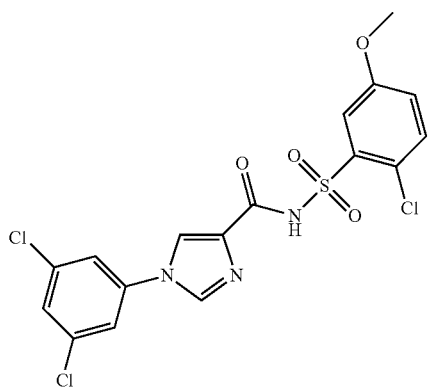 [SMILES: COc1ccc(Cl)c(S(=O)(=O)NC(=O)c2cn(-c3cc(Cl)cc(Cl)c3)cn2)c1] | Example I-188: 1H-NMR(400.0 MHz, d6-DMSO): δ = 8.672(3.36); 8.593(3.32); 7.945(6.44); 7.941(7.09); 7.71(1.59); 7.706 (2.91); 7.702(1.7); 7.618(2.73); 7.611(2.95); 7.573(2.53); 7.551(2.98); 7.293(1.51); 7.285(1.5); 7.271(1.33); 7.263(1.31); 3.859(16); 2.507 (30.03); 2.502(39.85); 2.498(31.03); 0(3.42) |

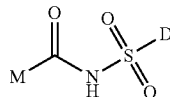
(I)
| Example No. | Structure | NMR peak list |
|---|---|---|
| I-189 | 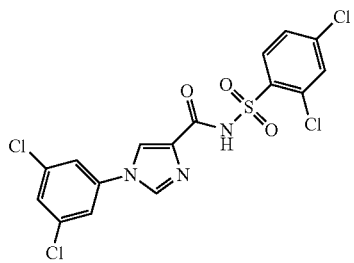 [SMILES: O=C(NS(=O)(=O)c1ccc(Cl)cc1Cl)c1cn(-c2cc(Cl)cc(Cl)c2)cn1] | Example I-189: 1H-NMR(400.0 MHz, d6-DMSO): δ = 8.668(9.05); 8.657(8.23); 8.158(6.64); 8.136(7.39); 7.958(15.04); 7.953 (16); 7.873(6.28); 7.868(6.88); 7.723(4.43); 7.718(7.66); 7.714(7.69); 7.71(4.16); 7.701(3.89); 7.696(3.71); 4.191(0.99); 3.859(0.35); 2.672 (0.4); 2.508(43.86); 2.504(57.67); 2.499(43.28); 2.33(0.37); 2.076(1.97); 0(0.88) |
| I-190 | 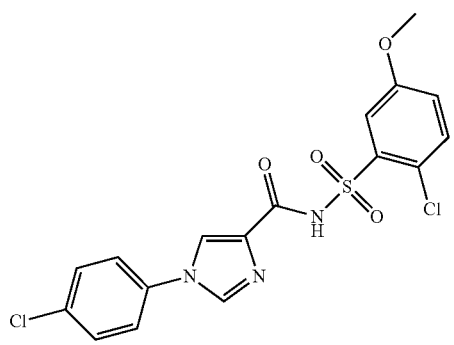 [SMILES: COc1ccc(Cl)c(S(=O)(=O)NC(=O)c2cn(-c3ccc(Cl)cc3)cn2)c1] | Example I-190: 1H-NMR(400.0 MHz, d6-DMSO): δ = 8.578(3.05); 8.575(3.68); 8.531(2.81); 8.529(2.75); 7.776(0.34); 7.768 (3.35); 7.763(1.33); 7.752(1.38); 7.746(5.08); 7.739(0.72); 7.662(0.58); 7.655(4.97); 7.65(1.6); 7.638(1.18); 7.633(3.58); 7.62(2.87); 7.613 (3.07); 7.566(2.71); 7.544(3.18); 7.284(1.6); 7.277(1.58); 7.262(1.4); 7.254(1.36); 5.756(0.71); 3.857(16); 3.816(0.92); 2.507(19.96); 2.503 (26.67); 2.498(20.21); 0(0.62) |
| I-191 | 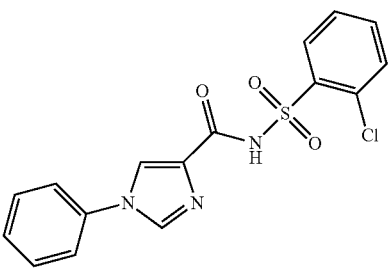 [SMILES: O=C(NS(=O)(=O)c1ccccc1Cl)c1cn(-c2ccccc2)cn1] | Example I-191: 1H-NMR(400.0 MHz, d6-DMSO): δ = 8.572(10.48); 8.568(13.77); 8.521(10.54); 8.316(0.37); 8.176(5.39); 8.172(6.23); 8.156(5.94); 8.152(6.54); 7.722(7.87); 7.719(11.47); 7.698 (16); 7.691(6.59); 7.677(5.8); 7.674(6.41); 7.663(7.32); 7.659(10.4); 7.643(3.73); 7.64(3.12); 7.628(4.43); 7.624(4.18); 7.608(6.11); 7.606 (6.08); 7.604(5.8); 7.591(4.19); 7.586(9.23); 7.567(12.68); 7.546(8.13); 7.471(4.98); 7.452(7.16); 7.434(2.66); 2.676(0.79); 2.671(1.1); 2.667(0.85); 2.524(3.28); 2.511(58.67); 2.507(119.1); 2.502(159.53); 2.498 (122.19); 2.333(0.75); 2.329(1.04); 2.325(0.82); 2.075(1.49); 0.008(0.83); 0(23.52); −0.008(1.22) |
| I-192 | 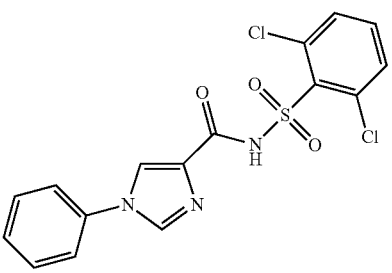 [SMILES: O=C(NS(=O)(=O)c1c(Cl)cccc1Cl)c1cn(-c2ccccc2)cn1] | Example I-192: 1H-NMR(400.0 MHz, d6-DMSO): δ = 8.704(6.2); 8.566(9.7); 7.915(0.64); 7.743(7.58); 7.724(10.03); 7.634 (6.72); 7.631(6.77); 7.613(16); 7.594(5.1); 7.575(9.73); 7.567(7.31); 7.555(6.36); 7.55(5.39); 7.544(3.81); 7.527(2.36); 7.519(0.64); 7.487(3.6); 7.469(4.97); 7.451(1.91); 7.374(0.38); 5.757(0.64); 2.672(0.4); 2.507 (52.27); 2.503(59.73); 2.33(0.37); 2.076(0.39); 0(6.95) |

-continued
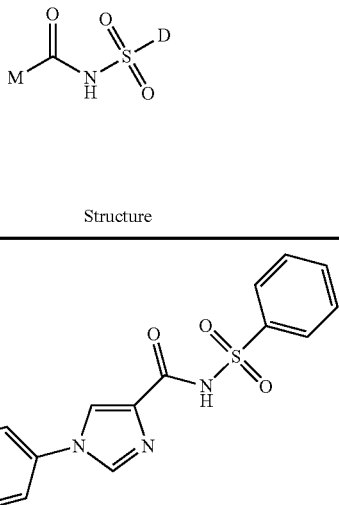
(I)
| Example No. | Structure | NMR peak list |
|---|---|---|
| I-193 | 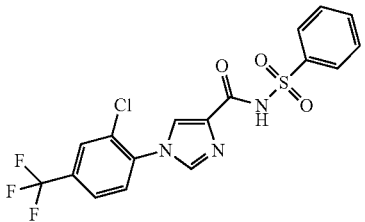 [SMILES: O=C(NS(=O)(=O)c1ccccc1)c1cn(-c2ccc(C(F)(F)F)cc2Cl)cn1] | Example I-193: 1H-NMR(400.0 MHz, d6-DMSO): δ = 8.577(13.95); 8.574(14.56); 8.515(14.63); 8.512(13.05); 8.15(12.13); 8.143(12.56); 8.02(11.72); 8.002(14.21); 7.998(10.26); 7.844(8.77); 7.822(16); 7.81(0.62); 7.805(0.59); 7.773(8.5); 7.767(8.06); 7.751(4.81); 7.745(4.81); 7.729(2.3); 7.716(1.7); 7.71(7.45); 7.705(2.32); 7.695(3.7); 7.692(5.77); 7.651(10.32); 7.632(14.57); 7.617(2.49); 7.614(5.68); 2.676(0.47); 2.672(0.66); 2.667(0.48); 2.525(1.86); 2.511(41.9); 2.507 (82.68); 2.503(108.26); 2.498(80.04); 2.494(40.51); 2.44.3(0.45); 2.334 (0.6); 2.33(0.8); 2.325(0.62); 1.76(0.34); 0.008(0.69); 0(19.18); −0.008(0.76) |
| I-194 | 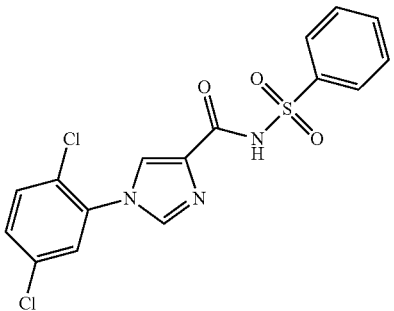 [SMILES: O=C(NS(=O)(=O)c1ccccc1)c1cn(-c2cc(Cl)ccc2Cl)cn1] | Example I-194: 1H-NMR(400.0 MHz, d6-DMSO): δ = 8.309(15.18); 8.306(15.55); 8.229(10.28); 8.226(10.44); 8.185(15.34); 8.182(14.53); 8.027(13.54); 8.008(15.7.3); 8.004(11.56); 7.962(4.35); 7.958(4.39); 7.941(7.01); 7.937(6.93); 7.877(10.44); 7.856(6.61); 7.734 (2.47); 7.722(1.95); 7.716(8.13); 7.698(6.24); 7.657(11.48); 7.637(16); 7.619(6.15); 7.586(0.35); 2.675(0.82); 2.671(1.07); 2.667(0.8); 2.506 (110.67); 2.502(142.26); 2.498(104.54); 2.333(0.68); 2.329(0.93); 2.324 (0.67); 2.074(1.01); 1.356(0.33); 0.008(1.1); 0(25.01); −0.008(0.93) |
| I-195 | 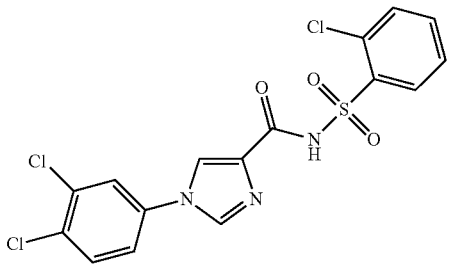 [SMILES: O=C(NS(=O)(=O)c1ccccc1Cl)c1cn(-c2ccc(Cl)c(Cl)c2)cn1] | Example I-195: 1H-NMR(400.0 MHz, d6-DMSO): δ = 8.267(10.14); 8.264(10.68); 8.142(9.76); 8.139(9.51); 8.025(8.34); 8.011(2.37); 8.006(9.94); 8.003(7.22); 7.891(0.35); 7.86(8.71); 7.854 (9.35); 7.841(0.6); 7.837(0.59); 7.822(0.61); 7.817(0.64); 7.776(7.38); 7.754(10.99); 7.734(1.59); 7.721(1.19); 7.716(5.25); 7.71(1.69); 7.697(4.1); 7.67(6.3); 7.664(6.23); 7.656(7.71); 7.649(5.03); 7.642(6.47); 7.64 (6.44); 7.636(10.59); 7.618(4.09); 7.601(0.48); 7.591(0.45); 7.586(1.06); 7.566(0.67); 7.349(0.85); 6.871(0.68); 6.64(0.34); 5.756(16); 3.618 (0.97); 3.611(0.96); 3.607(0.94); 3.601(2.39); 3.595(1.04); 3.591(0.75); 3.585(1.06); 2.675(0.33); 2.671(0.47); 2.666(0.35); 2.524(0.99); 2.511 (28.25); 2.506(57.68); 2.502(77.4); 2.497(58.15); 2.493(29.82); 2.444 (0.38); 2.333(0.44); 2.329(0.58); 2.324(0.45); 2.184(1.11); 1.776(0.97); 1.768(1.08); 1.759(2.82); 1.751(1.13); 1.743(1); 1.356(7.58); 1.233(0.4); 1.099(0.37); 0.008(0.67); 0(22.9); −0.008(0.97) |
| I-196 | 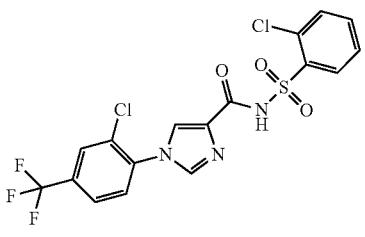 | Example I-196: 1H-NMR(400.0 MHz, d6-DMSO): δ = 8.633(14.18); 8.63(15.09); 8.557(13.95); 8.554(13.1); 8.176(6.35); 8.172(6.75); 8.156(7.39); 8.152(7.99); 8.147(13.44); 8.141(13.34); 7.859 (9.95); 7.837(16); 7.773(8.56); 7.766(8.07); 7.751(5.4); 7.744(5.34); 7.724(1.87); 7.72(1.95); 7.704(5.32); 7.7(5.03); 7.686(6.69); 7.682(6.56); 7.669(8.51); 7.666(11.37); 7.649(4.66); 7.646(3.41); 7.634(5.31); 7.63 (4.4); 7.614(6.47); 7.603(1.09); 7.597(3.3); 7.593(2.95); 2.676(0.63); 2.672(0.84); 2.667(0.62); 2.524(2.89); 2.511(47.9); 2.507(92.21); 2.502 (120.17); 2.498(88.12); 2.334(0.58); 2.329(0.79); 2.325(0.58); 2.075 (0.76); 0.008(0.95); 0(22.9); −0.008(0.82) |
| I-197 | 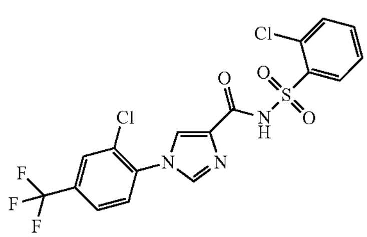 [SMILES: O=C(NS(=O)(=O)c1ccccc1Cl)c1cn(-c2ccc(C(F)(F)F)cc2Cl)cn1] | Example I-197: 1H-NMR(400.0 MHz, d6-DMSO): δ = 8.396(15.86); 8.393(15.86); 8.241(10.54); 8.238(10.67); 8.231(16); 8.228(14.98); 8.182(6.77); 8.179(7.03); 8.163(7.42); 8.159(7.31); 7.994 (0.47); 7.99(0.51); 7.975(4.19); 7.971(4.04); 7.954(7.34); 7.95(7.09); 7.907(10.81); 7.887(5.97); 7.734(1.91); 7.73(1.96); 7.714(5.65); 7.71(5.12); 7.697(7.25); 7.693(7.01); 7.683(9.3); 7.679(11.87); 7.663(4.59); 7.659 (3.03); 7.652(0.56); 7.641(5.17); 7.637(4.67); 7.621(6.76); 7.604(4.14); 7.6(3.24); 2.676(0.48); 2.671(0.64); 2.667(0.47); 2.524(2.05); 2.511 (38.6); 2.507(74.25); 2.502(95.95); 2.498(69.86); 2.494(34.35); 2.334 (0.48); 2.329(0.63); 2.324(0.47); 1.356(0.53); 1.291(0.33); 0.008(0.67); 0(18.14); −0.008(0.63) |

-continued
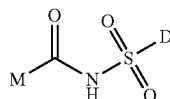
(I)
| Example No. | Structure | NMR peak list |
|---|---|---|
| I-198 | 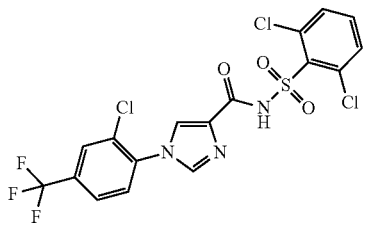 [SMILES: O=C(NS(=O)(=O)c1c(Cl)cccc1Cl)c1cn(-c2ccc(C(F)(F)F)cc2Cl)cn1] | Example I-198: 1H-NMR(400.0 MHz, d6-DMSO): δ = 8.395(8.44); 8.393(9.15); 8.308(7.84); 8.306(7.77); 8.247(5.99); 8.245 (6.09); 7.982(2.18); 7.978(2.14); 7.961(4.42); 7.957(4.44); 7.924(6.62); 7.904(3.25); 7.671(5.56); 7.667(6.67); 7.649(16); 7.624(0.33); 7.609 (6.46); 7.592(4.17); 7.586(3.2); 7.569(2.19); 2.675(0.44); 2.671(0.57); 2.666(0.44); 2.506(66.98); 2.502(86.76); 2.498(65.66); 2.471(0.49); 2.467 (0.84); 2.462(0.86); 2.333(0.42); 2.329(0.57); 2.324(0.44); 2.074(1.29); 0.007(1.84); 0(37.47); −0.036(0.34) |
| I-199 | 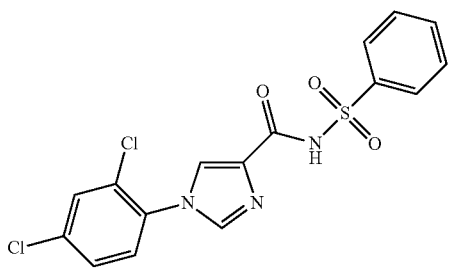 [SMILES: O=C(NS(=O)(=O)c1ccccc1)c1cn(-c2ccc(Cl)cc2Cl)cn1] | Example I-199: 1H-NMR(400.0 MHz, d6-DMSO): δ = 8.234(8.4); 8.232(7.95); 8.112(8.2); 8.109(7.29); 8.022(7.03); 8.004 (8.33); 8(6.01); 7.957(5.68); 7.952(5.82); 7.731(1.35); 7.718(1.19); 7.713 (4.3); 7.708(1.49); 7.694(3.35); 7.676(1.83); 7.654(16); 7.651(11.67); 7.646(8.07); 7.634(8.81); 7.624(2.15); 7.619(1.88); 7.616(3.45); 2.675 (0.48); 2.671(0.64); 2.666(0.45); 2.51(44.44); 2.506(79.95); 2.502 (100.66); 2.497(74.08); 2.333(0.55); 2.328(0.72); 2.324(0.53); 2.074(1.08); 0.008(2.22); 0(37.07); −0.008(1.81) |
| I-200 | 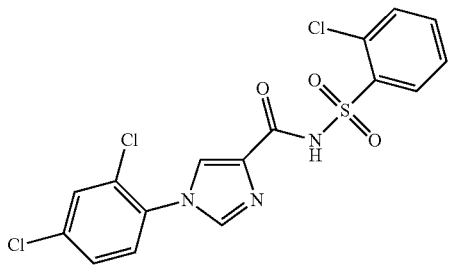 [SMILES: O=C(NS(=O)(=O)c1ccccc1Cl)c1cn(-c2ccc(Cl)cc2Cl)cn1] | Example I-200: 1H-NMR(400.0 MHz, d6-DMSO): δ = 8.316(10.38); 8.314(10.17); 8.175(4.83); 8.172(5.07); 8.164(9.92); 8.162(9.37); 8.156(5.48); 8.152(5.02); 7.97(7.59); 7.965(7.55); 7.728 (1.24); 7.724(1.28); 7.708(8.17); 7.686(16); 7.676(6.84); 7.672(8.1); 7.665 (7.56); 7.66(7.44); 7.644(2.88); 7.638(3.55); 7.635(3.85); 7.631(3.06); 7.615(4.49); 7.598(2.19); 7.594(1.9); 2.671(0.59); 2.506(70.98); 2.502 (88.74); 2.498(65.85); 2.329(0.59); 2.074(2); 0(34.72); −0.008(1.53) |
| I-201 | 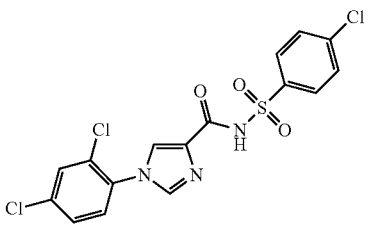 [SMILES: O=C(NS(=O)(=O)c1ccc(Cl)cc1)c1cn(-c2ccc(Cl)cc2Cl)cn1] | Example I-201: 1H-NMR(400.0 MHz, d6-DMSO): δ = 8.249(2.83); 8.246(2.85); 8.144(2.61); 8.02(3.04); 7.999(3.62); 7.959 (2.05); 7.955(1.9); 7.838(1.64); 7.816(2.1); 7.733(3.49); 7.711(3.01); 7.682(0.7); 7.667(2.53); 7.661(4.01); 7.655(2.75); 7.65(2.83); 7.646(2.1); 7.634(0.45); 7.628(0.47); 7.464(2.15); 2.502(20.99); 2.075(16); 1.356 (1.59); 0(5.49) |
| I-202 | 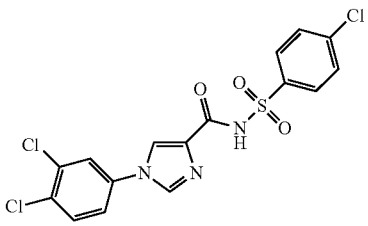 [SMILES: O=C(NS(=O)(=O)c1ccc(Cl)cc1)c1cn(-c2ccc(Cl)c(Cl)c2)cn1] | Example I-202: 1H-NMR(400.0 MHz, d6-DMSO): δ = 8.582(14.08); 8.544(12.79); 8.542(12.78); 8.157(9.79); 8.151(10.94); 8.015(13.36); 7.994(16); 7.848(6.24); 7.826(11.62); 7.805(0.54); 7.78 (6.82); 7.774(7.13); 7.758(3.74); 7.752(4.08); 7.729(15.27); 7.708(13.57); 2.672(0.9); 2.503(139.2); 2.33(0.97); 2.075(0.51); 0(29.77) |

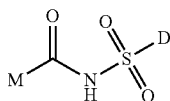
(I)
| Example No. | Structure | NMR peak list |
|---|---|---|
| I-203 | 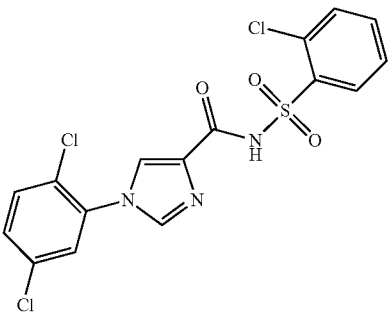 [SMILES: O=C(NS(=O)(=O)c1ccccc1Cl)c1cn(-c2cc(Cl)ccc2Cl)cn1] | Example I-203: 1H-NMR(400.0 MHz, d6-DMSO): δ = 8.348(14.01); 8.346(14.11); 8.212(0.47); 8.209(0.52); 8.192(12.71); 8.19(12.42); 8.177(6.14); 8.174(6.21); 8.158(6.41); 8.154(6.35); 8.071 (0.33); 8.068(0.32); 7.993(2.43); 7.99(2.43); 7.974(2.75); 7.97(2.67); 7.894(11.26); 7.888(11.71); 7.872(0.45); 7.79(9.29); 7.778(0.75); 7.768 (13.48); 7.757(0.66); 7.731(1.7); 7.727(1.75); 7.711(5.14); 7.708(4.72); 7.694(6.51); 7.69(6.47); 7.68(16); 7.676(13.73); 7.659(8.58); 7.652(7.18); 7.636(7.2); 7.619(7.38); 7.602(10.69); 7.587(1.79); 7.583(1.53); 7.573 (0.37); 7.54(1.92); 7.536(1.82); 7.521(2.54); 7.519(2.36); 7.503(1.28); 7.499(1.18); 6.871(0.93); 6.641(0.45); 4.273(0.41); 4.255(0.46); 3.204 (0.37); 2.675(0.8); 2.671(1.07); 2.666(0.81); 2.506(129.34); 2.502 (164.23); 2.497(122.78); 2.445(0.41); 2.411(0.37); 2.333(0.87); 2.328 (1.12); 2.324(0.86); 2.183(1.49); 2.074(10.78); 1.356(10.16); 1.304(0.44); 1.286(0.88); 1.268(0.45); 0.008(2.13); 0(46.31); −0.008(2.09) |
| I-204 | 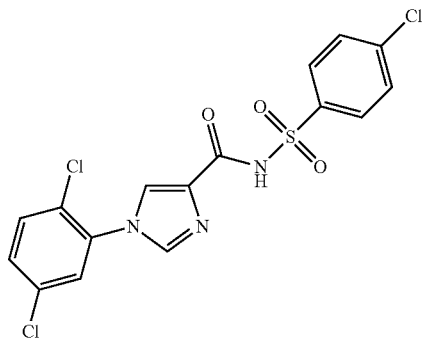 [SMILES: O=C(NS(=O)(=O)c1ccc(Cl)cc1)c1cn(-c2cc(Cl)ccc2Cl)cn1] | Example I-204: 1H-NMR(400.0 MHz, d6-DMSO): δ = 8.316(0.39); 8.273(9.32); 8.27(10.47); 8.167(9.71); 8.164(9.82); 8.025 (1.68); 8.019(13.65); 8.014(4.7); 8.002(4.81); 7.997(15.98); 7.991(2.03); 7.866(9.59); 7.86(10.05); 7.78(8.62); 7.758(12.65); 7.74(2.04); 7.733 (14.97); 7.729(5.01); 7.716(4.24); 7.712(12.79); 7.705(1.61); 7.675 (7.24); 7.669(6.72); 7.653(4.79); 7.647(4.6); 2.68(0.41); 2.675(0.79); 2.671 (1.08); 2.666(0.79); 2.524(3.45); 2.519(5.35); 2.511(58.82); 2.506 (117.66); 2.502(154.6); 2.497(111.46); 2.493(53.29); 2.338(0.35); 2.333 (0.75); 2.329(1.05); 2.324(0.76); 2.32(0.36); 2.074(16); 0.146(0.68); 0.008 (6); 0(158.33); −0.009(5.16); −0.15(0.67) |
| I-205 | 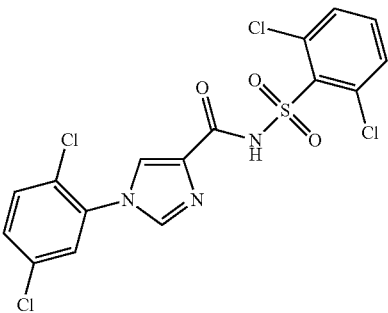 [SMILES: O=C(NS(=O)(=O)c1c(Cl)cccc1Cl)c1cn(-c2cc(Cl)ccc2Cl)cn1] | Exampple I-205: 1H-NMR(400.0 MHz, d6-DMSO): δ = 8.35(8.63); 8.348(8.9); 8.288(7.54); 7.917(7.5); 7.911(7.97); 7.796 (5.98); 7.774(8.76); 7.704(0.74); 7.689(4.99); 7.683(4.74); 7.667(8.01); 7.662(9.23); 7.644(16); 7.626(0.57); 7.603(6.24); 7.586(3.99); 7.58(3.07); 7.564(2.1); 7.394(0.51); 7.39(0.57); 7.372(1.4); 7.328(0.55); 7.311 (0.37); 5.756(0.99); 2.671(0.5); 2.506(66.56); 2.502(84.39); 2.498(63.11); 2.332(0.47); 2.328(0.6); 1.045(1.18); 1.03(1.15); 0(2.52) |
| I-206 | 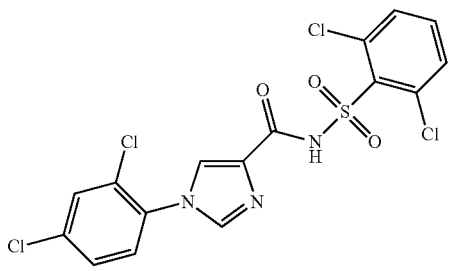 [SMILES: O=C(NS(=O)(=O)c1c(Cl)cccc1Cl)c1cn(-c2ccc(Cl)cc2Cl)cn1] | Example I-206: 1H-NMR(400.0 MHz, d6-DMSO): δ = 8.31(8.61); 8.265(7.53); 7.979(6.84); 7.974(7.16); 7.911(0.46); 7.728 (4.62); 7.706(9.76); 7.674(6.18); 7.669(6.31); 7.659(6.36); 7.654(8.69); 7.648(4.52); 7.637(16); 7.606(1.03); 7.595(5.79); 7.578(3.97); 7.573 (3.36); 7.556(2.11); 2.671(0.93); 2.505(159.4); 2.502(205.79); 2.498 (168.82); 2.328(1.93); 2.257(0.44); 2.25(0.43); 2.074(1.6); 0.146(0.45); 0(125.22); −0.15(0.86) |

-continued (I)

| Example No. | Structure | NMR peak list |
|---|---|---|
| I-207 | 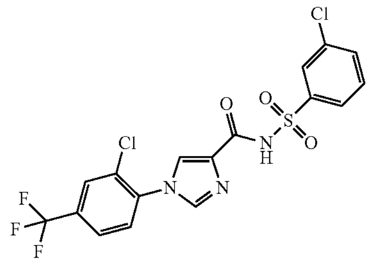 [SMILES: O=C(NS(=O)(=O)c1cccc(Cl)c1)c1cn(-c2ccc(C(F)(F)F)cc2Cl)cn1] | Example I-207: 1H-NMR(400.0 MHz, d6-DMSO): δ = 8.341(11.96); 8.24(15.09); 8.015(8.46); 7.978(5.26); 7.97(4.28); 7.959 (6.31); 7.949(5.94); 7.889(7.67); 7.868(4.73); 7.842(1.27); 7.823(3.61); 7.803(4.9); 7.801(4.95); 7.771(0.85); 7.706(5.76); 7.687(8.68); 7.667 (3.41); 7.638(0.9); 7.619(1.11); 7.599(0.47); 7.545(0.44); 7.515(2); 7.474 (0.33); 7.416(0.39); 3.803(0.49); 3.788(1.21); 3.773(1.61); 3.758(1.23); 3.743(0.51); 2.672(0.54); 2.503(95.94); 2.329(0.76); 1.356(0.97); 1.046(16); 1.03(15.94); 0(2.05) |
| I-208 | 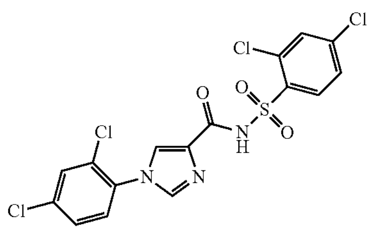 [SMILES: O=C(NS(=O)(=O)c1ccc(Cl)cc1Cl)c1cn(-c2ccc(Cl)cc2Cl)cn1] | Example I-208: 1H-NMR(400.0 MHz, d6-DMSO): δ = 8.316(12.75); 8.313(13); 8.247(10.06); 8.244(8.91); 8.157(10.55); 8.135(11.64); 7.974(10.02); 7.968(9.82); 7.874(10.23); 7.869(10.42); 7.721(8.52); 7.719(8.28); 7.716(7.33); 7.697(16); 7.682(0.35); 7.671(8.72); 7.665(7.85); 7.649(3.56); 7.644(3.63); 2.672(0.38); 2.525(1.35); 2.512 (22.53); 2.507(44.42); 2.503(58.04); 2.498(41.88); 2.494(20.12); 2.33 (0.38); 2.075(8.3); 0(8.62); −0.008(0.32) |
| I-209 | 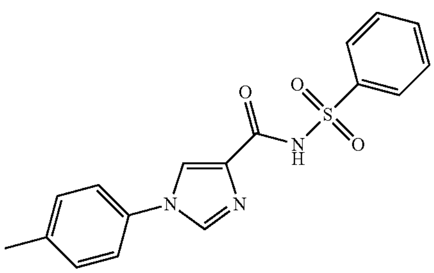 [SMILES: Cc1ccc(-n2cnc(C(=O)NS(=O)(=O)c3ccccc3)c2)cc1] | Example I-209: 1H-NMR(400.0 MHz, d6-DMSO): δ = 8.456(5.39); 8.453(5.99); 8.4(4.86); 8.397(4.48); 8.02(4.59); 8.007 (1.32); 8.002(5.65); 7.998(3.9); 7.724(0.86); 7.72(0.57); 7.711(0.64); 7.705 (2.84); 7.7(0.88); 7.69(1.36); 7.687(2.25); 7.684(1.24); 7.647(4.04); 7.628(5.62); 7.613(0.91); 7.61(2.15); 7.585(5.54); 7.564(6.67); 7.354 (5.29); 7.333(4.32); 5.756(1.14); 2.511(12.45); 2.507(25.69); 2.502(34.34); 2.498(25.82); 2.494(13.34); 2.351(16); 2.329(0.56); 2.325(0.44); 0(4.92) |
| I-210 | 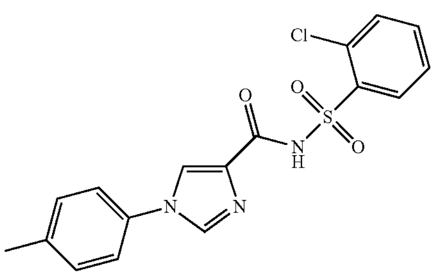 [SMILES: Cc1ccc(-n2cnc(C(=O)NS(=O)(=O)c3ccccc3Cl)c2)cc1] | Example I-210: 1H-NMR(400.0 MHz, d6-DMSO): δ = 8.517(4.66); 8.514(5.23); 8.481(3.93); 8.169(2.37); 8.166(2.51); 8.15 (2.58); 8.146(2.59); 7.705(0.64); 7.701(0.68); 7.685(1.86); 7.681(1.77); 7.668(2.54); 7.664(2.48); 7.653(3.14); 7.649(4.16); 7.633(1.67); 7.629 (1.19); 7.619(1.98); 7.615(1.61); 7.596(7.16); 7.574(6.81); 7.37(5.18); 7.349(4.32); 5.754(1.62); 2.512(17.73); 2.507(36.66); 2.502(49.17); 2.498 (36.97); 2.494(19.2); 2.36(16); 2.339(0.53); 2.334(0.54); 2.329(0.59); 2.325(0.49); 2.074(12.98); 0(6.73); −0.008(0.35) |
| I-211 | 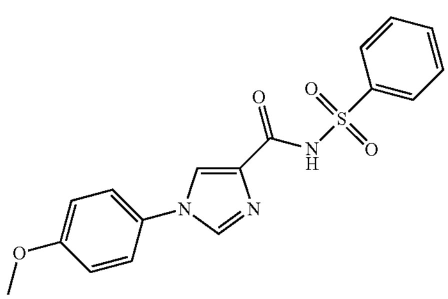 [SMILES: COc1ccc(-n2cnc(C(=O)NS(=O)(=O)c3ccccc3)c2)cc1] | Example I-211: 1H-NMR(400.0 MHz, d6-DMSO): δ = 8.399(3.17); 8.396(3.63); 8.341(2.73); 8.021(2.9); 8.003(3.3); 8(2.4); 7.722(0.51); 7.709(0.39); 7.703(1.72); 7.698(0.54); 7.685(1.34); 7.646 (2.51); 7.626(3.66); 7.617(3.96); 7.611(1.83); 7.609(1.88); 7.599(1.37); 7.594(4.22); 7.586(0.46); 7.104(0.42); 7.095(4.06); 7.09(1.31); 7.078 (1.24); 7.072(3.78); 7.064(0.34); 5.757(0.58); 3.804(16); 2.508(10.01); 2.503(13.02); 2.499(9.68); 0(1.71) |

-continued $$\underset{M}{\overset{O}{\|}}\overset{}{\underset{H}{\text{N}}}\overset{O}{\underset{O}{\overset{\|}{\text{S}}}}\text{D} \quad (I)$$

| Example No. | Structure | NMR peak list |
|---|---|---|
| I-212 | 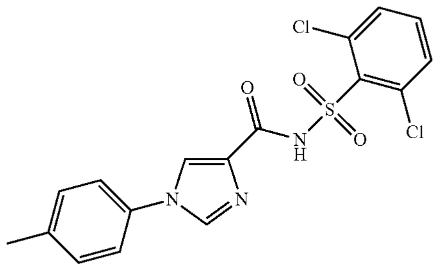 [SMILES: Cc1ccc(-n2cnc(C(=O)NS(=O)(=O)c3c(Cl)cccc3Cl)c2)cc1] | Example I-212: 1H-NMR(400.0 MHz, d6-DMSO): δ = 8.687(2.42); 8.514(6.04); 8.511(5.77); 7.912(0.4); 7.623(9.23); 7.619 (6.8); 7.601(16); 7.554(4.21); 7.537(2.89); 7.532(2.23); 7.515(1.67); 7.38(5.05); 7.359(4.18); 5.756(2.06); 3.601(0.33); 2.676(0.34); 2.671 (0.46); 2.666(0.33); 2.524(1.42); 2.52(2.23); 2.511(25.9); 2.506(51.98); 2.502(68.02); 2.497(48.13); 2.493(22.48); 2.364(15.53); 2.333(0.39); 2.329(0.48); 2.324(0.34); 2.074(0.38); 1.76(0.4); 0(7.56) |
| I-213 | 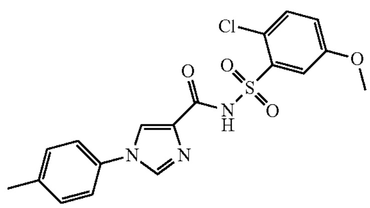 | Example I-213: 1H-NMR(400.0 MHz, d6-DMSO): δ = 8.526(2.41); 8.523(3.83); 8.513(1.93); 7.619(2.86); 7.612(3.04); 7.606 (0.51); 7.599(3.03); 7.582(1.17); 7.578(3.75); 7.557(2.65); 7.535(3.1); 7.373(2.87); 7.353(2.36); 7.274(1.56); 7.266(1.49); 7.252(1.35); 7.244 (1.31); 5.756(0.39); 3.854(16); 3.816(0.43); 2.524(0.57); 2.52(0.93); 2.511 (10.85); 2.507(21.97); 2.502(29); 2.498(20.87); 2.493(10); 2.362(8.74); 0(3.15) |
| I-214 | 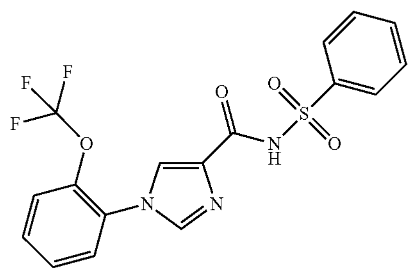 [SMILES: O=C(NS(=O)(=O)c1ccccc1)c1cn(-c2ccccc2OC(F)(F)F)cn1] | Example I-214: 1H-NMR(400.0 MHz, d6-DMSO): δ = 8.288(13.78); 8.285(14.53); 8.2(0.35); 8.174(13.16); 8.171(12.73); 8.065(0.37); 8.061(0.41); 8.039(1.29); 8.031(10.46); 8.027(5.52); 8.018 (2.98); 8.013(13.22); 8.009(8.96); 7.94(0.42); 7.937(0.41); 7.844(0.73); 7.84(0.75); 7.824(0.8); 7.82(0.87); 7.751(0.36); 7.737(7.03); 7.735(5.18); 7.719(11.43); 7.704(3.49); 7.7(5.6); 7.697(3.3); 7.689(1.22); 7.686 (1.15); 7.672(9.84); 7.665(6.34); 7.659(16); 7.656(9.48); 7.643(7.21); 7.64 (14.57); 7.624(6.87); 7.622(7.03); 7.618(5.17); 7.609(2.9); 7.605(4.29); 7.602(3.28); 7.599(3.09); 7.593(1.01); 7.588(3.06); 7.582(2.55); 7.577 (0.42); 7.572(0.46); 7.568(0.9); 7.354(0.96); 6.872(0.82); 3.349(0.34); 3.332(0.43); 2.672(0.34); 2.525(0.85); 2.512(22.76); 2.508(47); 2.503 (63.01); 2.498(46.53); 2.494(23.4); 2.444(0.49); 2.432(0.36); 2.416(0.42); 2.334(0.37); 2.33(0.49); 2.325(0.37); 2.185(1.39); 2.076(9.81); 1.989 (0.5); 1.654(0.4); 1.357(10.01); 1.291(0.47); 1.287(0.34); 1.27(0.64); 1.252(0.33); 0(6.58) |
| I-215 | 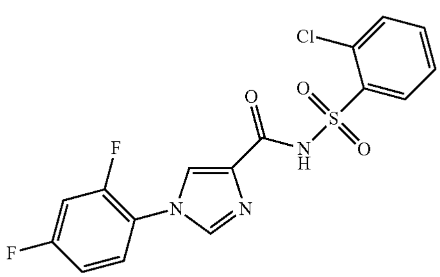 [SMILES: O=C(NS(=O)(=O)c1ccccc1Cl)c1cn(-c2ccc(F)cc2F)cn1] | Example I-215: 1H-NMR(400.0 MHz, d6-DMSO): δ = 8.386(1.59); 8.382(2.76); 8.379(1.68); 8.32(0.39); 8.268(0.71); 8.265 (0.76); 8.236(2.56); 8.192(0.34); 8.176(1.39); 8.172(1.66); 8.165(0.61); 8.156(1.7); 8.152(1.75); 8.146(0.44); 7.823(0.56); 7.808(0.61); 7.801 (1.16); 7.786(1.15); 7.778(0.65); 7.764(0.6); 7.728(0.4); 7.724(0.45); 7.708(1.14); 7.704(1.18); 7.69(1.69); 7.686(1.59); 7.68(1); 7.674(2.38); 7.67(2.98); 7.662(0.65); 7.657(1.3); 7.654(1.44); 7.651(1.71); 7.645(0.89); 7.636(1.26); 7.631(1.35); 7.623(0.88); 7.616(1.39); 7.614(1.33); 7.612 (1.38); 7.607(0.55); 7.598(0.83); 7.594(0.78); 7.59(0.46); 7.353(0.41); 7.349(0.46); 7.346(0.42); 7.343(0.4); 7.329(0.73); 7.327(0.75); 7.323 (0.72); 7.31(0.39); 7.307(0.41); 7.303(0.37); 7.3(0.34); 6.944(0.35); 4.148(0.71); 4.13(0.75); 4.119(0.51); 4.101(0.48); 2.524(0.81); 2.511 (13.18); 2.507(26.29); 2.502(34.61); 2.498(25.14); 2.493(12.22); 2.075 (16); 1.363(0.49); 1.345(1.01); 1.328(0.47); 1.298(0.74); 1.28(1.63); 1.263(0.8); 0(2.7) |
| I-216 | 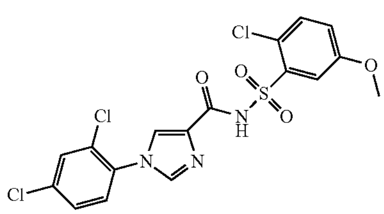 [SMILES: COc1ccc(Cl)c(S(=O)(=O)NC(=O)c2cn(-c3ccc(Cl)cc3Cl)cn2)c1] | Example I-216: 1H-NMR(400.0 MHz, d6-DMSO): δ = 8.309(1.95); 8.172(2.3); 8.17(2.36); 7.973(2.64); 7.968(2.64); 7.711 (1.55); 7.69(3.93); 7.668(2.41); 7.662(2.24); 7.646(0.98); 7.641(0.96); 7.617(2.81); 7.609(2.94); 7.575(2.17); 7.553(3.55); 7.292(1.26); 7.284 (1.22); 7.27(1.11); 7.262(1.08); 3.856(16); 2.675(0.6); 2.67(0.84); 2.666 (0.6); 2.524(2.18); 2.519(3.55); 2.51(48.99); 2.506(99.26); 2.501(131.21); 2.497(94.91); 2.492(46.04); 2.333(0.69); 2.328(0.93); 2.324(0.69); 2.074(0.79); 0.008(0.41); 0(14.4); −0.008(0.49) |

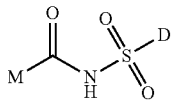
(I)
| Example No. | Structure | NMR peak list |
|---|---|---|
| I-217 | 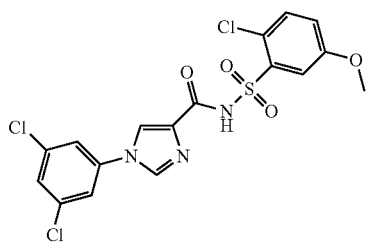 [SMILES: COc1ccc(Cl)c(S(=O)(=O)NC(=O)c2cn(-c3cc(Cl)cc(Cl)c3)cn2)c1] | Example I-217: 1H-NMR(400.0 MHz, d6-DMSO): δ = 8.348(3.66); 8.2(3.48); 7.899(2.91); 7.893(3.08); 7.791(2.35); 7.769 (3.38); 7.682(1.98); 7.676(1.92); 7.66(1.38); 7.654(1.33); 7.62(2.91); 7.612(3.16); 7.582(2.6); 7.56(3.01); 7.298(1.63); 7.29(1.61); 7.276(1.44); 7.268(1.39); 3.858(16); 3.816(1.17); 2.502(54.62); 2.328(0.56); 0(2.28) |
| I-218 | 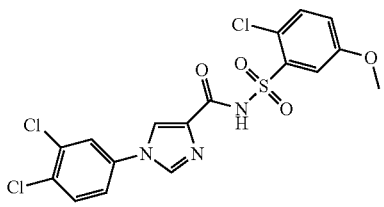 [SMILES: COc1ccc(Cl)c(S(=O)(=O)NC(=O)c2cn(-c3ccc(Cl)c(Cl)c3)cn2)c1] | Example I-218: 1H-NMR(400.0 MHz, d6-DMSO): δ = 8.632(2.86); 8.629(3.3); 8.567(3.06); 8.564(3.02); 8.148(2.97); 8.141 (3.03); 7.862(2.28); 7.84(3.6); 7.772(1.89); 7.766(1.78); 7.751(1.19); 7.744(1.19); 7.618(2.76); 7.611(2.89); 7.57(2.63); 7.548(3.09); 7.29(1.54); 7.282(1.49); 7.268(1.33); 7.26(1.28); 3.857(16); 2.524(0.49); 2.511 (15.53); 2.506(32.06); 2.502(43.06); 2.498(32.35); 2.493(16.76); 2.329 (0.32); 2.074(1.31); 0.008(0.87); 0(31.62); −0.008(1.56) |
| I-219 | 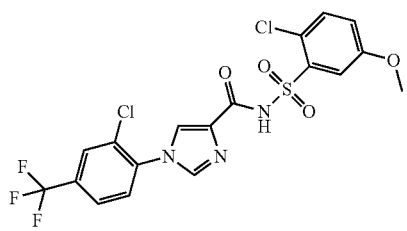 [SMILES: COc1ccc(Cl)c(S(=O)(=O)NC(=O)c2cn(-c3ccc(C(F)(F)F)cc3Cl)cn2)c1] | Example I-219: 1H-NMR(400.0 MHz, d6-DMSO): δ = 8.395(2.73); 8.392(2.91); 8.238(4.87); 8.235(3.68); 7.976(0.75); 7.972 (0.75); 7.955(1.46); 7.951(1.48); 7.91(2.21); 7.889(1.21); 7.624(2.75); 7.616(2.91); 7.584(2.59); 7.562(3.05); 7.301(1.51); 7.293(1.47); 7.279 (1.32); 7.271(1.29); 3.86(16); 2.524(0.85); 2.511(16.7); 2.506(33.21); 2.502(43.53); 2.497(31.86); 2.493(15.86); 2.074(0.56); 0.008(1.33); 0 (34.46); −0.008(1.34) |
| I-220 | 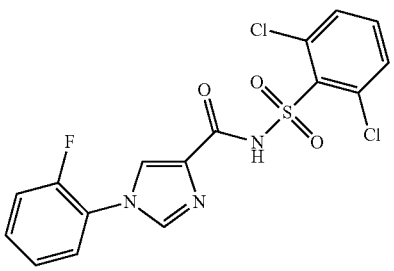 [SMILES: O=C(NS(=O)(=O)c1c(Cl)cccc1Cl)c1cn(-c2ccccc2F)cn1] | Example I-220: 1H-NMR(400.0 MHz, d6-DMSO): δ = 8.421(4.27); 8.418(7.63); 8.414(4.79); 8.372(6.3); 7.912(0.4); 7.75 (1.79); 7.73(3.74); 7.711(2); 7.663(5.7); 7.658(6.89); 7.641(16); 7.628 (0.52); 7.625(0.53); 7.606(1.07); 7.6(6.81); 7.583(4.47); 7.577(3.85); 7.572 (2.13); 7.567(3.84); 7.558(6.72); 7.541(4.7); 7.536(4.48); 7.52(0.92); 7.514(0.43); 7.429(2.1); 7.424(1.23); 7.419(1.25); 7.414(1.88); 7.408 (2.66); 7.395(1.56); 7.387(1.46); 5.756(0.54); 2.675(0.35); 2.671(0.54); 2.666(0.36); 2.524(0.9); 2.511(40.33); 2.506(83.33); 2.502(111.5); 2.497 (82.29); 2.493(41.49); 2.333(0.7); 2.329(0.91); 2.324(0.72); 0.146(0.33); 0.008(2.45); 0(86.53); −0.008(4); −0.15(0.45) |
| I-221 | 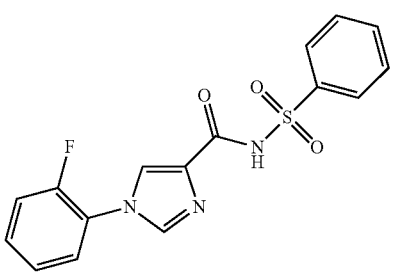 [SMILES: O=C(NS(=O)(=O)c1ccccc1)c1cn(-c2ccccc2F)cn1] | Example I-221: 1H-NMR(400.0 MHz, d6-DMSO): δ = 9.089(0.41); 8.381(0.37); 8.377(0.38); 8.34(14.51); 8.232(9.28); 8.229 (13.03); 8.027(13.14); 8.026(13.17); 8.008(16); 8.004(10.82); 7.844 (2.38); 7.84(2.52); 7.825(2.69); 7.82(2.67); 7.734(2.71); 7.716(11.29); 7.698(13.01); 7.677(4.07); 7.657(11.51); 7.637(15.42); 7.619(6.25); 7.606(1.13); 7.604(1.17); 7.593(1.97); 7.588(4.69); 7.577(1.19); 7.569 (3.05); 7.549(7.52); 7.538(11.37); 7.522(8.21); 7.518(7.85); 7.502(1.31); 7.423(0.47); 7.412(3.81); 7.407(2.38); 7.402(2.52); 7.397(3.52); 7.391 (5.03); 7.379(3.11); 7.37(2.87); 7.356(3.91); 6.874(0.34); 4.493(0.7); 4.476 (0.72); 3.789(0.32); 3.739(0.35); 3.696(0.35); 3.677(0.36); 3.654(0.36); 3.637(0.36); 3.618(0.36); 3.595(0.37); 3.588(0.37); 3.547(0.37); 3.542 (0.38); 3.527(0.37); 3.509(0.38); 3.5(0.38); 3.473(0.37); 3.468(0.37); 3.458(0.37); 3.44(0.36); 3.42(0.36); 3.414(0.35); 3.373(0.34); 3.359(0.34); 3.352(0.33); 2.672(0.56); 2.668(0.43); 2.508(57.56); 2.503(71.18); 2.499(51.06); 2.33(0.46); 2.326(0.34); 2.185(0.6); 2.076(1.4); 1.39(0.67); 1.373(1.39); 1.357(4.24); 1.269(0.33); 1.236(0.4); 0.008(0.64); 0(12.13); −0.008(0.52) |

-continued
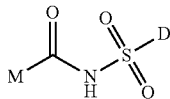
(I)
| Example No. | Structure | NMR peak list |
|---|---|---|
| I-222 | 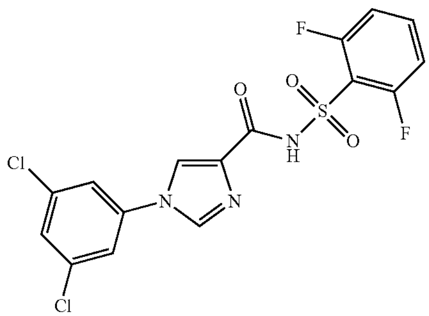 [SMILES: O=C(NS(=O)(=O)c1c(F)cccc1F)c1cn(-c2cc(Cl)cc(Cl)c2)cn1] | Example I-222: 1H-NMR(400.0 MHz, d6-DMSO): δ = 8.712(7.97); 8.669(9.03); 7.97(16); 7.967(15.07); 7.776(0.77); 7.76 (1.75); 7.754(1.89); 7.74(3.24); 7.719(8.34); 7.705(1.63); 7.314(4.74); 7.291(7.71); 7.268(4.62); 5.756(0.48); 2.502(84.36); 2.329(1.04); 2.074(5.26); 2.061(0.71); 0.006(0.82); −0.002(25.97); −0.014(2.86) |
| I-223 | 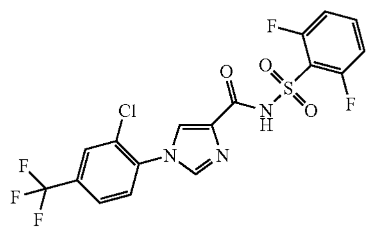 [SMILES: O=C(NS(=O)(=O)c1c(F)cccc1F)c1cn(-c2ccc(C(F)(F)F)cc2Cl)cn1] | Example I-223: 1H-NMR(400.0 MHz, d6-DMSO): δ = 8.384(14.26); 8.381(16); 8.339(12.82); 8.336(11.76); 8.316(0.36); 8.252(9.08); 8.248(9.12); 7.986(3.53); 7.982(3.5); 7.965(6.74); 7.961(6.58); 7.925(10.18); 7.904(5.2); 7.792(1.11); 7.777(2.51); 7.771(2.37); 7.762 (1.77); 7.756(4.48); 7.75(1.79); 7.741(2.45); 7.734(2.82); 7.72(1.15); 7.329(7.31); 7.307(11.1); 7.284(6.59); 5.756(2.48); 2.671(0.39); 2.511 (45.8); 2.506(103.16); 2.502(147.77); 2.497(113.37); 2.493(60.57); 2.333(1.25); 2.329(1.56); 2.324(1.32); 2.075(2.04); 1.018(0.44); 0.008 (0.39); 0(62.45); −0.009(3.75); −0.15(0.38) |
| I-224 | 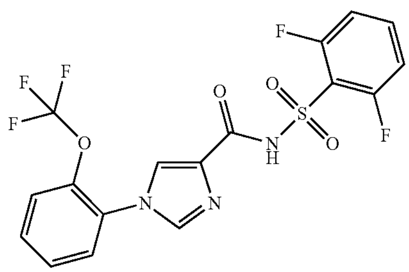 [SMILES: O=C(NS(=O)(=O)c1c(F)cccc1F)c1cn(-c2ccccc2OC(F)(F)F)cn1] | Example I-224: 1H-NMR(400.0 MHz, d6-DMSO): δ = 8.356(16); 8.338(13.37); 8.316(0.75); 7.984(0.65); 7.782(8.12); 7.764 (10.77); 7.762(10.49); 7.748(5.34); 7.733(3.11); 7.727(3.28); 7.711(2.3); 7.692(14.09); 7.68(10.35); 7.639(2.21); 7.655(2.58); 7.642(5.59); 7.634 (4.02); 7.627(3.57); 7.622(5.07); 7.616(3.75); 7.607(2.59); 7.6(2.26); 7.322(8.29); 7.299(13.07); 7.276(7.51); 7.242(0.39); 5.756(1.63); 4.492(0.32); 4.458(0.33); 4.427(0.35); 4.414(0.34); 4.383(0.36); 4.363 (0.36); 4.314(0.36); 4.296(0.38); 4.278(0.46); 4.268(0.41); 4.258(0.44); 4.242(0.4); 4.2(0.37); 4.164(0.42); 4.147(0.56); 4.13(0.56); 4.113(0.4); 4.062(0.37); 4.038(0.35); 4.002(0.35); 3.991(0.34); 3.96(0.34); 3.919 (0.33); 2.675(1.43); 2.671(1.97); 2.666(1.51); 2.506(235.6); 2.502(301.64); 2.497(231.43); 2.333(1.73); 2.328(2.24); 2.324(1.77); 2.074(0.57); 1.288(0.61); 0.146(0.4); 0(94.66); −0.15(0.47) |
| I-225 | 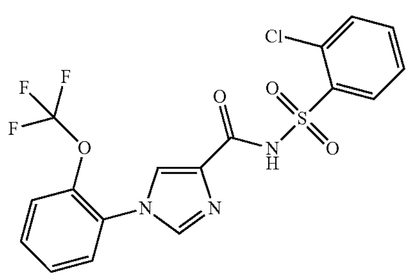 [SMILES: O=C(NS(=O)(=O)c1ccccc1Cl)c1cn(-c2ccccc2OC(F)(F)F)cn1] | Example I-225: 1H-NMR(400.0 MHz, d6-DMSO): δ = 8.378(8.93); 8.207(11.65); 8.178(5.89); 8.174(6.96); 8.158(6.44); 8.154(7.32); 7.768(5.75); 7.752(7.39); 7.748(7.91); 7.727(1.41); 7.724 (1.67); 7.707(5.43); 7.704(5.89); 7.685(16); 7.682(14.99); 7.677(12.9); 7.672(12.98); 7.669(11.59); 7.665(8.45); 7.656(4.49); 7.652(4.05); 7.648 (4.11); 7.644(3.17); 7.635(9.5); 7.629(5.9); 7.616(10.86); 7.6(5.37); 7.595 (4.02); 3.508(0.34); 2.675(1.71); 2.671(2.29); 2.666(1.68); 2.524(8.87); 2.51(128.94); 2.506(252.17); 2.502(328.38); 2.497(239.45); 2.493 (118.33); 2.333(1.64); 2.328(2.2); 2.324(1.64); 1.234(0.67); 0.146(0.33); 0.008(3.13); 0(74.11); −0.008(2.56) |
| I-226 | 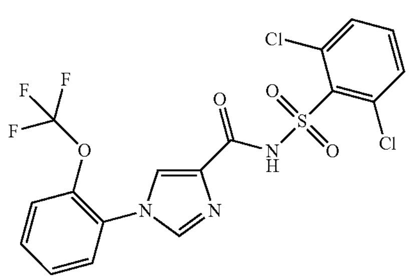 [SMILES: O=C(NS(=O)(=O)c1c(Cl)cccc1Cl)c1cn(-c2ccccc2OC(F)(F)F)cn1] | Example I-226: 1H-NMR(400.0 MHz, d6-DMSO): δ = 8.387(7.82); 8.384(8.86); 8.312(6.65); 8.309(6.72); 7.787(3.54); 7.77 (4.21); 7.766(4.21); 7.708(0.69); 7.705(0.68); 7.691(6.83); 7.678(4.92); 7.674(4.32); 7.669(6.32); 7.665(7.46); 7.657(1.93); 7.653(2.17); 7.647 (16); 7.642(4.66); 7.635(2.45); 7.626(2.19); 7.622(2.92); 7.619(2.22); 7.616(2.25); 7.605(7.64); 7.6(1.92); 7.588(4.5); 7.582(3.51); 7.565(2.49); 2.676(0.33); 2.671(0.46); 2.667(0.33); 2.524(1.57); 2.511(26.22); 2.507(51.57); 2.502(67.06); 2.498(48.25); 2.493(23.3); 2.329(0.44); 2.076(2.89); 1.291(0.41); 0.008(0.74); 0(18.37); −0.008(0.6) |

-continued
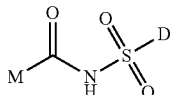
(I)
| Example No. | Structure | NMR peak list |
|---|---|---|
| I-227 | 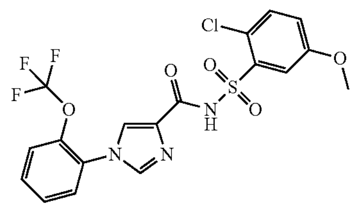 [SMILES: COc1ccc(Cl)c(S(=O)(=O)NC(=O)c2cn(-c3ccccc3OC(F)(F)F)cn2)c1] | Example I-227: 1H-NMR(400.0 MHz, d6-DMSO): δ = 8.392(2.91); 8.389(3.03); 8.228(2.8); 8.225(2.76); 7.774(1.19); 7.756 (1.53); 7.752(1.57); 7.684(2.52); 7.671(1.64); 7.667(1.37); 7.651(0.6); 7.647(0.48); 7.638(1.24); 7.631(0.93); 7.622(3.48); 7.618(1.63); 7.615 (3.92); 7.602(0.65); 7.596(0.52); 7.583(2.63); 7.561(3.07); 7.553(0.41); 7.531(0.38); 7.481(0.37); 7.473(0.38); 7.3(1.57); 7.292(1.5); 7.278(1.36); 7.27(1.31); 3.86(16); 3.816(2.17); 2.524(0.63); 2.511(13.78); 2.506 (27.6); 2.502(36.26); 2.497(26.35); 2.493(12.98); 0.008(0.37); 0(11.09); −0.008(0.41) |
| I-228 | 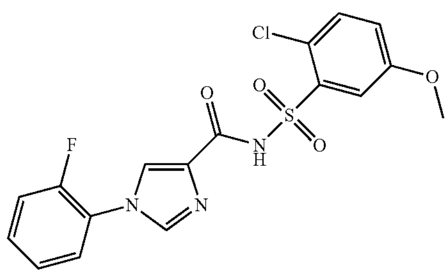 [SMILES: COc1ccc(Cl)c(S(=O)(=O)NC(=O)c2cn(-c3ccccc3F)cn2)c1] | Example I-228: 1H-NMR(400.0 MHz, d6-DMSO): δ = 8.427(2.77); 8.289(2.57); 7.74(0.72); 7.72(1.4); 7.701(0.81); 7.624 (2.88); 7.616(3.01); 7.58(2.73); 7.563(1.96); 7.558(3.69); 7.553(2.43); 7.537(1.3); 7.532(2); 7.426(0.77); 7.42(0.48); 7.413(0.68); 7.405(1.02); 7.394(0.71); 7.384(0.53); 7.298(1.62); 7.29(1.57); 7.276(1.43); 7.268 (1.39); 3.86(16); 3.816(0.42); 2.524(0.61); 2.511(9.94); 2.507(19.17); 2.502(24.63); 2.498(17.81); 2.493(8.72); 2.076(1.53); 1.292(0.32); 0(6.25) |
| I-229 | 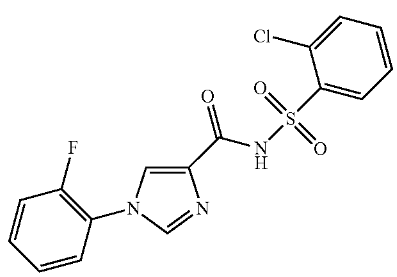 [SMILES: O=C(NS(=O)(=O)c1ccccc1Cl)c1cn(-c2ccccc2F)cn1] | Example I-229: 1H-NMR(400.0 MHz, d6-DMSO): δ = 8.431(9.3); 8.428(16); 8.424(9.73); 8.314(0.85); 8.311(0.92); 8.281 (8.78); 8.278(14.22); 8.209(0.55); 8.182(7.71); 8.178(8.27); 8.17(1.06); 8.162(8.45); 8.158(8.54); 7.738(4.03); 7.731(2.8); 7.726(3.13); 7.718 (8.04); 7.71(7); 7.707(6.67); 7.699(5.27); 7.693(9.21); 7.689(8.64); 7.678 (10.75); 7.674(14.3); 7.666(1.23); 7.658(5.63); 7.654(3.79); 7.639(6.33); 7.635(5.35); 7.62(7.35); 7.616(6.06); 7.608(1.2); 7.602(4.28); 7.598 (3.68); 7.591(0.48); 7.586(0.51); 7.561(9.19); 7.551(11.33); 7.536(6.67); 7.53(10.5); 7.516(1.48); 7.496(0.45); 7.492(0.54); 7.476(0.46); 7.473(0.7); 7.452(0.41); 7.434(0.66); 7.424(4.21); 7.419(2.52); 7.412(3.74); 7.403 (5.37); 7.398(2.55); 7.392(3.73); 7.382(2.93); 7.37(0.34); 7.283(0.47); 7.264(0.37); 7.094(0.43); 7.091(0.41); 4.139(0.89); 4.122(0.89); 2.676 (0.44); 2.672(0.6); 2.667(0.43); 2.525(2.11); 2.512(36.46); 2.507(71.89); 2.503(93.68); 2.498(67.67); 2.494(32.89); 2.334(0.47); 2.33(0.62); 2.325(0.46); 2.076(5.31); 1.31(0.94); 1.292(2.02); 1.275(0.91); 0.008 (0.95); 0(24.11); −0.008(0.86) |
| I-230 | 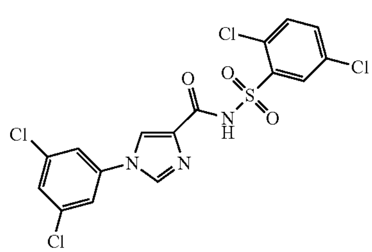 [SMILES: O=C(NS(=O)(=O)c1cc(Cl)ccc1Cl)c1cn(-c2cc(Cl)cc(Cl)c2)cn1] | Example I-230: 1H-NMR(400.0 MHz, d6-DMSO): δ = 8.756(5.68); 8.754(6.05); 8.675(7.61); 8.672(7.24); 8.092(6.52); 8.086 (6.76); 7.971(15.48); 7.967(16); 7.787(3.12); 7.781(2.9); 7.766(4.69); 7.76(4.63); 7.731(4.03); 7.727(7.13); 7.722(3.8); 7.712(0.43); 7.706 (0.49); 7.702(0.66); 7.694(8.37); 7.672(5.35); 5.758(4.01); 2.672(0.39); 2.525(1.64); 2.512(24.56); 2.507(47.36); 2.503(61.01); 2.498(44.22); 2.494(21.78); 2.329(0.39); 0.008(0.41); 0(9.27); −0.008(0.34) |

| Example No. | Structure | NMR peak list |
|---|---|---|
| I-231 | 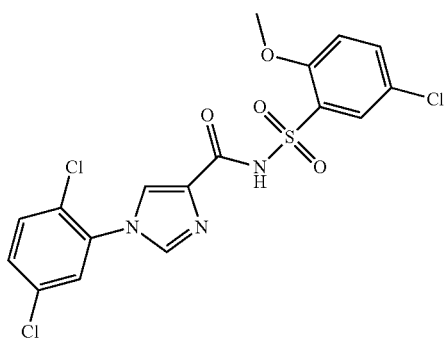 [SMILES: COc1ccc(Cl)cc1S(=O)(=O)NC(=O)c1cn(-c2cc(Cl)ccc2Cl)cn1] | Example I-231: 1H-NMR(400.0 MHz, d6-DMSO): δ = 8.35(3.29); 8.347(3.47); 8.153(3.58); 8.15(3.63); 7.886(3.26); 7.879 (3.44); 7.843(3.01); 7.836(3.49); 7.792(2.8); 7.771(4.12); 7.765(1.87); 7.758(1.5); 7.742(1.87); 7.736(1.67); 7.681(2.36); 7.675(2.24); 7.659(1.6); 7.653(1.59); 7.306(2.89); 7.284(2.63); 3.904(0.32); 3.875(16); 2.524 (1.05); 2.51(15); 2.506(29.28); 2.502(38.09); 2.497(27.76); 2.492(13.66); 2.075(1.25); 0(3) |
| I-232 | 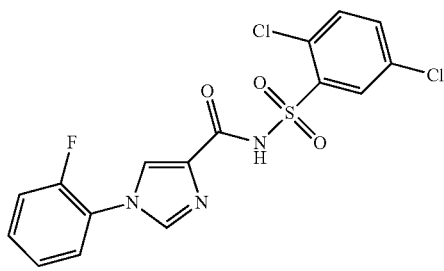 [SMILES: O=C(NS(=O)(=O)c1cc(Cl)ccc1Cl)c1cn(-c2ccccc2F)cn1] | Example I-232: 1H-NMR(400.0 MHz, d6-DMSO): δ = 8.454(8.99); 8.415(7.33); 8.412(11.51); 8.408(6.34); 8.268(0.52); 8.265(0.5); 8.093(12.67); 8.087(12.79); 8.073(0.38); 8.066(0.4); 7.79 (6.23); 7.783(5.65); 7.768(9.27); 7.762(9.21); 7.757(2.89); 7.754(2.94); 7.737(5.19); 7.735(5.97); 7.717(3.14); 7.714(3.44); 7.707(1.13); 7.697(16); 7.676(10.06); 7.652(0.52); 7.631(0.34); 7.599(0.45); 7.595(0.44); 7.584 (1.09); 7.578(2.98); 7.574(3.62); 7.57(5.11); 7.563(9.96); 7.561(8.99); 7.544(6.25); 7.539(4.99); 7.524(1.2); 7.518(0.61); 7.431(3.27); 7.427 (1.96); 7.422(1.94); 7.416(3.45); 7.41(4.11); 7.402(1.61); 7.396(2.43); 7.389(2.12); 4.145(0.59); 4.127(0.59); 2.68(0.37); 2.675(0.91); 2.671 (1.29); 2.666(0.9); 2.662(0.35); 2.524(3.94); 2.519(6.32); 2.511(76.16); 2.506(154.6); 2.502(204.65); 2.497(147.55); 2.493(70.92); 2.338(0.53); 2.333(1.04); 2.328(1.42); 2.324(1.03); 2.32(0.52); 2.075(1.57); 1.303 (0.56); 1.286(1.22); 1.268(0.55); 0.146(0.32); 0.008(2.69); 0(93.34); −0.008(3.48); −0.15(0.39) |
| I-233 | 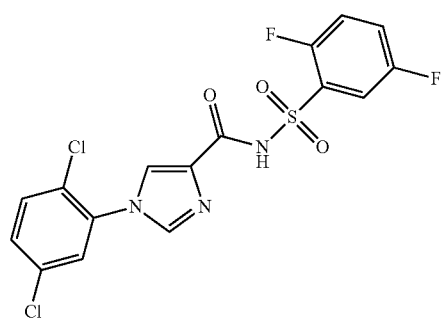 [SMILES: O=C(NS(=O)(=O)c1cc(F)ccc1F)c1cn(-c2cc(Cl)ccc2Cl)cn1] | Example I-233: 1H-NMR(400.0 MHz, d6-DMSO): δ = 8.355(13.39); 8.33(16); 7.911(12.37); 7.905(12.81); 7.799(9.58); 7.777 (14.22); 7.763(3.06); 7.734(3.82); 7.75(4.02); 7.742(3.25); 7.736(4.13); 7.731(3.67); 7.722(3.04); 7.696(8.47); 7.69(8.19); 7.675(5.94); 7.668 (6.68); 7.659(2.8); 7.645(3.31); 7.637(4.56); 7.627(3.38); 7.617(3.19); 7.609(1.68); 7.546(3.13); 7.536(3.41); 7.522(5.09); 7.512(4.98); 7.499 (2.38); 7.489(2.05); 2.671(1.16); 2.502(205.79); 2.354(0.42); 2.328(1.62); 2.075(0.35); 0(55.61); −0.15(0.32) |
| I-234 | 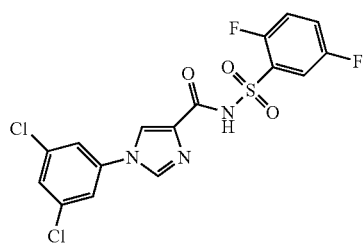 [SMILES: O=C(NS(=O)(=O)c1cc(F)ccc1F)c1cn(-c2cc(Cl)cc(Cl)c2)cn1] | Example I-234: 1H-NMR(400.0 MHz, d6-DMSO): δ = 8.75(5.42); 8.747(5.65); 8.665(7.43); 8.661(6.96); 7.974(15.53); 7.97 (16); 7.763(1.21); 7.755(1.55); 7.75(1.55); 7.742(2.12); 7.736(1.73); 7.729(4.83); 7.724(7.73); 7.72(4.19); 7.661(0.64); 7.652(1.09); 7.641 (1.06); 7.638(1.15); 7.629(1.75); 7.619(1.23); 7.609(1.42); 7.601(0.7); 7.536(1.47); 7.526(1.55); 7.513(2.37); 7.502(2.34); 7.49(1.07); 7.48(0.98); 5.758(1.62); 2.672(0.33); 2.525(1.18); 2.512(21.03); 2.507(41.82); 2.503 (54.82); 2.498(39.76); 2.494(19.36); 2.33(0.37); 0(1.01) |
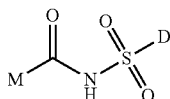
(I)

(I)
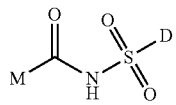
| Example No. | Structure | NMR peak list |
|---|---|---|
| I-235 | 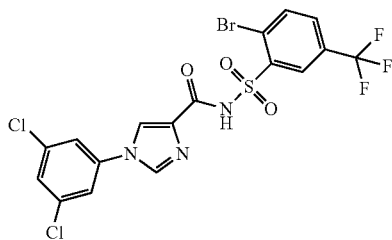 [SMILES: O=C(NS(=O)(=O)c1cc(C(F)(F)F)ccc1Br)c1cn(-c2cc(Cl)cc(Cl)c2)cn1] | Example I-235: 1H-NMR(400.0 MHz, d6-DMSO): δ = 8.88(5.25); 8.878(4.89); 8.687(7.57); 8.684(6.68); 8.374(4.38); 8.368 (4.13); 8.076(3.24); 8.055(4.28); 7.987(16); 7.983(15.51); 7.942(2.62); 7.936(2.45); 7.92(1.89); 7.915(1.75); 7.744(4.04); 7.739(6.78); 7.735 (3.23); 2.672(0.36); 2.526(1.29); 2.512(21.62); 2.508(42.52); 2.503(55.32); 2.499(39.88); 2.494(19.24); 2.33(0.36); 0(1.15) |
| I-236 | 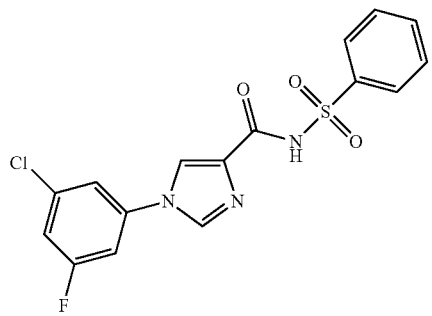 [SMILES: O=C(NS(=O)(=O)c1ccccc1)c1cn(-c2cc(F)cc(Cl)c2)cn1] | Example I-236: 1H-NMR(400.0 MHz, d6-DMSO): δ = 8.609(13.97); 8.606(15.8); 8.552(15.17); 8.549(14.14); 8.028(1.28); 8.02(12.55); 8.016(6.63); 8.007(3.46); 8.002(16); 7.998(11); 7.839(9.61); 7.799(3.56); 7.793(5.95); 7.788(3.28); 7.774(3.61); 7.768(5.96); 7.763 (3.24); 7.734(1.25); 7.731(2.4); 7.728(1.62); 7.718(1.74); 7.712(7.68); 7.707(2.48); 7.697(3.58); 7.694(6.21); 7.691(3.48); 7.653(10.66); 7.649(5.2); 7.636(7.8); 7.633(15.09); 7.619(2.46); 7.615(5.86); 7.613 (4.04); 7.548(3.46); 7.544(5.31); 7.539(3.24); 7.527(3.64); 7.522(5.42); 7.517(3.13); 3.336(0.42); 3.32(0.42); 3.221(0.33); 2.676(0.78); 2.671 (1.03); 2.667(0.78); 2.524(3.78); 2.511(57.22); 2.507(112.01); 2.502 (145.53); 2.498(104.69); 2.493(49.93); 2.333(0.67); 2.329(0.91); 2.324 (0.64); 2.076(1.48); 0(1.71) |
| I-237 | 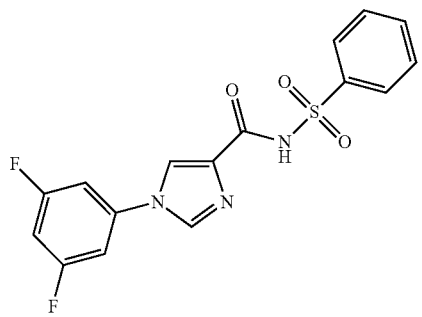 [SMILES: O=C(NS(=O)(=O)c1ccccc1)c1cn(-c2cc(F)cc(F)c2)cn1] | Example I-237: 1H-NMR(400.0 MHz, d6-DMSO): δ = 8.583(11.84); 8.58(13.96); 8.558(0.63); 8.54(14.54); 8.537(14.22); 8.506(0.43); 8.503(0.41); 8.016(13.58); 7.998(16); 7.994(12.22); 7.722 (2.38); 7.71(2.01); 7.704(8.25); 7.699(3.77); 7.682(12.36); 7.678(10.75); 7.662(10.19); 7.656(8.9); 7.646(12.38); 7.626(15.9); 7.608(6.06); 7.376 (1.75); 7.37(2.89); 7.365(1.7); 7.352(3.67); 7.347(5.77); 7.342(3.2); 7.329(1.97); 7.324(2.96); 7.318(1.54); 5.758(0.58); 4.132(0.46); 4.115 (0.45); 2.676(0.8); 2.672(1.03); 2.667(0.79); 2.511(57.79); 2.507(109.2); 2.503(140.14); 2.498(101.76); 2.494(49.95); 2.334(0.66); 2.329(0.91); 2.325(0.65); 1.356(0.45); 1.338(0.88); 1.321(0.4); 0(2.47) |
| I-238 | 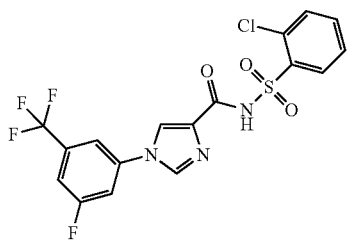 [SMILES: O=C(NS(=O)(=O)c1ccccc1Cl)c1cn(-c2cc(F)cc(C(F)(F)F)c2)cn1] | Example I-238: 1H-NMR(400.0 MHz, d6-DMSO): δ = 8.744(14.77); 8.741(16); 8.656(15.92); 8.652(15.58); 8.181(7.07); 8.177(7.8); 8.161(7.94); 8.157(8.24); 8.124(5.61); 8.12(3.86); 8.1(5.71); 8.095(3.82); 8.06(11.23); 7.815(5.16); 7.794(5.27); 7.728(2); 7.724(2.23); 7.708(5.88); 7.705(5.83); 7.691(7.53); 7.687(7.7); 7.674(9.74); 7.67 (13.15); 7.654(5.44); 7.65(4.19); 7.639(5.91); 7.635(5.28); 7.619(7.3); 7.602(3.89); 7.598(3.55); 5.757(2.77); 4.222(0.4); 4.205(0.4); 2.676(0.79); 2.672(1.09); 2.667(0.82); 2.511(69.54); 2.507(134.14); 2.503(174.13); 2.498(128.67); 2.494(65.53); 2.334(0.94); 2.33(1.22); 2.325(0.94); 2.075(0.55); 1.366(0.51); 0.008(2.64); 0(56.6); −0.008(2.57) |
| I-239 | 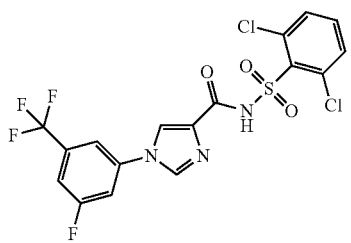 [SMILES: O=C(NS(=O)(=O)c1c(Cl)cccc1Cl)c1cn(-c2cc(F)cc(C(F)(F)F)c2)cn1] | Example I-239: 1H-NMR(400.0 MHz, d6-DMSO): δ = 8.743(16); 8.134(2.09); 8.129(1.4); 8.11(2.11); 8.104(1.42); 8.078 (4.15); 7.913(4.55); 7.828(1.93); 7.807(1.97); 7.662(4.16); 7.658(5.17); 7.64(12.01); 7.628(3.64); 7.626(3.93); 7.607(7.68); 7.599(4.96); 7.582 (3.08); 7.576(2.44); 7.559(1.67); 7.536(2.89); 7.518(2.16); 7.514(1.92); 7.496(1.36); 5.756(0.89); 2.511(26.6); 2.507(60.01); 2.502(84.2); 2.498 (65.97); 2.494(36.51); 2.334(0.7); 2.329(0.88); 2.325(0.75); 2.075(0.62); 0(27.95); −0.008(2.11) |

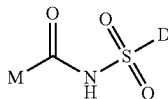
(I)
| Example No. | Structure | NMR peak list |
|---|---|---|
| I-240 | 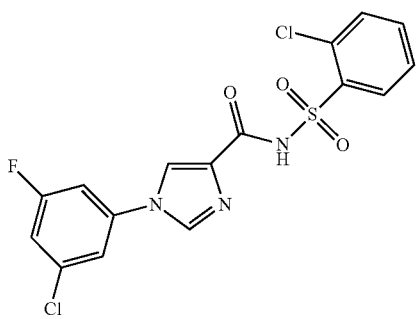 [SMILES: O=C(NS(=O)(=O)c1ccccc1Cl)c1cn(-c2cc(F)cc(Cl)c2)cn1] | Example I-240: 1H-NMR(400.0 MHz, d6-DMSO): δ = 8.661(15.17); 8.658(16); 8.585(15.53); 8.583(14.96); 8.177(6.95); 8.173(7.45); 8.157(7.66); 8.153(7.82); 7.832(12); 7.796(4.1); 7.791(6.42); 7.786(3.8); 7.771(4.15); 7.766(6.43); 7.761(3.74); 7.727(1.95); 7.723 (2.12); 7.707(6.1); 7.704(5.89); 7.69(7.04); 7.686(7.13); 7.672(9.71); 7.669(12.3); 7.653(5.09); 7.637(5.57); 7.633(5.04); 7.616(7.38); 7.6(3.57); 7.596(3.29); 7.564(4.05); 7.56(6.17); 7.555(4.01); 7.543(4.35); 7.538 (6.28); 7.534(3.81); 5.758(1.85); 2.676(0.32); 2.672(0.56); 2.668(0.36); 2.507(108.03); 2.503(141.16); 2.499(111.02); 2.334(1.07); 2.329(1.31); 2.326(1.11); 0(34.54); −0.058(0.33) |
| I-241 | 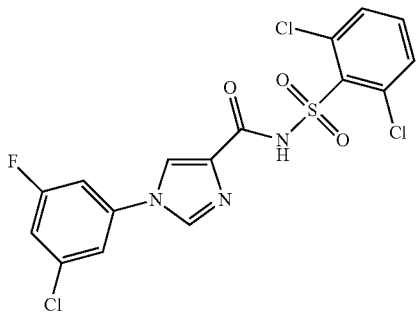 | Example I-241: 1H-NMR(400.0 MHz, d6-DMSO): δ = 8.674(9.54); 8.666(11.38); 7.915(0.62); 7.846(6.89); 7.808(2.47); 7.802(3.67); 7.783(2.49); 7.778(3.65); 7.661(6.07); 7.657(6.96); 7.639(16); 7.607(1.36); 7.599(6.45); 7.582(4.76); 7.576(5.76); 7.572(4.28); 7.559 (3.18); 7.555(2.96); 7.55(3.72); 7.537(0.62); 7.518(0.35); 7.374(0.45); 5.757(4.96); 2.673(0.39); 2.508(49.08); 2.504(60.12); 2.5(45.06); 2.33 (0.37); 0(16) |
| I-242 | 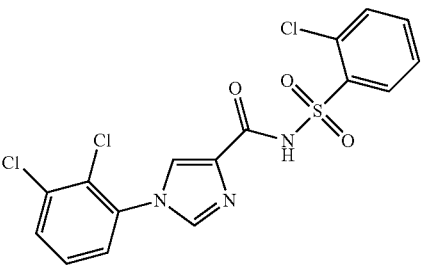 [SMILES: O=C(NS(=O)(=O)c1ccccc1Cl)c1cn(-c2cccc(Cl)c2Cl)cn1] | Example I-242: 1H-NMR(400.0 MHz, d6-DMSO): δ = 8.335(15.84); 8.332(16); 8.316(0.33); 8.193(15.3); 8.19(14.7); 8.178 (7.21); 8.174(7.33); 8.158(7.56); 8.154(7.41); 7.87(7.34); 7.866(7.84); 7.85(8.54); 7.846(8.61); 7.73(1.92); 7.726(2.02); 7.709(5.75); 7.706(5.4); 7.692(7.67); 7.688(7.72); 7.68(9.74); 7.676(12.38); 7.666(6.85); 7.661 (9.19); 7.656(3.89); 7.646(11.05); 7.642(10.08); 7.636(6.3); 7.632(5.02); 7.617(6.6); 7.613(5.33); 7.599(3.83); 7.595(3.91); 7.59(9.81); 7.57 (13.81); 7.55(5.56); 2.676(0.47); 2.671(0.68); 2.667(0.46); 2.511(47.69); 2.507(92.01); 2.502(118.97); 2.498(86.89); 2.493(43.53); 2.333(0.66); 2.329(0.85); 2.324(0.65); 2.075(3.3); 1.074(0.41); 0.008(3.04); 0(68.59); −0.008(3.31); −0.15(0.33) |
| I-243 | 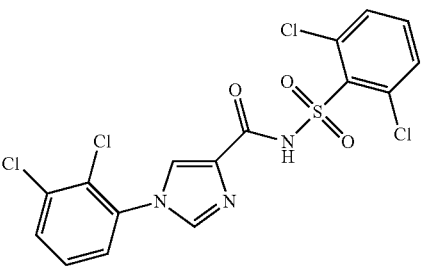 [SMILES: O=C(NS(=O)(=O)c1c(Cl)cccc1Cl)c1cn(-c2cccc(Cl)c2Cl)cn1] | Example I-243: 1H-NMR(400.0 MHz, d6-DMSO): δ = 8.341(9.48); 8.337(10.53); 8.293(7.75); 8.29(6.9); 7.879(4.69); 7.875 (5.19); 7.859(5.49); 7.855(5.62); 7.686(3.96); 7.682(4.37); 7.666(11.73); 7.661(11.19); 7.654(0.87); 7.644(14.82); 7.643(16); 7.602(7.97); 7.597 (6.45); 7.585(5.33); 7.577(9.72); 7.562(2.96); 7.557(3.84); 5.756(0.47); 2.676(0.34); 2.671(0.47); 2.667(0.34); 2.525(1.65); 2.52(2.57); 2.511 (27.81); 2.507(56.15); 2.502(73.6); 2.498(52.65); 2.493(24.85); 2.334 (0.35); 2.329(0.48); 2.324(0.34); 2.075(0.8); 1.073(0.5); 0.008(1.17); 0(34.45); −0.008(1.12) |

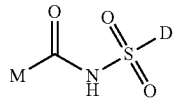
(I)
| Example No. | Structure | NMR peak list |
|---|---|---|
| I-244 | 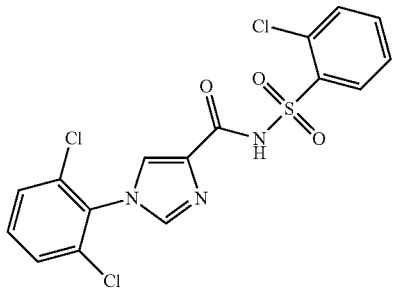 [SMILES: O=C(NS(=O)(=O)c1ccccc1Cl)c1cn(-c2c(Cl)cccc2Cl)cn1] | Example I-244: 1H-NMR(400.0 MHz, d6-DMSO): δ = 8.255(8.13); 8.252(8.54); 8.181(3.6); 8.177(3.84); 8.161(4.01); 8.157 (3.93); 8.136(8.15); 8.132(7.87); 7.769(8.56); 7.768(9.74); 7.748(16); 7.737(1.17); 7.733(1.11); 7.717(2.9); 7.713(2.89); 7.7(4.17); 7.696(4.23); 7.689(5.09); 7.685(6.42); 7.669(2.38); 7.665(1.41); 7.645(6.37); 7.642 (3.63); 7.638(2.79); 7.626(5.73); 7.623(7.26); 7.618(2.97); 7.604(5.2); 7.6(2.14); 2.524(0.77); 2.511(25.52); 2.506(52.73); 2.502(70.76); 2.497 (52.08); 2.493(26.16); 2.333(0.46); 2.328(0.58); 2.324(0.46); 2.075 (0.73); 0.008(1.29); 0(47.45); −0.009(2.17) |
| I-245 | 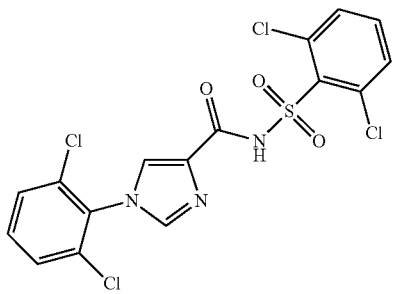 [SMILES: O=C(NS(=O)(=O)c1c(Cl)cccc1Cl)c1cn(-c2c(Cl)cccc2Cl)cn1] | Example I-245: 1H-NMR(400.0 MHz, d6-DMSO): δ = 8.264(7.21); 8.261(8.07); 8.206(7.23); 8.203(6.86); 7.912(0.47); 7.775 (8.78); 7.773(9.54); 7.753(16); 7.677(5.65); 7.673(7); 7.655(15.03); 7.652(7.48); 7.632(4.89); 7.629(4.65); 7.624(0.84); 7.615(6.68); 7.61 (3.85); 7.606(1.13); 7.598(4.19); 7.592(3.2); 7.575(2.24); 7.536(0.37); 2.676(0.45); 2.671(0.62); 2.666(0.45); 2.524(2.17); 2.511(37.39); 2.506 (75.57); 2.502(99.5); 2.497(71.78); 2.493(34.61); 2.333(0.49); 2.329(0.66); 2.324(0.49); 2.074(0.46); 1.355(0.35); 0.008(2.16); 0(61.89); −0.009(2.26) |
| I-246 | 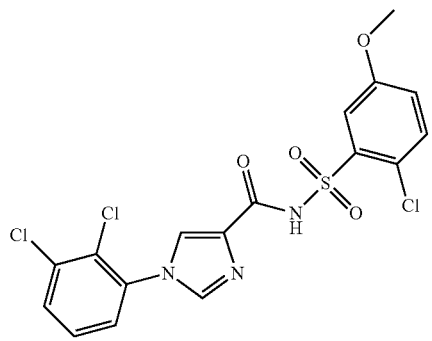 [SMILES: COc1ccc(Cl)c(S(=O)(=O)NC(=O)c2cn(-c3cccc(Cl)c3Cl)cn2)c1] | Example I-246: 1H-NMR(400.0 MHz, d6-DMSO): δ = 8.341(3.46); 8.338(3.42); 8.206(3.31); 8.203(3.13); 7.872(1.61); 7.868 (1.72); 7.852(1.87); 7.848(1.89); 7.67(1.34); 7.666(1.44); 7.65(2.26); 7.646(2.06); 7.622(2.9); 7.614(3.05); 7.592(2.14); 7.583(2.88); 7.572 (3.08); 7.561(3.29); 7.552(1.39); 7.298(1.65); 7.291(1.59); 7.276(1.43); 7.268(1.36); 3.859(16); 3.816(0.6); 2.506(24.8); 2.502(32.04); 2.498 (24.09); 2.075(0.95); 0.008(0.51); 0(11.45) |
| I-247 | 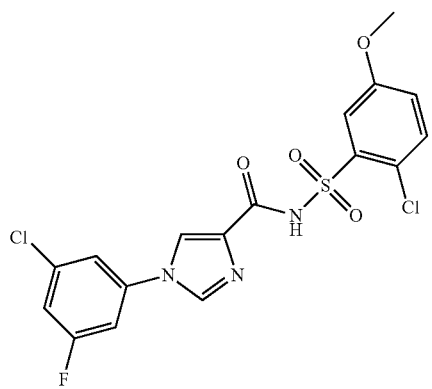 [SMILES: COc1ccc(Cl)c(S(=O)(=O)NC(=O)c2cn(-c3cc(F)cc(Cl)c3)cn2)c1] | Example I-247: 1H-NMR(400.0 MHz, d6-DMSO): δ = 8.662(2.69); 8.658(3.03); 8.594(2.9); 8.591(2.84); 7.83(2.2); 7.796 (0.79); 7.79(1.28); 7.785(0.73); 7.771(0.8); 7.766(1.3); 7.76(0.73); 7.619 (2.89); 7.611(3.22); 7.574(2.76); 7.567(0.98); 7.562(1.35); 7.557(0.98); 7.552(3.54); 7.546(1.04); 7.541(1.31); 7.536(0.76); 7.53(0.34); 7.294 (1.59); 7.286(1.56); 7.272(1.39); 7.264(1.35); 3.858(16); 3.816(1.3); 2.524 (0.52); 2.511(14.91); 2.507(31); 2.502(41.93); 2.498(32.02); 2.493 (16.99); 2.329(0.34); 2.075(1.78); 0.008(0.52); 0(18.02); −0.008(1.05) |

-continued $$\underset{M}{\overset{O}{\underset{H}{\parallel}}} \underset{\underset{O}{\overset{O}{\parallel}}}{\overset{O}{\underset{\parallel}{S}}} D \quad (I)$$

| Example No. | Structure | NMR peak list |
|---|---|---|
| I-248 | 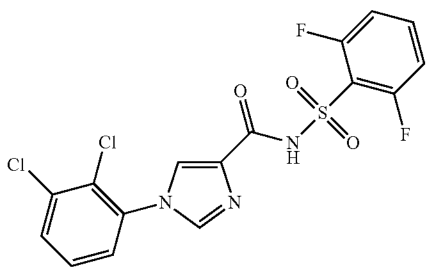 [SMILES: O=C(NS(=O)(=O)c1c(F)cccc1F)c1cn(-c2cccc(Cl)c2Cl)cn1] | Example I-248: 1H-NMR(400.0 MHz, d6-DMSO): δ = 8.357(0.33); 8.355(0.33); 8.33(16); 7.883(2.97); 7.88(3.27); 7.863 (3.44); 7.859(3.56); 7.782(0.52); 7.767(1.15); 7.761(1.16); 7.746(2.03); 7.731(1.2); 7.725(1.3); 7.709(0.58); 7.687(2.5); 7.684(2.79); 7.667(4.02); 7.664(3.76); 7.6(3.65); 7.58(5.35); 7.56(2.21); 7.321(3.35); 7.298(5.11); 7.276(2.88); 2.671(0.32); 2.506(41.42); 2.502(53.83); 2.498(41.02); 2.329(0.36); 2.075(2.1); 1.076(0.33); 0.008(0.96); 0(19.24) |
| I-249 | 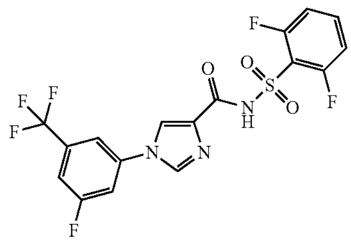 [SMILES: O=C(NS(=O)(=O)c1c(F)cccc1F)c1cn(-c2cc(F)cc(C(F)(F)F)c2)cn1] | Example I-249: 1H-NMR(400.0 MHz, d6-DMSO): δ = 8.781(3.46); 8.778(3.81); 8.747(5.03); 8.744(4.15); 8.147(1.54); 8.142 (0.97); 8.122(1.54); 8.117(0.99); 8.094(2.9); 7.985(0.58); 7.83(1.32); 7.809(1.33); 7.78(0.38); 7.765(0.86); 7.759(0.78); 7.749(0.58); 7.744 (1.49); 7.738(0.57); 7.728(0.84); 7.722(1.01); 7.707(0.46); 7.317(2.39); 7.295(3.6); 7.272(2.16); 6.871(0.51); 2.525(0.43); 2.52(0.77); 2.512(14.92); 2.507(31.15); 2.503(42.55); 2.498(31.65); 2.494(15.55); 2.184(0.84); 2.075(16); 1.369(0.37); 1.356(6.43); 0(5.57) |
| I-250 | 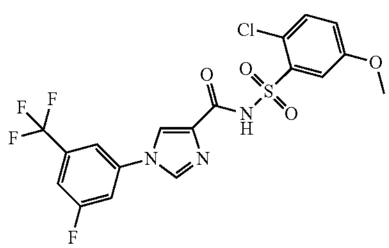 [SMILES: COc1ccc(Cl)c(S(=O)(=O)NC(=O)c2cn(-c3cc(F)cc(C(F)(F)F)c3)cn2)c1] | Example I-250: 1H-NMR(400.0 MHz, d6-DMSO): δ = 8.748(3.05); 8.745(3.16); 8.666(3.1); 8.662(2.88); 8.124(1.05); 8.12 (0.68); 8.1(1.07); 8.095(0.68); 8.06(2.08); 7.819(0.95); 7.798(0.96); 7.624 (2.93); 7.616(3.05); 7.577(2.71); 7.555(3.2); 7.297(1.68); 7.29(1.59); 7.275(1.43); 7.267(1.37); 3.861(16); 3.842(0.33); 3.817(1.36); 2.512 (11.87); 2.507(22.97); 2.503(30.26); 2.498(22.58); 2.494(11.28); 0.008 (0.32); 0(7.89) |
| I-251 | 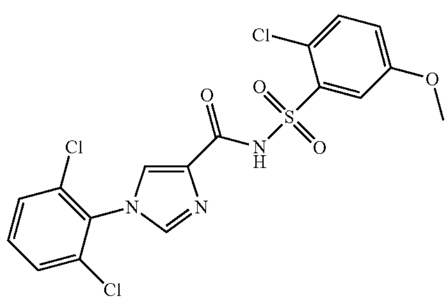 [SMILES: COc1ccc(Cl)c(S(=O)(=O)NC(=O)c2cn(-c3c(Cl)cccc3Cl)cn2)c1] | Example I-251: 1H-NMR(400.0 MHz, d6-DMSO): δ = 8.259(2.91); 8.256(3.08); 8.143(2.97); 8.14(2.88); 7.77(3.63); 7.75 (6.11); 7.647(2.13); 7.628(1.97); 7.624(3.93); 7.616(3.11); 7.606(1.42); 7.593(2.7); 7.571(3.12); 7.306(1.59); 7.299(1.53); 7.284(1.41); 7.277 (1.34); 3.858(16); 3.841(0.44); 3.816(0.6); 2.524(0.5); 2.511(15.73); 2.506 (32.58); 2.502(43.63); 2.497(32.68); 2.493(16.84); 2.328(0.33); 2.074 (3.12); 0.008(0.5); 0(16.14); −0.008(0.81) |
| I-252 | 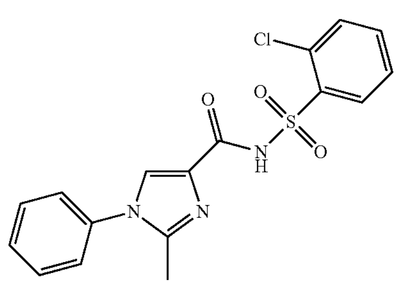 [SMILES: Cc1nc(C(=O)NS(=O)(=O)c2ccccc2Cl)cn1-c1ccccc1] | Example I-252: 1H-NMR(400.0 MHz, d6-DMSO): δ = 8.133(0.53); 8.113(1.82); 8.11(1.86); 8.093(2.01); 8.091(2.01); 8.073 (6.49); 8.044(0.35); 7.618(0.95); 7.613(0.99); 7.606(2.28); 7.597(3.25); 7.584(8.87); 7.578(11.58); 7.567(3.35); 7.559(5.98); 7.54(1.32); 7.532 (1.63); 7.527(1.01); 7.512(1.51); 7.496(0.9); 7.491(0.61); 7.476(0.36); 7.373(0.46); 2.671(0.34); 2.506(41.91); 2.502(53.13); 2.497(40.46); 2.415 (0.9); 2.374(16); 2.329(0.4); 2.074(1.06); 0(17.66) |

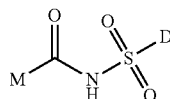
(I)
| Example No. | Structure | NMR peak list |
|---|---|---|
| I-253 | 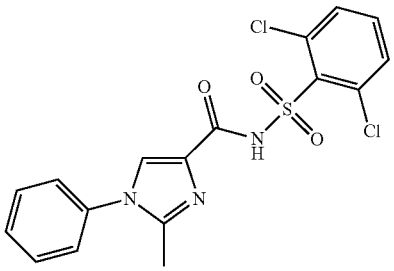 [SMILES: Cc1nc(C(=O)NS(=O)(=O)c2c(Cl)cccc2Cl)cn1-c1ccccc1] | Example I-253: 1H-NMR(400.0 MHz, d6-DMSO): δ = 8.044(4.97); 7.623(0.5); 7.616(1.39); 7.612(2.04); 7.606(11.77); 7.59 (0.6); 7.579(0.39); 7.497(2.25); 7.494(2.43); 7.476(4.6); 7.41(1.82); 7.393 (1.4); 7.388(1.2); 7.371(0.87); 2.524(0.6); 2.511(11.54); 2.506(23.06); 2.502(30.46); 2.497(22.38); 2.493(10.99); 2.415(11); 2.074(16) |
| I-254 | 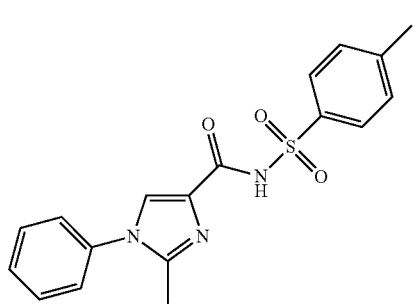 [SMILES: Cc1ccc(S(=O)(=O)NC(=O)c2cn(-c3ccccc3)c(C)n2)cc1] | Example I-254: 1H-NMR(400.0 MHz, d6-DMSO): δ = 8.047(5.81); 7.875(2.95); 7.871(1.07); 7.859(1.09); 7.854(3.32); 7.723 (0.84); 7.718(5.4); 7.714(1.93); 7.702(2.29); 7.697(6.57); 7.693(1.02); 7.594(0.42); 7.59(0.73); 7.585(0.39); 7.579(0.52); 7.573(2.06); 7.568 (1.29); 7.558(1.14); 7.555(2.77); 7.548(0.63); 7.545(0.67); 7.54(1.31); 7.536(1.16); 7.53(0.38); 7.523(1.44); 7.514(2.73); 7.51(2.92); 7.504(0.9); 7.498(0.93); 7.494(1.75); 7.49(1.25); 7.406(2.49); 7.386(2.42); 7.375 (4.22); 7.374(4.69); 7.354(4.15); 7.27(5.19); 3.767(0.59); 3.601(1.45); 3.562(1.32); 2.526(0.35); 2.521(0.56); 2.512(7.16); 2.508(14.5); 2.503 (19.26); 2.499(14.08); 2.494(6.86); 2.386(8.42); 2.372(16); 2.309(12.57); 2.184(0.37); 2.073(3.64); 1.357(2.63); 0(2) |
| I-255 | 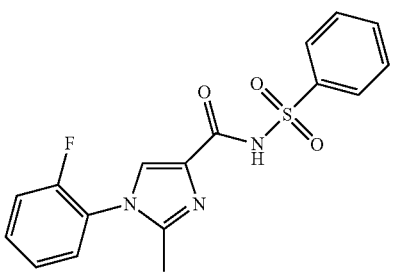 [SMILES: Cc1nc(C(=O)NS(=O)(=O)c2ccccc2)cn1-c1ccccc1F] | Example I-255: 1H-NMR(400.0 MHz, d6-DMSO): δ = 8.08(6.36); 8.079(6.28); 8.012(0.51); 8.004(4.2); 8.001(2.15); 7.991 (1.23); 7.986(5.53); 7.983(3.76); 7.843(2.56); 7.84(2.72); 7.836(1.09); 7.834(1.06); 7.829(0.99); 7.824(2.63); 7.819(3.06); 7.711(0.48); 7.708 (0.87); 7.705(0.57); 7.695(0.65); 7.689(2.64); 7.684(0.83); 7.674(1.33); 7.671(2.2); 7.668(1.19); 7.639(1.89); 7.632(4.49); 7.628(2.5); 7.622(2.38); 7.619(3.8); 7.616(5.2); 7.613(6.58); 7.605(2.66); 7.602(2.39); 7.6(2.64); 7.595(3.99); 7.592(4.21); 7.587(5.38); 7.582(2.44); 7.576(1); 7.571(1.44); 7.568(2.93); 7.56(0.54); 7.554(1.65); 7.552(2.07); 7.545(0.89); 7.533 (1.05); 7.529(2.02); 7.526(1.62); 7.507(0.93); 7.504(0.81); 7.424 (1.41); 7.422(1.37); 7.406(2.01); 7.403(2.33); 7.386(1.07); 7.383(1.06); 7.354(3.25); 6.872(0.71); 2.512(8.92); 2.507(19.73); 2.503(27.38); 2.498(20.8); 2.494(10.77); 2.22(16); 2.184(1.34); 2.075(4.15); 1.357(8.71); 0(3.34) |
| I-256 | 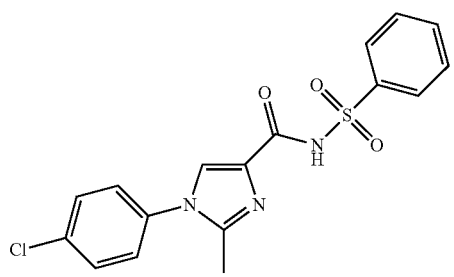 [SMILES: Cc1nc(C(=O)NS(=O)(=O)c2ccccc2)cn1-c1ccc(Cl)cc1] | Example I-256: 1H-NMR(400.0 MHz, d6-DMSO): δ = 8.062(7.52); 7.984(3.12); 7.971(0.96); 7.966(3.87); 7.963(2.68); 7.842 (1.05); 7.839(1.13); 7.828(0.41); 7.823(1.13); 7.818(1.25); 7.681(0.57); 7.668(0.51); 7.662(1.96); 7.652(3.88); 7.646(2.46); 7.635(2.14); 7.63 (6.65); 7.622(1.25); 7.61(2.93); 7.602(1.06); 7.59(4.3); 7.576(1.73); 7.57 (7.54); 7.553(1.54); 7.548(3.74); 7.541(0.45); 7.353(1.68); 6.871(0.67); 2.511(7.97); 2.507(17.48); 2.502(24.21); 2.498(18.6); 2.493(9.85); 2.363(0.46); 2.311(16); 2.287(0.59); 2.184(1.16); 2.075(2.47); 1.356 (7.89); 1.104(0.57); 1.089(0.59); 0(2.48) |

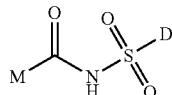
(I)
| Example No. | Structure | NMR peak list |
|---|---|---|
| I-257 | 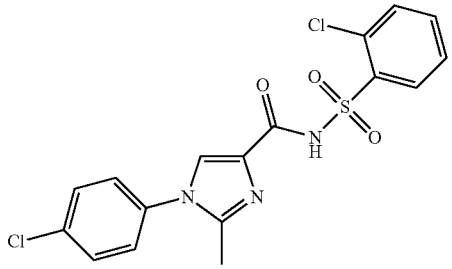 [SMILES: Cc1nc(C(=O)NS(=O)(=O)c2ccccc2Cl)cn1-c1ccc(Cl)cc1] | Example I-257: 1H-NMR(400.0 MHz, d6-DMSO): δ = 8.116(1.89); 8.113(1.95); 8.091(7.64); 7.68(3.31); 7.675(1.52); 7.658 (7.01); 7.621(6.92); 7.604(2.06); 7.599(3.53); 7.589(1.59); 7.586(1.46); 7.568(4.01); 7.564(3.49); 7.548(1.11); 7.541(1.59); 7.536(1.13); 7.521 (1.65); 7.505(0.76); 7.5(0.64); 2.506(24.75); 2.502(31.41); 2.498(23.97); 2.361(16); 2.329(0.32); 2.074(14.72); 0(7.05) |
| I-258 | 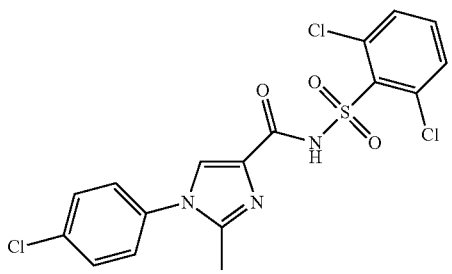 [SMILES: Cc1nc(C(=O)NS(=O)(=O)c2c(Cl)cccc2Cl)cn1-c1ccc(Cl)cc1] | Example I-258: 1H-NMR(400.0 MHz, d6-DMSO): δ = 8.067(6.57); 7.912(2.65); 7.702(2.81); 7.68(7.18); 7.654(7.09); 7.631 (3.03); 7.627(2.25); 7.626(2.41); 7.606(3.42); 7.536(1.21); 7.517(1.09); 7.514(1.04); 7.503(3.97); 7.483(7.05); 7.42(2.35); 7.402(1.9); 7.399(1.7); 7.38(1.07); 7.372(0.37); 2.502(44.72); 2.402(16); 2.328(0.33); 2.074 (1.47); 0(16.92) |
| I-259 | 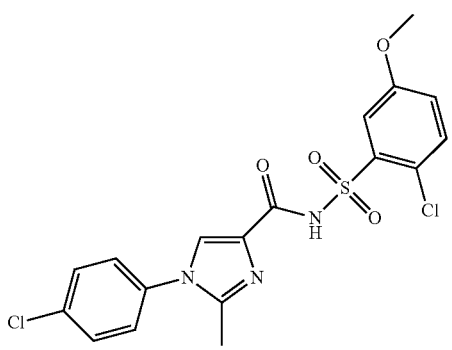 [SMILES: COc1ccc(Cl)c(S(=O)(=O)NC(=O)c2cn(-c3ccc(Cl)cc3)c(C)n2)c1] | Example I-259: 1H-NMR(400.0 MHz, d6-DMSO): δ = 8.084(5.92); 7.685(2.47); 7.68(0.98); 7.669(1.36); 7.663(5.72); 7.657 (0.78); 7.634(0.86); 7.628(5.44); 7.622(1.28); 7.611(1.11); 7.606(2.7); 7.599(0.36); 7.592(2.86); 7.584(2.9); 7.457(2.17); 7.435(2.52); 7.161 (1.26); 7.153(1.19); 7.139(1.08); 7.131(1.03); 3.825(16); 3.816(1.67); 2.524(0.6); 2.519(1.02); 2.511(13.69); 2.506(27.95); 2.502(37.32); 2.497 (27.34); 2.492(13.36); 2.369(12.44); 2.074(8.41); 0.008(0.77); 0(24.03); −0.009(0.91) |
| I-260 | 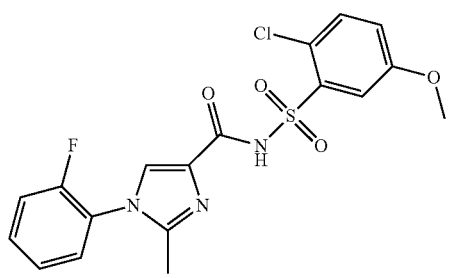 [SMILES: COc1ccc(Cl)c(S(=O)(=O)NC(=O)c2cn(-c3ccccc3F)c(C)n2)c1] | Example I-260: 1H-NMR(400.0 MHz, d6-DMSO): δ = 8.13(3.82); 7.695(0.87); 7.675(1.79); 7.656(1.53); 7.632(1.17); 7.618 (0.82); 7.598(2.84); 7.591(2.91); 7.578(1.31); 7.554(1.57); 7.531(0.88); 7.508(2.28); 7.487(2.63); 7.445(1.16); 7.425(1.83); 7.407(0.85); 7.217 (1.51); 7.21(1.47); 7.195(1.37); 7.188(1.27); 4.132(0.35); 4.017(0.68); 3.838(16); 3.816(2.17); 3.759(1.41); 3.654(0.96); 3.502(0.41); 2.671 (0.56); 2.502(74.17); 2.329(0.65); 2.278(11.34); 0(0.76) |

-continued (I)

| Example No. | Structure | NMR peak list |
|---|---|---|
| I-261 | 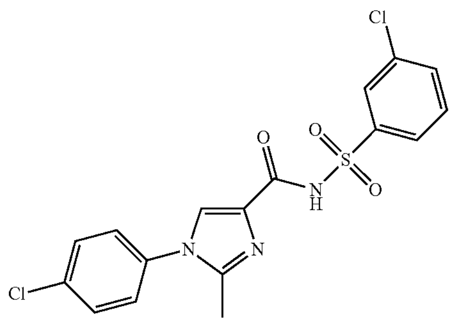 [SMILES: Cc1nc(C(=O)NS(=O)(=O)c2cccc(Cl)c2)cn1-c1ccc(Cl)cc1] | Example I-261: 1H-NMR(400.0 MHz, d6-DMSO): δ = 8.062(7.41); 7.936(2.9); 7.932(1.99); 7.866(1.67); 7.847(1.94); 7.679 (4.3); 7.657(8.01); 7.638(0.41); 7.608(6.43); 7.586(4.18); 7.57(2.81); 7.55(1.17); 7.515(0.38); 2.506(32.45); 2.502(47.08); 2.498(40); 2.358(16); 2.329(1.18); 2.192(0.38); 2.074(0.4); 0(3.27) |
| I-262 | 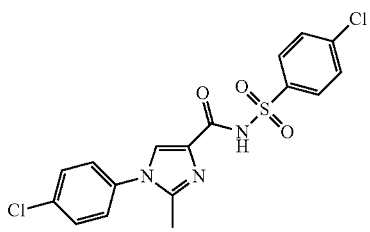 [SMILES: Cc1nc(C(=O)NS(=O)(=O)c2ccc(Cl)cc2)cn1-c1ccc(Cl)cc1] | Example I-262: 1H-NMR(400.0 MHz, d6-DMSO): δ = 8.052(7.21); 7.958(0.55); 7.951(4.62); 7.946(1.55); 7.935(1.61); 7.93 (5.44); 7.923(0.69); 7.836(0.36); 7.814(0.45); 7.674(0.41); 7.667(4.12); 7.662(1.51); 7.651(2.39); 7.646(11.32); 7.629(1.46); 7.624(4.11); 7.618 (0.62); 7.597(0.87); 7.591(6.42); 7.585(1.7); 7.574(1.31); 7.568(3.64); 7.561(0.39); 7.465(0.34); 2.671(0.33); 2.525(1.16); 2.511(17.18); 2.507 (33.61); 2.502(43.79); 2.498(31.25); 2.493(14.5); 2.362(0.34); 2.337 (16); 2.075(0.6); 0.008(0.55); 0(13.96); −0.008(0.35) |
| I-263 | 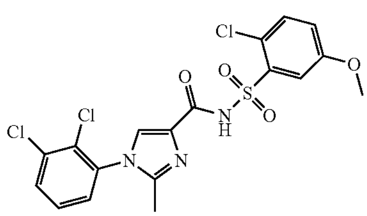 [SMILES: COc1ccc(Cl)c(S(=O)(=O)NC(=O)c2cn(-c3cccc(Cl)c3Cl)c(C)n2)c1] | Example I-263: 1H-NMR(400.0 MHz, d6-DMSO): δ = 8.108(4.26); 7.919(1.43); 7.916(1.58); 7.899(1.69); 7.895(1.73); 7.719 (1.23); 7.716(1.32); 7.699(1.9); 7.696(1.76); 7.62(1.88); 7.608(0.62); 7.599(5.31); 7.591(2.98); 7.58(1.25); 7.551(0.33); 7.529(0.42); 7.52(2.48); 7.498(2.89); 7.48(0.33); 7.472(0.33); 7.228(1.47); 7.22(1.42); 7.206 (1.28); 7.198(1.25); 3.839(16); 3.816(2.24); 3.61(5.48); 2.671(0.4); 2.511 (22.6); 2.507(43.89); 2.502(57.08); 2.498(42); 2.493(20.77); 2.329 (0.36); 2.208(12.56); 2.074(0.95) |
| I-264 | 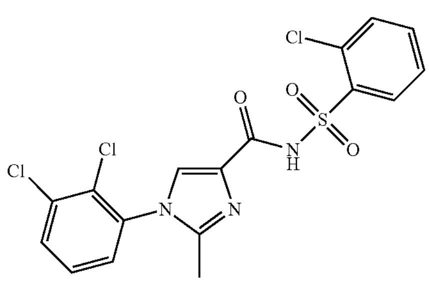 [SMILES: Cc1nc(C(=O)NS(=O)(=O)c2ccccc2Cl)cn1-c1cccc(Cl)c1Cl] | Example I-264: 1H-NMR(400.0 MHz, d6-DMSO): δ = 8.14(1.61); 8.136(1.67); 8.12(1.76); 8.116(1.82); 8.106(6.07); 7.916 (1.97); 7.912(2.12); 7.895(2.33); 7.891(2.31); 7.71(1.66); 7.706(1.77); 7.69(2.67); 7.687(2.37); 7.67(0.4); 7.666(0.41); 7.65(1.3); 7.646(1.21); 7.633(2.06); 7.629(2.44); 7.627(2.54); 7.622(2.98); 7.616(2.79); 7.607 (1.12); 7.602(0.77); 7.596(3.91); 7.586(1.41); 7.582(1.18); 7.576(1.82); 7.569(1.12); 7.567(1.47); 7.562(1.12); 7.55(0.84); 7.545(0.72); 3.722 (1.38); 3.714(1.39); 3.476(0.35); 2.676(0.35); 2.671(0.47); 2.666(0.33); 2.524(1.16); 2.52(1.99); 2.511(25.66); 2.506(51.58); 2.502(69.08); 2.497 (50.82); 2.493(24.13); 2.333(0.38); 2.328(0.5); 2.324(0.36); 2.197(16); 2.074(1.01); 0.008(0.66); 0(19.65); −0.008(0.63) |
| I-265 | 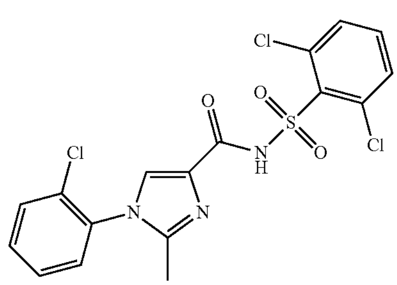 [SMILES: Cc1nc(C(=O)NS(=O)(=O)c2c(Cl)cccc2Cl)cn1-c1ccccc1Cl] | Example I-265: 1H-NMR(400.0 MHz, d6-DMSO): δ = 8.087(8.93); 7.806(1.72); 7.803(1.85); 7.786(2.23); 7.783(2.27); 7.752 (1.53); 7.748(1.65); 7.733(2.06); 7.729(2.11); 7.679(0.89); 7.675(0.98); 7.66(1.96); 7.656(1.66); 7.64(1.41); 7.636(1.16); 7.618(1.58); 7.614 (1.6); 7.606(0.51); 7.598(1.95); 7.595(1.92); 7.579(0.76); 7.576(0.7); 7.551(2.94); 7.548(3.38); 7.53(6.74); 7.472(2.5); 7.455(1.82); 7.45(1.55); 7.433(1.07); 7.372(0.6); 2.524(0.59); 2.519(1.05); 2.51(19.48); 2.506 (40.36); 2.501(54.17); 2.497(40.3); 2.492(20.32); 2.328(0.4); 2.255(16); 2.074(7.57); 0.008(0.61); 0(24.32); −0.008(1.11) |

-continued
(I)
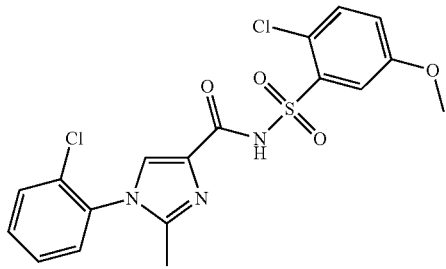 [SMILES: COc1ccc(Cl)c(S(=O)(=O)NC(=O)c2cn(-c3ccccc3Cl)c(C)n2)c1]
| Example No. | Structure | NMR peak list |
|---|---|---|
| I-266 | 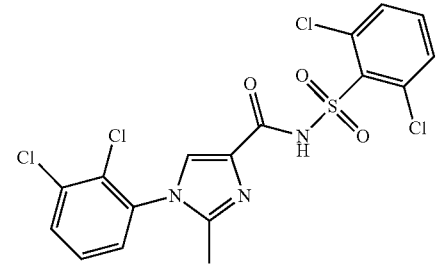 [SMILES: Cc1nc(C(=O)NS(=O)(=O)c2c(Cl)cccc2Cl)cn1-c1cccc(Cl)c1Cl] | Example I-266: 1H-NMR(400.0 MHz, d6-DMSO): δ = 8.084(4.36); 7.79(0.94); 7.787(1.03); 7.77(1.21); 7.767(1.26); 7.714 (0.82); 7.709(0.9); 7.694(1.15); 7.69(1.24); 7.659(0.54); 7.654(0.58); 7.64(1.23); 7.635(1.03); 7.62(1.24); 7.61(4.2); 7.601(3.48); 7.597(1.62); 7.593(2.53); 7.59(1.3); 7.582(1.21); 7.578(1.17); 7.563(0.46); 7.559(0.43); 7.552(2.72); 7.531(3.29); 7.525(1.12); 7.51(1.74); 7.488(2.06); 7.48 (2.67); 7.473(2.75); 7.307(0.46); 7.299(0.44); 7.285(0.41); 7.277(0.39); 7.215(0.99); 7.208(0.97); 7.194(2.42); 7.186(2.32); 7.172(1.42); 7.164 (1.36); 6.871(0.49); 5.757(8.06); 4.041(0.35); 4.023(1.12); 4.006(1.14); 3.988(0.4); 3.837(14.08); 3.816(16); 2.511(12.06); 2.506(26.18); 2.502 (35.89); 2.497(26.99); 2.493(13.9); 2.205(8.93); 2.183(0.94); 1.355(5.79); 1.101(1.31); 1.083(2.79); 1.066(1.42); 0(4.93) |
| I-267 | 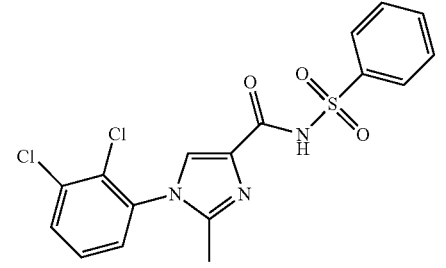 [SMILES: Cc1nc(C(=O)NS(=O)(=O)c2ccccc2)cn1-c1cccc(Cl)c1Cl] | Example I-267: 1H-NMR(400.0 MHz, d6-DMSO): δ = 8.111(7.67); 7.94(1.94); 7.937(2.07); 7.92(2.29); 7.916(2.33); 7.756 (1.72); 7.752(1.8); 7.736(2.48); 7.732(2.23); 7.67(0.53); 7.637(2.47); 7.617(3.89); 7.596(1.7); 7.564(2.9); 7.561(3.28); 7.543(7.07); 7.488(2.59); 7.47(1.85); 7.466(1.55); 7.448(1.08); 5.756(0.82); 4.04(0.33); 4.022 (0.33); 2.524(0.51); 2.519(0.95); 2.511(19.31); 2.506(40.1); 2.502(53.77); 2.497(39.58); 2.493(19.76); 2.328(0.39); 2.258(16); 1.102(0.45); 1.084(0.94); 1.066(0.45); 0.008(0.62); 0(24.31); −0.008(1.07) |
| I-268 | 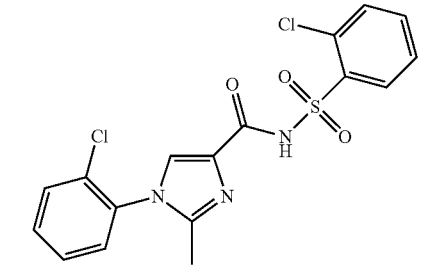 [SMILES: Cc1nc(C(=O)NS(=O)(=O)c2ccccc2Cl)cn1-c1ccccc1Cl] | Example I-268: 1H-NMR(400.0 MHz, d6-DMSO): δ = 8.06(7.51); 8.009(3.15); 7.991(3.88); 7.987(2.82); 7.909(1.83); 7.896 (2.25); 7.892(4.16); 7.888(2.02); 7.876(2.06); 7.872(2.12); 7.745(0.39); 7.726(1.21); 7.721(0.44); 7.711(0.99); 7.708(1.16); 7.7(0.48); 7.694 (1.91); 7.689(0.63); 7.676(1.55); 7.66(1.91); 7.656(2.04); 7.652(1.65); 7.636(5.73); 7.632(3.44); 7.617(4.22); 7.598(3.73); 7.587(0.59); 7.578 (3.44); 7.567(0.38); 7.558(1.37); 7.352(0.35); 5.757(4.91); 4.038(0.95); 4.021(3.01); 4.003(3.05); 3.985(1.01); 3.601(0.44); 2.525(0.41); 2.507 (26.28); 2.502(34.4); 2.498(25.27); 2.494(12.58); 2.184(0.36); 2.15(16); 2.135(0.38); 1.759(0.51); 1.356(2.36); 1.116(3.11); 1.099(6.46); 1.089 (0.65); 1.081(3.06); 0.008(0.54); 0(16.4); −0.008(0.62) |
| I-269 | 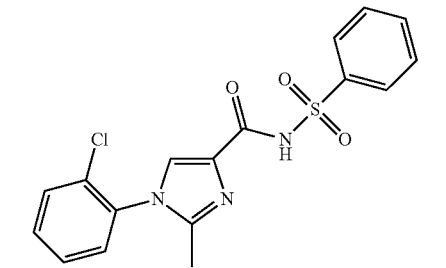 | Example I-269: 1H-NMR(400.0 MHz, d6-DMSO): δ = 8.137(1.91); 8.134(1.89); 8.118(2.02); 8.114(1.93); 8.079(6.44); 7.787 (1.84); 7.783(1.86); 7.767(2.32); 7.763(2.24); 7.703(1.58); 7.698(1.66); 7.684(2.17); 7.679(2.26); 7.654(1.36); 7.65(1.19); 7.635(3.38); 7.631 (2.22); 7.621(2.72); 7.616(4.86); 7.612(4.17); 7.597(2.63); 7.593(2.09); 7.578(3.24); 7.574(2.73); 7.558(2.2); 7.542(0.73); 7.537(0.6); 2.506 (27.94); 2.502(35.47); 2.497(26.17); 2.193(16); 2.075(0.36); 0.008(0.6); 0(12.83); −0.008(0.66) |
| I-270 | 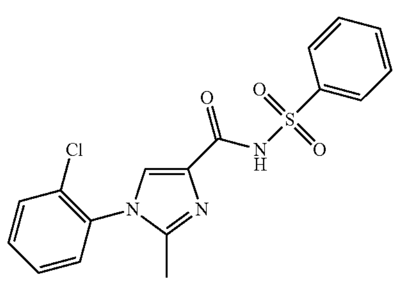 [SMILES: Cc1nc(C(=O)NS(=O)(=O)c2ccccc2)cn1-c1ccccc1Cl] | Example I-270: 1H-NMR(400.0 MHz, d6-DMSO): δ = 8.021(6.4); 8.007(3.92); 7.989(4.17); 7.764(1.71); 7.761(1.68); 7.744 (2.37); 7.707(0.72); 7.688(2.08); 7.67(1.75); 7.632(4.63); 7.612(7.17); 7.593(2.98); 7.576(1.85); 7.572(1.88); 7.556(1.59); 7.554(1.74); 7.538 (0.6); 7.535(0.56); 2.506(22.49); 2.502(27.94); 2.498(21.9); 2.141(16); 0(8.48) |

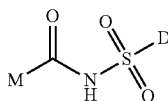
(I)
| Example No. | Structure | NMR peak list |
|---|---|---|
| I-271 | 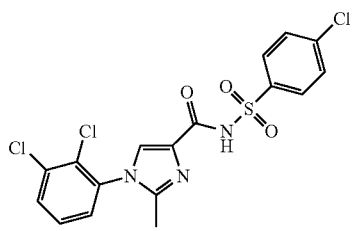 [SMILES: Cc1nc(C(=O)NS(=O)(=O)c2ccc(Cl)cc2)cn1-c1cccc(Cl)c1Cl] | Example I-271: 1H-NMR(400.0 MHz, d6-DMSO): δ = 8.078(5.04); 8.003(0.47); 7.996(3.34); 7.992(1.19); 7.98(1.28); 7.975 (3.87); 7.969(0.53); 7.914(2.08); 7.907(1.51); 7.903(1.51); 7.898(0.95); 7.893(2.72); 7.886(1.88); 7.883(1.59); 7.84(0.86); 7.824(0.35); 7.819 (1.12); 7.745(0.38); 7.738(2.61); 7.734(0.83); 7.722(0.74); 7.717(2.05); 7.71(0.4); 7.705(0.6); 7.699(3.68); 7.694(1.29); 7.682(1.2); 7.677(3.33); 7.669(2.24); 7.652(2.09); 7.648(2.35); 7.609(1.71); 7.588(2.35); 7.568 (0.93); 7.47(0.87); 4.055(0.7); 4.038(2.24); 4.02(2.26); 4.002(0.73); 3.602 (0.42); 2.513(6.15); 2.509(12.02); 2.504(15.61); 2.5(11.61); 2.176 (10.59); 2.077(16); 1.759(0.5); 1.357(1.89); 1.133(2.29); 1.124(0.39); 1.116(4.7); 1.109(0.49); 1.098(2.23); 1.058(0.4); 0.008(0.43); 0(11.67); −0.008(0.55) |
| I-272 | 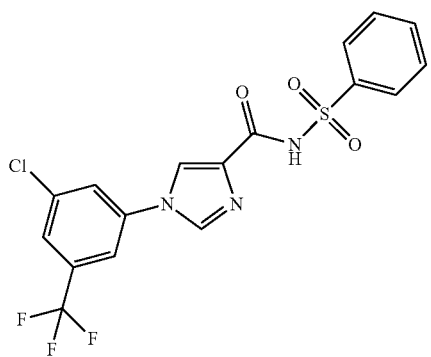 [SMILES: O=C(NS(=O)(=O)c1ccccc1)c1cn(-c2cc(Cl)cc(C(F)(F)F)c2)cn1] | Example I-272: 1H-NMR(400.0 MHz, d6-DMSO): δ = 8.718(4.01); 8.714(4.19); 8.633(4.13); 8.629(.3.81); 8.284(2.84); 8.28 (1.73); 8.172(2.57); 8.027(3.26); 8.014(1.06); 8.009(4.21); 8.006(2.97); 7.94(2.63); 7.911(1.28); 7.898(0.46); 7.893(1.77); 7.89(1.33); 7.734(0.8); 7.731(0.62); 7.728(0.99); 7.722(0.76); 7.716(2.18); 7.71(1.1); 7.706 (0.57); 7.701(1.1); 7.698(1.72); 7.694(0.93); 7.657(3.44); 7.641(4.02); 7.638(4.59); 7.623(1.4); 7.62(1.92); 4.04(0.69); 4.022(2.17); 4.005(2.19); 3.987(0.71); 2.526(0.44); 2.513(9.71); 2.509(18.95); 2.504(24.48); 2.5 (17.78); 2.495(8.69); 2.077(16); 1.357(1.48); 1.118(2.25); 1.106(0.98); 1.1(4.7); 1.09(0.84); 1.083(2.21); 0.008(0.62); 0(15.59); −0.008(0.57) |
| I-273 | 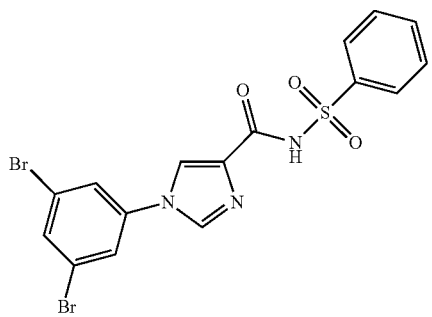 | Example I-273: 1H-NMR(400.0 MHz, d6-DMSO): δ = 8.62(6.78); 8.616(7.4); 8.544(7.49); 8.541(7.11); 8.138(0.48); 8.134 (0.5); 8.089(15.72); 8.085(16); 8.02(6.51); 8.002(7.91); 7.998(5.67); 7.908(6.92); 7.904(8.6); 7.9(4.26); 7.891(3.92); 7.887(2.96); 7.842(0.33); 7.839(0.36); 7.823(0.46); 7.818(0.43); 7.743(0.67); 7.74(0.5); 7.73(1.72); 7.725(2.33); 7.717(1.24); 7.711(4.29); 7.706(2.78); 7.696(2.04); 7.693 (3.17); 7.658(3.78); 7.653(6.12); 7.637(6.28); 7.633(8.37); 7.619(2.46); 7.615(3.34); 7.588(0.58); 7.568(0.35); 7.353(0.45); 5.758(4.43); 4.037 (1.44); 4.019(4.52); 4.001(4.57); 3.984(1.51); 3.618(0.82); 3.612(0.63); 3.608(0.82); 3.602(1.92); 3.596(0.84); 3.591(0.61); 3.585(0.86); 3.338 (0.37); 3.32(0.4); 2.672(0.42); 2.512(25.86); 2.508(49.57); 2.503(63.84); 2.499(46.21); 2.494(22.48); 2.334(0.34); 2.33(0.44); 2.325(0.32); 2.184(0.45); 1.776(0.78); 1.768(0.85); 1.76(2.2); 1.751(0.83); 1.743(0.73); 1.356(3.11); 1.22(0.51); 1.205(0.44); 1.201(0.36); 1.117(5.08); 1.104 (1.84); 1.099(10.45); 1.089(1.5); 1.081(4.96); 1.057(0.32); 0.008(1.56); 0(35.51); −0.008(1.25) |
| I-274 | 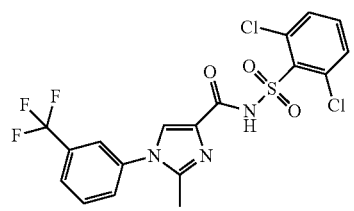 [SMILES: Cc1nc(C(=O)NS(=O)(=O)c2c(Cl)cccc2Cl)cn1-c1cccc(C(F)(F)F)c1] | Example I-274: 1H-NMR(400.0 MHz, d6-DMSO): δ = 8.159(4.37); 8.074(3.54); 7.976(1.89); 7.955(3.36); 7.93(2.59); 7.87 (1.9); 7.851(2.38); 7.831(0.98); 7.625(0.47); 7.606(0.62); 7.535(0.44); 7.514(4.02); 7.495(6.43); 7.432(2.1); 7.412(2.01); 7.392(1.06); 2.671 (0.78); 2.502(147.96); 2.412(16); 2.328(1.57); 2.255(0.47); 1.077(0.55); 1.059(0.33); 0(1.08) |

(I)
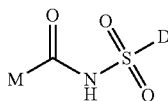
| Example No. | Structure | NMR peak list |
|---|---|---|
| I-275 | 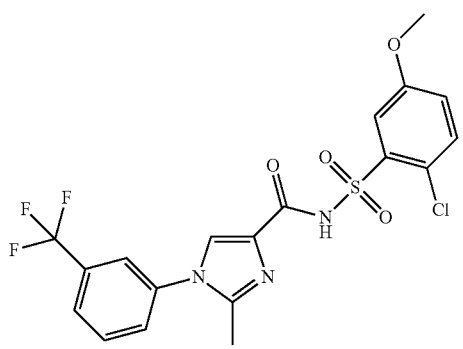 [SMILES: COc1ccc(Cl)c(S(=O)(=O)NC(=O)c2cn(-c3cccc(C(F)(F)F)c3)c(C)n2)c1] | Example I-275: 1H-NMR(400.0 MHz, d6-DMSO): δ = 8.186(5.05); 8.041(2.39); 7.954(1.2); 7.933(2.21); 7.908(1.62); 7.857 (1.39); 7.837(1.69); 7.817(0.62); 7.598(2.92); 7.591(3.03); 7.474(2.08); 7.452(2.4); 7.178(1.26); 7.171(1.26); 7.156(1.11); 7.149(1.07); 3.832 (16); 2.507(24.66); 2.502(31.26); 2.498(23.97); 2.384(12.65); 2.075(0.91) |
| I-276 | 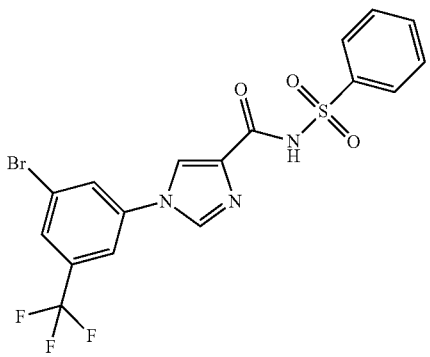 | Example I-276: 1H-NMR(400.0 MHz, d6-DMSO): δ = 8.713(10.18); 8.71(11.17); 8.624(10.88); 8.621(10.77); 8.566(0.35); 8.563(0.42); 8.489(0.36); 8.486(0.37); 8.392(8.34); 8.201(7.79); 8.038 (8.48); 8.025(10.07); 8.007(11.43); 8.004(9.01); 7.91(3.95); 7.892(4.86); 7.888(3.9); 7.824(0.33); 7.819(0.34); 7.745(0.86); 7.733(2.26); 7.726(3); 7.721(2.22); 7.715(6.08); 7.709(3.6); 7.696(4.61); 7.656(10.06); 7.64 (11.21); 7.636(13.38); 7.622(3.94); 7.618(5.46); 7.594(0.37); 7.588 (0.52); 7.568(0.32); 7.352(0.36); 6.872(0.37); 5.758(8.47); 4.039(1.82); 4.021(5.64); 4.003(5.72); 3.986(1.92); 3.858(0.39); 3.618(0.65); 3.608 (0.72); 3.602(1.59); 3.585(0.74); 3.368(0.35); 3.342(0.5); 3.324(0.56); 3.307(0.33); 3.227(0.35); 3.211(0.35); 2.677(0.4); 2.672(0.56); 2.668 (0.43); 2.508(67.25); 2.504(88.21); 2.499(67.62); 2.463(0.48); 2.445 (0.43); 2.418(0.37); 2.335(0.47); 2.33(0.62); 2.326(0.49); 2.184(0.63); 2.087(16); 1.776(0.64); 1.767(1.24); 1.76(1.8); 1.751(0.76); 1.743(0.65); 1.733(0.6); 1.648(0.44); 1.559(0.34); 1.546(0.34); 1.541(0.35); 1.356 (4.21); 1.232(0.39); 1.221(0.4); 1.196(0.53); 1.178(0.84); 1.159(0.46); 1.117(6.09); 1.105(2.21); 1.1(12.56); 1.09(1.75); 1.082(6.01); 1.057 (0.38); 0.008(2.63); 0(53.51) |
| I-277 | 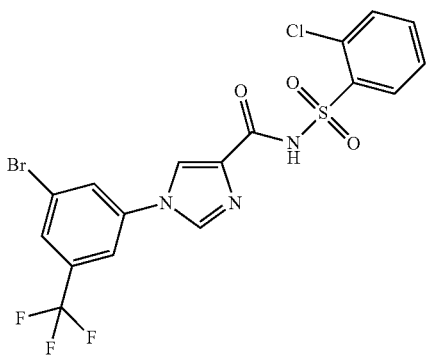 [SMILES: O=C(NS(=O)(=O)c1ccccc1Cl)c1cn(-c2cc(Cl)cc(C(F)(F)F)c2)cn1] | Example I-277: 1H-NMR(400.0 MHz, d6-DMSO): δ = 8.754(16); 8.651(15.83); 8.384(12.39); 8.19(12.15); 8.18(8.51); 8.176 (8.16); 8.159(7.97); 8.156(7.9); 8.093(0.33); 8.055(12.51); 7.726(1.89); 7.724(2.07); 7.706(6.37); 7.704(6.48); 7.689(7.07); 7.687(7.11); 7.669 (12.04); 7.652(5.26); 7.637(5.56); 7.635(5.05); 7.619(7.7); 7.617(7.7); 7.615(6.97); 7.6(3.65); 7.598(3.48); 4.012(0.64); 3.995(0.65); 3.975 (0.33); 2.671(1.5); 2.505(191.62); 2.502(232.82); 2.498(179.36); 2.328 (1.72); 2.075(0.52); 1.091(0.52); 1.073(1.04); 1.055(0.53); 0.145(0.43); 0(88.55); −0.002(77.76); −0.008(6.15); −0.151(0.45) |

-continued
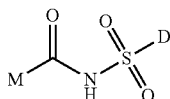
(I)
| Example No. | Structure | NMR peak list |
|---|---|---|
| I-278 | 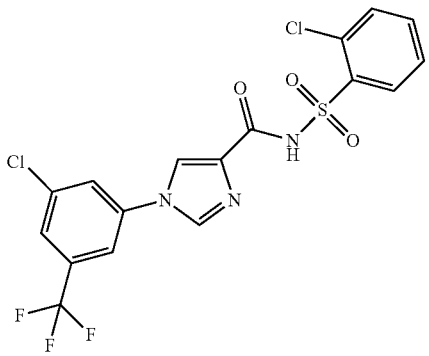 | Example I-278: 1H-NMR(400.0 MHz, d6-DMSO): δ = 8.759(14.22); 8.756(14.5); 8.659(14.91); 8.656(13.64); 8.316(0.42); 8.282(5.78); 8.277(10.46); 8.273(5.89); 8.181(6.87); 8.177(7.25); 8.161 (16); 8.157(13.16); 7.958(9.04); 7.729(2.09); 7.725(2.2); 7.72(0.51); 7.711(3.67); 7.709(5.24); 7.705(5.46); 7.701(1.09); 7.691(7.43); 7.687 (7.09); 7.674(8.54); 7.67(11.43); 7.654(4.76); 7.65(3.22); 7.639(5.61); 7.635(4.46); 7.621(4.86); 7.62(6.08); 7.618(4.88); 7.616(4.87); 7.608 (0.53); 7.602(3.68); 7.598(3.17); 5.757(5); 4.013(0.68); 3.995(0.69); 2.68(0.55); 2.676(1.08); 2.671(1.46); 2.667(1.07); 2.662(0.54); 2.541 (0.65); 2.525(4.35); 2.52(6.63); 2.511(75.66); 2.507(152.9); 2.502 (201.28); 2.498(142.4); 2.493(66.07); 2.338(0.44); 2.334(0.97); 2.329(1.34); 2.324(0.96); 2.32(0.42); 1.091(0.61); 1.073(1.31); 1.055(0.6); 0.146(0.49); 0.008(4.19); 0(130.47); −0.008(4.11); −0.15(0.51) |
| I-279 | 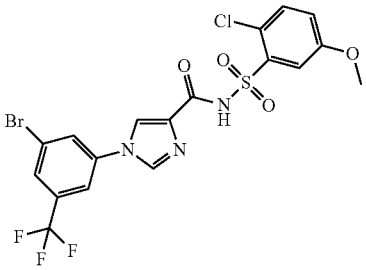 [SMILES: COc1ccc(Cl)c(S(=O)(=O)NC(=O)c2cn(-c3cc(Br)cc(C(F)(F)F)c3)cn2)c1] | Example I-279: 1H-NMR(400.0 MHz, d6-DMSO): δ = 8.761(3.3); 8.759(3.41); 8.665(3.36); 8.663(3.23); 8.385(2.68); 8.192 (2.53); 8.06(2.67); 7.624(2.86); 7.616(2.99); 7.577(2.68); 7.555(3.16); 7.297(1.65); 7.289(1.6); 7.275(1.43); 7.267(1.36); 5.757(0.4); 3.861(16); 3.84(0.56); 3.817(0.43); 2.507(21.59); 2.503(27.5); 2.499(20.76); 0(9.25) |
| I-280 | 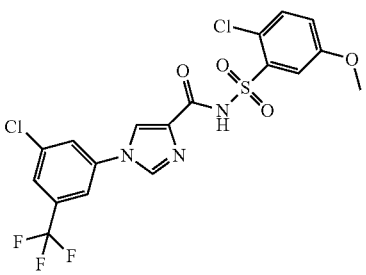 [SMILES: COc1ccc(Cl)c(S(=O)(=O)NC(=O)c2cn(-c3cc(Cl)cc(C(F)(F)F)c3)cn2)c1] | Example I-280: 1H-NMR(400.0 MHz, d6-DMSO): δ = 8.76(2.81); 8.758(2.95); 8.668(2.95); 8.665(2.81); 8.277(2.35); 8.272 (1.43); 8.16(2.1); 7.959(2.14); 7.623(2.89); 7.616(3.01); 7.576(2.6); 7.554 (3.06); 7.296(1.56); 7.288(1.49); 7.274(1.35); 7.266(1.3); 5.756(0.53); 3.86(16); 3.839(0.38); 2.525(0.65); 2.511(14.73); 2.507(29.55); 2.502 (39.03); 2.498(28.67); 2.494(14.21); 0.008(0.58); 0(16.38); −0.008(0.63) |
| I-281 | 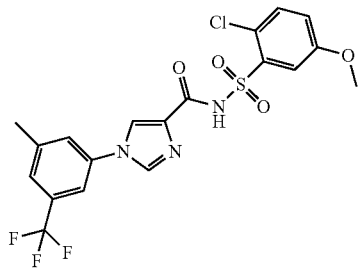 [SMILES: COc1ccc(Cl)c(S(=O)(=O)NC(=O)c2cn(-c3cc(C)cc(C(F)(F)F)c3)cn2)c1] | Example I-281: 1H-NMR(400.0 MHz, d6-DMSO): δ = 8.702(4.68); 8.625(4.37); 7.934(4.22); 7.916(4.21); 7.653(4.16); 7.625 (3.81); 7.618(3.62); 7.573(2.71); 7.551(3.11); 7.291(2.17); 7.284(2.06); 7.269(1.89); 7.262(1.64); 5.759(0.33); 3.86(16); 3.817(0.85); 2.503 (38.31); 2.474(15.6); 2.33(0.36); 1.085(0.35); 0(13.63) |

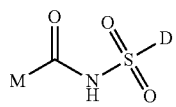
(I)
| Example No. | Structure | NMR peak list |
|---|---|---|
| I-282 | 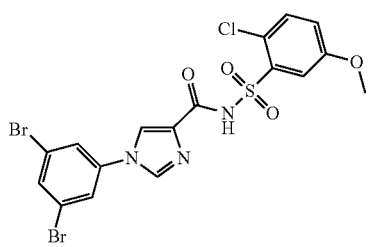 | Example I-282: 1H-NMR(400.0 MHz, d6-DMSO): δ = 8.679(3.92); 8.591(3.85); 8.082(7.56); 8.079(6.98); 7.925(3.33); 7.619 (2.94); 7.612(3.21); 7.576(2.65); 7.554(3.18); 7.295(1.67); 7.288(1.68); 7.273(1.47); 7.266(1.42); 3.86(16); 3.84(0.76); 3.817(0.55); 2.506 (23.78); 2.503(27.74); 0(17.81) |
| I-283 | 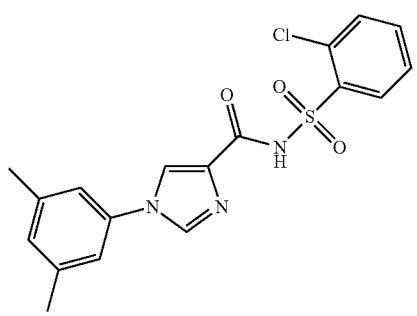 [SMILES: Cc1cc(C)cc(-n2cnc(C(=O)NS(=O)(=O)c3ccccc3Cl)c2)c1] | Example I-283: 1H-NMR(400.0 MHz, d6-DMSO): δ = 8.552(2.12); 8.549(2.19); 8.484(1.82); 8.173(1.1); 8.169(1.14); 8.153 (1.2); 8.149(1.18); 7.693(0.87); 7.689(0.77); 7.675(1.16); 7.671(1.11); 7.661(1.43); 7.657(1.91); 7.642(0.74); 7.637(0.51); 7.626(0.88); 7.622 (0.7); 7.606(1.05); 7.589(0.56); 7.585(0.48); 7.342(3.8); 7.084(1.66); 2.511(7.8); 2.507(15.88); 2.502(21.01); 2.498(15.35); 2.493(7.58); 2.339 (16); 2.075(0.95); 0.008(0.42); 0(14.06); −0.009(0.61) |
| I-284 | 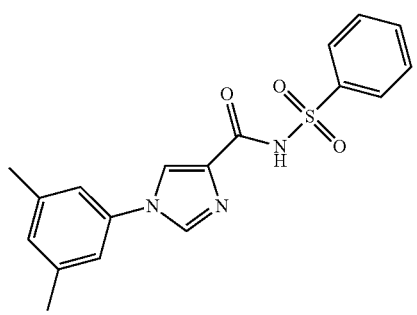 [SMILES: Cc1cc(C)cc(-n2cnc(C(=O)NS(=O)(=O)c3ccccc3)c2)c1] | Example I-284: 1H-NMR(400.0 MHz, d6-DMSO): δ = 8.473(2.64); 8.47(2.79); 8.409(2.38); 8.407(2.24); 8.024(2.29); 8.006 (2.81); 8.002(1.97); 7.727(0.44); 7.715(0.38); 7.709(1.36); 7.704(0.46); 7.694(0.74); 7.69(1.12); 7.688(0.64); 7.651(1.97); 7.635(1.63); 7.632 (2.7); 7.618(0.52); 7.614(1.05); 7.335(4.24); 7.065(1.88); 2.512(4.43); 2.508(8.15); 2.503(10.26); 2.499(7.5); 2.495(3.74); 2.328(16); 0(7.18) |
| I-285 | 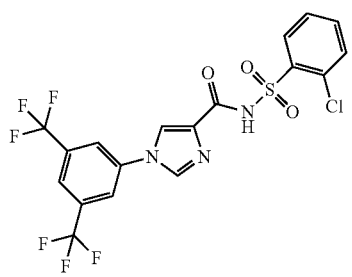 [SMILES: O=C(NS(=O)(=O)c1ccccc1Cl)c1cn(-c2cc(C(F)(F)F)cc(C(F)(F)F)c2)cn1] | Example I-285: 1H-NMR(400.0 MHz, d6-DMSO): δ = 8.822(4.6); 8.722(6.89); 8.506(16); 8.316(0.57); 8.184(7.32); 8.156 (4.21); 7.716(1.06); 7.697(2.95); 7.679(3.44); 7.662(5.49); 7.644(2.47); 7.631(2.96); 7.611(3.82); 7.594(1.79); 3.816(0.33); 3.602(0.95); 3.506 (1.84); 3.368(1.65); 3.21(1.01); 2.977(0.35); 2.671(3.01); 2.502(430.59); 2.328(3.12); 2.3(1.18); 1.76(0.34); 1.234(2.24); 0.852(0.35); 0(41.45) |

-continued
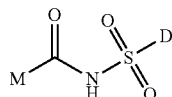
(I)
| Example No. | Structure | NMR peak list |
|---|---|---|
| I-286 | 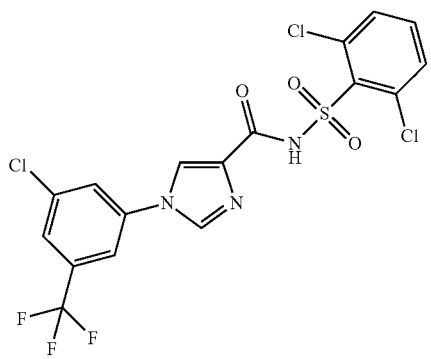 [SMILES: O=C(NS(=O)(=O)c1c(Cl)cccc1Cl)c1cn(-c2cc(Cl)cc(C(F)(F)F)c2)cn1] | Example I-286: 1H-NMR(400.0 MHz, d6-DMSO): δ = 8.756(11.23); 8.746(9.89); 8.289(7.56); 8.178(7.35); 7.969(7.37); 7.657(7); 7.639(16); 7.598(5.83); 7.581(4.02); 7.575(3.34); 7.558(2.05); 2.672(0.49); 2.503(102.61); 2.377(0.33); 2.33(0.88); 2.075(1.62); 0(9.75) |
| I-287 | 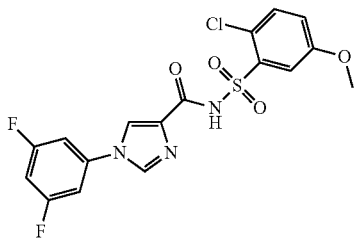 [SMILES: COc1ccc(Cl)c(S(=O)(=O)NC(=O)c2cn(-c3cc(F)cc(F)c3)cn2)c1] | Example I-287: 1H-NMR(400.0 MHz, d6-DMSO): δ = 8.647(3.72); 8.645(3.68); 8.59(3.8); 8.587(3.43); 7.674(2.54); 7.658 (2.53); 7.619(2.93); 7.612(3.19); 7.576(2.61); 7.554(3.11); 7.395(0.71); 7.372(1.38); 7.354(0.51); 7.348(0.72); 7.295(1.64); 7.287(1.69); 7.273 (1.43); 7.265(1.45); 5.758(0.49); 3.858(16); 3.84(0.51); 3.817(0.58); 2.506 (25.6); 2.503(31.51); 2.499(24.85); 0(1.72) |
| I-288 | 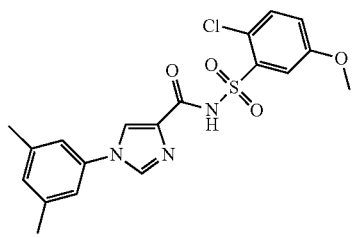 | Example I-288: 1H-NMR(400.0 MHz, d6-DMSO): δ = 8.557(2.42); 8.554(2.74); 8.511(2.02); 7.622(2.13); 7.614(2.22); 7.563 (2.03); 7.541(2.38); 7.344(4.18); 7.28(1.23); 7.272(1.19); 7.258(1.07); 7.25(1.03); 7.087(1.85); 3.857(11.87); 2.508(9.77); 2.503(12.71); 2.499 (9.49); 2.34(16); 0(1.03) |
| I-289 | 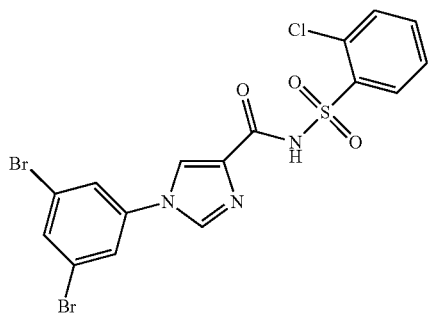 [SMILES: O=C(NS(=O)(=O)c1ccccc1Cl)c1cn(-c2cc(Br)cc(Br)c2)cn1] | Example I-289: 1H-NMR(400.0 MHz, d6-DMSO): δ = 8.678(7.11); 8.676(8.11); 8.582(7.05); 8.579(7.47); 8.178(3.29); 8.174 (3.74); 8.158(3.64); 8.155(3.94); 8.084(14.23); 8.08(16); 7.926(3.99); 7.922(6.88); 7.919(4.47); 7.728(0.93); 7.724(1.09); 7.708(3.14); 7.704 (3.15); 7.69(3.47); 7.687(3.64); 7.674(4.51); 7.67(6.14); 7.654(2.52); 7.65(2.07); 7.638(2.93); 7.634(2.77); 7.618(3.63); 7.601(1.94); 7.597 (1.78); 5.759(3.87); 2.508(33.23); 2.504(43.05); 2.5(33.22); 1.074(0.57); 1.066(0.49); 1.05(0.47); 0(3.25) |

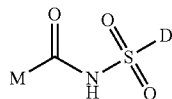
(I)
| Example No. | Structure | NMR peak list |
|---|---|---|
| I-290 | 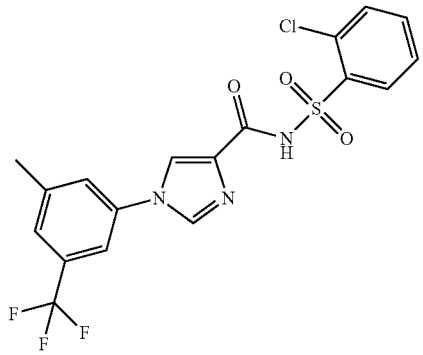 [SMILES: Cc1cc(-n2cnc(C(=O)NS(=O)(=O)c3ccccc3Cl)c2)cc(C(F)(F)F)c1] | Example I-290: 1H-NMR(400.0 MHz, d6-DMSO): δ = 8.699(4.91); 8.61(4.45); 8.181(2.14); 8.178(2.28); 8.162(2.38); 8.158 (2.42); 7.934(3.5); 7.915(3.63); 7.725(0.61); 7.721(0.67); 7.705(1.95); 7.702(1.86); 7.688(2.24); 7.684(2.28); 7.672(3.09); 7.668(3.86); 7.651 (4.95); 7.637(1.97); 7.633(1.65); 7.617(2.3); 7.6(1.11); 7.596(1.03); 5.759 (0.52); 2.507(27.11); 2.503(35); 2.499(27.67); 2.472(16); 0(2.19) |
| I-291 | 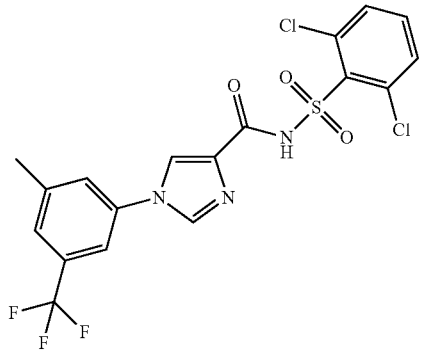 [SMILES: Cc1cc(-n2cnc(C(=O)NS(=O)(=O)c3c(Cl)cccc3Cl)c2)cc(C(F)(F)F)c1] | Example I-291: 1H-NMR(400.0 MHz, d6-DMSO): δ = 8.738(3.66); 8.694(4.68); 8.692(4.56); 7.957(3.48); 7.933(3.57); 7.664 (3.92); 7.65(3.43); 7.647(3.9); 7.628(8.05); 7.607(0.56); 7.585(3.01); 7.568(2.14); 7.562(1.82); 7.545(1.14); 2.672(0.37); 2.506(43.72); 2.502 (53.9); 2.474(16); 2.329(0.4); 2.076(1.23); 0(16.33) |
| I-292 | 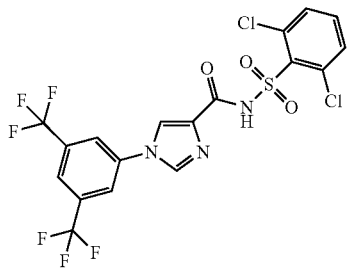 [SMILES: O=C(NS(=O)(=O)c1c(Cl)cccc1Cl)c1cn(-c2cc(C(F)(F)F)cc(C(F)(F)F)c2)cn1] | Example I-292: 1H-NMR(400.0 MHz, d6-DMSO): δ = 8.845(8.4); 8.843(9.02); 8.823(8.04); 8.524(14.94); 8.202(6.49); 7.664 (6.04); 7.66(6.86); 7.642(16); 7.601(6.25); 7.584(4.24); 7.578(3.29); 7.561(2.19); 2.672(0.64); 2.668(0.48); 2.507(80.93); 2.503(100.42); 2.499(75.03); 2.334(0.51); 2.33(0.65); 2.326(0.5); 2.075(4.76); 0(1.28) |
| I-293 | 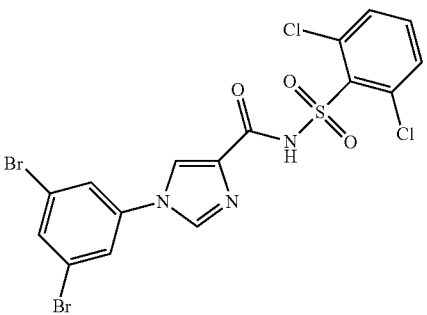 | Example I-293: 1H-NMR(400.0 MHz, d6-DMSO): δ = 8.671(16); 8.096(12.44); 8.092(12.79); 7.937(3.71); 7.934(5.87); 7.93 (3.38); 7.658(4.04); 7.654(4.86); 7.636(10.78); 7.606(0.41); 7.595(4.17); 7.578(2.8); 7.572(2.23); 7.556(1.43); 2.672(0.38); 2.507(50.21); 2.503 (62.81); 2.498(46.96); 2.334(0.35); 2.33(0.42); 2.325(0.33); 2.076 (7.97); 0(1.46) |

-continued
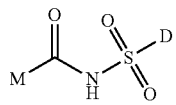
(I)
| Example No. | Structure | NMR peak list |
|---|---|---|
| I-294 | 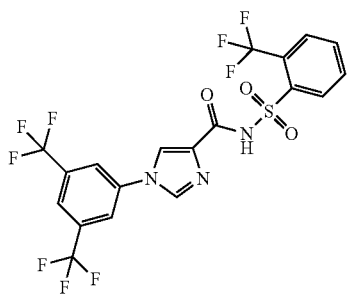 [SMILES: O=C(NS(=O)(=O)c1ccccc1C(F)(F)F)c1cn(-c2cc(C(F)(F)F)cc(C(F)(F)F)c2)cn1] | Example I-294: 1H-NMR(400.0 MHz, d6-DMSO): δ = 8.841(6.23); 8.782(5.88); 8.519(10.84); 8.374(2.82); 8.354(3.04); 8.195(4.72); 8.015(2.32); 7.995(3.41); 7.978(1.23); 7.961(2.82); 7.943 (2.19); 7.926(2.43); 7.908(2.51); 7.89(0.89); 2.671(0.34); 2.502(83.24); 2.329(0.76); 2.075(16); 0(1.48) |
| I-295 | 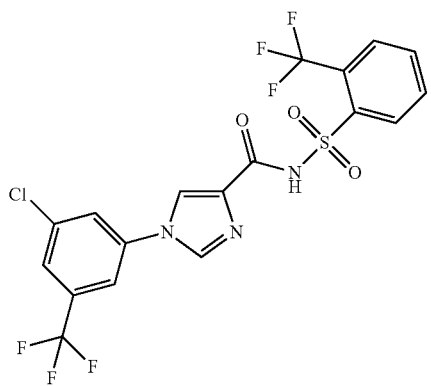 [SMILES: O=C(NS(=O)(=O)c1ccccc1C(F)(F)F)c1cn(-c2cc(Cl)cc(C(F)(F)F)c2)cn1] | Example I-295: 1H-NMR(400.0 MHz, d6-DMSO): δ = 8.754(15.24); 8.752(15.35); 8.704(16); 8.368(7.5); 8.349(8.2); 8.317 (0.73); 8.287(13.48); 8.173(12.57); 8.011(6.06); 7.994(8.73); 7.992(8.83); 7.973(4.01); 7.959(15.95); 7.939(6.37); 7.923(6.2); 7.904(6.4); 7.886 (2.09); 7.807(0.43); 7.722(1.32); 4.373(0.33); 4.342(0.35); 4.327(0.36); 4.307(0.37); 4.288(0.4); 4.268(0.39); 4.256(0.4); 4.248(0.4); 4.226(0.41); 4.22(0.41); 4.112(0.49); 4.083(0.51); 4.074(0.54); 4.045(0.55); 4.027 (0.62); 4.01(0.63); 3.99(0.61); 3.94(0.66); 3.852(0.71); 3.774(0.74); 3.762 (0.74); 3.737(0.75); 3.718(0.76); 3.673(0.78); 3.624(0.74); 3.615(0.74); 3.584(0.73); 3.575(0.74); 3.568(0.72); 3.506(0.78); 3.444(0.65); 3.423 (0.62); 3.409(0.6); 3.394(0.6); 3.387(0.59); 3.38(0.62); 3.368(0.63); 3.322(0.6); 3.284(0.51); 3.226(0.49); 3.21(0.5); 3.195(0.43); 3.129(0.38); 3.089(0.34); 3.051(0.32); 2.676(2.29); 2.671(2.94); 2.667(2.21); 2.649 (0.33); 2.507(329.4); 2.502(412.18); 2.498(301.44); 2.333(2.07); 2.329 (2.7); 2.325(2); 2.184(0.33); 2.075(1.18); 1.356(2.21); 1.234(0.52); 0.146(1.01); 0.008(11.85); 0(214.47); −0.008(10.2); −0.15(1.03) |
| I-296 | 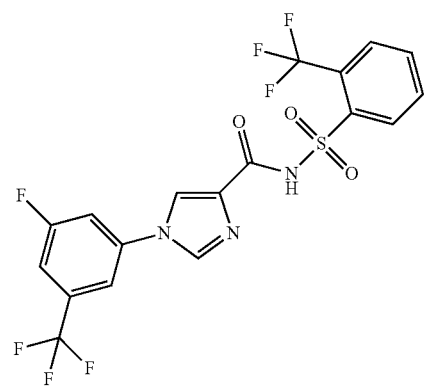 [SMILES: O=C(NS(=O)(=O)c1ccccc1C(F)(F)F)c1cn(-c2cc(F)cc(C(F)(F)F)c2)cn1] | Example I-296: 1H-NMR(400.0 MHz, d6-DMSO): δ = 8.749(14.87); 8.746(16); 8.724(0.53); 8.707(14.81); 8.704(13.08); 8.371(6.45); 8.352(6.96); 8.135(5.27); 8.13(3.47); 8.111(5.32); 8.106 (3.45); 8.076(10.35); 8.017(5); 8.015(5.11); 7.999(7.37); 7.995(7.64); 7.981(2.43); 7.978(2.64); 7.962(6.71); 7.959(5.74); 7.943(5.38); 7.939 (4.29); 7.927(5.4); 7.909(5.58); 7.89(1.89); 7.822(4.79); 7.801(4.85); 7.726(0.46); 5.759(2.29); 2.678(0.4); 2.673(0.6); 2.669(0.41); 2.526 (2.06); 2.513(40.5); 2.509(78.28); 2.504(101.16); 2.5(74.15); 2.495 (36.95); 2.335(0.57); 2.331(0.74); 2.326(0.57); 2.077(0.51); 1.366 (0.37); 0(1.73) |

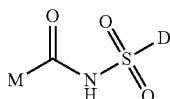
(I)
| Example No. | Structure | NMR peak list |
|---|---|---|
| I-297 | 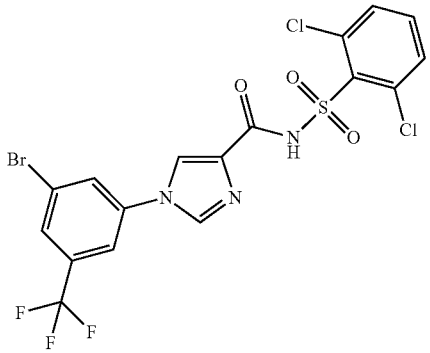 | Example I-297: 1H-NMR(400.0 MHz, d6-DMSO): δ = 8.756(7.34); 8.745(6.08); 8.397(4.83); 8.208(4.55); 8.068(4.83); 7.661 (4.2); 7.657(5.05); 7.639(11.65); 7.598(4.55); 7.581(3); 7.575(2.37); 7.558(1.57); 2.672(0.39); 2.507(46.02); 2.503(59.01); 2.499(44.73); 2.33(0.37); 2.075(16); 0(1.58) |
| I-298 | 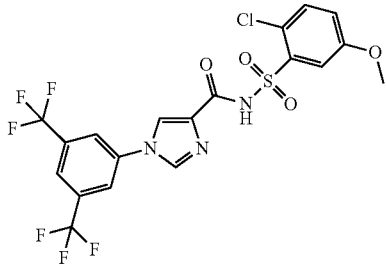 [SMILES: COc1ccc(Cl)c(S(=O)(=O)NC(=O)c2cn(-c3cc(C(F)(F)F)cc(C(F)(F)F)c3)cn2)c1] | Example I-298: 1H-NMR(400.0 MHz, d6-DMSO): δ = 8.847(3.17); 8.844(3.26); 8.745(3.17); 8.742(3.02); 8.508(5.44); 8.193 (2.38); 7.629(2.9); 7.621(3.05); 7.609(0.58); 7.58(2.77); 7.558(3.25); 7.53(0.4); 7.474(0.33); 7.3(1.68); 7.292(1.61); 7.278(1.46); 7.27(1.39); 3.863(16); 3.84(0.59); 3.817(1.91); 2.507(26.65); 2.503(34.55); 2.498 (26.04); 2.075(0.37); 1.356(0.42); 0(1.57) |
| I-299 | 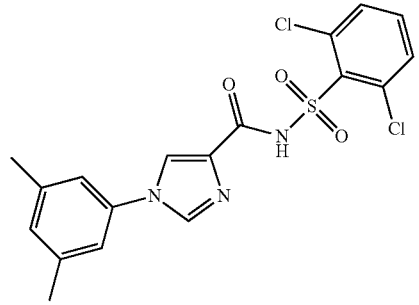 [SMILES: Cc1cc(C)cc(-n2cnc(C(=O)NS(=O)(=O)c3c(Cl)cccc3Cl)c2)c1] | Example I-299: 1H-NMR(400.0 MHz, d6-DMSO): δ = 8.673(1.29); 8.539(2.4); 8.536(2.28); 7.631(1.69); 7.627(2.08); 7.609 (4.37); 7.563(1.7); 7.546(1.13); 7.54(0.92); 7.523(0.63); 7.371(4); 7.103 (1.8); 5.757(0.59); 2.507(20.82); 2.502(26.68); 2.498(19.76); 2.364 (0.46); 2.342(16); 2.075(0.73); 0(0.79) |
| I-300 | 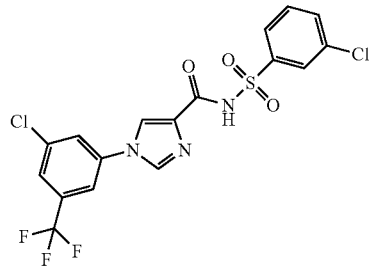 [SMILES: O=C(NS(=O)(=O)c1cccc(Cl)c1)c1cn(-c2cc(Cl)cc(C(F)(F)F)c2)cn1] | Example I-300: 1H-NMR(400.0 MHz, d6-DMSO): δ = 8.74(14.49); 8.737(14.37); 8.686(14.45); 8.683(12.78); 8.316(0.43); 8.297(11.18); 8.189(10.54); 8.014(11.23); 8.009(7.44); 7.971(6.19); 7.95 (16); 7.816(4.11); 7.814(4.66); 7.812(4.46); 7.796(5.96); 7.794(6.39); 7.791(6.43); 7.7(7.11); 7.68(11.07); 7.66(4.68); 7.609(0.36); 3.817 (1.08); 2.672(0.72); 2.507(122.22); 2.503(156.92); 2.499(120.82); 2.33(1.4); 2.076(0.67); 0(2.36) |

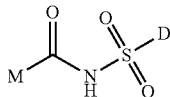
(I)
| Example No. | Structure | NMR peak list |
|---|---|---|
| I-301 | 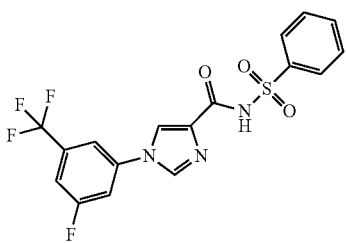 [SMILES: O=C(NS(=O)(=O)c1ccccc1)c1cn(-c2cc(F)cc(C(F)(F)F)c2)cn1] | Example I-301: 1H-NMR(400.0 MHz, d6-DMSO): δ = 8.7(14.34); 8.697(15.34); 8.676(0.5); 8.673(0.51); 8.628(15.48); 8.624 (14.12); 8.594(0.48); 8.591(0.44); 8.317(0.37); 8.131(2.47); 8.126(4.67); 8.121(2.99); 8.107(2.43); 8.102(4.66); 8.097(3.01); 8.072(8.81); 8.032 (1.37); 8.024(12.18); 8.011(3.45); 8.006(16); 8.003(10.87); 7.841(0.66); 7.838(0.7); 7.822(0.71); 7.817(0.8); 7.797(4.1); 7.776(4.11); 7.735 (1.31); 7.732(2.46); 7.729(1.59); 7.72(1.81); 7.714(7.79); 7.708(2.38); 7.698(3.73); 7.695(6.35); 7.692(3.52); 7.654(10.71); 7.638(7.95); 7.635 (15.2); 7.621(2.8); 7.617(6.11); 7.605(0.52); 7.602(0.6); 7.592(0.49); 7.587(1.13); 7.568(0.7); 7.352(0.87); 6.871(0.34); 4.215(0.5); 4.198(0.52); 3.368(0.41); 3.342(0.46); 3.323(0.49); 3.307(0.39); 3.28(0.4); 3.257 (0.41); 3.227(0.36); 3.212(0.42); 3.194(0.45); 2.681(0.42); 2.676(0.81); 2.672(1.08); 2.667(0.81); 2.663(0.4); 2.525(3.17); 2.52(4.87); 2.512 (58.59); 2.507(117.98); 2.503(154.62); 2.498(109.19); 2.494(50.72); 2.334(0.7); 2.33(0.97); 2.325(0.69); 2.184(0.55); 2.088(0.32); 2.075(4.83); 1.378(0.54); 1.36(1.56); 1.356(4.49); 1.343(0.55); 0.008(1.67); 0(48.59); −0.009(1.33) |
| I-302 | 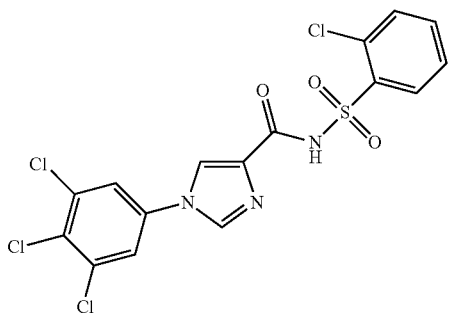 [SMILES: O=C(NS(=O)(=O)c1ccccc1Cl)c1cn(-c2cc(Cl)c(Cl)c(Cl)c2)cn1] | Example I-302: 1H-NMR(400.0 MHz, d6-DMSO): δ = 8.68(4.31); 8.678(4.64); 8.592(4.44); 8.59(4.42); 8.186(16); 8.176 (2.52); 8.172(2.41); 8.156(2.33); 8.152(2.38); 7.728(0.56); 7.724(0.61); 7.708(1.7); 7.704(1.66); 7.69(2.07); 7.686(2.08); 7.672(2.75); 7.669(3.64); 7.652(1.52); 7.649(1.17); 7.637(1.64); 7.633(1.43); 7.617(2.11); 7.6 (1.04); 7.596(0.97); 2.507(33.39); 2.503(44.69); 2.498(34.27); 2.329 (0.36); 0.008(1.43); 0(48.35); −0.008(3.08) |
| I-303 | 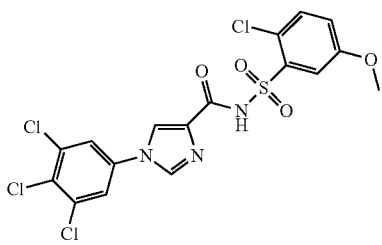 [SMILES: COc1ccc(Cl)c(S(=O)(=O)NC(=O)c2cn(-c3cc(Cl)c(Cl)c(Cl)c3)cn2)c1] | Example I-303: 1H-NMR(400.0 MHz, d6-DMSO): δ = 8.678(2.53); 8.675(2.75); 8.598(2.94); 8.595(2.82); 8.186(13.25); 7.617(2.82); 7.609(3.11); 7.573(2.54); 7.551(3.12); 7.293(1.48); 7.285 (1.44); 7.271(1.3); 7.263(1.26); 3.858(16); 3.816(0.87); 2.525(0.42); 2.511(14.82); 2.507(30.52); 2.502(40.54); 2.498(29.57); 2.493(14.56); 2.075(10.37); 0.008(1.6); 0(48.45); −0.008(2.09) |
| I-304 | 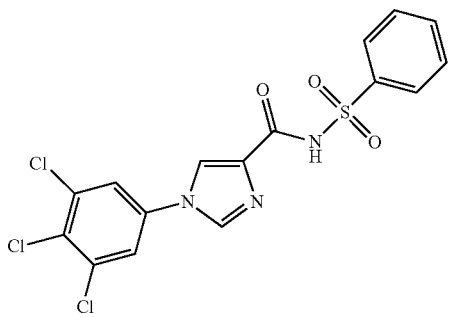 [SMILES: O=C(NS(=O)(=O)c1ccccc1)c1cn(-c2cc(Cl)c(Cl)c(Cl)c2)cn1] | Example I-304: 1H-NMR(400.0 MHz, d6-DMSO): δ = 8.627(3.56); 8.56(3.57); 8.194(9.01); 8.018(3.42); 7.999(3.63); 7.727 (0.69); 7.709(1.72); 7.691(1.5); 7.65(2.59); 7.631(3.5); 7.612(1.49); 2.672(0.4); 2.503(43.81); 2.075(16); 0.822(0.34); 0(24.23) |

-continued
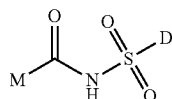
(I)
| Example No. | Structure | NMR peak list |
|---|---|---|
| I-305 | 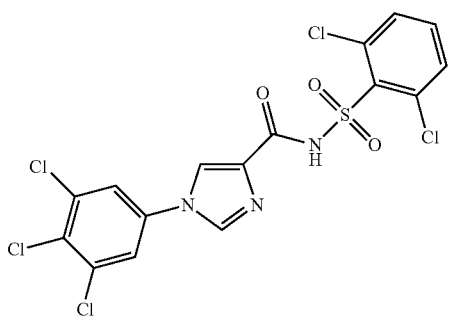 [SMILES: O=C(NS(=O)(=O)c1c(Cl)cccc1Cl)c1cn(-c2cc(Cl)c(Cl)c(Cl)c2)cn1] | Example I-305: 1H-NMR(400.0 MHz, d6-DMSO): δ = 8.667(9.75); 8.197(16); 7.656(4.03); 7.652(4.28); 7.634(9.79); 7.594 (3.64); 7.577(2.6); 7.571(2.05); 7.554(1.29); 2.503(59.31); 2.33(0.57); 2.075(0.87); 0(26.27) |
| I-306 | 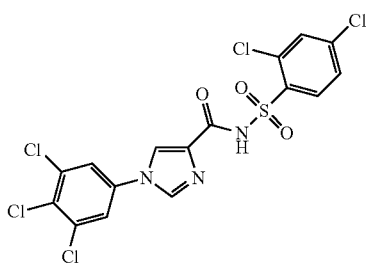 [SMILES: O=C(NS(=O)(=O)c1ccc(Cl)cc1Cl)c1cn(-c2cc(Cl)c(Cl)c(Cl)c2)cn1] | Example I-306: 1H-NMR(400.0 MHz, d6-DMSO): δ = 8.675(5.49); 8.653(4.86); 8.651(4.59); 8.197(16); 8.157(3.88); 8.136 (4.29); 7.875(3.95); 7.87(4.39); 7.724(2.64); 7.719(2.63); 7.703(2.31); 7.698(2.35); 2.507(42.1); 2.503(53.9); 2.499(43.58); 2.33(0.4); 2.076 (0.63); 0(28.13) |
| I-307 | 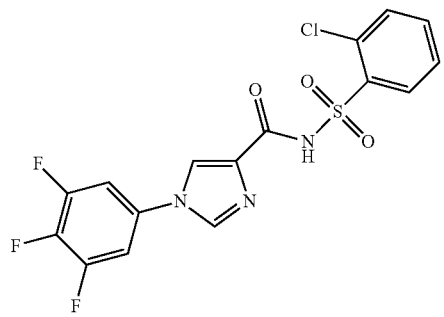 [SMILES: O=C(NS(=O)(=O)c1ccccc1Cl)c1cn(-c2cc(F)c(F)c(F)c2)cn1] | Example I-307: 1H-NMR(400.0 MHz, d6-DMSO): δ = 11.062(0.61); 8.578(15.27); 8.511(16); 8.474(2.43); 8.405(2.34); 8.316 (0.53); 8.171(8.4); 8.167(8.79); 8.151(9.23); 8.148(9.21); 7.989(0.68); 7.969(0.91); 7.963(0.91); 7.943(8.32); 7.927(9.16); 7.92(8.95); 7.905 (7.94); 7.885(0.76); 7.719(2.56); 7.702(7.15); 7.685(7.85); 7.681(8.24); 7.664(14.03); 7.647(5.93); 7.632(6.97); 7.612(9.15); 7.594(4.12); 7.591 (3.88); 7.541(0.49); 7.536(0.51); 7.521(0.63); 7.374(0.44); 7.368(0.52); 7.36(0.51); 7.353(0.52); 7.347(0.5); 7.34(0.52); 7.332(0.47); 7.075 (0.85); 7.058(0.84); 5.756(0.33); 4.262(0.46); 4.244(0.46); 3.844(0.35); 3.761(0.36); 3.695(0.39); 3.673(0.4); 3.625(0.43); 3.602(0.43); 3.365 (0.4); 3.349(0.39); 2.671(2.38); 2.506(275.11); 2.502(343.38); 2.498 (260.71); 2.328(2.32); 2.074(1.17); 1.381(0.6); 1.364(0.36); 1.356(0.49); 0.146(0.86); 0(171.61); −0.15(0.84) |
| I-308 | 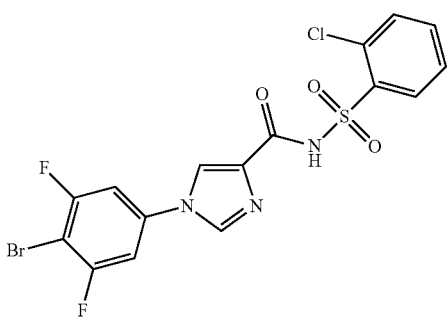 | Example I-308: 1H-NMR(400.0 MHz, d6-DMSO): δ = 8.658(9.1); 8.642(7.53); 8.586(10.66); 8.316(0.37); 8.17(7.61); 8.152 (7.92); 7.988(0.33); 7.972(0.36); 7.887(6.78); 7.867(6.68); 7.7(6.49); 7.682(7.84); 7.666(11.7); 7.646(5.92); 7.63(6.28); 7.611(8.09); 7.593 (3.95); 7.523(3.92); 7.518(4.05); 7.499(3.8); 7.494(3.72); 7.333(6.54); 7.072(0.43); 4.29(3.33); 4.273(8.15); 4.255(8.18); 4.238(3.27); 4.209 (0.95); 4.191(0.83); 4.14(0.54); 4.123(0.55); 4.067(0.57); 4.022(0.58); 3.971(0.61); 3.813(0.73); 3.772(0.74); 3.76(0.74); 3.662(0.78); 3.639 (0.77); 3.552(0.75); 3.507(0.73); 3.451(0.68); 3.44(0.68); 3.362(0.63); 3.226(0.44); 2.671(1.69); 2.502(272.34); 2.329(2.61); 2.182(0.5); 2.171 (0.48); 2.162(0.44); 2.074(1); 1.41(8.48); 1.393(16); 1.375(8.66); 1.304 (0.5); 1.285(0.37); 1.232(1.03); 0.146(0.42); 0(87.01); −0.15(0.64) |

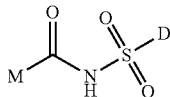
(I)
| Example No. | Structure | NMR peak list |
|---|---|---|
| I-309 | 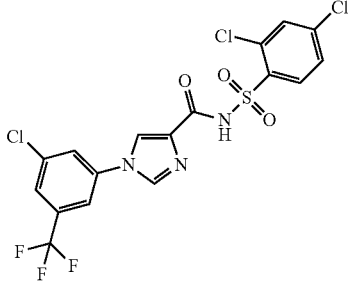 [SMILES: O=C(NS(=O)(=O)c1ccc(Cl)cc1Cl)c1cn(-c2cc(Cl)cc(C(F)(F)F)c2)cn1] | Example I-309: 1H-NMR(400.0 MHz, d6-DMSO): δ = 8.744(15.47); 8.72(16); 8.316(0.9); 8.288(13.97); 8.175(13.49); 8.158 (13.87); 8.137(15.01); 7.977(2.15); 7.964(13.56); 7.868(12.95); 7.864 (13.13); 7.853(1.48); 7.848(1.22); 7.721(9.53); 7.716(8.16); 7.699(7.73); 7.694(7.06); 7.643(0.68); 7.638(0.6); 7.622(0.58); 7.617(0.54); 4.296 (0.36); 4.289(0.34); 4.26(0.35); 4.252(0.35); 4.198(0.37); 4.143(0.39); 4.134(0.41); 4.1(0.41); 4.085(0.4); 4.056(0.49); 4.052(0.42); 4.038(0.62); 4.02(0.65); 4.003(0.5); 3.991(0.44); 3.963(0.42); 3.953(0.42); 3.899 (0.43); 3.89(0.41); 3.873(0.42); 3.871(0.41); 3.824(0.41); 3.81(0.42); 3.793(0.4); 3.776(0.4); 3.737(0.4); 3.728(0.38); 3.708(0.39); 3.682(0.37); 3.676(0.37); 3.656(0.37); 3.64(0.36); 3.629(0.37); 3.576(0.35); 3.559 (0.34); 3.54(0.34); 3.507(0.44); 3.478(0.34); 2.676(1.75); 2.671(2.25); 2.667(1.72); 2.506(283.08); 2.502(352.01); 2.498(261.23); 2.376(0.37); 2.333(1.93); 2.329(2.41); 2.075(0.64); 1.989(1.17); 1.341(0.44); 1.233 (1.22); 1.193(0.36); 1.175(0.64); 1.157(0.32); 0.146(0.5); 0.008(7.66); 0(121.9); −0.15(0.65) |
| I-310 | 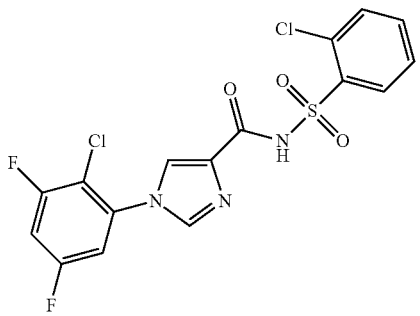 [SMILES: O=C(NS(=O)(=O)c1ccccc1Cl)c1cn(-c2cc(F)cc(F)c2Cl)cn1] | Example I-310: 1H-NMR(400.0 MHz, d6-DMSO): δ = 8.374(11.5); 8.198(11.06); 8.177(5.06); 8.157(5.3); 8.146(0.38); 8.084 (0.59); 7.994(1.78); 7.991(1.9); 7.972(1.93); 7.841(1.83); 7.834(2.01); 7.818(3.37); 7.811(3.4); 7.795(1.88); 7.788(1.81); 7.73(1.53); 7.711 (4.63); 7.697(7.8); 7.693(7.75); 7.678(10.74); 7.661(3.24); 7.652(1.96); 7.636(5.31); 7.62(6.71); 7.603(8.79); 7.587(1.48); 7.552(0.32); 7.54(1.27); 7.536(1.35); 7.52(1.8); 7.519(1.84); 7.503(0.8); 7.499(0.85); 6.871 (0.85); 6.638(0.43); 5.755(16); 2.671(0.39); 2.502(60.86); 2.329(0.4); 2.183(1.3); 2.074(0.48); 1.97(1.07); 1.356(8.33); 1.234(0.39); 1.221(0.56); 1.202(0.78); 1.184(0.43); 0.019(1.61); 0(45.53) |
| I-311 | 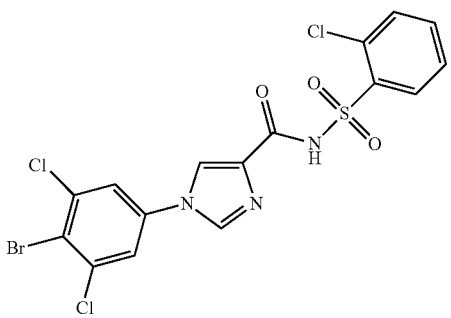 | Example I-311: 1H-NMR(400.0 MHz, d6-DMSO): δ = 9.382(0.46); 8.687(4.04); 8.684(4.43); 8.599(4.18); 8.596(4.14); 8.205 (0.57); 8.178(1.96); 8.174(2.12); 8.158(2.35); 8.154(2.62); 8.145(16); 7.838(0.43); 7.739(2.23); 7.729(0.6); 7.725(0.6); 7.708(1.61); 7.705 (1.56); 7.691(1.99); 7.687(1.96); 7.673(2.6); 7.669(3.46); 7.653(1.55); 7.649(1.18); 7.638(1.61); 7.634(1.53); 7.618(1.95); 7.601(1); 7.597(0.89); 2.526(0.6); 2.512(11.49); 2.508(22.41); 2.504(29.08); 2.5(21.23); 2.495 (10.58); 2.076(6.09); 0.008(0.76); 0(17.2); −0.008(0.71) |
| I-312 | 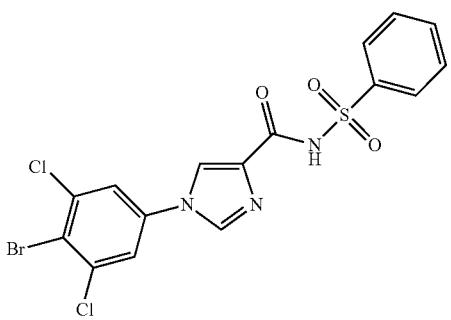 | Example I-312: 1H-NMR(400.0 MHz, d6-DMSO): δ = 9.382(0.64); 8.628(3.7); 8.565(4); 8.562(3.88); 8.154(16); 8.016(3.71); 7.998(4.25); 7.994(3.27); 7.741(3.05); 7.727(0.73); 7.709(2.09); 7.69 (1.65); 7.649(3.05); 7.63(4.21); 7.612(1.6); 3.39(0.34); 3.355(0.43); 3.336(0.45); 3.317(0.47); 2.671(0.58); 2.667(0.44); 2.524(2.37); 2.506 (70.19); 2.502(92.03); 2.498(68.77); 2.329(0.59); 2.324(0.45); 2.075 (1.1); 0.017(0.42); 0.008(1.78); 0(44.86); −0.008(2.23) |

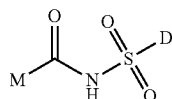
(I)
| Example No. | Structure | NMR peak list |
|---|---|---|
| I-313 | 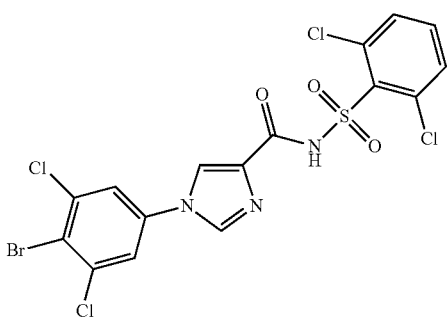 | Example I-313: 1H-NMR(400.0 MHz, d6-DMSO): δ = 9.889(0.47); 8.678(5.52); 8.673(5.18); 8.156(16); 7.841(2.07); 7.659 (2.7); 7.655(3.32); 7.637(7.9); 7.597(3.12); 7.58(2.01); 7.574(1.56); 7.557(1.08); 2.511(21.05); 2.507(47.98); 2.502(67.23); 2.498(51.9); 2.494(28.52); 2.334(0.58); 2.329(0.7); 2.325(0.61); 2.075(0.84); 0(10.97) |
| I-314 | 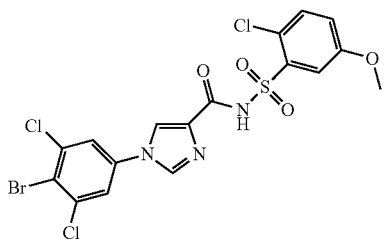 | Example I-314: 1H-NMR(400.0 MHz, d6-DMSO): δ = 8.686(3.2); 8.684(3.35); 8.604(3.28); 8.145(10.78); 7.617(2.96); 7.609 (3.67); 7.575(2.6); 7.553(3.34); 7.53(0.54); 7.48(0.45); 7.473(0.48); 7.296(1.57); 7.288(1.56); 7.273(1.39); 7.266(1.36); 6.746(0.37); 3.859 (16); 3.84(0.67); 3.834(0.51); 3.816(2.78); 2.507(34.48); 2.503(45.3); 2.498(35.02); 2.33(0.37); 2.075(7.66); 0(7.16) |
| I-315 | 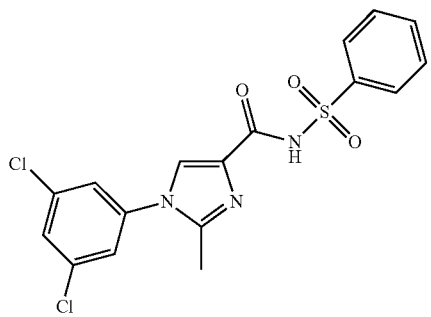 | Example I-315: 1H-NMR(400.0 MHz, d6-DMSO): δ = 8.098(2.86); 7.983(3.02); 7.965(3.52); 7.961(2.72); 7.816(1.61); 7.811 (3.19); 7.807(1.99); 7.738(7.78); 7.734(7.15); 7.687(0.46); 7.669(1.5); 7.651(1.28); 7.614(2.39); 7.595(3.33); 7.577(1.31); 3.405(1.22); 2.676 (0.58); 2.671(0.79); 2.667(0.58); 2.541(0.6); 2.524(1.89); 2.511(48.22); 2.507(94.36); 2.502(122.04); 2.498(90.44); 2.338(16); 2.075(0.46); 0.146(0.72); 0.008(6.83); 0(157.45); −0.008(6.77); −0.15(0.74) |
| I-316 | 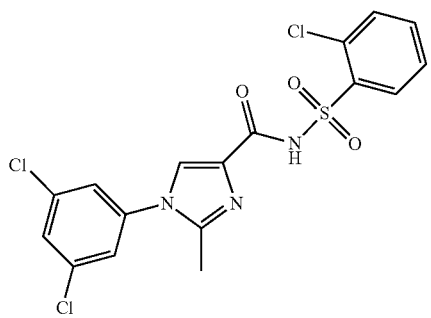 [SMILES: Cc1nc(C(=O)NS(=O)(=O)c2ccccc2Cl)cn1-c1cc(Cl)cc(Cl)c1] | Example I-316: 1H-NMR(400.0 MHz, d6-DMSO): δ = 8.147(5.49); 8.126(1.7); 8.122(1.86); 8.106(1.84); 8.103(1.95); 7.852 (1.71); 7.847(3.46); 7.843(2.21); 7.781(8.29); 7.777(7.64); 7.639(0.42); 7.636(0.46); 7.619(1.33); 7.616(1.32); 7.602(1.96); 7.596(2.73); 7.591 (3.18); 7.576(1.06); 7.564(1.38); 7.56(1.13); 7.544(1.59); 7.528(0.75); 7.523(0.68); 5.757(2.83); 2.507(36.42); 2.502(48.75); 2.498(37.81); 2.38(16); 2.329(0.4); 2.086(8.8); 1.234(2.38); 0.008(1.88); 0(53.1); −0.008(3.26) |

-continued (I)

| Example No. | Structure | NMR peak list |
|---|---|---|
| I-317 | 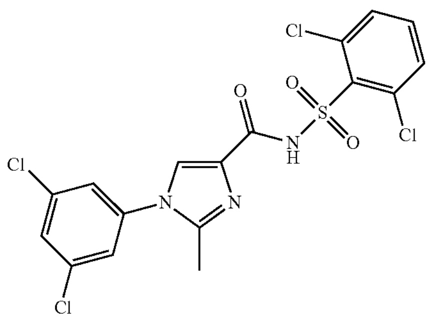 | Example I-317: 1H-NMR(400.0 MHz, d6-DMSO): δ = 8.317(0.38); 8.107(2.33); 7.888(1.61); 7.883(3.23); 7.879(2.02); 7.811 (8.17); 7.807(7.56); 7.781(0.38); 7.777(0.33); 7.527(2.88); 7.525(3.3); 7.506(6.66); 7.446(2.2); 7.429(1.66); 7.424(1.51); 7.407(0.98); 5.757 (2.28); 4.043(0.34); 3.964(0.41); 3.945(0.42); 3.902(0.49); 3.84(0.53); 3.824(0.55); 3.808(0.57); 3.79(0.57); 3.766(0.57); 3.749(0.58); 3.729 (0.57); 3.684(0.55); 3.524(0.38); 3.465(0.32); 2.675(0.86); 2.671(1.21); 2.666(0.89); 2.524(2.98); 2.519(4.6); 2.511(64.91); 2.506(131.89); 2.502 (175.24); 2.497(129.55); 2.493(64.73); 2.416(16); 2.379(0.8); 2.339(0.78); 2.333(0.94); 2.328(1.26); 2.324(0.93); 2.075(2.76); 1.233(0.51); 0.146 (1.01); 0.008(7.42); 0(212.52); −0.008(8.42); −0.15(1.01) |
| I-318 | 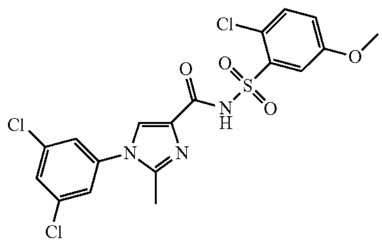 [SMILES: COc1ccc(Cl)c(S(=O)(=O)NC(=O)c2cn(-c3cc(Cl)cc(Cl)c3)c(C)n2)c1] | Example I-318: 1H-NMR(400.0 MHz, d6-DMSO): δ = 8.126(2.13); 7.856(1.37); 7.852(2.82); 7.847(1.78); 7.785(6.79); 7.78 (6.25); 7.59(2.84); 7.583(2.97); 7.481(1.96); 7.459(2.28); 7.187(1.11); 7.18(1.1); 7.166(0.98); 7.158(0.96); 3.832(16); 2.525(0.41); 2.52(0.68); 2.511(11.73); 2.507(24.37); 2.502(32.61); 2.498(24.42); 2.494(12.4); 2.385(12.4); 2.086(2.71); 0.008(1.38); 0(43.49); −0.008(1.93) |
| I-319 | 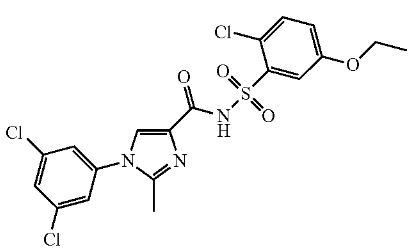 [SMILES: CCOc1ccc(Cl)c(S(=O)(=O)NC(=O)c2cn(-c3cc(Cl)cc(Cl)c3)c(C)n2)c1] | Example I-319: 1H-NMR(400.0 MHz, d6-DMSO): δ = 8.146(4.73); 7.859(1.74); 7.855(3.64); 7.85(2.23); 7.787(8.91); 7.782 (8.11); 7.573(3.55); 7.565(3.71); 7.47(2.68); 7.449(3.14); 7.177(1.49); 7.169(1.47); 7.155(1.32); 7.147(1.3); 4.121(1.28); 4.104(4.1); 4.087(4.19); 4.069(1.41); 2.671(0.39); 2.524(0.55); 2.52(1.07); 2.511(26.13); 2.507 (54.68); 2.502(73.02); 2.498(53.95); 2.493(27.02); 2.385(16); 2.333 (0.46); 2.329(0.58); 2.324(0.46); 2.086(11.15); 1.373(4.5); 1.355(9.92); 1.338(4.54); 0.146(0.41); 0.008(3.12); 0(103.31); −0.009(4.33); −0.025(0.37); −0.15(0.49) |
| I-320 | 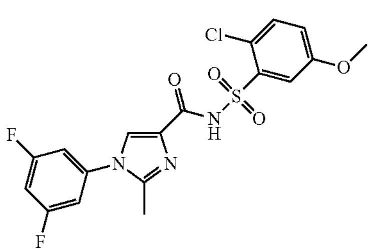 [SMILES: COc1ccc(Cl)c(S(=O)(=O)NC(=O)c2cn(-c3cc(F)cc(F)c3)c(C)n2)c1] | Example I-320: 1H-NMR(400.0 MHz, d6-DMSO): δ = 8.316(0.43); 8.098(1.6); 7.589(2.64); 7.581(2.74); 7.535(0.59); 7.53 (0.64); 7.51(1.28); 7.5(2.06); 7.496(1.98); 7.479(3.6); 7.456(2.22); 7.184 (1.11); 7.177(1.04); 7.162(0.97); 7.155(0.9); 3.83(16); 3.816(1.37); 3.647 (1.19); 3.564(1.43); 3.492(1.2); 3.478(1.15); 3.392(0.66); 3.376(0.6); 3.253(0.35); 2.676(0.86); 2.671(1.17); 2.666(0.88); 2.524(3.21); 2.51 (64.6); 2.506(127.85); 2.502(167.49); 2.497(123.97); 2.4(12.29); 2.333 (0.86); 2.329(1.15); 2.324(0.86); 2.074(2.16); 0.146(0.93); 0.008(7.7); 0(203.6); −0.008(8.47); −0.064(0.39); −0.15(0.97) |
| I-321 | 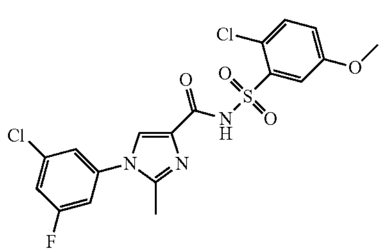 [SMILES: COc1ccc(Cl)c(S(=O)(=O)NC(=O)c2cn(-c3cc(F)cc(Cl)c3)c(C)n2)c1] | Example I-321: 1H-NMR(400.0 MHz, d6-DMSO): δ = 8.112(2.1); 7.71(0.65); 7.705(1.17); 7.7(0.85); 7.688(0.69); 7.683(1.2); 7.678(0.87); 7.652(2.4); 7.636(1.02); 7.63(1.28); 7.626(0.72); 7.612 (1.19); 7.608(1.42); 7.602(0.79); 7.59(2.81); 7.582(2.94); 7.479(2.18); 7.472(0.4); 7.457(2.36); 7.186(1.27); 7.178(1.2); 7.164(1.14); 7.156 (1.04); 3.831(16); 3.816(1.34); 2.524(0.98); 2.511(19.36); 2.507(38.26); 2.502(50.46); 2.498(38.47); 2.392(12.62); 2.329(0.37); 2.075(10.87); 0.008(2.56); 0(59.35); −0.008(3.61) |

-continued
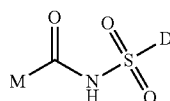
(I)
| Example No. | Structure | NMR peak list |
|---|---|---|
| I-322 | 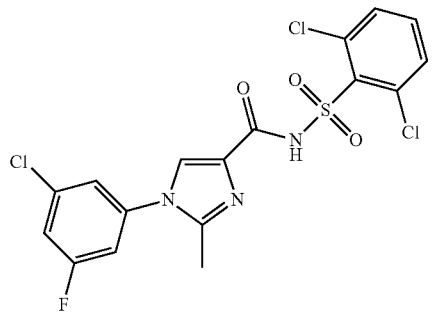 [SMILES: Cc1nc(C(=O)NS(=O)(=O)c2c(Cl)cccc2Cl)cn1-c1cc(F)cc(Cl)c1] | Example I-322: 1H-NMR(400.0 MHz, d6-DMSO): δ = 8.104(3.86); 7.744(0.86); 7.739(1.5); 7.734(1.07); 7.722(0.9); 7.717 (1.55); 7.712(1.09); 7.683(2.98); 7.661(1.22); 7.656(1.6); 7.651(0.92); 7.638(1.19); 7.633(1.61); 7.628(1.02); 7.529(2.97); 7.527(3.43); 7.508 (6.66); 7.449(2.33); 7.432(1.78); 7.427(1.61); 7.409(1.03); 2.507(36.76); 2.502(48.4); 2.498(37.03); 2.427(16); 2.329(0.4); 0.008(2.55); 0(58.15); −0.008(3.42) |
| I-323 | 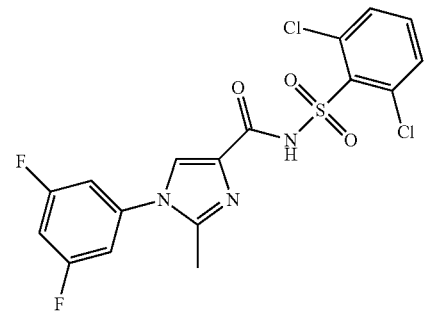 [SMILES: Cc1nc(C(=O)NS(=O)(=O)c2c(Cl)cccc2Cl)cn1-c1cc(F)cc(F)c1] | Example I-323: 1H-NMR(400.0 MHz, d6-DMSO): δ = 8.11(5.36); 7.575(0.82); 7.552(1.94); 7.547(1.91); 7.532(7.41); 7.513 (10.4); 7.455(2.34); 7.437(1.99); 7.415(1.06); 2.672(0.43); 2.502(69.02); 2.44(16); 2.329(0.53); 2.075(1.86); 0(60.18); −0.15(0.35) |
| I-324 | 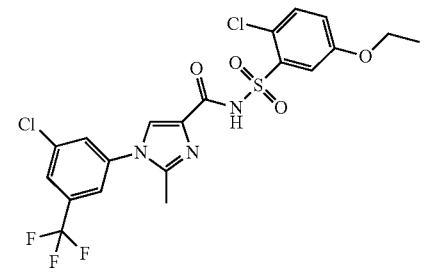 [SMILES: CCOc1ccc(Cl)c(S(=O)(=O)NC(=O)c2cn(-c3cc(Cl)cc(C(F)(F)F)c3)c(C)n2)c1] | Example I-324: 1H-NMR(400.0 MHz, d6-DMSO): δ = 8.211(6.62); 8.128(3.09); 8.124(2.42); 8.112(2.85); 8.052(2.83); 7.578 (3.64); 7.571(3.76); 7.477(2.88); 7.455(3.36); 7.184(1.64); 7.176(1.6); 7.162(1.43); 7.154(1.38); 4.125(1.22); 4.107(4.08); 4.09(4.15); 4.072 (1.31); 2.512(11.61); 2.507(24.42); 2.503(32.9); 2.498(24.87); 2.494 (12.92); 2.392(16); 1.374(4.54); 1.357(9.81); 1.34(4.64); 0.008(0.37); 0(15.85); −0.008(0.82) |
| I-325 | 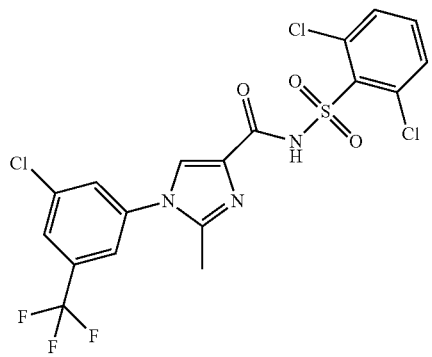 [SMILES: Cc1nc(C(=O)NS(=O)(=O)c2c(Cl)cccc2Cl)cn1-c1cc(Cl)cc(C(F)(F)F)c1] | Example I-325: 1H-NMR(400.0 MHz, d6-DMSO): δ = 8.18(5.41); 8.147(6.12); 8.086(3.1); 7.535(3.07); 7.533(3.44); 7.514 (7.02); 7.455(2.37); 7.438(1.78); 7.433(1.61); 7.416(1.04); 4.226(0.33); 4.181(0.36); 4.097(0.44); 4.074(0.46); 4.061(0.47); 4.014(0.51); 3.99 (0.51); 3.932(0.52); 3.907(0.51); 3.835(0.5); 3.741(0.36); 2.676(0.58); 2.671(0.76); 2.667(0.59); 2.506(77.45); 2.502(100.14); 2.498(75.17); 2.423(16); 2.333(0.5); 2.328(0.77); 2.086(1.87); 0.146(0.72); 0.008(7.46); 0(138.09); −0.008(7.15); −0.15(0.66) |

(I)
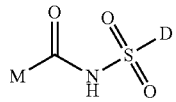
| Example No. | Structure | NMR peak list |
|---|---|---|
| I-326 | 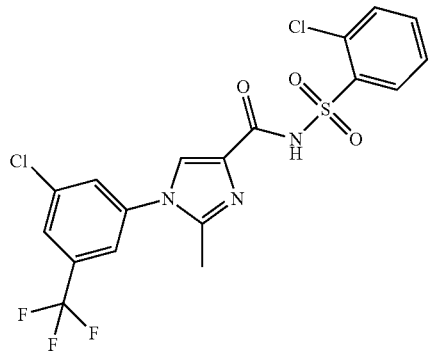 [SMILES: Cc1nc(C(=O)NS(=O)(=O)c2ccccc2Cl)cn1-c1cc(Cl)cc(C(F)(F)F)c1] | Example I-326: 1H-NMR(400.0 MHz, d6-DMSO): δ = 8.213(6.04); 8.128(3.11); 8.124(3.25); 8.119(2.43); 8.108(4.13); 8.044 (2.78); 7.647(0.34); 7.643(0.36); 7.626(1.2); 7.623(1.15); 7.61(1.8); 7.606(2.05); 7.602(2.38); 7.597(3.07); 7.582(1.03); 7.578(0.65); 7.571 (1.32); 7.566(1.04); 7.551(1.5); 7.547(1.21); 7.534(0.76); 7.53(0.68); 2.525(0.53); 2.511(18.69); 2.507(38.34); 2.502(51.28); 2.498(38.88); 2.494(20.65); 2.387(16); 2.334(0.33); 2.329(0.43); 2.325(0.35); 2.086 (0.38); 0.146(0.33); 0.008(2.47); 0(74.23); −0.008(4.4); −0.15(0.39) |
| I-327 | 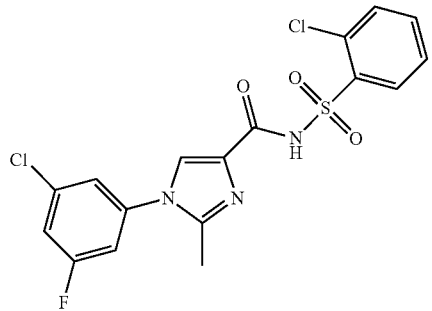 [SMILES: Cc1nc(C(=O)NS(=O)(=O)c2ccccc2Cl)cn1-c1cc(F)cc(Cl)c1] | Example I-327: 1H-NMR(400.0 MHz, d6-DMSO): δ = 8.146(5.75); 8.128(1.73); 8.124(1.83); 8.108(1.84); 8.105(1.86); 7.709 (0.91); 7.704(1.57); 7.698(1.1); 7.687(0.91); 7.682(1.59); 7.677(1.13); 7.652(3.09); 7.636(1.58); 7.631(1.74); 7.625(1.47); 7.622(1.53); 7.618 (1.43); 7.613(1.56); 7.605(2.67); 7.602(2.77); 7.598(2.66); 7.593(3.08); 7.578(0.97); 7.574(0.62); 7.566(1.29); 7.562(1.02); 7.547(1.51); 7.542 (1.17); 7.53(0.71); 7.525(0.64); 2.525(0.41); 2.511(10.57); 2.507(21.16); 2.503(27.78); 2.498(20.9); 2.391(16); 2.075(0.91); 0.008(1.31); 0(38.59); −0.008(2.08) |
| I-328 | 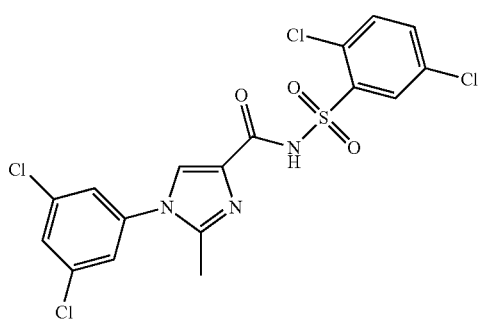 [SMILES: Cc1nc(C(=O)NS(=O)(=O)c2cc(Cl)ccc2Cl)cn1-c1cc(Cl)cc(Cl)c1] | Example I-328: 1H-NMR(400.0 MHz, d6-DMSO): δ = 8.111(5.05); 8.021(3.37); 8.015(3.48); 7.905(1.82); 7.9(3.57); 7.896 (2.17); 7.818(8.71); 7.814(8.11); 7.797(0.45); 7.706(0.34); 7.702(0.39); 7.618(1.29); 7.612(1.25); 7.597(2.39); 7.59(2.4); 7.55(4.38); 7.529(2.28); 2.676(0.39); 2.671(0.54); 2.667(0.41); 2.524(1.48); 2.511(33.39); 2.506 (66.19); 2.502(86.52); 2.498(64.7); 2.493(33.34); 2.432(16); 2.334 (0.54); 2.329(0.64); 2.325(0.46); 2.075(0.48); 0.146(0.56); 0.008(4.92); 0(123.6); −0.008(6.25); −0.15(0.58) |
| I-329 | 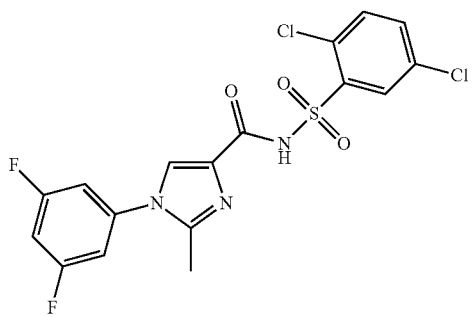 [SMILES: Cc1nc(C(=O)NS(=O)(=O)c2cc(Cl)ccc2Cl)cn1-c1cc(F)cc(F)c1] | Example I-329: 1H-NMR(400.0 MHz, d6-DMSO): δ = 8.109(6.8); 8.025(3.19); 8.019(3.41); 7.624(1.3); 7.617(1.29); 7.602 (2.49); 7.596(2.89); 7.57(1.59); 7.565(1.34); 7.555(4.88); 7.547(1.48); 7.54(3.3); 7.534(4.75); 7.522(3.13); 2.507(22.77); 2.502(30.06); 2.498 (23.99); 2.456(16); 2.075(7.79); 0.008(1.52); 0(34.98) |

-continued
(I)
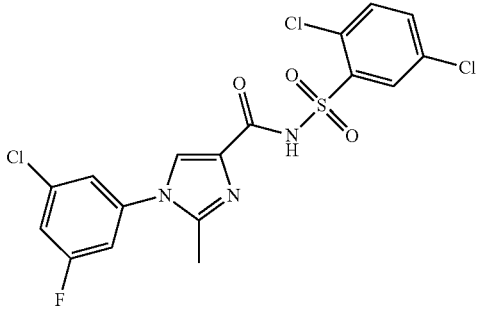 [SMILES: Cc1nc(C(=O)NS(=O)(=O)c2cc(Cl)ccc2Cl)cn1-c1cc(F)cc(Cl)c1]
| Example No. | Structure | NMR peak list |
|---|---|---|
| I-330 | 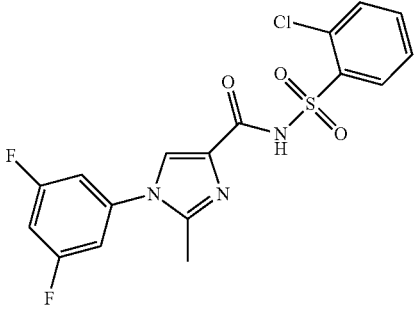 [SMILES: Cc1nc(C(=O)NS(=O)(=O)c2ccccc2Cl)cn1-c1cc(F)cc(F)c1] | Example I-330: 1H-NMR(400.0 MHz, d6-DMSO): δ = 8.115(7.15); 8.025(3.34); 8.018(3.46); 7.797(0.35); 7.764(0.92); 7.759 (1.58); 7.754(1.09); 7.742(0.94); 7.737(1.61); 7.732(1.11); 7.701(1.72); 7.696(2.93); 7.668(1.17); 7.663(1.59); 7.658(0.88); 7.646(1.17); 7.64 (1.63); 7.635(0.9); 7.622(1.33); 7.615(1.28); 7.6(2.42); 7.594(2.42); 7.554 (4.5); 7.532(2.37); 2.525(0.48); 2.511(10.61); 2.507(21.51); 2.503 (28.48); 2.498(21.28); 2.494(10.87); 2.446(16); 2.075(2.48); 0.008(1.38); 0(40.01); −0.008(1.99) |
| I-331 | 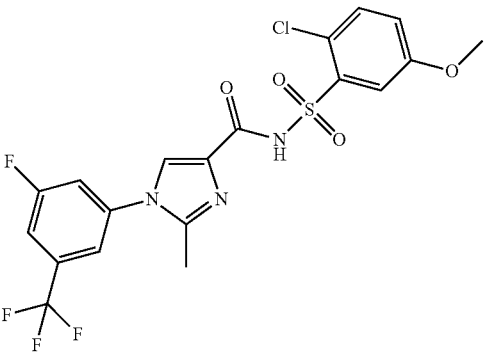 [SMILES: COc1ccc(Cl)c(S(=O)(=O)NC(=O)c2cn(-c3cc(F)cc(C(F)(F)F)c3)c(C)n2)c1] | Example I-331: 1H-NMR(400.0 MHz, d6-DMSO): δ = 8.123(2.28); 8.118(6.32); 8.104(1.87); 8.101(1.88); 7.635(0.44); 7.632 (0.46); 7.615(1.33); 7.611(1.33); 7.598(1.98); 7.592(2.66); 7.587(3.1); 7.572(1.02); 7.567(0.62); 7.561(1.36); 7.556(1.03); 7.541(1.64); 7.537 (1.53); 7.531(0.88); 7.524(1.27); 7.512(1.06); 7.506(1.79); 7.498(2.73); 7.493(2.41); 7.478(3.54); 2.542(0.84); 2.525(0.49); 2.511 (11.7); 2.507(22.9); 2.503(29.65); 2.498(21.83); 2.494(10.96); 2.397(16); 0.008(1.8); 0(41.22); −0.008(1.81) |
| I-332 | 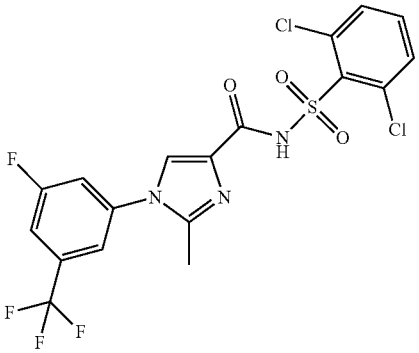 | Example I-332: 1H-NMR(400.0 MHz, d6-DMSO): δ = 8.162(5.17); 7.966(2.38); 7.944(2.67); 7.924(2.86); 7.614(0.56); 7.593 (2.94); 7.585(3.06); 7.553(0.44); 7.531(0.35); 7.479(2.63); 7.457(2.82); 7.185(1.59); 7.177(1.5); 7.163(1.41); 7.155(1.29); 3.832(16); 3.816 (2.1); 2.503(33.08); 2.499(26.75); 2.397(13.5); 2.34(0.33); 2.329(0.36); 2.075(4.41); 0(0.73) |
| I-333 | 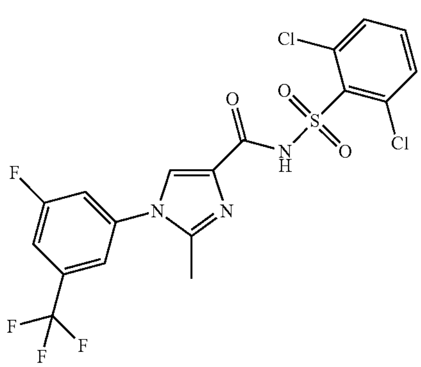 [SMILES: Cc1nc(C(=O)NS(=O)(=O)c2c(Cl)cccc2Cl)cn1-c1cc(F)cc(C(F)(F)F)c1] | Example I-333: 1H-NMR(400.0 MHz, d6-DMSO): δ = 8.179(4.96); 8.002(2.5); 7.98(2.2); 7.971(3.76); 7.538(3.23); 7.535 (3.44); 7.516(6.74); 7.458(2.27); 7.44(1.73); 7.436(1.51); 7.418(0.93); 2.671(0.41); 2.507(51.25); 2.502(66.98); 2.498(51.38); 2.433(16); 2.334 (0.37); 2.329(0.48); 0(7.86); −0.063(0.56) |

-continued
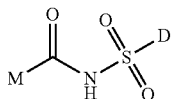
(I)
| Example No. | Structure | NMR peak list |
|---|---|---|
| I-334 | 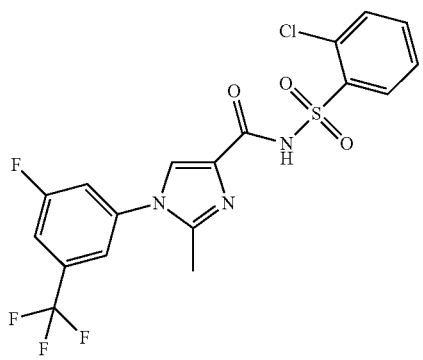 [SMILES: Cc1nc(C(=O)NS(=O)(=O)c2ccccc2Cl)cn1-c1cc(F)cc(C(F)(F)F)c1] | Example I-334: 1H-NMR(400.0 MHz, d6-DMSO): δ = 8.217(6.29); 8.134(1.67); 8.13(1.81); 8.114(1.84); 8.111(1.92); 7.971 (2.51); 7.948(2.78); 7.927(2.88); 7.65(0.37); 7.646(0.39); 7.63(1.29); 7.627(1.21); 7.613(1.9); 7.609(2.19); 7.605(2.5); 7.601(3.19); 7.586(1.03); 7.581(0.66); 7.574(1.33); 7.569(1.05); 7.554(1.59); 7.537(0.75); 7.533 (0.69); 5.758(5.97); 2.542(26.85); 2.525(0.5); 2.507(33.05); 2.503 (43.37); 2.498(32.81); 2.398(16); 2.33(0.35); 0.008(1.02); 0(30.91) |
| I-335 | 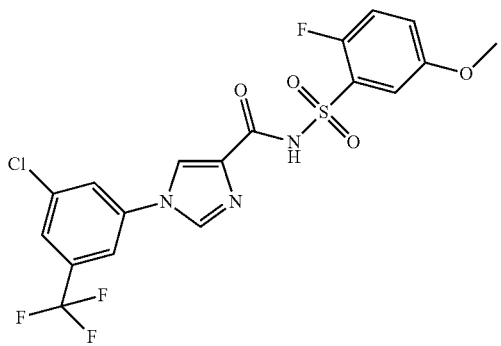 [SMILES: COc1ccc(F)c(S(=O)(=O)NC(=O)c2cn(-c3cc(Cl)cc(C(F)(F)F)c3)cn2)c1] | Example I-335: 1H-NMR(400.0 MHz, d6-DMSO): δ = 8.741(2.14); 8.679(2.43); 8.677(2.39); 8.283(2.22); 8.169(2.04); 7.96 (2.05); 7.422(1); 7.414(1.23); 7.408(1.19); 7.4(1.75); 7.378(1.55); 7.354 (1.1); 7.314(0.63); 7.305(1.07); 7.297(0.67); 7.292(0.51); 7.283(0.61); 7.274(0.34); 3.83(16); 3.795(0.36); 3.646(0.64); 3.441(1.89); 2.676 (0.68); 2.672(0.95); 2.667(0.73); 2.525(2.03); 2.52(3.44); 2.542(.1.71); 2.511(53.35); 2.507(109.91); 2.502(145.72); 2.498(108.59); 2.494(55.2); 2.334(0.75); 2.329(1.01); 2.325(0.79); 0.008(0.5); 0(15.79); −0.008(0.65) |
| I-336 | 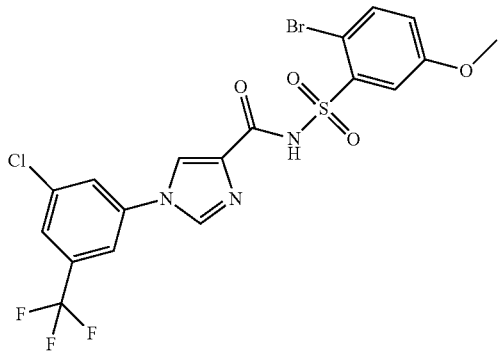 [SMILES: COc1ccc(Br)c(S(=O)(=O)NC(=O)c2cn(-c3cc(Cl)cc(C(F)(F)F)c3)cn2)c1] | Example I-336: 1H-NMR(400.0 MHz, d6-DMSO): δ = 8.768(2.98); 8.672(3.16); 8.67(3.1); 8.278(2.59); 8.16(2.37); 7.963 (2.43); 7.738(2.64); 7.717(2.93); 7.666(2.76); 7.659(2.87); 7.213(1.45); 7.206(1.41); 7.191(1.35); 7.184(1.3); 5.757(0.49); 3.856(16); 3.814(0.82); 2.672(0.39); 2.507(47.54); 2.503(62); 2.498(46.74); 2.334(0.36); 2.329(0.46); 2.325(0.36) |
| I-337 | 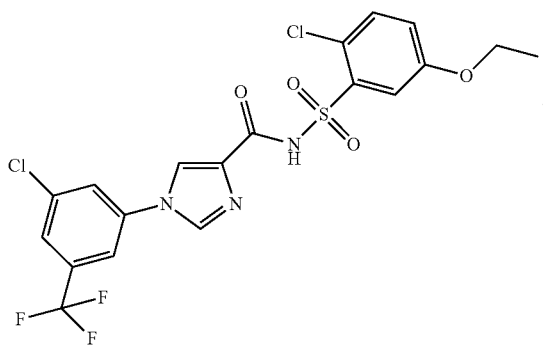 [SMILES: CCOc1ccc(Cl)c(S(=O)(=O)NC(=O)c2cn(-c3cc(Cl)cc(C(F)(F)F)c3)cn2)c1] | Example I-337: 1H-NMR(400.0 MHz, d6-DMSO): δ = 8.754(5.41); 8.663(6.43); 8.278(5.44); 8.162(5.07); 7.959(5.08); 7.601 (5.87); 7.594(6); 7.553(4.69); 7.531(5.65); 7.272(2.76); 7.264(2.68); 7.25(2.45); 7.242(2.33); 5.757(0.57); 4.15(2.31); 4.133(7.09); 4.116(7.21); 4.098(2.5); 4.086(0.62); 4.069(0.55); 4.052(0.4); 4.028(0.34); 3.962 (0.4); 3.948(0.42); 3.931(0.44); 3.911(0.45); 3.857(0.52); 3.667(0.78); 3.633(0.79); 3.618(0.8); 3.602(0.8); 3.566(0.81); 3.479(0.75); 3.463(0.7); 3.31(0.45); 3.299(0.42); 3.269(0.4); 2.676(0.65); 2.672(0.88); 2.668 (0.65); 2.507(103.12); 2.503(131.52); 2.498(97.87); 2.334(0.81); 2.329 (1.02); 2.325(0.79); 2.075(0.37); 1.382(7.61); 1.365(16); 1.347(7.51); 1.321(0.35); 0.146(0.39); 0.008(3.72); 0(85.73); −0.008(4.34); −0.058(0.38); −0.15(0.45) |

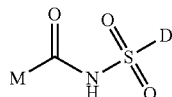
(I)
| Example No. | Structure | NMR peak list |
|---|---|---|
| I-338 | 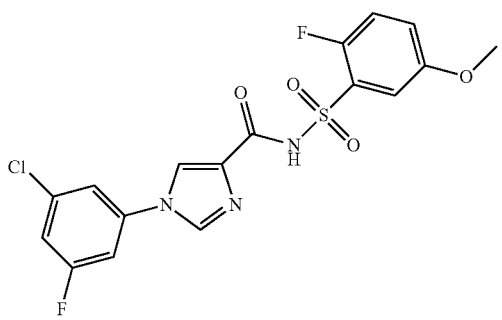 [SMILES: COc1ccc(F)c(S(=O)(=O)NC(=O)c2cn(-c3cc(F)cc(Cl)c3)cn2)c1] | Example I-338: 1H-NMR(400.0 MHz, d6-DMSO): δ = 8.654(3.03); 8.651(3.46); 8.611(3.18); 8.608(2.98); 7.838(2.37); 7.801 (0.81); 7.796(1.33); 7.79(0.74); 7.776(0.83); 7.771(1.34); 7.766(0.74); 7.565(0.84); 7.56(1.28); 7.556(0.79); 7.544(0.87); 7.539(1.29); 7.534 (0.75); 7.423(1.1); 7.415(1.38); 7.409(1.39); 7.401(1.57); 7.381(2.04); 7.357(1.52); 7.318(0.86); 7.308(1.39); 7.3(0.85); 7.295(0.6); 7.286(0.79); 7.277(0.42); 5.757(0.58); 3.831(16); 3.794(0.63); 2.509(15.5); 2.504 (20.8); 2.5(15.97); 0.008(0.76); 0(29.87) |
| I-339 | 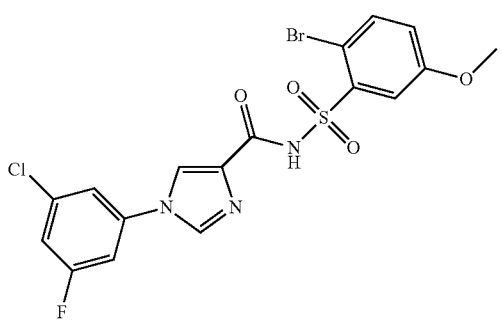 [SMILES: COc1ccc(Br)c(S(=O)(=O)NC(=O)c2cn(-c3cc(F)cc(Cl)c3)cn2)c1] | Example I-339: 1H-NMR(400.0 MHz, d6-DMSO): δ = 8.676(3.17); 8.673(3.48); 8.6(3.3); 8.598(3.32); 7.832(2.65); 7.799 (0.89); 7.794(1.4); 7.774(0.9); 7.769(1.4); 7.737(2.7); 7.715(2.99); 7.663 (2.9); 7.656(2.96); 7.57(0.88); 7.565(1.33); 7.548(0.9); 7.544(1.32); 7.212 (1.53); 7.204(1.49); 7.19(1.41); 7.183(1.35); 3.855(16); 3.815(0.52); 2.507(31.15); 2.503(40.49); 2.499(31.48); 2.076(0.65); 0.008(1.52); 0(30.93) |
| I-340 | 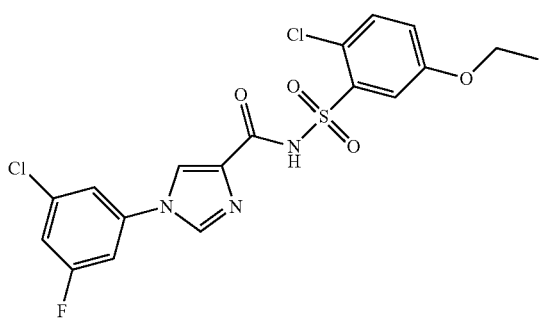 [SMILES: CCOc1ccc(Cl)c(S(=O)(=O)NC(=O)c2cn(-c3cc(F)cc(Cl)c3)cn2)c1] | Example I-340: 1H-NMR(400.0 MHz, d6-DMSO): δ = 20.008(0.51); 8.316(5.08); 5.92(0.55); 3.621(0.51); 3.541(0.75); 3.501 (0.66); 3.467(0.79); 3.454(0.86); 3.428(0.98); 3.329(1735.33); 2.938 (0.51); 2.88(0.67); 2.845(0.56); 2.671(16); 2.506(1891.72); 2.502 (2420.97); 2.499(1964.31); 2.329(15.21); 0.146(7.6); 0(1523.4); −0.058(1.3); −0.149(7.58) |
| I-341 | 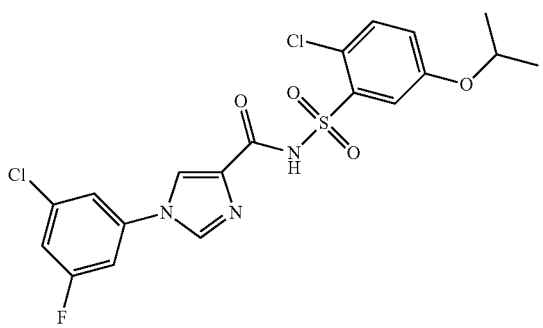 [SMILES: CC(C)Oc1ccc(Cl)c(S(=O)(=O)NC(=O)c2cn(-c3cc(F)cc(Cl)c3)cn2)c1] | Example I-341: 1H-NMR(400.0 MHz, d6-DMSO): δ = 8.676(3.22); 8.674(3.43); 8.596(3.42); 8.593(3.25); 7.835(2.46); 7.799 (0.84); 7.794(1.39); 7.789(0.78); 7.775(0.85); 7.77(1.4); 7.764(0.77); 7.586(2.82); 7.578(2.99); 7.564(0.89); 7.56(1.31); 7.555(0.82); 7.543(1); 7.537(3.89); 7.515(3.22); 7.266(1.55); 7.258(1.5); 7.243(1.34); 7.236 (1.3); 4.724(0.41); 4.709(1.08); 4.694(1.48); 4.679(1.12); 4.664(0.46); 2.508(22); 2.503(30.27); 2.499(23.58); 1.319(15.74); 1.304(16); 0(13.79); −0.008(0.84) |

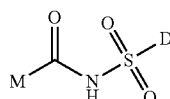
(I)
| Example No. | Structure | NMR peak list |
|---|---|---|
| I-342 | 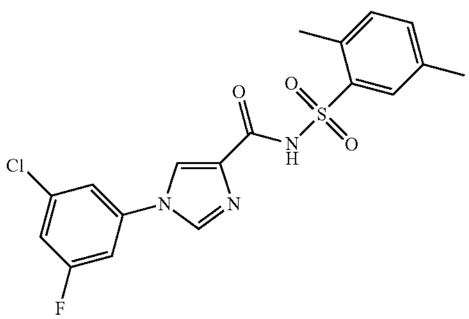 [SMILES: Cc1ccc(C)c(S(=O)(=O)NC(=O)c2cn(-c3cc(F)cc(Cl)c3)cn2)c1] | Example I-342: 1H-NMR(400.0 MHz, d6-DMSO): δ = 8.609(4.86); 8.55(5.03); 7.846(3.97); 7.83(3.88); 7.791(1.27); 7.786 (1.98); 7.782(1.15); 7.767(1.3); 7.762(1.98); 7.757(1.12); 7.55(1.31); 7.546(1.93); 7.528(1.36); 7.524(1.93); 7.393(1.64); 7.375(2.28); 7.282 (3.43); 7.263(2.41); 5.758(0.45); 2.56(16); 2.527(1.38); 2.508(27.71); 2.504(34.57); 2.5(26); 2.369(15.3); 2.326(0.75); 2.076(1.13); 0(8.34) |
| I-343 | 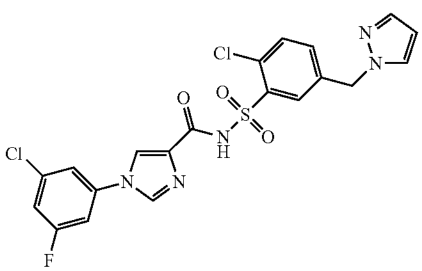 [SMILES: O=C(NS(=O)(=O)c1cc(Cn2cccn2)ccc1Cl)c1cn(-c2cc(F)cc(Cl)c2)cn1] | Example I-343: 1H-NMR(400.0 MHz, d6-DMSO): δ = 8.647(6.33); 8.595(6.7); 8.592(6.55); 8.317(0.42); 8.042(5.27); 8.036 (5.54); 7.904(5.57); 7.899(5.55); 7.831(5.25); 7.795(1.83); 7.79(2.99); 7.784(1.67); 7.77(1.86); 7.765(3.01); 7.76(1.68); 7.635(4.85); 7.614(6.25); 7.565(1.81); 7.56(2.75); 7.556(1.72); 7.544(1.88); 7.539(2.8); 7.534 (1.65); 7.513(5.18); 7.509(5.39); 7.469(2.95); 7.464(3.04); 7.449(2.36); 7.443(2.43); 6.315(3.97); 6.31(6.71); 6.305(4.1); 5.49(16); 3.96(0.32); 3.83(0.51); 3.768(0.57); 3.717(0.68); 3.587(0.86); 3.573(0.87); 3.543 (0.87); 3.463(0.77); 3.415(0.68); 3.357(0.57); 3.297(0.45); 3.268(0.41); 2.676(0.87); 2.671(1.24); 2.667(0.94); 2.542(11.93); 2.524(2.8); 2.511 (68.4); 2.507(139.65); 2.502(186.3); 2.498(141.15); 2.333(1.04); 2.329 (1.4); 2.325(1.09); 2.075(2.89); 0.146(0.43); 0.008(3.95); 0(105.04); −0.008(5.12); −0.15(0.51) |
| I-344 | 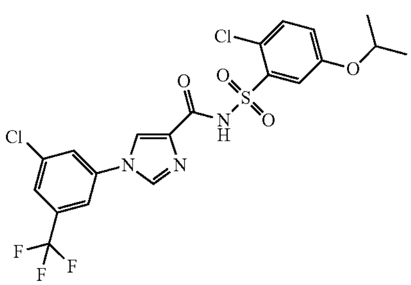 [SMILES: CC(C)Oc1ccc(Cl)c(S(=O)(=O)NC(=O)c2cn(-c3cc(Cl)cc(C(F)(F)F)c3)cn2)c1] | Example I-344: 1H-NMR(400.0 MHz, d6-DMSO): δ = 8.757(1.71); 8.66(2.53); 8.282(2.55); 8.165(2.32); 7.955(2.29); 7.587 (2.71); 7.58(2.9); 7.531(1.79); 7.508(2.11); 7.258(1.03); 7.25(1.03); 7.236 (0.9); 7.228(0.89); 4.723(0.4); 4.709(1.01); 4.694(1.37); 4.678(1.03); 4.664(0.42); 2.676(0.41); 2.671(0.57); 2.667(0.42); 2.542(0.4); 2.525 (1.29); 2.511(31.6); 2.507(65.29); 2.502(87.8); 2.498(66.99); 2.334(0.44); 2.329(0.61); 2.325(0.47); 2.075(0.47); 1.32(15.99); 1.304(16); 0.008 (1.19); 0(38.45); −0.008(1.98) |
| I-345 | 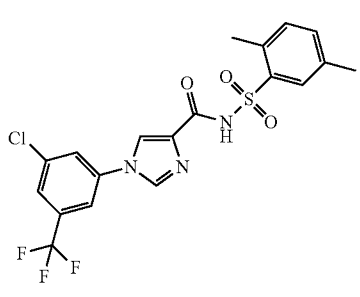 [SMILES: Cc1ccc(C)c(S(=O)(=O)NC(=O)c2cn(-c3cc(Cl)cc(C(F)(F)F)c3)cn2)c1] | Example I-345: 1H-NMR(400.0 MHz, d6-DMSO): δ = 8.695(2.8); 8.615(4.28); 8.317(0.35); 8.273(4.19); 8.159(3.89); 7.942 (3.75); 7.844(3.72); 7.388(1.44); 7.369(1.98); 7.278(2.88); 7.258(2.06); 3.332(1.45); 2.891(0.35); 2.676(0.78); 2.671(1.05); 2.667(0.8); 2.56 (16.81); 2.542(0.64); 2.524(2.97); 2.507(115.31); 2.502(150.78); 2.498 (113.21); 2.368(16); 2.333(0.8); 2.329(1.04); 2.325(0.81); 0.146(0.39); 0.008(3.47); 0(89.58); −0.008(3.98); −0.15(0.42) |

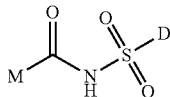
(I)
| Example No. | Structure | NMR peak list |
|---|---|---|
| I-346 | 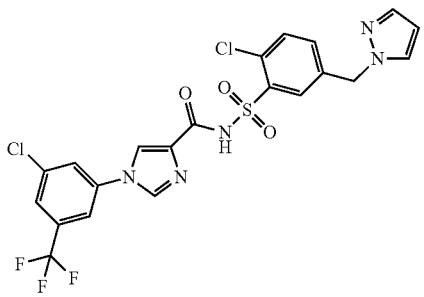 [SMILES: O=C(NS(=O)(=O)c1cc(Cn2cccn2)ccc1Cl)c1cn(-c2cc(Cl)cc(C(F)(F)F)c2)cn1] | Example I-346: 1H-NMR(400.0 MHz, d6-DMSO): δ = 8.755(6.69); 8.752(7.25); 8.673(6.95); 8.67(6.72); 8.277(5.54); 8.161 (5.1); 8.051(5.31); 8.046(5.62); 7.959(5.19); 7.905(5.46); 7.9(5.66); 7.639(5.14); 7.619(6.64); 7.514(5.31); 7.511(5.55); 7.476(3.07); 7.47 (3.14); 7.455(2.45); 7.45(2.54); 6.317(3.97); 6.312(6.69); 6.307(4.2); 5.494(16); 2.672(0.44); 2.542(1); 2.525(0.34); 2.521(0.89); 2.512(29.39); 2.507(62.85); 2.503(85.79); 2.498(66.24); 2.334(0.52); 2.33(0.69); 2.325 (0.56); 2.076(0.62); 0.008(1.21); 0(56.73); −0.008(3.22) |
| I-347 | 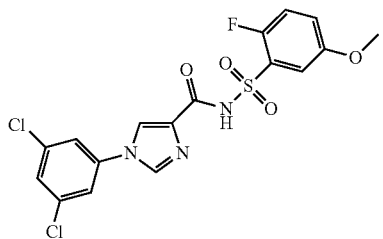 [SMILES: COc1ccc(F)c(S(=O)(=O)NC(=O)c2cn(-c3cc(Cl)cc(Cl)c3)cn2)c1] | Example I-347: 1H-NMR(400.0 MHz, d6-DMSO): δ = 8.662(2.64); 8.659(3.02); 8.611(2.85); 8.608(2.75); 7.952(6.16); 7.947 (6.68); 7.711(1.45); 7.707(2.7); 7.703(1.52); 7.419(1.03); 7.411(129); 7.405(1.35); 7.402(1.3); 7.398(1.4); 7.378(1.85); 7.355(1.37); 7.315 (0.77); 7.306(1.28); 7.298(0.79); 7.293(0.57); 7.284(0.74); 7.275((1.4); 3.83(16); 2.52(043); 2511(15.64); 2.507(33.69); 2.503(46.24); 2.498 (36.08); 2.494(19.65); 2.329(0.38); 0.008(0.62); 0(28.15); −0.008(1.66) |
| I-348 | 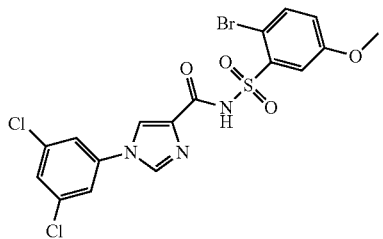 | Example I-348: 1H-NMR(400.0 MHz, d6-DMSO): δ = 8.685(3.27); 8.598(3.52); 7.946(6.64); 7.942(7.24); 7.735(2.56); 7.713 (4.6); 7.71(4.04); 7.661(2.74); 7.654(2.85); 7.21(1.43); 7.202(1.43); 7.188(1.34); 7.18(1.3); 3.854(16); 3.712(0.33); 3.705(0.33); 3.669(0.41); 3.647(0.35); 3.618(0.34); 3.596(0.35); 3.553(0.34); 3.52(0.34); 3.507 (0.33); 3.502(0.33); 2.672(0.56); 2.542(1.49); 2.502(90.69); 2.498(72.7); 2.329(0.65); 0(31.85) |
| I-349 | 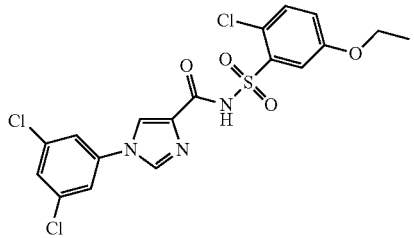 [SMILES: CCOc1ccc(Cl)c(S(=O)(=O)NC(=O)c2cn(-c3cc(Cl)cc(Cl)c3)cn2)c1] | Example I-349: 1H-NMR(400.0 MHz, d6-DMSO): δ = 8.68(8.51); 8.596(8.59); 8.002(0.33); 7.944(15.95); 7.707(6.91); 7.598 (6); 7.591(6.61); 7.555(5.11); 7.533(6.09); 7.51(0.36); 7.274(3.34); 7.267(3.53); 7.252(3.08); 7.245(3.07); 4.149(2.66); 4.132(7.66); 4.115 (7.97); 4.098(3.19); 4.069(0.71); 4.053(0.49); 4.009(0.35); 3.996(0.35); 3.963(0.35); 3.948(0.35); 3.932(0.34); 2.672(0.41); 2.503(93.39); 2.329 (0.9); 1.382(7.73); 1.364(16); 1.347(8.59); 1.232(0.41); 1.185(0.33); 0(6.98) |
| I-350 | 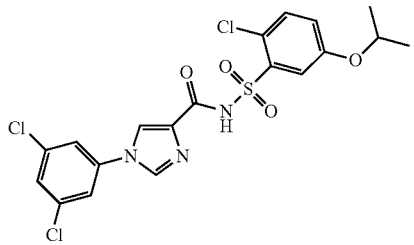 [SMILES: CC(C)Oc1ccc(Cl)c(S(=O)(=O)NC(=O)c2cn(-c3cc(Cl)cc(Cl)c3)cn2)c1] | Example I-350: 1H-NMR(400.0 MHz, d6-DMSO): δ = 8.672(1.55); 8.588(2.5); 7.95(7.06); 7.946(7.34); 7.706(1.63); 7.702 (2.78); 7.698(1.68); 7.582(2.64); 7.574(2.82); 7.528(1.61); 7.506(1.89); 7.255(0.95); 7.248(1.01); 7.233(0.89); 7.226(0.87); 5.757(0.58); 4.721 (0.4); 4.706(1); 4.691(1.34); 4.676(1.03); 4.661(0.42); 2.672(0.67); 2.667 (0.51); 2.542(28.24); 2.507(80.26); 2.502(103.69); 2.498(77.83); 2.334 (0.55); 2.329(0.72); 2.325(0.56); 1.318(16); 1.303(15.97); 0.146(0.49); 0.008(4.65); 0(105.64); −0.008(5.45); −0.15(0.52) |

-continued
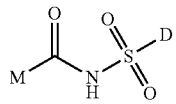
(I)
| Example No. | Structure | NMR peak list |
|---|---|---|
| I-351 | 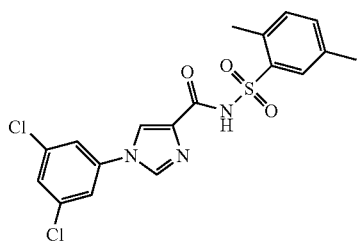 [SMILES: Cc1ccc(C)c(S(=O)(=O)NC(=O)c2cn(-c3cc(Cl)cc(Cl)c3)cn2)c1] | Example I-351: 1H-NMR(400.0 MHz, d6-DMSO): δ = 8.624(4.78); 8.622(5.23); 8.552(5.39); 8.549(5.4); 7.943(10); 7.939 (10.66); 7.844(4.05); 7.697(2.71); 7.693(4.59); 7.689(2.69); 7.661(0.56); 7.393(1.74); 7.374(2.4); 7.301(0.97); 7.282(3.69); 7.263(2.51); 7.252 (0.65); 3.586(0.34); 3552(0.41); 3.365(1.14); 3.343(1.15); 2.672(0.6); 2.558(16.79); 2.527(3.66); 2.507(59.14); 2.503(75.2); 2.499(58.2); 2.368 (16); 2.325(2.39); 2.076(0.86); 0(7.7) |
| I-352 | 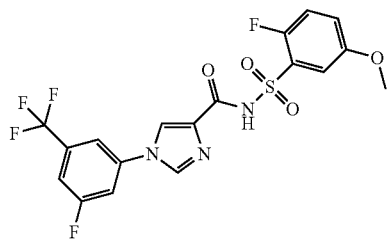 | Example I-352: 1H-NMR(400.0 MHz, d6-DMSO): δ = 8.738(4.04); 8.681(3.93); 8.13(1.78); 8.106(1.66); 8.071(3.31); 7.818 (1.65); 7.798(1.61); 7.425(1.9); 7.417(2.34); 7.411(2.42); 7.404(2.4); 7.382(2.37); 7.358(1.65); 7.318(1.5); 7.31(1.95); 7.301(1.3); 7.287(1.11); 7.279(0.56); 3.832(16); 3.794(0.79); 2.504(47.2); 2.33(0.37); 0(3.22) |
| I-353 | 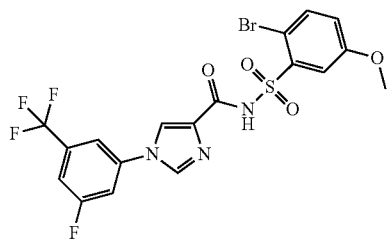 [SMILES: COc1ccc(Br)c(S(=O)(=O)NC(=O)c2cn(-c3cc(F)cc(C(F)(F)F)c3)cn2)c1] | Example I-353: 1H-NMR(400.0 MHz, d6-DMSO): δ = 8.757(3.49); 8.128(1.32); 8.103(1.33); 8.06(2.74); 7.822 (1.27); 7.801(1.31); 7.739(2.59); 7.717(2.86); 7.667(2.92); 7.66(3.14); 7.214(1.48); 7.206(1.52); 7.192(1.43); 7.184(1.42); 3.856(16); 3.815 (0.44); 2.503(48.5); 2.499(39.97); 2.33(0.37); 0(4.43) |
| I-354 | 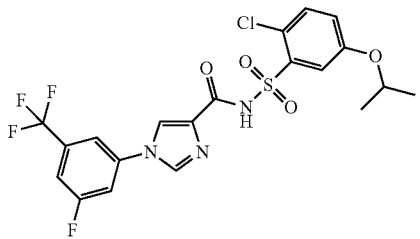 [SMILES: CC(C)Oc1ccc(Cl)c(S(=O)(=O)NC(=O)c2cn(-c3cc(F)cc(C(F)(F)F)c3)cn2)c1] | Example I-354: 1H-NMR(400.0 MHz, d6-DMSO): δ = 8.758(3.44); 8.668(3.5); 8.665(3.44); 8.129(1.27); 8.105(1.29); 8.066 (2.64); 7.817(1.21); 7.795(1.24); 7.59(2.83); 7.583(2.99); 7.538(2.59); 7.516(3.05); 7.266(1.54); 7.259(1.51); 7.244(1.33); 7.237(1.29); 4.727 (0.43); 4.712(1.11); 4.697(1.51); 4.682(1.13); 4.666(0.46); 2.508(28.28); 2.504(36.89); 2.5(28.73); 1.321(16); 1.306(15.95); 0(3.46) |
| I-355 | 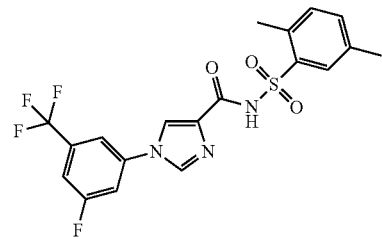 [SMILES: Cc1ccc(C)c(S(=O)(=O)NC(=O)c2cn(-c3cc(F)cc(C(F)(F)F)c3)cn2)c1] | Example I-355: 1H-NMR(400.0 MHz, d6-DMSO): δ = 8.696(4.57); 8.693(4.92); 8.647(0.33); 8.644(0.36); 8.622(5.29); 8.619 (5.06); 8.571(0.32); 8.119(1.78); 8.094(1.8); 8.061(3.63); 7.849(3.8); 7.803(1.67); 7.782(1.7); 7.394(1.6); 7.375(2.22); 7.284(3.34); 7.264 (2.37); 3.52(0.42); 3.351(0.92); 2.677(0.37); 2.672(0.51); 2.668(0.4); 2.562(16); 2.526(1.82); 2.508(52.66); 2.503(68.07); 2.499(51.33); 2.37(15.28); 2.326(0.69); 2.076(1.71); 0(7.38) |

-continued
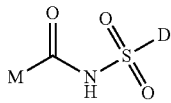
(I)
| Example No. | Structure | NMR peak list |
|---|---|---|
| I-356 | 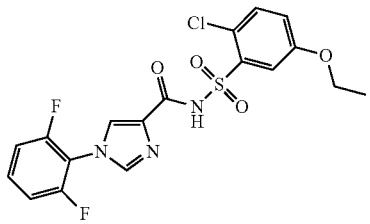 [SMILES: CCOc1ccc(Cl)c(S(=O)(=O)NC(=O)c2cn(-c3c(F)cccc3F)cn2)c1] | Example I-356: 1H-NMR(400.0 MHz, d6-DMSO): δ = 8.368(6.03); 8.214(5.54); 7.683(0.53); 7.667(1.21); 7.662(1.13); 7.646 (2.44); 7.629(1.27); 7.624(1.67); 7.608(0.97); 7.601(5.88); 7.594(6.2); 7.567(5.65); 7.545(6.62); 7.459(4.21); 7.438(7.15); 7.417(3.24); 7.286 (3.32); 7.278(3.25); 7.264(2.91); 7.256(2.85); 4.149(2.19); 4.132(7.15); 4.115(7.27); 4.097(2.38); 2.672(0.33); 2.507(43.31); 2.503(57.64); 2.498 (44.61); 2.33(0.43); 2.326(0.35); 2.076(1.69); 1.381(7.61); 1.364(16); 1.346(757); 0.008(1.29); 0(36.55); −0.008(2.06) |
| I-357 | 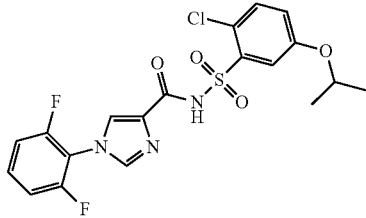 [SMILES: CC(C)Oc1ccc(Cl)c(S(=O)(=O)NC(=O)c2cn(-c3c(F)cccc3F)cn2)c1] | Example I-357: 1H-NMR(400.0 MHz, d6-DMSO): δ = 8.374(2.6); 8.216(2.56); 8.214(2.5); 7.667(0.58); 7.662(0.52); 7.651 (0.43); 7.646(1.16); 7.64(0.52); 7.629(0.56); 7.624(0.78); 7.608(0.35); 7.584(2.79); 7.577(2.99); 7.55(2.62); 7.528(3.09); 7.46(1.96); 7.439(3.35); 7.418(1.49); 7.278(1.48); 7.27(1.46); 7.255(1.28); 7.248(1.27); 5.758 (0.71); 4.724(0.4); 4.709(1.05); 4.694(1.44); 4.679(1.08); 4.664(0.43); 2.542(0.79); 2.508(22.92); 2.503(30.83); 2.499(23.32); 1.318(15.97); 1.303(16); 0.008(0.38); 0(17.45); −0.008(1.03) |
| I-358 | 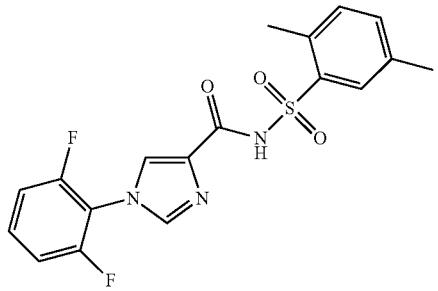 [SMILES: Cc1ccc(C)c(S(=O)(=O)NC(=O)c2cn(-c3c(F)cccc3F)cn2)c1] | Example I-358: 1H-NMR(400.0 MHz, d6-DMSO): δ = 8.297(4.06); 8.183(3.86); 8.18(3.91); 7.846(3.71); 7.675(0.43); 7.659 (0.93); 7.653(0.83); 7.643(0.69); 7.638(1.88); 7.632(0.83); 7.621(0.91); 7.616(1.26); 7.6(0.56); 7.45(3.17); 7.429(5.3); 7.408(2.47); 7.4(2.04); 7.38(2.16); 7.377(2.22); 7.288(3.45); 7.269(2.45); 2.569(16); 2.526(0.74); 2.512(10.97); 2.508(22.24); 2.503(29.64); 2.499(22.44); 2.369(15.36); 2.326(0.34); 2.076(1.54); 0.008(0.82); 0(21.75); −0.008(0.89) |
| I-359 | 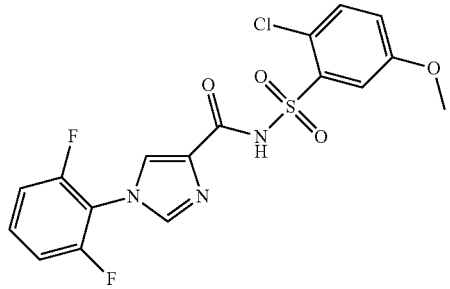 [SMILES: COc1ccc(Cl)c(S(=O)(=O)NC(=O)c2cn(-c3c(F)cccc3F)cn2)c1] | Example I-359: 1H-NMR(400.0 MHz, d6-DMSO): δ = 8.369(2.94); 8.216(2.66); 7.667(0.61); 7.662(0.59); 7.646(1.22); 7.623 (3.38); 7.615(3.23); 7.588(2.71); 7.566(3.16); 7.46(2.01); 7.438(3.41); 7.418(1.55); 7.308(1.65); 7.3(1.63); 7.285(1.45); 7.278(1.42); 3.861(16); 2.508(17.87); 2.503(24.23); 2.499(19.49); 2.076(0.38); 0.008(0.38); 0(12.68) |
| I-360 | 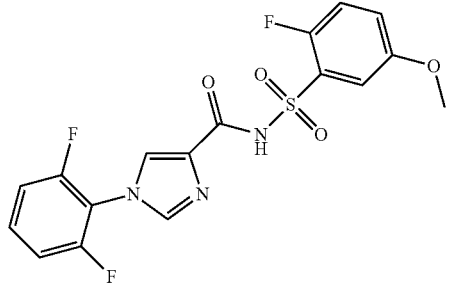 [SMILES: COc1ccc(F)c(S(=O)(=O)NC(=O)c2cn(-c3c(F)cccc3F)cn2)c1] | Example I-360: 1H-NMR(400.0 MHz, d6-DMSO): δ = 8.337(.1.77); 8.21(2.08); 7.666(0.62); 7.661(0.52); 7.65(0.39); 7.645 (1.09):7.629(0.53); 7.623(0.74); 7.458(1.85); 7.437(3.16); 7.42(1.33); 7.412(2.75); 7.407(1.56); 7.398(1.35); 7.389(1.73); 7.365(1.21); 7.325 (0.7); 7.316(1.16); 7.307(0.72); 7.303(0.54); 7.294(0.68); 7.285(0.36); 3.832(16); 3.793(0.41); 2.672(0.35); 2.524(0.66); 2.511(20.59); 2.507 (42.62); 2.502(57.29); 2.498(43.89); 2.329(0.4); 0.008(1.03); 0(34.15); −0.008(1.72) |

-continued
(I)
| Example No. | Structure | NMR peak list |
|---|---|---|
| I-361 | 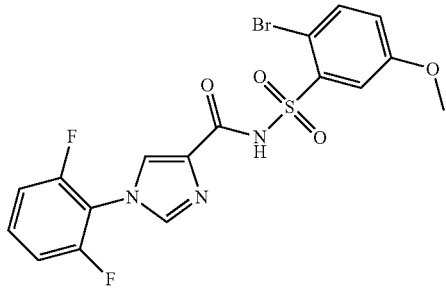 | Example I-361: 1H-NMR(400.0 MHz, d6-DMSO): δ = 8.38(2.7); 8.222(2.47); 8.22(2.45); 7.749(2.89); 7.727(3.19); 7.668 (3.48); 7.661(3.4); 7.653(0.5); 7.647(1.17); 7.642(0.51); 7.63(0.55); 7.626 (0.77); 7.61(0.34); 7.461(1.94); 7.44(3.27); 7.419(1.46); 7.225(1.61); 7.217(1.57); 7.203(1.49); 7.195(1.46); 3.857(16); 2.525(0.33); 2.512(7.5); 2.508(15.43); 2.503(20.57); 2.499(15.46); 2.494(7.92); 0.008(0.48); 0(15.06); −0.008(0.66) |
| I-362 | 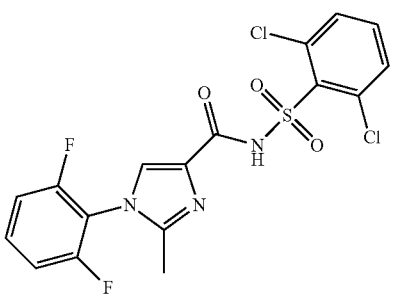 [SMILES: Cc1nc(C(=O)NS(=O)(=O)c2c(Cl)cccc2Cl)cn1-c1c(F)cccc1F] | Example I-362: 1H-NMR(400.0 MHz, d6-DMSO): δ = 8.212(6.35); 7.767(0.41); 7.751(0.93); 7.746(0.9); 7.729(1.69); 7.713 (0.97); 7.708(1.08); 7.692(0.49); 7.624(3.39); 7.62(3.71); 7.602(8.62); 7.558(3.16); 7.541(2.2); 7.536(1.79); 7.519(1.24); 7.493(2.75); 7.472 (4.74); 7.451(2.24); 2.507(26.4); 2.504(32.56); 2.5(25.09); 2.273(16); 0(43.65) |
| I-363 | 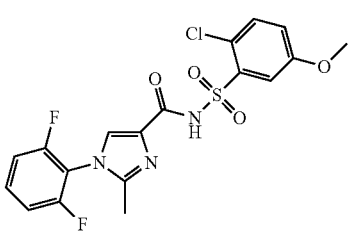 [SMILES: COc1ccc(Cl)c(S(=O)(=O)NC(=O)c2cn(-c3c(F)cccc3F)c(C)n2)c1] | Example I-363: 1H-NMR(400.0 MHz, d6-DMSO): δ = 8.206(4.05); 7.737(0.56); 7.731(0.49); 7.721(0.38); 7.715(1.07); 7.71 (0.44); 7.699(0.52); 7.694(0.71); 7.604(2.76); 7.597(2.92); 7.559(2.69); 7.537(3.16); 7.482(1.81); 7.461(2.86); 7.44(1.41); 7.275(1.57); 7.267 (1.53); 7.253(1.37); 7.245(1.34); 3.849(16); 2.542(1.69); 2.521(0.51); ; 2.512(9.59); 2.508(20.77); 2.503(28.25); 2.498(21.1); 2.494(10.72); 2.234(10.21); 0(11.08); −0.008(0.52) |
| I-364 | 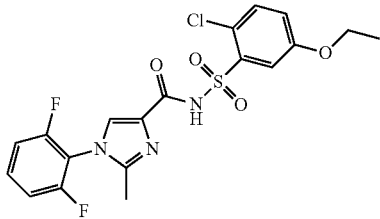 [SMILES: CCOc1ccc(Cl)c(S(=O)(=O)NC(=O)c2cn(-c3c(F)cccc3F)c(C)n2)c1] | Example I-364: 1H-NMR(400.0 MHz, d6-DMSO): δ = 9.562(1.03); 7.68(0.44); 7.67(0.41); 7.654(0.85); 7.648(0.77); 7.632 (1.66); 7.616(0.81); 7.611(1.09); 7.595(0.47); 7.515(4.2); 7.507(4.32); 7.475(5.61); 7.417(2.85); 7.397(4.62); 7.376(2.28); 7.266(4.05); 7.245 (4.66); 7.032(0.93); 6.948(2.32); 6.94(2.25); 6.927(2.04); 6.919(2); 4.062 (1.53); 4.045(5.07); 4.027(5.14); 4.01(1.6); 3.56(2.77); 3.546(2.11); 3.537 (2.73); 3.489(2.21); 3.474(3.95); 3.46(2.36); 3.342(2.66); 3.255(2.85); 2.672(0.44); 2.667(0.4); 2.654(2.48); 2.628(2.49); 2.542(14.42); 2.525 (0.89); 2.511(23.19); 2.507(46.64); 2.503(60.67); 2.498(44.27); 2.33 (0.39); 2.1(16); 1.941(0.77); 1.926(1.95); 1.912(3.01); 1.897(1.86); 1.883 (0.68); 1.672(1.76); 1.659(2.02); 1.647(1.69); 1.641(1.76); 1.623(2.77); 1.61(3.48); 1.599(3.08); 1.359(5.5); 1.342(11.72); 1.325(5.37); 0.008 (0.78); 0(23.6); −0.008(0.88) |
| I-365 | 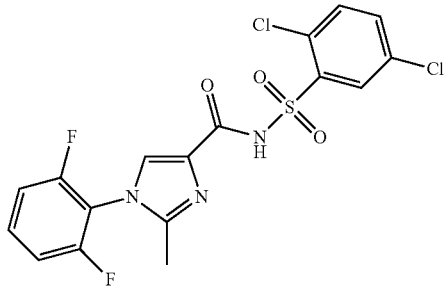 [SMILES: Cc1nc(C(=O)NS(=O)(=O)c2cc(Cl)ccc2Cl)cn1-c1c(F)cccc1F] | Example I-365: 1H-NMR(400.0 MHz, d6-DMSO): δ = 8.212(4.98); 8.058(3.99); 8.054(4.02); 7.774(0.45); 7.754(1.27); 7.729 (2.91); 7.723(3.03); 7.707(3.57); 7.703(3.54); 7.646(3.99); 7.625(2.44); 7.498(2.96); 7.476(5.21); 7.455(2.56); 4.764(0.38); 4.695(0.46); 4.596 (0.61); 4.581(0.62); 4.52(0.69); 4.489(0.71); 4.473(0.73); 4.425(0.73); 4.409(0.72); 4.384(0.7); 4.325(0.65); 4.307(0.63); 4.299(0.61); 4.273 (0.57); 4.167(0.43); 4.133(0.39); 4.084(0.33); 4.069(0.33); 2.671(0.51); 2.503(78.99); 2.329(0.81); 2.295(16); 2.075(0.35); 0(40.32) |

-continued
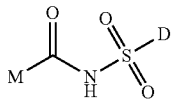
(I)
| Example No. | Structure | NMR peak list |
|---|---|---|
| I-366 | 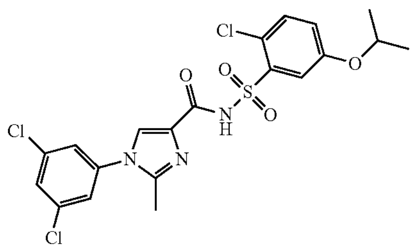 [SMILES: Cc1nc(C(=O)NS(=O)(=O)c2cc(OC(C)C)ccc2Cl)cn1-c1cc(Cl)cc(Cl)c1] | Example I-366: 1H-NMR(400.0 MHz, d6-DMSO): δ = 8.151(2.24); 7.933(4.46); 7.804(2.94); 7.744(6.83); 7.74(6.27); 7.596 (0.42); 7.543(2.65); 7.536(2.77); 7.378(2.28); 7.356(2.65); 7.254(5.57); 7.082(1.45); 7.075(1.45); 7.06(1.31); 7.053(1.27); 4.66(0.48); 4.645(1.1); 4.63(1.48); 4.615(1.12); 4.599(0.5); 3.477(0.36); 2.671(0.34); 2.502 (74.18); 2.353(12.69); 2.075(0.89); 1.933(0.33); 1.614(0.36); 1.303 (14.62); 1.288(16); 1.272(2.27); 0(58.54); −0.15(0.4) |
| I-367 | 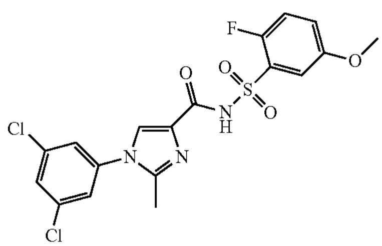 [SMILES: COc1ccc(F)c(S(=O)(=O)NC(=O)c2cn(-c3cc(Cl)cc(Cl)c3)c(C)n2)c1] | Example I-367: 1H-NMR(400.0 MHz, d6-DMSO): δ = 8.11(3.65); 7.859(2.98); 7.783(7.01); 7.666(0.59); 7.383(1.35); 7.375 (1.74); 7.37(1.58); 7.362(1.4); 7.282(0.83); 7.26(2.16); 7.236(1.34); 7.189 (1); 7.181(1.6); 7.172(1.08); 7.159(0.94); 4.21(0.35); 4.19(0.37); 4.13 (0.41); 4.085(0.44); 4.08(0.44); 4.067(0.45); 4.064(0.45); 4.039(0.45); 4.02(0.46); 3.98(0.53); 3.901(0.44); 3.884(0.43); 3.859(0.43); 3.802(16); 3.793(3.21); 2.671(0.38); 2.502(60.41); 2.386(13.24); 2.332(0.6); 2.074 (1.81); 1.177(0.39); −0.001(32.73) |
| I-368 | 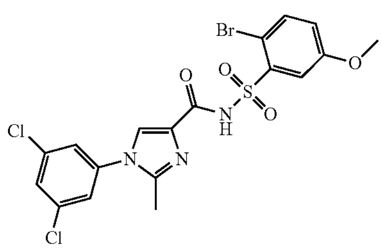 | Example I-368: 1H-NMR(400.0 MHz, d6-DMSO): δ = 8.155(5.2); 7.863(1.53); 7.858(3.17); 7.854(1.99); 7.792(7.31); 7.788 (6.73); 7.655(2.42); 7.636(3.41); 7.634(3.55); 7.629(3.3); 7.114(1.29); 7.106(1.27); 7.092(1.2); 7.085(1.18); 3.83(16); 3.814(0.46); 2.507(24); 2.502(32.32); 2.498(24.33); 2.392(13.38); 0.008(0.61); 0(23.56); −0.008(1.15) |
| I-369 | 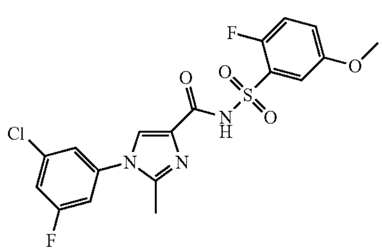 | Example I-369: 1H-NMR(400.0 MHz, d6-DMSO): δ = 8.129(5.01); 7.721(2.19); 7.7(2.16); 7.661(4.27); 7.636(2.29); 7.614 (2.07); 7.38(2.65); 7.294(1.19); 7.271(2.52); 7.248(1.71); 7.192(2.23); 7.171(1.35); 4.946(0.32); 4.911(0.34); 4.898(0.34); 4.862(0.37); 4.85 (0.38); 4.839(0.38); 4.806(0.41); 4.786(0.41); 4.774(0.42); 4.757(0.44); 4.746(0.44); 4.718(0.45); 4.711(0.44); 4.666(0.46); 4.639(0.46); 4.631 (0.46); 4.586(0.46); 4.575(0.45); 4.494(0.42); 4.467(0.41); 4.446(0.39); 4.43(0.38); 4.42(0.38); 4.412(0.37); 4.389(0.35); 4.332(0.32); 3.805(16); 2.504(38.7); 2.402(14.33); 2.332(0.46); 2.076(4.54); 0(7.54) |
| I-370 | 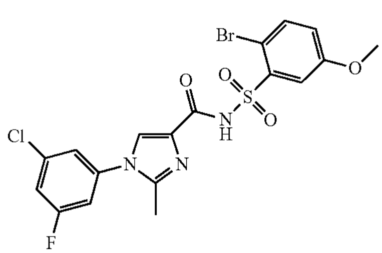 [SMILES: COc1ccc(Br)c(S(=O)(=O)NC(=O)c2cn(-c3cc(Cl)cc(Cl)c3)c(C)n2)c1] | Example I-370: 1H-NMR(400.0 MHz, d6-DMSO): δ = 8.154(5.66); 7.719(0.77); 7.714(1.44); 7.709(1); 7.698(0.79); 7.693 (1.47); 7.688(1.01); 7.658(4.33); 7.646(1.32); 7.637(5.41); 7.63(3.45); 7.623(1.22); 7.618(1.45); 7.613(0.78); 7.118(1.36); 7.11(1.38); 7.096 (1.27); 7.088(1.29); 3.831(16); 3.814(0.56); 2.507(23.86); 2.503(31.71); 2.498(24.17); 2.403(13.62); 2.075(10.95); 0.008(0.39); 0(11.35) |

-continued
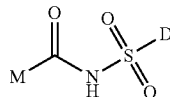
(I)
| Example No. | Structure | NMR peak list |
|---|---|---|
| I-371 | 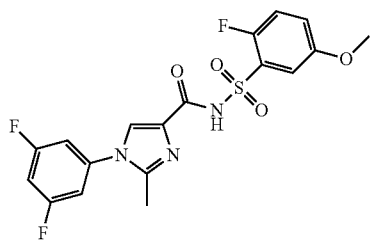 | Example I-371: 1H-NMR(400.0 MHz, d6-DMSO): δ = 8.126(5.25); 7.55(1.63); 7.527(3.17); 7.506(5.64); 7.491(4.66); 7.38 (2.74); 7.297(1.27); 7.274(2.59); 7.251(1.76); 7.195(2.28); 3.806(16); 2.504(28.88); 2.413(14.81); 2.332(0.38); 2.076(3.5); −0.001(5.65) |
| I-372 | 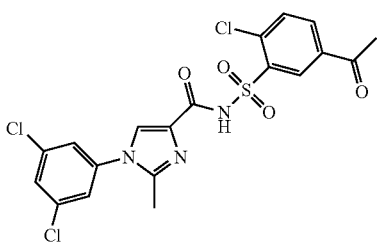 [SMILES: CC(=O)c1ccc(Cl)c(S(=O)(=O)NC(=O)c2cn(-c3cc(Cl)cc(Cl)c3)c(C)n2)c1] | Example I-372: 1H-NMR(400.0 MHz, d6-DMSO): δ = 8.576(3.14); 8.571(3.3); 8.11(6.03); 8.102(1.99); 8.086(1.68); 8.081 (1.69); 7.89(1.95); 7.886(3.38); 7.881(2.17); 7.808(7.71); 7.803(7.14); 7.701(2.82); 7.68(2.6); 2.632(16); 2.507(38.54); 2.503(49.34); 2.498 (38.77); 2.418(14); 2.333(0.35); 2.329(0.42); 2.325(0.36); 2.319(0.38); 2.075(1.44); 1.179(0.56); 1.175(0.55); 0(17.69) |
| I-373 | 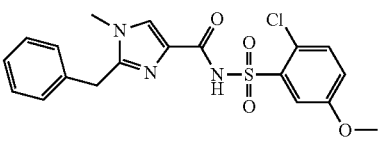 [SMILES: COc1ccc(Cl)c(S(=O)(=O)NC(=O)c2cn(C)c(Cc3ccccc3)n2)c1] | Example I-373: 1H-NMR(400.0 MHz, d6-DMSO): δ = 7.823(3.68); 7.563(2.76); 7.555(2.91); 7.393(2.11); 7.371(2.52); 7.366 (0.82); 7.363(1.1); 7.346(2.91); 7.327(2.5); 7.289(1.1); 7.286(0.88); 7.271 (1.46); 7.264(0.41); 7.248(2.57); 7.245(2.89); 7.227(2.09); 7.093(1.2); 7.085(1.21); 7.071(1.06); 7.063(1.05); 4.252(4.32); 3.815(0.73); 3.805 (16); 3.612(11.31); 2.52(0.59); 2.511(18.62); 2.507(40.58); 2.502(55.15); 2.498(41.21); 2.493(21.02); 2.329(0.41); 2.324(0.33); 2.075(6.06); 0.008 (0.5); 0(22.09); −0.008(0.97) |
| I-374 | 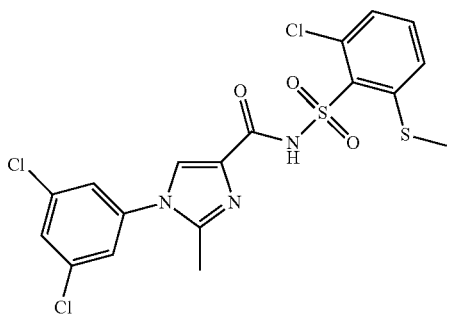 | Example I-374: 1H-NMR(400.0 MHz, d6-DMSO): δ = 8.139(3.44); 7.843(1.97); 7.839(3.59); 7.834(2.14); 7.776(9.1); 7.771 (7.75); 7.489(0.93); 7.469(2.29); 7.449(1.74); 7.359(2.05); 7.34(1.51); 7.317(2.24); 7.298(1.83); 5.753(6.87); 2.675(0.41); 2.67(0.58); 2.666 (0.38); 2.54(1.87); 2.524(1.19); 2.51(42.72); 2.506(82.03); 2.501(105.19); 2.496(77.4); 2.492(38.5); 2.431(13.16); 2.373(16); 2.332(0.76); 2.328 (0.91); 2.323(0.73); 2.086(0.47); 0.008(1.15); 0(29.86); −0.008(1.26) |
| I-375 | 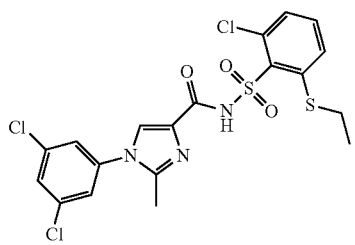 | Example I-375: 1H-NMR(400.0 MHz, d6-DMSO): δ = 8.152(5.15); 7.84(1.77); 7.836(3.47); 7.832(2.28); 7.773(8.26); 7.769 (7.62); 7.742(0.42); 7.737(0.39); 7.47(0.76); 7.449(2.22); 7.43(2.54); 7.414(2.7); 7.397(1.18); 7.32(2.07); 7.318(2.08); 7.302(1.69); 7.299(1.62); 2.984(0.98); 2.966(3.46); 2.947(3.64); 2.929(1.21); 2.54(3.9); 2.506 (46.87); 2.501(63.77); 2.497(51.17); 2.372(16); 2.352(1.34); 2.333(0.65); 2.328(0.75); 1.285(4.25); 1.267(9.26); 1.249(4.38); 1.183(0.5); 1.12 (1.96); 0(13.33) |

-continued
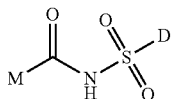
(I)
| Example No. | Structure | NMR peak list |
|---|---|---|
| I-376 | 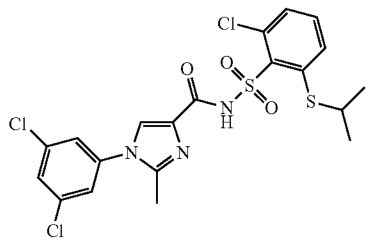 | Example I-376: 1H-NMR(400.0 MHz, d6-DMSO): δ = 8.16(2.74); 7.834(2.03); 7.83(3.72); 7.825(2.31); 7.766(8.64); 7.761 (7.77); 7.73(0.32); 7.522(1.05); 7.503(2.1); 7.477(1.46); 7.458(2.16); 7.445(0.33); 7.438(1.05); 7.348(1.86); 7.346(1.9); 7.329(1.4); 7.327(1.36); 5.753(16); 3.672(0.35); 3.656(0.92); 3.64(1.26); 3.623(0.98); 3.606 (0.43); 2.524(0.37); 2.511(11.84); 2.506(24.22); 2.502(32.17); 2.497 (24.27); 2.493(12.52); 2.372(15.1); 1.988(1.02); 1.397(15.99); 1.306(1.08); 1.282(0.98); 1.269(15.59); 1.252(15.35); 1.224(0.94); 1.207(0.88); 1.193 (0.45); 1.188(0.66); 1.175(0.71); 1.172(0.51); 1.158(0.33); 0.008(0.6); 0(23.33); −0.008(1.25) |
| I-377 | 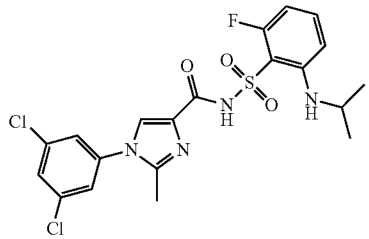 [SMILES: Cc1nc(C(=O)NS(=O)(=O)c2c(F)cccc2NC(C)C)cn1-c1cc(Cl)cc(Cl)c1] | Example I-377: 1H-NMR(400.0 MHz, d6-DMSO): δ = 8.159(4.77); 7.828(1.74); 7.824(3.36); 7.819(2.21); 7.761(8.02); 7.757 (7.33); 7.341(0.53); 7.32(1.13); 7.303(1.15); 7.283(0.58); 6.907(0.46); 6.606(1.8); 6.584(1.72); 6.368(0.98); 6.348(1.06); 6.341(1.15); 6.321 (0.95); 3.738(0.54); 3.723(0.71); 3.711(0.59); 2.541(0.64); 2.506(21.51); 2.502(28.3); 2.497(21.94); 2.358(14.67); 2.333(0.38); 2.328(0.34); 1.218 (15.91); 1.202(16); 0(2.11) |
| I-378 | 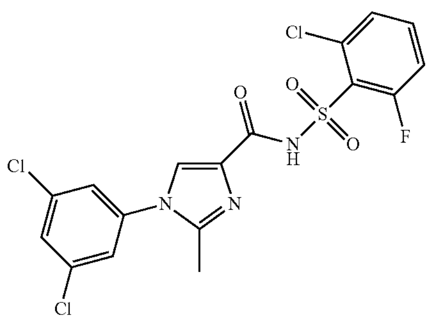 [SMILES: Cc1nc(C(=O)NS(=O)(=O)c2c(F)cccc2Cl)cn1-c1cc(Cl)cc(Cl)c1] | Example I-378: 1H-NMR(400.0 MHz, d6-DMSO): δ = 8.106(4.8); 7.877(3.7); 7.873(2.42); 7.808(8.7); 7.803 (8.12); 7.544(0.57); 7.53(0.69); 7.523(1.32); 7.51(1.35); 7.503(0.93); 7.489 (0.79); 7.374(2.29); 7.354(1.74); 7.305(1.01); 7.28(1.32); 7.259(0.83); 2.506(27.17); 2.502(36.23); 2.497(28.06); 2.416(16); 2.074(2.27); 0.008(1.15); 0(32.22) |
| I-379 | 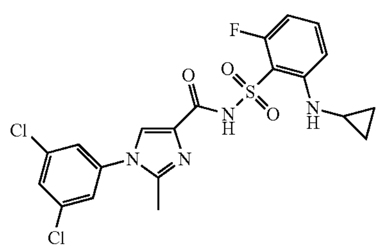 [SMILES: Cc1nc(C(=O)NS(=O)(=O)c2c(F)cccc2NC2CC2)cn1-c1cc(Cl)cc(Cl)c1] | Example I-379: 1H-NMR(400.0 MHz, d6-DMSO): δ = 8.141(6.18); 7.837(1.95); 7.832(3.86); 7.828(2.37); 7.764(9.11); 7.76 (8.24); 7.4(0.54); 7.379(1.15); 7.363(1.16); 7.343(0.6); 7.164(1.49); 6.943 (2.09); 6.922(1.94); 6.464(0.97); 6.444(1.04); 6.437(1.1); 6.416(0.93); 2.524(0.51); 2.51(10.03); 2.506(20.15); 2.502(26.68); 2.497(20.01); 2.493(10.6); 2.364(16); 2.074(5.52); 0.844(0.64); 0.832(2.14); 0.827 (2.75); 0.815(2.7); 0.81(2.34); 0.799(0.77); 0.51(0.78); 0.5(2.5); 0.494 (2.78); 0.492(2.75); 0.485(2.47); 0.474(0.72); 0.008(0.61); 0(18.68); −0.008(0.76) |
| I-380 | 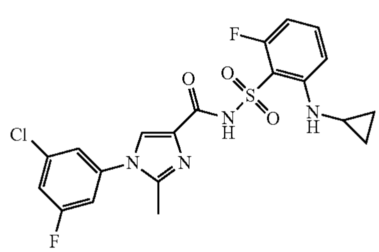 [SMILES: Cc1nc(C(=O)NS(=O)(=O)c2c(F)cccc2NC2CC2)cn1-c1cc(F)cc(Cl)c1] | Example I-380: 1H-NMR(400.0 MHz, d6-DMSO): δ = 9.57(0.84); 7.729(2.1); 7.562(0.78); 7.557(1.5); 7.552(1.11); 7.541 (0.72); 7.536(1.62); 7.53(2.53); 7.523(3.78); 7.518(6.89); 7.509(1.71); 7.504(0.75); 7.491(1.16); 7.486(1.55); 7.48(0.73); 7.147(0.61); 7.132 (0.76); 7.127(1.26); 7.111(1.26); 7.107(0.83); 7.091(0.66); 6.765(2.05); 6.744(1.85); 6.253(0.97); 6.232(1.06); 6.228(1.1); 6.208(0.92); 5.754 (10.25); 3.561(2.26); 3.548(1.7); 3.538(2.2); 3.49(1.74); 3.475(3.12); 3.46(1.82); 3.325(2.04); 3.268(1.65); 3.254(2.72); 3.24(1.66); 2.659 (2.09); 2.633(2.05); 2.54(13.89); 2.524(0.66); 2.51(12.31); 2.506(24.58); 2.501(32.65); 2.497(24.41); 2.492(12.32); 2.399(0.44); 2.391(0.67); 2.383(0.91); 2.377(0.92); 2.368(0.74); 2.361(0.49); 2.29(16); 1.943(0.61); 1.928(1.6); 1.913(2.52); 1.899(1.53); 1.884(0.57); 1.673(1.42); 1.66(1.63); 1.643(1.65); 1.625(2.13); 1.613(2.7); 1.6(2.41); 0.762(0.64); 0.75(2.04); 0.745(2.63); 0.734(2.6); 0.728(2.15); 0.718(0.74); 0.45(0.77); 0.44(2.5); 0.434(2.6); 0.431(2.58); 0.425(2.35); 0.414(0.68); 0.008(0.33); 0(9.51); −0.008(0.36) |

-continued
(I)
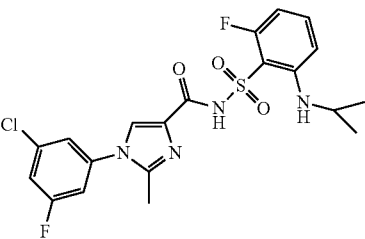 [SMILES: Cc1nc(C(=O)NS(=O)(=O)c2c(F)cccc2NC(C)C)cn1-c1cc(F)cc(Cl)c1]
| Example No. | Structure | NMR peak list |
|---|---|---|
| I-381 | 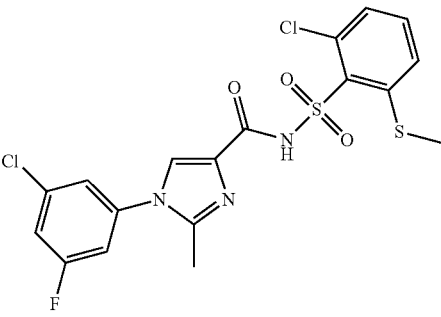 [SMILES: CSc1cccc(Cl)c1S(=O)(=O)NC(=O)c1cn(-c2cc(F)cc(Cl)c2)c(C)n1] | Example I-381: 1H-NMR(400.0 MHz, d6-DMSO): δ = 8.156(3.76); 7.684(0.75); 7.679(1.39); 7.673(1.01); 7.662(0.75); 7.657 (1.4); 7.652(1.03); 7.627(2.79); 7.614(1.36); 7.609(1.53); 7.604(0.77); 7.591(1.11); 7.586(1.49); 7.581(0.81); 7.342(0.49); 7.321(1.03); 7.304 (1.02); 7.284(0.54); 6.902(0.36); 6.607(1.65); 6.585(1.56); 6.369(0.9); 6.349(0.94); 6.341(1.01); 6.321(0.86); 5.752(2.91); 3.739(0.48); 3.724 (0.63); 3.709(051); 2.67(0.38); 2.523(0.75); 2.519(1.23); 251(21.55); 2.506(46.67); 2.501(65.76); 2.496(51.9); 2.492(27.46); 2.367(14.99); 2.332(0.44); 2.328(0.53); 2.323(0.44); 1.398(3.95); 1.217(15.95); 1.202(16); 1.177(0.68); 1.161(0.6); 0.008(0.34); 0(13.53); −0.008(0.59) |
| I-382 | 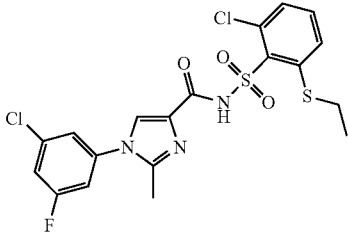 [SMILES: CCSc1cccc(Cl)c1S(=O)(=O)NC(=O)c1cn(-c2cc(F)cc(Cl)c2)c(C)n1] | Example I-382: 1H-NMR(400.0 MHz, d6-DMSO): δ = 7.789(0.44); 7.633(0.68); 7.628(1.19); 7.623(0.97); 7.607(1.18); 7.602 (1.09); 7.589(2.67); 7.58(1.38); 7.574(1.32); 7.556(1); 7.551(1.26); 7.546 (0.68); 7.356(0.44); 7.336(0.95); 7.316(0.71); 7.24(1.13); 7.22(0.89); 7.205(1.28); 7.186(0.95); 5.752(10.12); 4.038(0.97); 4.02(0.99); 4.003 (0.34); 2.51(6.39); 2.506(14.18); 2.502(20.14); 2.497(15.98); 2.493 (8.66); 2.432(0.32); 2.37(0.75); 2.345(16); 1.988(4.25); 1.397(2.85); 1.193(1.13); 1.175(2.26); 1.158(1.14); 0(4.93) |
| I-383 | 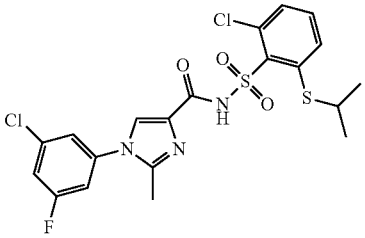 [SMILES: Cc1nc(C(=O)NS(=O)(=O)c2c(Cl)cccc2SC(C)C)cn1-c1cc(F)cc(Cl)c1] | Example I-383: 1H-NMR(400.0 MHz, d6-DMSO): δ = 8.177(0.55); 8.147(4.57); 7.695(0.85); 7.69(1.56); 7.685(1.1); 7.673 (0.98); 7.668(1.74); 7.663(1.3); 7.64(3.17); 7.628(1.48); 7.622(1.66); 7.618(0.87); 7.604(1.53); 7.6(1.84); 7.594(1.04); 7.471(0.75); 7.45(2.19); 7.431(2.56); 7.415(2.61); 7.398(1.02); 7.322(1.98); 7.318(1.99); 7.303 (1.61); 7.3(1.6); 4.056(0.71); 4.038(2.17); 4.02(2.21); 4.003(0.76); 2.985 (1.05); 2.967(3.59); 2.948(3.72); 2.93(1.25); 2.506(33.03); 2.501(45.97); 2.497(36.25); 2.382(16); 2.365(2.02); 2.333(0.37); 2.328(0.46); 2.324 (0.38); 1.988(9.32); 1.285(4.03); 1.267(8.83); 1.249(4.16); 1.236(0.55); 1.226(0.65); 1.208(1.13); 1.2(0.35); 1.193(2.62); 1.181(0.48); 1.175 (4.93); 1.163(0.37); 1.157(2.51); 0(8.22); −0.008(0.49) |
| I-384 | 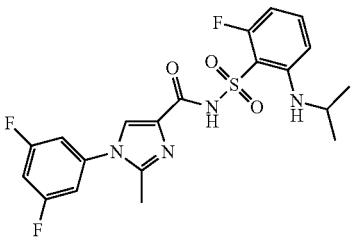 | Example I-384: 1H-NMR(400.0 MHz, d6-DMSO): δ = 7.622(1.03); 7.601(1.05); 7.577(2.59); 7.542(1.23); 7.364(0.74); 7.322 (0.62); 7.214(0.62); 4.056(1.29); 4.038(3.8); 4.02(3.86); 4.003(1.36); 3.558(0.68); 3.543(0.8); 3.528(0.74); 2.67(0.39); 2.524(0.53); 2.51(21.43); 2.506(45); 2.501(62.32); 2.497(48.72); 2.492(25.83); 2.344(10.8); 1.988(16); 1.398(0.33); 1.291(1.1); 1.258(15.12); 1.241(15.16); 1.22 (0.66); 1.204(0.49); 1.193(4.44); 1.175(8.56); 1.157(4.28); 0(11.37); −0.008(0.52) |
| I-385 | 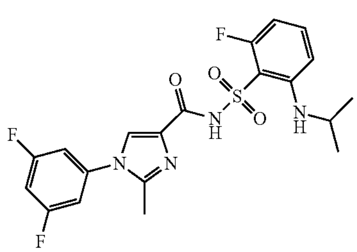 [SMILES: Cc1nc(C(=O)NS(=O)(=O)c2c(F)cccc2NC(C)C)cn1-c1cc(F)cc(F)c1] | Example I-385: 1H-NMR(400.0 MHz, d6-DMSO): δ = 8.153(4.21); 7.512(0.68); 7.506(0.54); 7.493(0.97); 7.488(1.74); 7.48 (2.73); 7.46(3.54); 7.344(0.53); 7.322(1.1); 7.306(1.09); 7.285(0.55); 6.897(0.39); 6.609(1.8); 6.587(1.7); 6.371(1); 6.351(1.03); 6.343(1.1); 6.324(0.95); 3.801(0.36); 3.739(0.93); 3.725(1.11); 3.711(0.99); 3.656 (0.57); 3.646(0.57); 3.604(0.61); 3.573(0.64); 3.556(0.64); 3.54(0.64); 3.517(0.63); 3.492(0.61); 3.48(0.6); 3.33(0.37); 3.321(0.36); 2.675(0.6); 2.671(0.81); 2.666(0.61); 2.541(1.94); 2.524(2.15); 2.506(93.16); 2.502 (121.85); 2.497(90.71); 2.377(15.25); 2.332(0.63); 2.328(0.83); 2.324 (0.63); 1.217(16); 1.202(15.9); 0.146(0.47); 0.008(3.78); 0(104.97); −0.007(4.95); −0.15(0.54) |

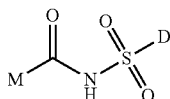
| Example No. | Structure | NMR peak list |
|---|---|---|
| I-386 | 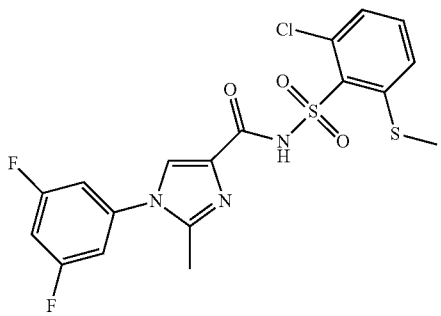 [SMILES: CSc1cccc(Cl)c1S(=O)(=O)NC(=O)c1cn(-c2cc(F)cc(F)c2)c(C)n1] | Example I-386: 1H-NMR(400.0 MHz, d6-DMSO): δ = 8.134(5.62); 7.532(0.43); 7.527(0.79); 7.521(0.68); 7.503(2.09); 7.494 (3.94); 7.475(5.39); 7.453(2.12); 7.364(2.3); 7.344(1.63); 7.32(2.38); 7.301(1.9); 5.753(8.72); 2.67(0.37); 2.54(5.29); 2.505(53.53); 2.501(70.7); 2.497(54.86); 2.434(13.75); 2.393(16); 2.37(1.04); 2.332(0.49); 2.328 (0.59); 0.007(2.15); 0(60.26); −0.15(0.34) |
| I-387 | 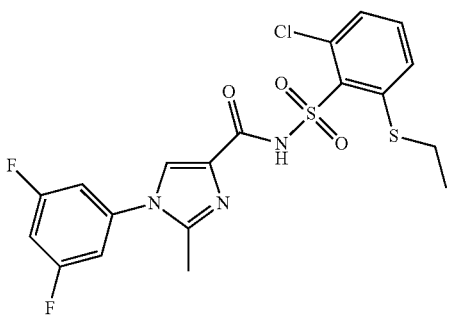 [SMILES: CCSc1cccc(Cl)c1S(=O)(=O)NC(=O)c1cn(-c2cc(F)cc(F)c2)c(C)n1] | Example I-387: 1H-NMR(400.0 MHz, d6-DMSO): δ = 8.141(4.28); 7.524(0.73); 7.518(0.67); 7.5(2.01); 7.493(3.29); 7.473 (4.81); 7.452(2.46); 7.433(2.55); 7.416(2.65); 7.399(1.11); 7.323(2.02); 7.319(2.02); 7.304(1.66); 7.301(1.6); 5.753(6.21); 3.896(0.35); 3.768 (0.38); 3.733(0.38); 3.69(0.37); 3.621(0.33); 2.986(1.11); 2.967(3.48); 2.949(3.59); 2.931(1.26); 2.675(0.57); 2.67(0.76); 2.666(0.58); 2.541 (5.92); 2.506(94.61); 2.501(124.08); 2.497(96.06); 2.391(16); 2.372(0.99); 2.332(0.8); 2.328(0.98); 2.324(0.79); 2.073(0.37); 1.284(4.21); 1.266 (9.07); 1.248(4.18); 0.146(0.5); 0.008(6.1); 0(114.82); −0.008(8.82); −0.041(0.59); −0.15(0.54) |
| I-388 | 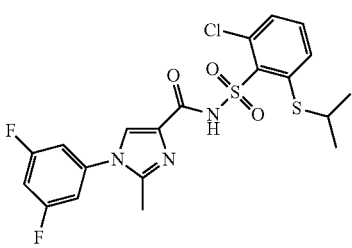 [SMILES: Cc1nc(C(=O)NS(=O)(=O)c2c(Cl)cccc2SC(C)C)cn1-c1cc(F)cc(F)c1] | Example I-388: 1H-NMR(400.0 MHz, d6-DMSO): δ = 8.164(6.09); 7.531(1.27); 7.512(3.24); 7.486(5.02); 7.468(6.42); 7.446 (1.51); 7.356(2.54); 7.337(1.97); 5.754(7.12); 3.678(0.42); 3.662(1.09); 3.645(1.49); 3.629(1.12); 3.613(0.45); 2.542(3.3); 2.503(16.73); 2.395 (15.14); 2.074(0.42); 1.268(16); 1.252(15.55); 0(15.77) |
| I-389 | 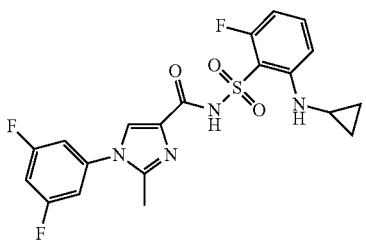 [SMILES: Cc1nc(C(=O)NS(=O)(=O)c2c(F)cccc2NC2CC2)cn1-c1cc(F)cc(F)c1] | Example I-389: 1H-NMR(400.0 MHz, d6-DMSO): δ = 8.136(5.7); 7.526(0.36); 7.521(0.72); 7.516(0.57); 7.498(1.57); 7.493 (1.81); 7.481(2.93); 7.478(2.95); 7.463(3.39); 7.404(0.6); 7.383(1.28); 7.367(1.27); 7.347(0.66); 7.153(1.65); 6.946(2.16); 6.924(2.03); 6.468 (1.03); 6.447(1.13); 6.44(1.24); 6.42(1.02); 5.753(9.27); 2.541(5.12); 2.506 (51.19); 2.501(68.76); 2.497(55.44); 2.434(0.59); 2.384(16); 2.332 (0.57); 2.328(0.69); 2.324(0.6); 2.073(0.88); 0.844(0.57); 0.828(2.88); 0.816(2.88); 0.811(2.63); 0.8(0.98); 0.51(0.71); 0.5(2.59); 0.492(3.14); 0.486(2.85); 0.474(0.95); 0.007(1.86); 0(57.62); −0.15(0.36) |

-continued (I)

M-C(O)-NH-S(O)(O)-D

| Example No. | Structure | NMR peak list |
|---|---|---|
| I-390 | 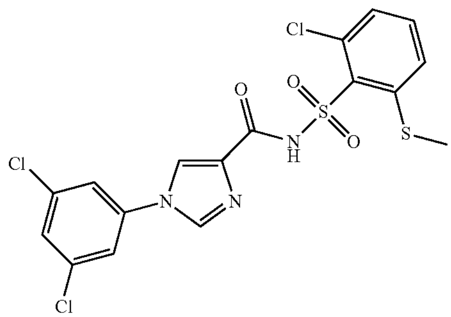 [SMILES: CSc1cccc(Cl)c1S(=O)(=O)NC(=O)c1cn(-c2cc(Cl)cc(Cl)c2)cn1] | Example I-390: 1H-NMR(400.0 MHz, d6-DMSO): δ = 8.656(3.7); 8.569(4.04); 8.566(4.01); 7.934(9.04); 7.93(10.08); 7.707 (2.21); 7.703(4.08); 7.698(2.23); 7.553(1.31); 7.533(3.03); 7.513(2.4); 7.421(2.46); 7.4(1.74); 7.372(2.53); 7.37(2.59); 7.353(2.11); 7.35(2.09); 7.236(0.35); 3.718(0.33); 3.664(0.38); 3.522(0.48); 3.47(0.49); 3.367 (0.4); 3.313(0.36); 2.675(0.5); 2.671(0.71); 2.666(0.52); 2.541(75.39); 2.524(1.96); 2.51(39.78); 2.506(81.89); 2.502(109.78); 2.497(81.6); 2.493 (41.35); 2.471(16); 2.444(2.19); 2.367(0.39); 2.333(0.62); 2.328(0.79); 2.324(0.6); 0.146(0.5); 0.008(3.92); 0(114.17); −0.008(4.92); −0.15(0.51) |
| I-391 | 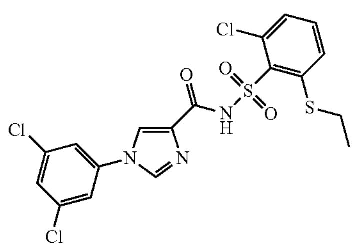 [SMILES: CCSc1cccc(Cl)c1S(=O)(=O)NC(=O)c1cn(-c2cc(Cl)cc(Cl)c2)cn1] | Example I-391: 1H-NMR(400.0 MHz, d6-DMSO): δ = 8.668(7.76); 8.571(8.5); 7.934(15.5); 7.702(6.42); 7.53(1.4); 7.509(4.3); 7.49(4.91); 7.476(5.77); 7.458(2.07); 7.373(4.44); 7.354(3.5); 5.754 (0.42); 3.775(0.33); 3.735(0.35); 3.724(0.35); 3.677(0.38); 3.655(0.38); 3.579(0.4); 3.554(0.4); 3.513(0.4); 3.447(0.39); 3.397(0.36); 3.383 (0.36); 3.351(0.34); 3.023(2.28); 3.005(6.98); 2.987(7.18); 2.968(2.5); 2.711(0.5); 2.671(0.79); 2.541(99.26); 2.502(129.3); 2.368(0.7); 2.328 (0.98); 1.278(7.69); 1.26(16); 1.242(7.65); 1.12(0.4); 0.146(0.44); 0(92.3); −0.15(0.51) |
| I-392 | 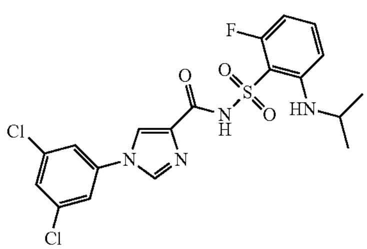 [SMILES: CC(C)Nc1cccc(F)c1S(=O)(=O)NC(=O)c1cn(-c2cc(Cl)cc(Cl)c2)cn1] | Example I-392: 1H-NMR(400.0 MHz, d6-DMSO): δ = 8.673(3.8); 8.671(3.67); 8.564(4.1); 7.942(7.51); 7.938(7.53); 7.695 (2.02); 7.691(3.37); 7.687(1.82); 7.389(0.62); 7.368(1.24); 7.351(1.25); 7.331(0.65); 6.654(2.04); 6632(1.93); 6.409(1.11); 6.389(1.15); 6.381 (124); 6.361(1.07); 3.79(0.39); 3.775(0.81); 3.759(1.05); 3.744(0.83); 3.728(0.43); 2.542(8.8); 2.507(27.98); 2.503(35.81); 2.498(26.94); 1.229(16); 1.213(15.83); 0.008(1.32); 0(30.77) |
| I-393 | 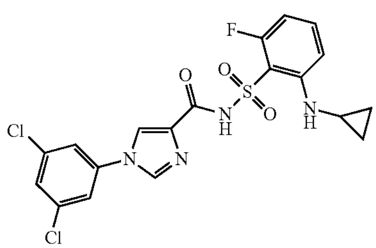 [SMILES: O=C(NS(=O)(=O)c1c(F)cccc1NC1CC1)c1cn(-c2cc(Cl)cc(Cl)c2)cn1] | Example I-393: 1H-NMR(400.0 MHz, d6-DMSO): δ = 8.658(7.19); 8.656(7.1); 8.573(7.98); 8.57(7.09); 7.941(15.98); 7.937 (16); 7.698(4.16); 7.694(6.87); 7.689(3.7); 7.464(1.18); 7.448(1.62); 7.443(2.47); 7.427(2.47); 7.423(1.74); 7.407(1.31); 7.055(2.51); 6.99 (4.27); 6.968(3.96); 6.518(2.04); 6.498(2.18); 6.49(2.32); 6.47(2.01); 5.754(2.59); 2.712(0.58); 2.676(0.37); 2.672(0.51); 2.667(0.36); 2.542(141.79); 2.524(3.35); 2.52(4.05); 2.507(66.22); 2.502(85.72); 2.498(64.14); 2.368(0.76); 2.334(0.52); 2.329(0.65); 2.325(0.52); 0.862(1.23); 0.85(4.35); 0.846(5.4); 0.834(5.4); 0.829(4.6); 0.817(1.54); 0.53(1.52); 0.519(5.01); 0.513(5.75); 0.505(4.96); 0.493(1.49); 0.146(0.36); 0.008(3.41); 0(84.69); −0.149(0.42) |
| I-394 | 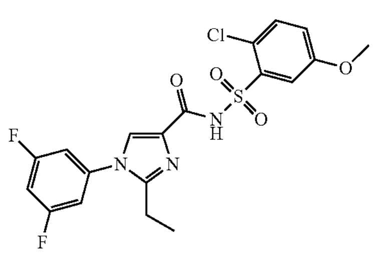 [SMILES: CCc1nc(C(=O)NS(=O)(=O)c2cc(OC)ccc2Cl)cn1-c1cc(F)cc(F)c1] | Example I-394: 1H-NMR(400.0 MHz, d6-DMSO): δ = 8.169(5.68); 7.611(2.78); 7.603(2.98); 7.545(0.38); 7.536(3.06); 7.522 (0.76); 7.514(4.1); 7.494(2.88); 7.489(2.79); 7.475(2.75); 7.458(0.4); 7.248(1.56); 7.24(1.56); 7.226(1.4); 7.218(1.38); 3.848(16); 2.73(1.08); 2.712(3.51); 2.693(3.62); 2.674(1.3); 2.507(19.59); 2.502(25.58); 2.498 (19.83); 1.154(3.81); 1.135(7.89); 1.116(3.67); 0.008(1.05); 0(23.23) |

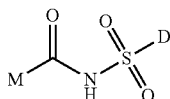
(I)
| Example No. | Structure | NMR peak list |
|---|---|---|
| I-395 | 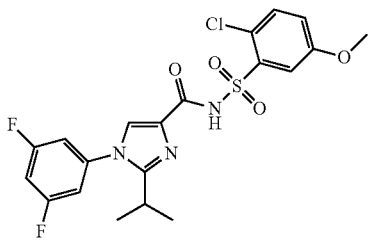 | Example I-395: 1H-NMR(400.0 MHz, d6-DMSO): δ = 8.157(5.92); 7.621(2.87); 7.613(3.01); 7.556(3.38); 7.533(4.26); 7.527 (1.14); 7.514(0.71); 7.508(0.97); 7.502(2.56); 7.497(2.2); 7.483(2.55); 7.269(1.64); 7.261(1.6); 7.247(1.43); 7.239(1.39); 3.854(16); 3.027 (0.36); 3.01(1.01); 2.993(1.42); 2.976(1.06); 2.959(0.41); 2.712(0.8); 2.543(116.95); 2.507(11.75); 2.503(15.6); 2.499(12.27); 2.368(0.89); 1.167(13.53); 1.15(13.29); 0.008(0.67); 0(16.49) |
| I-396 | 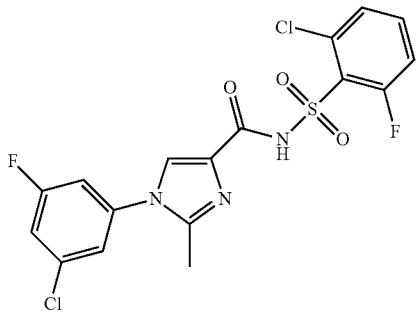 [SMILES: Cc1nc(C(=O)NS(=O)(=O)c2c(F)cccc2Cl)cn1-c1cc(F)cc(Cl)c1] | Example I-396: 1H-NMR(400.0 MHz, d6-DMSO): δ = 8.122(6.71); 7.742(0.86); 7.738(1.54); 7.733(1.09); 7.721(0.9); 7.716 (1.58); 7.711(1.11); 7.685(3.19); 7.661(1.19); 7.656(1.64); 7.652(0.95); 7.638(1.18); 7.633(1.67); 7.629(0.96); 7.552(0.58); 7.539(0.67); 7.532 (1.34); 7.519(1.38); 7.512(0.96); 7.498(0.84); 7.381(2.32); 7.361(1.81); 7.314(1.08); 7.289(1.36); 7.266(0.91); 2.506(17.22); 2.502(22.74); 2.498 (17.51); 2.431(16); 2.074(1.74); 0.008(1.56); 0(29.91) |
| I-397 | 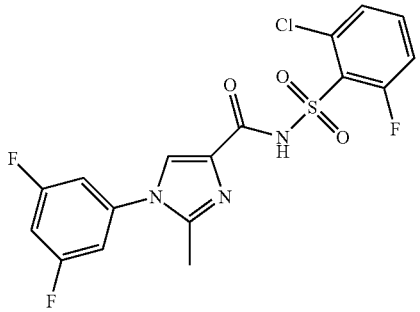 [SMILES: Cc1nc(C(=O)NS(=O)(=O)c2c(F)cccc2Cl)cn1-c1cc(F)cc(F)c1] | Example I-397: 1H-NMR(400.0 MHz, d6-DMSO): δ = 8.118(6.7); 7.578(0.48); 7.572(0.82); 7.566(0.62); 7.555(1.3); 7.55 (1.87); 7.543(2.11); 7.532(3.57); 7.526(3.36); 7.521(3.1); 7.513(3.77); 7.501(1.26); 7.383(2.26); 7.363(1.74); 7.317(1.05); 7.291(1.29); 7.27 (0.86); 2.506(23.03); 2.502(30.08); 2.498(22.76); 2.441(16); 0.008(1.71); 0(40.03); −0.008(2.6) |
| I-398 | 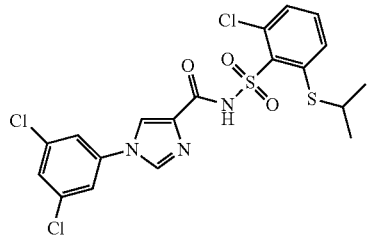 | Example I-398: 1H-NMR(400.0 MHz, d6-DMSO): δ = 8.679(2.42); 8.578(3.34); 8.314(0.39); 7.941(7.56); 7.937(8.07); 7.704 (1.86); 7.7(3.29); 7.696(1.89); 7.582(1.13); 7.562(2.15); 7.531(1.44); 7.511(2.27); 7.491(1.1); 7.4(2.06); 7.381(1.5); 5.754(1.31); 3.71(0.48); 3.693(1.09); 3.677(1.43); 3.66(1.12); 3.644(0.56); 3.521(0.37); 3.352 (0.77); 3.203(0.41); 2.71(0.33); 2.675(0.87); 2.67(1.19); 2.666(0.93); 2.54(64.72); 2.523(3.01); 2.506(134.31); 2.501(179.37); 2.497(135.53); 2.366(0.34); 2.332(0.83); 2.328(1.15); 2.324(0.87); 1.292(0.35); 1.276 (0.42); 1.254(16); 1.238(15.93); 1.152(0.41); 1.136(0.41); 1.122(1.11); 0.008(2.24); 0(65.38); −0.008(2.83) |

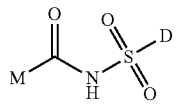
(I)
| Example No. | Structure | NMR peak list |
|---|---|---|
| I-399 | 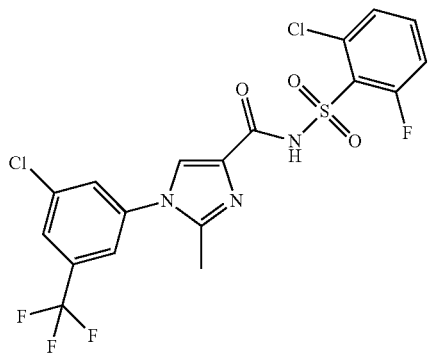 | Example I-399: 1H-NMR(400.0 MHz, d6-DMSO): δ = 8.182(5.84); 8.144(5.11); 8.082(3.07); 7.554(0.57); 7.541(0.67); 7.534 (1.33); 7.52(1.35); 7.513(0.93); 7.5(0.81); 7.383(2.31); 7.363(1.77); 7.316(1.05); 7.291(1.33); 7.269(0.88); 2.506(30.27); 2.502(39.92); 2.497(30.72); 2.423(16); 0.007(2); 0(43.65) |
| I-400 | 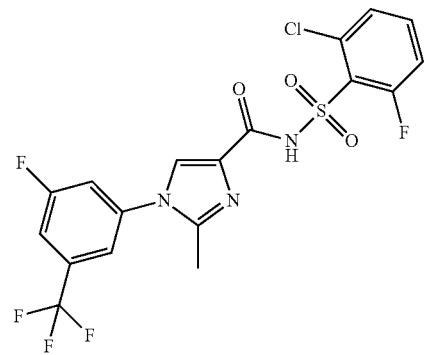 | Example I-400: 1H-NMR(400.0 MHz, d6-DMSO): δ = 8.188(5.9); 7.998(3.23); 7.971(4.79); 7.559(0.55); 7.545(0.71); 7.539 (1.37); 7.525(1.39); 7.518(1.04); 7.505(0.83); 7.387(2.4); 7.367(1.86); 7.32(1.16); 7.295(1.49); 7.273(0.96); 2.67(0.37); 2.502(61.54); 2.498 (50.54); 2.434(16); 2.329(0.42); 0.146(0.32); 0(67.08); 0.15(0.4) |
| I-401 | 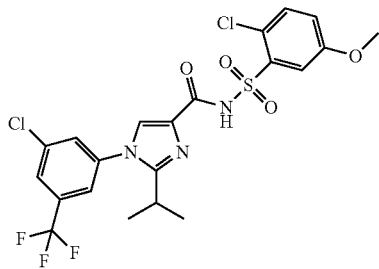 [SMILES: COc1ccc(Cl)c(S(=O)(=O)NC(=O)c2cn(-c3cc(Cl)cc(C(F)(F)F)c3)c(C(C)C)n2)c1] | Example I-401: 1H-NMR(400.0 MHz, d6-DMSO): δ = 8.216(5.29); 8.136(2.81); 8.132(2.84); 8.125(2.71); 8.055(2.5); 7.622 (2.9); 7.614(2.99); 7.555(2.61); 7.533(3.05); 7.268(1.59); 7.261(1.52); 7.246(1.38); 7.239(1.31); 5.754(0.33); 3.855(16); 2.968(0.34); 2.951 (0.95); 2.934(1.34); 2.917(0.99); 2.9(0.38); 2.542(45.04); 2.526(0.76); 2.507(18.68); 2.503(24.25); 2.498(18.15); 1.166(13.06); 1.149(12.86); 0(4.49) |
| I-402 | 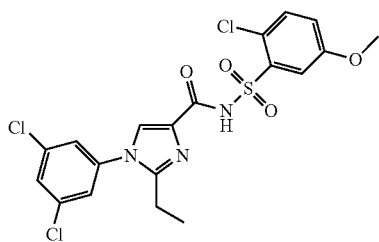 [SMILES: CCc1nc(C(=O)NS(=O)(=O)c2cc(OC)ccc2Cl)cn1-c1cc(Cl)cc(Cl)c1] | Example I-402: 1H-NMR(400.0 MHz, d6-DMSO): δ = 8.214(4.42); 7.982(2.4); 7.961(2.29); 7.932(2.28); 7.62(2.84); 7.613 (2.96); 7.556(2.52); 7.534(2.97); 7.27(1.51); 7.262(1.45); 7.248(1.32); 7.24(1.27); 3.854(16); 2.992(0.33); 2.975(0.92); 2.958(1.3); 2.941(0.96); 2.924(0.36); 2.541(49.08); 2.511(17.68); 2.506(35.01); 2.502(46.12); 2.498(34.44); 2.329(0.33); 1.164(12.87); 1.147(12.72); 0(6.12) |

-continued (I)

| Example No. | Structure | NMR peak list |
|---|---|---|
| I-403 | 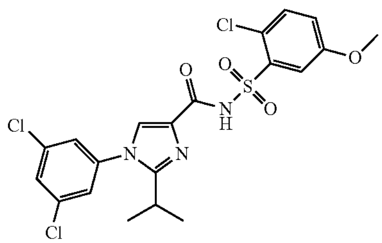 [SMILES: COc1ccc(Cl)c(S(=O)(=O)NC(=O)c2cn(-c3cc(Cl)cc(Cl)c3)c(C(C)C)n2)c1] | Example I-403: 1H-NMR(400.0 MHz, d6-DMSO): δ = 8.159(4.82); 7.87(1.77); 7.866(3.24); 7.861(1.9); 7.785(7.39); 7.781 (6.46); 7.618(2.92); 7.61(2.96); 7.551(2.58); 7.529(3.01); 7.264(1.57); 7.256(1.49); 7.242(1.36); 7.234(1.27); 3.852(16); 2.98(0.34); 2.964(0.96); 2.946(1.34); 2.929(1); 2.912(0.37); 2.712(0.7); 2.542(134.45); 2.525 (1.7); 2.507(23.73); 2.502(30.18); 2.498(22.24); 2.467(0.34); 2.368(0.77); 1.166(13.14); 1.149(12.87); 0.008(0.36); 0(6.9); −0.008(0.34) |
| I-404 | 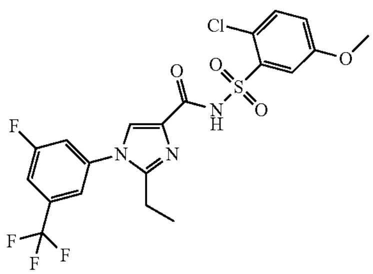 | Example I-404: 1H-NMR(400.0 MHz, d6-DMSO): δ = 8.234(4.77); 7.966(3.41); 7.944(3.47); 7.916(2.96); 7.612(2.79); 7.605 (2.93); 7.538(2.47); 7.516(2.86); 7.25(1.53); 7.242(1.5); 7.228(1.32); 7.22(1.27); 3.849(16); 2.717(1.09); 2.698(3.5); 2.68(3.73); 2.661(1.29); 2.341(21.34); 2.502(60.58); 2.328(0.44); 1.157(3.87); 1.139(7.85); 1.12 (3.75); 0(11.22) |
| I-405 | 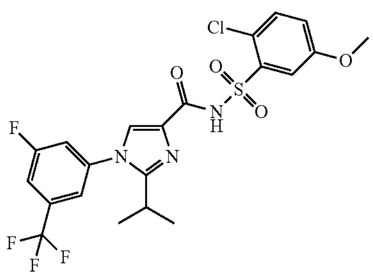 [SMILES: COc1ccc(Cl)c(S(=O)(=O)NC(=O)c2cn(-c3cc(F)cc(C(F)(F)F)c3)c(C(C)C)n2)c1] | Example I-405: 1H-NMR(400.0 MHz, d6-DMSO): δ = 8.178(5.58); 7.855(1.64); 7.85(3.16); 7.846(1.95); 7.776(7.17); 7.771 (6.52); 7.61(2.94); 7.602(3.05); 7.533(2.6); 7.511(3.03); 7.244(1.58); 7.237(1.52); 7.222(1.39); 7.215(1.33); 5.754(0.82); 3.847(16); 2.704(1.03); 2.685(3.37); 2.666(3.52); 2.647(1.1); 2.542(0.87); 2.507(17.15); 2.502 (21.96); 2.498(16.29); 1.155(3.8); 1.136(7.96); 1.117(3.63); 0(4.08) |
| I-406 | 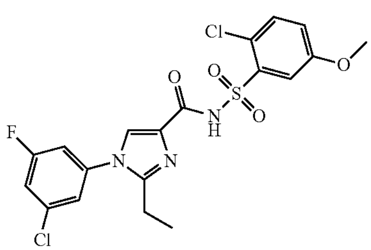 [SMILES: CCc1nc(C(=O)NS(=O)(=O)c2cc(OC)ccc2Cl)cn1-c1cc(F)cc(Cl)c1] | Example I-406: 1H-NMR(400.0 MHz, d6-DMSO): δ = 8.175(5.7); 7.711(0.77); 7.706(1.35); 7.701(0.95); 7.689(0.81); 7.684 (1.36); 7.679(0.93); 7.643(2.63); 7.629(1.18); 7.623(1.45); 7.618(0.91); 7.611(3.19); 7.603(3.9); 7.596(0.93); 7.534(2.64); 7.512(3.09); 7.246 (1.58); 7.238(1.54); 7.224(1.39); 7.216(1.33); 3.848(16); 3.817(0.49); 2.717 (1.06); 2.699(3.39); 2.68(3.5); 2.661(1.14); 2.542(39.66); 2.511(8.22); 2.507(15.62); 2.502(20.2); 2.498(14.97); 1.155(3.82); 1.136(7.97); 1.117(3.64); 0(4.06) |
| I-407 | 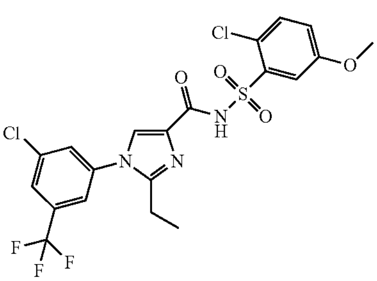 [SMILES: CCc1nc(C(=O)NS(=O)(=O)c2cc(OC)ccc2Cl)cn1-c1cc(Cl)cc(C(F)(F)F)c1] | Example I-407: 1H-NMR(400.0 MHz, d6-DMSO): δ = 8.159(5.13); 7.728(0.9); 7.723(1.47); 7.718(1); 7.706(0.9); 7.702(1.43); 7.696(0.91); 7.652(2.96); 7.638(1.23); 7.633(1.48); 7.628(0.92); 7.618 (3.47); 7.61(4.26); 7.553(2.58); 7.531(2.96); 7.266(1.62); 7.258(1.52); 7.244(1.36); 7.236(1.26); 3.853(16); 3.004(0.39); 2.986(1.01); 2.969 (1.41); 2.952(1.05); 2.935(0.4); 2.541(38.26); 2.506(22.29); 2.502(28.53); 2.498(21.68); 1.166(13.62); 1.148(13.29); 0.008(0.32); 0(5.82) |

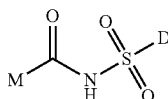
(I)
| Example No. | Structure | NMR peak list |
|---|---|---|
| I-408 | 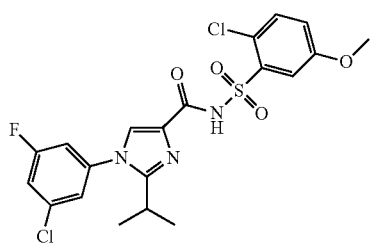 [SMILES: COc1ccc(Cl)c(S(=O)(=O)NC(=O)c2cn(-c3cc(F)cc(Cl)c3)c(C(C)C)n2)c1] | Example I-408: 1H-NMR(400.0 MHz, d6-DMSO): δ = 8.234(4.9); 8.119(3.18); 8.115(3.09); 8.107(3.13); 8.038(2.89); 7.612 (2.89); 7.605(2.98); 7.537(2.48); 7.515(2.88); 7.248(1.55); 7.241(1.49); 7.226(1.34); 7.219(1.27); 3.849(16); 2.703(1.06); 2.685(3.46); 2.666 (3.72); 2.647(1.18); 2.541(4.61); 2.502(47.04); 2.329(0.32); 1.159(3.77); 1.14(7.85); 1.121(3.7); 0(8.92) |
| I-409 | 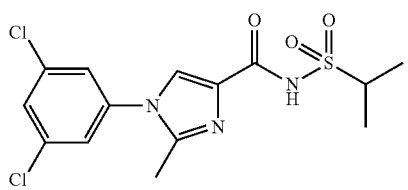 [SMILES: Cc1nc(C(=O)NS(=O)(=O)C(C)C)cn1-c1cc(Cl)cc(Cl)c1] | Example I-409: 1H-NMR(400.0 MHz, d6-DMSO): δ = 8.216(5.16); 7.819(1.61); 7.815(3.37); 7.81(2.24); 7.766(7.69); 7.762 (6.78); 3.791(0.45); 3.774(1.15); 3.756(1.58); 3.739(1.19); 3.722(0.5); 3.477(0.37); 3.346(0.7); 3.259(0.46); 2.506(38.81); 2.501(50.46); 2.497 (37.5); 2.356(16); 2.333(0.41); 2.328(0.42); 2.324(0.34); 2.073(9.63); 1.308(14.48); 1.291(14.28) |
| I-410 | 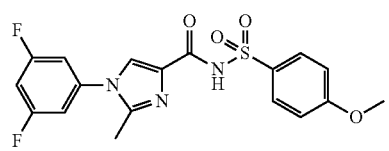 [SMILES: COc1ccc(S(=O)(=O)NC(=O)c2cn(-c3cc(F)cc(F)c3)c(C)n2)cc1] | Example I-410: 1H-NMR(400.0 MHz, d6-DMSO): δ = 8.083(4.59); 7.937(0.41); 7.929(3.85); 7.924(1.32); 7.912(1.25); 7.907 (4.29); 7.9(0.48); 7.486(0.57); 7.48(0.41); 7.463(1.22); 7.458(1.36); 7.446(2.1); 7.442(2.06); 7.427(2.42); 7.138(0.44); 7.131(3.9); 7.126(1.35); 7.113(1.21); 7.108(3.83); 7.101(0.46); 3.842(16); 3.444(0.35); 3.401 (0.36); 3.343(0.33); 2.524(0.86); 2.51(18.15); 2.506(35.94); 2.501(47.03); 2.497(34.13); 2.492(16.63); 2.35(14); 2.332(0.34); 2.328(0.41); 2.073 (0.32) |
| I-411 | 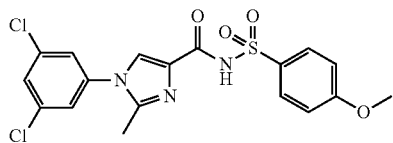 [SMILES: COc1ccc(S(=O)(=O)NC(=O)c2cn(-c3cc(Cl)cc(Cl)c3)c(C)n2)cc1] | Example I-411: 1H-NMR(400.0 MHz, d6-DMSO): δ = 8.105(5.63); 7.939(0.49); 7.932(4.13); 7.927(1.37); 7.914(1.37); 7.909 (4.41); 7.902(0.51); 7.807(1.47); 7.802(2.95); 7.798(1.82); 7.728(6.58); 7.723(6.05); 7.142(0.49); 7.134(4.16); 7.116(1.31); 7.112(3.97); 7.104 (0.46); 3.843(16); 3.361(0.48); 3.343(0.48); 3.332(0.48); 2.675(0.45); 2.67(0.6); 2.666(0.45); 2.51(37.34); 2.506(73.3); 2.501(96.45); 2.497 (71.78); 2.329(14.24); 2.073(1.11); 0.008(0.49); 0(12.36); −0.008(0.51) |
| I-412 | 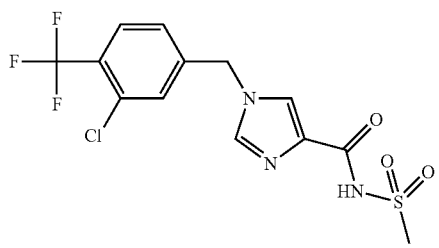 [SMILES: CS(=O)(=O)NC(=O)c1cn(Cc2ccc(C(F)(F)F)c(Cl)c2)cn1] | I-412; ¹H-NMR(400.0 MHz, d₆-DMSO): δ = 8.1462(9.6); 8.0276(8.7); 7.8997(5.6); 7.8793(6.1); 7.7263(7. 4); 7.4540(3.9); 7.4335(3.5); 5.3929(16.0); 3.4611(0.6); 3.398 4(0.4); 3.2895(39.6); 3.1138(0.4); 2.6715(0.7); 2.5066(85.5); 2.5024(112.4); 2.4980(85.9); 2.3292(0.7); 2.3247(0.6); 2.074 8(0.3); 0.1458(0.3); 0.0074(3.1); −0.0002(71.1); −0.1498(0.3) |

-continued
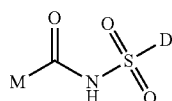
(I)
| Example No. | Structure | NMR peak list |
|---|---|---|
| I-413 | 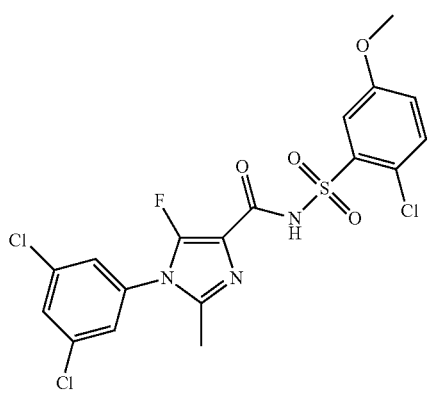 [SMILES: COc1ccc(Cl)c(S(=O)(=O)NC(=O)c2nc(C)n(-c3cc(Cl)cc(Cl)c3)c2F)c1] | I-413; $^1$H-NMR(601.6MHz, CD3CN): δ = 7.7567(1.6); 7.7516(1.7); 7.7251(0.9); 7.7220(1.8); 7.7190 (1.1); 7.5456(1.7); 7.5309(1.9); 7.4976(2.7); 7.4948(3.0); 7.2457 (1.0); 7.2406(1.0); 7.2310(0.9); 7.2259(0.9); 4.9467(0.4); 3.9023(11.0); 2.5347(16.0); 2.2305(4.7); 1.9923(2.5); 1.9842 (1.1); 1.9801(1.2); 1.9762(5.5); 1.9722(9.2); 1.9681(13.1); 1.9639 (9.2); 1.9598(5.0) |
| I-414 | 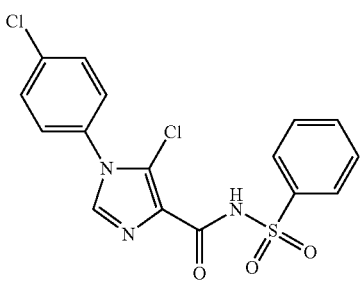 [SMILES: O=C(NS(=O)(=O)c1ccccc1)c1ncn(-c2ccc(Cl)cc2)c1Cl] | I-414; $^1$H-NMR(400.0 MHz, d$_6$-DMSO): δ = 8.2181(15.8); 8.0234(8.3); 8.0052(9.9); 8.0016(7.3); 7.7305 (1.4); 7.7179(1.1); 7.7120(4.9); 7.7069(1.7); 7.6929(13.4); 7.6879(4.6); 7.6762(4.4); 7.6708(16.0); 7.6637(2.5); 7.6556(7.1); 7.6360(9.8); 7.6219(1.7); 7.6181(3.8); 7.5971(2.0); 7.5900 (15.6); 7.5847(4.8); 7.5732(3.6); 7.5680(10.4); 7.5609(1.2); 3.3780(0.7); 3.3421(0.7); 3.1862(0.6); 3.1692(0.7); 2.6762(0.4); 2.6715(0.5); 2.6671(0.4); 2.5248(1.1); 2.5112(29.7); 2.5070 (60.6); 2.5025(80.4); 2.4980(59.1); 2.4937(29.2); 2.3337(0.4); 2.3291(0.5); 2.3247(0.4); 2.0754(0.6); −0.0002(8.4) |
| I-415 | 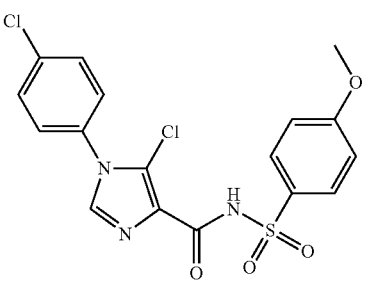 [SMILES: COc1ccc(S(=O)(=O)NC(=O)c2ncn(-c3ccc(Cl)cc3)c2Cl)cc1] | I-415; $^1$H-NMR(400.0 MHz, d$_6$-DMSO): δ = 8.2107(5.3); 8.0963(1.6); 7.9651(0.4); 7.9573(3.9); 7.9398 (1.2); 7.9350(4.3); 7.9281(0.5); 7.7012(0.5); 7.6940(3.8); 7.6891 (1.4); 7.6722(5.8); 7.6653(0.7); 7.5991(1.6); 7.5889(5.4); 7.5835(1.8); 7.5774(1.1); 7.5722(1.2); 7.5671(3.6); 7.5599(0.4); 7.1671(0.4); 7.1598(4.1); 7.1374(3.9); 7.1302(0.5); 3.8521 (16.0); 3.3280(1.5); 2.5106(18.1); 2.5065(36.6); 2.5020(48.7); 2.4976(35.9); 1.5303(11.3); −0.0002(7.7) |
| I-416 | 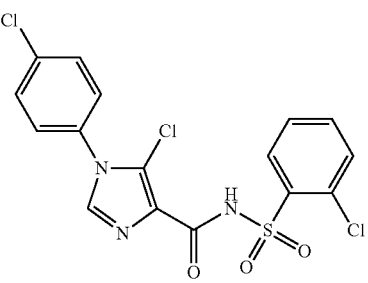 [SMILES: O=C(NS(=O)(=O)c1ccccc1Cl)c1ncn(-c2ccc(Cl)cc2)c1Cl] | I-416; $^1$H-NMR(400.0 MHz, d$_6$-DMSO): δ = 8.2301(5.4); 8.2226(2.9); 8.1607(3.1); 8.1413(3.4); 8.0249 (0.8); 8.0064(1.0); 7.7157(1.2); 7.6964(9.4); 7.6744(16.0); 7.657 9(1.9); 7.6541(2.0); 7.6389(1.4); 7.6201(2.9); 7.6128(12.3); 7.5910(9.4); 7.5743(0.7); 7.5691(1.2); 3.5073(0.5); 3.3858 (0.5); 3.2340(1.3); 3.1866(0.6); 2.6755(0.7); 2.6713(0.9); 2.6669 (0.7); 2.5065(102.1); 2.5022(133.0); 2.4978(99.8); 2.3332(0.6); 2.3290(0.8); 2.3245(0.6); 2.0750(0.8); −0.0002(6.5) |

-continued
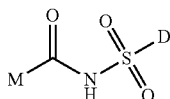
(I)
| Example No. | Structure | NMR peak list |
|---|---|---|
| I-417 | 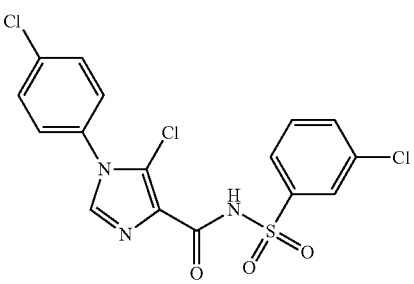 [SMILES: O=C(NS(=O)(=O)c1cccc(Cl)c1)c1ncn(-c2ccc(Cl)cc2)c1Cl] | I-417; ¹H-NMR(400.0 MHz, d₆-DMSO): δ = 8.2479(16.0); 8.0171(4.2); 8.0126(7.9); 8.0079(5.3); 7.9809 (3.9); 7.9771(2.8); 7.9611(4.4); 7.8248(2.8); 7.8221(2.7); 7.8198(2.6); 7.8047(3.8); 7.8018(3.9); 7.7116(5.2); 7.6993(10.1); 7.6919(9.2); 7.6828(4.7); 7.6775(15.5); 7.6717(5.0); 7.6058 (2.2); 7.5988(14.9); 7.5936(4.6); 7.5820(3.6); 7.5769(9.8); 7.5698(1.1); 5.7578(5.4); 3.5708(0.3); 3.5524(0.3); 3.5050(0.4); 3.4862(0.4); 3.4627(0.4); 3.4576(0.4); 3.4517(0.4); 3.4458(0.4); 3.3891(0.4); 3.3717(0.4); 3.3567(0.4); 3.3453(0.4); 3.3014(0.4); 3.2844(0.4); 3.2767(0.4); 3.2614(0.4); 3.2449(0.4); 3.1873 (0.3); 2.8908(2.4); 2.7312(2.0); 2.6762(0.6); 2.6717(0.9); 2.6671 (0.7); 2.5111(50.0); 2.5070(95.9); 2.5026(124.6); 2.4981 (92.9); 2.3381(0.3); 2.3336(0.6); 2.3294(0.8); 2.3249(0.6); 2.0864(0.4); 0.1458(0.8); 0.0077(9.5); −0.0002(178.6); −0.0085(8.9); −0.1498(0.8) |
| I-418 | 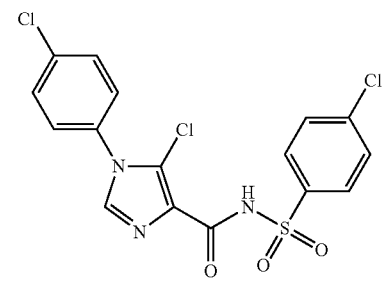 [SMILES: O=C(NS(=O)(=O)c1ccc(Cl)cc1)c1ncn(-c2ccc(Cl)cc2)c1Cl] | I-418; ¹H-NMR(400.0 MHz, d₆-DMSO): δ = 8.2352(16.0); 8.0295(1.2); 8.0230(10.8); 8.0183(3.7); 8.0061 (3.8); 8.0013(12.9); 7.9949(1.6); 7.9531(2.0); 7.7503(1.5); 7.7440(12.3); 7.7392(4.0); 7.7270(3.5); 7.7223(10.7); 7.7159 (1.3); 7.7043(1.0); 7.6971(9.3); 7.6920(3.3); 7.6805(3.9); 7.6752 (14.4); 7.6682(1.8); 7.6019(1.7); 7.5948(14.2); 7.5895(4.0); 7.5780(3.2); 7.5729(9.3); 7.5656(0.9); 5.7573(4.4); 3.5071 (0.4); 3.4346(0.4); 3.3791(0.5); 3.3663(0.5); 3.3153(0.5); 3.2874 (0.4); 3.2196(0.4); 3.1978(0.3); 3.1873(0.4); 2.8912(15.1); 2.7319(12.4); 2.6763(0.6); 2.6719(0.8); 2.6671(0.6); 2.5251(1.9); 2.5116(43.2); 2.5073(86.9); 2.5027(113.9); 2.4982(83.0); 2.4939(40.6); 2.3340(0.6); 2.3295(0.8); 2.3251(0.6); 0.1460 (0.9); 0.0078(7.3); −0.0002(195.6); −0.0086(7.6); −0.1497(0.9) |
| I-419 | 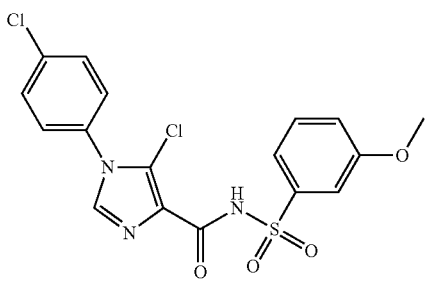 [SMILES: COc1cccc(S(=O)(=O)NC(=O)c2ncn(-c3ccc(Cl)cc3)c2Cl)c1] | I-419; ¹H-NMR(400.0 MHz, d₆-DMSO): δ = 8.2280(5.0); 7.6966(3.3); 7.6749(5.3); 7.5952(5.6); 7.5733 (6.9); 7.5528(2.3); 7.5311(2.0); 7.5258(2.4); 7.2901(1.2); 7.2852 (1.0); 7.2769(0.8); 7.2717(1.2); 7.2667(0.8); 3.8351(16.0); 3.3344(1.0); 3.2339(0.5); 3.2171(0.4); 2.6711(0.4); 2.5062 (46.9); 2.5020(63.0); 2.4978(50.7); 2.3286(0.4); 2.0751(0.6); 0.8935(0.4); 0.0078(2.4); −0.0002(55.4) |
| I-420 | 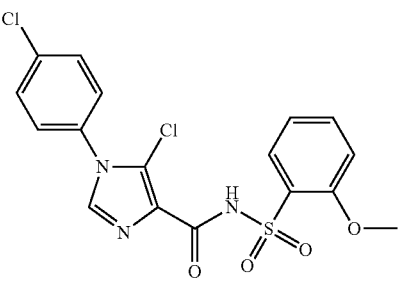 [SMILES: COc1ccccc1S(=O)(=O)NC(=O)c1ncn(-c2ccc(Cl)cc2)c1Cl] | I-420; ¹H-NMR(400.0 MHz, d₆-DMSO): δ = 8.2335(4.8); 7.9136(1.5); 7.9093(1.7); 7.8939(1.7); 7.8896 (1.8); 7.7069(0.4); 7.6999(4.0); 7.6947(1.6); 7.6830(2.3); 7.6778 (7.0); 7.6709(0.9); 7.6617(0.8); 7.6575(0.8); 7.6174(0.7); 7.6103(5.7); 7.6049(1.6); 7.5936(1.2); 7.5883(3.5); 7.5811(0.4); 7.2606(1.8); 7.2399(1.7); 7.1714(1.0); 7.1530(1.8); 7.1350(0.9); 7.1332(0.9); 5.7573(2.8); 3.8819(16.0); 3.3280(3.1); 2.6753 (0.3); 2.6711(0.4); 2.5243(1.0); 2.5196(1.6); 2.5108(22.8); 2.5064(46.8); 2.5019(62.0); 2.4973(45.3); 2.4928(22.1); 2.3286(0.4); 0.0080(2.3); −0.0002(71.9); −0.0086(2.6) |

-continued
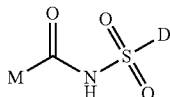
(I)
| Example No. | Structure | NMR peak list |
|---|---|---|
| I-421 | 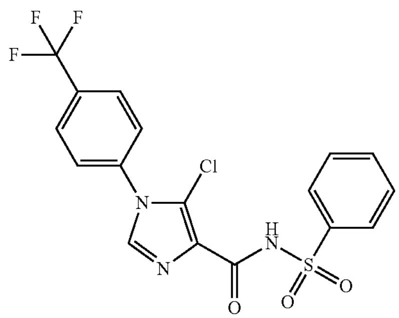 [SMILES: O=C(NS(=O)(=O)c1ccccc1)c1ncn(-c2ccc(C(F)(F)F)cc2)c1Cl] | I-421; ¹H-NMR(400.0 MHz, d₆-DMSO): δ = 8.3170(0.4); 8.2972(16.0); 8.0300(9.4); 8.0158(11.2); 8.0122 (14.9); 8.0089(10.1); 7.9946(10.7); 7.8154(10.0); 7.7946(8.5); 7.7384(1.5); 7.7194(4.8); 7.7015(3.9); 7.6625(7.3); 7.6430 (10.1); 7.6251(3.7); 3.3332(4.6); 2.8906(0.7); 2.7308(0.6); 2.6803(0.4); 2.6759(0.9); 2.6713(1.2); 2.6668(0.9); 2.6623(0.4); 2.5247(3.0); 2.5199(4.7); 2.5112(68.5); 2.5068(141.2); 2.5023 (188.4); 2.4977(138.5); 2.4933(68.0); 2.3336(0.9); 2.3290(1.3); 2.3245(0.9); 2.0752(8.4); 0.1459(0.5); 0.0080(3.5); −0.0002(113.1); −0.0085(4.0); −0.1498(0.5) |
| I-422 | 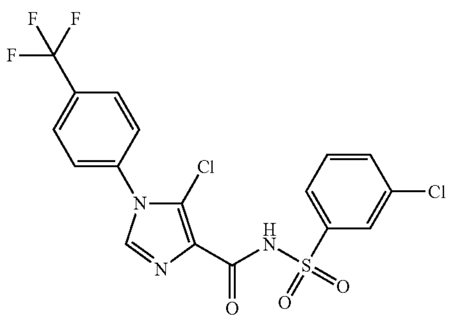 [SMILES: O=C(NS(=O)(=O)c1cccc(Cl)c1)c1ncn(-c2ccc(C(F)(F)F)cc2)c1Cl] | I-422; ¹H-NMR(400.0 MHz, d₆-DMSO): δ = 8.3192(16.0); 8.0217(10.2); 8.0168(9.6); 8.0119(5.5); 8.0011 (8.4); 7.9879(2.9); 7.9854(3.6); 7.9814(2.4); 7.9683(3.2); 7.9657(3.8); 7.9617(2.8); 7.9531(0.6); 7.8232(10.0); 7.8028(9.1); 7.7153(4.6); 7.6955(7.1); 7.6755(3.0); 5.7580(4.1); 3.6027 (0.4); 3.5339(0.5); 3.3680(1.0); 3.3561(1.0); 3.3481(1.0); 3.2528 (0.7); 3.1873(0.5); 3.0524(0.3); 2.8908(4.2); 2.7311(3.4); 2.6800(0.5); 2.6760(0.9); 2.6714(1.2); 2.6669(0.9); 2.5248(3.3); 2.5113(64.6); 2.5069(128.6); 2.5024(167.4); 2.4978(121.0); 2.4934(58.0); 2.3378(0.4); 2.3336(0.8); 2.3291(1.1); 2.3246 (0.8); 0.0079(1.0); −0.0002(30.8); −0.0085(1.0) |
| I-423 | 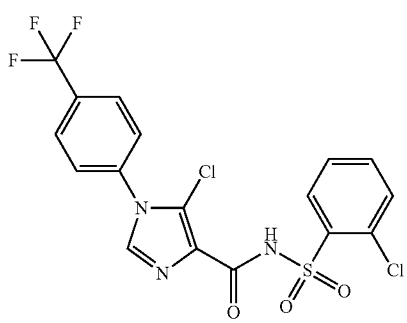 [SMILES: O=C(NS(=O)(=O)c1ccccc1Cl)c1ncn(-c2ccc(C(F)(F)F)cc2)c1Cl] | I-423; ¹H-NMR(400.0 MHz, d₆-DMSO): δ = 8.3211(16.0); 8.1774(3.9); 8.1736(4.2); 8.1575(4.3); 8.1540 (4.3); 8.0213(6.9); 8.0000(8.5); 7.8411(8.1); 7.8203(6.7); 7.7394(1.0); 7.7355(1.0); 7.7193(3.1); 7.7155(3.0); 7.7021(4.3); 7.6982(4.3); 7.6920(5.4); 7.6879(6.8); 7.6722(2.4); 7.6681(1.4); 7.6442(2.9); 7.6399(2.5); 7.6265(2.7); 7.6243(3.5); 7.6201 (2.8); 7.6072(2.0); 7.6027(1.8); 5.7578(4.8); 3.5230(0.5); 3.5062 (0.5); 3.4259(0.6); 3.4100(0.7); 3.3816(0.7); 3.3536(0.7); 3.3361(0.7); 3.3060(0.6); 3.3025(0.6); 3.2902(0.6); 3.2088(0.4); 3.1869(0.5); 3.1711(0.4); 2.8905(0.4); 2.6801(0.4); 2.6757(0.9); 2.6711(1.3); 2.6666(0.9); 2.6622(0.4); 2.5245(2.8); 2.5197 (4.4); 2.5110(70.8); 2.5066(145.1); 2.5021(192.3); 2.4975 (140.6); 2.4930(68.7); 2.3377(0.5); 2.3334(1.0); 2.3288(1.3); 2.3243(1.0); 2.3198(0.5); 0.0079(1.0); −0.0002(36.8); −0.0085(1.3) |
| I-424 | 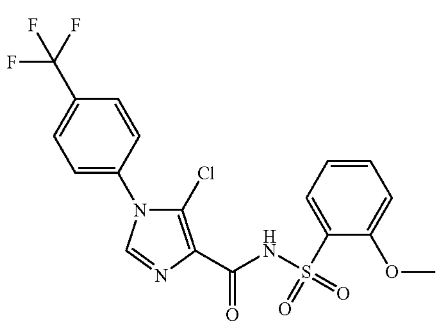 [SMILES: COc1ccccc1S(=O)(=O)NC(=O)c1ncn(-c2ccc(C(F)(F)F)cc2)c1Cl] | I-424; ¹H-NMR(400.0 MHz, d₆-DMSO): δ = 8.3102(5.1); 8.0229(2.8); 8.0016(3.4); 7.9190(1.6); 7.9148 (1.7); 7.8993(1.7); 7.8951(1.8); 7.8348(3.2); 7.8140(2.7); 7.7065(0.7); 7.7023(0.7); 7.6845(1.3); 7.6669(0.8); 7.6628 (0.8); 7.2660(1.9); 7.2453(1.7); 7.1761(1.0); 7.1577(1.9); 7.1395(0.9); 3.8876(16.0); 3.3271(6.5); 2.6753(0.4); 2.6709 (0.6); 2.6663(0.4); 2.5242(1.5); 2.5106(33.9); 2.5064(67.5); 2.5019(88.3); 2.4973(64.7); 2.4929(31.9); 2.3330(0.4); 2.3287(0.6); 2.3241(0.4); 2.0860(7.2); 2.0750(0.3); 0.0080(0.5); −0.0002(15.2); −0.0085(0.6) |

-continued (I)

| Example No. | Structure | NMR peak list |
|---|---|---|
| I-425 | 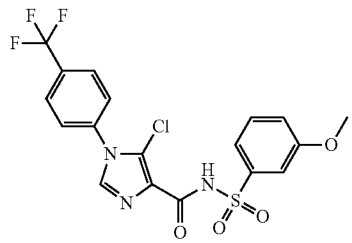 [SMILES: COc1cccc(S(=O)(=O)NC(=O)c2ncn(-c3ccc(C(F)(F)F)cc3)c2Cl)c1] | I-425; ¹H-NMR(400.0 MHz, d₆-DMSO): δ = 8.3040(5.3); 8.0202(2.5); 7.9990(3.1); 7.8205(2.9); 7.7998 (2.5); 7.6001(0.6); 7.5960(0.5); 7.5843(1.6); 7.5806(2.8); 7.5768 (3.2); 7.5583(2.2); 7.5373(1.8); 7.5310(2.0); 7.5269(1.5); 7.3012(0.8); 7.2970(1.1); 7.2903(0.8); 7.2821(0.8); 7.2776(1.0); 7.2717(0.7); 5.7579(0.7); 3.8381(16.0); 3.3340(1.0); 2.6711 (0.4); 2.5244(1.2); 2.5109(26.3); 2.5067(51.0); 2.5022(65.9); 2.4977(48.4); 2.4936(24.2); 2.3334(0.3); 2.3289(0.4); 2.3245 (0.3); 2.0862(0.8); 0.0078(0.4); −0.0002(10.8); −0.0085(0.4) |
| I-426 | 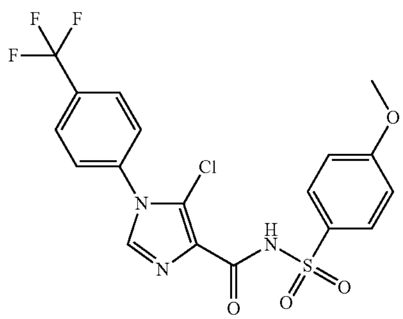 [SMILES: COc1ccc(S(=O)(=O)NC(=O)c2ncn(-c3ccc(C(F)(F)F)cc3)c2Cl)cc1] | I-426; ¹H-NMR(400.0 MHz, d₆-DMSO): δ = 8.2884(6.1); 8.0171(2.6); 7.9958(3.1); 7.9712(0.4); 7.9637 (4.1); 7.9589(1.4); 7.9464(1.2); 7.9414(4.5); 7.9341(0.5); 7.8144(3.0); 7.7936(2.5); 7.1725(0.4); 7.1650(4.3); 7.1601 (1.4); 7.1476(1.2); 7.1426(4.1); 7.1352(0.4); 5.7579(1.3); 3.8548(16.0); 3.3284(1.3); 2.5247(0.8); 2.5199(1.2); 2.5112 (17.4); 2.5068(36.0); 2.5023(48.2); 2.4978(35.8); 2.4934 (17.9); −0.0002(7.9) |
| I-427 | 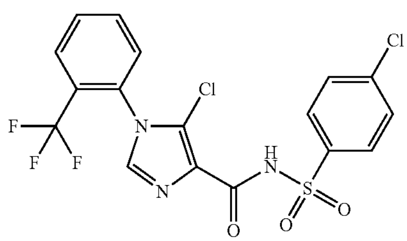 [SMILES: O=C(NS(=O)(=O)c1ccc(Cl)cc1)c1ncn(-c2ccccc2C(F)(F)F)c1Cl] | I-427; ¹H-NMR(400.0 MHz, d₆-DMSO): δ = 8.2664(10.6); 8.0477(5.0); 8.0403(13.8); 8.0351(6.1); 8.0237 (5.1); 8.0186(16.0); 8.0124(2.1); 7.9651(1.6); 7.9461(4.2); 7.9291(3.3); 7.8957(3.4); 7.8765(4.4); 7.8574(1.6); 7.7814(5.5); 7.7612(5.9); 7.7543(15.6); 7.7498(5.3); 7.7374(4.0); 7.7326 (13.5); 7.7265(1.7); 3.3624(0.4); 3.3520(0.4); 2.6771(0.4); 2.6725(0.6); 2.6682(0.4); 2.5258(1.1); 2.5120(30.5); 2.5078 (63.3); 2.5034(85.6); 2.4989(64.8); 2.4948(33.3); 2.3344(0.4); 2.3301(0.6); 2.3258(0.4); −0.0003(3.9) |
| I-428 | 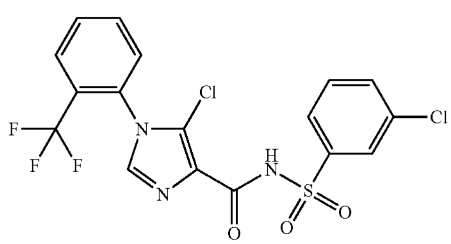 [SMILES: O=C(NS(=O)(=O)c1cccc(Cl)c1)c1ncn(-c2ccccc2C(F)(F)F)c1Cl] | I-428; ¹H-NMR(400.0 MHz, d₆-DMSO): δ = 8.2742(16.0); 8.0500(6.4); 8.0295(14.4); 8.0246(15.2); 8.0199(9.8); 7.9966(7.2); 7.9767(8.0); 7.9489(6.7); 7.9300(5.4); 7.8963(5.5); 7.8772(7.0); 7.8583(2.6); 7.8370(5.1); 7.8344(4.8); 7.8320(4.6); 7.8169(6.8); 7.8140(6.9); 7.8120(6.2); 7.7867 (8.7); 7.7675(7.0); 7.7224(9.0); 7.7025(14.0); 7.6825(6.0); 3.3562(2.4); 3.1185(0.6); 3.0497(0.4); 2.6759(1.4); 2.6715(1.9); 2.6671(1.4); 2.5248(4.4); 2.5112(104.4); 2.5069(211.0); 2.5024 (280.2); 2.4980(208.7); 2.4938(105.0); 2.3336(1.4); 2.3292 (1.8); 2.3247(1.4); −0.0002(8.1) |
| I-429 | 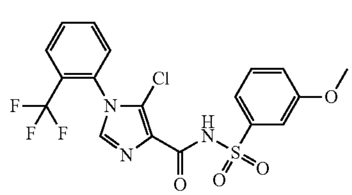 [SMILES: COc1cccc(S(=O)(=O)NC(=O)c2ncn(-c3ccccc3C(F)(F)F)c2Cl)c1] | I-429; ¹H-NMR(400.0 MHz, d₆-DMSO): δ = 8.2577(2.5); 8.0472(1.0); 8.0276(1.3); 7.9632(0.4); 7.9463 (1.1); 7.9439(1.1); 7.9275(0.9); 7.8937(0.9); 7.8747(1.2); 7.8561(0.4); 7.7809(1.4); 7.7616(1.1); 7.6111(0.7); 7.6071 (0.5); 7.5953(1.3); 7.5916(2.4); 7.5875(1.6); 7.5845(2.0); 7.5650(2.2); 7.5422(1.4); 7.5364(1.9); 7.5322(1.4); 7.3085 (0.8); 7.3048(0.9); 7.3022(0.9); 7.2981(0.8); 7.2890(0.7); 7.2852(0.8); 7.2831(0.8); 7.2789(0.7); 3.8415(16.0); 3.3285(1.4); 2.6711(0.4); 2.5245(0.8); 2.5197(1.2); 2.5111(19.7); 2.5066(41.4); 2.5020(56.1); 2.4975(42.0); 2.4930(21.1); 2.3289(0.4) |

-continued (I)

| Example No. | Structure | NMR peak list |
|---|---|---|
| I-430 | 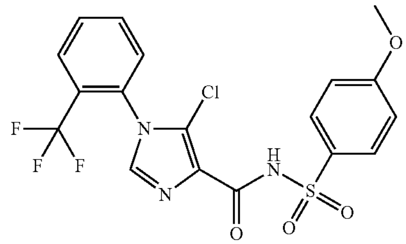 [SMILES: COc1ccc(S(=O)(=O)NC(=O)c2ncn(-c3ccccc3C(F)(F)F)c2Cl)cc1] | I-430; ¹H-NMR(400.0 MHz, d₆-DMSO): δ = 8.2410(2.9); 8.0447(1.2); 8.0250(1.4); 7.9810(0.4); 7.9735 (4.1); 7.9685(1.4); 7.9562(1.4); 7.9511(4.6); 7.9438(1.7); 7.9251(1.0); 7.8916(1.0); 7.8726(1.3); 7.8536(0.5); 7.7726 (1.6); 7.7534(1.3); 7.1771(0.5); 7.1696(4.3); 7.1646(1.4); 7.1521(1.2); 7.1471(4.1); 7.1397(0.4); 3.8573(16.0); 3.3283(1.8); 2.5246(0.6); 2.5112(15.1); 2.5068(31.0); 2.5022(41.3); 2.4977(30.7); 2.4933(15.3); 2.0752(2.5) |
| I-431 | 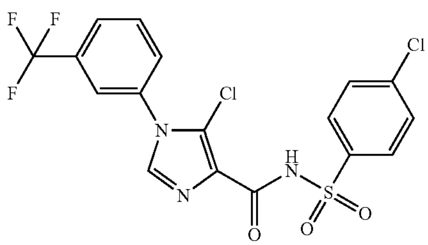 [SMILES: O=C(NS(=O)(=O)c1ccc(Cl)cc1)c1ncn(-c2cccc(C(F)(F)F)c2)c1Cl] | I-431; ¹H-NMR(400.0 MHz, d₆-DMSO): δ = 8.3541(0.5); 8.3165(0.7); 8.3059(16.0); 8.0376(6.4); 8.0329 (5.1); 8.0255(12.0); 8.0207(4.1); 8.0087(4.0); 8.0038(14.1); 7.9974(2.0); 7.9805(3.0); 7.9623(4.0); 7.8977(1.9); 7.8934 (1.4); 7.8814(4.0); 7.8774(6.1); 7.8671(5.2); 7.8483(4.1); 7.8284(1.4); 7.7518(1.6); 7.7454(12.9); 7.7406(4.2); 7.7284 (3.6); 7.7236(11.2); 7.7173(1.4); 3.3399(1.5); 3.2521(1.1); 3.1867(0.5); 2.6758(1.1); 2.6712(1.5); 2.6667(1.1); 2.6620 (0.6); 2.5246(3.8); 2.5198(5.6); 2.5111(78.5); 2.5067(161.9); 2.5021(217.0); 2.4976(159.6); 2.4931(77.6); 2.3378(0.4); 2.3335(1.0); 2.3289(1.4); 2.3243(1.0); −0.0002(1.2) |
| I-432 | 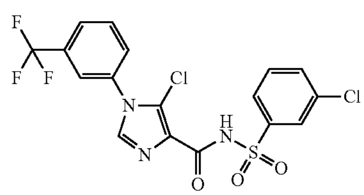 [SMILES: O=C(NS(=O)(=O)c1cccc(Cl)c1)c1ncn(-c2cccc(C(F)(F)F)c2)c1Cl] | I-432; ¹H-NMR(400.0 MHz, d₆-DMSO): δ = 8.3128(16.0); 8.0400(9.5); 8.0170(5.5); 8.0125(10.7); 8.0080 (7.5); 7.9805(9.3); 7.9626(10.8); 7.9007(3.0); 7.8803(8.8); 7.8685(7.5); 7.8496(6.3); 7.8296(2.3); 7.8205(3.7); 7.7975(5.2); 7.7096(6.2); 7.6897(9.6); 7.6697(4.1); 3.8907(0.3); 3.8617 (0.4); 3.8426(0.4); 3.7979(0.4); 3.7781(0.4); 3.7713(0.5); 3.7448 (0.5); 3.6977(0.6); 3.6602(0.8); 3.3446(15.1); 3.1416(1.5); 3.0532(0.9); 2.8910(0.4); 2.8671(0.4); 2.8561(0.3); 2.7720(0.3); 2.6755(3.2); 2.6710(4.4); 2.6666(3.3); 2.5243(10.3); 2.5106 (232.9); 2.5064(480.8); 2.5019(646.2); 2.4974(490.4); 2.4933 (250.0); 2.3331(3.2); 2.3287(4.4); 2.3241(3.2); 1.2349(0.4); 0.1459(4.1); 0.0486(0.4); 0.0413(0.4); 0.0079(30.8); −0.0002(913.4); −0.0085(37.5); −0.0203(1.4); −0.0284(0.7); −0.0364(0.4); −0.1498(4.1) |
| I-433 | 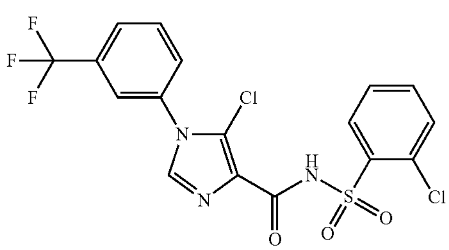 [SMILES: O=C(NS(=O)(=O)c1ccccc1Cl)c1ncn(-c2cccc(C(F)(F)F)c2)c1Cl] | I-433; ¹H-NMR(400.0 MHz, d₆-DMSO): δ = 19.9752(1.6); 8.3222(16.0); 8.1720(6.7); 8.1697(6.9); 8.1588 (7.4); 8.1565(7.1); 8.0645(10.1); 7.9782(5.4); 7.9654(6.6); 7.9153(4.3); 7.9025(6.6); 7.8646(5.6); 7.8514(7.8); 7.8384(3.2); 7.7281(2.0); 7.7148(5.3); 7.7028(5.2); 7.6862(9.1); 7.6748 (4.3); 7.6361(4.1); 7.6229(6.4); 7.6111(3.1); 3.4151(35.0); 2.6148(3.7); 2.5208(8.9); 2.5178(8.8); 2.5058(300.0); 2.5030 (390.8); 2.5001(280.0); 2.3870(2.6); 0.0965(1.8); −0.0002(399.9); −0.0057(16.6); −0.1001(1.8) |
| I-434 | 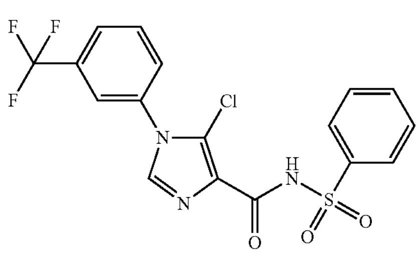 [SMILES: O=C(NS(=O)(=O)c1ccccc1)c1ncn(-c2cccc(C(F)(F)F)c2)c1Cl] | I-434; ¹H-NMR(400.0 MHz, d₆-DMSO): δ = 19.9713(1.2); 8.2966(16.0); 8.0343(11.7); 8.0260(15.5); 8.0135(15.4); 7.9747(6.1); 7.9620(7.5); 7.8897(4.2); 7.8759(8.6); 7.8593(7.1); 7.8462(8.2); 7.8331(3.1); 7.7288(2.8); 7.7165 (7.6); 7.7042(5.4); 7.6562(10.4); 7.6432(15.6); 7.6304(6.9); 3.3561(42.1); 2.6144(2.4); 2.5053(245.0); 2.5026(321.0); 2.4998(240.8); 2.3868(2.2); 0.0962(1.0); −0.0002(204.2); −0.1000(1.0) |

(I)
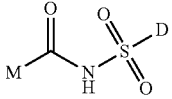
| Example No. | Structure | NMR peak list |
|---|---|---|
| I-435 | 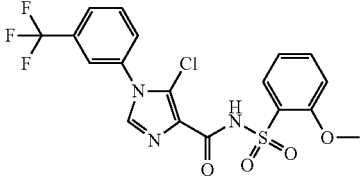 [SMILES: COc1ccccc1S(=O)(=O)NC(=O)c1ncn(-c2cccc(C(F)(F)F)c2)c1Cl] | I-435; ¹H-NMR(400.0 MHz, d₆-DMSO): δ = 8.3108(4.6); 8.0542(2.4); 7.9825(1.2); 7.9636(1.6); 7.9179 (2.1); 7.9140(2.5); 7.8980(3.2); 7.8942(3.7); 7.8712(1.7); 7.8517 (1.8); 7.8320(0.6); 7.7049(0.6); 7.7012(0.7); 7.6835(1.4); 7.6656(0.8); 7.6619(0.8); 7.2676(2.0); 7.2467(1.8); 7.1759(1.1); 7.1571(2.0); 7.1384(1.0); 3.8866(16.0); 3.8402(0.5); 3.3273 (6.7); 2.6758(0.7); 2.6711(0.5); 2.6666(0.4); 2.5240(1.1); 2.5062 (56.3); 2.5018(74.5); 2.4974(55.6); 2.3328(0.4); 2.3286(0.5); 2.3242(0.4); 0.1459(0.5); 0.0079(3.5); −0.0002(102.4); −0.0084(4.3); −0.1498(0.5) |
| I-436 | 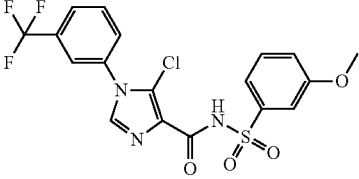 [SMILES: COc1cccc(S(=O)(=O)NC(=O)c2ncn(-c3cccc(C(F)(F)F)c3)c2Cl)c1] | I-436; ¹H-NMR(400.0 MHz, d₆-DMSO): δ = 8.3046(4.3); 8.0389(1.9); 7.9772(1.0); 7.9643(1.2); 7.8952 (0.7); 7.8813(1.4); 7.8633(1.2); 7.8504(1.4); 7.8372(0.5); 7.5945 (0.8); 7.5814(2.0); 7.5717(1.6); 7.5586(2.0); 7.5456(0.8); 7.5354(1.4); 7.5316(1.9); 7.5286(1.4); 7.2925(0.8); 7.2793(0.8); 3.8378(16.0); 3.3325(1.0); 2.6143(0.4); 2.5236(0.6); 2.5205 (0.7); 2.5174(0.7); 2.5085(20.8); 2.5056(45.6); 2.5026(63.4); 2.4996(46.2); 2.4966(21.5); 2.3867(0.4); 0.0965(0.4); 0.0052 (2.8); −0.0002(87.6); −0.0057(2.8); −0.1001(0.4) |
| I-437 | 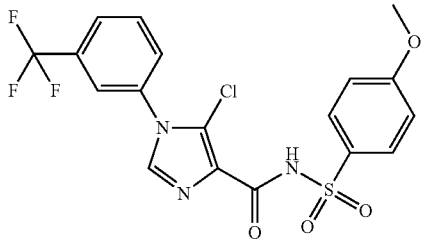 [SMILES: COc1ccc(S(=O)(=O)NC(=O)c2ncn(-c3cccc(C(F)(F)F)c3)c2Cl)cc1] | I-437; ¹H-NMR(400.0 MHz, d₆-DMSO): δ 5= 8.2861(3.0); 8.0308(1.9); 7.9744(1.0); 7.9580(3.9); 7.9430 (3.6); 7.8878(0.7); 7.8740(1.5); 7.8602(1.3); 7.8473(1.4); 7.8341 (0.5); 7.1587(3.2); 7.1438(3.0); 3.8536(16.0); 3.3323(5.9); 2.6143(0.5); 2.5236(0.8); 2.5205(1.0); 2.5174(1.0); 2.5086 (28.1); 2.5056(61.2); 2.5026(85.0); 2.4996(60.8); 2.4966(27.5); 2.3867(0.5); 0.0965(0.5); 0.0052(3.6); −0.0002(115.2); −0.0058(3.6); −0.1000(0.5) |
| I-438 | 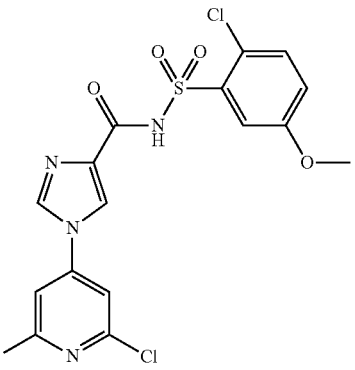 | I-438; ¹H-NMR(400.0 MHz, d₆-DMSO): δ = 8.8253(3.0); 8.8225(3.4); 8.7705(3.4); 8.7679(3.2); 8.1312 (11.2); 7.6178(2.9); 7.6101(3.0); 7.5809(2.6); 7.5589(3.0); 7.3033(1.6); 7.2957(1.5); 7.2814(1.4); 7.2736(1.3); 3.8596(16.0); 3.1687(10.7); 2.5064(31.8); 2.5021(41.9); 2.4978(31.3); 0.0073(0.5); −0.0002(13.3) |
| I-439 | 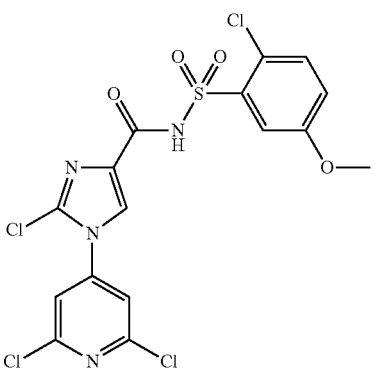 [SMILES: COc1ccc(Cl)c(S(=O)(=O)NC(=O)c2cn(-c3cc(Cl)nc(Cl)c3)c(Cl)n2)c1] | I-439; ¹H-NMR(400.0 MHz, d₆-DMSO): δ = 8.3808(6.0); 8.1035(1.1); 8.0141(12.4); 7.6120(2.9); 7.6043 (3.2); 7.5929(3.0); 7.5857(0.4); 7.5708(3.1); 7.5633(0.4); 7.3066(1.6); 7.2989(1.5); 7.2846(1.4); 7.2768(1.3); 3.8618(16.0); 3.8181(0.4); 3.1888(0.4); 3.1685(0.5); 2.6705(0.3); 2.5650 (0.4); 2.5059(41.9); 2.5015(55.8); 2.4972(41.7); 2.3279(0.3); 0.0072(0.3); −0.0003(8.7); −0.0084(0.4) |

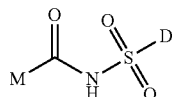
| Example No. | Structure | NMR peak list |
|---|---|---|
| I-440 | 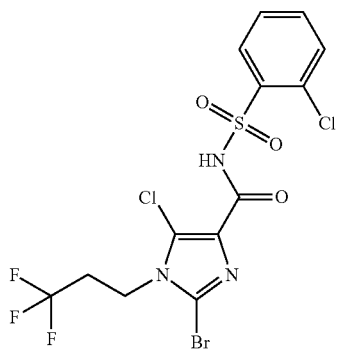 [SMILES: O=C(NS(=O)(=O)c1ccccc1Cl)c1nc(Br)n(CCC(F)(F)F)c1Cl] | I-440; ¹H-NMR(400.0 MHz, d$_6$-DMSO): δ = 8.1411(4.9); 8.1377(5.6); 8.1213(5.4); 8.1180(5.8); 7.7249 (1.3); 7.7212(1.5); 7.7018(4.2); 7.6872(4.4); 7.6837(4.9); 7.6660(8.5); 7.6494(3.1); 7.6465(3.1); 7.6280(3.2); 7.6250(3.4); 7.6079(4.9); 7.5907(2.1); 7.5875(2.2); 5.7559(16.0); 4.3081(4.9); 4.2907(10.7); 4.2728(6.7); 4.2540(1.5); 3.3411(3.8); 2.8872 (0.8); 2.8710(1.9); 2.8596(2.5); 2.8552(2.4); 2.8429(4.6); 2.8318(3.0); 2.8266(3.4); 2.8149(4.4); 2.7980(2.3); 2.7869(1.5); 2.7698(0.6); 2.6755(0.6); 2.6711(0.8); 2.6667(0.6); 2.5498(0.6); 2.5105(53.5); 2.5065(102.9); 2.5021(134.1); 2.4977(100.8); 2.3333(0.6); 2.3288(0.8); 2.3245(0.6); 1.2348(0.7); 0.0077 (2.4); −0.0002(48.6); −0.0077(2.4) |
| I-441 | 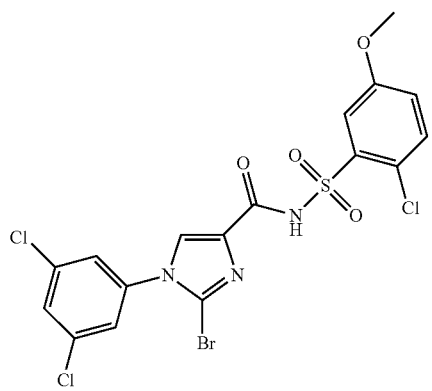 | I-441; ¹H-NMR(400.0 MHz, d$_6$-DMSO): δ = 8.3430(5.5); 7.9035(1.8); 7.8989(3.5); 7.8944(2.2); 7.8022 (7.3); 7.7977(7.0); 7.6140(2.9); 7.6063(3.2); 7.5977(2.7); 7.5757 (3.0); 7.3060(1.5); 7.2984(1.5); 7.2839(1.4); 7.2763(1.3); 3.8637(16.0); 2.6705(0.4); 2.5649(0.4); 2.5058(45.2); 2.5015 (58.5); 2.4971(43.5); 2.3283(0.3); 1.2581(1.1); −0.0001(1.2) |
| I-442 | 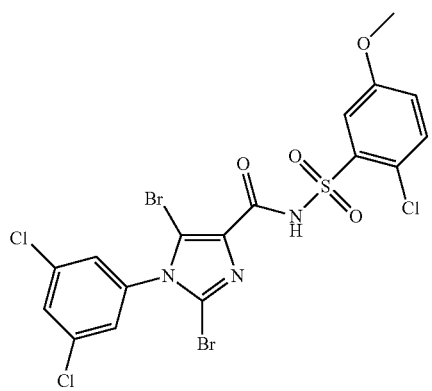 [SMILES: COc1ccc(Cl)c(S(=O)(=O)NC(=O)c2nc(Br)n(-c3cc(Cl)cc(Cl)c3)c2Br)c1] | I-442; ¹H-NMR(400.0 MHz, d$_6$-DMSO): δ = 8.3450(0.5); 7.9670(1.6); 7.9626(3.0); 7.9580(1.8); 7.8882 (1.4); 7.8836(1.2); 7.8679(5.6); 7.8633(5.2); 7.8027(0.5); 7.7981 (0.5); 7.6021(3.1); 7.5949(5.1); 7.5735(2.8); 7.3005(1.6); 7.2929(1.4); 7.2785(1.4); 7.2708(1.2); 3.8581(16.0); 3.3491(0.9); 2.6705(0.3); 2.5058(45.2); 2.5015(58.8); 2.4971(43.2); 2.3282(0.4); 2.0737(6.1); −0.0002(1.3) |

-continued
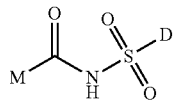
(I)
| Example No. | Structure | NMR peak list |
|---|---|---|
| I-443 | 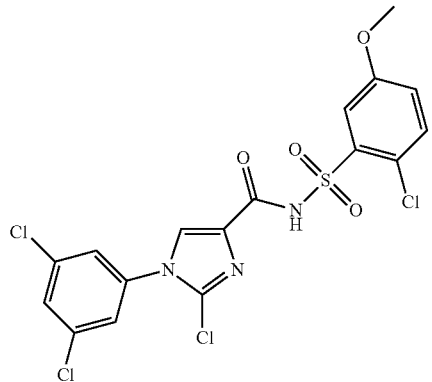 [SMILES: COc1ccc(Cl)c(S(=O)(=O)NC(=O)c2cn(-c3cc(Cl)cc(Cl)c3)c(Cl)n2)c1] | I-443; ¹H-NMR(400.0 MHz, d₆-DMSO): δ = 8.4048(0.8); 8.2933(6.2); 7.8990(1.8); 7.8945(3.4); 7.8899 (2.4); 7.8823(0.7); 7.8322(1.3); 7.8216(7.3); 7.8171(7.1); 7.6156 (3.0); 7.6080(3.6); 7.5978(3.0); 7.5757(3.2); 7.3083(1.8); 7.3007(1.8); 7.2862(1.6); 7.2785(1.6); 3.8627(16.0); 2.6989(0.5); 2.5657(6.2); 2.5067(33.0); 2.5024(43.3); 2.4982(35.6); −0.0002(3.5) |
| I-444 | 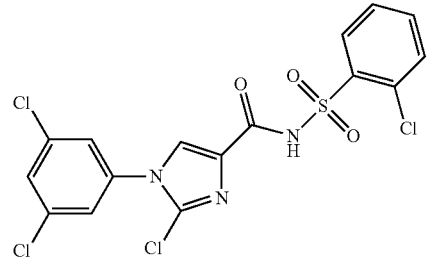 [SMILES: O=C(NS(=O)(=O)c1ccccc1Cl)c1cn(-c2cc(Cl)cc(Cl)c2)c(Cl)n1] | I-444; ¹H-NMR(400.0 MHz, d₆-DMSO): δ = 8.3920(0.4); 8.2875(13.8); 8.1750(3.1); 8.1713(3.4); 8.1551 (3.4); 8.1516(3.6); 7.8954(3.7); 7.8908(7.5); 7.8862(4.7); 7.8281(0.8); 7.8234(0.9); 7.8148(16.0); 7.8102(15.0); 7.7380(0.8); 7.7340(0.9); 7.7177(2.7); 7.7141(2.6); 7.7006(3.5); 7.6968 (3.6); 7.6895(4.5); 7.6855(5.7); 7.6696(2.1); 7.6657(1.4); 7.6431 (2.3); 7.6389(2.1); 7.6232(3.0); 7.6193(2.5); 7.6061(1.6); 7.6017(1.5); 2.6716(0.4); 2.5070(44.0); 2.5025(57.0); 2.4980 (42.6); 2.3290(0.3); 1.0459(0.3); 1.0307(0.3); 0.0079(0.3); −0.0002(7.8) |
| I-445 | 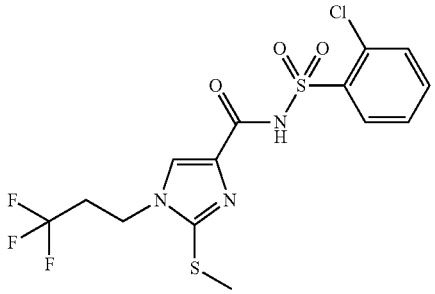 [SMILES: CSc1nc(C(=O)NS(=O)(=O)c2ccccc2Cl)cn1CCC(F)(F)F] | I-445; ¹H-NMR(400.0 MHz, d₆-DMSO): δ = 8.1572(4.8); 8.1496(1.6); 8.1460(1.6); 8.1297(1.6); 8.1263 (1.6); 7.7212(0.4); 7.7176(0.4); 7.7010(1.3); 7.6835(1.5); 7.6799 (1.4); 7.6655(2.0); 7.6626(2.5); 7.6463(1.0); 7.6262(1.1); 7.6227(0.9); 7.6062(1.5); 7.5887(0.7); 7.5854(0.6); 4.2226(1.7); 4.2054(3.6); 4.1881(1.8); 2.8738(0.4); 2.8633(0.7); 2.8459(1.4); 2.8351(0.9); 2.8289(0.8); 2.8181(1.4); 2.8008(0.7); 2.7906 (0.5); 2.6161(16.0); 2.5063(21.0); 2.5021(26.6); 2.4979(19.9); 2.0858(1.1); −0.0002(5.2) |
| I-446 | 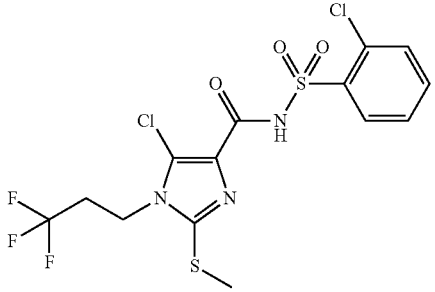 [SMILES: CSc1nc(C(=O)NS(=O)(=O)c2ccccc2Cl)c(Cl)n1CCC(F)(F)F] | I-446; ¹H-NMR(400.0 MHz, d₆-DMSO): δ = 8.1584(1.5); 8.1549(1.6); 8.1386(1.6); 8.1352(1.7); 7.7377 (0.4); 7.7343(0.4); 7.7176(1.3); 7.7156(1.2); 7.7000(1.5); 7.6964 (1.4); 7.6795(2.7); 7.6632(1.1); 7.6406(1.1); 7.6374(0.9); 7.6206(1.6); 7.6031(0.7); 7.5998(0.6); 4.2095(1.7); 4.1922(3.4); 4.1748(1.7); 2.8244(0.5); 2.8137(0.7); 2.7966(1.4); 2.7858(0.9); 2.7793(0.8); 2.7687(1.4); 2.7513(0.7); 2.7409(0.5); 2.7014 (16.0); 2.5066(19.0); 2.5025(24.2); 2.4986(18.2); 2.0743(1.4); 0.0078(0.5); −0.0002(10.5) |

-continued
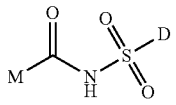
| Example No. | Structure | NMR peak list |
|---|---|---|
| I-447 | 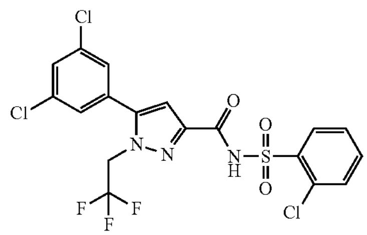 [SMILES: O=C(NS(=O)(=O)c1ccccc1Cl)c1cc(-c2cc(Cl)cc(Cl)c2)n(CC(F)(F)F)n1] | I-447; ¹H-NMR(400.0 MHz, d₆-DMSO): δ = 8.1880(3.4); 8.1687(3.7); 7.8089(3.9); 7.8045(7.4); 7.8002 (4.5); 7.7428(0.9); 7.7245(2.7); 7.7051(3.1); 7.6880(5.4); 7.6709 (2.2); 7.6448(16.0); 7.6404(14.6); 7.6297(3.6); 7.6120(1.4); 7.1951(7.9); 5.2346(1.5); 5.2128(4.6); 5.1908(4.7); 5.1687(1.6); 3.3808(1.7); 2.6720(1.0); 2.5069(133.8); 2.5027(175.4); 2.4988(133.6); 2.3295(1.0); 2.0745(4.6); 0.0077(1.1); −0.0002(32.0); −0.0081(1.4) |
| I-448 | 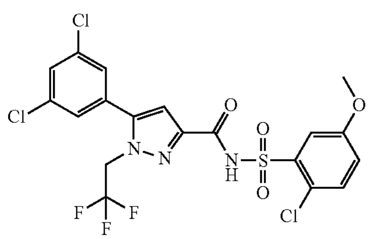 [SMILES: COc1ccc(Cl)c(S(=O)(=O)NC(=O)c2cc(-c3cc(Cl)cc(Cl)c3)n(CC(F)(F)F)n2)c1] | I-448; ¹H-NMR(400.0 MHz, d₆-DMSO): δ = 7.8094(1.9); 7.8049(3.3); 7.8004(1.9); 7.6450(7.0); 7.6405 (6.4); 7.6283(3.0); 7.6206(3.1); 7.5969(2.3); 7.5748(2.7); 7.3168 (1.4); 7.3092(1.3); 7.2948(1.2); 7.2870(1.1); 7.1958(4.0); 5.2331(0.7); 5.2114(2.1); 5.1895(2.2); 5.1669(0.7); 3.8640(16.0); 3.3524(5.2); 2.6717(0.4); 2.5069(62.0); 2.5026(78.7); 2.4987 (57.3); 2.3293(0.5); 2.0743(1.7); 1.3094(0.3); 0.0078(1.3); −0.0001(26.3) |
| I-449 | 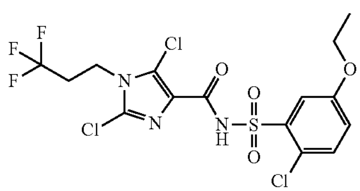 [SMILES: CCOc1ccc(Cl)c(S(=O)(=O)NC(=O)c2nc(Cl)n(CCC(F)(F)F)c2Cl)c1] | I-449; ¹H-NMR(400.0 MHz, d₆-DMSO): δ = 7.5605(6.0); 7.5524(8.2); 7.5286(5.5); 7.2704(2.8); 7.2628 (2.7); 7.2484(2.4); 7.2408(2.3); 5.7559(12.7); 4.2897(3.3); 4.2728(7.0); 4.2560(3.4); 4.1359(2.1); 4.1186(6.8); 4.1012(6.9); 4.0839(2.2); 3.3391(7.8); 2.9024(0.4); 2.8856(0.9); 2.8749(1.4); 2.8579(2.7); 2.8467(1.8); 2.8411(1.7); 2.8301(2.8); 2.8133 (1.4); 2.8022(1.0); 2.7852(0.4); 2.6749(0.7); 2.6706(1.0); 2.6661 (0.7); 2.5099(60.1); 2.5059(118.9); 2.5015(157.1); 2.4970 (117.8); 2.3327(0.7); 2.3282(1.0); 2.3237(0.7); 2.0085(0.5); 1.9895(0.5); 1.3744(7.5); 1.3570(16.0); 1.3396(7.4); 1.2354(2.9); 0.8540(0.7); 0.0077(2.3); −0.0003(58.1); −0.0083(2.8) |
| I-450 | 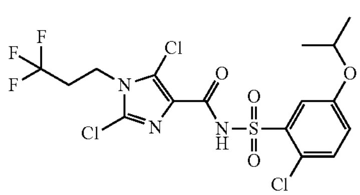 [SMILES: CC(C)Oc1ccc(Cl)c(S(=O)(=O)NC(=O)c2nc(Cl)n(CCC(F)(F)F)c2Cl)c1] | I-450; ¹H-NMR(400.0 MHz, d₆-DMSO): δ = 7.5390(2.9); 7.5321(4.6); 7.5108(2.5); 7.2617(1.2); 7.2542 (1.2); 7.2397(1.0); 7.2321(1.0); 7.5546(0.4); 4.7057(0.4); 4.6912 (1.0); 4.6761(1.4); 4.6612(1.0); 4.6464(0.4); 4.2913(1.6); 4.2745(3.4); 4.2577(1.6); 3.3370(162.7); 2.8846(0.4); 2.8738(0.7); 2.8570(1.3); 2.8455(0.9); 2.8410(0.8); 2.8290(1.4); 2.8122 (0.7); 2.8015(0.5); 2.6759(0.6); 2.6713(0.8); 2.6668(0.6); 2.5243(2.5); 2.5109(55.8); 2.5067(112.1); 2.5023(148.0); 2.4979 (108.4); 2.3333(0.7); 2.3290(0.8); 2.3245(0.7); 1.3090(16.0); 1.2940(15.9); 1.2350(0.6); 0.0079(1.5); −0.0002(43.1); −0.0082(1.8) |
| I-451 | 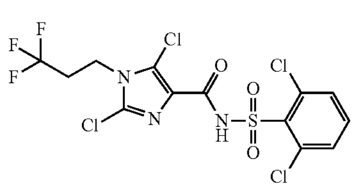 [SMILES: O=C(NS(=O)(=O)c1c(Cl)cccc1Cl)c1nc(Cl)n(CCC(F)(F)F)c1Cl] | I-451; ¹H-NMR(400.0 MHz, d₆-DMSO): δ = 7.6681(5.1); 7.6633(6.4); 7.6456(16.0); 7.6121(6.4); 7.5957 (3.9); 7.5890(2.8); 7.5727(1.9); 7.3939(0.6); 7.3901(0.7); 7.3719(1.6); 7.3276(0.6); 7.3109(0.4); 5.7564(6.2); 4.2896(4.4); 4.2729(9.3); 4.2558(4.6); 3.6095(0.3); 3.5919(0.4); 3.3974(3.0); 3.2313(0.5); 2.9046(0.7); 2.8881(1.4); 2.8767(2.0); 2.8599 (3.7); 2.8485(2.5); 2.8440(2.3); 2.8320(3.8); 2.8154(1.9); 2.8042(1.4); 2.7867(0.6); 2.6748(1.2); 2.6702(1.5); 2.6661(1.2); 2.5057(184.4); 2.5014(240.1); 2.4972(183.0); 2.3326(1.0); 2.3280(1.3); 1.2355(1.5); 0.8539(0.4); 0.1459(0.4); −0.0003(77.3); −0.1497(0.4) |

-continued (I)

| Example No. | Structure | NMR peak list |
|---|---|---|
| I-452 | (2,5-dichloro-1-(3,3,3-trifluoropropyl)imidazole-4-carboxamide with N-(2-methylphenyl)sulfonyl) | I-452; ¹H-NMR(400.0 MHz, d₆-DMSO): δ = 12.4480(0.4); 8.0141(2.1); 7.9966(2.2); 7.9943(2.2); 7.5874 (0.9); 7.5712(2.0); 7.5685(2.0); 7.5523(1.3); 7.5501(1.3); 7.4529(1.3); 7.4339(2.1); 7.4150(1.0); 7.3961(2.2); 7.3773(1.8); 5.7561(3.4); 4.2839(2.4); 4.2671(5.0); 4.2503(2.4); 3.3285(5.4); 2.8727(0.6); 2.8615(1.0); 2.8449(1.9); 2.8334(1.2); 2.8283 (1.2); 2.8170(2.0); 2.8002(1.0); 2.7892(0.7); 2.7719(0.3); 2.6748 (0.3); 2.6705(0.4); 2.6658(0.4); 2.5959(16.0); 2.5059(55.4); 2.5015(73.4); 2.4971(55.3); 2.3282(0.4); 1.2351(0.7); 0.0079 (1.1); −0.0002(27.7) |
| I-453 | (2,5-dichloro-1-(3,3,3-trifluoropropyl)imidazole-4-carboxamide with N-(2-chloro-6-methylthiophenyl)sulfonyl) | I-453; ¹H-NMR(400.0 MHz, d₆-DMSO): δ = 7.4874(1.6); 7.4701(1.3); 7.3693(2.2); 7.3491(1.9); 7.3271 (2.3); 7.3088(1.8); 5.7564(14.7); 5.3252(0.4); 4.2785(4.6); 4.2616(9.2); 4.2448(4.5); 4.0381(0.6); 4.0204(0.6); 3.3244(2.3); 2.8936(0.6); 2.8769(1.3); 2.8661(2.1); 2.8493(3.7); 2.8379(2.6); 2.8331(2.4); 2.8214(3.8); 2.8047(1.9); 2.7935(1.4); 2.7764 (0.6); 2.7167(0.5); 2.6748(0.5); 2.6709(0.6); 2.6665(0.4); 2.5238 (1.8); 2.5061(70.3); 2.5017(90.0); 2.4974(63.9); 2.4372(16.0); 2.3326(0.4); 2.3285(0.6); 2.3246(0.4); 2.0278(0.4); 2.0097 (0.8); 1.9889(3.2); 1.9738(0.4); 1.4576(0.3); 1.2990(1.2); 1.2842 (1.0); 1.2587(2.2); 1.2358(8.0); 1.1922(0.9); 1.1746(1.4); 1.1569(0.7); 0.8699(0.6); 0.8539(1.6); 0.8368(0.7); −0.0002(0.6) |
| I-454 | (2,5-dichloro-1-(3,3,3-trifluoropropyl)imidazole-4-carboxamide with N-(2-methoxy-5-chlorophenyl)sulfonyl) | I-454; ¹H-NMR(400.0 MHz, d₆-DMSO): δ = 7.8028(3.1); 7.7961(3.8); 7.7519(1.5); 7.7452(1.2); 7.7296 (1.6); 7.7229(1.3); 7.2888(2.6); 7.2664(2.4); 5.7558(1.0); 4.2921 (1.8); 4.2753(3.8); 4.2584(1.8); 3.8511(16.0); 3.3266(13.0); 2.8854(0.5); 2.8744(0.7); 2.8578(1.4); 2.8463(0.9); 2.8414(0.8); 2.8299(1.5); 2.8132(0.7); 2.8018(0.5); 2.6750(0.4); 2.6706 (0.5); 2.6661(0.4); 2.5236(1.5); 2.5101(31.7); 2.5059(64.1); 2.5014(84.8); 2.4970(61.9); 2.4928(30.6); 2.3323(0.4); 2.3282 (0.5); 2.3240(0.4); 0.0078(1.2); −0.0002(31.6); −0.0085(1.2) |
| I-455 | (2,5-dichloro-1-(3,3,3-trifluoropropyl)imidazole-4-carboxamide with N-(2-bromo-5-methoxyphenyl)sulfonyl) | I-455; ¹H-NMR(400.0 MHz, d₆-DMSO): δ = 7.7329(2.4); 7.7110(2.6); 7.6248(2.8); 7.6170(2.9); 7.2080 (1.3); 7.2003(1.3); 7.1860(1.2); 7.1784(1.2); 4.2914(1.6); 4.2746 (3.4); 4.2576(1.6); 3.8454(16.0); 3.3351(6.9); 2.8878(0.4); 2.8769(0.7); 2.8603(1.3); 2.8487(0.8); 2.8435(0.8); 2.8324(1.4); 2.8154(0.7); 2.8045(0.5); 2.6749(0.4); 2.6705(0.6); 2.6660 (0.4); 2.5236(1.6); 2.5100(35.7); 2.5059(72.6); 2.5015(96.8); 2.4970(71.8); 2.3325(0.4); 2.3282(0.6); 2.3238(0.4); 1.2353 (1.5); 0.8542(0.4); 0.0078(1.2); −0.0002(33.1); −0.0080(1.5) |
| I-456 | (2,5-dichloro-1-(3,3,3-trifluoropropyl)imidazole-4-carboxamide with N-(2-methyl-5-ethylphenyl)sulfonyl) | I-456; ¹H-NMR(400.0 MHz, d₆-DMSO): δ = 12.3723(0.7); 7.8339(4.5); 7.8304(4.6); 7.8035(0.4); 7.4301 (1.9); 7.4107(2.5); 7.3301(0.4); 7.3029(3.7); 7.2833(2.7); 4.2854(3.3); 4.2686(6.8); 4.2517(3.3); 3.3240(62.5); 2.9940(0.4); 2.9753(0.4); 2.8902(0.4); 2.8733(0.9); 2.8626(1.4); 2.8456(2.6); 2.8345(1.8); 2.8296(1.6); 2.8179(2.7); 2.8010(1.3); 2.7898 (1.0); 2.7731(0.4); 2.6983(1.6); 2.6793(5.3); 2.6706(1.7); 2.6605 (5.3); 2.6415(1.7); 2.5471(21.0); 2.5233(3.5); 2.5058(136.5); 2.5014(179.9); 2.4970(133.0); 2.3622(1.8); 2.3326(0.8); 2.3282(1.1); 2.3239(0.8); 1.2355(1.7); 1.2112(7.6); 1.1924(16.0); 1.1734(7.3); 1.1370(0.6); 1.1186(1.2); 1.0998(0.6); 0.8538 (0.4); 0.0078(2.2); −0.0002(61.2); −0.0082(2.7) |
| I-457 | (2,5-dichloro-1-(3,3,3-trifluoropropyl)imidazole-4-carboxamide with N-(2-fluoro-5-methoxyphenyl)sulfonyl) | I-457; ¹H-NMR(400.0 MHz, d₆-DMSO): δ = 7.4008(0.7); 7.3831(1.3); 7.3761(2.5); 7.3694(1.3); 7.3613 (1.4); 7.3540(1.2); 7.3155(0.7); 7.3061(1.1); 7.2979(0.7); 7.2837(0.6); 7.2752(0.3); 4.2900(1.5); 4.2731(3.1); 4.2561(1.5); 3.8208(16.0); 3.3383(3.6); 2.8812(0.4); 2.8701(0.6); 2.8537(1.2); 2.8420(0.8); 2.8370(0.7); 2.8256(1.2); 2.8089(0.6); 2.7977 (0.4); 2.6750(0.4); 2.6706(0.5); 2.6663(0.4); 2.5234(1.6); 2.5101(31.4); 2.5059(63.6); 2.5014(84.5); 2.4970(61.8); 2.4926 (30.4); 2.3328(0.4); 2.3282(0.5); 2.3236(0.4); 1.2354(0.9); 0.0080 (1.1); −0.0001(31.2); −0.0083(1.3) |

-continued (I)

[Structure: M-C(=O)-NH-S(=O)2-D]

| Example No. | Structure | NMR peak list |
|---|---|---|
| I-458 | [Structure] | I-458; ¹H-NMR(400.0 MHz, d$_6$-DMSO): δ = 8.3182(10.9); 8.1062(4.7); 8.0846(5.7); 7.9333(8.2); 7.9120 (6.6); 7.8362(1.0); 7.4314(0.5); 7.4139(0.6); 7.3067(0.8); 7.2865(0.6); 5.7562(0.6); 5.3247(0.4); 5.3131(0.3); 4.2843(7.9); 4.2675(16.0); 4.2508(8.1); 4.0885(0.4); 3.9755(0.4); 3.9634(0.4); 3.9410(0.5); 3.9048(0.5); 3.8820(0.5); 3.8559(0.5); 3.7910 (0.7); 3.7679(0.7); 3.7346(0.9); 3.3909(10.3); 3.1075(1.1); 3.1021(1.0); 3.0312(0.7); 2.9946(0.7); 2.9765(0.6); 2.8940(1.4); 2.8776(2.7); 2.8667(3.9); 2.8504(6.7); 2.8391(5.0); 2.8229(6.8); 2.8058(3.7); 2.7947(2.7); 2.7781(1.4); 2.7394(0.4); 2.6981 (0.7); 2.6708(3.6); 2.6438(0.7); 2.5984(0.6); 2.5475(5.8); 2.5019 (552.7); 2.3629(0.6); 2.3284(3.2); 2.0252(0.4); 2.0097(0.7); 1.9898(0.8); 1.2359(4.3); 1.2120(1.7); 1.1929(2.6); 1.1740 (1.2); 0.8696(0.5); 0.8533(0.9); 0.8361(0.5); 0.1458(0.7); 0.0000(141.3); −0.1492(0.8) |
| I-459 | [Structure] | I-459; ¹H-NMR(400.0 MHz, d$_6$-DMSO): δ = 7.5569(6.1); 7.5488(7.5); 7.5463(7.1); 7.5238(6.4); 7.2680 (3.2); 7.2604(3.1); 7.2460(2.8); 7.2383(2.7); 5.7543(1.3); 4.1360 (2.2); 4.1187(7.1); 4.1013(7.2); 4.0840(2.3); 3.7889(1.2); 3.7772(2.0); 3.7685(2.6); 3.7594(1.9); 3.7479(1.3); 3.3431(2.7); 2.8148(0.6); 2.8062(0.7); 2.7978(1.1); 2.7891(1.4); 2.7807(1.3); 2.7720(1.4); 2.7634(1.1); 2.7547(0.8); 2.7461(0.6); 2.6706 (0.5); 2.5056(60.1); 2.5014(77.7); 2.4973(58.3); 2.3281(0.5); 2.0088(0.5); 1.9899(0.5); 1.7761(0.8); 1.7591(2.5); 1.7402(2.8); 1.7239(2.1); 1.7134(1.8); 1.7003(1.7); 1.6882(1.7); 1.6720 (0.7); 1.3751(7.7); 1.3578(16.0); 1.3404(7.5); 1.2922(0.3); 1.2356(3.1); 0.8540(0.7); 0.0073(1.9); −0.0002(43.0) |
| I-460 | [Structure] | I-460; ¹H-NMR(400.0 MHz, d$_6$-DMSO): δ = 7.5371(2.9); 7.5299(5.3); 7.5081(3.0); 7.2631(1.5); 7.2555 (1.4); 7.2410(1.2); 7.2335(1.2); 5.7541(1.5); 4.7093(0.4); 4.6944 (1.0); 4.6794(1.4); 4.6644(1.1); 4.6492(0.4); 3.7910(0.6); 3.7790(0.9); 3.7705(1.2); 3.7617(0.9); 3.7497(0.6); 3.3395(2.3); 2.7979(0.5); 2.7891(0.6); 2.7808(0.6); 2.7717(0.6); 2.7631(0.5); 2.7548(0.4); 2.5060(31.9); 2.5016(41.3); 2.4972(30.0); 1.7772 (0.4); 1.7598(1.1); 1.7407(1.2); 1.7248(1.0); 1.7129(0.8); 1.7004(0.8); 1.6885(0.7); 1.3100(16.0); 1.2950(15.8); 1.2356 (0.4); 0.0078(1.0); −0.0002(24.6); −0.0083(1.2) |
| I-461 | [Structure] | I-461; ¹H-NMR(400.0 MHz, d$_6$-DMSO): δ = 7.6626(5.1); 7.6578(6.4); 7.6404(16.0); 7.6069(6.2); 7.5905 (3.8); 7.5837(2.8); 7.5674(1.8); 3.7885(1.5); 3.7766(2.5); 3.7680(3.2); 3.7592(2.4); 3.7473(1.7); 3.3631(1.5); 2.8164(0.8); 2.8076(0.9); 2.7996(1.4); 2.7909(1.8); 2.7824(1.6); 2.7737(1.8); 2.7652(1.4); 2.7567(1.0); 2.7480(0.8); 2.6704(0.7); 2.6662 (0.6); 2.5058(90.0); 2.5015(115.6); 2.4973(85.6); 2.3282(0.7); 2.0736(10.0); 1.7767(1.0); 1.7595(3.0); 1.7405(3.5); 1.7237 (2.4); 1.7146(2.2); 1.7016(2.1); 1.6891(2.0); 1.6728(0.8); 0.0077 (3.1); −0.0002(65.0) |

-continued
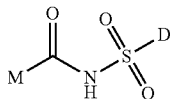
(I)
| Example No. | Structure | NMR peak list |
|---|---|---|
| I-462 | 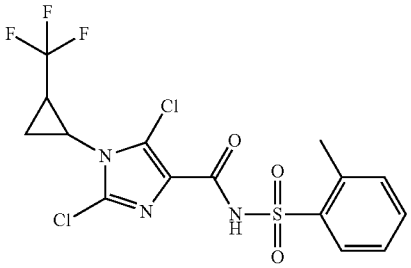 [SMILES: Cc1ccccc1S(=O)(=O)NC(=O)c1nc(Cl)n(C2CC2C(F)(F)F)c1Cl] | I-462; ¹H-NMR(400.0 MHz, d₆-DMSO): δ = 12.4360(0.4); 8.0057(2.1); 7.9859(2.2); 7.5805(0.8); 7.5620 (1.9); 7.5431(1.2); 7.4473(1.3); 7.4282(2.0); 7.4092(0.9); 7.3878(2.2); 7.3691(1.8); 5.7542(3.7); 3.7792(0.8); 3.7674(1.2); 3.7588(1.6); 3.7499(1.2); 3.7381(0.8); 3.3229(14.9); 2.7946(0.4); 2.7857(0.5); 2.7776(0.7); 2.7691(0.9); 2.7607(0.8); 2.7519 (0.9); 2.7433(0.7); 2.7349(0.5); 2.7260(0.4); 2.6700(0.5); 2.6662 (0.4); 2.5874(16.0); 2.5056(64.1); 2.5012(83.5); 2.4969 (61.2); 2.3326(0.4); 2.3281(0.5); 2.3239(0.4); 1.7704(0.5); 1.7532 (1.5); 1.7340(1.7); 1.7162(0.9); 1.7105(0.9); 1.6966(1.0); 1.6835(1.0); 1.6714(1.0); 1.6554(0.4); 1.2356(0.6); 0.0079(1.9); −0.0002(45.6); −0.0081(2.0) |
| I-463 | 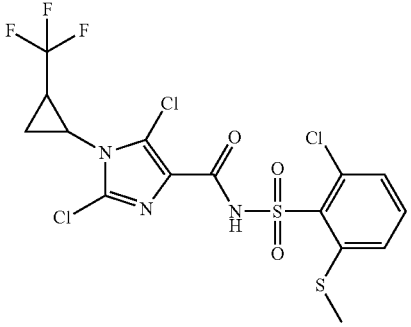 [SMILES: CSc1cccc(Cl)c1S(=O)(=O)NC(=O)c1nc(Cl)n(C2CC2C(F)(F)F)c1Cl] | I-463; ¹H-NMR(400.0 MHz, d₆-DMSO): δ = 7.6643(0.4); 7.5467(2.0); 7.5264(4.7); 7.5064(3.6); 7.4895 (0.4); 7.4837(0.4); 7.4795(0.5); 7.4594(0.4); 7.4043(4.0); 7.3838 (3.0); 7.3596(4.5); 7.3578(4.5); 7.3403(3.5); 7.3382(3.4); 5.7561 (16.0); 3.7912(1.2); 3.7791(2.0); 3.7706(2.5); 3.7620(1.9); 3.7500(1.3); 3.3500(1.6); 2.8190(0.6); 2.8108(0.7); 2.8023 (1.0); 2.7936(1.4); 2.7851(1.3); 2.7764(1.4); 2.7678(1.1); 2.7594 (0.8); 2.7506(0.6); 2.7186(0.8); 2.6742(0.3); 2.6698(0.4); 2.6344 (0.8); 2.5230(1.4); 2.5053(55.7); 2.5009(72.6); 2.4965(53.3); 2.4627(22.6); 2.4402(1.6); 2.4180(1.9); 2.3321(0.3); 2.3276 (0.4); 2.3233(0.3); 1.7753(0.8); 1.7582(2.5); 1.7390(2.8); 1.7223(1.9); 1.7137(1.7); 1.7006(1.6); 1.6882(1.6); 1.6719(0.7); 1.3779(0.5); 1.2352(1.0); 1.1173(7.8); 1.0999(0.8); 1.0952(0.5); −0.0002(0.7) |
| I-464 | 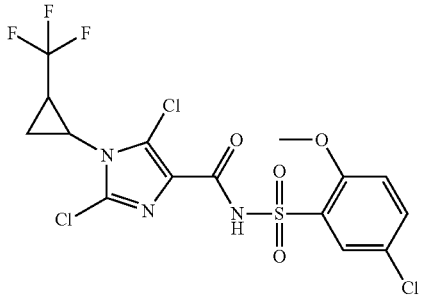 [SMILES: COc1ccc(Cl)cc1S(=O)(=O)NC(=O)c1nc(Cl)n(C2CC2C(F)(F)F)c1Cl] | I-464; ¹H-NMR(400.0 MHz, d₆-DMSO): δ = 7.7975(3.1); 7.7907(3.8); 7.7504(1.8); 7.7436(1.4); 7.7281 (1.8); 7.7213(1.6); 7.2858(2.9); 7.2634(2.6); 3.8542(16.0); 3.7923(0.6); 3.7803(1.0); 3.7717(1.3); 3.7630(0.9); 3.7511(0.7); 3.6511(0.8); 3.3303(8.8); 2.8061(0.4); 2.7977(0.5); 2.7893(0.7); 2.7806(0.6); 2.7720(0.7); 2.7633(0.5); 2.7548(0.4); 2.6749 (0.4); 2.6705(0.5); 2.6660(0.3); 2.5100(30.6); 2.5059(57.5); 2.5014(73.7); 2.4969(54.4); 2.3326(0.3); 2.3282(0.4); 2.3238 (0.3); 2.0733(2.6); 1.7784(0.4); 1.7610(1.2); 1.7417(1.3); 1.7244 (1.2); 1.7108(0.8); 1.6980(0.8); 1.6860(0.8); 1.6693(0.3); 0.0079(0.8); −0.0002(18.8); −0.0084(0.8) |
| I-465 | 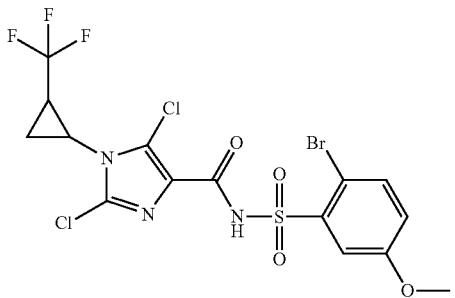 [SMILES: COc1ccc(Br)c(S(=O)(=O)NC(=O)c2nc(Cl)n(C3CC3C(F)(F)F)c2Cl)c1] | I-465; ¹H-NMR(400.0 MHz, d₆-DMSO): δ = 7.7295(2.6); 7.7076(2.9); 7.6221(2.9); 7.6144(3.0); 7.2065 (1.5); 7.1988(1.4); 7.1846(1.4); 7.1768(1.3); 3.8464(16.0); 3.7931(0.6); 3.7813(1.0); 3.7725(1.2); 3.7633(0.9); 3.7519(0.6); 3.3390(2.3); 2.8111(0.4); 2.8032(0.5); 2.7943(0.7); 2.7858(0.6); 2.7771(0.7); 2.7686(0.5); 2.7603(0.4); 2.5057(33.6); 2.5015 (43.6); 2.4973(32.4); 2.0734(2.8); 1.7771(0.4); 1.7601(1.2); 1.7410(1.3); 1.7238(0.9); 1.7162(0.8); 1.7034(0.8); 1.6907(0.8); 0.0075(1.0); −0.0002(23.3) |

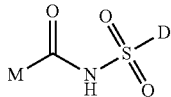
(I)
| Example No. | Structure | NMR peak list |
|---|---|---|
| I-466 | 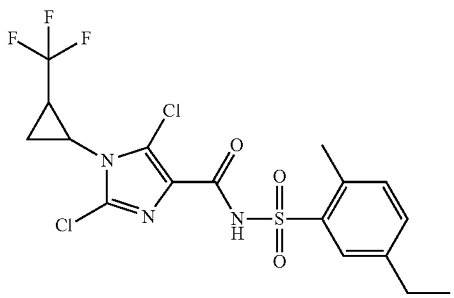 [SMILES: CCc1ccc(C)c(S(=O)(=O)NC(=O)c2nc(Cl)n(C3CC3C(F)(F)F)c2Cl)c1] | I-466; ¹H-NMR(400.0 MHz, d₆-DMSO): δ = 12.3682(0.7); 7.8278(4.4); 7.8240(4.4); 7.7995(0.4); 7.4264 (1.9); 7.4228(1.8); 7.4071(2.4); 7.4036(2.4); 7.3273(0.4); 7.3071 (0.4); 7.2973(3.8); 7.2778(2.8); 5.7564(2.0); 3.7847(1.0); 3.7728(1.7); 3.7642(2.2); 3.7554(1.5); 3.7435(1.0); 3.3257(14.2); 2.9880(0.5); 2.9691(0.5); 2.7991(0.5); 2.7909(0.6); 2.7821 (0.9); 2.7735(1.2); 2.7649(1.1); 2.7562(1.2); 2.7474(0.9); 2.7390 (0.7); 2.7305(0.5); 2.6963(1.7); 2.6773(5.1); 2.6586(5.0); 2.6395(1.7); 2.5386(20.6); 2.5232(2.4); 2.5096(47.2); 2.5054 (93.6); 2.5010(121.3); 2.4966(86.4); 2.3599(1.8); 2.3321(0.5); 2.3278(0.7); 2.3233(0.5); 1.7731(0.7); 1.7559(2.1); 1.7367(2.3); 1.7191(1.2); 1.7118(1.1); 1.6982(1.3); 1.6849(1.4); 1.6730 (1.3); 1.6570(0.6); 1.2353(0.8); 1.2098(7.5); 1.1908(16.0); 1.1719(7.2); 1.1468(0.6); 1.1282(1.3); 1.1096(0.6); −0.0002(1.2) |
| I-467 | 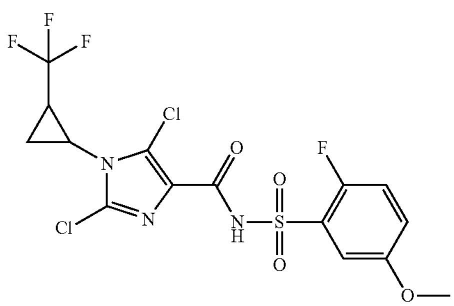 [SMILES: COc1ccc(F)c(S(=O)(=O)NC(=O)c2nc(Cl)n(C3CC3C(F)(F)F)c2Cl)c1] | I-467; ¹H-NMR(400.0 MHz, d₆-DMSO): δ = 7.3992(0.8); 7.3762(2.8); 7.3690(1.6); 7.3628(1.3); 7.3533 (2.0); 7.3147(0.8); 7.3054(1.3); 7.2972(0.7); 7.2924(0.6); 7.2831 (0.7); 7.2745(0.3); 5.7565(1.3); 3.8206(16.0); 3.7880(0.6); 3.7765(0.9); 3.7677(1.1); 3.7589(0.8); 3.7471(0.6); 3.3594(0.6); 2.7897(0.4); 2.7810(0.6); 2.7727(0.6); 2.7640(0.6); 2.7553 (0.5); 2.7470(0.3); 2.5054(38.3); 2.5010(50.3); 2.4966(36.7); 1.7788(0.4); 1.7616(1.1); 1.7427(1.2); 1.7238(0.8); 1.7080(0.7); 1.6947(0.7); 1.6823(0.7); −0.0002(0.4) |
| I-468 | 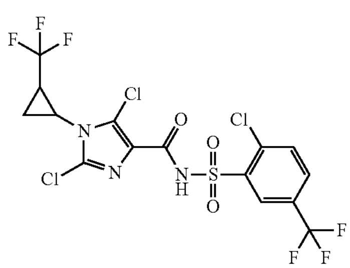 [SMILES: O=C(NS(=O)(=O)c1cc(C(F)(F)F)ccc1Cl)c1nc(Cl)n(C2CC2C(F)(F)F)c1Cl] | I-468; ¹H-NMR(400.0 MHz, d₆-DMSO): δ = 8.3204(15.0); 8.3156(16.0); 8.1646(0.5); 8.1173(6.8); 8.1124 (6.7); 8.0963(8.5); 8.0914(8.4); 7.9382(13.5); 7.9174(11.1); 7.8363(0.5); 7.7512(0.3); 7.6130(0.5); 7.5927(0.4); 5.7566(2.2); 3.9885(0.4); 3.9482(0.5); 3.7852(4.5); 3.7733(7.0); 3.7646 (8.9); 3.7562(6.7); 3.7440(5.0); 3.4571(2.3); 2.8080(2.0); 2.7991 (2.4); 2.7912(3.5); 2.7823(4.5); 2.7739(4.2); 2.7651(4.8); 2.7561(3.7); 2.7480(2.7); 2.7392(2.2); 2.7317(0.9); 2.7217(0.7); 2.6747(2.8); 2.6704(3.7); 2.6658(2.8); 2.5236(10.8); 2.5100 (226.1); 2.5058(460.3); 2.5013(608.0); 2.4968(439.0); 2.4926 (215.2); 2.3324(2.5); 2.3280(3.5); 2.3236(2.6); 1.7758(2.7); 1.7588(7.8); 1.7394(8.4); 1.7214(6.8); 1.7069(4.9); 1.6937(5.0); 1.6814(4.9); 1.6652(2.2); 1.2352(1.4); 0.8543(0.4); −0.0002(5.9) |
| I-469 | 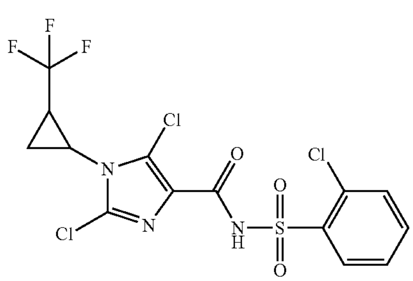 [SMILES: O=C(NS(=O)(=O)c1ccccc1Cl)c1nc(Cl)n(C2CC2C(F)(F)F)c1Cl] | I-469; ¹H-NMR(400.0 MHz, d₆-DMSO): δ = 12.6175(0.4); 12.6100(0.3); 8.1349(7.7); 8.1312(8.2); 8.1152 (8.6); 8.1114(8.6); 7.7200(2.3); 7.7160(2.4); 7.6999(6.4); 7.6963 (5.8); 7.6822(7.5); 7.6783(7.2); 7.6610(10.4); 7.6578(13.1); 7.6413(5.8); 7.6379(4.5); 7.6242(5.9); 7.6206(5.0); 7.6044 (7.8); 7.5867(3.8); 7.5830(3.3); 5.7565(16.0); 5.3364(0.4); 5.3250(0.6); 5.3133(0.4); 3.7875(2.8); 3.7754(4.6); 3.7668(6.0); 3.7582(4.4); 3.7462(3.1); 3.5069(0.3); 3.3517(3.8); 2.8286(0.3); 2.8116(1.3); 2.8027(1.6); 2.7945(2.4); 2.7859(3.2); 2.7774 (2.9); 2.7686(3.3); 2.7600(2.5); 2.7516(1.8); 2.7428(1.4); 2.7346 (0.5); 2.7252(0.4); 2.6748(0.9); 2.6701(1.2); 2.6659(0.9); 2.5234(3.8); 2.5099(82.1); 2.5057(164.0); 2.5012(213.3); 2.4967 (152.3); 2.3324(1.0); 2.3279(1.3); 2.3236(1.0); 2.0739(0.8); 2.0274(0.7); 2.0088(1.2); 1.9900(1.2); 1.9739(0.6); 1.7747(1.9); 1.7576(5.8); 1.7383(6.3); 1.7214(5.8); 1.7087(3.8); 1.6958 (3.8); 1.6835(3.7); 1.6673(1.6); 1.4747(0.3); 1.4571(0.4); 1.2919(0.7); 1.2357(6.9); 0.8708(0.6); 0.8539(1.8); 0.8365(0.7); −0.0001(2.1) |

(I)
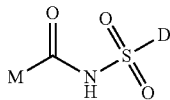
| Example No. | Structure | NMR peak list |
|---|---|---|
| I-470 | 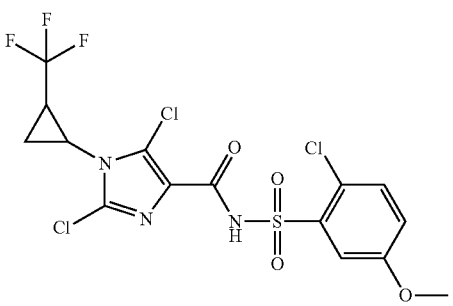 | I-470; $^1$H-NMR(400.0 MHz, $d_6$-DMSO): δ = 7.5755(2.9); 7.5672(4.4); 7.5438(2.8); 7.2878(1.4); 7.2801 (1.3); 7.2657(1.2); 7.2580(1.2); 5.7564(1.6); 3.8497(16.0); 3.7903(0.5); 3.7783(0.8); 3.7697(1.1); 3.7609(0.8); 3.7491(0.6); 3.3493(1.2); 2.7991(0.4); 2.7905(0.6); 2.7822(0.6); 2.7735(0.6); 2.7651(0.5); 2.7564(0.3); 2.6702(0.4); 2.5231(1.1); 2.5054 (48.2); 2.5010(62.8); 2.4966(45.0); 2.3278(0.4); 1.7772(0.4); 1.7601(1.1); 1.7410(1.2); 1.7246(1.0); 1.7129(0.7); 1.6994(0.7); 1.6879(0.7); −0.0002(0.6) |
| I-471 | 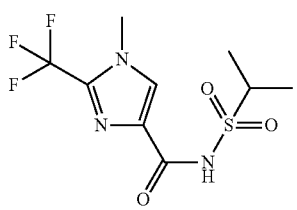 [SMILES: CC(C)S(=O)(=O)NC(=O)c1cn(C)c(C(F)(F)F)n1] | I-471; $^1$H-NMR(400.0 MHz, $d_6$-DMSO): δ = 11.6208(0.6); 8.2908(4.9); 3.8638(7.9); 3.8620(8.2); 3.7770 (0.4); 3.7598(1.2); 3.7426(1.6); 3.7254(1.2); 3.7083(0.4); 3.3318(8.3); 2.5239(0.5); 2.5191(0.8); 2.5105(13.4); 2.5061 (28.6); 2.5015(38.8); 2.4969(27.6); 2.4923(12.8); 1.3035(16.0); 1.2863(15.7); 1.2329(1.5); 1.2159(1.4); −0.0002(3.0) |
| I-472 | 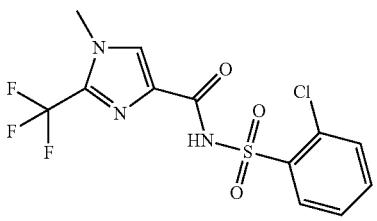 [SMILES: Cn1cc(C(=O)NS(=O)(=O)c2ccccc2Cl)nc1C(F)(F)F] | I-472; $^1$H-NMR(400.0 MHz, $d_6$-DMSO): δ = 8.2731(9.7); 8.1601(3.2); 8.1561(3.4); 8.1403(3.5); 8.1364 (3.6); 7.7304(1.0); 7.7264(1.0); 7.7104(2.5); 7.7065(2.5); 7.6927 (3.2); 7.6886(3.1); 7.6712(4.1); 7.6677(5.4); 7.6513(2.4); 7.6477 (1.8); 7.6335(2.5); 7.6297(2.1); 7.6137(3.0); 7.6102(2.5); 7.5959 (1.6); 7.5921(1.5); 5.7543(4.0); 3.8457(15.9); 3.8439(16.0); 3.3435(1.3); 2.5251(0.6); 2.5118(14.9); 2.5073(31.6); 2.5028(42.4); 2.4982(30.4); 2.4937(14.4); −0.0002(0.7) |
| I-473 | 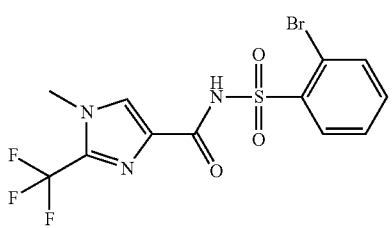 [SMILES: Cn1cc(C(=O)NS(=O)(=O)c2ccccc2Br)nc1C(F)(F)F] | I-473; $^1$H-NMR(400.0 MHz, $d_6$-DMSO): δ = 8.2857(9.5); 8.1874(3.1); 8.1830(3.4); 8.1678(3.4); 8.1635 (3.5); 7.8534(3.1); 7.8501(3.3); 7.8341(3.8); 7.8308(3.9); 7.6770(1.3); 7.6738(1.5); 7.6582(3.3); 7.6548(3.2); 7.6390(2.6); 7.6355(2.4); 7.6200(2.4); 7.6153(2.7); 7.6007(3.0); 7.5962(3.1); 7.5819(1.3); 7.5774(1.2); 3.8463(16.0); 3.3460(1.2); 2.5248 (0.6); 2.5114(15.3); 2.5070(32.5); 2.5025(44.0); 2.4979(31.9); 2.4934(15.3); −0.0002(0.9) |
| I-474 | 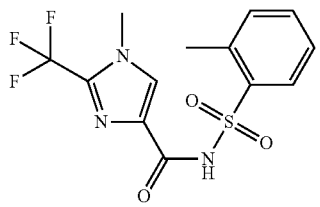 [SMILES: Cc1ccccc1S(=O)(=O)NC(=O)c1cn(C)c(C(F)(F)F)n1] | I-474; $^1$H-NMR(400.0 MHz, $d_6$-DMSO): δ = 12.4383(0.4); 8.2148(6.9); 8.0240(1.9); 8.0210(2.1); 8.0042 (2.1); 8.0011(2.2); 7.5933(0.8); 7.5900(0.9); 7.5746(2.0); 7.5713 (2.1); 7.5559(1.4); 7.5526(1.3); 7.4549(1.3); 7.4352(1.9); 7.4162 (0.9); 7.3995(2.2); 7.3806(1.8); 7.3569(0.6); 5.7539(1.2); 3.8355 (10.2); 3.8334(10.4); 3.3292(4.6); 2.6003(16.0); 2.5877(1.5); 2.5249(0.4); 2.5201(0.7); 2.5116(10.4); 2.5071(22.3); 2.5025(30.2); 2.4979(21.7); 2.4933(10.2); 1.9888(1.0); 1.1753(0.5); −0.0002(0.6) |
| I-475 | 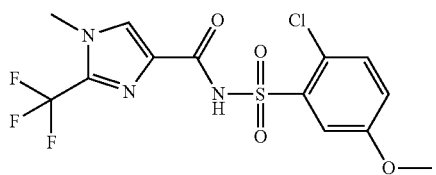 [SMILES: COc1ccc(Cl)c(S(=O)(=O)NC(=O)c2cn(C)c(C(F)(F)F)n2)c1] | I-475; $^1$H-NMR(400.0 MHz, $d_6$-DMSO): δ = 8.2689(3.5); 7.5987(2.7); 7.5910(2.8); 7.5744(2.4); 7.5524 (2.8); 7.2995(1.4); 7.2917(1.4); 7.2774(1.2); 7.2696(1.2); 4.0385 (0.4); 4.0207(0.4); 3.8527(16.0); 3.8461(6.8); 3.8442(6.6); 3.8164(0.5); 3.3358(2.2); 2.5243(0.4); 2.5111(10.4); 2.5066 (22.2); 2.5021(30.0); 2.4975(21.6); 2.4929(10.3); 1.9886(1.9); 1.1930(0.5); 1.1752(1.0); 1.1574(0.5); −0.0002(0.5) |

(I)
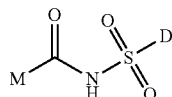
| Example No. | Structure | NMR peak list |
|---|---|---|
| I-476 | 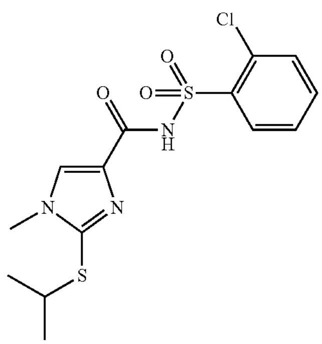 [SMILES: CC(C)Sc1nc(C(=O)NS(=O)(=O)c2ccccc2Cl)cn1C] | I-476; ¹H-NMR(400.0 MHz, d₆-DMSO): δ = 8.1397(1.5); 8.1364(1.6); 8.1200(1.6); 8.1167(1.6); 8.0649 (3.5); 7.6954(0.4); 7.6784(1.2); 7.6613(1.4); 7.6580(1.4); 7.6431 (2.4); 7.6267(0.9); 7.6097(1.0); 7.6064(0.9); 7.5898(1.4); 7.5726 (0.6); 7.5689(0.6); 5.7575(0.7); 3.6826(0.4); 3.6657(1.1); 3.6490 (1.5); 3.6320(1.3); 3.6171(14.4); 3.1860(0.8); 2.7653(0.6); 2.5068(13.9); 2.5027(17.9); 2.4985(13.1); 1.2924(16.0); 1.2755(15.7); −0.0002(1.8) |
| I-477 | 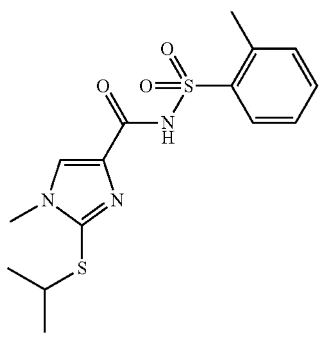 [SMILES: Cc1ccccc1S(=O)(=O)NC(=O)c1cn(C)c(SC(C)C)n1] | I-477; ¹H-NMR(400.0 MHz, d₆-DMSO): δ = 8.0267(4.4); 8.0120(1.8); 7.9920(1.9); 7.5805(0.7); 7.5620 (1.8); 7.5434(1.2); 7.4479(1.0); 7.4288(1.7); 7.4097(0.8); 7.3918 (1.9); 7.3729(1.5); 5.7572(0.6); 3.6800(0.5); 3.6632(1.2); 3.6464 (1.6); 3.6296(1.3); 3.6106(14.6); 2.5965(12.5); 2.5057(23.4); 2.5021(28.0); 1.2908(16.0); 1.2739(15.8); −0.0002(2.3) |
| I-478 | 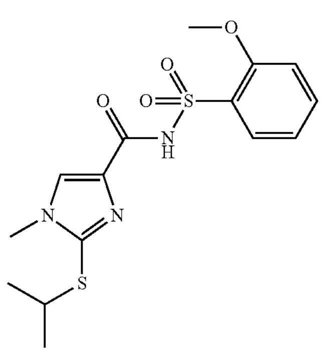 [SMILES: COc1ccccc1S(=O)(=O)NC(=O)c1cn(C)c(SC(C)C)n1] | I-478; ¹H-NMR(400.0 MHz, d₆-DMSO): δ = 8.0515(4.2); 7.8882(1.5); 7.8845(1.5); 7.8685(1.6); 7.8647 (1.6); 7.6803(0.7); 7.6767(0.7); 7.6590(1.4); 7.6409(0.8); 7.6373 (0.8); 7.2303(2.1); 7.2095(1.9); 7.1579(1.1); 7.1387(2.0); 7.1197 (1.0); 3.8382(14.9); 3.7027(0.4); 3.6859(1.1); 3.6690(1.5); 3.6523(1.2); 3.6353(0.5); 3.6050(14.3); 3.3305(0.4); 2.6705 (0.3); 2.5053(48.4); 2.5012(62.0); 2.4971(45.6); 2.3283(0.4); 1.3108(16.0); 1.2939(15.8); −0.0003(4.8) |

-continued
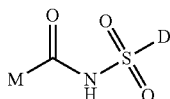
(I)
| Example No. | Structure | NMR peak list |
|---|---|---|
| I-479 | 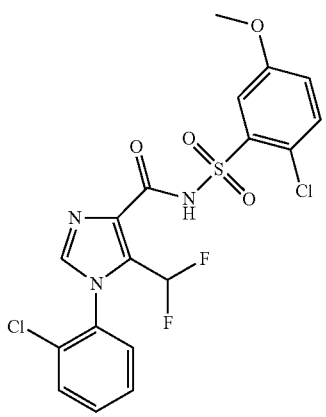 [SMILES: COc1ccc(Cl)c(S(=O)(=O)NC(=O)c2ncn(-c3ccccc3Cl)c2C(F)F)c1] | I-479; ¹H-NMR(400.0 MHz, d₆-DMSO): δ = 8.2906(3.6); 7.7490(1.7); 7.7292(2.4); 7.7127(1.6); 7.6929 (1.9); 7.6454(1.0); 7.6256(2.2); 7.6198(3.3); 7.6119(3.6); 7.5963 (2.5); 7.5741(2.9); 7.5671(1.6); 7.5458(1.8); 7.5292(1.1); 7.4022 (1.3); 7.2992(1.5); 7.2917(1.5); 7.2767(1.7); 7.2703(1.8); 4.0768 (0.3); 4.0339(0.4); 3.9025(14.7); 3.8546(16.0); 3.8160(1.0); 3.7204(1.4); 3.6910(1.4); 3.6820(1.4); 3.6703(1.5); 3.5092 (1.0); 3.4168(0.5); 3.3816(0.5); 3.3406(0.4); 3.3236(0.4); 3.3061(0.3); 3.1688(3.2); 2.6713(0.8); 2.5403(0.7); 2.5061 (106.9); 2.5022(136.9); 2.4984(107.1); 2.3288(0.8); 1.2346(0.3); −0.0002(3.6) |
| I-480 | 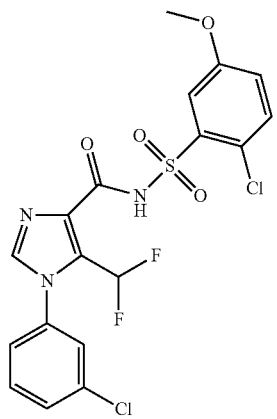 [SMILES: COc1ccc(Cl)c(S(=O)(=O)NC(=O)c2ncn(-c3cccc(Cl)c3)c2C(F)F)c1] | I-480; ¹H-NMR(400.0 MHz, d₆-DMSO): δ = 8.2989(1.9); 7.7403(1.2); 7.7371(2.4); 7.7338(1.4); 7.6675 (0.7); 7.6658(0.8); 7.6643(0.8); 7.6626(0.7); 7.6541(1.1); 7.6524 (1.3); 7.6509(1.3); 7.6492(1.1); 7.6120(3.2); 7.6067(3.0); 7.6003 (2.6); 7.5869(1.4); 7.5676(1.8); 7.5529(2.3); 7.5351(0.8); 7.4920 (0.4); 7.2716(1.0); 7.2665(1.0); 7.2569(0.9); 7.2518(0.9); 3.8519(16.0); 3.4170(26.6); 3.1696(0.6); 2.6162(0.4); 2.6132 (0.6); 2.6101(0.4); 2.5224(1.1); 2.5193(1.4); 2.5162(1.4); 2.5075(31.0); 2.5044(65.5); 2.5014(90.9); 2.4983(66.5); 2.4953 (31.8); 2.3886(0.4); 2.3856(0.6); 2.3825(0.4); 1.9085(1.2); −0.0002(3.8) |
| I-481 | 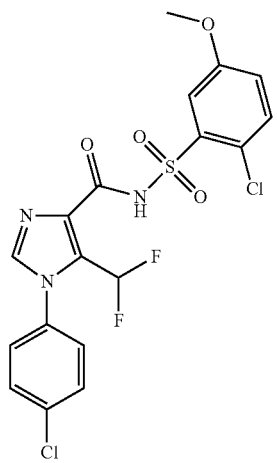 [SMILES: COc1ccc(Cl)c(S(=O)(=O)NC(=O)c2ncn(-c3ccc(Cl)cc3)c2C(F)F)c1] | I-481; ¹H-NMR(400.0 MHz, d₆-DMSO): δ = 8.2993(2.4); 7.6668(1.8); 7.6453(3.6); 7.6119(2.4); 7.6045 (5.0); 7.5817(3.5); 7.5591(1.9); 7.4578(0.9); 7.3284(0.5); 7.2864(1.0); 7.2797(1.0); 7.2647(0.9); 7.2576(0.9); 4.0307(0.4); 3.9024(16.0); 3.8527(10.7); 3.7398(1.3); 3.5071(0.5); 3.1688 (7.3); 2.6710(0.6); 2.5059(75.6); 2.5021(95.4); 2.4981(72.5); 2.3285(0.5); −0.0002(2.6) |

-continued
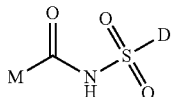
(I)
| Example No. | Structure | NMR peak list |
|---|---|---|
| I-482 | 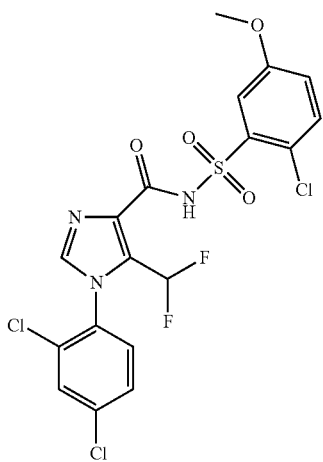 [SMILES: COc1ccc(Cl)c(S(=O)(=O)NC(=O)c2ncn(-c3ccc(Cl)cc3Cl)c2C(F)F)c1] | I-482; ¹H-NMR(400.0 MHz, d₆-DMSO): δ = 8.2685(2.9); 7.9836(2.5); 7.9786(2.7); 7.7732(1.4); 7.7518 (2.1); 7.6748(1.5); 7.6698(1.6); 7.6538(1.1); 7.6486(1.1); 7.6151(2.3); 7.6077(2.4); 7.5890(1.9); 7.5670(2.2); 7.5502(0.6); 7.4194(1.0); 7.2923(1.6); 7.2854(1.5); 7.2703(1.1); 7.2636(1.1); 4.0311(0.3); 3.9024(16.0); 3.8521(12.9); 3.7048(1.3); 3.6668 (1.4); 3.6312(1.4); 3.5079(1.1); 3.3236(0.4); 3.1688(2.4); 2.6713 (0.7); 2.5413(0.4); 2.5062(90.8); 2.5022(119.0); 2.4981(93.4); 2.3292(0.7); 1.2354(0.4); −0.0002(3.4) |
| I-483 | 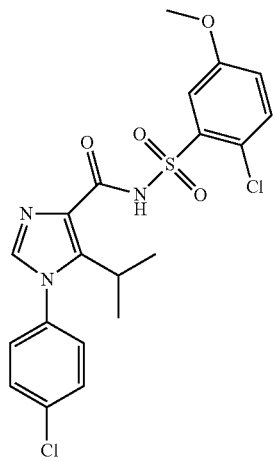 [SMILES: COc1ccc(Cl)c(S(=O)(=O)NC(=O)c2ncn(-c3ccc(Cl)cc3)c2C(C)C)c1] | I-483; ¹H-NMR(400.0 MHz, d₆-DMSO): δ = 8.0517(2.6); 7.6829(2.6); 7.6614(3.6); 7.6152(2.4); 7.6077 (2.4); 7.5791(1.9); 7.5574(5.6); 7.5362(2.6); 7.2774(1.0); 7.2699(1.1); 7.2553(1.0); 7.2477(0.9); 3.9025(16.0); 3.8571(12.3); 3.8159(0.6); 3.5960(1.8); 3.5082(1.3); 3.4789(1.0); 3.4188(0.6); 3.3244(0.8); 3.2678(0.4); 3.1691(1.3); 3.0566(0.7); 3.0389 (0.9); 3.0214(0.7); 2.6718(0.4); 2.5067(58.5); 2.5026(75.8); 2.4988(58.5); 2.3293(0.5); 1.2938(0.5); 1.2357(0.4); 1.2237 (0.9); 1.2059(0.9); 1.1116(9.4); 1.0940(9.3); −0.0001(2.0) |
| I-484 | 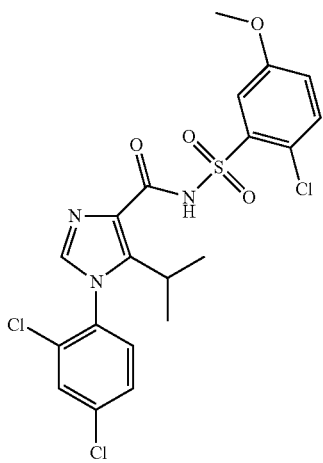 [SMILES: COc1ccc(Cl)c(S(=O)(=O)NC(=O)c2ncn(-c3ccc(Cl)cc3Cl)c2C(C)C)c1] | I-484; ¹H-NMR(400.0 MHz, d₆-DMSO): δ = 8.0120(3.0); 8.0066(3.1); 7.9787(4.1); 7.7716(1.9); 7.7503 (3.2); 7.6948(1.9); 7.6894(1.8); 7.6736(1.1); 7.6682(1.1); 7.6184 (2.9); 7.6108(3.1); 7.6010(2.4); 7.5790(2.7); 7.2976(1.4); 7.2900 (1.4); 7.2756(1.3); 7.2679(1.2); 3.9025(13.0); 3.8597(16.0); 3.8181(0.6); 3.6750(1.2); 3.5859(1.3); 3.5654(1.3); 3.5591 (1.3); 3.5081(1.2); 3.3258(0.5); 3.3015(0.4); 3.1687(0.5); 2.9036 (0.3); 2.8854(0.8); 2.8682(1.1); 2.8505(0.8); 2.8326(0.3); 2.6711 (0.5); 2.5062(76.5); 2.5020(98.9); 2.4978(74.8); 2.3288 (0.7); 1.1301(6.1); 1.1125(6.0); 1.0382(5.9); 1.0206(5.8); −0.0002(2.5) |

US 10,820,591 B2
-continued
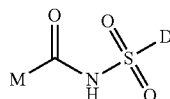
(I)
| Example No. | Structure | NMR peak list |
|---|---|---|
| I-485 | 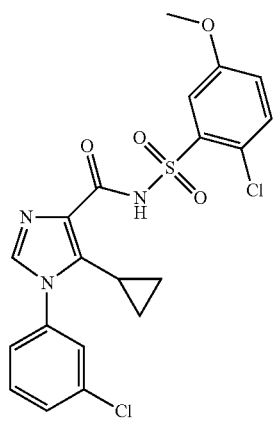 [SMILES: COc1ccc(Cl)c(S(=O)(=O)NC(=O)c2ncn(-c3cccc(Cl)c3)c2C2CC2)c1] | I-485; ¹H-NMR(400.0 MHz, d₆-DMSO): δ = 8.0939(3.3); 7.7645(2.0); 7.6169(2.6); 7.6094(4.2); 7.5901 (3.6); 7.5735(2.2); 7.5676(3.0); 7.2941(1.0); 7.2865(1.0); 7.2720(0.9); 7.2643(0.9); 3.9023(16.0); 3.8640(11.3); 3.8249(0.4); 3.8152(0.4); 3.7880(0.6); 3.7257(0.8); 3.6673(1.1); 3.5479(2.0); 3.5087(1.8); 3.3542(0.5); 3.3242(0.9); 3.2675(0.5); 3.1687 (1.4); 2.6705(0.4); 2.5061(57.7); 2.5020(74.8); 2.4978(56.9); 2.3287(0.4); 1.9028(0.4); 1.8953(0.5); 1.8897(0.4); 1.8815(0.9); 1.8680(0.5); 1.8605(0.5); 0.7186(0.4); 0.7068(1.4); 0.7022 (1.5); 0.6858(1.4); 0.6809(1.5); 0.6703(0.5); 0.3910(0.5); 0.3761(1.8); 0.3628(1.7); 0.3509(0.4); −0.0002(1.6) |
| I-486 | 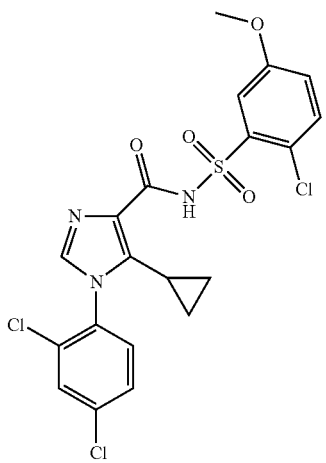 [SMILES: COc1ccc(Cl)c(S(=O)(=O)NC(=O)c2ncn(-c3ccc(Cl)cc3Cl)c2C2CC2)c1] | I-486; ¹H-NMR(400.0 MHz, d₆-DMSO): δ = 7.9937(2.2); 7.9883(2.3); 7.9742(3.3); 7.7763(1.4); 7.7550 (2.2); 7.6837(1.3); 7.6784(1.3); 7.6626(0.8); 7.6571(0.8); 7.6159(2.1); 7.6083(2.3); 7.6036(2.0); 7.5814(1.9); 7.3053(1.0); 7.2977(1.0); 7.2833(0.9); 7.2757(0.9); 3.9025(16.0); 3.8619(10.8); 3.7801(0.4); 3.7515(0.5); 3.6768(0.8); 3.6217(1.0); 3.5597 (1.2); 3.5468(1.2); 3.5370(1.2); 3.5073(1.2); 3.4579(1.0); 3.4307 (0.8); 3.3982(0.7); 3.3239(0.6); 3.3050(0.4); 3.2667(0.4); 3.1685(0.9); 2.6709(0.4); 2.5059(64.1); 2.5018(83.0); 2.4977 (64.0); 2.3285(0.5); 1.7120(0.4); 1.7040(0.5); 1.6982(0.4); 1.6906(0.9); 1.6830(0.4); 1.6771(0.6); 1.6695(0.5); 1.1215(0.3); 0.6708(1.3); 0.6658(1.5); 0.6495(1.3); 0.6444(1.5); 0.4854(0.9); −0.0002(2.3) |
| I-487 | 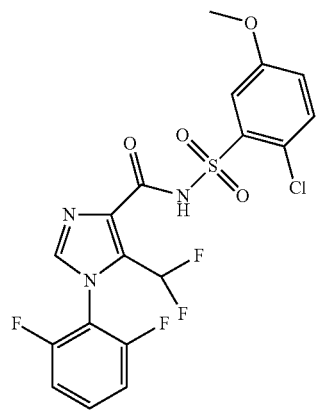 [SMILES: COc1ccc(Cl)c(S(=O)(=O)NC(=O)c2ncn(-c3c(F)cccc3F)c2C(F)F)c1] | I-487; ¹H-NMR(400.0 MHz, d₆-DMSO): δ = 8.3632(2.0); 7.7534(0.5); 7.7497(0.4); 7.7391(0.8); 7.7284 (0.4); 7.7248(0.5); 7.6170(2.8); 7.6118(2.9); 7.5778(1.8); 7.5632 (2.1); 7.4502(1.5); 7.4363(2.3); 7.4228(1.2); 7.2850(1.0); 7.2799 (1.0); 7.2704(0.9); 7.2652(0.9); 3.8518(16.0); 3.4648(0.5); 3.1693(1.5); 2.6154(0.3); 2.6124(0.4); 2.6093(0.3); 2.5217 (0.8); 2.5186(1.0); 2.5155(1.0); 2.5067(23.8); 2.5037(51.0); 2.5006(71.0); 2.4975(52.0); 2.4945(24.9); 2.3878(0.3); 2.3848 (0.4); 2.3817(0.3); 1.9083(0.9); −0.0002(3.2) |

(I)
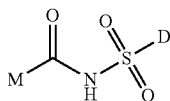
| Example No. | Structure | NMR peak list |
|---|---|---|
| I-488 | 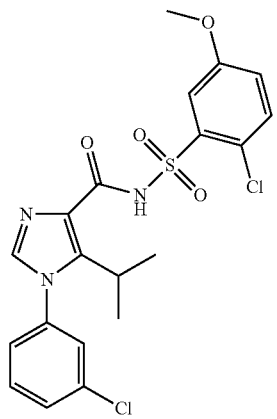 [SMILES: COc1ccc(Cl)c(S(=O)(=O)NC(=O)c2ncn(-c3cccc(Cl)c3)c2C(C)C)c1] | I-488; ¹H-NMR(400.0 MHz, d₆-DMSO): δ = 8.0078(0.4); 7.7039(1.9); 7.6820(1.1); 7.6685(1.6); 7.6669 (1.4); 7.6276(1.7); 7.6143(3.2); 7.6114(3.3); 7.6062(3.2); 7.6011(1.5); 7.5531(0.8); 7.5387(0.9); 7.4791(1.3); 7.4662(1.1); 7.2443(0.6); 7.2324(0.6); 3.9007(15.6); 3.8521(16.0); 3.7287(0.3); 3.4508(1.2); 3.1690(0.8); 3.0714(0.5); 2.6151(0.5); 2.6121(0.7); 2.6091(0.5); 2.5213(1.1); 2.5183(1.4); 2.5152(1.5); 2.5062 (43.2); 2.5033(89.6); 2.5003(121.9); 2.4973(89.8); 2.4944 (43.8); 2.3875(0.6); 2.3845(0.8); 2.3815(0.6); 1.9079(1.4); 1.1196(13.2); 1.1078(13.4); 1.0975(0.6); −0.0002(5.1) |
| I-489 | 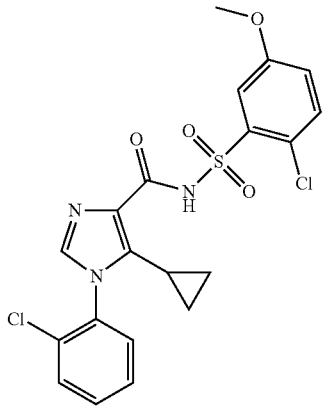 [SMILES: COc1ccc(Cl)c(S(=O)(=O)NC(=O)c2ncn(-c3ccccc3Cl)c2C2CC2)c1] | I-489; ¹H-NMR(400.0 MHz, d₆-DMSO): δ = 7.9905(4.0); 7.7655(1.2); 7.7481(1.6); 7.7456(1.6); 7.7163 (1.0); 7.7125(1.2); 7.6972(1.4); 7.6935(1.4); 7.6431(0.6); 7.6393 (0.6); 7.6194(3.5); 7.6116(2.9); 7.6045(3.1); 7.5821(3.1); 7.5614(1.2); 7.5587(1.3); 7.5425(0.4); 7.3049(1.2); 7.2972(1.2); 7.2828(1.1); 7.2752(1.0); 3.9024(16.0); 3.8868(0.6); 3.8629 (13.3); 3.8520(1.2); 3.8160(0.5); 3.7605(0.6); 3.7213(0.7); 3.7071(0.8); 3.6787(0.9); 3.6435(0.8); 3.6358(0.9); 3.6080(0.9); 3.5712(0.8); 3.5076(0.7); 3.4587(0.5); 3.4132(0.5); 3.3972(0.5); 3.3820(0.4); 3.3243(0.4); 3.1687(1.4); 2.6711(0.5); 2.5063 (62.0); 2.5020(80.4); 2.4977(59.3); 2.3287(0.4); 2.3244(0.3); 1.7360(0.6); 1.7279(0.6); 1.7223(0.4); 1.7146(1.1); 1.7065(0.4); 1.7010(0.6); 1.6933(0.6); 0.6431(1.4); 0.6382(1.7); 0.6219(1.4); 0.6168(1.6); 0.4861(1.4); −0.0001(2.5) |
| I-490 | 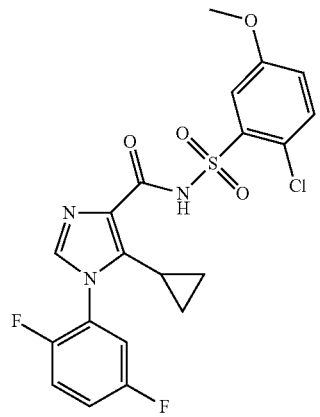 [SMILES: COc1ccc(Cl)c(S(=O)(=O)NC(=O)c2ncn(-c3cc(F)ccc3F)c2C2CC2)c1] | I-490; ¹H-NMR(400.0 MHz, d₆-DMSO): δ = 8.0358(3.9); 7.7661(0.5); 7.7588(0.6); 7.7513(0.7); 7.7444 (1.1); 7.7375(0.7); 7.7304(0.7); 7.7231(0.6); 7.6411(0.4); 7.6291 (0.5); 7.6167(3.5); 7.6088(3.4); 7.6020(3.0); 7.5799(3.0); 7.5527(0.4); 7.5438(0.7); 7.5338(0.7); 7.5231(0.9); 7.5015(0.4); 7.3082(1.4); 7.3007(1.3); 7.2862(1.2); 7.2785(1.2); 3.9023 (16.0); 3.8647(14.2); 3.8163(0.4); 3.7878(0.6); 3.7254(0.8); 3.6962(0.8); 3.6673(1.1); 3.5084(2.6); 3.4788(2.5); 3.3242(1.4); 3.2862(0.7); 3.2676(0.9); 3.1905(0.4); 3.1686(1.4); 2.6711(0.6); 2.5062(73.8); 2.5021(97.6); 2.4978(77.6); 2.3289(0.6); 1.7762 (0.5); 1.7685(0.6); 1.7552(1.0); 1.7422(0.6); 1.7345(0.6); 0.7060(0.6); 0.6943(1.8); 0.6893(2.1); 0.6734(1.9); 0.6682(2.0); 0.6575(0.7); 0.4327(0.7); 0.4175(2.4); 0.4083(2.1); 0.4040(2.3); 0.3926(0.6); −0.0002(2.0) |

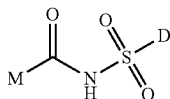
(I)

| Example No. | Structure | NMR peak list |
|---|---|---|
| I-491 | 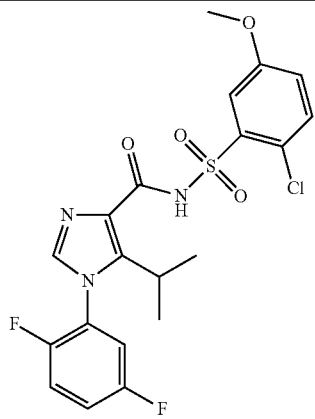 | I-491; ¹H-NMR(400.0 MHz, d₆-DMSO): δ = 8.0151(4.5); 7.7813(0.5); 7.7733(0.6); 7.7660(0.7); 7.7594 (1.1); 7.7530(0.7); 7.7454(0.6); 7.7380(0.6); 7.6618(0.3); 7.6499 (0.4); 7.6389(1.0); 7.6269(1.1); 7.6170(3.6); 7.6095(3.4); 7.6022(3.5); 7.5916(0.9); 7.5801(3.5); 7.5721(1.0); 7.5639(0.6); 7.5494(0.4); 7.3025(1.4); 7.2948(1.4); 7.2804(1.3); 7.2728(1.2); 3.9024(13.1); 3.8614(16.0); 3.8159(0.4); 3.7883(0.5); 3.6766 (1.0); 3.5092(3.0); 3.3245(0.9); 3.2673(0.5); 3.1855(0.3); 3.1685(1.9); 3.0127(0.4); 2.9951(0.8); 2.9778(1.0); 2.9603(0.8); 2.9435(0.4); 2.6709(0.6); 2.6665(0.4); 2.5063(74.7); 2.5020 (98.1); 2.4977(73.3); 2.3287(0.6); 1.0920(6.6); 1.0746(6.5); −0.0002(2.3) |
| I-492 | 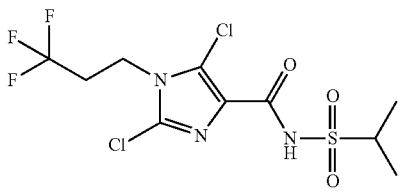 [SMILES: CC(C)S(=O)(=O)NC(=O)c1nc(Cl)n(CCC(F)(F)F)c1Cl] | I-492; ¹H-NMR(400.0 MHz, d₆-DMSO): δ = 11.5588(1.1); 4.3264(2.2); 4.3094(4.7); 4.2926(2.3); 3.9021 (4.4); 3.7524(0.4); 3.7353(1.0); 3.7181(1.4); 3.7010(1.0); 3.6832(0.4); 3.3254(58.4); 3.2674(0.4); 2.9113(0.6); 2.9006(1.0); 2.8839(1.8); 2.8723(1.2); 2.8674(1.2); 2.8559(1.8); 2.8394(0.9); 2.8282(0.6); 2.6711(0.7); 2.5063(93.4); 2.5021(119.4); 2.4978 (92.3); 2.3290(0.7); 1.2920(16.0); 1.2749(15.9); 1.2324(0.5); −0.0002(1.0) |

USE EXAMPLES

*Boophilus microplus*—Injection Test
Solvent: dimethyl sulfoxide

To produce a suitable active compound preparation, 10 mg of active compound are mixed with 0.5 ml of solvent and the concentrate is diluted to the desired concentration with solvent.

1 μl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 μg/animal: I-035, I-059, I-284

In this test, for example, the following compounds from the preparation examples show an efficacy of 90% at an application rate of 20 μg/animal: I-032:

In this test, for example, the following compounds from the preparation examples show an efficacy of 80% at an application rate of 20 μg/animal I-268

In this test, for example, the following compounds from the preparation examples show an efficacy of 70% at an application rate of 20 μg/animal: I-060

*Ctenocephalides felis*—Oral Test
Solvent: dimethyl sulfoxide

To produce a suitable active compound preparation, 10 mg of active compound are mixed with 0.5 ml of dimethyl sulfoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 70% at an application rate of 100 ppm: I-032

*Lucilia cuprina* Test
Solvent: dimethyl sulfoxide

To produce a suitable active compound preparation, 10 mg of active compound are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: I-035

*Diabrotica balteata*—Spray Test

| Solvent: | 78 parts by weight of acetone |
| --- | --- |
| | 1.5 parts by weight of dimethylformamide |
| Emulsifier: | alkylaryl polyglycol ether |

To produce a suitable active compound preparation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Pre-swollen wheat grains (*Triticum aestivum*) are incubated in a multiwell plate filled with agar and a little water for one day (5 seed grains per cavity). The germinated wheat grains are sprayed with an active compound preparation of the desired concentration. Subsequently, each cavity is infected with 10-20 beetle larvae of *Diabrotica* balteata.

After 7 days, the efficacy in % is determined. 100% means that all maize plants have grown as in the untreated, uninfected control; 0% means that no maize plant has grown.

In this test, for example, the following compounds from the preparation examples show an efficacy of 100% at an application rate of 160 μg/well: I-118

*Meloidogyne incognita* Test

| Solvent: | 125.0 parts by weight of acetone |
| --- | --- |

To produce a suitable active compound preparation, 1 part by weight of active compound is mixed with the stated amount of solvent and the concentrate is diluted to the desired concentration with water.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compound from the preparation examples shows an efficacy of 100% at an application rate of 20 ppm: I-005, I-006, I-008, I-012, I-028, I-036, I-037, I-039, I-041, I-042, I-043, I-044, I-045, I-046, I-047, I-057, I-059, I-063, I-064, I-069, I-070, I-071, I-072, I-073, I-074, I-077, I-078, I-079, I-082, I-084, I-089, I-093, I-101, I-102, I-103, I-104, I-106, I-107, I-108, I-109, I-110, I-111, I-112, I-113, I-114, I-115, I-118, I-120, I-124, I-125, I-126, I-134, I-136, I-137, I-138, I-139, I-140, I-142, I-146, I-147, I-148, I-150, I-151, I-152, I-153, I-155, I-156, I-158, I-159, I-161, I-162, I-165, I-166, I-168, I-170, I-171, I-172, I-173, I-174, I-175, I-176, I-177, I-178, I-180, I-181, I-184, I-185, I-187, I-188, I-190, I-191, I-192, I-193, I-194, I-195, I-196, I-197, I-198, I-199, I-200, I-203, I-204, I-205, I-206, I-207, I-208, I-210, I-211, I-215, I-220, I-222, I-223, I-225, I-226, I-227, I-229, I-230, I-231, I-232, I-233, I-239, I-240, I-242, I-243, I-244, I-245, I-246, I-247, I-248, I-249, I-250, I-252, I-253, I-254, I-255, I-256, I-259, I-261, I-262, I-266, I-267, I-268, I-271, I-275, I-286, I-287, I-288, I-290, I-293, I-301, I-302, I-307, I-310, I-315, I-316, I-317, I-318, I-319, I-320, I-322, I-323, I-324, I-326, I-327, I-329, I-330, I-331, I-332, I-334, I-336, I-337, I-338, I-339, I-340, I-341, I-345, I-347, I-348, I-349, I-350, I-351, I-352, I-353, I-354, I-355, I-358, I-365, I-366, I-367, I-369, I-372, I-374, I-375, I-378, I-379, I-380, I-381, I-382, I-383, I-384, I-385, I-386, I-387, I-388, I-389, I-390, I-391, I-392, I-393, I-394, I-405, I-406, I-407, I-408, I-409, I-410, I-411, I-412, I-413, I-414, I-416, I-417, I-418, I-419, I-420, I-421, I-422, I-423, I-424, I-425, I-427, I-433, I-434, I-435, I-436, I-440, I-441, I-442, I-443, I-444, I-448, I-449, I-450, I-452, I-453, I-454, I-455, I-456, I-457, I-458, I-459, I-460, I-461, I-462, I-463, I-465, I-466, I-467, I-468, I-469, I-470, I-474, I-487, I-491

In this test, for example, the following compound from the preparation examples shows an efficacy of 90% at an application rate of 20 ppm: I-001, I-002, I-003, I-004, I-009, I-010, I-014, I-015, I-016, I-017, I-018, I-019, I-020, I-021, I-022, I-023, I-024, I-025, I-026, I-027, I-030, I-031, I-032, I-033, I-034, I-035, I-038, I-048, I-049, I-050, I-051, I-052, I-053, I-054, I-055, I-056, I-060, I-061, I-062, I-065, I-066, I-068, I-076, I-080, I-081, I-083, I-085, I-088, I-090, I-091, I-094, I-095, I-096, I-097, I-098, I-100, I-105, I-116, I-117, I-119, I-122, I-123, I-129, I-130, I-131, I-132, I-135, I-141, I-143, I-144, I-154, I-157, I-163, I-164, I-167, I-169, I-179, I-182, I-183, I-186, I-189, I-209, I-212, I-213, I-214, I-216, I-217, I-219, I-221, I-224, I-228, I-235, I-236, I-237, I-238, I-241, I-251, I-257, I-263, I-264, I-265, I-269, I-270, I-272, I-273, I-274, I-278, I-279, I-280, I-281, I-282, I-283, I-285, I-289, I-291, I-292, I-294, I-295, I-296, I-297, I-298, I-299, I-303, I-304, I-305, I-306, I-308, I-309, I-311, I-312, I-313, I-314, I-321, I-325, I-328, I-335, I-342, I-343, I-344, I-359, I-360, I-361, I-362, I-363, I-364, I-368, I-371, I-376, I-377, I-395, I-396, I-398, I-399, I-400, I-402, I-403, I-404, I-415, I-426, I-428, I-429, I-430, I-431, I-432, I-437, I-439, I-445, I-446, I-447, I-451, I-464, I-471, I-472, I-473, I-475, I-477, I-479, I-480, I-482, I-485, I-488, I-489, I-490

In this test, for example, the following compounds from the preparation examples show an efficacy of 80% at an application rate of 20 ppm: I-201

In this test, for example, the following compounds from the preparation examples show an efficacy of 70% at an application rate of 20 ppm: I-007, I-011, I-013, I-029, I-040, I-058, I-067, I-075, I-086, I-087, I-092, I-099, I-121, I-127, I-128, I-133, I-145, I-160, I-202, I-218, I-234, I-258, I-260, I-276, I-277, I-284, I-300, I-33, I-346, I-370, I-373, I-397, I-401, I-476, I-478, I-481, I-483, I-484, I-486

In this test, for example, the following compounds from the preparation examples show an efficacy of 90% at an application rate of 4 ppm: I-145, I-149, I-356, I-357

*Aphis gossypii*—Oral Test

| Solvent: | 100 parts by weight of acetone |
| --- | --- |

To produce a suitable active compound preparation, 1 part by weight of active compound is dissolved with the stated parts by weight of solvent and made up to the desired concentration with water.

50 μl of the active compound preparation are transferred into microtitre plates and made up to a final volume of 200 μl with 150 μl of IPL41 insect medium (33%+15% sugar). Subsequently, the plates are sealed with parafilm, which a mixed population of the cotton aphid (*Aphis gossypii*) within a second microtitre plate is able to puncture and imbibe the solution through it.

After 5 days, the efficacy in % is determined. 100% means that all the aphids have been killed; 0% means that no aphids have been killed.

In this test, for example, the following compound from the preparation examples shows an efficacy of 90% at an application rate of 100 ppm: I-412

*Myzus persicae*—Oral Test

| Solvent: | 100 parts by weight of acetone |
|---|---|

To produce a suitable active compound preparation, 1 part by weight of active compound is dissolved with the stated parts by weight of solvent and made up to the desired concentration with water.

50 µl of the active compound preparation are transferred into microtitre plates and made up to a final volume of 200 µl with 150 µl of IPL41 insect medium (33%+15% sugar). Subsequently, the plates are sealed with parafilm, which a mixed population of green peach aphids (*Myzus persicae*) within a second microtitre plate is able to puncture and imbibe the solution through it.

After 5 days, the efficacy in % is determined. 100% means that all the aphids have been killed; 0% means that no aphids have been killed.

In this test, for example, the following compound from the preparation examples shows an efficacy of 100% at an application rate of 100 ppm: I-250, I-253, I-254, I-264

In this test, for example, the following compound from the preparation examples shows an efficacy of 100% at an application rate of 20 ppm: I-284, I-316, I-387, I-392

In this test, for example, the following compound from the preparation examples shows an efficacy of 90% at an application rate of 20 ppm: I-116, I-170, I-266, I-268, I-286, I-291, I-317

In this test, for example, the following compound from the preparation examples shows an efficacy of 70% at an application rate of 20 ppm: I-004, I-007, I-127, I-269, I-460

In this test, for example, the following compounds from the preparation examples show an efficacy of 100% at an application rate of 4 ppm: I-106

*Myzus persicae*—Spray Test

| Solvent: | 78 parts by weight of acetone |
|---|---|
| | 1.5 parts by weight of dimethylformamide |
| Emulsifier: | alkylaryl polyglycol ether |

To produce a suitable active compound preparation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After 6 days, the efficacy in % is determined. 100% means that all the aphids have been killed; 0% means that no aphids have been killed.

In this test, for example, the following compounds from the preparation examples show an efficacy of 90% at an application rate of 500 g/ha: I-006, I-120, I-122, I-127, I-158, I-253, I-254, I-268, I-317, I-392, I-401

In this test, for example, the following compounds from the preparation examples show an efficacy of 70% at an application rate of 500 g/ha: I-010, I-042, I-059, I-060, I-085, I-116, I-171, I-214, I-220, I-264, I-269, I-314, I-346, I-385, I-387, I-47³

In this test, for example, the following compounds from the preparation examples show an efficacy of 90% at an application rate of 100 g/ha: I-010

*Nezara viridula*—Spray Test

| Solvent: | 78.0 parts by weight of acetone |
|---|---|
| | 1.5 parts by weight of dimethylformamide |
| Emulsifier: | alkylaryl polyglycol ether |

To produce a suitable active compound preparation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Barley plants (*Hordeum vulgare*) infected with larvae of the Southern green shield bug (*Nezara viridula*) are sprayed with an active compound preparation of the desired concentration.

After 4 days, the efficacy in % is determined. 100% means that all of the shield bugs have been killed; 0% means that none of the shield bugs have been killed.

In this test, for example, the following compounds from the preparation examples show an efficacy of 100% at an application rate of 500 g/ha: I-032, I-035

*Nilaparvata lugens* Test

| Solvent: | 78.0 parts by weight of acetone |
|---|---|
| | 1.5 parts by weight of dimethylformamide |
| Emulsifier: | alkylaryl polyglycol ether |

To produce a suitable active compound preparation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Rice plants (*Oryza sativa*) are sprayed with the active compound preparation of the desired concentration and then infected with larvae of the brown planthopper (*Nilaparvata lugens*).

After 4 days, the efficacy in % is determined. 100% means that all of the planthoppers have been killed; 0% means that none of the planthoppers have been killed.

In this test, for example, the following compounds from the preparation examples show an efficacy of 100% at an application rate of 500 g/ha: I-032, I-035, I-070, I-107, I-456

*Phaedon cochleariae*—Spray Test

| Solvent: | 78.0 parts by weight of acetone |
|---|---|
| | 1.5 parts by weight of dimethylformamide |
| Emulsifier: | alkylaryl polyglycol ether |

To produce a suitable active compound preparation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 500 g/ha: I-035, I-300

In this test, for example, the following compounds from the preparation examples show an efficacy of 83% at an application rate of 500 g/ha: I-032, I-037, I-059

*Spodoptera frugiperda*—Spray Test

| Solvent: | 78.0 parts by weight of acetone |
| | 1.5 parts by weight of dimethylformamide |
| Emulsifier: | alkylaryl polyglycol ether |

To produce a suitable active compound preparation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active compound preparation of the desired concentration and, after drying, populated with caterpillars of the armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 500 g/ha: I-059, I-060, I-156

*Tetranychus urticae*—Spray Test, OP-Resistant

| Solvent: | 78.0 parts by weight of acetone |
| | 1.5 parts by weight of dimethylformamide |
| Emulsifier: | alkylaryl polyglycol ether |

To produce a suitable active compound preparation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active compound preparation of the desired concentration.

After 6 days, the efficacy in % is determined. 100% means that all the spider mites have been killed; 0% means that no spider mites have been killed.

In this test, for example, the following compounds from the preparation examples show an efficacy of 100% at an application rate of 500 g/ha: I-122, I-172

In this test, for example, the following compounds from the preparation examples show an efficacy of 90% at an application rate of 500 g/ha: I-028, I-032, I-059, I-060, I-073, I-083, I-121, I-170, I-171, I-173, I-373, I-492

In this test, for example, the following compounds from the preparation examples show an efficacy of 80% at an application rate of 500 g/ha: I-483

In this test, for example, the following compounds from the preparation examples show an efficacy of 70% at an application rate of 500 g/ha: I-085, I-160, I-197, I-255, I-330, I-391

*Myzus persicae*—Spray Test

| Solvent: | 14 parts by weight of dimethylformamide |
| Emulsifier: | alkylaryl polyglycol ether |

To produce a suitable active compound preparation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water. If the addition of ammonium salts or/and penetrants is required, these are each added in a concentration of 1000 ppm to the formulation solution.

Bell pepper plants (*Capsicum annuum*) severely infested with the green peach aphid (*Myzus persicae*) are treated by spraying with the active compound preparation in the desired concentration.

After 6 days, the kill in % is determined. 100% means that all of the aphids have been killed; 0% means that none of the aphids have been killed.

In this test, for example, the following compound from the preparation examples shows an efficacy of 99% at an application rate of 100 ppm: I-387

In this test, for example, the following compound from the preparation examples shows an efficacy of 95% at an application rate of 100 ppm: I-316

COMPARATIVE EXAMPLES

*Meloidogyne incognita* Test

| Solvent: | 7 parts by weight of dimethylformamide |
| Emulsifier: | 2.5 parts by weight of alkylaryl polyglycol ether |

To produce a suitable active compound preparation, 1 part by weight of active compound is mixed with the specified amounts of solvent and emulsifier, and the concentrate is diluted with water to the desired concentration, it being necessary to include the volume of soil which is drenched in the calculation. It should be ensured that a concentration of 20 ppm of emulsifier in the soil is not exceeded. To produce further test concentrations, water is used for dilution.

Pots filled with soil (loamy sand) are watered with the active compound solution. An egg/larvae suspension of the southern root-knot nematode (*Meloidogyne incognita*) is added, lettuce seeds are scattered over the surface of the soil, and they are covered over with quartz sand. The lettuce seeds germinate and the plants develop. The galls develop on the roots.

After 21 days, the nematicidal efficacy in % is determined by the formation of galls. 100% means that no galls have been found; 0% means that the number of galls on the treated plants corresponds to the untreated control.

In this test, for example, the following compounds of the Preparation Examples show superior efficacy to the prior art: see tables

| Substance | Structure | Animal species | Concentration | % Efficacy |
|---|---|---|---|---|
| Ex. I-137 according to the invention | 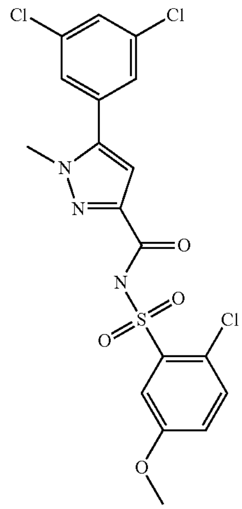 [SMILES: COc1ccc(Cl)c(S(=O)(=O)NC(=O)c2cc(-c3cc(Cl)cc(Cl)c3)n(C)n2)c1] | MELGIN | 1 ppm | 85 21dat |
| Ex. Prior art according to WO2015/169776 | 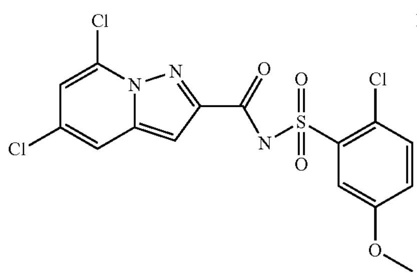 | MELGIN | 1 ppm | 0 21dat |
40
| Substance | Structure | Animal species | concentration | % Efficacy |
|---|---|---|---|---|
| Ex. I-141 according to the invention | 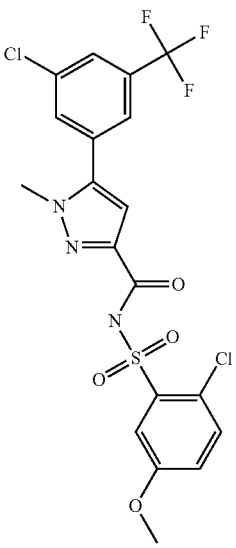 [SMILES: COc1ccc(Cl)c(S(=O)(=O)NC(=O)c2cc(-c3cc(Cl)cc(C(F)(F)F)c3)n(C)n2)c1] | MELGIN | 8 ppm | 99 21dat |

-continued
| Substance | Structure | Animal species | concentration | % Efficacy |
|---|---|---|---|---|
| Ex. Prior art according to WO2015/169776 | 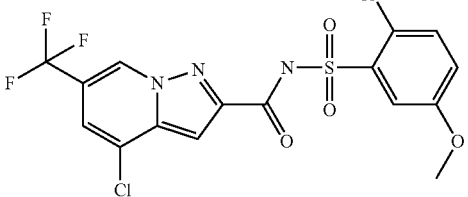 | MELGIN | 8 ppm | 30 21dat |
| Ex. I-113 according to the invention | 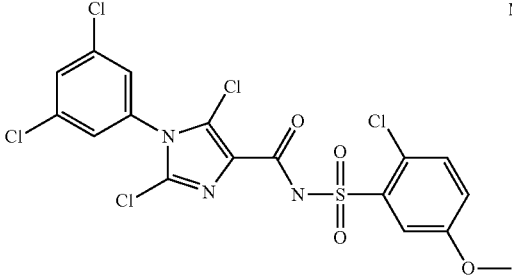 [SMILES: COc1ccc(Cl)c(S(=O)(=O)NC(=O)c2nc(Cl)n(-c3cc(Cl)cc(Cl)c3)c2Cl)c1] | MELGIN | 0.5 ppm | 100 21dat |
| Ex. I-470 according to the invention | 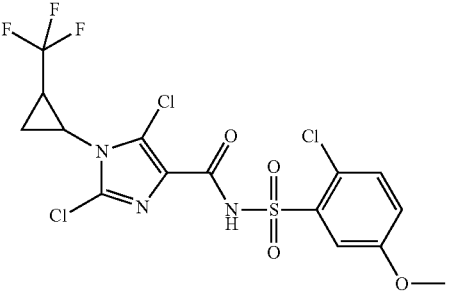 [SMILES: COc1ccc(Cl)c(S(=O)(=O)NC(=O)c2nc(Cl)n(C3CC3C(F)(F)F)c2Cl)c1] | MELGIN | 0.5 ppm | 100 21dat |
| Ex. Prior art according to WO2010/129500 | 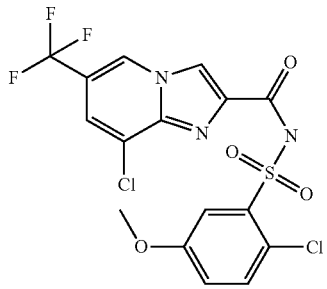 [SMILES: COc1ccc(Cl)c(S(=O)(=O)NC(=O)c2cn3cc(C(F)(F)F)cc(Cl)c3n2)c1] | MELGIN | 0.5 ppm | 55 21dat |

The invention claimed is:
1. A composition comprising at least one compound of formula (I'), and customary extenders and/or surfactants:

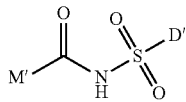
(I')

wherein:
M' is a radical of formula (IIa'), (IIb') or (IIc'):

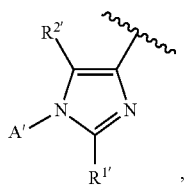
(IIa')

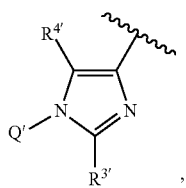
(IIb')

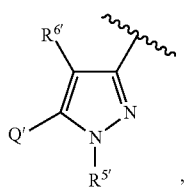
(IIc')

wherein:
R¹ is hydroxy, cyano, carboxyl, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-alkylsulfoximino, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl-$(C_1-C_6)$-alkyl or hetaryl-$(C_1-C_6)$-alkyl, each of which is optionally monosubstituted or polysubstituted by identical or different substituents, wherein hetaryl optionally comprises at least one carbonyl group, and wherein each substituent is independently selected from the group consisting of:

cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino or $(C_1-C_6)$-alkylcarbonylamino;

R²' is hydrogen, cyano, halogen, nitro, acetyl, hydroxy, carboxyl, amino, SCN, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-

$C_6$)-alkoxy, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-alkylsulfoximino, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino, or aryl or hetaryl, each of which is optionally mono- or polysubstituted by identical or different substituents, wherein hetaryl optionally comprises at least one carbonyl group, and wherein each substituent is independently: cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino or ($C_1$-$C_6$)-alkylcarbonylamino;

$R^{3'}$ is cyano, halogen, hydroxy, carboxyl, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-alkylsulfoximino, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino or aryl-($C_1$-$C_6$)-alkyl or hetaryl-($C_1$-$C_6$)-alkyl, each of which is optionally monosubstituted or polysubstituted by identical or different substituents, wherein hetaryl optionally comprises at least one carbonyl group, and wherein each substituent is independently:

cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-

$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino or ($C_1$-$C_6$)-alkylcarbonylamino;

$R^{4'}$ is hydrogen, cyano, halogen, nitro, acetyl, hydroxy, carboxyl, amino, SCN, tri-($C_1$-$C_6$)-alkylsilyl, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl ($C_1$-$C_6$)-alkylsulfinyl, ($C_1$-$C_6$)-haloalkylsulfinyl, ($C_1$-$C_6$)-alkylsulfoximino, ($C_1$-$C_6$)-alkoxy-($C_1$-$C_6$)-alkylsulfinyl, ($C_1$-$C_6$)-alkylsulfinyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino or aryl or hetaryl, each of which is optionally mono- or polysubstituted by identical or different substituents, wherein hetaryl optionally comprises at least one carbonyl group, and wherein each substituent is independently: cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino or ($C_1$-$C_6$)-alkylcarbonylamino;

$R^{5'}$ is ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxycarbonyl-($C_1$-$C_6$)-alkyl, ($C_1$-$C_6$)-alkoxy-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl or halo-($C_1$-$C_6$)-alkylsulfonyl-($C_1$-$C_6$)-alkyl;

$R^{6'}$ is hydrogen, cyano, halogen, nitro, acetyl, hydroxy, carboxyl, amino, tri-($C_1$-$C_6$)-alkylsilyl, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino or aryl-($C_1$-$C_6$)-alkyl or hetaryl-($C_1$-$C_6$)-alkyl, each of which is optionally monosubstituted or polysubstituted by identical or different substituents, wherein hetaryl optionally comprises at least one carbonyl group, present and wherein each substituent is independently:

cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino or ($C_1$-$C_6$)-alkylcarbonylamino;

A' is ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_1$-$C_6$)-alkyl-($C_3$-$C_8$)-cycloalkyl, halo-($C_3$-$C_8$)-cycloalkyl, halo-($C_1$-$C_3$)-alkoxy-($C_1$-$C_4$)-alkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxycarbonyl-($C_1$-$C_6$)-alkyl, ($C_1$-$C_6$)-alkoxy-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, halo-($C_3$-$C_8$)-alkynyl, halo-($C_3$-$C_8$)-alkenyl or an aryl-($C_1$-$C_6$)-alkyl or hetaryl-($C_1$-$C_6$)-alkyl radical, each of which is optionally monosubstituted or polysubstituted by identical or different substituents, wherein hetaryl optionally comprises at least one carbonyl group, and each substituent is independently:

cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino or ($C_1$-$C_6$)-alkylcarbonylamino;

Q' is a 6-membered aryl or hetaryl radical, each of which is unsubstituted or substituted by one or more radicals $R^{7'}$, wherein hetaryl optionally comprises at least one carbonyl group, and each $R^{7'}$ is independently:

cyano, halogen, nitro, acetyl, hydroxy, carboxyl, amino, SCN, tri-($C_1$-$C_6$)-alkylsilyl, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di- ($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino or aryl or hetaryl, each of which is optionally mono- or polysubstituted by identical or different substituents, wherein hetaryl optionally comprises at least one carbonyl group, and each substituent is independently: cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino or ($C_1$-$C_6$)-alkylcarbonylamino;

and

D' is a $C_1$-$C_6$-alkyl, phenyl, phenyl-($C_1$-$C_2$)-alkyl, benzdioxolyl or 5- or 6-membered hetaryl radical which is unsubstituted or substituted by one or more radicals $R^{8'}$ and which optionally contains one to three heteroatoms selected from the group consisting of oxygen, sulfur, and nitrogen, wherein each $R^{8'}$ is independently of:

cyano, halogen, nitro, acetyl, hydroxy, carboxyl, amino, SCN, tri-($C_1$-$C_6$)-alkylsilyl, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkylsulfonyloxy, ($C_1$-$C_6$)-alkyl-carbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino), (1-pyrazolyl) ($C_1$-$C_3$)-alkyl or aryl, hetaryl, aryloxy, or hetaryloxy, each of which is optionally mono- or polysubstituted by identical or different substituents, wherein hetaryl optionally comprises at least one carbonyl group, and each substituent is independently: cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)- alkylaminothiocarbonyl, $(C_3-C_8)$-cycloalkylamino or $(C_1-C_6)$-alkylcarbonylamino.

2. The composition of claim 1, wherein the composition is an agrochemical formulation comprising at least one compound of formula (I') in a biologically effective amount of from 0.00000001 to 98% by weight based on the weight of the agrochemical formulation, and also extenders and/or surfactants.

3. The agrochemical formulation according to claim 2, further comprising an additional agrochemically active compound.

4. A compound of formula (I')

$$\underset{M'}{\overset{O}{\underset{}{\bigvee}}}\underset{H}{\overset{}{N}}\underset{O}{\overset{O}{\underset{}{\overset{}{S}}}}D' \quad (I')$$

wherein:
M' is a radical of formula (IIa'), (IIb') or (IIc'):

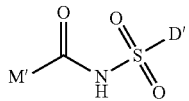
(IIa')

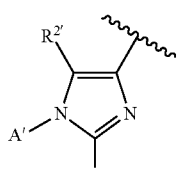
(IIb')

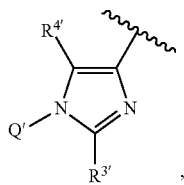
(IIc')

wherein:
$R^{1'}$ is hydroxy, cyano, carboxyl, halogen, nitro, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-alkylsulfoximino, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl-$(C_1-C_6)$-alkyl or hetaryl-$(C_1-C_6)$-alkyl, each of which is optionally monosubstituted or polysubstituted by identical or different substituents, wherein hetaryl optionally comprises at least one carbonyl group, and wherein each substituent is independently:

cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino or $(C_1-C_6)$-alkylcarbonylamino;

$R^{2'}$ is hydrogen, cyano, halogen, nitro, acetyl, hydroxy, carboxyl, amino, SCN, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-alkylsulfoximino, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino, or aryl or hetaryl, each of which is optionally mono- or polysubstituted by identical or different substituents, wherein hetaryl optionally comprises at least one carbonyl group, and wherein each substituent is independently: cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino or ($C_1$-$C_6$)-alkylcarbonylamino;

$R^{3'}$ is cyano, halogen, hydroxy, carboxyl, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-alkylsulfoximino, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino or aryl-($C_1$-$C_6$)-alkyl or hetaryl-($C_1$-$C_6$)-alkyl, each of which is optionally monosubstituted or polysubstituted by identical or different substituents, wherein hetaryl optionally comprises at least one carbonyl group, and wherein each substituent is independently:

cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)- alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino or $(C_1-C_6)$-alkylcarbonylamino;

$R^{4'}$ is hydrogen, cyano, halogen, nitro, acetyl, hydroxy, carboxyl, amino, SCN, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkylsulfoximino, $(C_1-C_6)$-alkoxy-$(C_1-C_6)$-alkylsulfinyl, $(C_1-C_6)$-alkylsulfinyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino or aryl or hetaryl, each of which is optionally mono- or polysubstituted by identical or different substituents, wherein hetaryl optionally comprises at least one carbonyl group, and wherein each substituent is independently: cyano, carboxyl, halogen, nitro, acetyl, hydroxy, amino, SCN, tri-$(C_1-C_6)$-alkylsilyl, $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, di-$(C_1-C_6)$-alkylaminocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino or $(C_1-C_6)$-alkylcarbonylamino;

$R^{5'}$ is $(C_3-C_8)$-cycloalkyl, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl or halo-$(C_1-C_6)$-alkylsulfonyl-$(C_1-C_6)$-alkyl;

$R^{6'}$ is hydrogen, cyano, halogen, nitro, acetyl, hydroxy, carboxyl, amino, tri-$(C_1-C_6)$-alkylsilyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, halo-$(C_1-C_6)$-alkylthio-$(C_1-C_6)$-alkyl, halo-$(C_1-C_6)$-alkylsulfinyl-$(C_1-C_6)$-alkyl, halo-$(C_1-C_6)$-alkylsulfonyl-$(C_1-C_6)$-alkyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$- alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino or aryl-($C_1$-$C_6$)-alkyl or hetaryl-($C_1$-$C_6$)-alkyl, each of which is optionally monosubstituted or polysubstituted by identical or different substituents, wherein hetaryl optionally comprises at least one carbonyl group, present and wherein each substituent is independently:

cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino or ($C_1$-$C_6$)-alkylcarbonylamino;

A' is ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_1$-$C_6$)-alkyl-($C_3$-$C_8$)-cycloalkyl, halo-($C_3$-$C_8$)-cycloalkyl, halo-($C_1$-$C_3$)-alkoxy-($C_1$-$C_4$)-alkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxycarbonyl-($C_1$-$C_6$)-alkyl, ($C_1$-$C_6$)-alkoxy-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, halo-($C_3$-$C_8$)-alkynyl, halo-($C_3$-$C_8$)-alkenyl or an aryl-($C_1$-$C_6$)-alkyl or hetaryl-($C_1$-$C_6$)-alkyl radical, each of which is optionally monosubstituted or polysubstituted by identical or different substituents, wherein hetaryl optionally comprises at least one carbonyl group, and each substituent is independently:

cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino or ($C_1$-$C_6$)-alkylcarbonylamino;

Q' is a 6-membered aryl or hetaryl radical, each of which is unsubstituted or substituted by one or more radicals $R^{7'}$, wherein hetaryl optionally comprises at least one carbonyl group, and each $R^{7'}$ is independently:

cyano, halogen, nitro, acetyl, hydroxy, carboxyl, amino, SCN, tri-($C_1$-$C_6$)-alkylsilyl, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino or aryl or hetaryl, each of which is optionally mono- or polysubstituted by identical or different substituents, wherein hetaryl optionally comprises at least one carbonyl group, and each substituent is independently: cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino or ($C_1$-$C_6$)-alkylcarbonylamino;

and

D' is a $C_1$-$C_6$-alkyl, phenyl, phenyl-($C_1$-$C_2$)-alkyl, benzdioxolyl or 5- or 6-membered hetaryl radical which is unsubstituted or substituted by one or more radicals $R^{8'}$ and which optionally contains one to three heteroatoms selected from the group consisting of oxygen, sulfur, and nitrogen, wherein each $R^{8'}$ is independently of:

cyano, halogen, nitro, acetyl, hydroxy, carboxyl, amino, SCN, tri-($C_1$-$C_6$)-alkylsilyl, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylcarbonylamino), (1-pyrazolyl) ($C_1$-$C_3$)-alkyl or aryl, hetaryl, aryloxy, or hetaryloxy, each of which is optionally mono- or polysubstituted by identical or different substituents, wherein hetaryl optionally comprises at least one carbonyl group, and each substituent is independently: cyano, carboxyl, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl, ($C_1$-$C_6$)-haloalkylsulfinyl, ($C_1$-$C_6$)-alkoxy-($C_1$-$C_6$)-alkylsulfinyl, ($C_1$-$C_6$)-alkylsulfinyl-($C_1$-$C_6$)-alkyl, ($C_1$-$C_6$)-alkylsulfonyl, ($C_1$-$C_6$)-haloalkylsulfonyl, ($C_1$-$C_6$)-alkoxy-($C_1$-$C_6$)-alkylsulfonyl, ($C_1$-$C_6$)-alkylsulfonyl-($C_1$-$C_6$)-alkyl, ($C_1$-$C_6$)-alkylsulfonyloxy, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, di-($C_1$-

$C_6$)-alkylaminocarbonyl, ($C_2$-$C_6$)-alkenylaminocarbonyl, di-($C_2$-$C_6$)-alkenylaminocarbonyl, ($C_3$-$C_8$)-cycloalkylaminocarbonyl, ($C_1$-$C_6$)-alkylsulfonylamino, ($C_1$-$C_6$)-alkylamino, di-($C_1$-$C_6$)-alkylamino, aminosulfonyl, ($C_1$-$C_6$)-alkylaminosulfonyl, di-($C_1$-$C_6$)-alkylaminosulfonyl, ($C_1$-$C_6$)-alkylsulfoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino or ($C_1$-$C_6$)-alkylcarbonylamino.

5. The compound of claim 4, wherein:
$R^{1'}$ is cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, ($C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl, ($C_1$-$C_6$)-alkylcarbonylamino) or benzyl which is unsubstituted or monosubstituted or polysubstituted by identical or different substituents, wherein each substituent is independently:
cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl or ($C_1$-$C_6$)-alkylsulfonyl-($C_1$-$C_6$)-alkyl;
$R^{2'}$ is hydrogen, cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl or ($C_1$-$C_6$)-alkylcarbonylamino);
$R^{3'}$ is cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, ($C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl, ($C_1$-$C_6$)-alkylcarbonylamino) or benzyl which is unsubstituted or monosubstituted or polysubstituted by identical or different substituents, wherein each substituent is independently:
cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl or ($C_1$-$C_6$)-alkylsulfonyl-($C_1$-$C_6$)-alkyl;
$R^{4'}$ is hydrogen, cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl or ($C_1$-$C_6$)-alkylcarbonylamino);
$R^{5'}$ is ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, ($C_1$-$C_6$)-alkylthio-($C_1$-$C_6$)-alkyl, halo-($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, halo-($C_1$-$C_6$)-alkylsulfinyl-($C_1$-$C_6$)-alkyl or halo-($C_1$-$C_6$)-alkylsulfonyl-($C_1$-$C_6$)-alkyl;
$R^{6'}$ is hydrogen, cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl or ($C_1$-$C_6$)-alkylcarbonylamino);
A' is halo-($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, halo-($C_1$-$C_3$)-alkoxy-($C_1$-$C_4$)-alkyl, ($C_1$-$C_6$)-alkylthio-($C_1$-$C_6$)-alkyl, ($C_1$-$C_6$)-alkylsulfinyl-($C_1$-$C_6$)-alkyl, halo-($C_1$-$C_6$)-alkylthio-($C_1$-$C_6$)-alkyl, halo-($C_1$-$C_6$)-alkylsulfinyl-($C_1$-$C_6$)-alkyl, halo-($C_1$-$C_6$)-alkylsulfonyl-($C_1$-$C_6$)-alkyl, halo-($C_3$-$C_6$)-alkenyl or
a benzyl radical which is optionally monosubstituted or polysubstituted by identical or different substituents, wherein each substituent is independently:
cyano, halogen, ($C_3$-$C_6$)-cycloalkyl, ($C_3$-$C_6$)-cycloalkyloxy, ($C_3$-$C_6$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)- alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, halo-$(C_1-C_6)$-alkylthio-$(C_1-C_6)$-alkyl, halo-$(C_1-C_6)$-alkylsulfinyl-$(C_1-C_6)$-alkyl or halo-$(C_1-C_6)$-alkylsulfonyl-$(C_1-C_6)$-alkyl;

Q' is a phenyl or pyridyl radical which is unsubstituted or substituted by one or more radicals $R^{7'}$, wherein each is independently:

cyano, halogen, nitro, $(C_3-C_6)$-cycloalkyl, $(C_3-C_6)$-cycloalkyloxy, $(C_3-C_6)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_6)$-alkoxycarbonyl, $(C_1-C_6)$-haloalkoxycarbonyl, $(C_1-C_6)$-alkylaminocarbonyl, $(C_1-C_6)$-alkylcarbonylamino), halo-$(C_1-C_6)$-alkylthio-$(C_1-C_6)$-alkyl, halo-$(C_1-C_6)$-alkylsulfinyl-$(C_1-C_6)$-alkyl or halo-$(C_1-C_6)$-alkylsulfonyl-$(C_1-C_6)$-alkyl;

and

D' is a $C_1-C_6$-alkyl, phenyl, thiophenyl, isoxazolyl, phenyl-$(C_1-C_2)$-alkyl or benzdioxolyl radical which is unsubstituted or substituted by one or more radicals $R^{8'}$, wherein each $R^{8'}$ is independently:

cyano, halogen, nitro, acetyl, $(C_3-C_8)$-cycloalkyl, $(C_3-C_8)$-cycloalkyloxy, $(C_3-C_8)$-cycloalkyl-$(C_3-C_8)$-cycloalkyl, $(C_1-C_6)$-alkyl-$(C_3-C_8)$-cycloalkyl, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulfinyl, $(C_1-C_6)$-haloalkylsulfinyl, $(C_1-C_6)$-alkoxy-$(C_1-C_6)$-alkylsulfinyl, $(C_1-C_6)$-alkylsulfinyl-$(C_1-C_6)$-alkyl, $(C_1-C_6)$-alkylsulfonyl, $(C_1-C_6)$-haloalkylsulfonyl, $(C_1-C_6)$-alkoxy-$(C_1-C_6)$-alkylsulfonyl, $(C_1-C_6)$-alkylsulfonyl-$(C_1-C_6)$-alkyl, $(C_1-C_6)$-alkylsulfonyloxy, $(C_1-C_6)$-alkylcarbonyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulfonylamino, $(C_1-C_6)$-alkylamino, di-$(C_1-C_6)$-alkylamino, aminosulfonyl, $(C_1-C_6)$-alkylaminosulfonyl, di-$(C_1-C_6)$-alkylaminosulfonyl, $(C_1-C_6)$-alkylsulfoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylcarbonylamino, (1-pyrazolyl)$(C_1-C_3)$-alkyl or $(C_1-C_3)$-alkoxypyrimidinyloxy.

6. The compound of claim 4, wherein:

$R^{1'}$ is cyano, halogen, cyclopropyl, $(C_1-C_4)$-alkyl, halocyclopropyl, halo-$(C_1-C_3)$-alkylcyclopropyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylthio-$(C_1-C_4)$-alkyl, $(C_1-C_4)$-alkylsulfinyl-$(C_1-C_4)$-alkyl, $(C_1-C_4)$-alkylsulfonyl-$(C_1-C_4)$-alkyl, or benzyl which is unsubstituted, monosubstituted or polysubstituted by identical or different substituents, wherein each substituent is indepedently:

cyano, halogen, $(C_1-C_4)$-haloalkyl, $(C_1-C_4)$-alkoxy, $(C_1-C_4)$-haloalkoxy, $(C_1-C_6)$-alkylthio or $(C_1-C_6)$-haloalkylthio;

$R^{2'}$ is hydrogen, cyano, halogen, $(C_1-C_4)$-haloalkyl, $(C_1-C_4)$-alkoxy, $(C_1-C_4)$-haloalkoxy, $(C_1-C_6)$-alkylthio or $(C_1-C_6)$-haloalkylthio;

$R^{3'}$ is cyano, halogen, cyclopropyl, $(C_1-C_4)$-alkyl, halocyclopropyl, halo-$(C_1-C_3)$-alkylcyclopropyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylthio-$(C_1-C_4)$-alkyl, $(C_1-C_4)$-alkylsulfinyl-$(C_1-C_4)$-alkyl, or $(C_1-C_4)$-alkylsulfonyl-$(C_1-C_4)$-alkyl;

$R^{4'}$ is hydrogen, cyano, halogen, $(C_1-C_4)$-haloalkyl, $(C_1-C_4)$-alkoxy, $(C_1-C_4)$-alkyl, $(C_3-C_4)$-cycloalkyl, $(C_1-C_4)$-haloalkoxy, $(C_1-C_6)$-alkylthio or $(C_1-C_6)$-haloalkylthio;

$R^{5'}$ is cyclopropyl, $(C_1-C_4)$-alkyl, halocyclopropyl, halo-$(C_1-C_3)$-alkylcyclopropyl or $(C_1-C_4)$-haloalkyl;

$R^{6'}$ is hydrogen, cyano, halogen, $(C_1-C_4)$-haloalkyl, $(C_1-C_4)$-alkoxy, $(C_1-C_4)$-haloalkoxy, $(C_1-C_6)$-alkylthio or $(C_1-C_6)$-haloalkylthio;

A' is halo-$(C_1-C_4)$-alkyl-$(C_3-C_4)$-cycloalkyl, halo-$(C_3-C_6)$-cycloalkyl, $(C_1-C_6)$-alkyl, $(C_1-C_5)$-haloalkyl, $(C_1-C_6)$-cyanoalkyl, $(C_1-C_4)$-alkoxy-$(C_1-C_4)$-alkyl, halo-$(C_1-C_3)$-alkoxy-$(C_1-C_4)$-alkyl, $(C_1-C_4)$-alkylthio-$(C_1-C_4)$-alkyl, $(C_1-C_4)$-alkylsulfinyl-$(C_1-C_4)$-alkyl, halo-$(C_3-C_4)$-alkenyl or a benzyl radical which is optionally monosubstituted or polysubstituted by identical or different substituents, wherein each substituent is independently:

cyano, halogen, $(C_3-C_6)$-cycloalkyl, $(C_3-C_6)$-cycloalkyloxy, halo-$(C_3-C_8)$-cycloalkyl, $(C_1-C_6)$-alkyl, $(C_1-C_6)$-haloalkyl, $(C_1-C_6)$-cyanoalkyl, $(C_1-C_6)$-alkoxy-$(C_1-C_6)$-alkyl, $(C_1-C_6)$-alkoxy, $(C_1-C_6)$-haloalkoxy, $(C_1-C_6)$-cyanoalkoxy, $(C_1-C_6)$-alkoxy-$(C_1-C_6)$-alkoxy, $(C_1-C_6)$-alkylthio or $(C_1-C_6)$-haloalkylthio;

Q' is a phenyl or pyridyl radical which is unsubstituted or substituted by one or more radicals $R^{7'}$, wherein each $R^{7'}$ is independently:

cyano, halogen, $(C_3-C_6)$-cycloalkyl, halo-$(C_3-C_8)$-cycloalkyl, $(C_1-C_6)$-alkyl, $(C_1-C_6)$-haloalkyl, $(C_1-C_6)$-alkoxy-$(C_1-C_6)$-alkyl, $(C_1-C_6)$-alkoxy or $(C_1-C_6)$-haloalkoxy;

and

D' is a $C_1-C_6$-alkyl, phenyl, thiophenyl, isoxazolyl, benzyl or benzdioxolyl radical which is unsubstituted or substituted by one or more radicals $R^{8'}$, wherein each $R^{8'}$ is independently:

cyano, halogen, acetyl, $(C_3-C_6)$-cycloalkyl, $(C_3-C_6)$-cycloalkyloxy, $(C_3-C_6)$-cycloalkyl-$(C_3-C_8)$-cycloalkyl, $(C_1-C_6)$-alkyl-$(C_3-C_6)$-cycloalkyl, halo-$(C_3-C_6)$-cycloalkyl, $(C_1-C_6)$-alkyl, $(C_1-C_6)$-haloalkyl, $(C_1-C_6)$-cyanoalkyl, $(C_1-C_6)$-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, (C₁-C₆)-alkoxy, (C₁-C₆)-haloalkoxy, (C₁-C₆)-cyanoalkoxy, (C₁-C₆)-alkoxycarbonyl-(C₁-C₆)-alkoxy, (C₁-C₆)-alkoxy-(C₁-C₆)-alkoxy, (C₁-C₆)-alkoxyimino, (C₁-C₆)-alkyl-(C₁-C₆)-alkoxyimino, (C₁-C₆)-haloalkyl-(C₁-C₆)-alkoxyimino, (C₁-C₆)-alkylthio, (C₁-C₆)-haloalkylthio, (C₁-C₆)-alkoxy-(C₁-C₆)-alkylthio, (C₁-C₆)-alkylthio-(C₁-C₆)-alkyl, (C₁-C₆)-alkylsulfinyl, (C₁-C₆)-haloalkylsulfinyl, (C₁-C₆)-alkoxy-(C₁-C₆)-alkylsulfinyl, (C₁-C₆)-alkylsulfinyl-(C₁-C₆)-alkyl, (C₁-C₆)-alkylsulfonyl, (C₁-C₆)haloalkylsulfonyl, (C₁-C₆)-alkoxy-(C₁-C₆)-alkylsulfonyl, (C₁-C₆)-alkylsulfonyl-(C₁-C₆)-alkyl, (C₁-C₆)-alkylsulfonyloxy, (C₁-C₆)-alkylcarbonyl, (C₁-C₆)-haloalkylcarbonyl, (C₁-C₆)-alkylcarbonyloxy, (C₁-C₆)-alkoxycarbonyl, (C₁-C₆)-haloalkoxycarbonyl, aminocarbonyl, (C₁-C₆)-alkylaminocarbonyl, di-(C₁-C₆)-alkylaminocarbonyl, (C₂-C₆)-alkenylaminocarbonyl, di-(C₂-C₆)-alkenylaminocarbonyl, (C₃-C₈)-cycloalkylaminocarbonyl, (C₁-C₆)-alkylsulfonylamino, (C₁-C₆)-alkylamino, di-(C₁-C₆)-alkylamino, (C₃-C₈)-cycloalkylamino, (C₁-C₆)-alkylcarbonylamino, (1-pyrazolyl)(C₁-C₃)alkyl or (C₁-C₃)-alkoxypyrimidinyloxy.

7. The compound of claim 4, wherein:
R¹' is halogen, cyclopropyl, (C₁-C₄)-alkyl, (C₁-C₄)-alkylthio, halocyclopropyl, (C₁-C₄)-haloalkyl or benzyl which is unsubstituted or monosubstituted or polysubstituted by identical or different substituents, wherein each substituent is independently: cyano, halogen, (C₁-C₄)-haloalkyl or (C₁-C₄)-alkoxy;
R²' is hydrogen, halogen, cyano, (C₁-C₄)-alkyl, or (C₁-C₄)-haloalkyl;
R³' is halogen, cyclopropyl, (C₁-C₄)-alkyl, halocyclopropyl or (C₁-C₄)-haloalkyl;
R⁴' is hydrogen, halogen, cyano, (C₁-C₄)-alkyl, cyclopropyl, or (C₁-C₄)-haloalkyl;
R⁵' is cyclopropyl, (C₁-C₄)-alkyl or halo-(C₁-C₄)-alkyl;
R⁶' is hydrogen, halogen, cyano, (C₁-C₄)-alkyl or (C₁-C₄)-haloalkyl;
A' is halo-(C₁-C₄)-alkyl-(C₃-C₄)-cycloalkyl, halo-(C₃-C₆)-cycloalkyl, (C₁-C₆)-alkyl, (C₁-C₅)-haloalkyl, (C₁-C₆)-cyanoalkyl, (C₁-C₄)-alkoxy-(C₁-C₄)-alkyl, halo-(C₁-C₃)-alkoxy-(C₁-C₄)-alkyl, (C₁-C₄)-alkylthio-(C₁-C₄)-alkyl, (C₁-C₄)-alkylsulfinyl-(C₁-C₄)-alkyl, halo-(C₃-C₄)-alkenyl or
a benzyl radical which is optionally monosubstituted or polysubstituted by identical or different substituents, wherein each substituent is independently:
cyano, halogen, (C₃-C₆)-cycloalkyl, (C₃-C₆)-cycloalkyloxy, halo-(C₃-C₈)-cycloalkyl, (C₁-C₆)-alkyl, (C₁-C₆)-haloalkyl, (C₁-C₆)-alkoxy-(C₁-C₆)-alkyl, (C₁-C₆)-alkoxy, (C₁-C₆)-haloalkoxy, (C₁-C₆)-alkylthio or (C₁-C₆)-haloalkylthio;
Q' is a phenyl or pyridyl radical which is unsubstituted or substituted by one or more radicals R⁷',
wherein each R⁷' is independently:
cyano, halogen, (C₃-C₆)-cycloalkyl, halo-(C₃-C₆)-cycloalkyl, (C₁-C₆)-alkyl, (C₁-C₆)-haloalkyl, (C₁-C₆)-alkoxy-(C₁-C₆)-alkyl, (C₁-C₆)-alkoxy or (C₁-C₆)-haloalkoxy;
and
D' is a C₁-C₆-alkyl, phenyl, thiophenyl, isoxazolyl, benzyl or benzdioxolyl radical which is unsubstituted or substituted by one or more radicals R⁸',
wherein each R⁸' is independently:
cyano, halogen, acetyl, (C₃-C₆)-cycloalkyl, (C₃-C₆)-cycloalkyloxy, (C₃-C₆)-cycloalkyl-(C₃-C₈)-cycloalkyl, (C₁-C₆)-alkyl-(C₃-C₆)-cycloalkyl, halo-(C₃-C₆)-cycloalkyl, (C₁-C₆)-alkyl, (C₁-C₆)-haloalkyl, (C₁-C₆)-cyanoalkyl, (C₁-C₆)-hydroxyalkyl, hydroxycarbonyl-(C₁-C₆)-alkoxy, (C₁-C₆)-alkoxycarbonyl-(C₁-C₆)-alkyl, (C₁-C₆)-alkoxy-(C₁-C₆)-alkyl, (C₁-C₆)-alkoxy, (C₁-C₆)-haloalkoxy, (C₁-C₆)-cyanoalkoxy, (C₁-C₆)-alkoxy-(C₁-C₆)-alkoxy, (C₁-C₆)-alkoxyimino, (C₁-C₆)-alkyl-(C₁-C₆)-alkoxyimino, (C₁-C₆)-haloalkyl-(C₁-C₆)-alkoxyimino, (C₁-C₆)-alkylthio, (C₁-C₆)-haloalkylthio, (C₁-C₆)-alkoxy-(C₁-C₆)-alkylthio, (C₁-C₆)-alkylthio-(C₁-C₆)-alkyl, (C₁-C₆)-alkylsulfinyl, (C₁-C₆)-haloalkylsulfinyl, (C₁-C₆)-alkoxy-(C₁-C₆)-alkylsulfinyl, (C₁-C₆)-alkylsulfinyl-(C₁-C₆)-alkyl, (C₁-C₆)-alkylsulfonyl, (C₁-C₆)-haloalkylsulfonyl, (C₁-C₆)-alkoxy-(C₁-C₆)-alkylsulfonyl, (C₁-C₆)-alkylsulfonyl-(C₁-C₆)-alkyl, (C₁-C₆)-alkylsulfonyloxy, (C₁-C₆)-alkylcarbonyl, (C₁-C₆)-haloalkylcarbonyl, (C₁-C₆)-alkylcarbonyloxy, (C₁-C₆)-alkoxycarbonyl, (C₁-C₆)-haloalkoxycarbonyl, aminocarbonyl, (C₁-C₆)-alkylaminocarbonyl, di-(C₁-C₆)-alkylaminocarbonyl, (C₂-C₆)-alkenylaminocarbonyl, (C₃-C₈)-cycloalkylaminocarbonyl, (C₁-C₆)-alkylsulfonylamino, (C₁-C₆)-alkylamino, di-(C₁-C₆)-alkylamino, (C₃-C₆)-cycloalkylamino, (C₁-C₆)-alkylcarbonylamino, (1-pyrazolyl)(C₁-C₃)-alkyl or (C₁-C₃)-alkoxypyrimidinyloxy.

8. The compound of claim 4, wherein:
R¹' is chlorine, bromine, methyl, benzyl, 2-chlorobenzyl, 3-chlorobenzyl, 4-chlorobenzyl, trifluoromethyl, methylthio or isopropylthio;
R²' is hydrogen, cyano, chlorine, bromine or iodine;
R³' is chlorine, methyl, isopropyl, ethyl or bromine;
R⁴' is hydrogen, chlorine, bromine, iodine, fluorine, difluoromethyl, isopropyl or cyclopropyl;
R⁵' is methyl or 2,2,2-trifluoroethyl;
R⁶' is hydrogen or chlorine;
A' is a radical selected from the radicals of formula (III1-III19):

(III1)

(III2)

(III3)

(III4)

(III5)

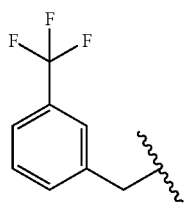 (III6)
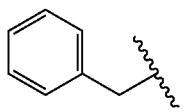 (III7)
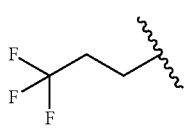 (III8)
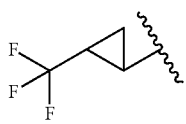 (III9)
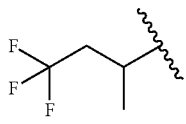 (III10)
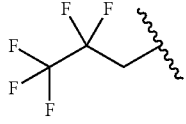 (III11)
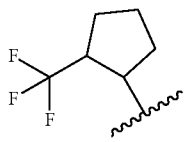 (III12)
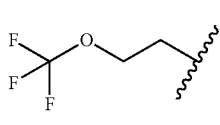 (III13)
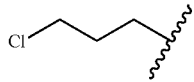 (III14)
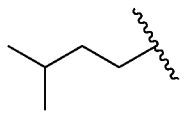 (III15)
 (III16)
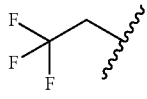 (III17)
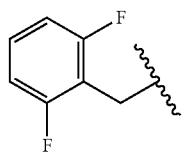 (III18)
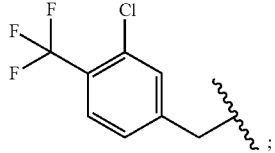 (III19)
Q' is a radical selected from the radicals of formula (IV1-IV40):
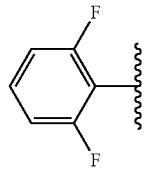 (IV1)
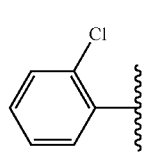 (IV2)
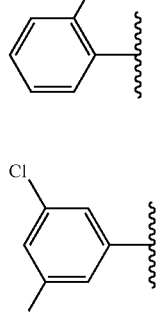 (IV3)
(IV4)
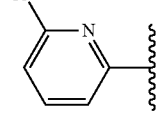 (IV5)
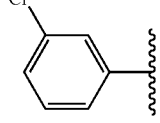 (IV6)
(IV7)

-continued
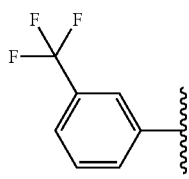 (IV8)
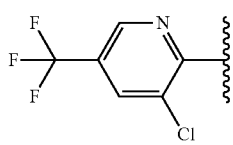 (IV9)
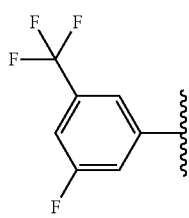 (IV10)
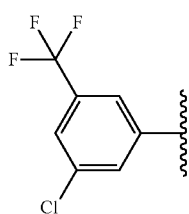 (IV11)
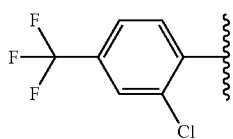 (IV12)
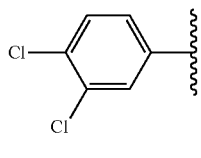 (IV13)
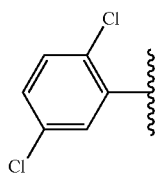 (IV14)
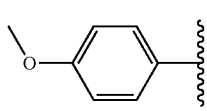 (IV16)
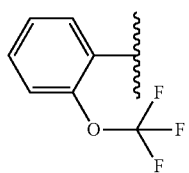 (IV17)
-continued
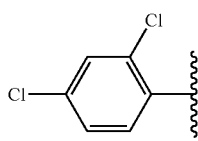 (IV18)
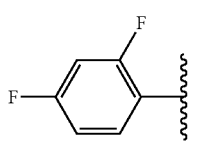 (IV19)
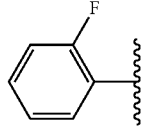 (IV20)
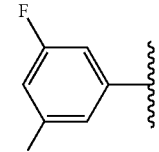 (IV21)
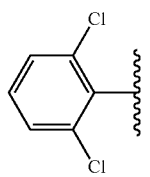 (IV22)
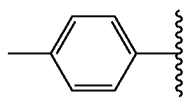 (IV23)
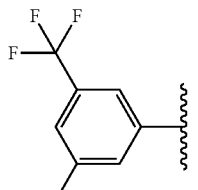 (IV24)
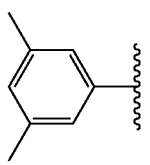 (IV25)
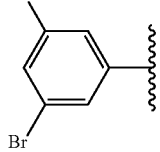 (IV26)

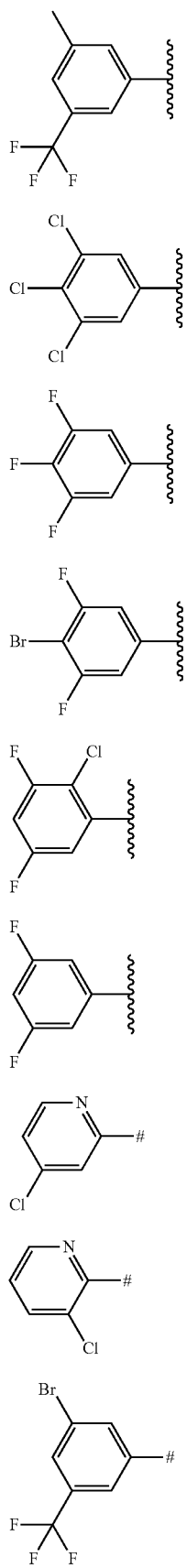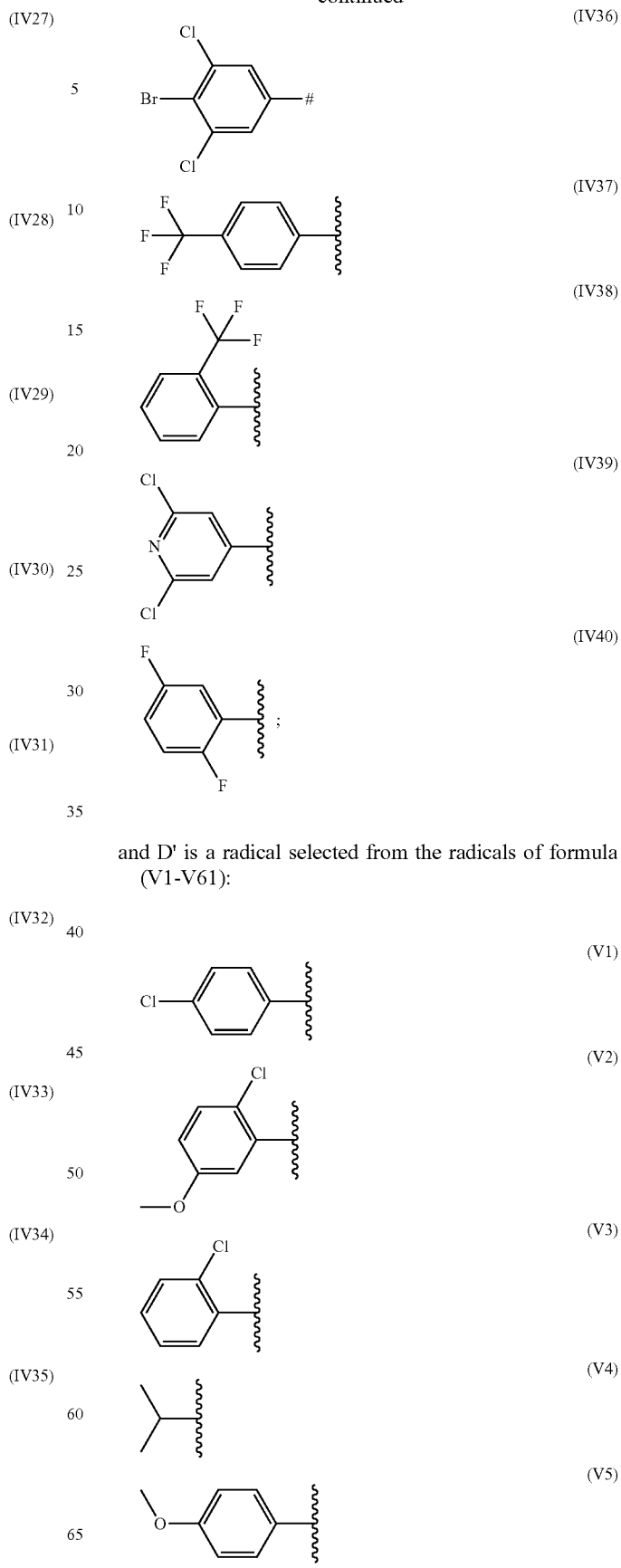
and D' is a radical selected from the radicals of formula (V1-V61):

-continued
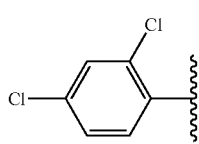 (V6)
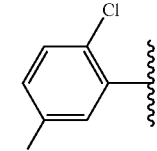 (V7)
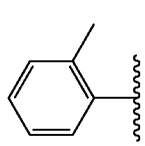 (V8)
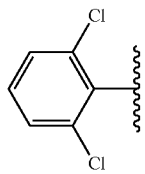 (V9)
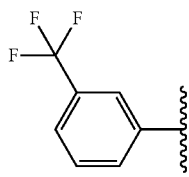 (V10)
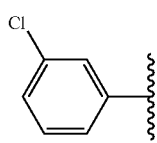 (V11)
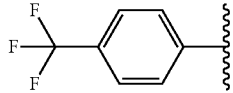 (V12)
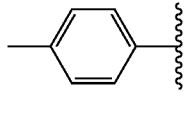 (V13)
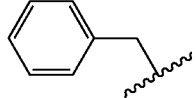 (V14)
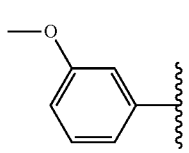 (V15)
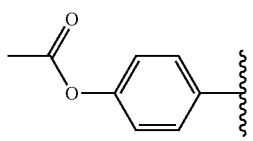 (V16)
-continued
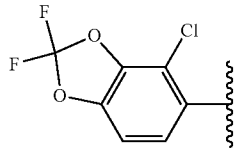 (V17)
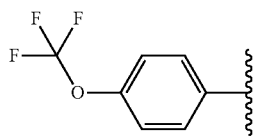 (V18)
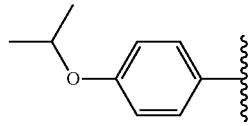 (V19)
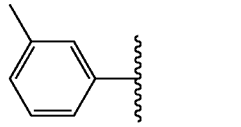 (V20)
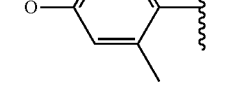 (V21)
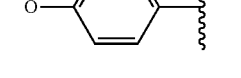 (V22)
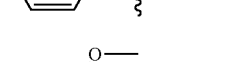 (V23)
 (V24)
 (V25)
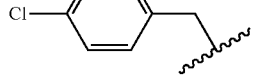 (V26)
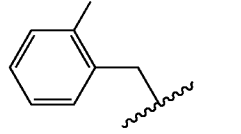 (V27)

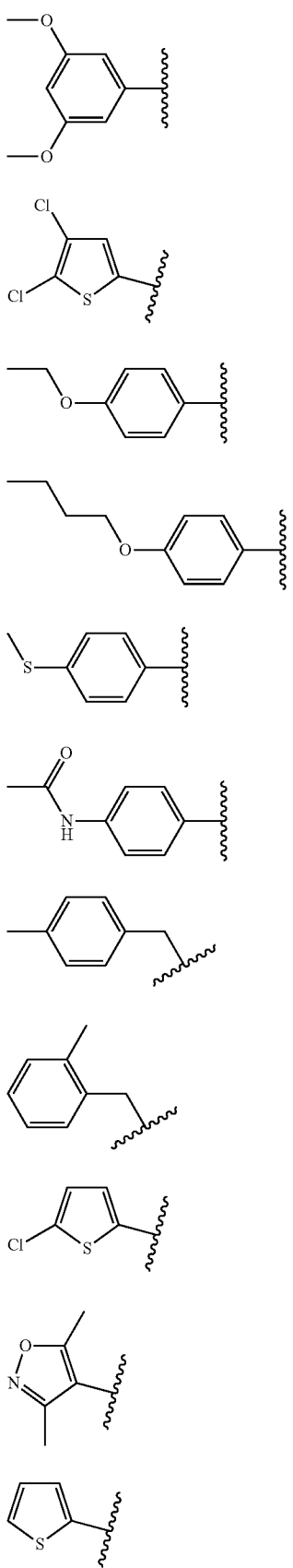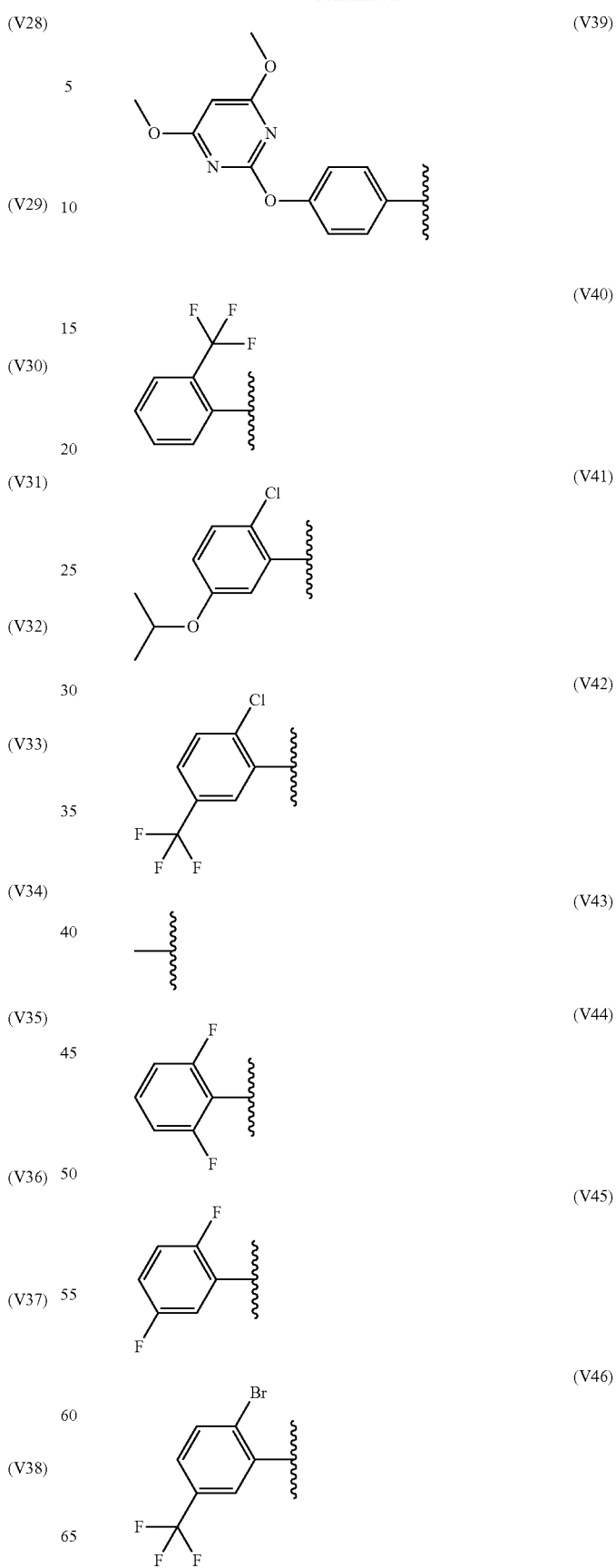

(V47) 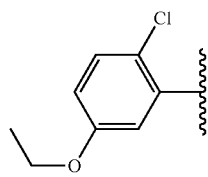
(V48) 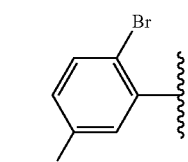
(V49) 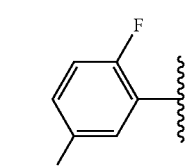
(V50) 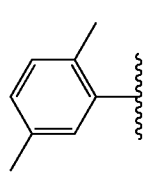
(V51) 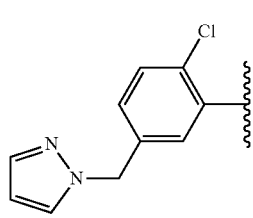
(V52) 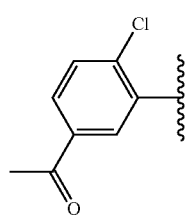
(V53) 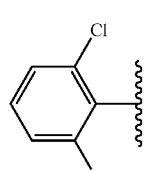
(V54) 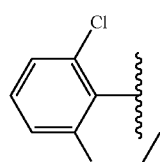
(V55) 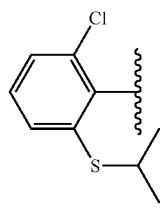
(V56) 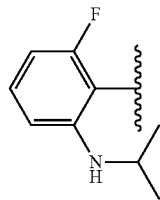
(V57) 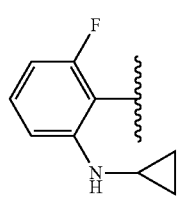
(V58) 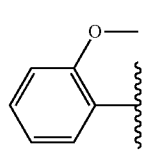
(V59) 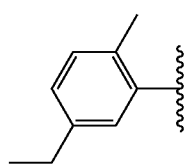
(V60) 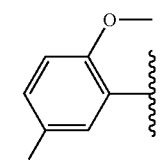
(V61) 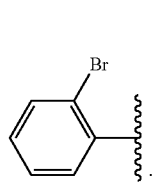
9. The compound of claim 4, wherein M is a radical selected from the group consisting of formulae IIa' and IIb', wherein the radicals $R^{1'}$, $R^{2'}$, $A'$, $R^{3'}$, $R^{4'}$, $R^{7'}$, $R^{8'}$, $Q'$ and $D'$ are as defined in claim 4.

10. The compound according to claim 4, wherein the compound of formula (I') is a compound of formula (Ia'), (Ib') or (Ic'),

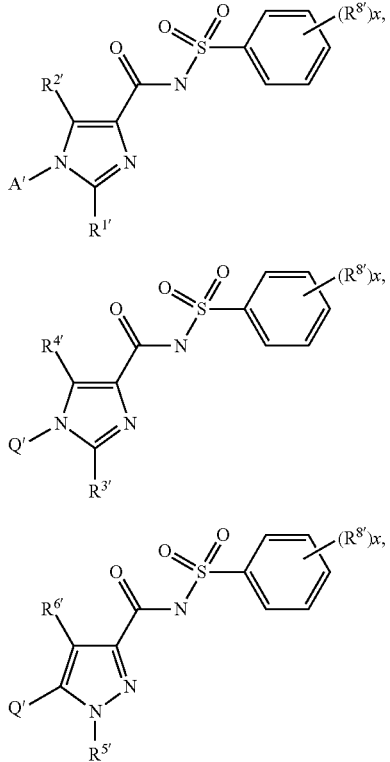

wherein the radicals R¹', R²', R³', R⁴', R⁵', R⁶', R⁷', A', Q' and R⁸' are as defined in claim 4.

11. An intermediate of formula (VIa), (Xa) or (IXa)

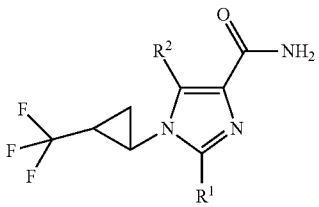

wherein

R¹ is hydrogen, cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, ($C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl, ($C_1$-$C_6$)-alkylcarbonylamino) or benzyl which is unsubstituted or monosubstituted or polysubstituted by identical or different substituents, wherein each substituent is independently:

cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, $C_1$-$C_6$)-alkoxy-($C_1$-$C_6$)-alkoxy, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl or ($C_1$-$C_6$)-alkylsulfonyl-($C_1$-$C_6$)-alkyl;

R² is hydrogen, cyano, halogen, nitro, ($C_3$-$C_8$)-cycloalkyl, ($C_3$-$C_8$)-cycloalkyloxy, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkoxy, ($C_1$-$C_6$)-haloalkoxy, ($C_1$-$C_6$)-cyanoalkoxy, ($C_1$-$C_6$)-alkoxy-($C_1$-$C_6$)-alkoxy, ($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-alkylsulfonyl-($C_1$-$C_6$)-alkyl, ($C_1$-$C_6$)-alkoxycarbonyl, ($C_1$-$C_6$)-haloalkoxycarbonyl, ($C_1$-$C_6$)-alkylaminocarbonyl or ($C_1$-$C_6$)-alkylcarbonylamino; and $R^x$ is ($C_1$-$C_6$)-alkyl or ($C_3$-$C_8$)-cycloalkyl.

* * * * *